(12) United States Patent
Castro et al.

(10) Patent No.: US 9,115,141 B2
(45) Date of Patent: Aug. 25, 2015

(54) SUBSTITUTED ISOQUINOLINONES AND METHODS OF TREATMENT THEREOF

(71) Applicant: Infinity Pharmaceuticals, Inc., Cambridge, MA (US)

(72) Inventors: Alfredo C. Castro, Winchester, MA (US); Catherine A. Evans, Somerville, MA (US); Somarajannair Janardanannair, Woburn, MA (US); Andre Lescarbeau, Somerville, MA (US); Tao Liu, Ashland, MA (US); Daniel A. Snyder, Somerville, MA (US); Martin R. Tremblay, Melrose, MA (US); Pingda Ren, San Diego, CA (US); Yi Liu, San Diego, CA (US); Liansheng Li, San Diego, CA (US); Katrina Chan, Fremont, CA (US)

(73) Assignee: Infinity Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 14/099,831

(22) Filed: Dec. 6, 2013

(65) Prior Publication Data

US 2014/0100214 A1    Apr. 10, 2014

Related U.S. Application Data

(63) Continuation of application No. 13/552,516, filed on Jul. 18, 2012, now Pat. No. 8,785,470.

(60) Provisional application No. 61/645,982, filed on May 11, 2012, provisional application No. 61/595,947, filed on Feb. 7, 2012, provisional application No. 61/562,278, filed on Nov. 21, 2011, provisional application No. 61/547,343, filed on Oct. 14, 2011, provisional application No. 61/528,585, filed on Aug. 29, 2011.

(51) Int. Cl.

| | |
|---|---|
| *A61K 31/472* | (2006.01) |
| *C07D 217/24* | (2006.01) |
| *C07D 495/04* | (2006.01) |
| *C07D 401/14* | (2006.01) |
| *C07D 413/14* | (2006.01) |
| *C07D 401/12* | (2006.01) |
| *C07D 411/14* | (2006.01) |
| *C07D 417/14* | (2006.01) |
| *C07D 487/04* | (2006.01) |
| *A61K 31/506* | (2006.01) |
| *A61K 31/517* | (2006.01) |
| *A61K 31/5377* | (2006.01) |
| *A61K 45/06* | (2006.01) |
| *C07D 403/12* | (2006.01) |
| *C07D 405/14* | (2006.01) |
| *C07D 471/04* | (2006.01) |
| *C07D 403/14* | (2006.01) |
| *C07D 513/04* | (2006.01) |

(52) U.S. Cl.
CPC ............ *C07D 495/04* (2013.01); *A61K 31/506* (2013.01); *A61K 31/517* (2013.01); *A61K 31/5377* (2013.01); *A61K 45/06* (2013.01); *C07D 401/12* (2013.01); *C07D 401/14* (2013.01); *C07D 403/12* (2013.01); *C07D 403/14* (2013.01); *C07D 405/14* (2013.01); *C07D 411/14* (2013.01); *C07D 413/14* (2013.01); *C07D 417/14* (2013.01); *C07D 471/04* (2013.01); *C07D 487/04* (2013.01); *C07D 513/04* (2013.01)

(58) Field of Classification Search
CPC ............................ A61K 31/472; C07D 217/24
USPC ................... 514/309; 544/328; 546/141, 290
See application file for complete search history.

(56) References Cited

U.S. PATENT DOCUMENTS

| | | | |
|---|---|---|---|
| 4,547,508 | A | 10/1985 | Konz et al. |
| 4,656,159 | A | 4/1987 | McPherson et al. |
| 4,704,381 | A | 11/1987 | Schaumann et al. |
| 4,795,627 | A | 1/1989 | Fisher et al. |
| 5,240,941 | A | 8/1993 | Bruneau |
| 5,294,612 | A | 3/1994 | Bacon et al. |
| 5,310,731 | A | 5/1994 | Olsson et al. |
| 5,364,862 | A | 11/1994 | Spada et al. |
| 5,420,419 | A | 5/1995 | Wood |
| 5,428,125 | A | 6/1995 | Hefner, Jr. et al. |
| 5,442,039 | A | 8/1995 | Hefner, Jr. et al. |
| 5,504,103 | A | 4/1996 | Bonjouklian et al. |
| 5,506,347 | A | 4/1996 | Erion et al. |
| 5,561,134 | A | 10/1996 | Spada et al. |

(Continued)

FOREIGN PATENT DOCUMENTS

| | | |
|---|---|---|
| CA | 1338379 C | 6/1996 |
| CN | 101602768 A | 12/2009 |

(Continued)

OTHER PUBLICATIONS

Jordan, V. C. Nature Reviews: Drug Discovery, 2, 2003, 205.*
Hackam, et al. JAMA, 296(14), 2006, 1731-1732.*
Abdel-Mohsen, "Synthesis, Reactions and Antimicrobial Activity of 2-Amino-4-(8-quinolinol-5-yl)-1-(p-tolyl)-pyrrole-3-carbonitrile," *Bull. Korean Chem. Soc.* 26(5):719-728 (2005).
Abe et al., "T cell receptor-mediated recognition of self-ligand induces signaling in immature thymocytes before negative selection," *J. Exp. Med.* 176(2):459-468 (1992).

(Continued)

Primary Examiner — Douglas M Willis
(74) *Attorney, Agent, or Firm* — Jones Day

(57) ABSTRACT

Substituted isoquinolinone compounds and pharmaceutical compositions that modulate kinase activity, including PI3 kinase activity, and compounds, pharmaceutical compositions, and methods of treatment of diseases and conditions associated with kinase activity, including PI3 kinase activity, are described herein.

49 Claims, No Drawings

(56) References Cited

U.S. PATENT DOCUMENTS

| | | |
|---|---|---|
| 5,563,257 A | 10/1996 | Zilch et al. |
| 5,593,997 A | 1/1997 | Dow et al. |
| 5,646,128 A | 7/1997 | Firestein et al. |
| 5,652,366 A | 7/1997 | Spada et al. |
| 5,654,307 A | 8/1997 | Bridges et al. |
| 5,665,721 A | 9/1997 | Bhagwat et al. |
| 5,674,998 A | 10/1997 | Boyer et al. |
| 5,686,455 A | 11/1997 | Adams et al. |
| 5,736,554 A | 4/1998 | Spada et al. |
| 5,747,235 A | 5/1998 | Farid et al. |
| 5,756,711 A | 5/1998 | Zilch et al. |
| 5,763,596 A | 6/1998 | Boyer et al. |
| 5,763,597 A | 6/1998 | Ugarkar et al. |
| 5,763,885 A | 6/1998 | Murphy et al. |
| 5,795,977 A | 8/1998 | Ugarkar et al. |
| 5,811,454 A | 9/1998 | Springer |
| 5,824,492 A | 10/1998 | Hiles et al. |
| 5,858,753 A | 1/1999 | Chantry et al. |
| 5,914,488 A | 6/1999 | Sone |
| 5,919,808 A | 7/1999 | Petrie et al. |
| 5,922,753 A | 7/1999 | Petrie et al. |
| 5,948,776 A | 9/1999 | Petrie et al. |
| 5,965,573 A | 10/1999 | Petrie et al. |
| 5,977,061 A | 11/1999 | Holy et al. |
| 5,981,533 A | 11/1999 | Traxler et al. |
| 5,985,589 A | 11/1999 | Chantry et al. |
| 5,990,169 A | 11/1999 | Petrie et al. |
| 5,994,358 A | 11/1999 | Petrie et al. |
| 6,001,839 A | 12/1999 | Calderwood et al. |
| 6,057,305 A | 5/2000 | Holy et al. |
| 6,084,095 A | 7/2000 | Bridges et al. |
| 6,093,737 A | 7/2000 | Anthony et al. |
| 6,127,121 A | 10/2000 | Meyer, Jr. et al. |
| 6,153,631 A | 11/2000 | Petrie et al. |
| 6,191,170 B1 | 2/2001 | Medina |
| 6,251,901 B1 | 6/2001 | Petrie et al. |
| 6,265,410 B1 | 7/2001 | Bridges et al. |
| 6,268,370 B1 | 7/2001 | Adams et al. |
| 6,312,894 B1 | 11/2001 | Hedgpeth et al. |
| 6,323,201 B1 | 11/2001 | Carson et al. |
| 6,342,514 B1 | 1/2002 | Petrie et al. |
| 6,350,741 B1 | 2/2002 | Golec et al. |
| 6,383,790 B1 | 5/2002 | Shokat |
| 6,384,039 B1 | 5/2002 | Fossa |
| 6,387,894 B1 | 5/2002 | Fossa |
| 6,390,821 B1 | 5/2002 | Shokat |
| 6,455,534 B2 | 9/2002 | Bridges et al. |
| 6,472,153 B1 | 10/2002 | Dempcy et al. |
| 6,482,623 B1 | 11/2002 | Vanhaesebroeck et al. |
| 6,485,906 B2 | 11/2002 | Meyer, Jr. et al. |
| 6,492,346 B1 | 12/2002 | Hedgpeth et al. |
| 6,506,769 B2 | 1/2003 | Snow et al. |
| 6,518,277 B1 | 2/2003 | Sadhu et al. |
| 6,521,417 B1 | 2/2003 | Shokat |
| 6,521,620 B1 | 2/2003 | Bridges et al. |
| 6,531,491 B1 | 3/2003 | Kania et al. |
| 6,534,524 B1 | 3/2003 | Kania et al. |
| 6,545,005 B1 | 4/2003 | Baxter et al. |
| 6,552,192 B1 | 4/2003 | Hanus et al. |
| 6,562,819 B2 | 5/2003 | Carson et al. |
| 6,583,161 B1 | 6/2003 | Medina |
| 6,613,798 B1 | 9/2003 | Porter et al. |
| 6,630,495 B1 | 10/2003 | Cooke et al. |
| 6,632,789 B1 | 10/2003 | June |
| 6,645,989 B2 | 11/2003 | Adams et al. |
| 6,649,631 B1 | 11/2003 | Orme et al. |
| 6,653,296 B1 | 11/2003 | Holy et al. |
| 6,653,306 B1 | 11/2003 | Alexander et al. |
| 6,660,744 B1 | 12/2003 | Hirst et al. |
| 6,660,845 B1 | 12/2003 | Gall et al. |
| 6,664,269 B2 | 12/2003 | Martin et al. |
| 6,667,300 B2 | 12/2003 | Sadhu et al. |
| 6,690,583 B1 | 2/2004 | Bergstedt et al. |
| 6,713,484 B2 | 3/2004 | Bridges et al. |
| 6,720,344 B2 | 4/2004 | Kerwin et al. |
| 6,734,187 B1 | 5/2004 | Tanaka et al. |
| 6,770,639 B2 | 8/2004 | Snow et al. |
| 6,777,425 B2 | 8/2004 | Burli et al. |
| 6,777,439 B2 | 8/2004 | Durden |
| 6,790,844 B2 | 9/2004 | Ueno et al. |
| 6,800,620 B2 | 10/2004 | Sadhu et al. |
| 6,849,420 B2 | 2/2005 | Vanhasebroeck et al. |
| 6,849,713 B2 | 2/2005 | Zhang et al. |
| 6,852,727 B2 | 2/2005 | Goulet et al. |
| 6,906,103 B2 | 6/2005 | Zhang et al. |
| 6,916,949 B2 | 7/2005 | Springer et al. |
| 6,919,332 B2 | 7/2005 | Noe et al. |
| 6,921,763 B2 | 7/2005 | Hirst et al. |
| 6,949,535 B2 | 9/2005 | Sadhu et al. |
| 7,026,461 B1 | 4/2006 | Shokat |
| 7,041,676 B2 | 5/2006 | McDonald et al. |
| 7,049,116 B2 | 5/2006 | Shokat |
| 7,049,312 B1 | 5/2006 | Rafferty et al. |
| 7,064,218 B2 | 6/2006 | Dyatkina et al. |
| 7,071,355 B2 | 7/2006 | Leban et al. |
| 7,115,627 B2 | 10/2006 | Pinto et al. |
| 7,115,653 B2 | 10/2006 | Baxter et al. |
| 7,144,903 B2 | 12/2006 | Collins et al. |
| 7,157,487 B2 | 1/2007 | Nakayama et al. |
| 7,166,293 B2 | 1/2007 | Teng et al. |
| 7,208,601 B2 | 4/2007 | Mjalli et al. |
| 7,217,794 B2 | 5/2007 | Abdel-Meguid et al. |
| 7,235,585 B2 | 6/2007 | Springer et al. |
| 7,244,741 B2 | 7/2007 | Simon et al. |
| 7,247,736 B2 | 7/2007 | Leban et al. |
| 7,262,204 B2 | 8/2007 | Collins et al. |
| 7,265,111 B2 | 9/2007 | Bigot et al. |
| 7,265,131 B2 | 9/2007 | Johnson et al. |
| 7,329,765 B2 | 2/2008 | Burli et al. |
| 7,332,497 B2 | 2/2008 | Hirst et al. |
| 7,348,427 B2 | 3/2008 | Burli et al. |
| 7,365,094 B2 | 4/2008 | Leban et al. |
| 7,384,967 B2 | 6/2008 | Polisetti et al. |
| 7,396,836 B2 | 7/2008 | Harada et al. |
| 7,414,036 B2 | 8/2008 | Sevillano et al. |
| 7,429,596 B2 | 9/2008 | Tanaka et al. |
| 7,439,254 B2 | 10/2008 | Bergnes |
| 7,449,477 B2 | 11/2008 | Barda et al. |
| 7,459,462 B2 | 12/2008 | Simon et al. |
| 7,459,472 B2 | 12/2008 | Mjalli et al. |
| 7,470,721 B2 | 12/2008 | Durden |
| 7,501,538 B2 | 3/2009 | Mjalli et al. |
| 7,514,445 B2 | 4/2009 | Freyne et al. |
| 7,534,797 B2 | 5/2009 | Arnold et al. |
| 7,541,373 B2 | 6/2009 | Polisetti et al. |
| 7,569,571 B2 | 8/2009 | Dong et al. |
| 7,572,913 B2 | 8/2009 | McKerracher et al. |
| 7,579,348 B2 | 8/2009 | Wang et al. |
| 7,585,868 B2 | 9/2009 | Knight et al. |
| 7,608,594 B2 | 10/2009 | Blagg et al. |
| 7,615,552 B2 | 11/2009 | Ono et al. |
| 7,622,451 B2 | 11/2009 | Blagg et al. |
| 7,678,803 B2 | 3/2010 | Huang et al. |
| 7,700,607 B2 | 4/2010 | Hu et al. |
| 7,705,018 B2 | 4/2010 | Chen et al. |
| 7,745,485 B2 | 6/2010 | Durden |
| 7,932,260 B2 | 4/2011 | Fowler et al. |
| 8,106,146 B2 | 1/2012 | Benz et al. |
| 8,193,182 B2 | 6/2012 | Ren et al. |
| 8,399,483 B2 | 3/2013 | Allen et al. |
| 2001/0019829 A1 | 9/2001 | Nelson et al. |
| 2001/0027197 A1 | 10/2001 | Bridges et al. |
| 2002/0016460 A1 | 2/2002 | Snow et al. |
| 2002/0016976 A1 | 2/2002 | Shokat |
| 2002/0037856 A1 | 3/2002 | Zhang et al. |
| 2002/0102590 A1 | 8/2002 | Taing et al. |
| 2002/0127625 A1 | 9/2002 | Oxelius |
| 2002/0146690 A1 | 10/2002 | Meyer et al. |
| 2002/0147160 A1 | 10/2002 | Bhat et al. |
| 2002/0156081 A1 | 10/2002 | Hirst et al. |
| 2002/0161014 A1 | 10/2002 | Sadhu et al. |
| 2002/0173524 A1 | 11/2002 | Collins et al. |
| 2003/0001141 A1 | 1/2003 | Sun et al. |
| 2003/0008896 A1 | 1/2003 | Martin et al. |

(56) References Cited

U.S. PATENT DOCUMENTS

| | | |
|---|---|---|
| 2003/0018022 A1 | 1/2003 | Collins et al. |
| 2003/0022344 A1 | 1/2003 | Williams et al. |
| 2003/0064997 A1 | 4/2003 | Adams et al. |
| 2003/0073218 A1 | 4/2003 | Shokat |
| 2003/0083268 A1 | 5/2003 | Burli et al. |
| 2003/0113765 A1 | 6/2003 | Dempcy et al. |
| 2003/0119479 A1 | 6/2003 | Arima et al. |
| 2003/0119791 A1 | 6/2003 | Kerwin et al. |
| 2003/0139427 A1 | 7/2003 | Castelhano et al. |
| 2003/0143602 A1 | 7/2003 | Meyer et al. |
| 2003/0166929 A1 | 9/2003 | Snow et al. |
| 2003/0180924 A1 | 9/2003 | DeSimone |
| 2003/0186987 A1 | 10/2003 | Bridges et al. |
| 2003/0187001 A1 | 10/2003 | Calderwood et al. |
| 2003/0195211 A1 | 10/2003 | Sadhu et al. |
| 2003/0199516 A1 | 10/2003 | Moser et al. |
| 2003/0208800 A1 | 11/2003 | Eby et al. |
| 2003/0212113 A1 | 11/2003 | Dyatkina et al. |
| 2003/0232849 A1 | 12/2003 | Noe et al. |
| 2003/0235822 A1 | 12/2003 | Lokhov et al. |
| 2004/0039035 A1 | 2/2004 | Collins et al. |
| 2004/0043959 A1 | 3/2004 | Bloom et al. |
| 2004/0043983 A1 | 3/2004 | Li |
| 2004/0067901 A1 | 4/2004 | Bhat et al. |
| 2004/0067915 A1 | 4/2004 | McMahon et al. |
| 2004/0072766 A1 | 4/2004 | June |
| 2004/0072788 A1 | 4/2004 | Bhat et al. |
| 2004/0102423 A1 | 5/2004 | MacLaughlan et al. |
| 2004/0102437 A1 | 5/2004 | Takami et al. |
| 2004/0110717 A1 | 6/2004 | Carroll et al. |
| 2004/0110945 A1 | 6/2004 | Nakayama et al. |
| 2004/0116689 A1 | 6/2004 | Gall et al. |
| 2004/0122235 A1 | 6/2004 | Polisetti et al. |
| 2004/0127434 A1 | 7/2004 | Bigot et al. |
| 2004/0176458 A1 | 9/2004 | Leban et al. |
| 2004/0176601 A1 | 9/2004 | Goulet et al. |
| 2004/0192758 A1 | 9/2004 | Leban et al. |
| 2004/0266780 A1 | 12/2004 | Sadhu et al. |
| 2005/0004149 A1 | 1/2005 | Harada et al. |
| 2005/0043239 A1 | 2/2005 | Douangpanya et al. |
| 2005/0049310 A1 | 3/2005 | Mjalli et al. |
| 2005/0054614 A1 | 3/2005 | Diacovo et al. |
| 2005/0059713 A1 | 3/2005 | Mjalli et al. |
| 2005/0085472 A1 | 4/2005 | Tanaka et al. |
| 2005/0101551 A1 | 5/2005 | Sevillano et al. |
| 2005/0124637 A1 | 6/2005 | Cheng et al. |
| 2005/0143317 A1 | 6/2005 | Abdel-Meguid et al. |
| 2005/0153997 A1 | 7/2005 | Simon et al. |
| 2005/0171148 A1 | 8/2005 | Mjalli et al. |
| 2005/0182045 A1 | 8/2005 | Nagase et al. |
| 2005/0187418 A1 | 8/2005 | Small et al. |
| 2005/0197340 A1 | 9/2005 | Arora et al. |
| 2005/0214310 A1 | 9/2005 | Toki et al. |
| 2005/0215579 A1 | 9/2005 | Simon et al. |
| 2005/0239809 A1 | 10/2005 | Watts et al. |
| 2005/0250770 A1 | 11/2005 | Ono et al. |
| 2005/0256066 A1 | 11/2005 | Abel et al. |
| 2005/0261317 A1 | 11/2005 | Sadhu et al. |
| 2005/0272751 A1 | 12/2005 | McKerracher et al. |
| 2006/0019988 A1 | 1/2006 | McDonald et al. |
| 2006/0069034 A1 | 3/2006 | Burli et al. |
| 2006/0079538 A1 | 4/2006 | Hallahan et al. |
| 2006/0106038 A1 | 5/2006 | Bouscary et al. |
| 2006/0116326 A1 | 6/2006 | Burli et al. |
| 2006/0135790 A1 | 6/2006 | Hyett et al. |
| 2006/0156485 A1 | 7/2006 | Lim |
| 2006/0183783 A1 | 8/2006 | Polisetti et al. |
| 2006/0199776 A1 | 9/2006 | Blagg et al. |
| 2006/0205694 A1 | 9/2006 | Alonso et al. |
| 2006/0235031 A1 | 10/2006 | Arnold et al. |
| 2006/0276470 A1 | 12/2006 | Jackson et al. |
| 2006/0287295 A1 | 12/2006 | Barlaam et al. |
| 2006/0293274 A1 | 12/2006 | Wu |
| 2007/0015773 A1 | 1/2007 | Bergeron et al. |
| 2007/0017915 A1 | 1/2007 | Weder et al. |
| 2007/0027193 A1 | 2/2007 | Leban et al. |
| 2007/0032640 A1 | 2/2007 | Varghese et al. |
| 2007/0054915 A1 | 3/2007 | Arora et al. |
| 2007/0072897 A1 | 3/2007 | Mahaney et al. |
| 2007/0099871 A1 | 5/2007 | Davis et al. |
| 2007/0142405 A1 | 6/2007 | Dong et al. |
| 2007/0179151 A1 | 8/2007 | Chen et al. |
| 2007/0224672 A1 | 9/2007 | Leban et al. |
| 2007/0249598 A1 | 10/2007 | Wang et al. |
| 2007/0270452 A1 | 11/2007 | Blagg et al. |
| 2008/0032960 A1 | 2/2008 | Knight et al. |
| 2008/0058521 A1 | 3/2008 | Krishnan et al. |
| 2008/0070935 A1 | 3/2008 | Huang et al. |
| 2008/0119454 A1 | 5/2008 | Polisetti et al. |
| 2008/0119455 A1 | 5/2008 | Polisetti et al. |
| 2008/0119461 A1 | 5/2008 | Sin et al. |
| 2008/0200465 A1 | 8/2008 | Burli et al. |
| 2008/0249090 A1 | 10/2008 | Hu et al. |
| 2008/0261956 A1 | 10/2008 | Choi et al. |
| 2008/0287469 A1 | 11/2008 | Diacovo et al. |
| 2008/0292626 A1 | 11/2008 | Wang et al. |
| 2008/0293674 A1 | 11/2008 | Schwarz et al. |
| 2008/0306053 A1 | 12/2008 | Tachdjian et al. |
| 2008/0306093 A1 | 12/2008 | Servant et al. |
| 2008/0312180 A1 | 12/2008 | Liang et al. |
| 2008/0318942 A1 | 12/2008 | Simon et al. |
| 2009/0030023 A1 | 1/2009 | Harada et al. |
| 2009/0053192 A1 | 2/2009 | Millan et al. |
| 2009/0088452 A1 | 4/2009 | Coleman et al. |
| 2009/0099214 A1 | 4/2009 | Fairhurst et al. |
| 2009/0105233 A1 | 4/2009 | Chua et al. |
| 2009/0118283 A1 | 5/2009 | Defert et al. |
| 2009/0124638 A1 | 5/2009 | Shokat et al. |
| 2009/0124654 A1 | 5/2009 | Mjalli et al. |
| 2009/0137581 A1 | 5/2009 | Chen et al. |
| 2009/0163481 A1 | 6/2009 | Murphy et al. |
| 2009/0163709 A1 | 6/2009 | Blagg |
| 2009/0170879 A1 | 7/2009 | Szucova et al. |
| 2009/0181920 A1 | 7/2009 | Watkins et al. |
| 2009/0181988 A1 | 7/2009 | Tanaka et al. |
| 2009/0187014 A1 | 7/2009 | Blagg |
| 2009/0203689 A1 | 8/2009 | Dhalla et al. |
| 2009/0232768 A1 | 9/2009 | Birkus et al. |
| 2009/0247513 A1 | 10/2009 | Burli et al. |
| 2009/0253694 A1 | 10/2009 | Ono et al. |
| 2009/0264409 A1 | 10/2009 | Dong et al. |
| 2009/0264423 A2 | 10/2009 | Chua et al. |
| 2009/0270426 A1 | 10/2009 | Knight et al. |
| 2009/0270567 A1 | 10/2009 | Small et al. |
| 2009/0312319 A1 | 12/2009 | Ren et al. |
| 2009/0312406 A1 | 12/2009 | Hsieh et al. |
| 2009/0318411 A1 | 12/2009 | Castanedo et al. |
| 2009/0325967 A1 | 12/2009 | Fairhurst et al. |
| 2010/0009963 A1 | 1/2010 | Knight et al. |
| 2010/0022585 A1 | 1/2010 | deLong et al. |
| 2010/0029658 A1 | 2/2010 | Gavish et al. |
| 2010/0029693 A1 | 2/2010 | Douangpanya et al. |
| 2010/0048540 A1 | 2/2010 | Boyle et al. |
| 2010/0048882 A1 | 2/2010 | Blagg et al. |
| 2010/0056494 A1 | 3/2010 | Winzeler et al. |
| 2010/0105630 A1 | 4/2010 | Blagg |
| 2010/0168153 A1 | 7/2010 | Stowasser et al. |
| 2010/0179167 A1 | 7/2010 | Xu et al. |
| 2010/0190749 A1 | 7/2010 | Ren et al. |
| 2011/0046165 A1 | 2/2011 | Ren et al. |
| 2011/0124641 A1 | 5/2011 | Ren et al. |
| 2011/0144134 A1 | 6/2011 | Shokat et al. |
| 2011/0172228 A1 | 7/2011 | Ren et al. |
| 2011/0224223 A1 | 9/2011 | Shokat et al. |
| 2011/0269779 A1 | 11/2011 | Wilson et al. |
| 2011/0281866 A1 | 11/2011 | Ren et al. |
| 2011/0301144 A1 | 12/2011 | Knight et al. |
| 2012/0059000 A1 | 3/2012 | Ren et al. |
| 2012/0065154 A1 | 3/2012 | Tanaka et al. |
| 2012/0122838 A1 | 5/2012 | Ren et al. |
| 2012/0149701 A1 | 6/2012 | Ren et al. |
| 2012/0184568 A1 | 7/2012 | Ren et al. |
| 2012/0202784 A1 | 8/2012 | Aronov et al. |
| 2012/0220575 A1 | 8/2012 | Chang et al. |

(56) References Cited

U.S. PATENT DOCUMENTS

| | | |
|---|---|---|
| 2012/0245169 A1 | 9/2012 | Ren et al. |
| 2012/0329776 A1 | 12/2012 | Ren et al. |
| 2013/0029982 A1 | 1/2013 | Castro et al. |
| 2013/0029984 A1 | 1/2013 | Castro et al. |
| 2013/0053362 A1 | 2/2013 | Castro et al. |
| 2014/0275135 A1 | 9/2014 | Genov et al. |
| 2014/0288048 A1 | 9/2014 | Castro et al. |

FOREIGN PATENT DOCUMENTS

| | | |
|---|---|---|
| DE | 2139107 A1 | 2/1973 |
| EP | 773023 A1 | 5/1997 |
| EP | 1020445 B1 | 8/2008 |
| GB | 812366 A | 4/1959 |
| GB | 937725 A | 9/1963 |
| JP | 61-109797 A | 5/1986 |
| JP | 05-256693 A | 10/1993 |
| JP | 08295667 A | 11/1996 |
| JP | 09143163 A | 6/1997 |
| JP | 10206995 A | 8/1998 |
| JP | 2000072773 A | 3/2000 |
| JP | 2002131859 A | 5/2002 |
| JP | 2003073357 A | 3/2003 |
| JP | 2004161716 A | 6/2004 |
| WO | WO 83/01446 A1 | 4/1983 |
| WO | WO 91/17161 A1 | 11/1991 |
| WO | WO 92/14733 A1 | 9/1992 |
| WO | WO 95/12588 A1 | 5/1993 |
| WO | WO 93/16091 A1 | 8/1993 |
| WO | WO 93/16092 A1 | 8/1993 |
| WO | WO 93/18035 A1 | 9/1993 |
| WO | WO 93/19767 A1 | 10/1993 |
| WO | WO 93/22443 A1 | 11/1993 |
| WO | WO 94/13677 A1 | 6/1994 |
| WO | WO 94/17803 A1 | 8/1994 |
| WO | WO 94/29436 A1 | 12/1994 |
| WO | WO 95/10628 A2 | 4/1995 |
| WO | WO 95/29673 A1 | 11/1995 |
| WO | WO 95/32984 A1 | 12/1995 |
| WO | WO 95/10628 A3 | 9/1996 |
| WO | WO 96/40706 A1 | 12/1996 |
| WO | WO 97/28133 A1 | 8/1997 |
| WO | WO 97/28161 A1 | 8/1997 |
| WO | WO 98/41525 A1 | 9/1998 |
| WO | WO 98/52611 A1 | 11/1998 |
| WO | WO 98/57952 A1 | 12/1998 |
| WO | WO 00/17202 A1 | 3/2000 |
| WO | WO 01/02369 A2 | 1/2001 |
| WO | WO 01/16114 A2 | 3/2001 |
| WO | WO 01/19829 A2 | 3/2001 |
| WO | WO 01/25238 A2 | 4/2001 |
| WO | WO 01/31063 A1 | 5/2001 |
| WO | WO 01/38584 A2 | 5/2001 |
| WO | WO 01/16114 A3 | 8/2001 |
| WO | WO 01/55140 A1 | 8/2001 |
| WO | WO 01/56988 A1 | 8/2001 |
| WO | WO 01/19829 A3 | 9/2001 |
| WO | WO 01/25238 A3 | 10/2001 |
| WO | WO 01/38584 A3 | 10/2001 |
| WO | WO 01/81346 A2 | 11/2001 |
| WO | WO 02/06192 A1 | 1/2002 |
| WO | WO 01/81346 A3 | 3/2002 |
| WO | WO 01/02369 A3 | 4/2002 |
| WO | WO 02/30944 A2 | 4/2002 |
| WO | WO 02/057425 A2 | 7/2002 |
| WO | WO 02/076986 A1 | 10/2002 |
| WO | WO 02/080926 A1 | 10/2002 |
| WO | WO 02/083143 A1 | 10/2002 |
| WO | WO 02/088025 A1 | 11/2002 |
| WO | WO 02/090334 A1 | 11/2002 |
| WO | WO 02/30944 A3 | 1/2003 |
| WO | WO 03/000187 A2 | 1/2003 |
| WO | WO 03/016275 A1 | 2/2003 |
| WO | WO 03/020880 A2 | 3/2003 |
| WO | WO 03/024969 A1 | 3/2003 |
| WO | WO 03/028341 A2 | 4/2003 |
| WO | WO 03/035075 A1 | 5/2003 |
| WO | WO 03/059884 A1 | 7/2003 |
| WO | WO 03/020880 A3 | 10/2003 |
| WO | WO 03/082341 A1 | 10/2003 |
| WO | WO 03/106426 A1 | 12/2003 |
| WO | WO 2004/006906 A2 | 1/2004 |
| WO | WO 2004/006906 A3 | 3/2004 |
| WO | WO 2004/018058 A2 | 3/2004 |
| WO | WO 2004/031177 A1 | 4/2004 |
| WO | WO 2004/039774 A2 | 5/2004 |
| WO | WO 2004/018058 A3 | 7/2004 |
| WO | WO 2004/039774 A3 | 7/2004 |
| WO | WO 2004/058717 A1 | 7/2004 |
| WO | WO 03/000187 A3 | 8/2004 |
| WO | WO 2004/087053 A2 | 10/2004 |
| WO | WO 2004/111014 A1 | 12/2004 |
| WO | WO 2005/002585 A1 | 1/2005 |
| WO | WO 2005/007085 A2 | 1/2005 |
| WO | WO 2005/012323 A2 | 2/2005 |
| WO | WO 2005/016348 A1 | 2/2005 |
| WO | WO 2005/016349 A1 | 2/2005 |
| WO | WO 2005/016528 A2 | 2/2005 |
| WO | WO 2005/021533 A1 | 3/2005 |
| WO | WO 2002/057425 A3 | 4/2005 |
| WO | WO 2005/012323 A3 | 5/2005 |
| WO | WO 2005/016528 A3 | 5/2005 |
| WO | WO 2005/044181 A2 | 5/2005 |
| WO | WO 2005/047289 A1 | 5/2005 |
| WO | WO 2005/061460 A1 | 7/2005 |
| WO | WO 2005/063258 A1 | 7/2005 |
| WO | WO 2005/067901 A2 | 7/2005 |
| WO | WO 2005/074603 A2 | 8/2005 |
| WO | WO 2005/007085 A3 | 9/2005 |
| WO | WO 2005/097800 A1 | 10/2005 |
| WO | WO 2005/105760 A1 | 11/2005 |
| WO | WO 2005/067901 A3 | 12/2005 |
| WO | WO 2005/112935 A1 | 12/2005 |
| WO | WO 2005/113556 A1 | 12/2005 |
| WO | WO 2005/117889 AI | 12/2005 |
| WO | WO 2005/120511 A1 | 12/2005 |
| WO | WO 2005/044181 A3 | 3/2006 |
| WO | WO 2006/030032 A1 | 3/2006 |
| WO | WO 2006/038865 A1 | 4/2006 |
| WO | WO 2006/050501 A2 | 5/2006 |
| WO | WO 2006/050946 A1 | 5/2006 |
| WO | WO 2006/068760 A2 | 6/2006 |
| WO | WO 2004/087053 A3 | 8/2006 |
| WO | WO 2006/089106 A2 | 8/2006 |
| WO | WO 2006/108107 A1 | 10/2006 |
| WO | WO 2006/112666 A1 | 10/2006 |
| WO | WO 2005/074603 A3 | 11/2006 |
| WO | WO 2006/114064 A2 | 11/2006 |
| WO | WO 2006/114065 A2 | 11/2006 |
| WO | WO 2006/068760 A3 | 12/2006 |
| WO | WO 2006/089106 A3 | 12/2006 |
| WO | WO 2007/002293 A2 | 1/2007 |
| WO | WO 2007/006547 A1 | 1/2007 |
| WO | WO 2007/020046 A1 | 2/2007 |
| WO | WO 2007/002293 A3 | 3/2007 |
| WO | WO 2007/025090 A2 | 3/2007 |
| WO | WO 2006/050501 A3 | 5/2007 |
| WO | WO 2007/061737 A2 | 5/2007 |
| WO | WO 2006/114064 A3 | 6/2007 |
| WO | WO 2006/114065 A3 | 6/2007 |
| WO | WO 2007/025090 A3 | 6/2007 |
| WO | WO 2007/075554 A2 | 7/2007 |
| WO | WO 2007/079164 A2 | 7/2007 |
| WO | WO 2007/079164 A3 | 9/2007 |
| WO | WO 2007/103308 A2 | 9/2007 |
| WO | WO 2007/112005 A2 | 10/2007 |
| WO | WO 2007/114926 A2 | 10/2007 |
| WO | WO 2007/121453 A2 | 10/2007 |
| WO | WO 2007/121920 A2 | 11/2007 |
| WO | WO 2007/121924 A2 | 11/2007 |
| WO | WO 2007/124854 A1 | 11/2007 |
| WO | WO 2007/125310 A2 | 11/2007 |
| WO | WO 2007/125315 A2 | 11/2007 |

(56) References Cited

FOREIGN PATENT DOCUMENTS

| | | |
|---|---|---|
| WO | WO 2007/126841 A2 | 11/2007 |
| WO | WO 2007/134828 A1 | 11/2007 |
| WO | WO 2007/135380 A2 | 11/2007 |
| WO | WO 2007/135398 A1 | 11/2007 |
| WO | WO 2007/061737 A3 | 12/2007 |
| WO | WO 2007/125315 A3 | 12/2007 |
| WO | WO 2007/121920 A3 | 1/2008 |
| WO | WO 2008/001236 A2 | 1/2008 |
| WO | WO 2008/012326 A1 | 1/2008 |
| WO | WO 2007/103308 A3 | 2/2008 |
| WO | WO 2007/112005 A3 | 2/2008 |
| WO | WO 2007/125310 A3 | 3/2008 |
| WO | WO 2008/025755 A1 | 3/2008 |
| WO | WO 2008/047821 A1 | 4/2008 |
| WO | WO 2008/063625 A2 | 5/2008 |
| WO | WO 2008/064018 A1 | 5/2008 |
| WO | WO 2007/121453 A3 | 7/2008 |
| WO | WO 2008/079028 A1 | 7/2008 |
| WO | WO 2008/082487 A2 | 7/2008 |
| WO | WO 2008/094737 A2 | 8/2008 |
| WO | WO 2007/121924 A3 | 9/2008 |
| WO | WO 2008/112715 A3 | 9/2008 |
| WO | WO 2007/114926 A3 | 10/2008 |
| WO | WO 2008/118454 A2 | 10/2008 |
| WO | WO 2008/118455 A1 | 10/2008 |
| WO | WO 2008/118468 A1 | 10/2008 |
| WO | WO 2008/125014 A1 | 10/2008 |
| WO | WO 2008/125207 A1 | 10/2008 |
| WO | WO 2008/127226 A2 | 10/2008 |
| WO | WO 2007/126841 A3 | 11/2008 |
| WO | WO 2008/112715 A3 | 11/2008 |
| WO | WO 2008/118454 A3 | 11/2008 |
| WO | WO 2008/136457 A1 | 11/2008 |
| WO | WO 2008/082487 A3 | 12/2008 |
| WO | WO 2008/127226 A3 | 12/2008 |
| WO | WO 2009/000412 A1 | 12/2008 |
| WO | WO 2009/004621 A1 | 1/2009 |
| WO | WO 2009/010925 A2 | 1/2009 |
| WO | WO 2009/023718 A2 | 2/2009 |
| WO | WO 2008/094737 A3 | 3/2009 |
| WO | WO 2009/029617 A1 | 3/2009 |
| WO | WO 2009/023718 A3 | 4/2009 |
| WO | WO 2009/044707 A1 | 4/2009 |
| WO | WO 2009/050506 A2 | 4/2009 |
| WO | WO 2009/064802 A2 | 5/2009 |
| WO | WO 2009/010925 A3 | 7/2009 |
| WO | WO 2009/064802 A3 | 7/2009 |
| WO | WO 2009/088986 A1 | 7/2009 |
| WO | WO 2009/088990 A1 | 7/2009 |
| WO | WO 2009/100406 A2 | 8/2009 |
| WO | WO 2009/117157 A1 | 9/2009 |
| WO | WO 2009/050506 A3 | 11/2009 |
| WO | WO 2009/100406 A3 | 11/2009 |
| WO | WO 2010/006086 A1 | 1/2010 |
| WO | WO 2010/009207 A1 | 1/2010 |
| WO | WO 2010/019210 A2 | 2/2010 |
| WO | WO 2010/036380 A1 | 4/2010 |
| WO | WO 2010/039534 A2 | 4/2010 |
| WO | WO 2010/019210 A3 | 5/2010 |
| WO | WO 2010/065923 A2 | 6/2010 |
| WO | WO 2010/070032 A1 | 6/2010 |
| WO | WO 2010/039534 A3 | 8/2010 |
| WO | WO 2010/092340 A1 | 8/2010 |
| WO | WO 2010/133836 A1 | 11/2010 |
| WO | WO 2011/008302 A1 | 1/2011 |
| WO | WO 2011/058108 A1 | 5/2011 |
| WO | WO 2011/058109 A1 | 5/2011 |
| WO | WO 2011/058110 A1 | 5/2011 |
| WO | WO 2011/075628 A1 | 6/2011 |
| WO | WO 2011/146882 A1 | 11/2011 |
| WO | WO 2012/032334 A1 | 3/2012 |
| WO | WO 2012/061696 A1 | 5/2012 |
| WO | WO 2012/064973 A2 | 5/2012 |
| WO | WO 2012/097000 A1 | 7/2012 |
| WO | WO 2014/151386 A1 | 9/2014 |
| WO | WO 2014/201409 A1 | 12/2014 |

OTHER PUBLICATIONS

Abrahamian et al., "Immunological and Clinical Profile of Adult Patients with Selective Immunoglobulin Subclass deficiency: response to intravenous immunoglobulin therapy," *Clin. Exp. Immunol.* 159(3):344-350 (2010).

Abraham, T., "Thermally induced intramolecular cycloaddition reaction of N-phenyl-2-phenylethynlbenzamide potential cure reaction for thermosetting polymers," *J. Polym. Sci. Polym. Chem. Ed.* 20(7):1953-1957 (1982).

Ames et al., "Heterocyclic Syntheses from o-Halogeno-acids. Part II. Thienopyridinones and Thienopyranones from 3-Bromothiophen-2- and 4-Bromothiophen-3-carboxylic Acids," *J.C.S. Perkin I* 1390-1395 (1975).

Anderson et al., "Paradoxical inhibition of T-cell function in response to CTLA-4 blockade; heterogeneity within the human T-cell population," *Nat. Med.* 6(2):211-214 (2000).

Andrews et al., "Effects of the 11β-hydroxysteroid dehydrogenase inhibitor carbenoxolone on insulin sensitive in men with type 2 diabetes," *J. Clin. Endocrinol. Metab.* 88(1):285-291 (2003).

Arcaro et al., "Wortmannin is a potent phosphatidylinositol 3-kinase inhibitor: the role of phosphatidylinositol 3,4,5-triphosphate in neutrophil responses," *Biochem. J.*, 296(Pt 2):297-301 (1993).

Arnold et al., "Pyrrolo[2,3-d]pyrimidines containing an extended 5-substituent as potent and selective inhibitors of lck I," *Bioorg. Med. Chem. Lett.* 10(19):2167-2170 (2000).

Augustine et al., "Interleukin 2- and polyomavirus middle T antigen-induced modification of phosphatidylinositol 3-kinase activity in activated T lymphocytes," *Mol. Cell. Biol.* 11(9):4431-4440 (1991).

Baggiolini et al., "Inhibition of the phagocytosis-induced respiratory burst by the fungal metabolite wortmannin and some analogues," *Exp. Cell. Res.* 169(2): 408-418 (1987).

Ballell et al. "New Thiopyrazolo[3,4-d] pyrimidine derivatives as anti-mycobacterial agents," *Bioorg. Med. Chem. Lett.* 17(6):1736-1740 (2007).

Banker et al., Modern Pharmaceutics, pp. 451, 596, 3$^{rd}$ ed, Marcel Dekker, New York (1996).

Bansal et al., "The Molecular Biology of Endometrial Cancers and the Implications for Pathogenesis, Classification, and Targeted Therapies," *Cancer Control* 16(1):8-13 (2009).

Barber et al., "PI3Kgamma inhibition blocks glomerulonephritis and extends lifespan in a mouse model of systemic lupus," *Nat. Med.* 11(9):933-935 (2005). (Epub Aug. 28, 2005).

Barf et al., "Arylsulfonamidothiazoles as a new class of potential antidiabetic drugs. Discovery of potent and selective inhibitors of the 11β-hydroxysteroid dehydrogenase Type 1," *J. Med. Chem.* 45(18):3813-3815 (2002).

Barnes et al., "Efficacy and Safety of Inhaled Corticosteroids in Asthma—Report of a Workshop Held in Eze, France Oct. 1992," *Am. Rev. Respir. Dis.* 148:S1-S26 (1993).

Bartholomeusz et al., "Targeting the PI3 Signaling Pathway in Cancer Therapy," *Expert Opin. Ther. Targets* 16(1):121-130 (2012).

BASOTEST®, Test Kit for the Quantitative Determination of the Degranulation of Basophilic Granulocytes in Heparinized Human Whole Blood, version Apr. 2002, pp. 1-10, [www.biocarta.com/TDS/10-0500.pdf], Retreived from the Internet Nov. 29, 2011.

Beeram et al., "Akt-induced endocrine therapy resistance is reversed by inhibition of mTOR signaling," *Ann Oncol.* 18(8):1323-1328 (2007).

Bell et al., "Glucokinase mutations insulin secretion, and diabetes mellitus", *Annu. Rev. Physiol.* 58:171-186 (1996).

Berndt et al., "The p110δ crystal structure uncovers mechanisms for selectivity and potency of novel PI3K inhibitors," *Nat. Chem. Biol.* 6(2):117-124 (2010).

Bhat et al., "Pyrazolopyrimidine nucleosides. 12. Synthesis and biological activity of certain pyrazolo[3,4-d]pyrimidine nucleosides related to adenosine," *J. Med. Chem.* 24(10):1165-1172 (1981).

(56) References Cited

OTHER PUBLICATIONS

Bhatt et al., "Dual inhibition of PI3K and mTOR inhibits autocrine and paracrine proliferative loops in PI3K/Akt/mTOR-addicted lymphomas," *Blood* 115(22):4455-4463 (2010).
Bi et al., "Proliferative defect and embryonic lethality in mice homozygous for a deletion in the p110α subunit of phosphoinositide 3-kinase," *J. Biol. Chem.* 274:10963-10968 (1999).
Billottet et al., "A selective inhibitor of the p110δ isoform of PI 3-kinase inhibits AML cell proliferation and survival and increases the cytotoxic effects of VP16," *Oncogene* 25:6648-6659 (2006).
Billottet et al., "Inhibition of Class 1 Phosphoinositide 3-Kinase Activity Impairs Proliferation and Triggers Apoptosis in Acute Promyelocytic Leukemia without Affecting Atra-Induced Differentiation," *Cancer Res.* 69(3):1027-1036 (2009).
Bishop et al., "Generation of monospecific nanomolar tyrosine kinase inhibitors via a chemical genetic approach," *J. Am. Chem. Soc.* 121(4):627-631 (1999).
Blunden et al., "Mycotoxins in food," *Med. Lab. Sci.* 48(4):271-282 (1991).
Bochner et al., "Immunological aspects of allergic asthma," *Annu. Rev. Immunol.* 12:295-335 (1994).
Bohren et al., "Expression, crystallization and preliminary crystallographic analysis of human carbonyl reductase," *J. Mol. Biol.* 224:659-664 (1994).
Bone et al., "Phosphoinositide 3-kinase signalling regulates early development and developmental haemopoiesis," *J. Cell. Sci.* 120(Pt 10):1752-1762 (2007).
Bowers et al., "A platelet biomarker for assessing phosphoinositide 3-kinase inhibition during cancer chemotherapy," *Mol. Cancer Ther.* 6(9):2600-2607 (2007).
Brzezianska et al., "A Minireview: The Role of MAPK/ERK and PI3K/Akt Pathways in Thyroid Follicular Cell-Derived Neoplasm," *Front. Biosci.* 16:422-439 (2011).
Buitenhuis et al., "The role of the PI3k-PKB signaling module in regulation of hematopoiesis," *Cell Cycle* 8(4):560-566 (2009).
Burger et al., "High-level expression of the T-cell chemokines CCL3 and CCL4 by chronic lymphocytic leukemia B cells in nurselike cell cocultures and after BCR stimulation," *Blood* 113(13):3050-3058 (2009).
Burger et al., "Phosphoinositide 3'-kinase delta: turning off BCR signaling in Chronic Lymphocytic Leukemia," *Oncotarget* 2(10):737-738 (2011).
Burger, "Inhibiting B-Cell Receptor Signaling Pathways in Chronic Lymphocytic Leukemia," *Curr. Mematol. Malig. Rep.* 7:26-33 (2012).
Byrd et al., "Translating PI3K-Delta Inhibitors to the Clinic in Chronic Lymphocytic Leukemia: The Story of CAL-101 (GS1101)," *ASCO Program Proceedings*, pp. 691-694 (2012).
Campora et al., "Binuclear complexes of nickel bridged by hydrocarbon ligands. Isocyanide insertion chemistry and amide formation by intramolecular coupling of acyl and imidoyl functionalities," *Organometallics* 11(1):11-13 (1992).
Campora et al., "Isocyanide insertion chemistry. Synthesis and structural characterization of bridging imidoyl complexes of nickel and amide formation by intramolecular coupling of acyl and imidoyl functionalities," *Organometallics* 12(10):4025-4031 (1993).
Camps et al., "Blockade of PI3Kγ suppresses joint inflammation and damage in mouse models of rheumatoid arthritis," *Nat. Med.* 11(9):936-943 (2005).
Chaisuparat et al., "Dual inhibition of PI3Kα and mTOR as an alternative treatment for Kaposi's Sarcoma," *Cancer Res.* 68:8361-8368 (2008).
Chang et al., "The Bruton tyrosine kinase inhibitor PCI-32765 ameliorates autoimmune arthritis by inhibition of multiple effector cells," *Arthritis Research & Therapy* 13:R115 (2011).
Chappelow et al., "Neovascular age-related macular degeneration: potential therapies," *Drugs* 68(8):1029-1036 (2008).
Chapuis et al., "Dual Inhibition of PI3K and mTORC1/2 Signaling by NVP-BEZ235 as a New Therapeutic Strategy for Acute Myeloid Leukemia," *Clin. Cancer Res.* 16(22):5424-5435 (2010).
Chawla et. al., "Challenges in Polymorphism of Pharmaceuticals," *Current Research & Information on Pharmaceutical Science* 5(1):9-12 (2004).
Chen et al., "Characterization of Structurally Distinct, Isoform-Selective Phosphoinositide 3'-Kinase Inhibitors in Combination with Radiation in the Treatment of Glioblastoma," *Mol. Cancer. Ther.* 7(4):841-850 (2008).
Cheson et al., "Bendamustine: Rebirth of an Old Drug," *J. Clin. Oncol.* 27(9):1492-1501 (2009).
Chiarini et al., "Activity of the Novel Dual Phosphatidylinositol 3-Kinase/Mammalian Target of Rapamycin Inhibitor NVP-BEZ235 against T-Cell Acute Lymphoblastic Leukemia," *Cancer Res.* 70(20):8097-8107 (2010).
Chiarini et al., "Dual Inhibition of Class IA Phosphatidylinositol 3-Kinase and Mammalian Target of Rapamycin as a New Therapeutic Option for T-Cell Acute Lymphoblastic Leukemia," *Cancer Res.* 69(8): 3520-3528 (2009).
Cho et al., "A novel synthesis of benzo[c]phenanthridine skeleton and biological evaluation of isoquinoline derivatives," *Chem. Pharm. Bull.*(Tokyo) 47(6):900-902 (1999).
Clayton et al., "A crucial role for the p110delta subunit of phosphatidylinositol 3-kinase in B cell development and activation," *J. Exp. Med.* 196:753-763 (2002).
Closse et al., "2,3-dihydrobenzofuran-2-ones: a new class of highly potent antiinflammatory agents," *J. Med. Chem.* 24:1465-1471 (1981).
Courtney et al., "The PI3K Pathway as Drug Target in Human Cancer," *J. Clin. Oncol.* 28(6):1075-1083 (2010).
Cox et al., "Human colorectal cancer cells efficiently conjugate the cyclopentenone prostaglandin, prostaglandin $J_2$, to glutathione," *Biochem. Biophys. Acta.* 1584:37-45 (2002).
Cushing et al., "PI3Kδ and PI3Kγ as Targets for Autoimmune and Inflammatory Diseases," *J. Med. Chem.* 55:8559-8581 (2012).
Dai et al., "Distinct Roles of Phosphoinositide-3 Kinase and Phospholipase Cγ2 in B-Cell Receptor-Mediated Signal Transduction," *Mol. Cell. Biol.* 26(1):88-99 (2006).
Davids et al., "Decreased mitochondrial apoptotic priming underlies stroma-mediated treatment resistance in chronic lymphocytic leukemia," *Blood* 120(17):3501-3509 (2012).
Davies et al., "The Human T3 γ Chain is Phosphorylated at Serine 126 in Response to T Lymphocyte Activation," *J. Biol. Chem.* 262(23):10918-10921 (1987).
Davis et al., "The preparation of substituted 1(2H)-isoquinolinones from dilithiated 2-methyl-N-arylbenzamides, 2-methyl-N-(arylmethyl)-benzamides, or 2-methylbenzoic acid, 2,2-dimethylhydrazide," *Synthetic Commun.* 27(17):2961-2969 (1997).
Davis et al., "Chronic active B-cell-receptor signaling in diffuse large B-cell lymphoma," *Nature* 463:88-92 (2010).
De Weers et al., "The Bruton's tyrosine kinase gene is expressed throughout B cell differentiation, from early precursor B cell stages preceding immunoglobulin gene rearrangement up to mature B cell stages," *Eur. J. Immunol.* 23:3109-3114 (1993).
Diederich et al., "In search for specific inhibitors of human 11β-hydroxysteroid-dehydrogenases (11βHSDs): chenodeoxycholic acid selectively inhibits 11β-HSD-I," *Eur. J. Endocrinol.* 142(2):200-207 (2000).
Dijksman et al., "271.1 : 2-dihydro-2-thianaphthalene derivatives. Part I. Preparation and reactions of 1 : 2-dihydro-1-keto-2-thianaphthalenes," *J. Chem. Soc.* 1213-1218 (1951).
Ding et al., "A combinatorial scaffold approach toward kinase-directed heterocycle libraries," *J. Am. Chem. Soc.* 124(8):1594-1596 (2002).
Ding et al., "A concise and traceless linker strategy toward combinatorial libraries of 2,6,9-substituted purines," *J. Org. Chem.* 66(24):8273-8276 (2001).
Ding et al., "Resin-capture and release strategy toward combinatorial libraries of 2,6,9-substituted purines," *J. Comb. Chem.* 4(2):183-186 (2002).
Donati, G., "Emerging therapies for neovascular age-related macular degeneration: state of the art," *Ophthalmologica* 221(6):366-377 (2007).

(56) References Cited

OTHER PUBLICATIONS

European Examination Report for EP Application No. 07873406.8 dated Sep. 14, 2011.
European Search Report for EP Application No. 05857011.0 dated Feb. 4, 2011.
European Search Report for EP Application No. 09700784.3 dated Oct. 28, 2011.
European Search Report and Search Opinion for EP Application No. 09700424.6 dated Oct. 26, 2011.
European Search Report for EP Application No. 07873406.8 dated Mar. 1, 2010.
European Search Report for EP Application No. 07754845.1 dated Sep. 20, 2011.
Examination Report for GB Application No. GB 0819947.3 dated Oct. 27, 2010.
Extended European Search Report for EP Application No. 09816603.6 dated Mar. 19, 2012.
Extended European Search Report from European Application No. 09700784.3 dated Oct. 28, 2011.
Fajans et al., "Maturity onset diabetes of the young (MODY)," *Diabet. Med.* 13(9 Suppl 6):S90-S95 (1996).
Feinstein et al., "Regulation of the action of hydrocotisone in airway epithelial cells by 11b-hydroxysteroid dehydrogenase," *Am. J. Respir. Cell. Mol. Biol.* 21(3):403-408 (1999).
Feldman et al., "Active-Site Inhibitors of mTOR Target Rapamycin-Resistant Outputs of mTORC1 and mTORC2," *PLoS Biol.* 7(2):371-383 (2009).
Fingl et al., "Chapter 1—General Principles," The Pharmacological Basis of Therapeutics, 5th edition, Goodman and Gilman editors, MacMillan Publishings Co., Inc., New York, pp. 1-46, (1975).
Flinn et al., "Preliminary Evidence of Clinical Activity in a Phase I Study of CAL-101, a Selective Inhibitor of the p110δ Isoform of Phosphatidylinositol 3-Kinase (PI3K), in Patients with Select Hematologic Malignancies," *J. Clin. Oncol.* 27(15s) (Suppl: Abstr 3543) (2009).
Forrest et al., "Carbonyl Reductase," *Chem. Biol. Interact.* 129(1-2): 21-40 (2000).
Forrest et al., "Induction of a human carbonyl reductase gene located on chromosome 21," *Biochem. Biophys. Acta.* 1048(2-3):149-155 (1990).
Franzen, "The Suzuki, the Heck, and the Stille reaction—three versatile methods for the introduction of new C-C bonds on solid support," *Can. J. Chem.* 78:957-962 (2000).
Funder et al., "Mineralocorticoid action: target tissue specificity is enzyme, not receptor, mediated," *Science* 242:583-585 (1998).
Fung-Leung, W. P., "Phosphoinositide 3-kinase delta (PI3Kδ) in leukocyte signaling and function," *Cell Signal* 23:603-608 (2011).
Furukawa, T., "Molecular Targeting Therapy for Pancreatic Cancer: Current Knowledge and Perspectives from Bench to Bedside," *J. Gastroenterol.* 43(12):905-911 (2008).
Garber et al., "Diversity of gene expression in adenocarcinoma of the lung," *Proc. Natl. Acad. Sci. U.S.A.* 98(24):13784-13789 (2001).
Gillespie et al., "Antagonists of the human adenosine $A_{2A}$ receptor. Part 3: Design and synthesis of pyrazolo[3,4-d]pyrimidines, pyrrolo[2,3-d]pyrimidines and 6-arylpurines," *Bioorg. Med. Chem. Lett.* 18(9):2924-2929 (2008).
Gonzalez et al., "Protection against daunorubicin cytotoxicity by expression of a cloned human carbonyl reductase cDNA in K562 leukemia cells," *Cancer Res.* 55(20):4646-4650 (1995).
Graber et al., "The protein tyrosine kinase inhibitor herbimycin A, but not genistein, specifically inhibits signal transduction by the T cell antigen receptor," *Int. Immunol.* 41(1):1201-1210 (1992).
Graupera et al., "Angiogenesis selectively requires the p110α isoform of PI3K to control endothelial cell migration," *Nature* 453(7195):662-666 (2008).
Gunther et al., "Acute pathological effects on rats of orally administered wortmannin-containing preparations and purified wortmannin from *Fusarium oxysporum*," *Food Chem. Toxicol.* 27(3):173-179 (1989).
Gunther et al., "Immunosuppressive effects of dietary wortmannin on rats and mice," *Immunopharmacol. Immunotoxicol.* 11(4):559-570 (1989).
Haase et al., "Detection of viral nucleic acids by in situ hybridization," *Methods in Virology* 7:189-226 (1984).
Haluska et al., "The RTK/RAS/BRAF/PI3K Pathways in Melanoma: Biology, Small Molecule Inhibitors, and Potential Applications," *Semin. Oncol.* 34(6):546-554 (2007).
Hanefeld et al., "One-pot synthesis of tetrasubstituted pyrazoles proof of regiochemistry," *J. Chem. Soc. Perkin 1* 1545-1552 (1996).
Harada et al., "Novel role of phosphatidylinositol 3-kinase in CD28-mediated costimulation," *J. Biol. Chem.* 276(12):9003-9008 (2001).
Harding et al., "CD28-mediated signalling co-stimulates murine T cells and prevents induction of anergy in T-cell clones," *Nature* 356(6370):607-609 (1992).
Hasselblom et al., "High immunohistochemical expression of p-AKT predicts inferior survival in patients with diffuse large B-cell lymphoma treated with immunochemotherapy," *Brit. J. Haematol.* 149:560-568 (2010).
Haylock-Jacobs et al., "PI3Kδ drives the pathogenesis of experimental autoimmune encephalomyelitis by inhibiting effector T cell apoptosis and promoting Th17 differentiation," *J. Autoimmun.* 36:278-287 (2011).
Hellwinkel et al., "Heterocyclensynthesen mit MF/Al203-basensystemen; 2-arylbenzofurane and 2,3-diarylisochinolin-1(2H)-one," *Synthesis* 1995( 9):1135-1141 (1995).
Herishanu et al., "The lymph node microenvironment promotes B-cell receptor signaling, NF-κB activation, and tumor proliferation in chronic lymphocytic leukemia," *Blood* 117(2):563-574 (2011).
Herman et al., "Phosphatidylinositol 3-kinase-δ inhibitor CAL-101 shows promising preclinical activity in chronic lymphocytic leukemia by antagonizing intrinsic and extrinsic cellular survival signals," *Blood* 116(12):2078-2088 (2010).
Herman et al., "The role of phosphatidylinositol 3-kinase-δ in the immunomodulatory effects of lenalidomide in chronic lymphocytic leukemia," *Blood* 117(16):4323-4327 (2011).
Herrera et al., "The dual PI3K/mTOR inhibitor BEZ235 is effective in lung cancer cell lines," *Anticancer Res.* 31:849-854 (2011).
Hickey et al., "BCR-ABL Regulates Phosphatidylinositol 3-Kinase-p110γ Transcription and Activation and Is Required for Proliferation and Drug Resistance," *J. Biol. Chem.* 281(5):2441-2450 (2006).
Hirsch et al., "CALming Down T Cell Acute Leukemia," *Cancer Cell* 21:449-450 (2012).
Hirsch et al., "Central Role for G Protein-Coupled Phosphoinositide 3-Kinase γ in Inflammation," *Science* 287:1049-1053 (2000).
Hoellenriegel and Burger, "Phosphoinositide 3'-kinase delta: turning off BCR signaling in Chronic Lymphocytic Leukemia," *Oncotarget* 2(10):737-738 (2011).
Hoellenriegel et al., "The phosphoinositide 3'-kinase delta inhibitor, CAL-101, inhibits B-cell receptor signaling and chemokine networks in chronic lymphocytic leukemia," *Blood* 118(13):3603-3612 (2011).
Hoellenriegel et al., "Phosphoinositide 3'-kinase (PI3K) Delta Inhibition with CAL-101 Blocks B-cell Receptor (BCR) Signaling and the Prosurvival Actions of Nurse-Like Cells (NLC) in Chronic Lymphocytic Leukemia (CLL)," (ASH Annual Meeting 2010).
Honigberg et al., "The Bruton tyrosine kinase inhibitor PCI-32765 blocks B-Cell activation and is efficacious in models of autoimmune disease and B-cell malignancy," *PNAS* 107(29):13075-13080 (2010).
Ikeda et al., "PI3K/p110δ is a novel therapeutic target in multiple myeloma," *Blood* 116(9):1460-1468 (2010).
International Preliminary Report on Patentability and Written Opinion for PCT/US2005/042524 dated May 22, 2007.
International Preliminary Report on Patentability and Written Opinion for PCT/US2007/008355 dated Nov. 4, 2008.
International Preliminary Report on Patentability and Written Opinion for PCT/US2007/008395 dated Oct. 8, 2008.
International Preliminary Report on Patentability and Written Opinion for PCT/US2009/049969 dated Jan. 11, 2011.
International Preliminary Report on Patentability and Written Opinion for PCT/US2009/060985 dated Apr. 19, 2011.
International Preliminary Report on Patentability for PCT/US2009/000038 dated Jul. 6, 2010.

(56) References Cited

OTHER PUBLICATIONS

International Preliminary Report on Patentability for PCT/US2009/005380 dated Apr. 7, 2011.
International Preliminary Report on Patentability for PCT/US2010/002020 dated Jan. 26, 2012.
International Preliminary Report on Patentability for PCT/US2009/000042 dated Jul. 6, 2010.
International Search Report & Written Opinion for PCT/US2011/060212 dated Jun. 1, 2012.
International Search Report & Written Opinion issued after Submission of Request for Additional Search for PCT/US2011/060212 dated Jul. 6, 2012.
International Search Report and Written Opinion for PCT/US2009/005380 dated Nov. 20, 2009.
International Search Report and Written Opinion for PCT/US2009/049969 dated Mar. 15, 2010.
International Search Report and Written Opinion for PCT/US2010/033939, dated Nov. 5, 2010.
International Search Report and Written Opinion for PCT/US2012/047190 dated Oct. 2, 2012.
International Search Report and Written Opinion for PCT/US2012/020831 dated May 2, 2012.
International Search Report for PCT/US2011/037412 dated Aug. 22, 2011.
International Search Report for PCT/US1995/005213 dated Aug. 21, 1995.
International Search Report for PCT/US2007/008395 (4 pages) dated Aug. 27, 2008.
International Search Report for PCT/US2009/000038 dated Mar. 11, 2009.
International Search Report for PCT/US2009/000042 dated Mar. 23, 2009.
International Search Report for PCT/US2005/042524 (7 pages) dated Oct. 2, 2006.
International Search Report for PCT/US2007/008355 dated Sep. 25, 2008.
International Search Report for PCT/US2009/060985 dated Jun. 28, 2010.
International Search Report for PCT/US2010/002020 dated Nov. 2, 2010.
Ishiyama et al., "A stoichiometric aromatic C—H borylation catalyzed by iridium(I)/2,2'-bipyridine complexes at room temperature," *Angew. Chem. Int. Ed. Engl.* 41(16):3056-3058 (2002).
Ishiyama et al., "Mild iridium-catalyzed borylation of arenes. High turnover numbers, room temperature reactions, and isolation of a potential intermediate," *J. Am. Chem. Soc.* 124(3):390-391 (2002).
Jackson et al., "PI 3-kinase p110β: a new target for antithrombotic therapy," *Nat. Med.* 11:507-514 (2005).
Jimeno et al., "Phase I Trial of PX-866, a Novel Phosphoinositide-3-Kinase (PI-3K) Inhibitor," *J. Clin. Oncol.* 27:15s (Suppl; Abstract 3542) (2009).
Johnson et al., "Accessory cell-derived signals required for T cell activation," *Immunol. Res.* 48-64 (1993).
Jou et al., "Essential, nonredundant role for the phosphoinositide 3-kinase p110delta in signaling by the B-cell receptor complex," *Mol. Cell. Biol.* 22:8580-8591 (2002).
June et al., "Evidence for the involvement of three distinct signals in the induction of IL-2 gene expression in human T lymphocytes," *J. Immunol.* 143(1):153-161 (1989).
June et al., "Inhibition of tyrosine phosphorylation prevents T-cell receptor mediated signal transduction," *Proc. Natl. Acad. Sci. U.S.A.* 87:7722-7726 (1990).
June et al., "Role of CD28 receptor in T-cell activation," *Immunol. Today* 11(6):211-216 (1990).
June, C.H., "Signaling transduction in T cells," *Curr. Opin. Immunol.* 3(3):287-293 (1991).
Kajita et al., "Nickel-catalyzed decarbonylative addition of phthalimides to alkynes," *J. Am. Chem. Soc.* 130(19):6058-6059 (2008).

Kallberg et al., "Short-chain dehydrogenase/reductase (SDR) relationships: a large family with eight clusters common to human, animal, and plant genomes," *Protein Sci.* 11(3):636-641 (2002).
Kallberg et al., "Short-Chain Dehydrogenases/Reductases (SDRs)—Coenzyme-Based Functional Assignments in Completed Genomes," *Eur. J. Biochem.* 269(18):4409-4417 (2002).
Kang et al., "Oncogenic transformation induced by the p110β, -γ, and -δ isoforms of class I phosphoinositide 3-kinase," *PNAS* 103(5):1289-1294 (2006).
Karpeiskii et al., "Pyridoxal-5'-Derivatives of Nucleobases," *Bioorganicheskaya Khimiya* 11(8): 1097-1104 (1985).
Khwaja, A., "PI3K as a Target for Therapy in Haematological Malignancies," *Curr. Top. Microbiol. Immunol.* 347:169-188 (2010).
Kim et al., "Activation and Function of the mTORC1 Pathway in Mast Cells," *J. Immunol.* 180(7):4586-4595 (2008).
Knight et al., "A Pharmacological Map of the PI3-K Family Defines a Role for p110α in Insulin Signaling," *Cell* 125(4):733-747 (2006).
Kong, D. and Yamori, T., "Advances in Development of Phosphatidylinositol 3-Kinase Inhibitors," *Curr. Med. Chem.* 16:2839-2854 (2009).
Kost et al., "Recyclization of 3-Alkyl- and 1,3-Dialkylisoquinolinium Salts to Naphthylamines," *Chemistry of Heterocyclic Compounds* 16(9): 965-970 (1981).
Kraybill et al., "Inhibitor scaffolds as new allele specific kinase substrates," *J. Am. Chem. Soc.* 124(41):12118-12128 (2002).
Kreutzberger et al. "5-Substituierte 4-Aminopyrimidine durch Aminomethylierung von Acetonitrilen," *Liebigs Ann. Chem.* 537-544 (1977).
Kulkarni et al., "PI3Kbeta plays a critical role in neutrophil activation by immune complexes," *Sci. Signal* 2011, vol. 4, ra23.
Kumar et al., "Keten Dithioacetals. Part 11. Reaction of 3-Cyano-4-Methylthio-2(1H)-pyridones with Hydrazine and Guanidine: Synthesis of Novel Substituted and Fused Pyrazolo[4,3-c]pyridone and Pyrido[4,3-d]pyrimidine derivatives," *J. Chem. Soc. Perkin 1* 8:857-862 (1978).
Kundu et al., "Palladium-catalysed heteroannualation with terminal alkynes; a highly regio- and stereoselective synthesis of (Z)-3-aryl(alykl)idene isoindolin-1-ones," *Tetrahedron* 56(27):4777-4792 (2000).
Kurtova et al., "Diverse marrow stromal cells protect CLL cells from spontaneous and drug-induced apoptosis: development of a reliable and reproducible system to assess stromal cell adhesion-mediated drug resistance," *Blood* 114(20): 4441-4450 (2009).
Kwok et al., "The anti-inflammatory natural product parthenolide from the medicinal herb Feverfew directly binds to and inhibits IκB kinase," *Chem. Biol.* 8(8):759-766 (2001).
Lannutti et al., "CAL-101 a p110δ selective phosphatidylinositol-3-kinase inhibitor for the treatment of B-cell malignancies, inhibits PI3K signaling and cellular viability," *Blood* 117(2):591-594 (2011).
Larabi et al., "Crystal Structure and Mechanism of Activation of TANK-Binding Kinase 1," *Cell Reports* 3:734-746 (2013).
Ledbetter et al., "CD28 ligation in T-cell activation: evidence for two signal transduction pathways," *Blood* 75(7):1531-1539 (1990).
Ledbetter et al., "Crosslinking of surface antigens causes mobilization of intracellular ionized calcium in T lymphocytes," *Proc. Natl. Acad. Sci. U. S. A.* 84(5):1384-1388 (1987).
Lee et al., "All roads lead to mTOR: integrating inflammation and tumor angiogenesis," *Cell Cycle* 6(24):3011-3014 (2007).
Lee et al., "The CD28 signal transduction pathway in T cell activation", Advances in Cell Regulation of Cell Growth, vol. 2, pp. 141-160, New York: Raven Press, Ltd. (1991).
Ley et al., "The T cell receptor/CD3 complex and CD2 stimulate the tyrosine phosphorylation of indistinguishable patterns of polypeptides in the human T leukemic cell line Jurkat," *Eur. J. Immunol.* 21(9):2203-2209 (1991).
Li et al., "Roles of PLC-beta2 and -beta3 and PI3Kgamma in chemoattractant-mediated signal transduction," *Science* 287(5455):1046-1049 (2000).
Liu et al., "Costimulation of T-cell growth," *Curr. Opin. Immunol.* 4(3):265-270 (1992).
Lu et al., "CD28-induced T cell activation. Evidence for a protein-tyrosine kinase signal transduction pathway," *J. Immunol.* 149(1):24-29 (1992).

(56) References Cited

OTHER PUBLICATIONS

Majumder et al., "mTOR inhibition reverses Akt-dependent prostate intraepithelial neoplasia through regulation of apoptotic and HIF-1-dependent pathways," *Nat. Med.* 10(6):594-601 (2004).
Markman et al., "Status of PI3K inhibition and biomarker development in cancer therapeutics," *Ann. Oncol.* 21(4):683-691 (2010).
Martelli et al., "The emerging role of the phosphatidylinositol 3-kinase/Akt/mammalian target of rapamycin signaling network in normal myelopoiesis and leukemogenesis," *Biochim. Biophys. Acta.* 803:991-1002 (2010).
Martinez et al., "The Molecular Signature of Mantle Cell Lymphoma Reveals Multiple Signals Favoring Cell Survival," *Cancer Res.* 63:8226-8232 (2003).
Martin-Sanchez et al., "PI3K Inhibition as a Potential Therapeutic Strategy in Peripheral T-Cell Lymphomas," *Blood (ASH Annual Meeting Abstracts)* 118: Abstract 3493 (2011).
Mattes et al., "DNA sequence selectivity of guanine-N7 alkylation by nitrogen mustards," *Nucleic Acids Res.* 14(7):2971-2987 (1986).
Maxwell et al., "Attenuation of phosphoinositide 3-kinase δ signaling restrains autoimmune disease," *J. Autoimmun.* 38:381-391 (2012).
Mayer et al., "Small molecule inhibitor of mitotic spindle bipolarity identified in a phenotype-based screen," *Science* 286(5441):971-974 (1999).
Mazzoletti and Broggini, "PI3K/AKT/mTOR inhibitors in ovarian cancer," *Curr. Med. Chem.* 17(36):4433-4447 (2010).
Meadows, S.A., et al., "CAL-101, a Potent Selective Inhibitor of the p110δ Isoform of Phosphatidylinositol 3-Kinase, Attenuates Pathway Signaling, Induces Apoptosis, and Overcomes Signals From the Microenvironment in Cellular Models of Hodgkin Lymphoma," *Blood (ASH Annual Meeting Abstracts)*, 116:Abstract 3926 (2010).
Mellinghoff et al., "TORward AKTually useful mouse models," *Nat. Med.* 10(6):579-580 (2004).
Merida et al., "IL-2 binding activates a tyrosine-phosphorylated phosphatidylinositol-3-kinase," *J. Immunol.* 147(7): 2202-2207 (1991).
Miyaura et al., "Palladium-catalyzed cross-coupling reactions of organoboron compounds," *Chem. Rev.* 95(7):2457-2483 (1995).
Modi et al., "Isoquinolones; part IV-synthesis of methyl, 3-formyl & other 3-substituted N-arylisoquinolones." *Indian J. Chem.* 18B:304-306 (1979).
Moon et al., "A novel microtubule destabilizing entity from orthogonal synthesis of triazine library and zebrafish embryo screening," *J. Am. Chem. Soc.* 124(39):11608-11609 (2002).
Mosmann et al., "The expanding universe of T-cell subsets: Th1, Th2 and more," *Immunology Today* 17(3):138-146 (1996).
Nakanishi et al., "Cloning and sequence analysis of a cDNA encoding tetrameric carbonyl reductase of pig lung," *Biochem. Biophys. Res. Commun.* (3):1311-1316 (1993).
Nemazanyi et al., "3-Amino-4-aryl-1(2H)-isoquinolones," *Chemistry of Heterocyclic Compounds* 27(3):307-308 (1991).
Newman et al., "Solid state analysis of the active pharmaceutical ingredient in drug products," *Drug Discov. Today* 8(19):898-905 (2003).
Nisitani et al., "Posttranscriptional regulation of Bruton's tyrosine kinase expression in antigen receptor-stimulated splenic B cells," *PNAS* 97(6):2737-2742 (2000).
Niswender et al., "Protein engineering of protein kinase a catalytic subunits results in the acquisition of novel inhibitor sensitivity," *J. Biol. Chem.* 277(32):28916-28922 (2002).
Nobel et al., "Purification of full-length recombinant human and rat type 1 11β-hydroxysteroid dehydrogenases with retained oxidoreductase activities," *Protein Expr. Purif.* 26(3):349-356 (2002).
Norman, "Selective PI3K-delta Inhibitors, a Review of the Patent Literature," *Expert Opinion on Therapeutic Patents*, 21(11): 1773-1790 (2011).
Nunes et al., "Signalling through CD28 T-cell activation pathway involves an inositol phospholipid-specific phospholipase C activity," *Biochem. J.* 293(Pt 3):835-842 (1993).

Oda et al., "PIK3CA cooperates with other phosphatidylinositol 3'-kinase pathway mutations to effect oncogenic transformation," *Cancer Res.* 68(19):8127-8136 (2008).
Office Action dated Dec. 13, 2012 for 7004 US1, U.S. Appl. No. 13/112,611.
Okada et al., "Essential role of phosphatidylinositol 3-kinase in insulin-induced glucose transport and antilipolysis in rat adipocytes. Studies with a selective inhibitor wortmannin," *J. Biol. Chem.* 269(5):3568-3573 (1994).
Okada et al., "Blockage of chemotactic peptide-induced stimulation of neutrophils by wortmannin as a result of selective inhibition of phosphatidylinositol 3-kinase," *J. Biol. Chem.* 269(5):3563-3567 (1994).
Oppermann et al., "Forms and functions of human SDR enzymes," *Chem. Biol. Interact.* 130-132(1-3):699-705 (2001).
O'Shea et al., "Activation of human peripheral blood T lymphocytes by pharmacological induction of protein-tyrosine phosphorylation," *Proc. Natl. Acad. Sci. U. S. A.* 89(21):10306-10310 (1992).
Ozaki et al., "Studies on 4(1H)-quinazolinones. IV. Convenient synthesis of 12-methyl-6H-isoquino [2,1-a] quinazolin-6-one and 6-methyl-13H-quinazolino [3,4-a] quinazolin-13-one," *Chem. Pharm. Bull.* 32(6):2160-2164 (1984).
Ozol et al., "Autoxidative transformations of 2-substituted 3-alkyl-4-hydroxy-1-oxo-1, 2-dihydroisoquinolines," *Chemistry of Heterocyclic Compounds* 14(6):644-648 (1978).
Patel et al., "Immunopathological aspects of age-related macular degeneration," *Semin. Immunopathol.* 30(2):97-110 (2008).
Pérez-Blas et al., "Impaired T cell signal transduction through CD28 in a patient with idiopathic thrombocytopenia," *Clin. Exp. Immunol.* 85(3):424-428 (1991).
Persson, "Glucocorticoids for asthma—early contributions," *Pulm. Pharmacol.* 2(3):163-166 (1989).
Petrie et al., "Novel biotinylated adenylate analogue derived from pyrazolo[3,4-d]pyrimidine for labeling DNA probes," *Bioconjug. Chem.* 2(6):441-446 (1991).
Pighi et al., "Phospho-proteomic analysis of mantle cell lymphoma cells suggests a pro-survival role of B-cell receptor signaling," *Cell Oncol. (Dordr)* 34(2):141-153 (2011).
Polak et al., "The PI3K/PKB signaling module as key regulator of hematopoiesis: implications for therapeutic strategies in leukemia," *Blood* 119(4):911-923 (2012).
Porta and Figlin, "Phosphatidylinositol-3-kinase/Akt signaling pathway and kidney cancer, and the therapeutic potential of phosphatidylinositol-3-kinase/Akt inhibitors," *J. Urol.* 182(6):2569-2577 (2009).
Prasad et al., "Phosphatidylinositol (PI) 3-kinase and PI 4-kinase binding to the CD4-p56$^{lck}$ complex: the p56$^{lck}$ SH3 domain binds to PI 3-kinase but not PI 4-kinase," *Mol. Cell. Biol.* 13(12): 7708-7717 (1993).
Prasad et al., "Src-homology 3 domain of protein kinase p59$^{fyn}$ mediates binding to phosphatidylinositol 3-kinase in T cells," *Proc. Natl. Acad. Sci. U. S. A.* 90(15): 7366-7370 (1993).
Prasad et al., "T-cell antigen CD28 interacts with the lipid kinase phosphatidylinositol 3-kinase by a cytoplasmic Tyr(P)-Met-Xaa-Met motif," *Proc. Natl. Acad. Sci. U. S. A.* 91(7): 2834-2838 (1994).
Pudlo et al., "Synthesis, antiproliferative, and antiviral activity of certain 4-substituted and 4,5 disubstituted 7-[1,3-dihydroxy-2-propoxy)methyl]pyrrolo[2,3-d]pyrimidines," *J. Med. Chem.* 33(7):1984-1992 (1990).
Puri and Gold, "Selective inhibitors of phosphoinositide 3-kinase delta: modulators of B-cell function with potential for treating autoimmune inflammatory disease and B-cell malignancies," *Front. Immunol.* 3:256 (2012).
Quiroga et al., "B-cell antigen receptor signaling enhances chronic lymphocytic leukemia cell migration and survival: specific targeting with a novel spleen tyrosine kinase inhibitor, R406," *Blood* 114(5):1029-1037 (2009).
Reif et al., "Divergent regulation of phosphatidylinositol 3-kinase P85α and P85β isoforms upon T cell activation," *J. Biol. Chem.* 268(15):10780-10788 (1993).
Report of the Expert Committee on the Diagnosis and Classification of Diabetes Mellitus, *Diabetes Care* 2( Suppl. 1):S5-S19 (1992).

(56) References Cited

OTHER PUBLICATIONS

Rizzatti et al., "Gene expression profiling of mantle cell lymphoma cells reveals aberrant expression of genes from the PI3K-AKT, WNT and TGFβ signaling pathways," *Brit. J. Haematol.* 130:516-526 (2005).
Robertson, "Eicosanoids and human disease", Harrison's Principles of Internal Medicine, Isselbacher K.J. et al. (eds.), vol. 1, pp. 431-435, McGraw-Hill, New York City (1994).
Roller et al., "Blockade of Phosphatidylinositol 3-Kinase (PI3K)δ or PI3Kγ Reduces 1L-17 and Ameliorates Imiquimod-Induced Psoriasis-like Dermatitis," *J. Immunol.* 189:4612-4620 (2012).
Romero et al., "Cloning and expression of the bovine 1 lb-hydroxysteroid dehydrogenase type-2," *J. Steroid Biochem. Mol. Biol.* 72(5):231-237 (2000).
Rommel et al., "P13Kδ and PI3Kγ: partners in crime in inflammation in rheumatoid arthritis and beyond?" *Nat. Rev. Immunol.* 7:191-201 (2007).
Rott et al., "Recent developments in the use of biologics in psoriasis and autoimmune disorders. The role of autoantibodies," *BMJ* 330(7493):716-720 (2005).
Rudelius et al., "Constitutive activation of Akt contributes to the pathogenesis and survival of mantle cell lymphoma," *Blood* 108(5):1668-1676 (2006).
Saif and Chu, "Biology of colorectal cancer," *Cancer J.* 16(3):196-201 (2010).
Salmena et al., "Tenets of PTEN Tumor Suppression," *Cell* 133(3):403-414 (2008).
Sarker et al., "Targeting the PI3K/AKT pathway for the treatment of prostate cancer," *Clin. Cancer Res.* 15(15):4799-4805 (2009).
Sasaki et al., "Function of PI3Kγ in Thymocyte Development, T Cell Activation, and Neutrophil Migration," *Science* 287:1040-1046 (2000).
Schwartz et al., "Quercetin inhibition of the induction and function of cytotoxic T lymphocytes," *Immunopharmacology* 4(2):125-138 (1982).
Schwartz, "A cell culture model for T lymphocyte clonal anergy," *Science* 248(4961):1349-1356 (1990).
Shapiro et al., "Phase I Dose-Escalation Study of XL147, A PI3K Inhibitor Administered Orally to Patients with Solid Tumors," *J. Clin. Oncol.* 27:146x (Suppl Abstr 3500) (2009).
Shibasaki et al., "Different properties of monomer and heterodimer forms of phosphatidylinositol 3-kinases," *Biochem. J.* 289 (Pt 1):227-231 (1993).
Sinclair et al., "Phosphatidylinositol-3 Kinase Delta (PI3Kδ) Inhibitor AMG 319 Is a Potent, Selective and Orally Bioavailable Small Molecule Inhibitor That Suppresses PI3K-Mediated Signaling and Viability in Neoplastic B Cells," *Blood (ASH Annual Meeting Abstracts)* 118:Abstract 4964 (2011).
Singer et al., "Optimization of in situ hybridization using isotopic and non-isotopic detection methods," *Biotechniques* 4(3):230-250 (1986).
Smith et al., "Expression of Bruton's Agammaglobulinemia Tyrosine Kinase Gene, BTK, Is Selectively Down-Regulated in T Lymphocytes and Plasma Cells," *J. Immunol.* 152:557-565 (1994).
Soldan et al., "Induction of daunorubicin carbonyl reducing enzymes by daunorubicin in sensitive and resistant pancreas carcinoma cells," *Biochem. Pharmacol.* 51(2):117-123 (1996).
Soond et al., "PI3K p110δ regulates T-cell cytokine production during primary and secondary immune responses in mice and humans," *Blood* 115(11):2203-2213 (2010).
Srinivasan et al., "P13 Kinase Signals BCR-Dependent Mature B Cell Survival," *Cell* 139:573-586 (2009).
Stanoeva et al., "Homophthalic anhydrides and their application to the synthesis of heterocyclic compounds (review)," *Chemistry of Heterocyclic Compounds* 20(12):1305-1315 (1984).
Subramaniam et al., "Targeting Nonclassical Oncogenes for Therapy in T-ALL," *Cancer Cell* 21:459-472 (2012).
Sujobert et al., "Essential role for the p110δ isoform in phosphoinositide 3-kinase activation and cell proliferation in acute myeloid leukemia," *Blood* 106(3):1063-1066 (2005).

Supplementary European Examination Report EP Application No. 07754845.1 dated Sep. 20, 2011.
Supplementary European Search Report for EP Application No. 07754845 (4 pages) dated Feb. 24, 2010.
Supplementary European Search Report for EP Application No. 10800175.1 dated Nov. 7, 2012.
Sykes et al., "Treatment of severe autoimmune disease by stem-cell transplantation," *Nature* 35(7042):620-627 (2005).
Takeuchi et al., "Synergistic Augmentation of Rapamycin-Induced Autophagy in Malignant Glioma Cells by Phosphatidylinositol 3-Kinase/Protein Kinase B Inhibitors," *Cancer Res.* 65(8):3336-3346 (2005).
Tanaka et al., "An unbiased cell morphology-based screen for new, biologically active small molecules," *PLoS Biol.* 3(5):0764-0776 (2005).
Thompson et al., "Identification of distinct populations of PI-3 kinase activity following T-cell activation," *Oncogene* 7(4):719-725 (1992).
Torbett et al., "A chemical screen in diverse breast cancer cell lines reveals genetic enhancers and suppressors of sensitivity to PI3K isoform-selective inhibition," *Biochem. J.* 415(1):97-110 (2008).
Truitt et al., "Stimulation of CD28 triggers an association between CD28 and phosphatidylinositol 3-kinase in Jurkat T cells," *J. Exp. Med.* 179(3):1071-1076 (1994).
Tyukavkina et al., Bioorganicheskaya Khimiya, Moskva, DROFA, pp. 83-85 (2004).
Uddin et al., "Role of phosphatidylinositol 3'-kinase/AKT pathway in diffuse large B-cell lymphoma survival," *Blood* 108(13):4178-4186 (2006).
Ugarkar et al., "Adenosine kinase inhibitors. 2. Synthesis, enzyme inhibition, and antiseizure activity of diaryltubercidin analogues," *J. Med. Chem.* 43(15):2894-2905 (2000).
Vandenberghe et al., "Antibody and B7/BB1-mediated ligation of the CD28 receptor induces tyrosine phosphorylation in human T cells," *J. Exp. Med.* 175(4):951-960 (1992).
Vanhaesebroeck et al., "PI3K: from the bench to the clinic and back," *Curr. Top. Microbiol. Immunol.* 347:1-19 (2010).
Vara et al., "PI3K/Akt Signalling Pathway and Cancer," *Cancer Treat. Rev.* 30(2):193-204(2004).
Vasilevsky et al., "Study of the Heterocyclization of vic-Substituted Hydrazides of Acetylenylpyrazolecarboxylic Acids into N-Amino Pyrazolopyridinones," *Journal of Heterocyclic Chemistry* 39(6):1229-1233 (2002).
Vasilevsky et al., "Unexpected results in the heterocyclization of 5-acetylenylpyrazole-4-carboxylic acid hydrazides under the influence of CuCl: formation of a diazepinone and dehydrodimerization into the corresponding bis(pyrazolo [4,3-d] [1,2] diazepinone)," *Tetrahedron Lett.* 46(26):4457-4459 (2005).
Vippagunta et al., "Crystalline Solids," *Adv. Drug Deliv. Rev.* 48(1):3-26 (2001).
Vitali et al., "Immunotherapy in rheumatoid arthritis: a review," *Int. J. Artif. Organs* 16 Suppl. 5:196-200 (1993).
Vlahos et al., "A specific inhibitor of phosphatidylinositol 3-kinase, 2-(4-morpholinyl)-8-phenyl-4H-1-benzopyran-4-one (LY294002)," *J. Biol. Chem.* 269(7):5241-5248 (1994).
Vogt et al., "Phosphatidylinositol 3-kinase: the oncoprotein," *Curr. Top. Microbiol. Immunol.* 347:79-104 (2010).
Vogt et al., "Phosphoinositide 3-kinase: from viral oncoprotein to drug target," *Virology* 344(l):131-138 (2006).
Wagner et al., "A First-in-Human Phase I Study to Evaluate the Pan-PI3K Inhibitor GDC-0941 Administered QD or BID in Patients with Advanced Solid Tumors," *J. Clin. Oncol.* 27:146s (Suppl, Abstr 3501) (2009).
Wahlstrom et al., "Aberrant MAPK and PI3K Signaling Contribute to Chemotherapy Resistance in T Cell Acute Lymphobalstic Leukemia by Altering the Balance of Apoptosis Mediators," *Blood (ASH Annual Meeting Abstracts)* 118: Abstract 3490 (2011).
Ward et al., "Inhibition of CD28-mediated T cell costimulation by the phosphoinositide 3-kinase inhibitor wortmannin," *Eur. J. Immunol.* 25(2):526-532 (1995).
Ward et al., "Ligation of CD28 receptor by B7 induces formation of D-3 phosphoinositides in T lymphocytes independently of T cell receptor/CD3 activation." *Eur. J. Immunol.* 23(10):2572-2577 (1993).

(56) References Cited

OTHER PUBLICATIONS

Ward et al., "Regulation of D-3 phosphoinositides during T cell activation via the T cell antigen receptor/CD3 complex and CD2 antigens," *Eur. J. Immunol.* 22(1):45-49 (1992).

Ward et al., "Regulation of phosphoinositide kinases in T cells. Evidence that phosphatidylinositol 3-kinase is not a substrate for T cell antigen receptor-regulated tyrosine kinases," *J. Biol. Chem.* 267(33):23862-23869 (1992).

Ward et al., "Therapeutic potential of phosphoinositide 3-kinase inhibitors," *Chem. Biol.* 10(3):207-213 (2003).

White et al., "11β-Hydroxysteroid Dehyrdogenase and the Syndrome of Apparent Mineralocorticoid Excess," *Endocr. Rev.* 18(1):135-156 (1997).

Widler et al., "7-alkyl- and 7-Cycloalkyl-5-aryl-pyrrolo[2,3-d]pyrimidines-potent inhibitors of the tyrosine kinase c-Src," Bioorg. Med. Chem. Lett. 11(6):849-852 (2001).

Wiesinger et al., "Antiinflammatory activity of the new mould metabolite 11-desacetoxy-wortmannin and of some of its derivatives," *Experientia* 30(2):135-136 (1974).

Wolff, Burger's Medicinal Chemistry, 5$^{th}$ ed, Part 1, pp. 975-977, John Wiley & Sons (1995).

Woscholski et al., "A comparison of demethoxyviridin and wortmannin as inhibitors of phosphatidylinositol 3-kinase," *FEBS Lett.* 342(2):109-114 (1994).

Wu et al., "Decreased immunological responses by wortmannin-containing rice culture of *Fusarium oxysporum* and by purified wortmannin in avian species," *Immunopharmacol. Immunotoxicol.* 14(4):913-923 (1992).
Wu et al., "Wortmannin (a mycotoxin) inhibited immune responses in chickens," *Poultry Sci.* Vo. 71, Suppl 1, pp. 13 (1992).
Yaguchi et al., "Antitumor activity of ZSTK474, a new phosphatidylinositol 3-kinase inhibitor," *J. Natl. Cancer Inst.* 98(8):545-556 (2006).
Yang et al., "A novel activation pathway for mature thymocytes. Costimulation of CD2 (T,p50) and CD28 (T,p44) induces autocrine interleukin 2/interleukin 2 receptor-mediated cell proliferation," *J. Exp. Med.* 168(4):1457-1468 (1988).
Yano et al., "Inhibition of histamine secretion by wortmannin through the blockade of phosphatidylinositol 3-kinase in RBL-2H3 cells," *J. Biol. Chem.* 268(34):25846-25856 (1993).
Yoshida et al., "Quercetin arrests human leukemic T-cells in late G1 phase of the cell cycle," *Cancer Res.* 52(23):6676-6681 (1992).
Zhao and Vogt, "Class I PI3K in oncogenic cellular transformation," *Oncogene* 27(41):5486-5496 (2008).

* cited by examiner

SUBSTITUTED ISOQUINOLINONES AND METHODS OF TREATMENT THEREOF

CROSS-REFERENCE TO RELATED APPLICATIONS

This application is a continuation application of U.S. application Ser. No. 13/552,516, filed Jul. 18, 2012, which claims priority to U.S. Provisional Application Nos. 61/528,585, filed Aug. 29, 2011, 61/547,343, filed Oct. 14, 2011, 61/562,278, filed Nov. 21, 2011, 61/595,947, filed Feb. 7, 2012, and 61/645,982, filed May 11, 2012, the entireties of which are incorporated herein by reference.

BACKGROUND

The activity of cells can be regulated by external signals that stimulate or inhibit intracellular events. The process by which stimulatory or inhibitory signals are transmitted into and within a cell to elicit an intracellular response is referred to as signal transduction. Over the past decades, cascades of signal transduction events have been elucidated and found to play a central role in a variety of biological responses. Defects in various components of signal transduction pathways have been found to account for a vast number of diseases, including numerous forms of cancer, inflammatory disorders, metabolic disorders, vascular and neuronal diseases (Gaestel et al. *Current Medicinal Chemistry* (2007) 14:2214-2234).

Kinases represent a class of important signaling molecules. Kinases can generally be classified into protein kinases and lipid kinases, and certain kinases exhibit dual specificities. Protein kinases are enzymes that phosphorylate other proteins and/or themselves (i.e., autophosphorylation). Protein kinases can be generally classified into three major groups based upon their substrate utilization: tyrosine kinases which predominantly phosphorylate substrates on tyrosine residues (e.g., erb2, PDGF receptor, EGF receptor, VEGF receptor, src, abl), serine/threonine kinases which predominantly phosphorylate substrates on serine and/or threonine residues (e.g., mTorC1, mTor C2, ATM, ATR, DNA-PK, Akt), and dual-specificity kinases which phosphorylate substrates on tyrosine, serine and/or threonine residues.

Lipid kinases are enzymes that catalyze the phosphorylation of lipids. These enzymes, and the resulting phosphorylated lipids and lipid-derived biologically active organic molecules play a role in many different physiological processes, including cell proliferation, migration, adhesion, and differentiation. Certain lipid kinases are membrane associated and they catalyze the phosphorylation of lipids contained in or associated with cell membranes. Examples of such enzymes include phosphoinositide(s) kinases (e.g., PI3-kinases, PI4-Kinases), diacylglycerol kinases, and sphingosine kinases.

The phosphoinositide 3-kinases (PI3Ks) signaling pathway is one of the most highly mutated systems in human cancers. PI3K signaling is also a key factor in many other diseases in humans. PI3K signaling is involved in many disease states including allergic contact dermatitis, rheumatoid arthritis, osteoarthritis, inflammatory bowel diseases, chronic obstructive pulmonary disorder, psoriasis, multiple sclerosis, asthma, disorders related to diabetic complications, and inflammatory complications of the cardiovascular system such as acute coronary syndrome.

PI3Ks are members of a unique and conserved family of intracellular lipid kinases that phosphorylate the 3'-OH group on phosphatidylinositols or phosphoinositides. The PI3K family comprises 15 kinases with distinct substrate specificities, expression patterns, and modes of regulation. The class I PI3Ks (p110α, p110β, p110δ, and p110γ) are typically activated by tyrosine kinases or G-protein coupled receptors to generate PIP3, which engages downstream effectors such as those in the Akt/PDK1 pathway, mTOR, the Tec family kinases, and the Rho family GTPases. The class II and III PI3Ks play a key role in intracellular trafficking through the synthesis of PI(3)P and PI(3,4)P2. The PI3Ks are protein kinases that control cell growth (mTORC1) or monitor genomic integrity (ATM, ATR, DNA-PK, and hSmg-1).

The delta (δ) isoform of class I PI3K has been implicated, in particular, in a number of diseases and biological processes. PI3K-δ is expressed primarily in hematopoietic cells including leukocytes such as T-cells, dendritic cells, neutrophils, mast cells, B-cells, and macrophages. PI3K-δ is integrally involved in mammalian immune system functions such as T-cell function, B-cell activation, mast cell activation, dendritic cell function, and neutrophil activity. Due to its integral role in immune system function, PI3K-δ is also involved in a number of diseases related to undesirable immune response such as allergic reactions, inflammatory diseases, inflammation mediated angiogenesis, rheumatoid arthritis, and autoimmune diseases such as lupus, asthma, emphysema and other respiratory diseases. Other class I PI3K involved in immune system function includes PI3K-γ, which plays a role in leukocyte signaling and has been implicated in inflammation, rheumatoid arthritis, and autoimmune diseases such as lupus.

Unlike PI3K-δ, the beta (β) isoform of class I PI3K appears to be ubiquitously expressed. PI3K-β has been implicated primarily in various types of cancer including PTEN-negative cancer (Edgar et al. *Cancer Research* (2010) 70(3):1164-1172), and HER2-overexpressing cancer such as breast cancer and ovarian cancer.

SUMMARY

Described herein are compounds capable of selectively inhibiting certain isoform(s) of class I PI3K without substantially affecting the activity of the remaining isoforms of the same class. For example, non-limiting examples of inhibitors capable of selectively inhibiting PI3K-δ and/or PI3K-γ, but without substantially affecting the activity of PI3K-β are disclosed. Such inhibitors can be effective in ameliorating disease conditions associated with PI3K-δ/γ activity.

In one aspect, provided herein are compounds of Formula (I):

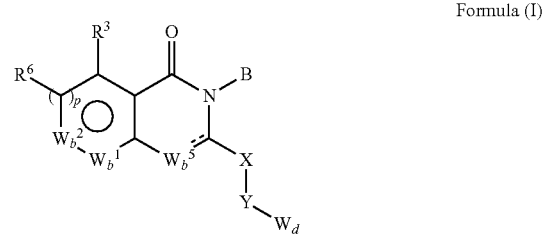

Formula (I)

or an enantiomer, a mixture of enantiomers, or a mixture of two or more diastereomers thereof, or a pharmaceutically acceptable form thereof, wherein $W_b^1$ and $W_b^2$ are each independently $CR^6$, S, O, N or $NR^{14}$, wherein at least one of $W_b^1$ and $W_b^2$ is $CR^6$, N or $NR^{14}$;

$W_b^5$ is $CR^8$, $CHR^8$, or N;

p is 0, 1, 2 or 3;

B is hydrogen, alkyl, alkenyl, alkynyl, amino, heteroalkyl, cycloalkyl, heterocyclyl, aryl or heteroaryl, each of which is substituted with 0-4 $R^2$;

each $R^2$ is independently alkyl, heteroalkyl, alkenyl, alkynyl, cycloalkyl, heterocyclyl, aryl, arylalkyl, heteroaryl, heteroarylalkyl, alkoxy, amido, amino, acyl, acyloxy, alkoxycarbonyl, sulfonamido, halo, cyano, hydroxyl, nitro, phosphate, urea or carbonate;

X is absent or is $—(CH(R^9))_z—$;

Y is absent, $—O—$, $—S—$, $—S(=O)—$, $—S(=O)_2—$, $—N(R^9)—$, $—C(=O)—(CHR^9)_z—$, $—C(=O)—$, $—N(R^9)—C(=O)—$, $—N(R^9)—C(=O)NH—$, $—N(R^9)C(R^9)_2—$, $—C(=O)—N(R^9)_2$ or $—C(=O)—N(R^9)—(CHR^9)_z—$;

each z is independently an integer of 1, 2, 3, or 4;

$R^3$ is $C_{2-6}$alkyl, fluoro, bromo, iodo, cycloalkyl, cycloalkylalkyl, aryl, heteroaryl, heterocyclyl, aralkyl, heteroaralkyl, heterocyclylalkyl, alkenyl, or alkynyl, or $R^3$ is a heteroatom selected from N, S, and O, wherein the heteroatom has a covalent bond, either directly or through a $C_1$-$C_6$ alkyl group, to an aryl, heteroaryl or heterocyclyl, or $R^3$ and $R^6$ are taken together with the carbons to which they are attached form a cyclic moiety; wherein each of the above substituents can be substituted with 0, 1, 2, or 3 $R^{13}$;

each $R^6$ is independently hydrogen, alkyl, alkenyl, alkynyl, cycloalkyl, heterocyclyl, fluoroalkyl, heteroalkyl, alkoxy, amido, amino, acyl, acyloxy, sulfinyl, sulfonyl, sulfoxide, sulfone, sulfonamido, halo, cyano, heteroaryl, aryl, hydroxyl, or nitro;

$R^8$ is hydrogen, alkyl, alkenyl, alkynyl, cycloalkyl, heteroalkyl, alkoxy, amino, acyl, acyloxy, sulfonamido, halo, cyano, hydroxyl, or nitro;

each $R^9$ is independently hydrogen, alkyl, cycloalkyl, heterocyclyl or heteroalkyl;

$W_d$ is

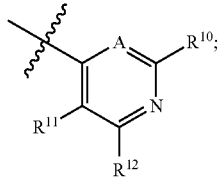

A is N or $CR^{19}$;

$R^{10}$, $R^{11}$, $R^{12}$, $R^{13}$, and $R^{19}$ are independently hydrogen, alkyl, heteroalkyl, alkenyl, alkynyl, cycloalkyl, heterocyclyl, aryl, arylalkyl, heteroaryl, heteroarylalkyl, alkoxy, heterocyclyloxy, amido, amino, acyl, acyloxy, alkoxycarbonyl, sulfonamido, halo, haloalkyl, cyano, hydroxyl, nitro, phosphate, urea, carbonate, oxo, or NR'R" wherein R' and R" are taken together with nitrogen to form a cyclic moiety;

each $R^{14}$ is independently hydrogen, alkyl, cycloalkyl, heterocyclyl or heteroalkyl; and wherein the compound of Formula (I) is not one of the following compounds:

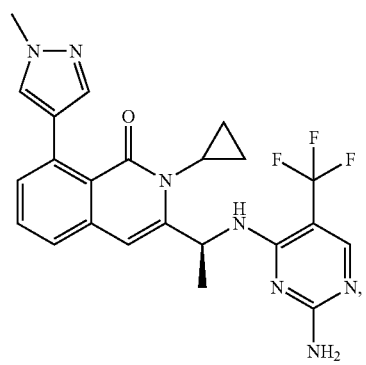

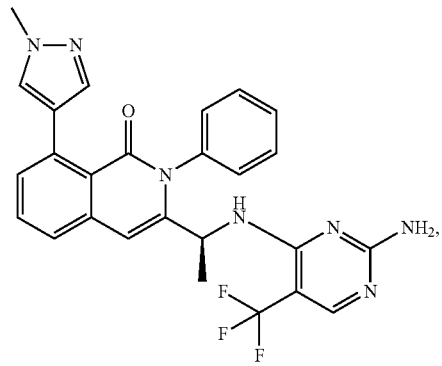

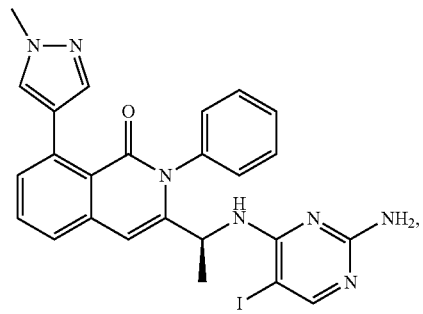

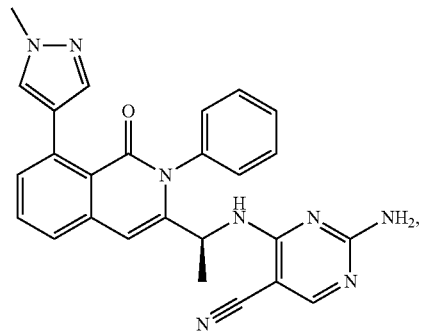

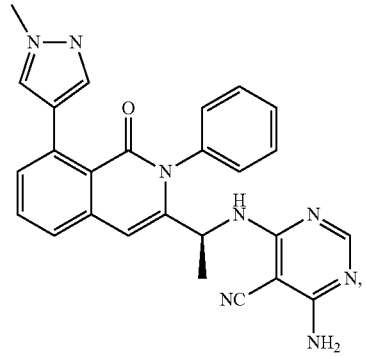

-continued

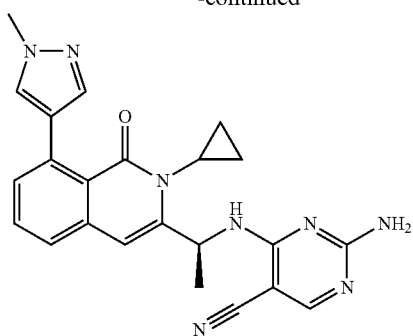

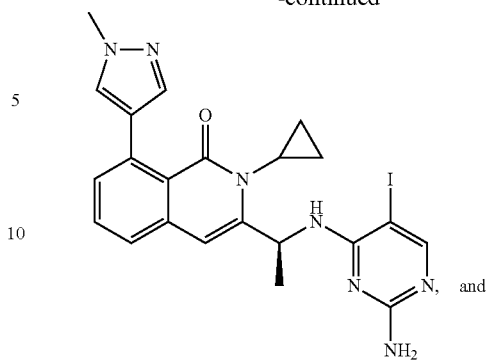

In one embodiment, provided herein are compounds of Formula (I):

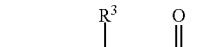

Formula (I)

or an enantiomer, a mixture of enantiomers, or a mixture of two or more diastereomers thereof, or a pharmaceutically acceptable form thereof, wherein $W_b^1$ and $W_b^2$ are each independently $CR^6$, S, O, N or $NR^{14}$, wherein at least one of $W_b^1$ and $W_b^2$ is $CR^6$, N or $NR^{14}$;

$W_b^5$ is $CR^8$, $CHR^8$, or N;

p is 0, 1, 2 or 3;

B is hydrogen, alkyl, alkenyl, alkynyl, amino, heteroalkyl, cycloalkyl, heterocyclyl, aryl or heteroaryl, each of which is substituted with 0-4 $R^2$;

each $R^2$ is independently alkyl, heteroalkyl, alkenyl, alkynyl, cycloalkyl, heterocyclyl, aryl, arylalkyl, heteroaryl, heteroarylalkyl, alkoxy, amido, amino, acyl, acyloxy, alkoxycarbonyl, sulfonamido, halo, cyano, hydroxyl, nitro, phosphate, urea or carbonate;

X is absent or is —$(CH(R^9))_z$—;

Y is absent, —O—, —S—, —S(=O)—, —S(=O)$_2$—, —N($R^9$)—, —C(=O)—$(CHR^9)_z$—, —C(=O)—, —N($R^9$)—C(=O)—, —N($R^9$)—C(=O)NH—, —N($R^9$)C($R^9$)$_2$—, —C(=O)—N($R^9$)$_2$, or —C(=O)—N($R^9$)—$(CHR^9)_z$;

each z is independently an integer of 1, 2, 3, or 4;

$R^3$ is $C_{2-6}$alkyl, fluoro, bromo, iodo, cycloalkyl, cycloalkylalkyl, aryl, heteroaryl, heterocyclyl, aralkyl, heteroaralkyl, heterocyclylalkyl, alkenyl, or alkynyl, or $R^3$ is a heteroatom selected from N, S, and O, wherein the heteroatom has a covalent bond, either directly or through a $C_1$-$C_6$ alkyl group, to an aryl, heteroaryl or heterocyclyl, or $R^3$ and $R^6$ are taken together with the carbons to which they are attached form a cyclic moiety; wherein each of the above substituents can be substituted with 0, 1, 2, or 3 $R^{13}$;

each $R^6$ is independently hydrogen, alkyl, alkenyl, alkynyl, cycloalkyl, heterocyclyl, fluoroalkyl, heteroalkyl, alkoxy, amido, amino, acyl, acyloxy, sulfinyl, sulfonyl, sulfoxide, sulfone, sulfonamido, halo, cyano, heteroaryl, aryl, hydroxyl, or nitro;

$R^8$ is hydrogen, alkyl, alkenyl, alkynyl, cycloalkyl, heteroalkyl, alkoxy, amino, acyl, acyloxy, sulfonamido, halo, cyano, hydroxyl, or nitro;

each $R^9$ is independently hydrogen, alkyl, cycloalkyl, heterocyclyl or heteroalkyl;

$W_d$ is

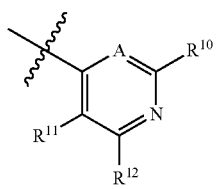

A is N or $CR^{19}$;

$R^{10}$, $R^{11}$, $R^{12}$, $R^{13}$ and $R^{19}$ are independently hydrogen, alkyl, heteroalkyl, alkenyl, alkynyl, cycloalkyl, heterocyclyl, aryl, arylalkyl, heteroaryl, heteroarylalkyl, alkoxy, heterocyclyloxy, amido, amino, acyl, acyloxy, alkoxycarbonyl, sulfonamido, halo, haloalkyl, cyano, hydroxyl, nitro, phosphate, urea, carbonate, oxo, or NR'R" wherein R' and R" are taken together with nitrogen to form a cyclic moiety;

each $R^{14}$ is independently hydrogen, alkyl, cycloalkyl, heterocyclyl or heteroalkyl; and wherein $R^3$ is not 1-methyl-4-pyrazolyl.

In certain embodiments, the compound of Formula (I) has a structure of Formula (II):

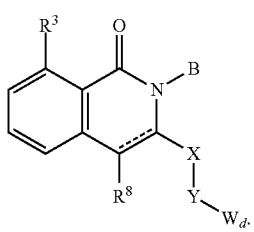

Formula (II)

In some embodiments, the compound of Formula (II) has a structure of Formula (IIa) or (IIb):

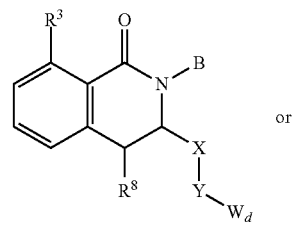

Formula (IIa)

or

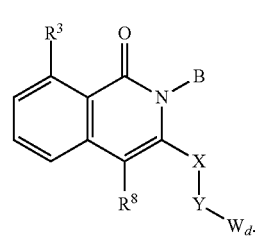

Formula (IIb)

In some embodiments, the compound of Formula (II) has a structure of Formula (IIIa) or (IIIb):

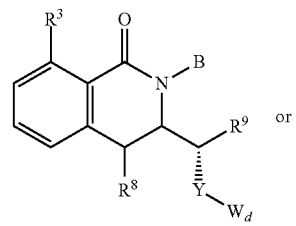

Formula (IIIa)

or

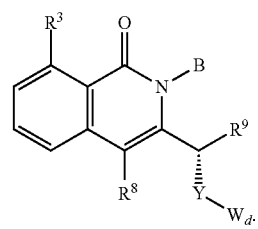

Formula (IIIb)

In certain embodiments, the compound of Formula (I) has a structure of Formula (IV):

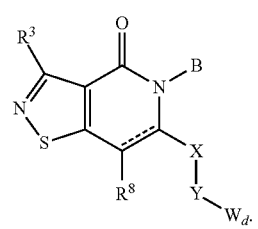

Formula (IV)

In some embodiments, the compound of Formula (IV) has a structure of Formula (V):

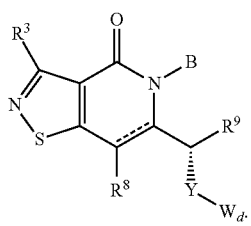

Formula (V)

In certain embodiments, the compound of Formula (I) has a structure of Formula (VI):

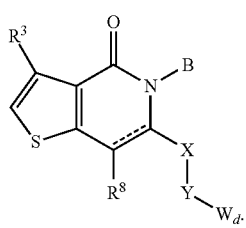

Formula (VI)

In certain embodiments, the compound of Formula (VI) has a structure of Formula (VII):

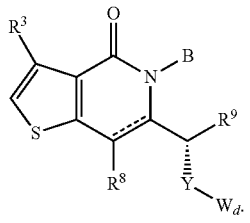

Formula (VII)

In certain embodiments, the compound of Formula (VI) has a structure of Formula (VIII):

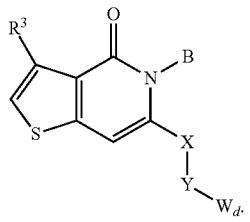

Formula (VIII)

In some embodiments, the compound of Formula (VIII) has a structure of Formula (IX):

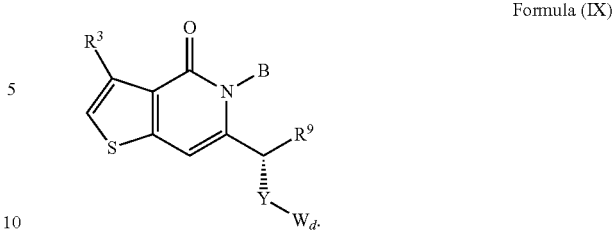

Formula (IX)

In another aspect, provided herein are compounds of Formula (XV):

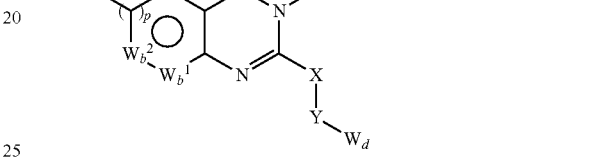

Formula (XV)

or an enantiomer, a mixture of enantiomers, or a mixture of two or more diastereomers thereof, or a pharmaceutically acceptable form thereof, wherein $W_b^1$ and $W_b^2$ are each independently $CR^6$, S, O, N or $NR^{14}$, wherein at least one of $W_b^1$ and $W_b^2$ is $CR^6$, N or $NR^{14}$;

p is 0, 1, 2 or 3;

B is hydrogen, alkyl, alkenyl, alkynyl, amino, heteroalkyl, cycloalkyl, heterocyclyl, aryl or heteroaryl, wherein cycloalkyl, heterocyclyl, aryl or heteroaryl are substituted with 0-4 $R^2$;

each $R^2$ is independently alkyl, heteroalkyl, alkenyl, alkynyl, cycloalkyl, heterocyclyl, aryl, arylalkyl, heteroaryl, heteroarylalkyl, alkoxy, amido, amino, acyl, acyloxy, alkoxycarbonyl, sulfonamido, halo, cyano, hydroxyl, nitro, phosphate, urea or carbonate;

X is absent or is —$(CH(R^9))_z$—;

Y is absent, —O—, —S—, —S(=O)—, —S(=O)$_2$—, —N($R^9$)—, —C(=O)—(CHR$^9$)$_z$—, —C(=O)—, —N($R^9$)—C(=O)—, —N($R^9$)—C(=O)NH—, —N($R^9$)C($R^9$)$_2$—, —C(=O)—N($R^9$)$_2$, or —C(=O)—N($R^9$)—(CHR$^9$)$_z$;

each z is independently an integer of 1, 2, 3, or 4;

each $R^6$ is independently hydrogen, alkyl, alkenyl, alkynyl, cycloalkyl, heterocyclyl, fluoroalkyl, heteroalkyl, alkoxy, amido, amino, acyl, acyloxy, sulfinyl, sulfonyl, sulfoxide, sulfone, sulfonamido, halo, cyano, heteroaryl, aryl, hydroxyl, or nitro;

each $R^9$ is independently hydrogen, alkyl, cycloalkyl, heterocyclyl or heteroalkyl;

$W_d$ is

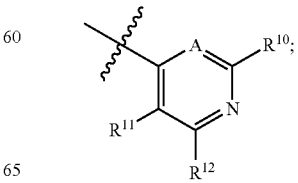

A is N or $CR^{19}$;

$R^{10}$, $R^{11}$, $R^{12}$, $R^{13}$ and $R^{19}$ are independently hydrogen, alkyl, heteroalkyl, alkenyl, alkynyl, cycloalkyl, heterocyclyl, aryl, arylalkyl, heteroaryl, heteroarylalkyl, alkoxy, heterocyclyloxy, amido, amino, acyl, acyloxy, alkoxycarbonyl, sulfonamido, halo, cyano, hydroxyl, nitro, phosphate, urea, carbonate, oxo, or NR'R" wherein R' and R" are taken together with nitrogen to form a cyclic moiety;

each $R^{14}$ is independently hydrogen, alkyl, cycloalkyl, heterocyclyl or heteroalkyl;

$R^{18}$ is hydrogen, alkyl, haloalkyl, halo, alkoxy, cycloalkyl, cycloalkylalkyl, aryl, heteroaryl, heterocyclyl, aralkyl, heteroaralkyl, heterocyclylalkyl, alkenyl, or alkynyl, or $R^{18}$ is a heteroatom selected from N, S, and O, wherein the heteroatom has a covalent bond either directly or through a $C_1$-$C_6$ alkyl group to an aryl, heteroaryl or heterocyclyl, or $R^{18}$ and $R^6$ are taken together with the carbons to which they are attached form a 5- or 6-membered ring; wherein each of the above substituents can be substituted with 0, 1, 2, or 3 $R^{13}$; and wherein both B and $R^{18}$ are not hydrogen.

In certain embodiments, the compound of Formula (XV) has a structure of Formula (XVI):

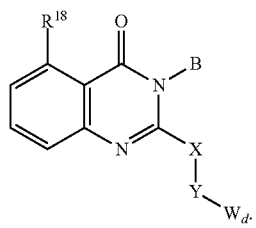

Formula (XVI)

In some embodiments, the compound of Formula (XVI) has a structure of Formula (XVII):

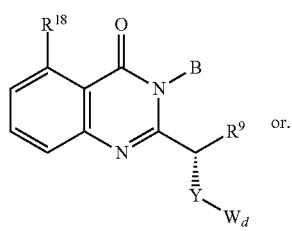

Formula (XVII)

In certain embodiments, the compound of Formula (XV) has a structure of Formula (XVIII):

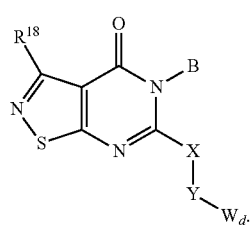

Formula (XVIII)

In some embodiments, the compound of Formula (XVIII) has a structure of Formula (XVIV):

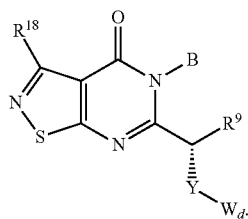

Formula (XVIV)

In certain embodiments, the compound of Formula (XV) has a structure of Formula (XX):

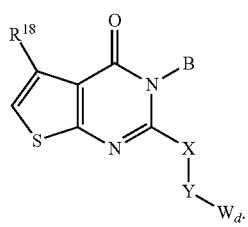

Formula (XX)

In certain embodiments, the compound of Formula (XX) has a structure of Formula (XXI):

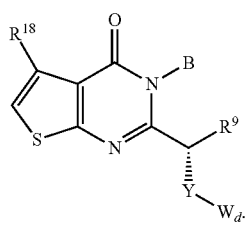

Formula (XXI)

In another aspect, provided herein are compounds of Formula (X) or (XI):

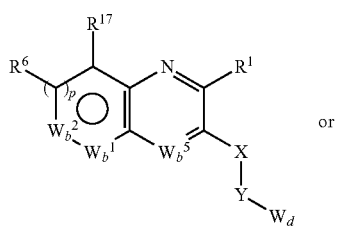

Formula (X)

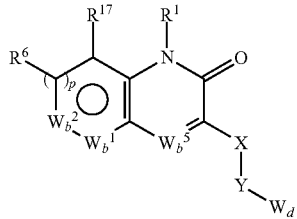

Formula (XI)

or an enantiomer, a mixture of enantiomers, or a mixture of two or more diastereomers thereof, or a pharmaceutically acceptable form thereof, wherein:

$W_b^1$ and $W_b^2$ are each independently $CR^6$, S, O, N or $NR^{14}$, wherein at least one of $W_b^1$ and $W_b^2$ is $CR^6$, N or $NR^{14}$;

each $R^6$ is independently hydrogen, alkyl, alkenyl, alkynyl, cycloalkyl, heterocyclyl, fluoroalkyl, heteroalkyl, alkoxy, amido, amino, acyl, acyloxy, sulfinyl, sulfonyl, sulfoxide, sulfone, sulfonamido, halo, cyano, heteroaryl, aryl, hydroxyl, or nitro;

each $R^{14}$ is independently hydrogen, alkyl, cycloalkyl, heterocyclyl or heteroalkyl;

$R^1$ is -(L)-$R^{1'}$;

L is a bond, —S—, —N($R^{15}$)—, —C($R^{15}$)$_2$—, —C(=O)—, or —O—;

$R^{1'}$ is hydrogen, alkyl, heteroalkyl, alkenyl, alkynyl, cycloalkyl, cycloalkylalkyl, heterocyclyl, heterocyclylalkyl, aryl, arylalkyl, heteroaryl, heteroarylalkyl, alkoxy, heterocyclyloxy, amido, amino, acyl, acyloxy, alkoxycarbonyl, sulfonamido, halo, cyano, hydroxyl, nitro, phosphate, urea, carbonate, substituted nitrogen, or NR'R" wherein R' and R" are taken together with nitrogen to form a cyclic moiety;

p is 0, 1, 2 or 3;

$W_b^5$ is $CR^8$ or N;

$R^8$ is hydrogen, alkyl, alkenyl, alkynyl, cycloalkyl, heteroalkyl, alkoxy, amido, amino, acyl, acyloxy, sulfonamido, halo, cyano, hydroxyl, or nitro;

$R^{17}$ is alkyl, haloalkyl, alkoxy, cycloalkyl, cycloalkylalkyl, aryl, heteroaryl, heterocyclyl, aralkyl, heteroaralkyl, heterocyclylalkyl, alkenyl, or alkynyl, or $R^{17}$ is a heteroatom selected from N, S, and O, wherein the heteroatom has a covalent bond either directly or through a $C_1$-$C_6$ alkyl group to an aryl, heteroaryl or heterocyclyl, or $R^{17}$ and $R^6$ are taken together with the carbons to which they are attached form a 5- or 6-membered ring; wherein each of the above substituents can be substituted with 0, 1, 2, or 3 $R^{13}$;

X is absent or is —(CH($R^{16}$))$_z$;

Y is absent, —O—, —S—, —S(=O)—, —S(=O)$_2$—, —N($R^{16}$)—, —C(=O)—(CH$R^{16}$)$_z$—, —C(=O)—, —N($R^{16}$)—C(=O)—, or —N($R^{16}$)—C(=O)NH—, —N($R^{16}$)C($R^{16}$)$_2$—, —C(=O)—N($R^9$)$_2$, or —C(=O)—N($R^{16}$)—(CH$R^{16}$)$_z$—;

each z is an integer of 1, 2, 3, or 4;

each $R^{16}$ is independently hydrogen, alkyl, cycloalkyl, heterocyclyl, heteroalkyl, aryl, halo or heteroaryl;

$W_d$ is

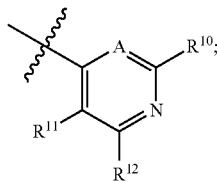

A is N or $CR^{19}$; and $R^{10}$, $R^{11}$, $R^{12}$, $R^{13}$, and $R^{19}$ are independently hydrogen, alkyl, heteroalkyl, alkenyl, alkynyl, cycloalkyl, heterocyclyl, aryl, arylalkyl, heteroaryl, heteroarylalkyl, alkoxy, heterocyclyloxy, amido, amino, acyl, acyloxy, alkoxycarbonyl, sulfonamido, halo, cyano, hydroxyl, nitro, phosphate, urea, carbonate, oxo, or NR'R" wherein R' and R" are taken together with nitrogen to form a cyclic moiety.

In certain embodiments, a compound as provided herein selectively modulates phosphatidyl inositol-3 kinase (PI3 kinase) delta isoform. In certain embodiments, the compound selectively inhibits the delta isoform over the beta isoform. By way of non-limiting example, the ratio of selectivity can be greater than a factor of about 10, greater than a factor of about 50, greater than a factor of about 100, greater than a factor of about 200, greater than a factor of about 400, greater than a factor of about 600, greater than a factor of about 800, greater than a factor of about 1000, greater than a factor of about 1500, greater than a factor of about 2000, greater than a factor of about 5000, greater than a factor of about 10,000, or greater than a factor of about 20,000, where selectivity can be measured by $IC_{50}$, among other means. In certain embodiments, the PI3 kinase delta isoform $IC_{50}$ activity of a compound as provided herein can be less than about 1000 nM, less than about 100 nM, less than about 10 nM, or less than about 1 nM.

In certain embodiments, provided herein is a composition (e.g., a pharmaceutical composition) comprising a compound as described herein and one or more pharmaceutically acceptable excipients. In some embodiments, provided herein is a method of inhibiting a phosphatidyl inositol-3 kinase (PI3 kinase), comprising contacting the PI3 kinase with an effective amount of a compound or pharmaceutical composition as described herein. In certain embodiments, a method is provided for inhibiting a phosphatidyl inositol-3 kinase (PI3 kinase) wherein said PI3 kinase is present in a cell. The inhibition can take place in a subject suffering from a disorder selected from cancer, bone disorder, inflammatory disease, immune disease, nervous system disease (e.g., a neuropsychiatric disorder), metabolic disease, respiratory disease, thrombosis, and cardiac disease. In certain embodiments, a second therapeutic agent is administered to the subject.

In certain embodiments, a method is provided of selectively inhibiting a phosphatidyl inositol-3 kinase (PI3 kinase) delta isoform over PI3 kinase beta isoform wherein the inhibition takes place in a cell. Non-limiting examples of the methods provided herein can comprise contacting PI3 kinase delta isoform with an effective amount of a compound or pharmaceutical composition as provided herein. In an embodiment, such contact can occur in a cell.

In certain embodiments, a method is provided of selectively inhibiting a phosphatidyl inositol-3 kinase (PI3 kinase) delta isoform over PI3 kinase beta isoform wherein the inhibition takes place in a subject suffering from a disorder selected from cancer, bone disorder, inflammatory disease, immune disease, nervous system disease (e.g., a neuropsychiatric disorder), metabolic disease, respiratory disease, thrombosis, and cardiac disease, said method comprising administering an effective amount of a compound or pharmaceutical composition to said subject. In certain embodiments, provided herein is a method of treating a subject suffering from a disorder associated with phosphatidyl inositol-3 kinase (PI3 kinase), said method comprising selectively modulating the phosphatidyl inositol-3 kinase (PI3 kinase) delta isoform over PI3 kinase beta isoform by administering an amount of a compound or pharmaceutical composition to said subject, wherein said amount is sufficient for selective modulation of PI3 kinase delta isoform over PI3 kinase beta isoform.

In some embodiments, provided herein is a method of making a compound as described herein.

In certain embodiments, provided herein is a reaction mixture comprising a compound as described herein.

In certain embodiments, provided herein is a kit comprising a compound as described herein.

In some embodiments, a method is provided for treating a disease or disorder described herein, the method comprising administering a therapeutically effective amount of a compound or pharmaceutical composition described herein to a subject.

In some embodiments, a method is provided for treating a PI3K mediated disorder in a subject, the method comprising administering a therapeutically effective amount of a compound or pharmaceutical composition described herein to a subject.

In some embodiments, provided herein is a use of a compound or a pharmaceutical composition described herein for the treatment of a disease or disorder described herein in a subject.

In some embodiments, provided herein is a use of a compound or a pharmaceutical composition described herein for the treatment of a PI3K mediated disorder in a subject.

In some embodiments, provided herein is a use of a compound or a pharmaceutical composition described herein in the manufacture of a medicament for the treatment of a disease or disorder described herein in a subject.

In certain embodiments, provided herein is use of a compound or a pharmaceutical composition described herein in the manufacture of a medicament for the treatment of a PI3K mediated disorder in a subject.

INCORPORATION BY REFERENCE

All publications, patents, and patent applications mentioned in this specification are herein incorporated by reference to the same extent as if each individual publication, patent, or patent application was specifically and individually indicated to be incorporated by reference. In case of conflict, the present application, including any definitions herein, will control.

DETAILED DESCRIPTION

In one embodiment, provided are heterocyclyl compounds, and pharmaceutically acceptable forms, including, but not limited to, salts, hydrates, solvates, isomers, prodrugs, and isotopically labeled derivatives thereof.

In another embodiment, provided are methods of treating and/or managing various diseases and disorders, which comprises administering to a patient a therapeutically effective amount of a compound provided herein, or a pharmaceutically acceptable form (e.g., salts, hydrates, solvates, isomers, prodrugs, and isotopically labeled derivatives) thereof. Examples of diseases and disorders are described herein.

In another embodiment, provided are methods of preventing various diseases and disorders, which comprises administering to a patient in need of such prevention a prophylactically effective amount of a compound provided herein, or a pharmaceutically acceptable form (e.g., salts, hydrates, solvates, isomers, prodrugs, and isotopically labeled derivatives) thereof. Examples of diseases and disorders are described herein.

In other embodiments, a compound provided herein, or a pharmaceutically acceptable form (e.g., salts, hydrates, solvates, isomers, prodrugs, and isotopically labeled derivatives) thereof, is administered in combination with another drug ("second active agent") or treatment. Second active agents include small molecules and large molecules (e.g., proteins and antibodies), examples of which are provided herein, as well as stem cells. Other methods or therapies that can be used in combination with the administration of compounds provided herein include, but are not limited to, surgery, blood transfusions, immunotherapy, biological therapy, radiation therapy, and other non-drug based therapies presently used to treat, prevent or manage various disorders described herein.

Also provided are pharmaceutical compositions (e.g., single unit dosage forms) that can be used in the methods provided herein. In one embodiment, pharmaceutical compositions comprise a compound provided herein, or a pharmaceutically acceptable form (e.g., salts, hydrates, solvates, isomers, prodrugs, and isotopically labeled derivatives) thereof, and optionally one or more second active agents.

While specific embodiments have been discussed, the specification is illustrative only and not restrictive. Many variations of this disclosure will become apparent to those skilled in the art upon review of this specification.

Unless defined otherwise, all technical and scientific terms used herein have the same meaning as is commonly understood by one of skill in the art to which this specification pertains.

As used in the specification and claims, the singular form "a", "an" and "the" includes plural references unless the context clearly dictates otherwise.

As used herein, "agent" or "biologically active agent" or "second active agent" refers to a biological, pharmaceutical, or chemical compound or other moiety. Non-limiting examples include simple or complex organic or inorganic molecules, a peptide, a protein, an oligonucleotide, an antibody, an antibody derivative, an antibody fragment, a vitamin, a vitamin derivative, a carbohydrate, a toxin, or a chemotherapeutic compound, and metabolites thereof. Various compounds can be synthesized, for example, small molecules and oligomers (e.g., oligopeptides and oligonucleotides), and synthetic organic compounds based on various core structures. In addition, various natural sources can provide compounds for screening, such as plant or animal extracts, and the like. A skilled artisan can readily recognize that there is no limit as to the structural nature of the agents of this disclosure.

The term "agonist" as used herein refers to a compound or agent having the ability to initiate or enhance a biological function of a target protein or polypeptide, such as increasing the activity or expression of the target protein or polypeptide. Accordingly, the term "agonist" is defined in the context of the biological role of the target protein or polypeptide. While some agonists herein specifically interact with (e.g., bind to) the target, compounds and/or agents that initiate or enhance a biological activity of the target protein or polypeptide by interacting with other members of the signal transduction pathway of which the target polypeptide is a member are also specifically included within this definition.

The terms "antagonist" and "inhibitor" are used interchangeably, and they refer to a compound or agent having the ability to inhibit a biological function of a target protein or polypeptide, such as by inhibiting the activity or expression of the target protein or polypeptide. Accordingly, the terms "antagonist" and "inhibitor" are defined in the context of the biological role of the target protein or polypeptide. While some antagonists herein specifically interact with (e.g., bind to) the target, compounds that inhibit a biological activity of the target protein or polypeptide by interacting with other members of the signal transduction pathway of which the target protein or polypeptide are also specifically included within this definition. Non-limiting examples of biological activity inhibited by an antagonist include those associated with the development, growth, or spread of a tumor, or an undesired immune response as manifested in autoimmune disease.

An "anti-cancer agent", "anti-tumor agent" or "chemotherapeutic agent" refers to any agent useful in the treatment of a neoplastic condition. One class of anti-cancer agents comprises chemotherapeutic agents. "Chemotherapy" means the administration of one or more chemotherapeutic drugs and/or other agents to a cancer patient by various methods, including intravenous, oral, intramuscular, intraperitoneal, intravesical, subcutaneous, transdermal, buccal, or inhalation or in the form of a suppository.

The term "cell proliferation" refers to a phenomenon by which the cell number has changed as a result of division. This term also encompasses cell growth by which the cell morphology has changed (e.g., increased in size) consistent with a proliferative signal.

The term "co-administration," "administered in combination with," and their grammatical equivalents, as used herein, encompasses administration of two or more agents to subject so that both agents and/or their metabolites are present in the subject at the same time. Co-administration includes simultaneous administration in separate compositions, administration at different times in separate compositions, or administration in a composition in which both agents are present.

The term "effective amount" or "therapeutically effective amount" refers to that amount of a compound or pharmaceutical composition described herein that is sufficient to effect the intended application including, but not limited to, disease treatment, as illustrated below. The therapeutically effective amount can vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g., reduction of platelet adhesion and/or cell migration. The specific dose will vary depending on, for example, the particular compounds chosen, the dosing regimen to be followed, whether it is administered in combination with other agents, timing of administration, the tissue to which it is administered, and the physical delivery system in which it is carried.

As used herein, the terms "treatment", "treating", "palliating" and "ameliorating" are used interchangeably herein. These terms refer to an approach for obtaining beneficial or desired results including, but not limited to, therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient can still be afflicted with the underlying disorder. For prophylactic benefit, the pharmaceutical compositions can be administered to a patient at risk of developing a particular disease, or to a patient reporting one or more of the physiological symptoms of a disease, even though a diagnosis of this disease may not have been made.

A "therapeutic effect," as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

"Signal transduction" is a process during which stimulatory or inhibitory signals are transmitted into and within a cell to elicit an intracellular response. A "modulator" of a signal transduction pathway refers to a compound which modulates the activity of one or more cellular proteins mapped to the same specific signal transduction pathway. A modulator can augment (agonist) or suppress (antagonist) the activity of a signaling molecule.

The term "selective inhibition" or "selectively inhibit" as applied to a biologically active agent refers to the agent's ability to selectively reduce the target signaling activity as compared to off-target signaling activity, via direct or interact interaction with the target. For example, a compound that selectively inhibits one isoform of PI3K over another isoform of PI3K has an activity of at least 2× against a first isoform relative to the compound's activity against the second isoform (e.g., at least about 3×, 5×, 10×, 20×, 50×, or 100×).

"Radiation therapy" means exposing a patient, using routine methods and compositions known to the practitioner, to radiation emitters such as, but not limited to, alpha-particle emitting radionuclides (e.g., actinium and thorium radionuclides), low linear energy transfer (LET) radiation emitters (i.e., beta emitters), conversion electron emitters (e.g., strontium-89 and samarium-153-EDTMP), or high-energy radiation, including without limitation x-rays, gamma rays, and neutrons.

"Subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or other primates (e.g., cynomolgus monkeys, rhesus monkeys); mammals, including commercially relevant mammals such as cattle, pigs, horses, sheep, goats, cats, and/or dogs; and/or birds, including commercially relevant birds such as chickens, ducks, geese, quail, and/or turkeys.

The term "in vivo" refers to an event that takes place in a subject's body.

The term "in vitro" refers to an event that takes places outside of a subject's body. For example, an in vitro assay encompasses any assay conducted outside of a subject. In vitro assays encompass cell-based assays in which cells, alive or dead, are employed. In vitro assays also encompass a cell-free assay in which no intact cells are employed.

As used herein, "pharmaceutically acceptable esters" include, but are not limited to, alkyl, alkenyl, alkynyl, aryl, aralkyl, and cycloalkyl esters of acidic groups, including, but not limited to, carboxylic acids, phosphoric acids, phosphinic acids, sulfonic acids, sulfinic acids and boronic acids.

As used herein, "pharmaceutically acceptable enol ethers" include, but are not limited to, derivatives of formula —C=C(OR) where R can be selected from alkyl, alkenyl, alkynyl, aryl, aralkyl and cycloalkyl. Pharmaceutically acceptable enol esters include, but are not limited to, derivatives of formula —C=C(OC(O)R) where R can be selected from hydrogen, alkyl, alkenyl, alkynyl, aryl, aralkyl and cycloalkyl.

As used herein, a "pharmaceutically acceptable form" of a disclosed compound includes, but is not limited to, pharmaceutically acceptable salts, hydrates, solvates, isomers, prodrugs, and isotopically labeled derivatives of disclosed compounds. In one embodiment, a "pharmaceutically acceptable form" includes, but is not limited to, pharmaceutically acceptable salts, isomers, prodrugs and isotopically labeled derivatives of disclosed compounds.

In certain embodiments, the pharmaceutically acceptable form is a pharmaceutically acceptable salt. As used herein, the term "pharmaceutically acceptable salt" refers to those salts which are, within the scope of sound medical judgment, suitable for use in contact with the tissues of subjects without undue toxicity, irritation, allergic response and the like, and are commensurate with a reasonable benefit/risk ratio. Pharmaceutically acceptable salts are well known in the art. For example, Berge et al. describes pharmaceutically acceptable salts in detail in *J. Pharmaceutical Sciences* (1977) 66:1-19. Pharmaceutically acceptable salts of the compounds provided herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, besylate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. In some embodiments, organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

Pharmaceutically acceptable salts derived from appropriate bases include alkali metal, alkaline earth metal, ammonium and $N^+(C_{1-4}alkyl)^4$-salts. Representative alkali or alkaline earth metal salts include sodium, lithium, potassium, calcium, magnesium, iron, zinc, copper, manganese, aluminum, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate. Organic bases from which salts can be derived include, for example, primary, secondary, and tertiary amines, substituted amines including naturally occurring substituted amines, cyclic amines, basic ion exchange resins, and the like, such as isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts.

In certain embodiments, the pharmaceutically acceptable form is a "solvate" (e.g., a hydrate). As used herein, the term "solvate" refers to compounds that further include a stoichiometric or non-stoichiometric amount of solvent bound by non-covalent intermolecular forces. The solvate can be of a disclosed compound or a pharmaceutically acceptable salt thereof. Where the solvent is water, the solvate is a "hydrate". Pharmaceutically acceptable solvates and hydrates are complexes that, for example, can include 1 to about 100, or 1 to about 10, or one to about 2, about 3 or about 4, solvent or water molecules. It will be understood that the term "compound" as used herein encompasses the compound and solvates of the compound, as well as mixtures thereof.

In certain embodiments, the pharmaceutically acceptable form is a prodrug. As used herein, the term "prodrug" refers to compounds that are transformed in vivo to yield a disclosed compound or a pharmaceutically acceptable form of the compound. A prodrug can be inactive when administered to a subject, but is converted in vivo to an active compound, for example, by hydrolysis (e.g., hydrolysis in blood). In certain cases, a prodrug has improved physical and/or delivery properties over the parent compound. Prodrugs are typically designed to enhance pharmaceutically and/or pharmacokinetically based properties associated with the parent compound. The prodrug compound often offers advantages of solubility, tissue compatibility or delayed release in a mammalian organism (see, e.g., Bundgard, H., *Design of Prodrugs* (1985), pp. 7-9, 21-24 (Elsevier, Amsterdam). A discussion of prodrugs is provided in Higuchi, T., et al., "Pro-drugs as Novel Delivery Systems," *A.C.S. Symposium Series*, Vol. 14, and in *Bioreversible Carriers in Drug Design*, ed. Edward B. Roche, American Pharmaceutical Association and Pergamon Press, 1987, both of which are incorporated in full by reference herein. Exemplary advantages of a prodrug can include, but are not limited to, its physical properties, such as enhanced water solubility for parenteral administration at physiological pH compared to the parent compound, or it enhances absorption from the digestive tract, or it can enhance drug stability for long-term storage.

The term "prodrug" is also meant to include any covalently bonded carriers, which release the active compound in vivo when such prodrug is administered to a subject. Prodrugs of an active compound, as described herein, can be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like. Other examples of prodrugs include compounds that comprise —NO, —$NO_2$, —ONO, or —$ONO_2$ moieties. Prodrugs can typically be prepared using well-known methods, such as those described in *Burger's Medicinal Chemistry and Drug Discovery*, 172-178, 949-982 (Manfred E. Wolff ed., 5th ed., 1995), and *Design of Prodrugs* (H. Bundgaard ed., Elsevier, New York, 1985).

For example, if a disclosed compound or a pharmaceutically acceptable form of the compound contains a carboxylic acid functional group, a prodrug can comprise a pharmaceutically acceptable ester formed by the replacement of the hydrogen atom of the acid group with a group such as ($C_1$-$C_8$)alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholino($C_2$-$C_3$)alkyl.

Similarly, if a disclosed compound or a pharmaceutically acceptable form of the compound contains an alcohol functional group, a prodrug can be formed by the replacement of the hydrogen atom of the alcohol group with a group such as ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl($C_1$-$C_6$)alkoxycarbonyloxymethyl, N—($C_1$-$C_6$)alkoxycarbonylaminomethyl, succinoyl, ($C_1$-$C_6$)alkanoyl, α-amino($C_1$-$C_4$)alkanoyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1$-$C_6)alkyl)_2$ or glycosyl (the radical resulting from the removal of a hydroxyl group of the hemiacetal form of a carbohydrate).

If a disclosed compound or a pharmaceutically acceptable form of the compound incorporates an amine functional group, a prodrug can be formed by the replacement of a hydrogen atom in the amine group with a group such as R-carbonyl, RO-carbonyl, NRR'-carbonyl where R and R' are each independently ($C_1$-$C_{10}$)alkyl, ($C_3$-$C_7$)cycloalkyl, benzyl, a natural α-aminoacyl or natural α-aminoacyl-natural α-aminoacyl, —$C(OH)C(O)OY^1$ wherein $Y^1$ is H, ($C_1$-$C_6$) alkyl or benzyl, —$C(OY^2)Y^3$ wherein $Y^2$ is ($C_1$-$C_4$)alkyl and $Y^3$ is ($C_1$-$C_6$)alkyl, carboxy($C_1$-$C_6$)alkyl, amino($C_1$-$C_4$)alkyl or mono-N— or di-N,N—($C_1$-$C_6$)alkylaminoalkyl, —$C(Y^4)Y^5$ wherein $Y^4$ is H or methyl and $Y^5$ is mono-N— or di-N, N—($C_1$-$C_6$)alkylamino, morpholino, piperidin-1-yl or pyrrolidin-1-yl.

In certain embodiments, the pharmaceutically acceptable form is an isomer. "Isomers" are different compounds that have the same molecular formula. "Stereoisomers" are isomers that differ only in the way the atoms are arranged in space. As used herein, the term "isomer" includes any and all geometric isomers and stereoisomers. For example, "isomers" include geometric double bond cis- and trans-isomers, also termed E- and Z-isomers; R- and S-enantiomers; diastereomers, (d)-isomers and (l)-isomers, racemic mixtures thereof; and other mixtures thereof, as falling within the scope of this disclosure.

Geometric isomers can be represented by the symbol ===== which denotes a bond that can be a single, double or triple bond as described herein. Provided herein are various geometric isomers and mixtures thereof resulting from the arrangement of substituents around a carbon-carbon double bond or arrangement of substituents around a carbocyclic ring. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers.

Substituents around a carbon-carbon double bond alternatively can be referred to as "cis" or "trans," where "cis" represents substituents on the same side of the double bond and "trans" represents substituents on opposite sides of the double bond. The arrangement of substituents around a carbocyclic ring can also be designated as "cis" or "trans." The term "cis" represents substituents on the same side of the plane of the ring, and the term "trans" represents substituents on opposite sides of the plane of the ring. Mixtures of compounds wherein the substituents are disposed on both the same and opposite sides of plane of the ring are designated "cis/trans."

"Enantiomers" are a pair of stereoisomers that are non-superimposable mirror images of each other. A mixture of a pair of enantiomers in any proportion can be known as a "racemic" mixture. The term "(±)" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is an enantiomer, the stereochemistry at each chiral carbon can be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and can thus give rise to enantiomers, diastereomers, and other stereoisomeric forms that can be defined, in terms of absolute stereochemistry at each asymmetric atom, as (R)— or (S)—. The present chemical entities, pharmaceutical compositions and methods are meant to include all such possible isomers, including racemic mixtures, optically substantially pure forms and intermediate mixtures. Optically active (R)- and (S)-isomers can be prepared, for example, using chiral synthons or chiral reagents, or resolved using conventional techniques.

The "enantiomeric excess" or "% enantiomeric excess" of a composition can be calculated using the equation shown below. In the example shown below, a composition contains 90% of one enantiomer, e.g., the S enantiomer, and 10% of the other enantiomer, e.g., the R enantiomer.

$$ee = (90-10)/100 = 80\%.$$

Thus, a composition containing 90% of one enantiomer and 10% of the other enantiomer is said to have an enantiomeric excess of 80%. Some compositions described herein contain an enantiomeric excess of at least about 50%, about 75%, about 90%, about 95%, or about 99% of the S enantiomer. In other words, the compositions contain an enantiomeric excess of the S enantiomer over the R enantiomer. In other embodiments, some compositions described herein contain an enantiomeric excess of at least about 50%, about 75%, about 90%, about 95%, or about 99% of the R enantiomer. In other words, the compositions contain an enantiomeric excess of the R enantiomer over the S enantiomer.

For instance, an isomer/enantiomer can, in some embodiments, be provided substantially free of the corresponding enantiomer, and can also be referred to as "optically enriched," "enantiomerically enriched," "enantiomerically pure" and "non-racemic," as used interchangeably herein. These terms refer to compositions in which the percent by weight of one enantiomer is greater than the amount of that one enantiomer in a control mixture of the racemic composition (e.g., greater than 1:1 by weight). For example, an enantiomerically enriched preparation of the S enantiomer, means a preparation of the compound having greater than about 50% by weight of the S enantiomer relative to the R enantiomer, such as at least about 75% by weight, further such as at least about 80% by weight. In some embodiments, the enrichment can be much greater than about 80% by weight, providing a "substantially enantiomerically enriched," "substantially enantiomerically pure" or a "substantially non-racemic" preparation, which refers to preparations of compositions which have at least about 85% by weight of one enantiomer relative to other enantiomer, such as at least about 90% by weight, and further such as at least about 95% by weight. In certain embodiments, the compound provided herein is made up of at least about 90% by weight of one enantiomer. In other embodiments, the compound is made up of at least about 95%, about 98%, or about 99% by weight of one enantiomer.

In some embodiments, the compound is a racemic mixture of (S)- and (R)-isomers. In other embodiments, provided herein is a mixture of compounds wherein individual compounds of the mixture exist predominately in an (S)- or (R)-isomeric configuration. For example, the compound mixture has an (S)-enantiomeric excess of greater than about 55%, about 60%, about 65%, about 70%, about 75%, about 80%, about 85%, about 90%, about 95%, about 96%, about 97%, about 98%, about 99%, about 99.5%, or more. In other embodiments, the compound mixture has an (S)-enantiomeric excess of greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5%, or more.

In other embodiments, the compound mixture has an (R)-enantiomeric purity of greater than about 55%, about 60%, about 65%, about 70%, about 75%, about 80%, about 85%, about 90%, about 95%, about 96%, about 97%, about 98%, about 99%, about 99.5% or more. In some other embodiments, the compound mixture has an (R)-enantiomeric excess of greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5% or more.

In other embodiments, the compound mixture contains identical chemical entities except for their stereochemical orientations, namely (S)- or (R)-isomers. For example, if a compound provided herein has —CH(R)— unit, and R is not hydrogen, then the —CH(R)— is in an (S)- or (R)-stereochemical orientation for each of the identical chemical entities. In some embodiments, the mixture of identical chemical entities is a racemic mixture of (S)- and (R)-isomers. In another embodiment, the mixture of the identical chemical entities (except for their stereochemical orientations), contain predominately (S)-isomers or predominately (R)-isomers. For example, the (S)-isomers in the mixture of identical chemical entities are present at about 55%, about 60%, about 65%, about 70%, about 75%, about 80%, about 85%, about 90%, about 95%, about 96%, about 97%, about 98%, about 99%, about 99.5%, or more, relative to the (R)-isomers. In some embodiments, the (S)-isomers in the mixture of identical chemical entities are present at an (S)-enantiomeric excess of greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5% or more.

In another embodiment, the (R)-isomers in the mixture of identical chemical entities (except for their stereochemical orientations), are present at about 55%, about 60%, about 65%, about 70%, about 75%, about 80%, about 85%, about 90%, about 95%, about 96%, about 97%, about 98%, about 99%, about 99.5%, or more, relative to the (S)-isomers. In some embodiments, the (R)-isomers in the mixture of identical chemical entities (except for their stereochemical orientations) are present at a (R)-enantiomeric excess greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5%, or more.

Enantiomers can be isolated from racemic mixtures by any method known to those skilled in the art, including chiral high pressure liquid chromatography (HPLC), the formation and crystallization of chiral salts, or prepared by asymmetric syntheses. See, for example, *Enantiomers, Racemates and Resolutions* (Jacques, Ed., Wiley Interscience, New York, 1981); Wilen et al., *Tetrahedron* 33:2725 (1977); *Stereochemistry of Carbon Compounds* (E. L. Eliel, Ed., McGraw-Hill, NY, 1962); and *Tables of Resolving Agents and Optical Resolutions* p. 268 (E. L. Eliel, Ed., Univ. of Notre Dame Press, Notre Dame, Ind. 1972).

In certain embodiments, the pharmaceutically acceptable form is a tautomer. As used herein, the term "tautomer" is a type of isomer that includes two or more interconvertable compounds resulting from at least one formal migration of a hydrogen atom and at least one change in valency (e.g., a single bond to a double bond, a triple bond to a single bond, or vice versa). "Tautomerization" includes prototropic or proton-shift tautomerization, which is considered a subset of acid-base chemistry. "Prototropic tautomerization" or "proton-shift tautomerization" involves the migration of a proton accompanied by changes in bond order. The exact ratio of the tautomers depends on several factors, including temperature, solvent, and pH. Where tautomerization is possible (e.g., in solution), a chemical equilibrium of tautomers can be reached. Tautomerizations (i.e., the reaction providing a tautomeric pair) can be catalyzed by acid or base, or can occur without the action or presence of an external agent. Exemplary tautomerizations include, but are not limited to, keto-to-enol; amide-to-imide; lactam-to-lactim; enamine-to-imine; and enamine-to-(a different) enamine tautomerizations. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$— or $^{14}C$-enriched carbon are within the scope of this disclosure.

The disclosure also embraces isotopically labeled compounds which are identical to those recited herein, except that one or more atoms are replaced by an atom having an atomic mass or mass number different from the atomic mass or mass number usually found in nature. Examples of isotopes that can be incorporated into disclosed compounds include isotopes of hydrogen, carbon, nitrogen, oxygen, phosphorus, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$ and $^{36}Cl$, respectively. Certain isotopically-labeled disclosed compounds (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes can allow for ease of preparation and detectability. Further, substitution with heavier isotopes such as deuterium (i.e., $^{2}H$) can afford certain therapeutic advantages resulting from greater metabolic stability (e.g., increased in vivo half-life or reduced dosage requirements). Isotopically labeled disclosed compounds can generally be prepared by substituting an isotopically labeled reagent for a non-isotopically labeled reagent. In some embodiments, provided herein are compounds that can also contain unnatural proportions of atomic isotopes at one or more of atoms that constitute such compounds. All isotopic variations of the compounds as provided herein, whether radioactive or not, are encompassed within the scope of the present disclosure.

"Pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions as provided herein is contemplated. Supplementary active ingredients can also be incorporated into the pharmaceutical compositions.

Definitions of specific functional groups and chemical terms are described in more detail below. The chemical elements are identified in accordance with the Periodic Table of the Elements, CAS version, Handbook of Chemistry and Physics, 75th ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5th ed., John Wiley & Sons, Inc., New York, 2001; Larock, *Comprehensive Organic Transformations*, VCH Publishers, Inc., New York, 1989; and Carruthers, Some *Modern Methods of Organic Synthesis*, 3rd ed., Cambridge University Press, Cambridge, 1987.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

"Alkyl" refers to a straight or branched hydrocarbon chain radical consisting solely of carbon and hydrogen atoms, containing no unsaturation, having from one to ten carbon atoms (e.g., $C_1$-$C_{10}$ alkyl). Whenever it appears herein, a numerical range such as "1 to 10" refers to each integer in the given range; e.g., "1 to 10 carbon atoms" means that the alkyl group can consist of 1 carbon atom, 2 carbon atoms, 3 carbon atoms, etc., up to and including 10 carbon atoms, although the present definition also covers the occurrence of the term "alkyl" where no numerical range is designated. In some embodiments, it is a $C_1$-$C_6$ alkyl group. In some embodiments, alkyl groups have 1 to 10, 1 to 6, or 1 to 3 carbon atoms. Representative saturated straight chain alkyls include, but are not limited to, -methyl, -ethyl, -n-propyl, -n-butyl, -n-pentyl, and -n-hexyl; while saturated branched alkyls include, but are not limited to, -isopropyl, -sec-butyl, -isobutyl, -tert-butyl, -isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, and the like. The alkyl is attached to the parent molecule by a single bond. Unless stated otherwise in the specification, an alkyl group is optionally substituted by one or more of substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$—, —$OR^a$, —$SR^a$, —OC(O)—$R^a$, —N($R^a$)$_2$, —C(O)$R^a$, —C(O)O$R^a$, —C(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, —N($R^a$)C(N$R^a$)N($R^a$)$_2$, —N($R^a$)S(O)$_t$$R^a$ (where t is 1 or 2), —S(O)$_t$O$R^a$ (where t is 1 or 2), —S(O)$_t$N($R^a$)$_2$ (where t is 1 or 2), or —O—P(=O)(O$R^a$)$_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

"Perhaloalkyl" refers to an alkyl group in which all of the hydrogen atoms have been replaced with a halogen selected from fluoro, chloro, bromo, and iodo. In some embodiments, all of the hydrogen atoms are each replaced with fluoro. In some embodiments, all of the hydrogen atoms are each replaced with chloro. Examples of perhaloalkyl groups include —$CF_3$, —$CF_2CF_3$, —$CF_2CF_2CF_3$, —$CCl_3$, —$CFCl_2$, —$CF_2Cl$ and the like.

"Alkyl-cycloalkyl" refers to an -(alkyl)cycloalkyl radical where alkyl and cycloalkyl are as provided herein and which are optionally substituted by one or more of the substituents described as suitable substituents for alkyl and cycloalkyl respectively. The "alkyl-cycloalkyl" is bonded to the parent molecular structure through the alkyl group. The terms "alkenyl-cycloalkyl" and "alkynyl-cycloalkyl" mirror the above description of "alkyl-cycloalkyl" wherein the term "alkyl" is replaced with "alkenyl" or "alkynyl" respectively, and "alkenyl" or "alkynyl" are as described herein.

"Alkylaryl" refers to an -(alkyl)aryl radical where aryl and alkyl are as provided herein and which are optionally substituted by one or more of the substituents described as suitable substituents for aryl and alkyl respectively. The "alkylaryl" is bonded to the parent molecular structure through the alkyl group. The terms "-(alkenyl)aryl" and "-(alkynyl)aryl" mirror the above description of "-(alkyl)aryl" wherein the term "alkyl" is replaced with "alkenyl" or "alkynyl" respectively, and "alkenyl" or "alkynyl" are as described herein.

"Alkyl-heteroaryl" refers to an -(alkyl)heteroaryl radical where heteroaryl and alkyl are as provided herein and which are optionally substituted by one or more of the substituents described as suitable substituents for heteroaryl and alkyl respectively. The "alkyl-heteroaryl" is bonded to the parent molecular structure through the alkyl group. The terms "-(alkenyl)heteroaryl" and "-(alkynyl)heteroaryl" mirror the above description of "-(alkyl)heteroaryl" wherein the term "alkyl" is replaced with "alkenyl" or "alkynyl" respectively, and "alkenyl" or "alkynyl" are as described herein.

"Alkyl-heterocyclyl" refers to an -(alkyl)heterocycyl radical where alkyl and heterocyclyl are as provided herein and which are optionally substituted by one or more of the substituents described as suitable substituents for heterocyclyl and alkyl respectively. The "alkyl-heterocyclyl" is bonded to the parent molecular structure through the alkyl group. The terms "-(alkenyl)heterocyclyl" and "-(alkynyl)heterocyclyl" mirror the above description of "-(alkyl)heterocyclyl" wherein the term "alkyl" is replaced with "alkenyl" or "alkynyl" respectively, and "alkenyl" or "alkynyl" are as described herein.

"Alkenyl" refers to a straight or branched hydrocarbon chain radical group consisting solely of carbon and hydrogen atoms, containing at least one double bond, and having from two to ten carbon atoms (i.e., $C_2$-$C_{10}$ alkenyl). Whenever it appears herein, a numerical range such as "2 to 10" refers to each integer in the given range; e.g., "2 to 10 carbon atoms" means that the alkenyl group can consist of 2 carbon atoms, 3 carbon atoms, etc., up to and including 10 carbon atoms. In certain embodiments, an alkenyl comprises two to eight carbon atoms. In other embodiments, an alkenyl comprises two to five carbon atoms (e.g., $C_2$-$C_5$ alkenyl). The alkenyl is attached to the parent molecular structure by a single bond, for example, ethenyl (i.e., vinyl), prop-1-enyl (i.e., allyl), but-1-enyl, pent-1-enyl, penta-1,4-dienyl, and the like. The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$) and the like. Examples of $C_{2-6}$ alkenyl groups include the aforementioned $C_{2-4}$ alkenyl groups as well as pentenyl ($C_5$), pentadienyl ($C_5$), hexenyl ($C_6$) and the like. Additional examples of alkenyl include heptenyl ($C_7$), octenyl ($C_8$), octatrienyl ($C_8$) and the like. Unless stated otherwise in the specification, an alkenyl group is optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfonyl, sulfonyl, sulfonamidyl, sulfoxyl, sulfonate, urea, —Si($R^a$)$_3$—, —O$R^a$, —S$R^a$, —OC(O)—$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, N($R^a$)C(N$R^a$)N($R^a$)$_2$, —N($R^a$)S(O)$_t$$R^a$ (where t is 1 or 2), —S(O)$_t$O$R^a$ (where t is 1 or 2), —S(O)N($R^a$)$_2$ (where t is 1 or 2), or —O—P(=O)(O$R^a$)$_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

"Alkynyl" refers to a straight or branched hydrocarbon chain radical group consisting solely of carbon and hydrogen atoms, containing at least one triple bond, having from two to ten carbon atoms (i.e., $C_2$-$C_{10}$ alkynyl). Whenever it appears herein, a numerical range such as "2 to 10" refers to each integer in the given range; e.g., "2 to 10 carbon atoms" means that the alkynyl group can consist of 2 carbon atoms, 3 carbon atoms, etc., up to and including 10 carbon atoms. In certain embodiments, an alkynyl comprises two to eight carbon atoms. In other embodiments, an alkynyl has two to five carbon atoms (e.g., $C_2$-$C_5$ alkynyl). The alkynyl is attached to the parent molecular structure by a single bond, for example, ethynyl, propynyl, butynyl, pentynyl, hexynyl, and the like. Unless stated otherwise in the specification, an alkynyl group is optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfonyl, sulfonyl, sulfonamidyl, sulfoxyl, sulfonate, urea, —Si($R^a$)$_3$—, —O$R^a$, —S$R^a$, —OC(O)—$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, N($R^a$)C(N$R^a$)N($R^a$)$_2$, —N($R^a$)S(O)$_t$$R^a$ (where t is 1 or 2), —S(O)$_t$O$R^a$ (where t is 1 or 2), —S(O)N($R^a$)$_2$ (where t is 1 or 2), or —O—P(=O)(O$R^a$)$_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

The term "alkoxy" refers to the group —O-alkyl, including from 1 to 10 carbon atoms of a straight, branched, cyclic configuration and combinations thereof, attached to the parent molecular structure through an oxygen. Examples include methoxy, ethoxy, propoxy, isopropoxy, cyclopropyloxy, cyclohexyloxy and the like. "Lower alkoxy" refers to alkoxy groups containing one to six carbons. In some embodiments, $C_1$-$C_4$ alkoxy is an alkoxy group which encompasses both straight and branched chain alkyls of from 1 to 4 carbon atoms. Unless stated otherwise in the specification, an alkoxy group is optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfonyl, sulfonyl, sulfonamidyl, sulfoxyl, sulfonate, urea, —Si($R^a$)$_3$—, —O$R^a$, —S$R^a$, —OC(O)—$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, N($R^a$)C(N$R^a$)N($R^a$)$_2$, —N($R^a$)S(O)$_t$$R^a$ (where t is 1 or 2), —S(O)$_t$O$R^a$ (where t is 1 or 2), —S(O)$_t$N($R^a$)$_2$ (where t is 1 or 2), or —O—P(=O)(O$R^a$)$_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein. The terms "alkenoxy" and "alkynoxy" mirror the above description of "alkoxy" wherein the prefix "alk" is replaced with "alken" or "alkyn" respectively, and the parent "alkenyl" or "alkynyl" terms are as described herein.

The term "alkoxycarbonyl" refers to a group of the formula (alkoxy)(C=O)— attached to the parent molecular structure through the carbonyl carbon having from 1 to 10 carbon atoms. Thus a $C_1$-$C_6$ alkoxycarbonyl group is an alkoxy group having from 1 to 6 carbon atoms attached through its oxygen to a carbonyl linker. The $C_1$-$C_6$ designation does not include the carbonyl carbon in the atom count. "Lower alkoxycarbonyl" refers to an alkoxycarbonyl group wherein the alkyl portion of the alkoxy group is a lower alkyl group. In some embodiments, $C_1$-$C_4$ alkoxy is an alkoxy group which encompasses both straight and branched chain alkoxy groups of from 1 to 4 carbon atoms. Unless stated otherwise in the specification, an alkoxycarbonyl group is optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfonyl, sulfonyl, sulfonamidyl, sulfoxyl, sulfonate, urea, —Si($R^a$)$_3$—, —O$R^a$, —S$R^a$, —OC(O)—$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, N($R^a$)C(N$R^a$)N($R^a$)$_2$, —N($R^a$)S(O)$_t$$R^a$ (where t is 1 or 2), —S(O)$_t$O$R^a$ (where t is 1 or 2), —S(O)$_t$N($R^a$)$_2$ (where t is 1 or 2), or —O—P(=O)(O$R^a$)$_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein. The terms "alkenoxycarbonyl" and "alkynoxycarbonyl" mirror the above description of "alkoxycarbonyl" wherein the prefix "alk" is replaced with "alken" or "alkyn" respectively, and the parent "alkenyl" or "alkynyl" terms are as described herein.

"Acyl" refers to R—C(O)— groups such as, but not limited to, (alkyl)-C(O)—, (alkenyl)-C(O)—, (alkynyl)-C(O)—, (aryl)-C(O)—, (cycloalkyl)-C(O)—, (heteroaryl)-C(O)—, (heteroalkyl)-C(O)—, and (heterocycloalkyl)-C(O)—, wherein the group is attached to the parent molecular structure through the carbonyl functionality. In some embodiments, it is a $C_1$-$C_{10}$ acyl radical which refers to the total number of chain or ring atoms of the, for example, alkyl, alkenyl, alkynyl, aryl, cyclohexyl, heteroaryl or heterocycloalkyl portion plus the carbonyl carbon of acyl. For example, a $C_4$-acyl has three other ring or chain atoms plus carbonyl. If the R radical is heteroaryl or heterocycloalkyl, the hetero ring or chain atoms contribute to the total number of chain or ring atoms. Unless stated otherwise in the specification, the "R" of an acyloxy group can be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$—, —$OR^a$, —$SR^a$, —OC(O)—$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, N($R^a$)C(N$R^a$)N($R^a$)$_2$, —N($R^a$)S(O)$_t$ $R^a$ (where t is 1 or 2), —S(O)$_t$O$R^a$ (where t is 1 or 2), —S(O)$_t$N($R^a$)$_2$ (where t is 1 or 2), or —O—P(=O)(O$R^a$)$_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

"Acyloxy" refers to a R(C=O)O— radical wherein "R" can be alkyl, alkenyl, alkynyl, heteroalkyl, heteroalkenyl, heteroalkynyl, aryl, cyclohexyl, heteroaryl or heterocycloalkyl, which are as described herein. The acyloxy group is attached to the parent molecular structure through the oxygen functionality. In some embodiments, an acyloxy group is a $C_1$-$C_4$ acyloxy radical which refers to the total number of chain or ring atoms of the alkyl, alkenyl, alkynyl, aryl, cyclohexyl, heteroaryl or heterocycloalkyl portion of the acyloxy group plus the carbonyl carbon of acyl, i.e., a $C_4$-acyloxy has three other ring or chain atoms plus carbonyl. If the R radical is heteroaryl or heterocycloalkyl, the hetero ring or chain atoms contribute to the total number of chain or ring atoms. Unless stated otherwise in the specification, the "R" of an acyloxy group is optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$—, —$OR^a$, —$SR^a$, —OC(O)—$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, N($R^a$)C(N$R^a$)N($R^a$)$_2$, —N($R^a$)S(O)$_t$$R^a$ (where t is 1 or 2), —S(O)$_t$O$R^a$ (where t is 1 or 2), —S(O)$_t$N($R^a$)$_2$ (where t is 1 or 2), or —O—P(=O)(O$R^a$)$_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl and each of these moieties can be optionally substituted as defined herein.

"Amino" or "amine" refers to a —N($R^b$)$_2$, —N($R^b$)$R^b$—, or —$R^b$N($R^b$)$R^b$— radical group, where each $R^b$ is independently selected from hydrogen, alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein. When a —N($R^b$)$_2$ group has two $R^b$ other than hydrogen, they can be combined with the nitrogen atom to form a 3-, 4-, 5-, 6-, or 7-membered ring. For example, —N($R^b$)$_2$ is meant to include, but not be limited to, 1-pyrrolidinyl and 4-morpholinyl. Unless stated otherwise in the specification, an amino group is optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$—, —$OR^a$, —$SR^a$, —OC(O)—$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, N($R^a$)C(N$R^a$)N($R^a$)$_2$, —N($R^a$)S(O)$_t$ $R^a$ (where t is 1 or 2), —S(O)$_t$O$R^a$ (where t is 1 or 2), —S(O)$_t$N($R^a$)$_2$ (where t is 1 or 2), or —O—P(=O)(O$R^a$)$_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

The terms "amine" and "amino" also refer to N-oxides of the groups —N$^+$(H)($R^a$)O$^-$, and —N$^+$($R^a$)($R^a$)O—, $R^a$ as described above, where the N-oxide is bonded to the parent molecular structure through the N atom. N-oxides can be prepared by treatment of the corresponding amino group with, for example, hydrogen peroxide or m-chloroperoxybenzoic acid. The person skilled in the art is familiar with reaction conditions for carrying out the N-oxidation.

"Amide" or "amido" refers to a chemical moiety with formula —C(O)N($R^b$)$_2$ or —N$R^b$C(O)$R^b$, where $R^b$ is independently selected from hydrogen, alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein. In some embodiments, this radical is a $C_1$-$C_4$ amido or amide radical, which includes the amide carbonyl in the total number of carbons in the radical. When a —C(O)N($R^b$)$_2$ has two $R^b$ other than hydrogen, they can be combined with the nitrogen atom to form a 3-, 4-, 5-, 6-, or 7-membered ring. For example, N($R^b$)$_2$ portion of a —C(O)N($R^b$)$_2$ radical is meant to include, but not be limited to, 1-pyrrolidinyl and 4-morpholinyl. Unless stated otherwise in the specification, an amido $R^b$ group is optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si$(R^a)_3$—, —OR$^a$, —SR$^a$, —OC(O)—R$^a$, —N$(R^a)_2$, —C(O)R$^a$, —C(O)OR$^a$, —OC(O)N$(R^a)_2$, —C(O)N$(R^a)_2$, —N$(R^a)$C(O)OR$^a$, —N$(R^a)$C(O)R$^a$, —N$(R^a)$C(O)N$(R^a)_2$, N$(R^a)$C(NR$^a$)N$(R^a)_2$, —N$(R^a)$S(O)$_t$R$^a$ (where t is 1 or 2), —S(O)$_t$OR$^a$ (where t is 1 or 2), —S(O)$_t$N$(R^a)_2$ (where t is 1 or 2), or —O—P(=O)(OR$^a$)$_2$ where each R$^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

The term "amide" or "amido" is inclusive of an amino acid or a peptide molecule. Any amine, hydroxy, or carboxyl side chain on the compounds described herein can be transformed into an amide group. The procedures and specific groups to make such amides are known to those of skill in the art and can readily be found in reference sources such as Greene and Wuts, *Protective Groups in Organic Synthesis*, 3rd Ed., John Wiley & Sons, New York, N.Y., 1999, which is incorporated herein by reference in its entirety.

"Amidino" refers to both the —C(=NR$^b$)N(R$^b$)$_2$ and —N(R$^b$)—C(=NR$^b$)— radicals, where each R$^b$ is independently selected from hydrogen, alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein.

"Aromatic" or "aryl" refers to a radical with six to ten ring atoms (e.g., $C_6$-$C_{10}$ aromatic or $C_6$-$C_{10}$ aryl) which has at least one ring having a conjugated pi electron system which is carbocyclic (e.g., phenyl, fluorenyl, and naphthyl). For example, bivalent radicals formed from substituted benzene derivatives and having the free valences at ring atoms are named as substituted phenylene radicals. In other embodiments, bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Whenever it appears herein, a numerical range such as "6 to 10 aryl" refers to each integer in the given range; e.g., "6 to 10 ring atoms" means that the aryl group can consist of 6 ring atoms, 7 ring atoms, etc., up to and including 10 ring atoms. The term includes monocyclic or fused-ring polycyclic (i.e., rings which share adjacent pairs of ring atoms) groups. Unless stated otherwise in the specification, an aryl moiety can be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfonyl, sulfonyl, sulfonamidyl, sulfoxyl, sulfonate, urea, —Si$(R^a)_3$—, —OR$^a$, —SR$^a$, —OC(O)—R$^a$, —N$(R^a)_2$, —C(O)R$^a$, —C(O)OR$^a$, —OC(O)N$(R^a)_2$, —C(O)N$(R^a)_2$, —N$(R^a)$C(O)OR$^a$, —N$(R^a)$C(O)R$^a$, —N$(R^a)$C(O)N$(R^a)_2$, N$(R^a)$C(NR$^a$)N$(R^a)_2$, —N$(R^a)$S(O)$_t$R$^a$ (where t is 1 or 2), —S(O)$_t$OR$^a$ (where t is 1 or 2), —S(O)$_t$N$(R^a)_2$ (where t is 1 or 2), or —O—P(=O)(OR$^a$)$_2$ where each R$^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

"Aralkyl" or "arylalkyl" refers to an (aryl)alkyl-radical where aryl and alkyl are as provided herein and which are optionally substituted by one or more of the substituents described as suitable substituents for aryl and alkyl respectively. The "aralkyl/arylalkyl" is bonded to the parent molecular structure through the alkyl group. The terms "aralkenyl/arylalkenyl" and "aralkynyl/arylalkynyl" mirror the above description of "aralkyl/arylalkyl" wherein the "alkyl" is replaced with "alkenyl" or "alkynyl" respectively, and the "alkenyl" or "alkynyl" terms are as described herein.

"Azide" refers to a —N$_3$ radical.

"Carbamate" refers to any of the following radicals: —O—(C=O)—N(R$^b$)—, —O—(C=O)—N(R$^b$)$_2$, —N(R$^b$)—(C=O)—O—, and —N(R$^b$)—(C=O)—OR$^b$, wherein each R$^b$ is independently selected from alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein.

"Carbonate" refers to a —O—(C=O)—O— radical.

"Carbonyl" refers to a —(C=O)— radical.

"Carboxaldehyde" refers to a —(C=O)H radical.

"Carboxyl" refers to a —(C=O)OH radical.

"Cyano" refers to a —CN radical.

"Cycloalkyl" and "carbocyclyl" each refer to a monocyclic or polycyclic radical that contains only carbon and hydrogen, and can be saturated or partially unsaturated. Partially unsaturated cycloalkyl groups can be termed "cycloalkenyl" if the carbocycle contains at least one double bond, or "cycloalkynyl" if the carbocycle contains at least one triple bond. Cycloalkyl groups include groups having from 3 to 10 ring atoms (i.e., $C_3$-$C_{10}$ cycloalkyl). Whenever it appears herein, a numerical range such as "3 to 10" refers to each integer in the given range; e.g., "3 to 10 carbon atoms" means that the cycloalkyl group can consist of 3 carbon atoms, 4 carbon atoms, 5 carbon atoms, etc., up to and including 10 carbon atoms. The term "cycloalkyl" also includes bridged and spiro-fused cyclic structures containing no heteroatoms. The term also includes monocyclic or fused-ring polycyclic (i.e., rings which share adjacent pairs of ring atoms) groups. In some embodiments, it is a $C_3$-$C_8$ cycloalkyl radical. In some embodiments, it is a $C_3$-$C_5$ cycloalkyl radical. Illustrative examples of cycloalkyl groups include, but are not limited to the following moieties: $C_{3-6}$ carbocyclyl groups include, without limitation, cyclopropyl ($C_3$), cyclobutyl ($C_4$), cyclopentyl ($C_5$), cyclopentenyl ($C_5$), cyclohexyl ($C_6$), cyclohexenyl ($C_6$), cyclohexadienyl ($C_6$) and the like. Examples of $C_{3-8}$ carbocyclyl groups include the aforementioned $C_{3-6}$ carbocyclyl groups as well as cycloheptyl ($C_7$), cycloheptadienyl ($C_7$), cycloheptatrienyl ($C_7$), cyclooctyl ($C_8$), bicyclo[2.2.1]heptanyl, bicyclo[2.2.2]octanyl, and the like. Examples of $C_{3-10}$ carbocyclyl groups include the aforementioned $C_{3-8}$ carbocyclyl groups as well as octahydro-1H-indenyl, decahydronaphthalenyl, spiro[4.5]decanyl and the like. Unless stated otherwise in the specification, a cycloalkyl group is optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$—, —O$R^a$, —S$R^a$, —OC(O)—$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, N($R^a$)C(N$R^a$)N($R^a$)$_2$, —N($R^a$)S(O)$_t$$R^a$ (where t is 1 or 2), —S(O)$_t$O$R^a$ (where t is 1 or 2), —S(O)$_t$N($R^a$)$_2$ (where t is 1 or 2), or —O—P(=O)(O$R^a$)$_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

"Cycloalkyl-alkyl" refers to a -(cycloalkyl)alkyl radical where cycloalkyl and alkyl are as provided herein and which are optionally substituted by one or more of the substituents described as suitable substituents for cycloalkyl and alkyl respectively. The "cycloalkyl-alkyl" is bonded to the parent molecular structure through the cycloalkyl group. The terms "cycloalkyl-alkenyl" and "cycloalkyl-alkynyl" mirror the above description of "cycloalkyl-alkyl" wherein the term "alkyl" is replaced with "alkenyl" or "alkynyl" respectively, and "alkenyl" or "alkynyl" are as described herein.

"Cycloalkyl-heterocycloalkyl" refers to a -(cycloalkyl)heterocycylalkyl radical where cycloalkyl and heterocycloalkyl are as provided herein and which are optionally substituted by one or more of the substituents described as suitable substituents for heterocycloalkyl and cycloalkyl respectively. The "cycloalkyl-heterocycloalkyl" is bonded to the parent molecular structure through the cycloalkyl group.

"Cycloalkyl-heteroaryl" refers to a -(cycloalkyl)heteroaryl radical where cycloalkyl and heteroaryl are as provided herein and which are optionally substituted by one or more of the substituents described as suitable substituents for heteroaryl and cycloalkyl respectively. The "cycloalkyl-heteroaryl" is bonded to the parent molecular structure through the cycloalkyl group.

As used herein, a "covalent bond" or "direct bond" refers to a single bond joining two groups.

"Ester" refers to a radical of formula —COOR, where R is selected from alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl. Any amine, hydroxy, or carboxyl side chain on the compounds described herein can be esterified. The procedures and specific groups to make such esters are known to those of skill in the art and can readily be found in reference sources such as Greene and Wuts, *Protective Groups in Organic Synthesis,* 3rd Ed., John Wiley & Sons, New York, N.Y., 1999, which is incorporated herein by reference in its entirety. Unless stated otherwise in the specification, an ester group can be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfonyl, sulfonyl, sulfonamidyl, sulfoxyl, sulfonate, urea, —Si($R^a$)$_3$—, —O$R^a$, —S$R^a$, —OC(O)—$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, N($R^a$)C(N$R^a$)N($R^a$)$_2$, —N($R^a$)S(O)$_t$$R^a$ (where t is 1 or 2), —S(O)$_t$O$R^a$ (where t is 1 or 2), —S(O)$_t$N($R^a$)$_2$ (where t is 1 or 2), or —O—P(=O)(O$R^a$)$_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

"Ether" refers to a —$R^b$—O—$R^b$— radical where each $R^b$ is independently selected from hydrogen, alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein.

"Halo", "halide", or, alternatively, "halogen" means fluoro, chloro, bromo or iodo. The terms "haloalkyl," "haloalkenyl," "haloalkynyl" and "haloalkoxy" include alkyl, alkenyl, alkynyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine, such as, but not limited to, trifluoromethyl, difluoromethyl, 2,2,2-trifluoroethyl, 1-fluoromethyl-2-fluoroethyl, and the like. Each of the alkyl, alkenyl, alkynyl and alkoxy groups are as defined herein and can be optionally further substituted as defined herein.

"Heteroalkyl", "heteroalkenyl" and "heteroalkynyl" include alkyl, alkenyl and alkynyl radicals, respectively, which have one or more skeletal chain atoms selected from an atom other than carbon, e.g., oxygen, nitrogen, sulfur, phosphorus or combinations thereof. A numerical range can be given, e.g., $C_1$-$C_4$ heteroalkyl which refers to the chain length in total, which in this example is 4 atoms long. For example, a —CH$_2$OCH$_2$CH$_3$ radical is referred to as a "$C_4$" heteroalkyl, which includes the heteroatom center in the atom chain length description. Connection to the parent molecular structure can be through either a heteroatom or a carbon in the heteroalkyl chain. For example, an N-containing heteroalkyl moiety refers to a group in which at least one of the skeletal atoms is a nitrogen atom. One or more heteroatom(s) in the heteroalkyl radical can be optionally oxidized. One or more nitrogen atoms, if present, can also be optionally quaternized. For example, heteroalkyl also includes skeletal chains substituted with one or more nitrogen oxide (—O—) substituents. Exemplary heteroalkyl groups include, without limitation, ethers such as methoxyethanyl (—CH$_2$CH$_2$OCH$_3$), ethoxymethanyl (—CH$_2$OCH$_2$CH$_3$), (methoxymethoxy) ethanyl (—CH$_2$CH$_2$OCH$_2$OCH$_3$), (methoxymethoxy) methanyl (—CH$_2$OCH$_2$OCH$_3$) and (methoxyethoxy)methanyl (—CH$_2$OCH$_2$ CH$_2$OCH$_3$) and the like; amines such as —CH$_2$CH$_2$NHCH$_3$, —CH$_2$CH$_2$N(CH$_3$)$_2$, —CH$_2$NHCH$_2$CH$_3$, —CH$_2$N(CH$_2$CH$_3$)(CH$_3$) and the like. Heteroalkyl, heteroalkenyl, and heteroalkynyl groups can each be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfonyl, sulfonyl, sulfonamidyl, sulfoxyl, sulfonate, urea, —Si($R^a$)$_3$—, —O$R^a$, —S$R^a$, —OC(O)—$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, N($R^a$)C(N$R^a$)N($R^a$)$_2$, —N($R^a$)S(O)$_t$$R^a$ (where t is 1 or 2), —S(O)$_t$O$R^a$ (where t is 1 or 2), —S(O)$_t$N($R^a$)$_2$ (where t is 1 or 2), or —O—P(=O)(O$R^a$)$_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

"Heteroalkyl-aryl" refers to a -(heteroalkyl)aryl radical where heteroalkyl and aryl are as provided herein and which are optionally substituted by one or more of the substituents described as suitable substituents for heteroalkyl and aryl respectively. The "heteroalkyl-aryl" is bonded to the parent molecular structure through an atom of the heteroalkyl group.

"Heteroalkyl-heteroaryl" refers to a -(heteroalkyl)heteroaryl radical where heteroalkyl and heteroaryl are as provided herein and which are optionally substituted by one or more of the substituents described as suitable substituents for heteroalkyl and heteroaryl respectively. The "heteroalkyl-heteroaryl" is bonded to the parent molecular structure through an atom of the heteroalkyl group.

"Heteroalkyl-heterocycloalkyl" refers to a -(heteroalkyl)heterocycloalkyl radical where heteroalkyl and heterocycloalkyl are as provided herein and which are optionally substituted by one or more of the substituents described as suitable substituents for heteroalkyl and heterocycloalkyl respectively. The "heteroalkyl-heterocycloalkyl" is bonded to the parent molecular structure through an atom of the heteroalkyl group.

"Heteroalkyl-cycloalkyl" refers to a -(heteroalkyl)cycloalkyl radical where heteroalkyl and cycloalkyl are as provided herein and which are optionally substituted by one or more of the substituents described as suitable substituents for heteroalkyl and cycloalkyl respectively. The "heteroalkyl-cycloalkyl" is bonded to the parent molecular structure through an atom of the heteroalkyl group.

"Heteroaryl" or, alternatively, "heteroaromatic" refers to a refers to a radical of a 5-18 membered monocyclic or polycyclic (e.g., bicyclic or tricyclic) aromatic ring system (e.g., having 6, 10 or 14 electrons shared in a cyclic array) having ring carbon atoms and 1-6 ring heteroatoms provided in the aromatic ring system, wherein each heteroatom is independently selected from nitrogen, oxygen, phosphorous and sulfur ("5-18 membered heteroaryl"). Heteroaryl polycyclic ring systems can include one or more heteroatoms in one or both rings. Whenever it appears herein, a numerical range such as "5 to 18" refers to each integer in the given range; e.g., "5 to 18 ring atoms" means that the heteroaryl group can consist of 5 ring atoms, 6 ring atoms, etc., up to and including 18 ring atoms. For example, bivalent radicals derived from univalent heteroaryl radicals whose names end in "-yl" by removal of one hydrogen atom from the atom with the free valence are named by adding "-idene" to the name of the corresponding univalent radical, e.g., a pyridyl group with two points of attachment is a pyridylidene.

For example, an N-containing "heteroaromatic" or "heteroaryl" moiety refers to an aromatic group in which at least one of the skeletal atoms of the ring is a nitrogen atom. One or more heteroatom(s) in the heteroaryl radical can be optionally oxidized. One or more nitrogen atoms, if present, can also be optionally quaternized. Heteroaryl also includes ring systems substituted with one or more nitrogen oxide (—O—) substituents, such as pyridinyl N-oxides. The heteroaryl is attached to the parent molecular structure through any atom of the ring(s).

"Heteroaryl" also includes ring systems wherein the heteroaryl ring, as defined above, is fused with one or more aryl groups wherein the point of attachment to the parent molecular structure is either on the aryl or on the heteroaryl ring, or wherein the heteroaryl ring, as defined above, is fused with one or more cycloalkyl or heterocycyl groups wherein the point of attachment to the parent molecular structure is on the heteroaryl ring. For polycyclic heteroaryl groups wherein one ring does not contain a heteroatom (e.g., indolyl, quinolinyl, carbazolyl and the like), the point of attachment to the parent molecular structure can be on either ring, i.e., either the ring bearing a heteroatom (e.g., 2-indolyl) or the ring that does not contain a heteroatom (e.g., 5-indolyl). In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, phosphorous, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, phosphorous, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, phosphorous, and sulfur ("5-6 membered heteroaryl"). In some embodiments, the 5-6 membered heteroaryl has 1-3 ring heteroatoms selected from nitrogen, oxygen, phosphorous, and sulfur. In some embodiments, the 5-6 membered heteroaryl has 1-2 ring heteroatoms selected from nitrogen, oxygen, phosphorous, and sulfur. In some embodiments, the 5-6 membered heteroaryl has 1 ring heteroatom selected from nitrogen, oxygen, phosphorous, and sulfur.

Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranyl, benzofuranonyl, benzofurazanyl, benzothiazolyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furazanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno[2,3-c]pridinyl, and thiophenyl (i.e., thienyl). Unless stated otherwise in the specification, a heteroaryl moiety is optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si(R$^a$)$_3$—, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or —O—P(=O)(OR$^a$)$_2$ where each R$^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl and each of these moieties can be optionally substituted as defined herein.

"Heteroaryl-alkyl" refers to a -(heteroaryl)alkyl radical where heteroaryl and alkyl are as provided herein and which are optionally substituted by one or more of the substituents described as suitable substituents for heteroaryl and alkyl respectively. The "heteroaryl-alkyl" is bonded to the parent molecular structure through any atom of the heteroaryl group.

"Heteroaryl-heterocycloalkyl" refers to an -(heteroaryl)heterocycloalkyl radical where heteroaryl and heterocycloalkyl are as provided herein and which are optionally substituted by one or more of the substituents described as suitable substituents for heteroaryl and heterocycloalkyl respectively. The "heteroaryl-heterocycloalkyl" is bonded to the parent molecular structure through an atom of the heteroaryl group.

"Heteroaryl-cycloalkyl" refers to an -(heteroaryl)cycloalkyl radical where heteroaryl and cycloalkyl are as provided herein and which are optionally substituted by one or more of the substituents described as suitable substituents for heteroaryl and cycloalkyl respectively. The "heteroaryl-cycloalkyl" is bonded to the parent molecular structure through a carbon atom of the heteroaryl group.

"Heterocyclyl", "heterocycloalkyl" or 'heterocarbocyclyl" each refer to any 3- to 18-membered non-aromatic radical monocyclic or polycyclic moiety comprising at least one heteroatom selected from nitrogen, oxygen, phosphorous and sulfur. A heterocyclyl group can be a monocyclic, bicyclic, tricyclic or tetracyclic ring system, wherein the polycyclic ring systems can be a fused, bridged or spiro ring system. Heterocyclyl polycyclic ring systems can include one or more heteroatoms in one or both rings. A heterocyclyl group can be saturated or partially unsaturated. Partially unsaturated heterocycloalkyl groups can be termed "heterocycloalkenyl" if the heterocyclyl contains at least one double bond, or "heterocycloalkynyl" if the heterocyclyl contains at least one triple bond. Whenever it appears herein, a numerical range such as "5 to 18" refers to each integer in the given range; e.g., "5 to 18 ring atoms" means that the heterocyclyl group can consist of 5 ring atoms, 6 ring atoms, etc., up to and including 18 ring atoms. For example, bivalent radicals derived from univalent heterocyclyl radicals whose names end in "-yl" by removal of one hydrogen atom from the atom with the free valence are named by adding "-idene" to the name of the corresponding univalent radical, e.g., a piperidine group with two points of attachment is a piperidylidene.

An N-containing heterocyclyl moiety refers to an non-aromatic group in which at least one of the ring atoms is a nitrogen atom. The heteroatom(s) in the heterocyclyl radical can be optionally oxidized. One or more nitrogen atoms, if present, can be optionally quaternized. Heterocyclyl also includes ring systems substituted with one or more nitrogen oxide (—O—) substituents, such as piperidinyl N-oxides. The heterocyclyl is attached to the parent molecular structure through any atom of any of the ring(s).

"Heterocyclyl" also includes ring systems wherein the heterocycyl ring, as defined above, is fused with one or more carbocycyl groups wherein the point of attachment is either on the carbocycyl or heterocyclyl ring, or ring systems wherein the heterocyclyl ring, as defined above, is fused with one or more aryl or heteroaryl groups, wherein the point of attachment to the parent molecular structure is on the heterocyclyl ring. In some embodiments, a heterocyclyl group is a 3-10 membered non-aromatic ring system having ring carbon atoms and 1-4 ring heteroatoms, wherein each heteroatom is independently selected from nitrogen, oxygen, phosphorous and sulfur ("3-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, phosphorous and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, phosphorous and sulfur ("5-6 membered heterocyclyl"). In some embodiments, the 5-6 membered heterocyclyl has 1-3 ring heteroatoms selected from nitrogen, oxygen phosphorous and sulfur. In some embodiments, the 5-6 membered heterocyclyl has 1-2 ring heteroatoms selected from nitrogen, oxygen, phosphorous and sulfur. In some embodiments, the 5-6 membered heterocyclyl has 1 ring heteroatom selected from nitrogen, oxygen, phosphorous and sulfur.

Exemplary 3-membered heterocyclyls containing 1 heteroatom include, without limitation, azirdinyl, oxiranyl, thiorenyl. Exemplary 4-membered heterocyclyls containing 1 heteroatom include, without limitation, azetidinyl, oxetanyl and thietanyl. Exemplary 5-membered heterocyclyls containing 1 heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyls containing 2 heteroatoms include, without limitation, dioxolanyl, oxathiolanyl and dithiolanyl. Exemplary 5-membered heterocyclyls containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, dioxanyl, and triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano [3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c] pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo

[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

Unless stated otherwise, heterocyclyl moieties are optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si(R$^a$)$_3$—, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or —O—P(=O)(OR$^a$)$_2$ where each R$^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl and each of these moieties can be optionally substituted as defined herein.

"Heterocyclyl-alkyl" refers to a -(heterocyclyl)alkyl radical where heterocyclyl and alkyl are as provided herein and which are optionally substituted by one or more of the substituents described as suitable substituents for heterocyclyl and alkyl respectively. The "heterocyclyl-alkyl" is bonded to the parent molecular structure through any atom of the heterocyclyl group. The terms "heterocyclyl-alkenyl" and "heterocyclyl-alkynyl" mirror the above description of "heterocyclyl-alkyl" wherein the term "alkyl" is replaced with "alkenyl" or "alkynyl" respectively, and "alkenyl" or "alkynyl" are as described herein.

"Imino" refers to the "—(C=N)—R$^b$" radical where R$^b$ is selected from hydrogen, alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein.

"Moiety" refers to a specific segment or functional group of a molecule. Chemical moieties are often recognized chemical entities embedded in or appended to a molecule.

"Nitro" refers to the —NO$_2$ radical.

"Oxa" refers to the —O— radical.

"Oxo" refers to the =O radical.

"Phosphate" refers to a —O—P(=O)(OR$^b$)$_2$ radical, where each R$^b$ is independently selected from hydrogen, alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein. In some embodiments, when R$^a$ is hydrogen and depending on the pH, the hydrogen can be replaced by an appropriately charged counter ion.

"Phosphonate" refers to a —O—P(=O)(R$^b$)(OR$^b$) radical, where each R$^b$ is independently selected from hydrogen, alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein. In some embodiments, when R$^a$ is hydrogen and depending on the pH, the hydrogen can be replaced by an appropriately charged counter ion.

"Phosphinate" refers to a —P(=O)(R$^b$)(OR$^b$) radical, where each R$^b$ is independently selected from hydrogen, alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein. In some embodiments, when R$^a$ is hydrogen and depending on the pH, the hydrogen can be replaced by an appropriately charged counter ion.

A "leaving group or atom" is any group or atom that will, under the reaction conditions, cleave from the starting material, thus promoting reaction at a specified site. Suitable non-limiting examples of such groups unless otherwise specified include halogen atoms, mesyloxy, p-nitrobenzensulphonyloxy, trifluoromethyloxy, and tosyloxy groups.

"Protecting group" has the meaning conventionally associated with it in organic synthesis, i.e., a group that selectively blocks one or more reactive sites in a multifunctional compound such that a chemical reaction can be carried out selectively on another unprotected reactive site and such that the group can readily be removed after the selective reaction is complete. A variety of protecting groups are disclosed, for example, in T. H. Greene and P. G. M. Wuts, *Protective Groups in Organic Synthesis*, Third Edition, John Wiley & Sons, New York (1999), incorporated herein by reference in its entirety. For example, a hydroxy protected form is where at least one of the hydroxy groups present in a compound is protected with a hydroxy protecting group. Likewise, amines and other reactive groups can similarly be protected.

As used herein, the terms "substituted" or "substitution" mean that at least one hydrogen present on a group atom (e.g., a carbon or nitrogen atom) is replaced with a permissible substituent, e.g., a substituent which upon substitution for the hydrogen results in a stable compound, e.g., a compound which does not spontaneously undergo transformation such as by rearrangement, cyclization, elimination, or other reaction. Unless otherwise indicated, a "substituted" group can have a substituent at one or more substitutable positions of the group, and when more than one position in any given structure is substituted, the substituent is either the same or different at each position. Substituents include one or more group(s) individually and independently selected from acyl, alkyl, alkenyl, alkynyl, alkoxy, alkylaryl, cycloalkyl, aralkyl, aryl, aryloxy, amino, amido, azide, carbonate, carbonyl, heteroalkyl, heteroaryl, heteroarylalkyl, heterocycloalkyl, hydroxy, cyano, halo, haloalkoxy, haloalkyl, ester, mercapto, thio, alkylthio, arylthio, thiocarbonyl, nitro, oxo, phosphate, phosphonate, phosphinate, silyl, sulfonyl, sulfonamidyl, sulfoxyl, sulfonate, urea, —Si(R$^a$)$_3$, OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), —O—P(=O)(OR$^a$)$_2$, where each R$^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl and each of these moieties can be optionally substituted as defined herein. For example, a cycloalkyl substituent can have a halide substituted at one or more ring carbons, and the like. The protecting groups that can form the protective derivatives of the above substituents are known to those of skill in the art and can be found in references such as Greene and Wuts, above.

"Silyl" refers to a —Si($R^b$)$_3$ radical where each $R^b$ is independently selected from alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein.

"Sulfanyl", "sulfide", and "thio" each refer to the radical —S—$R^b$, wherein $R^b$ is selected from alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein. For instance, an "alkylthio" refers to the "alkyl-S-" radical, and "arylthio" refers to the "aryl-S-" radical, each of which are bound to the parent molecular group through the S atom. The terms "sulfide", "thiol", "mercapto", and "mercaptan" can also each refer to the group —$R^b$SH.

"Sulfinyl" or "sulfoxide" refers to the —S(O)—$R^b$ radical, wherein for "sulfinyl", $R^b$ is H and for "sulfoxide", $R^b$ is selected from alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein.

"Sulfonyl" or "sulfone" refers to the —S($O_2$)—$R^b$ radical, wherein $R^b$ is selected from hydrogen, alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein.

"Sulfonamidyl" or "sulfonamido" refers to the following radicals: —S(=O)$_2$—N($R^b$)$_2$, —N($R^b$)—S(=O)$_2$—$R^b$, —S(=O)$_2$—N($R^b$)—, or —N($R^b$)—S(=O)$_2$—, where each $R^b$ is independently selected from hydrogen, alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein. The $R^b$ groups in —S(=O)$_2$—N($R^b$)$_2$ can be taken together with the nitrogen to which they are attached to form a 4-, 5-, 6-, or 7-membered heterocyclyl ring. In some embodiments, the term designates a $C_1$-$C_4$ sulfonamido, wherein each $R^b$ in the sulfonamido contains 1 carbon, 2 carbons, 3 carbons, or 4 carbons total.

"Sulfoxyl" or "sulfoxide" refers to a —S(=O)$_2$OH radical.

"Sulfonate" refers to a —S(=O)$_2$—O$R^b$ radical, wherein $R^b$ is selected from alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein.

"Thiocarbonyl" refers to a —(C=S)— radical.

"Urea" refers to a —N($R^b$)—(C=O)—N($R^b$)$_2$ or —N($R^b$)—(C=O)—N($R^b$)— radical, where each $R^b$ is independently selected from alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein.

Where substituent groups are specified by their conventional chemical formulae, written from left to right, they equally encompass the chemically identical substituents that would result from writing the structure from right to left, e.g., —$CH_2$O— is equivalent to —O$CH_2$—.

COMPOUNDS

In one aspect, provided herein are compounds of Formula (I):

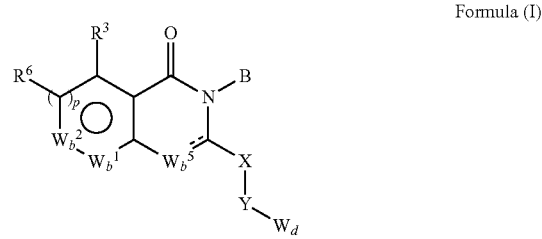

Formula (I)

or an enantiomer, a mixture of enantiomers, or a mixture of two or more diastereomers thereof, or a pharmaceutically acceptable form thereof, wherein $W_b^1$ and $W_b^2$ are each independently $CR^6$, S, O, N or $NR^{14}$, wherein at least one of $W_b^1$ and $W_b^2$ is $CR^6$, N or $NR^{14}$;

$W_b^5$ is $CR^8$, $CHR^8$, or N;

p is 0, 1, 2 or 3;

B is hydrogen, alkyl, alkenyl, alkynyl, amino, heteroalkyl, cycloalkyl, heterocyclyl, aryl or heteroaryl, each of which is substituted with 0-4 $R^2$;

each $R^2$ is independently alkyl, heteroalkyl, alkenyl, alkynyl, cycloalkyl, heterocyclyl, aryl, arylalkyl, heteroaryl, heteroarylalkyl, alkoxy, amido, amino, acyl, acyloxy, alkoxycarbonyl, sulfonamido, halo, cyano, hydroxyl, nitro, phosphate, urea or carbonate;

X is absent or is —(CH($R^9$))$_z$—;

Y is absent, —O—, —S—, —S(=O)—, —S(=O)$_2$—, —N($R^9$)—, —C(=O)—(CH$R^9$)$_z$—, —C(=O)—, —N($R^9$)—C(=O)—, —N($R^9$)—C(=O)NH—, —N($R^9$)C($R^9$)$_2$—, —C(=O)—N($R^9$)$_2$, or —C(=O)—N($R^9$)—(CH$R^9$)$_z$;

each z is independently an integer of 1, 2, 3, or 4;

$R^3$ is $C_{2-6}$alkyl, fluoro, bromo, iodo, cycloalkyl, cycloalkylalkyl, aryl, heteroaryl, heterocyclyl, aralkyl, heteroaralkyl, heterocyclylalkyl, alkenyl, or alkynyl, or $R^3$ is a heteroatom selected from N, S, and O, wherein the heteroatom has a covalent bond, either directly or through a $C_1$-$C_6$ alkyl group, to an aryl, heteroaryl or heterocyclyl, or $R^3$ and $R^6$ are taken together with the carbons to which they are attached form a cyclic moiety; wherein each of the above substituents can be substituted with 0, 1, 2, or 3 $R^{13}$;

each $R^6$ is independently hydrogen, alkyl, alkenyl, alkynyl, cycloalkyl, heterocyclyl, fluoroalkyl, heteroalkyl, alkoxy, amido, amino, acyl, acyloxy, sulfinyl, sulfonyl, sulfoxide, sulfone, sulfonamido, halo, cyano, heteroaryl, aryl, hydroxyl, or nitro;

$R^8$ is hydrogen, alkyl, alkenyl, alkynyl, cycloalkyl, heteroalkyl, alkoxy, amino, acyl, acyloxy, sulfonamido, halo, cyano, hydroxyl, or nitro;

each $R^9$ is independently hydrogen, alkyl, cycloalkyl, heterocyclyl or heteroalkyl;

$W_d$ is

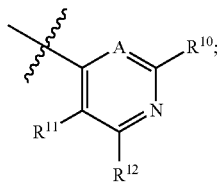

A is N or $CR^{19}$;

$R^{10}$, $R^{11}$, $R^{12}$, $R^{13}$, and $R^{19}$ are independently hydrogen, alkyl, heteroalkyl, alkenyl, alkynyl, cycloalkyl, heterocyclyl, aryl, arylalkyl, heteroaryl, heteroarylalkyl, alkoxy, heterocyclyloxy, amido, amino, acyl, acyloxy, alkoxycarbonyl, sulfonamido, halo, haloalkyl, cyano, hydroxyl, nitro, phosphate, urea, carbonate, oxo, or NR'R" wherein R' and R" are taken together with nitrogen to form a cyclic moiety;

each $R^{14}$ is independently hydrogen, alkyl, cycloalkyl, heterocyclyl or heteroalkyl; and wherein the compound of Formula (I) is not one of the following compounds:

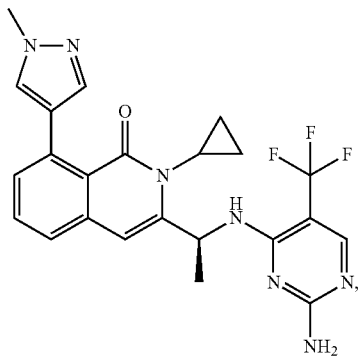

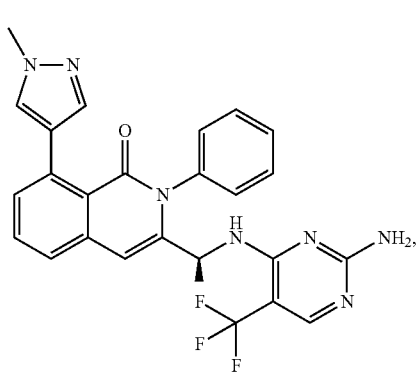

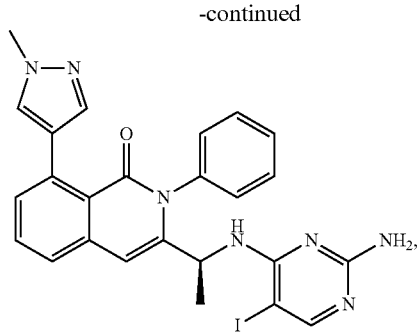

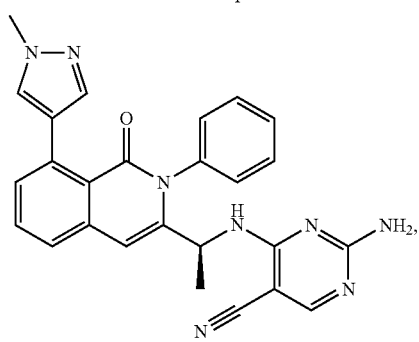

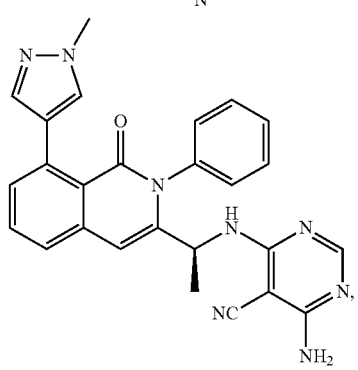

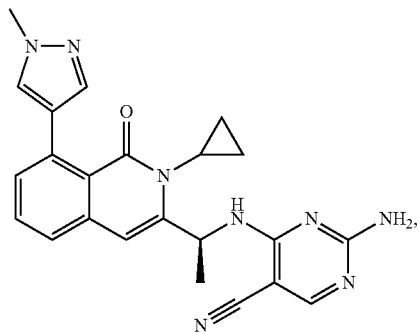

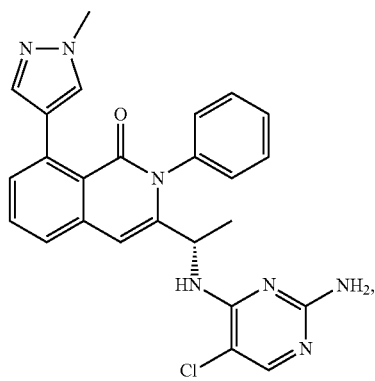

-continued

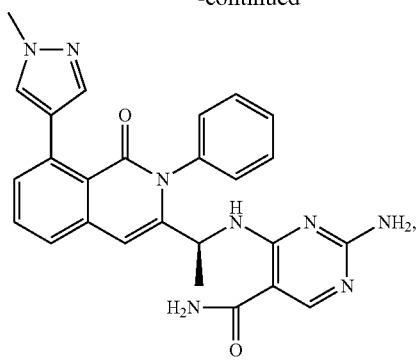

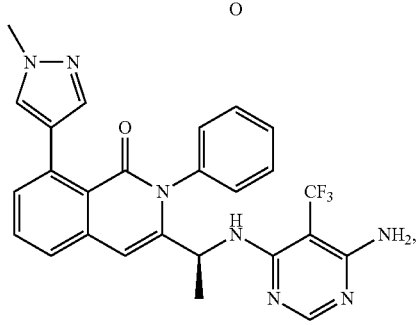

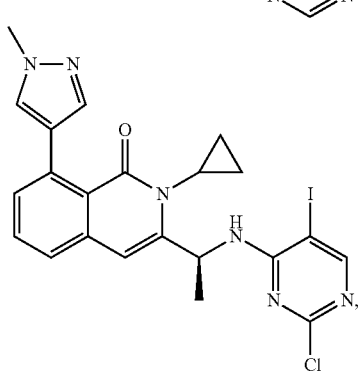

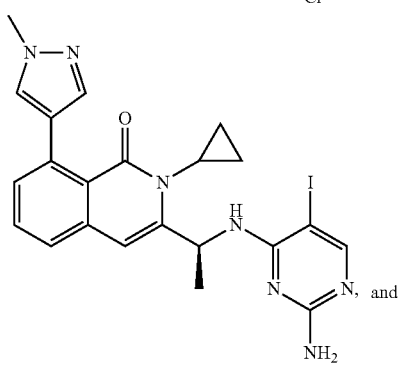

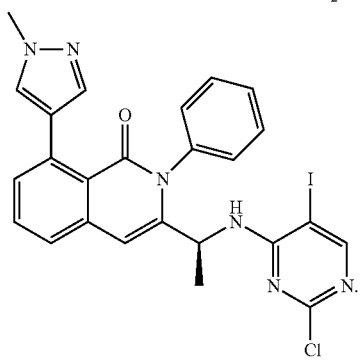

In some embodiments, when $R^3$ is 1-methyl-4-pyrazolyl, B is not phenyl substituted with 0 occurrences of $R^{13}$ or cyclopropyl substituted with 0 occurrences of $R^{13}$.

In one embodiment, provided herein are compounds of Formula (I):

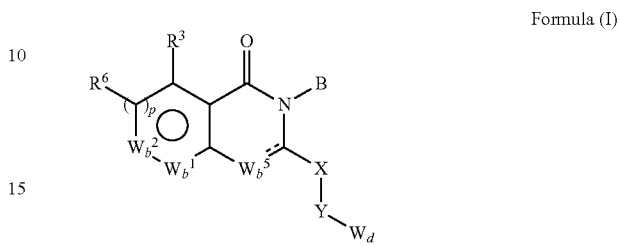

Formula (I)

or an enantiomer, a mixture of enantiomers, or a mixture of two or more diastereomers thereof, or a pharmaceutically acceptable form thereof, wherein $W_b^1$ and $W_b^2$ are each independently $CR^6$, S, O, N or $NR^{14}$, wherein at least one of $W_b^1$ and $W_b^2$ is $CR^6$, N or $NR^{14}$;

$W_b^5$ is $CR^8$, $CHR^8$, or N;

p is 0, 1, 2 or 3;

B is hydrogen, alkyl, alkenyl, alkynyl, amino, heteroalkyl, cycloalkyl, heterocyclyl, aryl or heteroaryl, each of which is substituted with 0-4 $R^2$;

each $R^2$ is independently alkyl, heteroalkyl, alkenyl, alkynyl, cycloalkyl, heterocyclyl, aryl, arylalkyl, heteroaryl, heteroarylalkyl, alkoxy, amido, amino, acyl, acyloxy, alkoxycarbonyl, sulfonamido, halo, cyano, hydroxyl, nitro, phosphate, urea or carbonate;

X is absent or is —$(CH(R^9))_z$—;

Y is absent, —O—, —S—, —S(=O)—, —S(=O)$_2$—, —N($R^9$)—, —C(=O)—$(CHR^9)_z$—, —C(=O)—, —N($R^9$)—C(=O)—, —N($R^9$)—C(=O)NH—, —N($R^9$)C($R^9$)$_2$—, —C(=O)—N($R^9$)$_2$, or —C(=O)—N($R^9$)—$(CHR^9)_z$;

each z is independently an integer of 1, 2, 3, or 4;

$R^3$ is $C_{2-6}$alkyl, fluoro, bromo, iodo, cycloalkyl, cycloalkylalkyl, aryl, heteroaryl, heterocyclyl, aralkyl, heteroaralkyl, heterocyclylalkyl, alkenyl, or alkynyl, or $R^3$ is a heteroatom selected from N, S, and O, wherein the heteroatom has a covalent bond, either directly or through a $C_1$-$C_6$ alkyl group, to an aryl, heteroaryl or heterocyclyl, or $R^3$ and $R^6$ are taken together with the carbons to which they are attached form a cyclic moiety; wherein each of the above substituents can be substituted with 0, 1, 2, or 3 $R^{13}$;

each $R^6$ is independently hydrogen, alkyl, alkenyl, alkynyl, cycloalkyl, heterocyclyl, fluoroalkyl, heteroalkyl, alkoxy, amido, amino, acyl, acyloxy, sulfinyl, sulfonyl, sulfoxide, sulfone, sulfonamido, halo, cyano, heteroaryl, aryl, hydroxyl, or nitro;

$R^8$ is hydrogen, alkyl, alkenyl, alkynyl, cycloalkyl, heteroalkyl, alkoxy, amino, acyl, acyloxy, sulfonamido, halo, cyano, hydroxyl, or nitro;

each $R^9$ is independently hydrogen, alkyl, cycloalkyl, heterocyclyl or heteroalkyl;

$W_d$ is

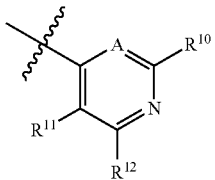

A is N or $CR^{19}$;

$R^{10}$, $R^{11}$, $R^{12}$, $R^{13}$, and $R^{19}$ are independently hydrogen, alkyl, heteroalkyl, alkenyl, alkynyl, cycloalkyl, heterocyclyl, aryl, arylalkyl, heteroaryl, heteroarylalkyl, alkoxy, heterocyclyloxy, amido, amino, acyl, acyloxy, alkoxycarbonyl, sulfonamido, halo, haloalkyl, cyano, hydroxyl, nitro, phosphate, urea, carbonate, oxo, or NR'R" wherein R' and R" are taken together with nitrogen to form a cyclic moiety;

each $R^{14}$ is independently hydrogen, alkyl, cycloalkyl, heterocyclyl or heteroalkyl; and wherein $R^3$ is not 1-methyl-4-pyrazolyl.

In certain embodiments, $W_b^1$ is $CR^6$. In some embodiments, $W_b^1$ is N. In some embodiments, $W_b^1$ is S. In some embodiments, $W_b^1$ is O.

In certain embodiments, $W_b^2$ is $CR^6$. In some embodiments, $W_b^2$ is N. In some embodiments, $W_b^2$ is S. In some embodiments, $W_b^2$ is O.

In some embodiments, $W_b^1$ and $W_b^2$ are $CR^6$. In some embodiments, $W_b^1$ is S and $W_b^2$ is $CR^6$.

In some embodiments, $W_b^1$ is S and $W_b^2$ is N.

In certain embodiments, $R^8$ is hydrogen.

In certain embodiments, each $R^6$ is independently hydrogen, alkyl, alkenyl, alkynyl, cycloalkyl, heterocyclyl, fluoroalkyl, heteroalkyl, alkoxy, amido, amino, acyl, acyloxy, sulfinyl, sulfonyl, sulfoxide, sulfone, sulfonamido, halo, cyano, heteroaryl, aryl, hydroxyl, or nitro. In some embodiments, each $R^6$ is independently hydrogen, alkyl, cycloalkyl, heterocyclyl, fluoroalkyl, alkoxy, halo, cyano, heteroaryl or aryl. In some embodiments, $R^6$ is hydrogen, alkyl, fluoroalkyl, alkoxy or aryl. In some embodiments, each $R^6$ is hydrogen.

In certain embodiments, p is 0 or 1. In certain embodiments, p is 0. In some embodiments, p is 1.

In certain embodiments, the compound of Formula (I) has a structure of Formula (II):

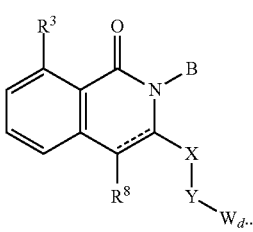

Formula (II)

In some embodiments, the compound of Formula (II) has a structure of Formula (IIa) or (IIb):

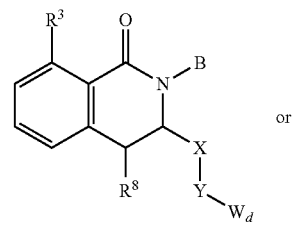

Formula (IIa)

or

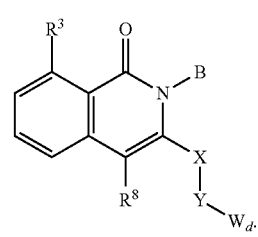

Formula (IIb)

In some embodiments, the compound of Formula (I) has a structure of Formula (III):

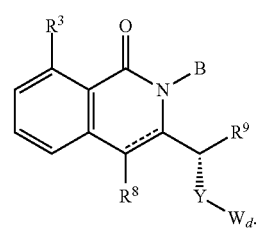

Formula (III)

In some embodiments, the compound of Formula (II) has a structure of Formula (IIIa) or (IIIb):

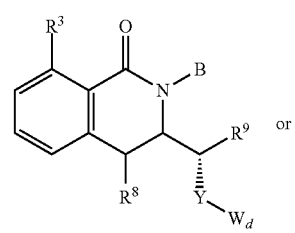

Formula (IIIa)

or

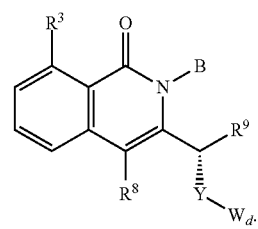

Formula (IIIb)

In some embodiments, the compound of Formula (I) has a structure of Formula (IIIb):

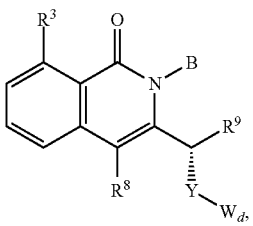

Formula (IIIb)

wherein $R^3$ is pyridyl substituted with 0, 1, 2, or 3 $R^{13}$. In some embodiments, the compound of Formula (I) has a structure of Formula (IIIb), wherein $R^3$ is pyridyl substituted with 1 or 2 $R^{13}$, wherein each occurrence of $R^{13}$ is independently $C_{1-4}$ alkyl, $C_{3-6}$ cycloalkyl, $C_{3-6}$ heterocyclyl, $C_{1-4}$ alkoxy, halo, $C_{1-4}$ haloalkyl, hydroxyl, or oxo. In some embodiments, the compound of Formula (I) has a structure of Formula (IIIb), wherein $R^3$ is pyridyl substituted with 1 or 2 $R^{13}$, wherein each occurrence of $R^{13}$ is independently methyl, methoxy, or oxo.

In some embodiments, X is —(CH($R^9$))$_z$—. In some embodiments, z is 1. In some embodiments, $R^9$ is $C_{1-10}$ alkyl (e.g., methyl). In some embodiments, $R^9$ is methyl.

In certain embodiments, Y is absent or —N($R^9$)—. In certain embodiments, Y is absent. In some embodiments, Y is —N($R^9$)—. In some embodiments, $R^9$ is hydrogen.

In certain embodiments, X—Y is

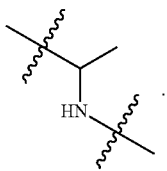 [SMILES: *NC(*)C]

In certain embodiments, X—Y is (S)—CH(CH$_3$)—NH—. In certain embodiments, X—Y is (R)—CH(CH$_3$)—NH—.

In certain embodiments, $R^3$ is $C_2$-$C_6$alkyl, fluoro, bromo, iodo, cycloalkyl, cycloalkylalkyl, aryl, heteroaryl, heterocyclyl, aralkyl, heteroaralkyl, heterocyclylalkyl, alkenyl, or alkynyl, or $R^3$ is a heteroatom selected from N, S, and O, wherein the heteroatom has a covalent bond either directly or through a $C_1$-$C_6$ alkyl group to an aryl, heteroaryl or heterocyclyl, or $R^3$ and $R^6$ are taken together with the carbons to which they are attached form a 5- or 6-membered ring; wherein each of the above substituents can be substituted with 0, 1, 2, or 3 $R^{13}$.

In certain embodiments, $R^3$ is cycloalkyl, cycloalkylalkyl, aryl, heteroaryl, heterocyclyl, aralkyl, heteroaralkyl, heterocyclylalkyl, alkenyl, or alkynyl, or $R^3$ is a heteroatom selected from N, S, and O, wherein the heteroatom has a covalent bond either directly or through a $C_1$-$C_6$ alkyl group to an aryl, heteroaryl or heterocyclyl, or $R^3$ and $R^6$ are taken together with the carbons to which they are attached form a 5- or 6-membered ring; wherein each of the above substituents can be substituted with 0, 1, 2, or 3 $R^{13}$.

In certain embodiments, $R^3$ is cycloalkyl, cycloalkylalkyl, aryl, 6-10 membered heteroaryl, heterocyclyl, aralkyl, heteroaralkyl, heterocyclylalkyl, alkenyl, or alkynyl, or $R^3$ is a heteroatom selected from N, S, and O, wherein the heteroatom has a covalent bond either directly or through a $C_1$-$C_6$ alkyl group to an aryl, heteroaryl or heterocyclyl, or $R^3$ and $R^6$ are taken together with the carbons to which they are attached form a 5- or 6-membered ring; wherein each of the above substituents can be substituted with 0, 1, 2, or 3 $R^{13}$.

In certain embodiments, $R^3$ is heteroaryl substituted with 0, 1, 2 or 3 $R^{13}$. In certain embodiments, $R^3$ is 6-10 membered heteroaryl substituted with 0, 1, 2 or 3 $R^{13}$. In some embodiments, $R^3$ is 6-membered heteroaryl substituted with 0, 1, 2 or 3 $R^{13}$. In some embodiments, $R^3$ is 6-membered heteroaryl substituted with 0 $R^{13}$ (e.g., 4-pyridazinyl). In some embodiments, $R^3$ is 6-membered heteroaryl substituted with 1 $R^{13}$ (e.g., 2-methoxy-5-pyrimidyl, 2-methyl-5-pyrimidyl, 5-methyl-2-pyridyl, 2-methoxy-4-pyridyl, 5-methoxy-2-pyridyl or 2-methyl-4-pyridyl). In some embodiments, $R^3$ is pyridyl substituted with 0, 1, 2 or 3 $R^{13}$. In some embodiments, $R^3$ is pyridyl substituted with 1 or 2 $R^{13}$. In some embodiments, $R^3$ is pyridyl substituted with 1 $R^{13}$. In some embodiments, $R^3$ is pyridyl substituted with 2 $R^{13}$. In some embodiments, the substituted pyridyl is a pyridinonyl.

In some embodiments, $R^3$ is 9-membered heteroaryl substituted with 0, 1, 2 or 3 $R^{13}$. In some embodiments, $R^3$ is 10-membered heteroaryl substituted with 0, 1, 2 or 3 $R^{13}$.

In certain embodiments, $R^3$ is a fused 5/6-bicyclic heteroaryl substituted with 0, 1, 2 or 3 $R^{13}$. In some embodiments, $R^3$ is a fused 5/6-bicyclic heteroaryl substituted with 0 $R^{13}$ (e.g., 5-1H-pyrrolo[2,3-b]pyridine). In some embodiments, $R^3$ is fused 6/6-bicyclic heteroaryl substituted with 0, 1, 2 or 3 $R^{13}$. In some embodiments, $R^3$ is fused 6/6-bicyclic heteroaryl substituted with 0 $R^{13}$ (e.g., 3-quinolinyl).

In certain embodiments of a compound of the Formulas provided herein and elsewhere (e.g., Formula (I), (II), (IIa), (IIb), (IIIa), or (IIIb)), each occurrence of $R^{13}$ is independently alkyl, cycloalkyl, heterocyclyl, alkoxy, amino, sulfonamido, halo, haloalkyl, hydroxyl, or oxo. In some embodiments, each occurrence of $R^{13}$ is independently $C_{1-4}$ alkyl, $C_{3-6}$ cycloalkyl, $C_{3-6}$ heterocyclyl, $C_{1-4}$ alkoxy, halo, $C_{1-4}$ haloalkyl, hydroxyl, or oxo. In some embodiments, each occurrence of $R^{13}$ is independently methyl, methoxy, halo, or oxo. In some embodiments, each occurrence of $R^{13}$ is independently methyl, methoxy, or oxo.

In certain embodiments, —X—Y—W$_d$ is selected from:

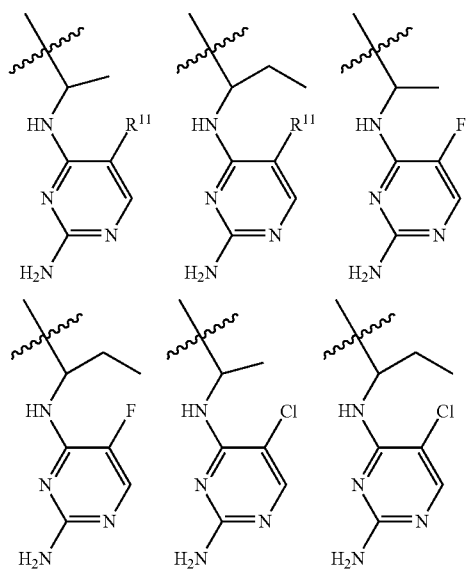

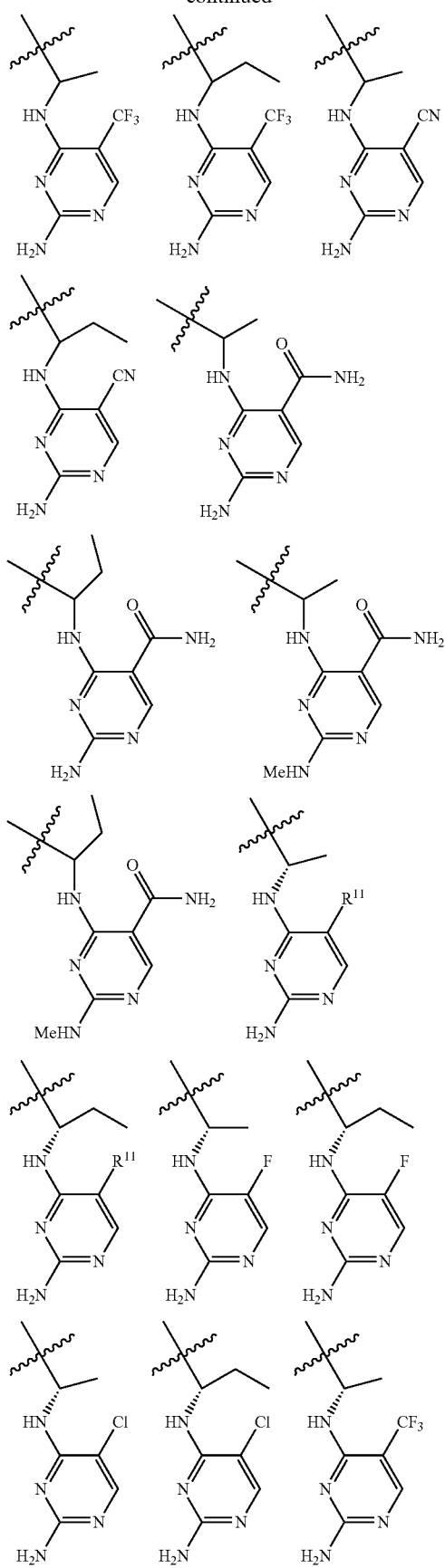
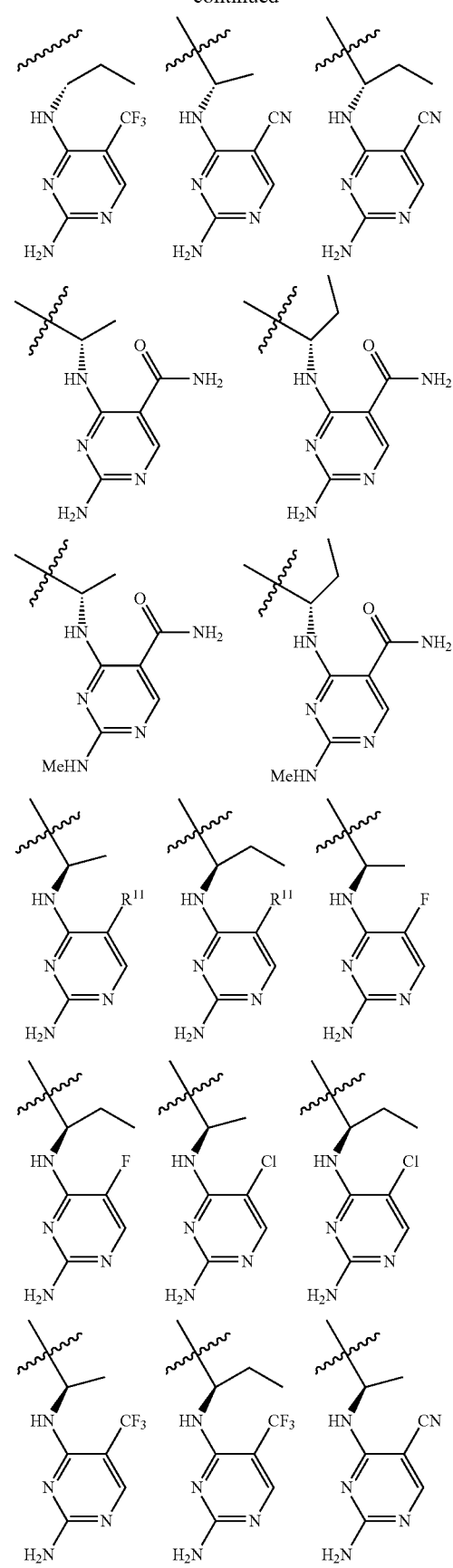

-continued
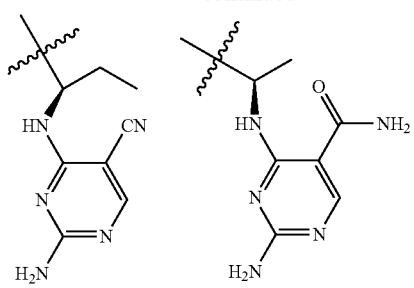 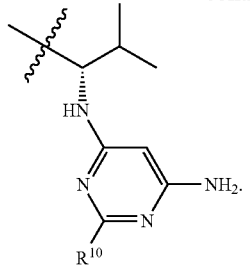
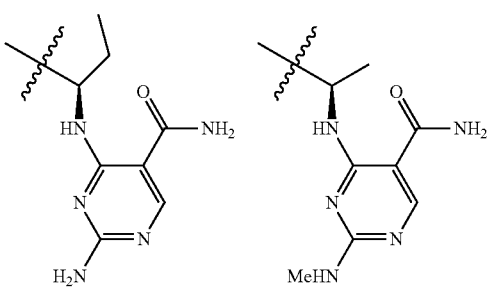 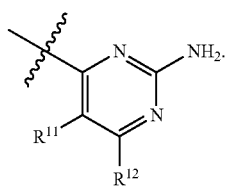
In certain embodiments, $W_d$ is
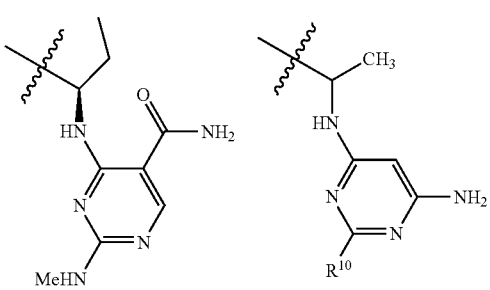 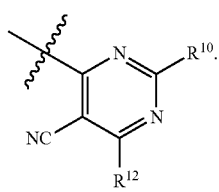
In some embodiments, $W_d$ is
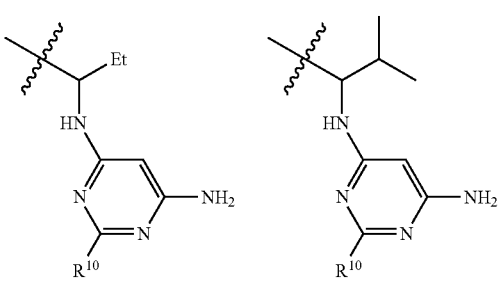 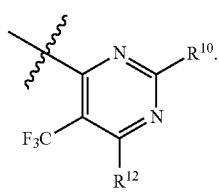
In some embodiments, $W_d$ is
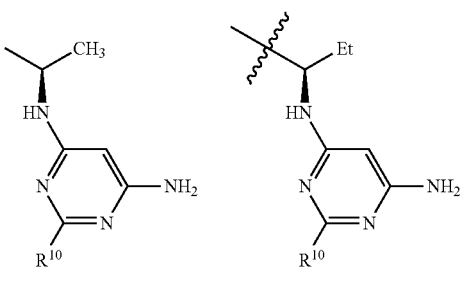 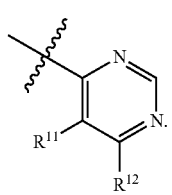
In some embodiments, $W_d$ is
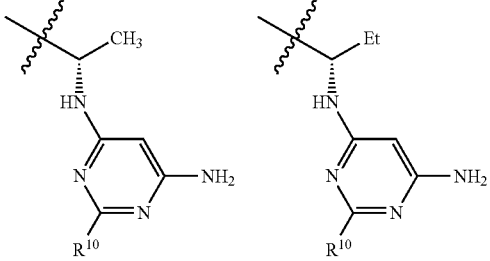 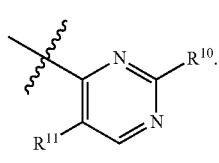
In some embodiments, $W_d$ is In some embodiments, $W_d$ is

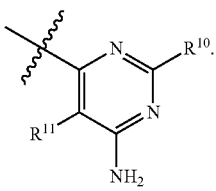

In some embodiments, $W_d$ is

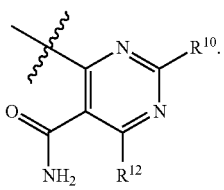

In certain embodiments, $R^{10}$ is hydrogen. In some embodiments, $R^{10}$ is amino.

In certain embodiments, $R^{11}$ is haloalkyl (e.g., trifluoromethyl). In some embodiments, $R^{11}$ is cyano. In some embodiments, $R^{11}$ is amido.

In certain embodiments, $R^{12}$ is hydrogen. In some embodiments, $R^{12}$ is amino.

In certain embodiments, $W_d$ is

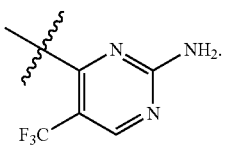 [SMILES: *c1nc(N)ncc1C(F)(F)F]

In some embodiments, $W_d$ is

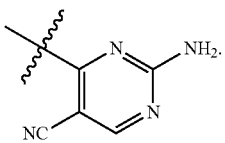 [SMILES: *c1nc(N)ncc1C#N]

In some embodiments, $W_d$ is

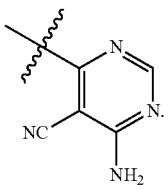 [SMILES: *c1ncnc(N)c1C#N]

In some embodiments, $W_d$ is

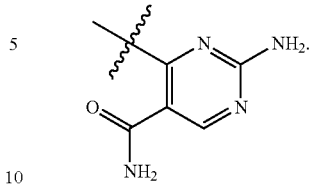

In some embodiments, A is N. In other embodiments, A is $CR^{19}$, wherein $R^{19}$ is hydrogen, alkyl, haloalkyl, arylalkyl, heterocyclyl, heteroaryl, heteroalkyl, amido, amino, halo, hydroxyl, alkoxy, or cyano. In some embodiments, $R^{19}$ is hydrogen, alkyl, haloalkyl, halo, amido, amino or cyano.

In certain embodiments, when $R^3$ is methyl, B is not phenyl or cyclopropyl substituted with 0 occurrences of $R^{13}$.

In certain embodiments, when $R^3$ is 1-methyl-4-pyrazolyl, B is not phenyl or cyclopropyl substituted with 0 occurrences of $R^{13}$.

In certain embodiments, when $R^3$ is chloro, $R^{11}$ is not hydrogen, methyl or trifluoromethyl.

In certain embodiments, $R^3$ is methyl and $R^{11}$ is cyano. In some embodiments, $R^3$ is chloro and $R^{11}$ is cyano.

In some embodiments, $R_{10}$ is hydrogen and $R_{12}$ is —$NH_2$.

In some embodiments of the compound of Formula (I), at least one of $R^{10}$, $R^{11}$ and $R^{12}$ is hydrogen, cyano, halo, unsubstituted or substituted alkyl, unsubstituted or substituted alkynyl, or unsubstituted or substituted alkenyl. In some embodiments, at least one of $R^{10}$, $R^{11}$ and $R^{12}$ is unsubstituted or substituted aryl. In some embodiments, at least one of $R^{10}$, $R^{11}$ and $R^{12}$ is unsubstituted or substituted heteroaryl, which includes, but is not limited to, heteroaryl having a five membered ring, heteroaryl having a six membered ring, heteroaryl with at least one nitrogen ring atom, heteroaryl with two nitrogen ring atoms, monocylic heteroaryl, and bicylic heteroaryl. In some embodiments, at least one of $R^{10}$, $R^{11}$ and $R^{12}$ is unsubstituted or substituted heterocyclyl, which includes, but is not limited to, heterocyclyl with one nitrogen ring atom, heterocyclyl with one oxygen ring atom, heterocyclyl with one sulfur ring atom, 5 membered heterocyclyl, 6 membered heterocyclyl, saturated heterocyclyl, unsaturated heterocyclyl, heterocyclyl having an unsaturated moiety connected to the heterocyclyl ring, heterocyclyl substituted by oxo, and heterocyclyl substituted by two oxo. In some embodiments, at least one of $R^{10}$, $R^{11}$ and $R^{12}$ is unsubstituted or substituted cycloalkyl, including, but not limited to, cyclopropyl, cyclobutyl, cyclopentyl, cyclohexyl, cycloalkyl, each of which can be substituted by one oxo, and cycloalkyl having an unsaturated moiety connected to the cycloalkyl ring. In some embodiments, at least one of $R^{10}$, $R^{11}$ and $R^{12}$ is unsubstituted or substituted amido, unsubstituted or substituted acyloxy, unsubstituted or substituted alkoxycarbonyl, unsubstituted or substituted acyl, or unsubstituted or substituted sulfonamido.

In some embodiments, when at least one of $R^{10}$, $R^{11}$ and $R^{12}$ is alkyl, alkynyl, alkenyl, aryl, heteroaryl, heterocyclyl, cycloalkyl, alkoxycarbonyl, amido, acyloxy, acyl, or sulfonamido, it is substituted with one or more of alkyl, heteroalkyl, alkenyl, alkynyl, cycloalkyl, heterocyclyl, aryl, heteroaryl, alkoxy, amido, amino, acyl, acyloxy, alkoxycarbonyl, sulfonamido, halo, cyano, hydroxyl or nitro, each of which alkyl, heteroalkyl, alkenyl, alkynyl, cycloalkyl, heterocyclyl, aryl, heteroaryl, alkoxy, amido, amino, acyl, acyloxy, alkoxycarbonyl, or sulfonamido can itself be substituted.

In some embodiments, B is alkyl, heteroalkyl, cycloalkyl, heterocyclyl, aryl, or heteroaryl, each of which is substituted with 0-4 $R^2$. In certain embodiments, B is aryl (e.g., 6-membered aryl) substituted with 0-4 occurrences of $R^2$. In some embodiments, B is phenyl substituted with 0-4 occurrences of $R^2$. In some embodiments, B is phenyl substituted with 0 occurrences of $R^2$. In some embodiments, B is phenyl substituted with 1 occurrence of $R^2$. In some embodiments, $R^2$ is halo (e.g., fluoro).

In some embodiments, B is unsubstituted or substituted alkyl, including, but not limited to —$(CH_2)_2$—$NR^aR^a$, wherein each $R^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl, or Nine are combined together to form a cyclic moiety, which includes, but is not limited to, piperidinyl, piperazinyl, and morpholinyl. In some embodiments, B is unsubstituted or substituted amino. In some embodiments, B is unsubstituted or substituted heteroalkyl. In some embodiments, B is alkyl or cycloalkyl substituted with 0-4 occurrences or $R^2$. In some embodiments, B is isopropyl.

In some embodiments, B is selected from unsubstituted or substituted aryl, including, but not limited to, unsubstituted or substituted phenyl; unsubstituted or substituted heteroaryl including, but not limited to, pyridin-2-yl, pyridin-3-yl, pyridin-4-yl, pyrimidin-4-yl, pyrimidin-2-yl, pyrimidin-5-yl, or pyrazin-2-yl; unsubstituted or substituted monocyclic heteroaryl; unsubstituted or substituted bicyclic heteroaryl; a heteroaryl having two heteroatoms as ring atoms; unsubstituted or substituted heteroaryl comprising a nitrogen ring atom; unsubstituted or substituted heteroaryl having two nitrogen ring atoms; unsubstituted or substituted heteroaryl having a nitrogen and a sulfur as ring atoms; unsubstituted or substituted heterocyclyl including, but not limited to, morpholinyl, tetrahydropyranyl, piperazinyl, and piperidinyl; and unsubstituted or substituted cycloalkyl including, but not limited to, cyclopentyl and cyclohexyl.

In some embodiments, B is one of the following moieties:

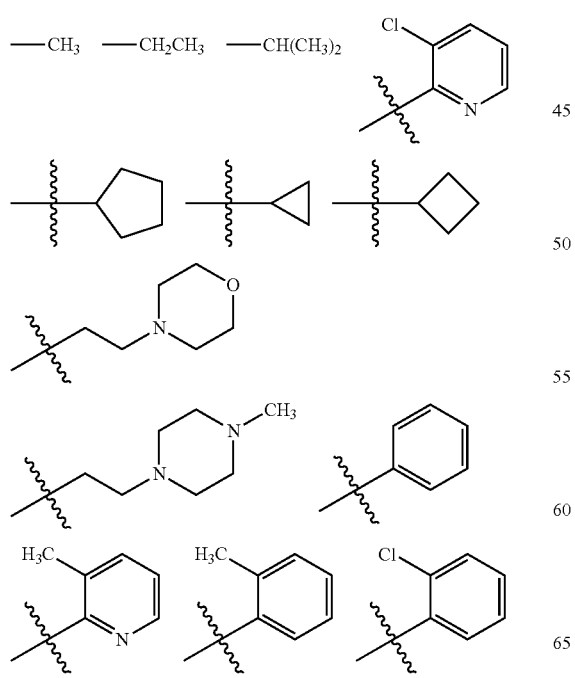

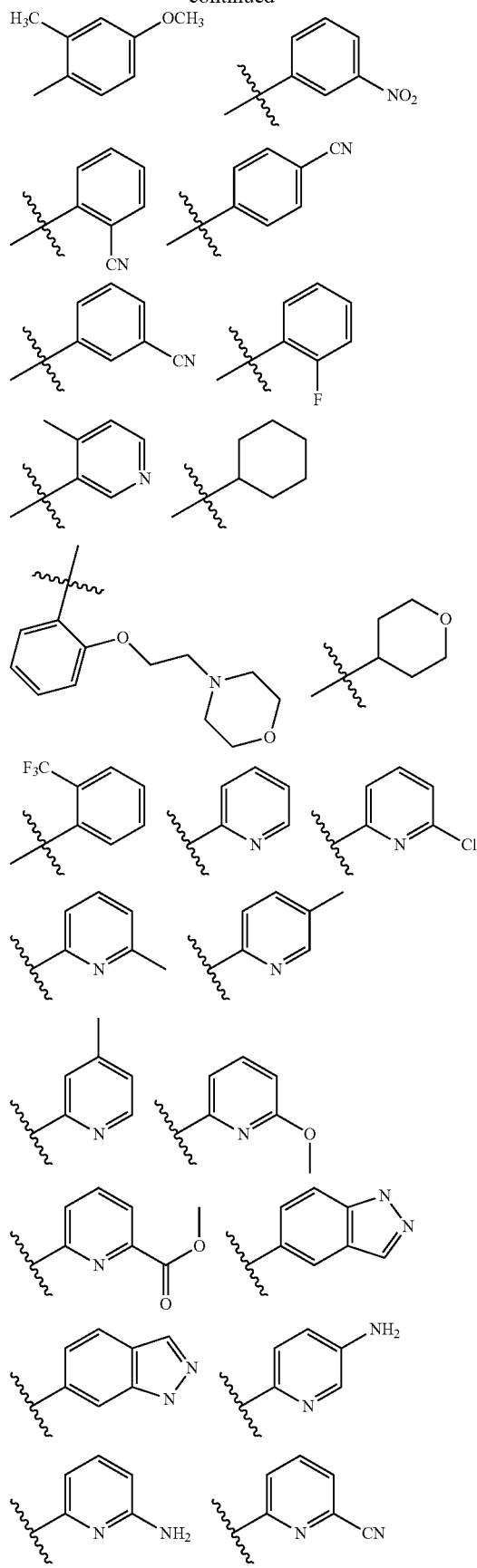

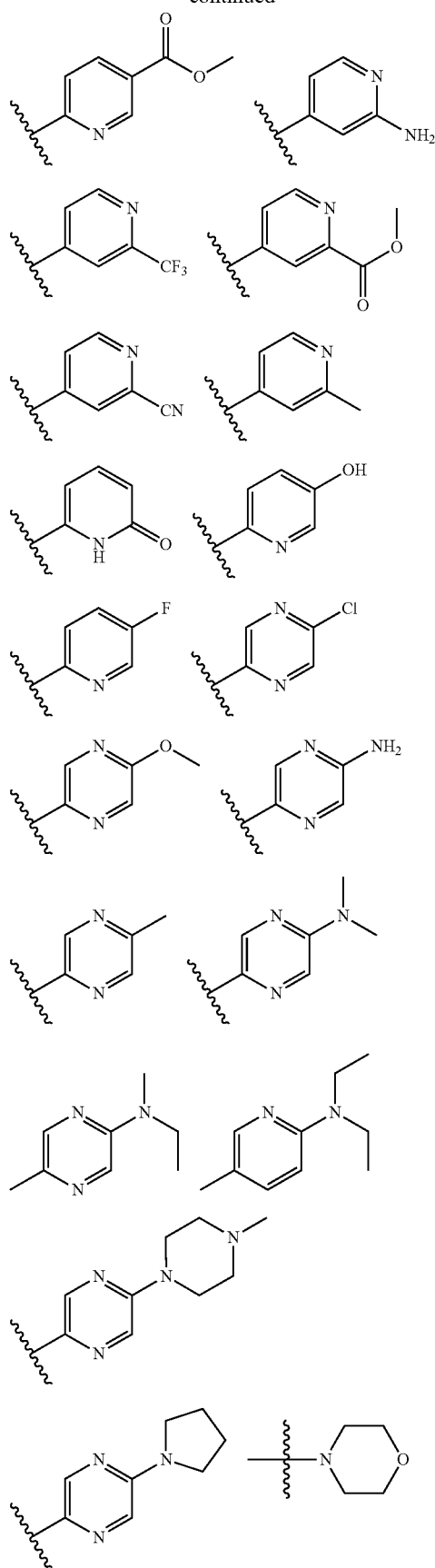
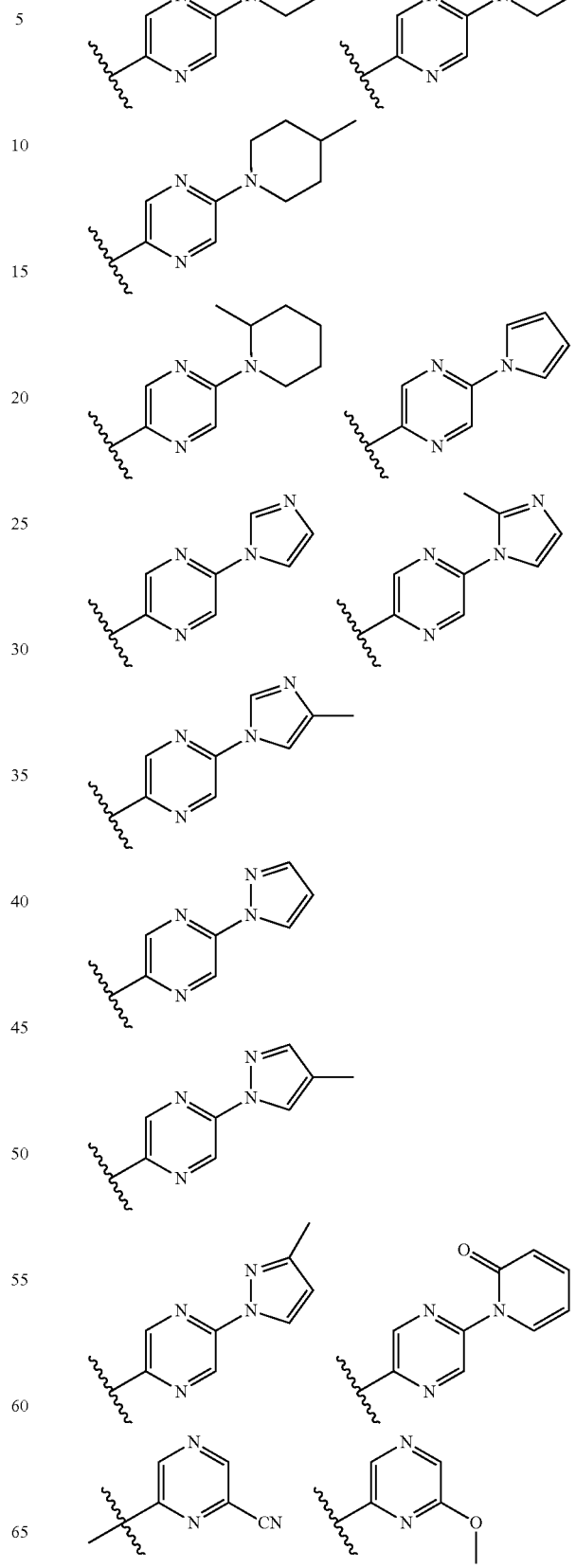

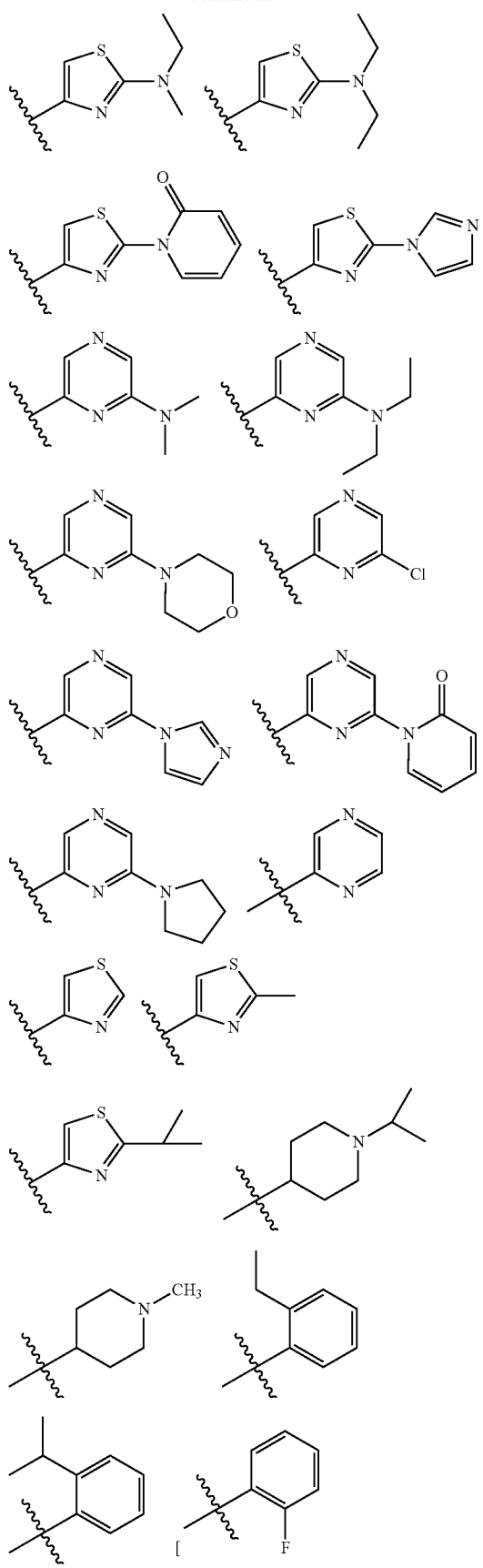
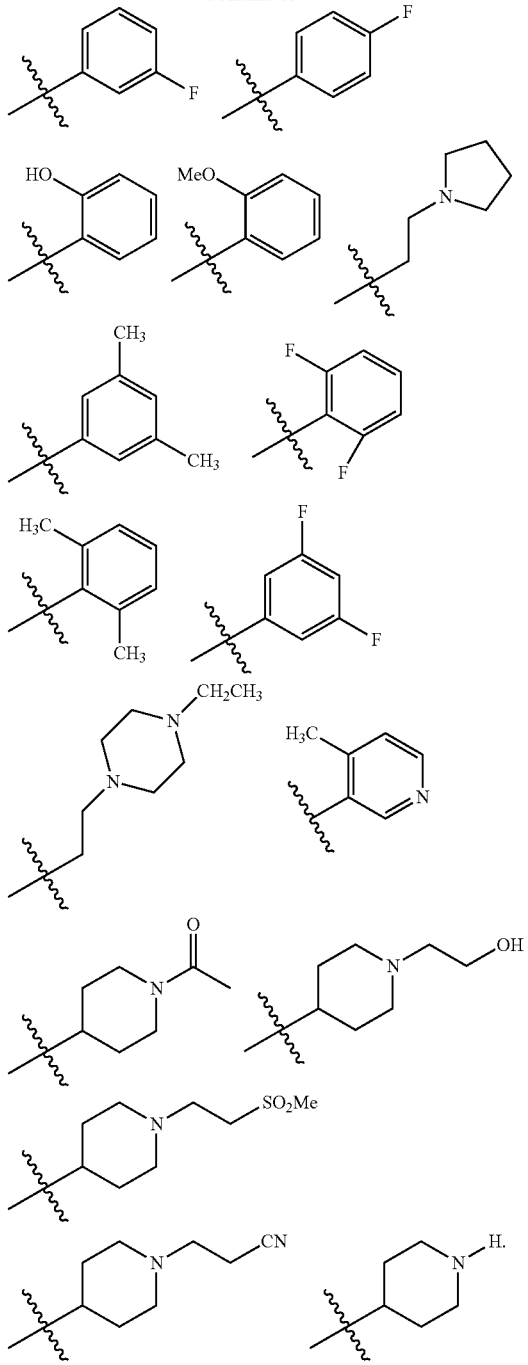

In some embodiments, B is unsubstituted or substituted with one or more $R^2$ substituents. In some embodiments, $R^2$ is alkyl, heteroalkyl, alkenyl, alkynyl, cycloalkyl, heterocyclyl, aryl, heteroaryl, alkoxy, amido, amino, acyl, acyloxy, alkoxycarbonyl, sulfonamido, halo, cyano, hydroxyl or nitro, each of which alkyl, heteroalkyl, alkenyl, alkynyl, cycloalkyl, heterocyclyl, aryl, heteroaryl, alkoxy, amido, amino, acyl, acyloxy, alkoxycarbonyl or sulfonamido, can itself be substituted.

In some embodiments, $R^2$ is unsubstituted or substituted alkyl, unsubstituted or substituted heteroalkyl, unsubstituted or substituted alkenyl, unsubstituted or substituted alkynyl, unsubstituted or substituted cycloalkyl, or unsubstituted or substituted heterocyclyl. In some embodiments, $R^2$ is unsubstituted or substituted aryl, unsubstituted or substituted arylalkyl, unsubstituted or substituted heteroaryl, or unsubstituted or substituted heteroarylalkyl. In some embodiments, $R^2$ is unsubstituted or substituted alkoxy, unsubstituted or substituted amido, or unsubstituted or substituted amino. In some embodiments, $R^2$ is unsubstituted or substituted acyl, unsubstituted or substituted acyloxy, unsubstituted or substituted alkoxycarbonyl, or unsubstituted or substituted sulfonamido. In some embodiments, $R^2$ is halo, selected from —I, —F, —Cl, and —Br. In some embodiments, $R^2$ is selected from cyano, hydroxyl, nitro, and a carbonate. In some embodiments, $R^2$ is unsubstituted or substituted phosphate. In some embodiments, $R^2$ is unsubstituted or substituted urea. In some embodiments, when $R^2$ is alkyl, $R^2$ is methyl, ethyl, propyl, isopropyl, n-butyl, tert-butyl, sec-butyl, pentyl, hexyl or heptyl.

In some embodiments, when $R^2$ is alkyl, heteroalkyl, alkenyl, alkynyl, cycloalkyl, heterocyclyl, aryl, arylalkyl, heteroaryl, heteroarylalkyl, alkoxy, amido, amino, acyl, acyloxy, alkoxycarbonyl, sulfonamido, or hydroxyl, it is substituted by phosphate, substituted by urea, or substituted by carbonate.

In some embodiments, when $R^2$ is alkyl, heteroalkyl, alkenyl, alkynyl, cycloalkyl, heterocyclyl, aryl, arylalkyl, heteroaryl, heteroarylalkyl, alkoxy, amido, amino, acyl, acyloxy, alkoxycarbonyl, or sulfonamido, it is substituted by one or more of alkyl, heteroalkyl, alkenyl, alkynyl, cycloalkyl, heterocyclyl, aryl, heteroaryl, alkoxy, amido, amino, acyl, acyloxy, alkoxycarbonyl, sulfonamido, halo, cyano, hydroxyl or nitro, each of which alkyl, heteroalkyl, alkenyl, alkynyl, cycloalkyl, heterocyclyl, aryl, heteroaryl, alkoxy, amido, amino, acyl, acyloxy, alkoxycarbonyl, or sulfonamido can itself be substituted.

In some embodiments, there are no occurrences of $R^2$. In other embodiments, there is one occurrence of $R^2$. In still other embodiments, there are two occurrences of $R^2$. In yet other embodiments, there are three occurrences of $R^2$. In yet other embodiments, there are four occurrences of $R^2$. For example, in some embodiments B is aryl or heteroaryl and there are no occurrences of $R^2$. In other instances, B is aryl or heteroaryl and there is one occurrence of $R^2$ where $R^2$ is alkyl or halo.

In some embodiments, $R^3$ is hydrogen. In some embodiments, $R^3$ is unsubstituted or substituted alkyl, unsubstituted or substituted alkenyl, or unsubstituted or substituted alkynyl. In some embodiments, $R^3$ is unsubstituted or substituted aryl, unsubstituted or substituted heteroaryl, unsubstituted or substituted cycloalkyl, or unsubstituted or substituted heterocyclyl. In some embodiments, $R^3$ is unsubstituted or substituted alkoxy, unsubstituted or substituted amido, or unsubstituted or substituted amino. In some embodiments, $R^3$ is unsubstituted or substituted acyl, unsubstituted or substituted acyloxy, or unsubstituted or substituted sulfonamido. In some embodiments, $R^3$ is halo, selected from —I, —F, —Cl, and —Br. In some embodiments, $R^3$ is H, halo, alkyl, alkoxy, heteroaryl, or cycloalkyl. For example, $R^3$ is H, $CH_3$, $CH_2CH_3$, $CF_3$, Cl, or F. In some instances, $R^3$ is $CH_3$, $CF_3$, or Cl.

In some embodiments, $R^3$ is selected from cyano, hydroxyl, and nitro. In some embodiments, when $R^3$ is alkyl, $R^3$ is methyl, ethyl, propyl, isopropyl, n-butyl, tert-butyl, sec-butyl, pentyl, hexyl or heptyl. In some embodiments, $R^3$ is —$CF_3$, —$CH_2F$ or —$CHF_2$.

In some embodiments, when $R^3$ is alkyl, alkenyl, alkynyl, aryl, heteroaryl, cycloalkyl, heterocyclyl, alkoxy, amido, amino, acyl, acyloxy, or sulfonamido, it is substituted with one or more of alkyl, heteroalkyl, alkenyl, alkynyl, cycloalkyl, heterocyclyl, aryl, heteroaryl, alkoxy, amido, amino, acyl, acyloxy, alkoxycarbonyl, sulfonamido, halo, cyano, hydroxyl or nitro, each of which alkyl, heteroalkyl, alkenyl, alkynyl, cycloalkyl, heterocyclyl, aryl, heteroaryl, alkoxy, amido, amino, acyl, acyloxy, alkoxycarbonyl, or sulfonamido can itself be substituted.

In some embodiments, $R^3$ is a 5-membered heteroaryl group. Such groups include, for example, pyrrole, furan, thiophene, triazole, oxazole, pyrazole, and isoxazole. In other embodiments, $R^3$ is a 5-membered heterocycle, including, but not limited to, oxazoline and oxazolidinone. In still other embodiments, $R^3$ is a 6-membered heteroaryl group including, but not limited to, pyridine, pyrazine, pyrimidine and pyridazine. Alternatively, $R^3$ is a 6-membered heterocycle, including moieties such as morpholino or piperidino. In other embodiments, $R^3$ is a fused 5/6-bicyclic heteroaryl, for example, benzothiazole, benzoxazole, benzisoxazole, indazole, benzimidazole, benzothiophene, indole, isoindole, purine, or pyrazolopyrimidine. In yet other embodiments, $R^3$ is a fused 5/6-bicyclic heterocycle.

In some embodiments, $R^3$ is a $C_1$-$C_6$ alkyl group substituted with a 5-membered heteroaryl, a 5-membered heterocycle, a 6-membered heteroaryl, a 6-membered heterocycle, a fused 5/6-bicyclic heteroaryl, or a fused 5/6-bicyclic heterocycle. Alternatively, $R^3$ is amino, sulfonyl, sulfonyl, sulfoxide, sulfone, or alkoxy where the N, S or O heteroatom has a covalent bond either directly or through a $C_1$-$C_6$ alkyl group to a 5-membered heteroaryl, a 5-membered heterocycle, a 6-membered heteroaryl, a 6-membered heterocycle, a fused 5/6-bicyclic heteroaryl, or a fused 5/6-bicyclic nonaromatic heterocycle.

In other embodiments, $R^3$ is a $C_1$-$C_6$ alkyl group substituted with a fused polycyclic group, wherein the polycyclic group has greater than two rings and is carbocyclic or heterocyclic; $C_1$-$C_6$ alkyl group substituted with a bridged cycloalkyl or bridged heterocyclic group; $C_1$-$C_6$ alkyl group substituted with a spirocyclic cycloalkyl or spirocyclic heterocyclic group; or branched $C_4$-$C_{12}$ alkyl group, wherein said branched alkyl group contains at least one terminal t-butyl group.

Each of the embodiments named above for $R^3$ is unsubstituted or optionally additionally substituted with an alkyl, heteroalkyl, alkenyl, alkynyl, cycloalkyl, heterocyclyl, aryl, heteroaryl, alkoxy, amido, amino, acyl, acyloxy, alkoxycarbonyl, sulfonamido, halo, cyano, hydroxyl or nitro group.

In certain embodiments, $R^3$ is a substituted or unsubstituted heterocyclyl or heteroaryl group selected from pyridine, pyrazole, piperazine, and pyrrolidine, wherein the substituent can be a $C_1$-$C_6$ alkyl group or a halogen.

In some embodiments, a compound is provided wherein $R^3$ is selected from a 5-membered heteroaryl such as a pyrrole, a furan, or a thiophene group; 5-membered nonaromatic heterocyclyl such as a pyrrolidine, a tetrahydrofuran, or a tetrahydrothiophene group; 6-membered heteroaryl such as pyridine, pyrazine, pyrimidine, or pyridazine; 6-membered nonaromatic heterocyclyl such as piperidine, tetrahydropyran, or thiane; and fused 5/6-bicyclic heteroaryl such as indole, isoindole, benzofuran, isobenzofuran, benzothiophene, benzimidazole, indazole, benzoxazole, benzisoxazole, or purine. In certain embodiments, $R^3$ is a substituted or unsubstituted group such as pyridine, pyrazole, piperazine, or pyrrolidine. By way of non-limiting example, the $R^3$ group can be substituted with a $C_1$-$C_6$ alkyl group or a halogen. For example, the $R^3$ group can be substituted with a methyl group.

In some embodiments, a compound is provided wherein $R^3$ is selected from

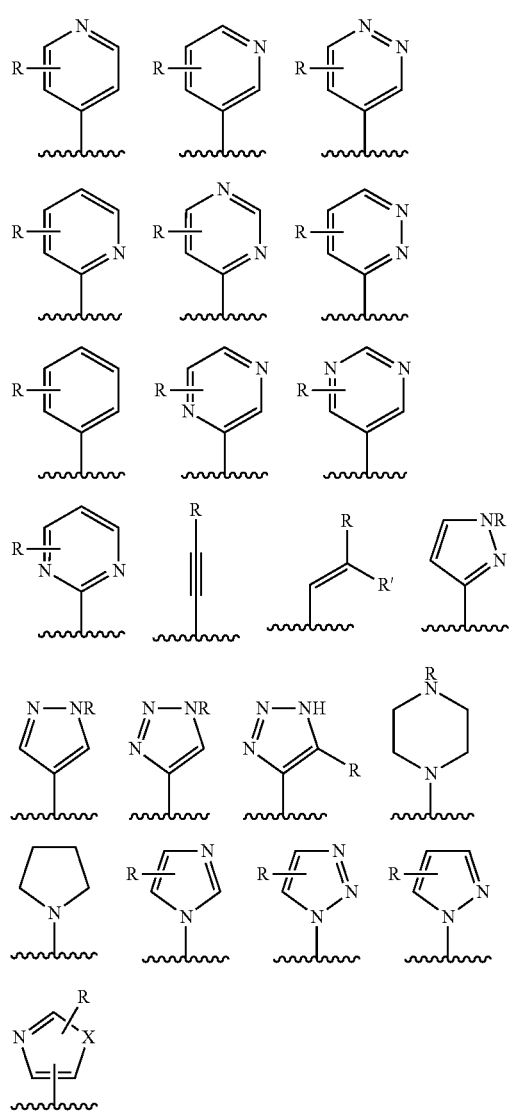

wherein R is H, $C_1$-$C_6$ alkyl, $C_1$-$C_6$ alkoxy, halo, and haloalkyl. In certain embodiments, R is methyl. In other embodiments, a compound is provided wherein $R^3$ is selected from:

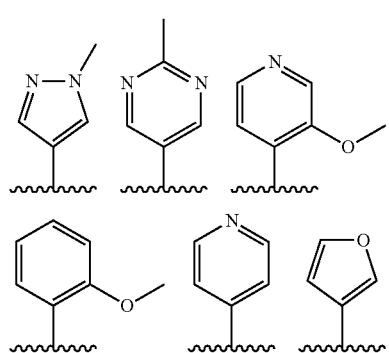

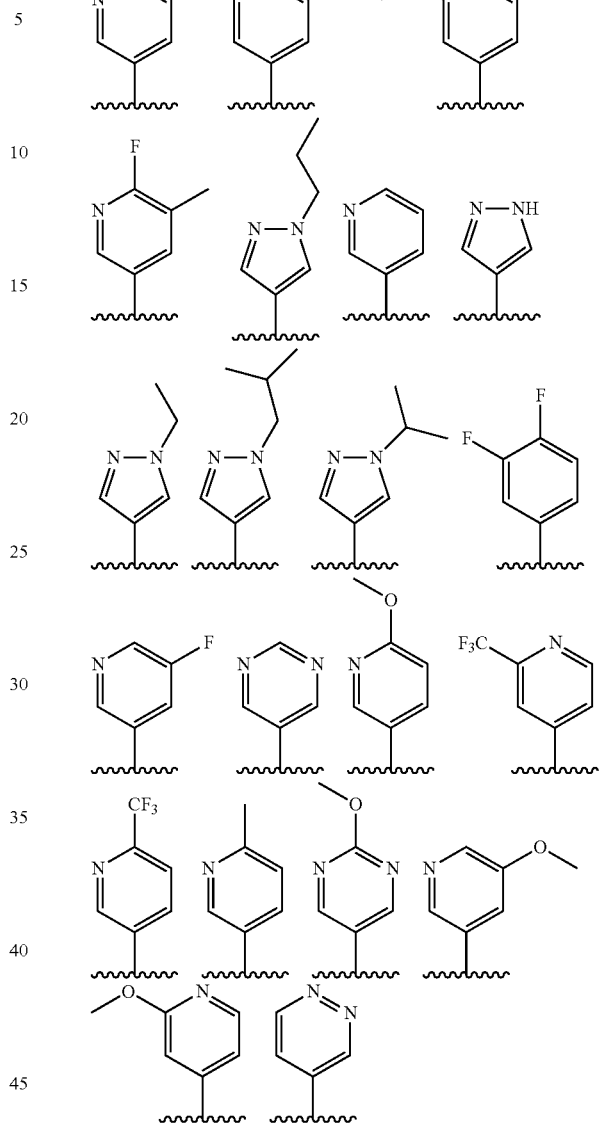

In some embodiments, X is absent. In some embodiments, X is —(CH($R^9$))$_z$—, and z is an integer of 1, 2, 3 or 4.

In some embodiments, $R^9$ is unsubstituted or substituted alkyl including, but not limited to unsubstituted or substituted $C_1$-$C_{10}$alkyl. In some embodiments, $R^9$ is unsubstituted or substituted cycloalkyl including, but not limited to unsubstituted or substituted $C_3$-$C_7$ cycloalkyl. In some embodiments, $R^9$ is ethyl, methyl or hydrogen. In some embodiments, $R^9$ is unsubstituted or substituted heterocyclyl including, but not limited to, unsubstituted or substituted $C_2$-$C_{10}$heteroalkyl. In some embodiments, $R^9$ is unsubstituted or substituted heteroalkyl including, but not limited to, unsubstituted or substituted $C_2$-$C_{10}$heteroalkyl.

Also provided herein is a compound of Formula (I) wherein $R^9$ is hydrogen, and X is —$CH_2$—, —$CH_2CH_2$—, —$CH_2CH_2CH_2$—, —$CH(CH_3)$—, or —$CH(CH_2CH_3)$—. In other embodiments, X is —(CH($R^9$))$_z$—, $R^9$ is not hydrogen, and z is an integer of 1. When X is —CH($R^9$)— and $R^9$ is not hydrogen, then the compound can adopt either an (S)- or (R)-stereochemical configuration with respect to the CH carbon. In some embodiments, the compound is a racemic mixture of (S)- and (R) isomers with respect to the CH carbon. In other embodiments, provided herein is a mixture of compounds of Formula (I), wherein individual compounds of the mixture exist predominately in an (S)— or (R)-isomeric configuration. For example, the compound mixture has an (S)-enantiomeric excess of greater than about 55%, about 60%, about 65%, about 70%, about 75%, about 80%, about 85%, about 90%, about 95%, about 96%, about 97%, about 98%, about 99%, about 99.5%, or more at the X carbon. In other embodiments, the compound mixture has an (S)-enantiomeric excess of greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5%, or more.

In other embodiments, the compound mixture has an (R)-enantiomeric excess of greater than about 55%, about 60%, about 65%, about 70%, about 75%, about 80%, about 85%, about 90%, about 95%, about 96%, about 97%, about 98%, about 99%, about 99.5%, or more at the CH carbon. In some other embodiments, the compound mixture has an (R)-enantiomeric excess of greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5%, or more.

In some embodiments of the compound of Formula (I), X is —CH($R^9$)—, $R^9$ is methyl or ethyl, and the compound is the (S)-isomer.

In some embodiments of the compound of Formula (I), Y is absent.

In some embodiments, Y is —O—, —S—, —S(═O)—, —S(═O)$_2$—, —C(═O)—, —N($R^9$)(C═O)—, —N($R^9$)(C═O)NH—, —N($R^9$)C($R^9$)$_2$— (such as —N($R^9$)CH$_2$—, including, but not limited to, —N(CH$_3$)CH$_2$—, N(CH(CH$_3$)$_2$)CH$_2$— or —N(CH$_2$CH$_3$)CH$_2$—), —N($R^9$)—, —N(CH$_3$)—, —N(CH$_2$CH$_3$)—, or —N(CH(CH$_3$)$_2$)—. In some embodiments, Y is —C(═O)—(CHR$^9$)$_z$— and z is an integer of 1, 2, 3, or 4.

In some embodiments, at least one of X and Y is present. In some embodiments of the compound of Formula I, —XY— is —CH$_2$—, —CH$_2$—N(CH$_3$), —CH$_2$—N(CH$_2$CH$_3$), —CH(CH$_3$)—NH—, (S)—CH(CH$_3$)—NH—, or (R)—CH(CH$_3$)—NH—. In other embodiments, X—Y is —N(CH$_3$)—CH$_2$—, N(CH$_2$CH$_3$) CH$_2$—, —N(CH(CH$_3$)$_2$)CH$_2$—, or —NHCH$_2$—.

In certain embodiments, the compound of Formula (I) has a structure of Formula (IV):

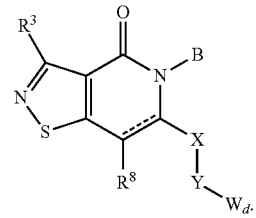

Formula (IV)

In some embodiments, the compound of Formula (IV) has a structure of Formula (V):

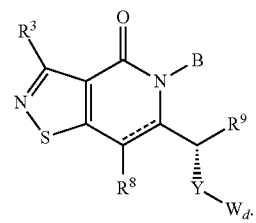

Formula (V)

In certain embodiments, the compound of Formula (I) has a structure of Formula (VI):

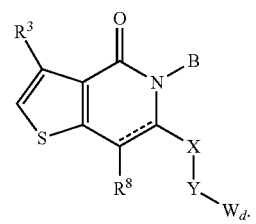

Formula (VI)

In certain embodiments, the compound of Formula (VI) has a structure of Formula (VII):

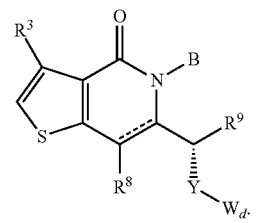

Formula (VII)

In certain embodiments, the compound of Formula (VI) has a structure of Formula (VIII):

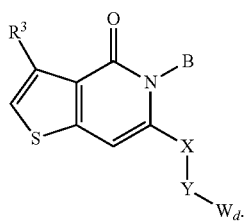

Formula (VIII)

In some embodiments, the compound of Formula (VIII) has a structure of Formula (IX):

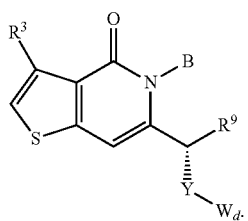

Formula (IX)

In one aspect, B is selected from the moieties presented in Table 1.

TABLE 1

Illustrative B moieties of the compounds described herein.

| Subclass # | B |
|---|---|
| B-1 | cyclopentyl |
| B-2 | 1-isopropylpiperidin-4-yl |
| B-3 | —CH(CH₃)₂ |
| B-4 | 2-(trifluoromethyl)phenyl |
| B-5 | cyclopropyl |
| B-6 | 2-chlorophenyl |

TABLE 1-continued

Illustrative B moieties of the compounds described herein.

| Subclass # | B |
|---|---|
| B-7 | 2-methylphenyl |
| B-8 | 3-methylpyridin-2-yl |
| B-9 | 2-ethylphenyl |
| B-10 | 2-fluorophenyl |
| B-11 | 1-methylpiperidin-4-yl |
| B-12 | 2-isopropylphenyl |
| B-13 | 2-methoxyphenyl |
| B-14 | 3-fluorophenyl |
| B-15 | 2-hydroxyphenyl |

TABLE 1-continued
Illustrative B moieties of the compounds described herein.
| Sub-class # | B |
|---|---|
| B-16 | 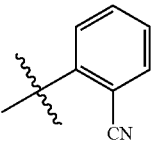 |
| B-17 | 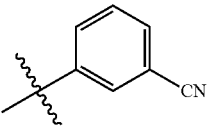 [SMILES: *c1cccc(C#N)c1] |
| B-18 | 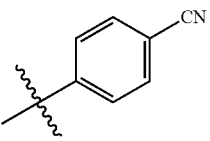 [SMILES: *c1ccc(C#N)cc1] |
| B-19 | 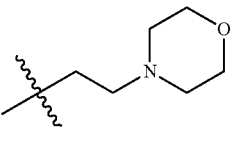 [SMILES: *CCN1CCOCC1] |
| B-20 | 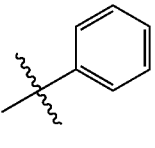 |
| B-21 | 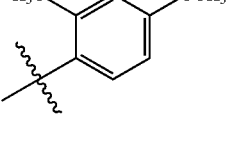 |
| B-22 | 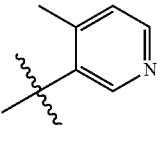 [SMILES: *c1cnccc1C] |
| B-23 | 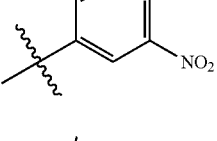 |
| B-24 | 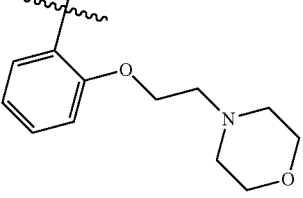 |
| B-25 | 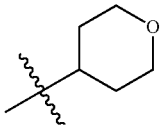 [SMILES: *C1CCOCC1] |
| B-26 | 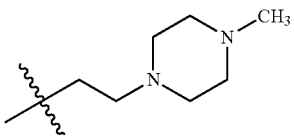 [SMILES: *CCN1CCN(C)CC1] |
| B-27 | 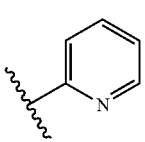 [SMILES: *c1ccccn1] |
| B-28 | 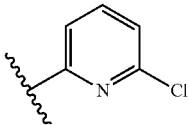 [SMILES: *c1cccc(Cl)n1] |
| B-29 | 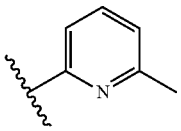 [SMILES: *c1cccc(C)n1] |
| B-30 | 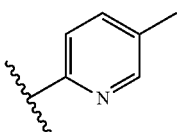 [SMILES: *c1ccc(C)cn1] |
| B-31 | 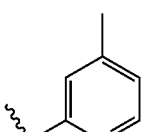 |
| B-32 | 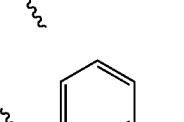 |
| B-33 | 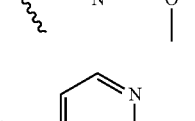 |
| B-34 | 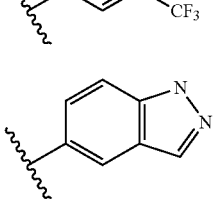 |

TABLE 1-continued

Illustrative B moieties of the compounds described herein.

| Sub-class # | B |
|---|---|
| B-35 | (6-indazolyl) |
| B-36 | (5-amino-2-pyridyl) |
| B-37 | (6-amino-2-pyridyl) |
| B-38 | (6-cyano-2-pyridyl) |
| B-39 | (methyl 6-pyridyl-3-carboxylate) |
| B-40 | (5-chloro-2-pyrazinyl) |
| B-41 | (methyl 6-pyridyl-2-carboxylate) |
| B-42 | (methyl 4-pyridyl-2-carboxylate) |
| B-43 | (2-cyano-4-pyridyl) |
| B-44 | (6-methyl-3-pyridyl) |
| B-45 | (6-oxo-1,6-dihydropyridin-2-yl) |
| B-46 | (5-hydroxy-2-pyridyl) |
| B-47 | (5-fluoro-2-pyridyl) |
| B-48 | (2-amino-4-pyridyl) |
| B-49 | (5-methoxy-2-pyrazinyl) |
| B-50 | (5-amino-2-pyrazinyl) |
| B-51 | (5-methyl-2-pyrazinyl) |
| B-52 | (5-(dimethylamino)-2-pyrazinyl) |

TABLE 1-continued

Illustrative B moieties of the compounds described herein.

| Subclass # | B |
|---|---|
| B-53 | (pyrazine with N(methyl)(ethyl)) |
| B-54 | (pyrazine with N(ethyl)2) |
| B-55 | (pyrazine with 4-methylpiperazin-1-yl) |
| B-56 | (pyrazine with pyrrolidin-1-yl) |
| B-57 | (pyrazine with piperidin-1-yl) |
| B-58 | (pyrazine with morpholin-4-yl) |
| B-59 | (pyrazine with 4-methylpiperidin-1-yl) |
| B-60 | (pyrazine with 2-methylpiperidin-1-yl) |
| B-61 | (pyrazine with 1H-pyrrol-1-yl) |
| B-62 | (pyrazine with 1H-imidazol-1-yl) |
| B-63 | (pyrazine with 2-methyl-1H-imidazol-1-yl) |
| B-64 | (pyrazine with 4-methyl-1H-imidazol-1-yl) |
| B-65 | (pyrazine with 1H-pyrazol-1-yl) |
| B-66 | (pyrazine with 4-methyl-1H-pyrazol-1-yl) |

TABLE 1-continued

Illustrative B moieties of the compounds described herein.

| Sub-class # | B |
|---|---|
| B-67 | (3-methyl-pyrazol-1-yl)pyrazinyl |
| B-68 | (2-oxopyridin-1-yl)pyrazinyl |
| B-69 | (cyano)pyrazinyl |
| B-70 | (methoxy)pyrazinyl |
| B-71 | (dimethylamino)pyrazinyl |
| B-72 | (diethylamino)pyrazinyl |
| B-73 | (morpholin-4-yl)pyrazinyl |
| B-74 | (chloro)pyrazinyl |
| B-75 | (imidazol-1-yl)pyrazinyl |
| B-76 | (2-oxopyridin-1-yl)pyrazinyl |
| B-77 | (pyrrolidin-1-yl)pyrazinyl |
| B-78 | (methyl)pyrazinyl |
| B-79 | thiazol-4-yl |
| B-80 | (2-methyl)thiazol-4-yl |
| B-81 | (2-isopropyl)thiazol-4-yl |
| B-82 | (2-(N-ethyl-N-methylamino))thiazol-4-yl |
| B-83 | (2-diethylamino)thiazol-4-yl |

TABLE 1-continued
Illustrative B moieties of the compounds described herein.
| Sub-class # | B |
|---|---|
| B-84 | 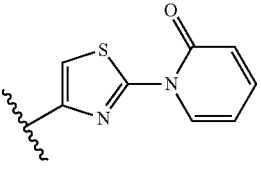 [SMILES: *c1csc(-n2ccccc2=O)n1] |
| B-85 | 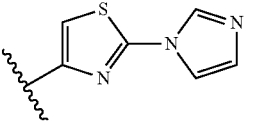 |
| B-86 | 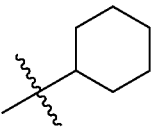 |
| B-87 | —CH$_3$ |
| B-88 | —CH$_2$CH$_3$ |
| B-89 |  |
| B-90 |  |
| B-91 | 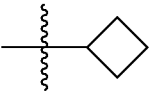 [SMILES: *C1CCC1] |
| B-92 | 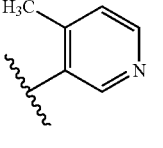 |
| B-93 | 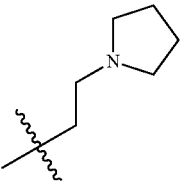 [SMILES: *CCN1CCCC1] |
| B-94 | 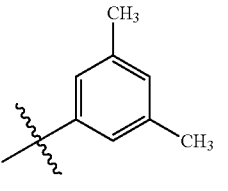 [SMILES: *c1cc(C)cc(C)c1] |
| B-95 | 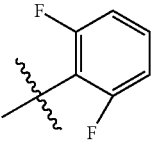 [SMILES: *c1c(F)cccc1F] |
| B-96 | 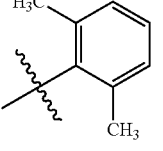 |
| B-97 | 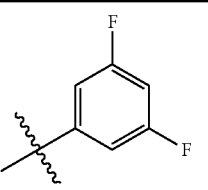 |
| B-98 | 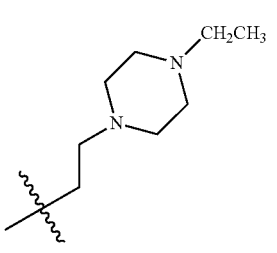 [SMILES: *CCN1CCN(CC)CC1] |
| B-99 | 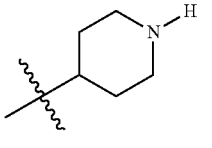 [SMILES: *C1CCNCC1] |
| B-100 | 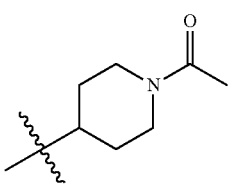 [SMILES: *C1CCN(C(C)=O)CC1] |
| B-101 | 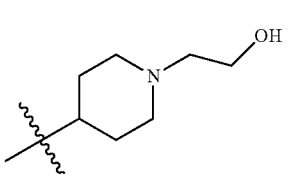 [SMILES: *C1CCN(CCO)CC1] |
| B-102 | 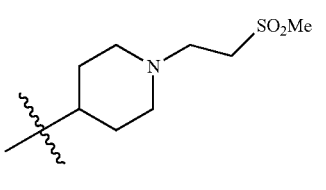 [SMILES: *C1CCN(CCS(C)(=O)=O)CC1] |
In some embodiments, provided herein are the following compounds:

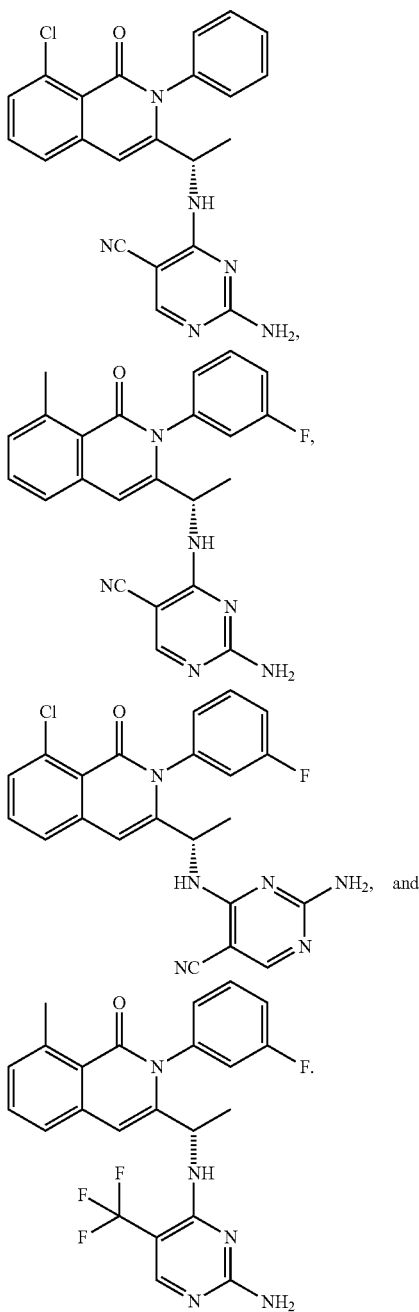

In another aspect, provided herein are compounds of Formula (XV):

Formula (XV)

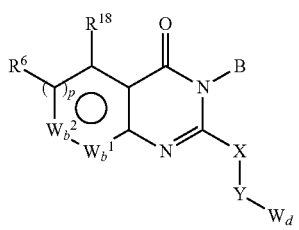

or an enantiomer, a mixture of enantiomers, or a mixture of two or more diastereomers thereof, or a pharmaceutically acceptable form thereof, wherein $W_b^1$ and $W_b^2$ are each independently $CR^6$, S, O, N or $NR^{14}$, wherein at least one of $W_b^1$ and $W_b^2$ is $CR^6$, N or $NR^{14}$;

p is 0, 1, 2 or 3;

B is hydrogen, alkyl, alkenyl, alkynyl, amino, heteroalkyl, cycloalkyl, heterocyclyl, aryl or heteroaryl, wherein cycloalkyl, heterocyclyl, aryl or heteroaryl are substituted with 0-4 $R^2$;

each $R^2$ is independently alkyl, heteroalkyl, alkenyl, alkynyl, cycloalkyl, heterocyclyl, aryl, arylalkyl, heteroaryl, heteroarylalkyl, alkoxy, amido, amino, acyl, acyloxy, alkoxycarbonyl, sulfonamido, halo, cyano, hydroxyl, nitro, phosphate, urea or carbonate;

X is absent or is $-(CH(R^9))_z-$;

Y is absent, $-O-$, $-S-$, $-S(=O)-$, $-S(=O)_2-$, $-N(R^9)-$, $-C(=O)-(CHR^9)_z-$, $-C(=O)-$, $-N(R^9)-C(=O)-$, $-N(R^9)-C(=O)NH-$, $-N(R^9)C(R^9)_2-$, $-C(=O)-N(R^9)_2$, or $-C(=O)-N(R^9)-(CHR^9)_z-$;

each z is independently an integer of 1, 2, 3, or 4;

each $R^6$ is independently hydrogen, alkyl, alkenyl, alkynyl, cycloalkyl, heterocyclyl, fluoroalkyl, heteroalkyl, alkoxy, amido, amino, acyl, acyloxy, sulfinyl, sulfonyl, sulfoxide, sulfone, sulfonamido, halo, cyano, heteroaryl, aryl, hydroxyl, or nitro;

each $R^9$ is independently hydrogen, alkyl, cycloalkyl, heterocyclyl or heteroalkyl;

$W_d$ is

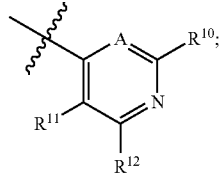

A is N or $CR^{19}$;

$R^{10}$, $R^{11}$, $R^{12}$, $R^{13}$ and $R^{19}$ are independently hydrogen, alkyl, heteroalkyl, alkenyl, alkynyl, cycloalkyl, heterocyclyl, aryl, arylalkyl, heteroaryl, heteroarylalkyl, alkoxy, heterocyclyloxy, amido, amino, acyl, acyloxy, alkoxycarbonyl, sulfonamido, halo, cyano, hydroxyl, nitro, phosphate, urea, carbonate, oxo, or NR'R" wherein R' and R" are taken together with nitrogen to form a cyclic moiety;

each $R^{14}$ is independently hydrogen, alkyl, cycloalkyl, heterocyclyl or heteroalkyl;

$R^{18}$ is hydrogen, alkyl, haloalkyl, halo, alkoxy, cycloalkyl, cycloalkylalkyl, aryl, heteroaryl, heterocyclyl, aralkyl, heteroaralkyl, heterocyclylalkyl, alkenyl, or alkynyl, or $R^{18}$ is a heteroatom selected from N, S, and O, wherein the heteroatom has a covalent bond either directly or through a $C_1$-$C_6$ alkyl group to an aryl, heteroaryl or heterocyclyl, or $R^{18}$ and $R^6$ are taken together with the carbons to which they are attached form a 5- or 6-membered ring; wherein each of the above substituents can be substituted with 0, 1, 2, or 3 $R^{13}$; and wherein both B and $R^{18}$ are not hydrogen.

In certain embodiments, $W_b^1$ is $CR^6$. In some embodiments, $W_b^1$ is N. In some embodiments, $W_b^1$ is S. In some embodiments, $W_b^1$ is O.

In certain embodiments, $W_b^2$ is $CR^6$. In some embodiments, $W_b^2$ is N. In some embodiments, $W_b^2$ is S. In some embodiments, $W_b^2$ is O.

In some embodiments, $W_b^1$ and $W_b^2$ are $CR^6$. In some embodiments, $W_b^1$ is S and $W_b^2$ is $CR^6$. In some embodiments, $W_b^1$ is S and $W_b^2$ is N.

In certain embodiments, p is 0. In some embodiments, p is 1.

In certain embodiments, $R^{18}$ is hydrogen, alkyl, halo, alkoxy, cycloalkyl, cycloalkylalkyl, aryl, heteroaryl, heterocyclyl, aralkyl, heteroaralkyl, heterocyclylalkyl, alkenyl, or alkynyl, or $R^{18}$ is a heteroatom selected from N, S, and O, wherein the heteroatom has a covalent bond either directly or through a $C_1$-$C_6$ alkyl group to an aryl, heteroaryl or heterocyclyl, or $R^{18}$ and $R^6$ are taken together with the carbons to which they are attached form a 5- or 6-membered ring; wherein each of the above substituents can be substituted with 0, 1, 2, or 3 $R^{13}$.

In some embodiments of the compound of Formula (XV), at least one of $R^{10}$, $R^{11}$ and $R^{12}$ is hydrogen, cyano, halo, unsubstituted or substituted alkyl, unsubstituted or substituted alkynyl, or unsubstituted or substituted alkenyl. In some embodiments, at least one of $R^{10}$, $R^{11}$ and $R^{12}$ is unsubstituted or substituted aryl. In some embodiments, at least one of $R^{10}$, $R^{11}$ and $R^{12}$ is unsubstituted or substituted heteroaryl, which includes, but is not limited to, heteroaryl having a 5 membered ring, heteroaryl having a six membered ring, heteroaryl with at least one nitrogen ring atom, heteroaryl with two nitrogen ring atoms, monocylic heteroaryl, and bicylic heteroaryl. In some embodiments, at least one of $R^{10}$, $R^{11}$ and $R^{12}$ is unsubstituted or substituted heterocyclyl, which includes, but is not limited to, heterocyclyl with one nitrogen ring atom, heterocyclyl with one oxygen ring atom, heterocyclyl with one sulfur ring atom, 5 membered heterocyclyl, 6 membered heterocyclyl, saturated heterocyclyl, unsaturated heterocyclyl, heterocyclyl having an unsaturated moiety connected to the heterocyclyl ring, heterocyclyl substituted by oxo, and heterocyclyl substituted by two oxo. In some embodiments, at least one of $R^{10}$, $R^{11}$ and $R^{12}$ is unsubstituted or substituted cycloalkyl, including, but not limited to, cyclopropyl, cyclobutyl, cyclopentyl, cyclohexyl, cycloalkyl, each of which can be substituted by one oxo, and cycloalkyl having an unsaturated moiety connected to the cycloalkyl ring. In some embodiments, at least one of $R^{10}$, $R^{11}$ and $R^{12}$ is unsubstituted or substituted amido, unsubstituted or substituted acyloxy, unsubstituted or substituted alkoxycarbonyl, unsubstituted or substituted acyl, or unsubstituted or substituted sulfonamido.

In some embodiments, when at least one of $R^{10}$, $R^{11}$ and $R^{12}$ is alkyl, alkynyl, alkenyl, aryl, heteroaryl, heterocyclyl, cycloalkyl, alkoxycarbonyl, amido, acyloxy, acyl, or sulfonamido, it is substituted with one or more of alkyl, heteroalkyl, alkenyl, alkynyl, cycloalkyl, heterocyclyl, aryl, heteroaryl, alkoxy, amido, amino, acyl, acyloxy, alkoxycarbonyl, sulfonamido, halo, cyano, hydroxyl or nitro, each of which alkyl, heteroalkyl, alkenyl, alkynyl, cycloalkyl, heterocyclyl, aryl, heteroaryl, alkoxy, amido, amino, acyl, acyloxy, alkoxycarbonyl, or sulfonamido can itself be substituted.

In some embodiments, B is unsubstituted or substituted alkyl, including, but not limited to —$(CH_2)_2$—$NR^aR^a$, where in each $R^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl, or Nine are combined together to form a cyclic moiety, which includes but is not limited to piperidinyl, piperazinyl, and morpholinyl. In some embodiments, B is unsubstituted or substituted amino. In some embodiments, B is unsubstituted or substituted heteroalkyl.

In some embodiments, B is selected from unsubstituted or substituted aryl, including, but not limited to, unsubstituted or substituted phenyl; unsubstituted or substituted heteroaryl including, but not limited to, pyridin-2-yl, pyridin-3-yl, pyridin-4-yl, pyrimidin-4-yl, pyrimidin-2-yl, pyrimidin-5-yl, or pyrazin-2-yl; unsubstituted or substituted monocyclic heteroaryl; unsubstituted or substituted bicyclic heteroaryl; a heteroaryl having two heteroatoms as ring atoms; unsubstituted or substituted heteroaryl comprising a nitrogen ring atom; unsubstituted or substituted heteroaryl having two nitrogen ring atoms; unsubstituted or substituted heteroaryl having a nitrogen and a sulfur as ring atoms; unsubstituted or substituted heterocyclyl including, but not limited to, morpholinyl, tetrahydropyranyl, piperazinyl, and piperidinyl; and unsubstituted or substituted cycloalkyl including, but not limited to, cyclopentyl and cyclohexyl.

In some embodiments, B is one of the following moieties:

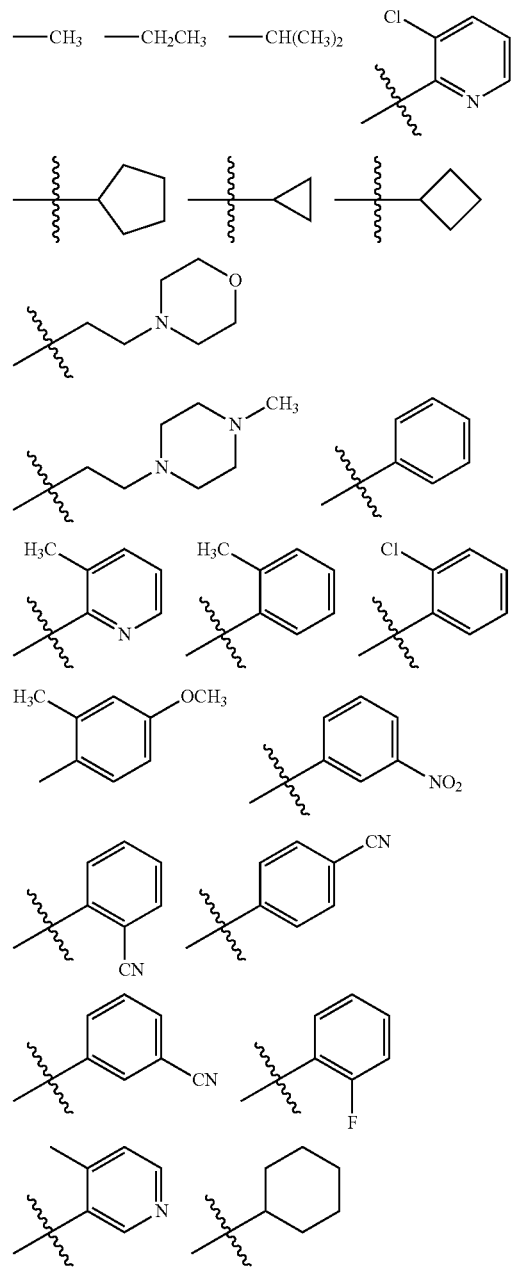

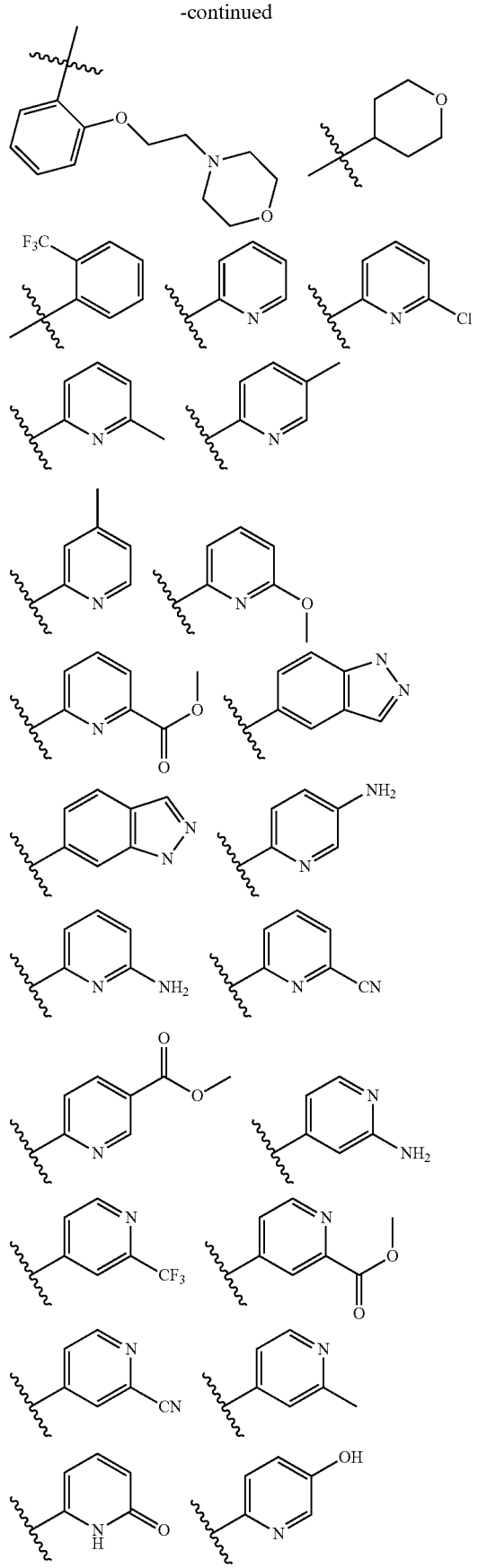
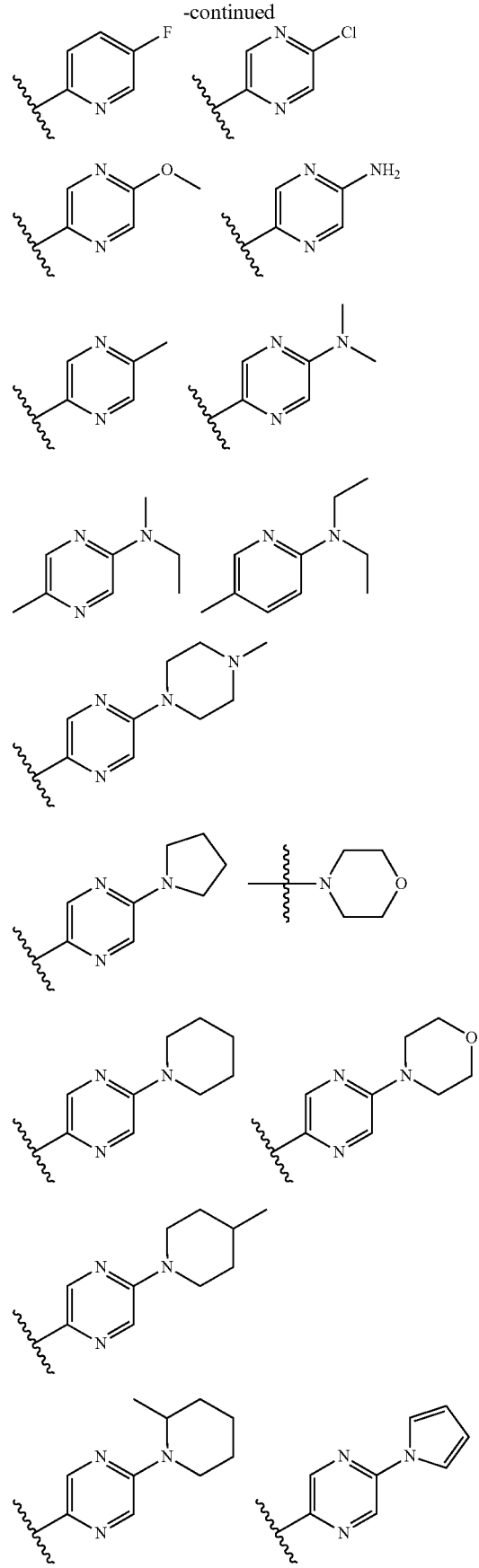

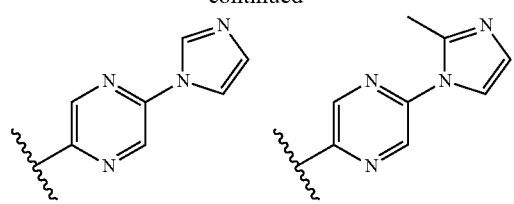
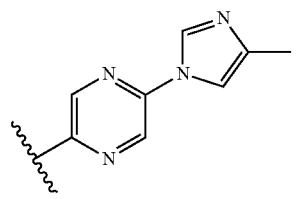
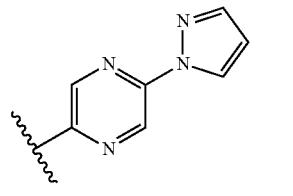
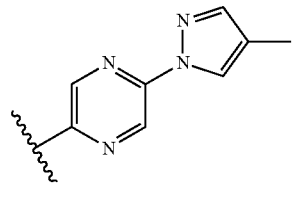
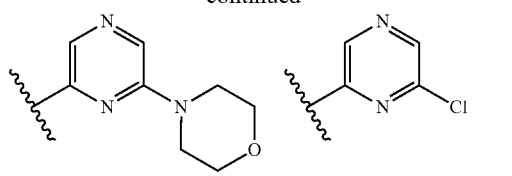
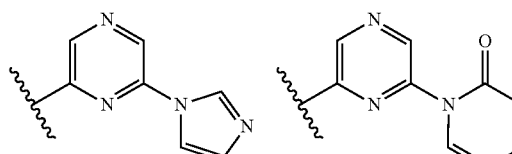
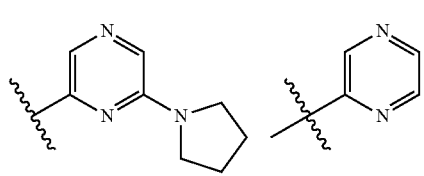
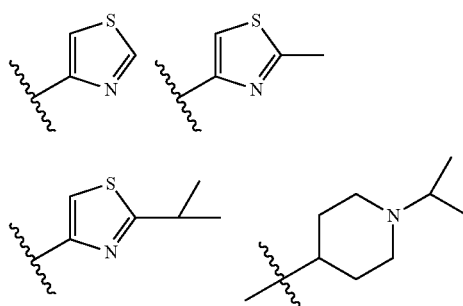
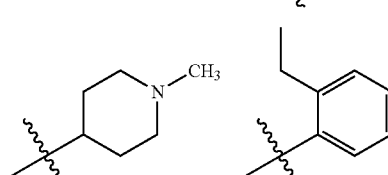
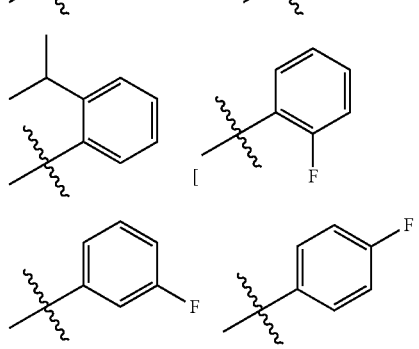
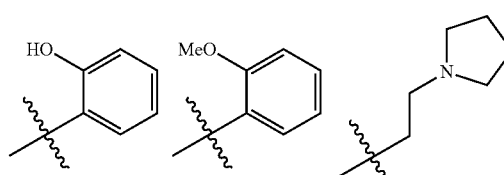
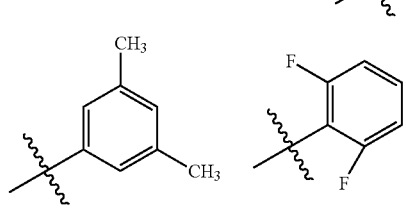

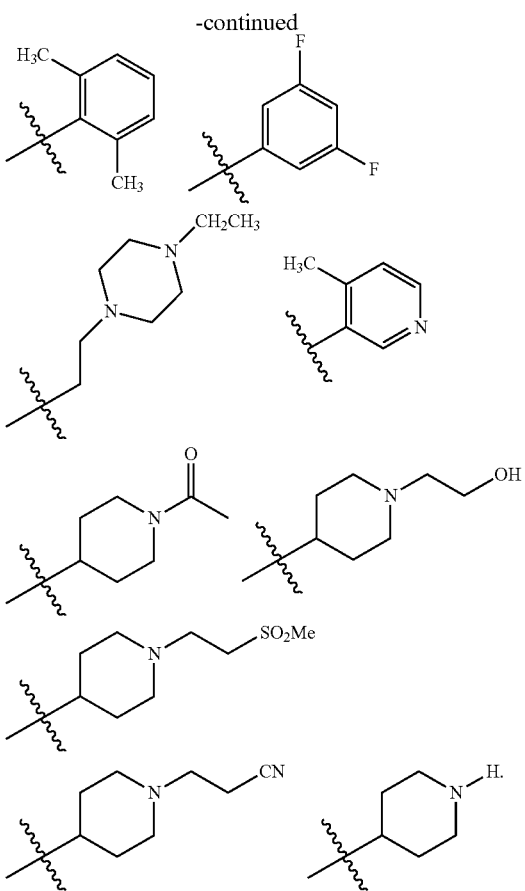

In some embodiments, B is unsubstituted or substituted with one or more $R^2$ substituents. In some embodiments, $R^2$ is alkyl, heteroalkyl, alkenyl, alkynyl, cycloalkyl, heterocyclyl, aryl, heteroaryl, alkoxy, amido, amino, acyl, acyloxy, alkoxycarbonyl, sulfonamido, halo, cyano, hydroxyl or nitro, each of which alkyl, heteroalkyl, alkenyl, alkynyl, cycloalkyl, heterocyclyl, aryl, heteroaryl, alkoxy, amido, amino, acyl, acyloxy, alkoxycarbonyl or sulfonamido, can itself be substituted.

In some embodiments, $R^2$ is unsubstituted or substituted alkyl, unsubstituted or substituted heteroalkyl, unsubstituted or substituted alkenyl, unsubstituted or substituted alkynyl, unsubstituted or substituted cycloalkyl, or unsubstituted or substituted heterocyclyl. In some embodiments, $R^2$ is unsubstituted or substituted aryl, unsubstituted or substituted arylalkyl, unsubstituted or substituted heteroaryl, or unsubstituted or substituted heteroarylalkyl. In some embodiments, $R^2$ is unsubstituted or substituted alkoxy, unsubstituted or substituted amido, or unsubstituted or substituted amino. In some embodiments, $R^2$ is unsubstituted or substituted acyl, unsubstituted or substituted acyloxy, unsubstituted or substituted alkoxycarbonyl, or unsubstituted or substituted sulfonamido. In some embodiments, $R^2$ is halo, selected from —I, —F, —Cl, and —Br. In some embodiments, $R^2$ is selected from cyano, hydroxyl, nitro, and a carbonate. In some embodiments, $R^2$ is unsubstituted or substituted phosphate. In some embodiments, $R^2$ is unsubstituted or substituted urea. In some embodiments, when $R^2$ is alkyl, $R^2$ is methyl, ethyl, propyl, isopropyl, n-butyl, tert-butyl, sec-butyl, pentyl, hexyl or heptyl.

In some embodiments, when $R^2$ is alkyl, heteroalkyl, alkenyl, alkynyl, cycloalkyl, heterocyclyl, aryl, arylalkyl, heteroaryl, heteroarylalkyl, alkoxy, amido, amino, acyl, acyloxy, alkoxycarbonyl, sulfonamido, or hydroxyl, it is substituted by phosphate, substituted by urea, or substituted by carbonate.

In some embodiments, when $R^2$ is alkyl, heteroalkyl, alkenyl, alkynyl, cycloalkyl, heterocyclyl, aryl, arylalkyl, heteroaryl, heteroarylalkyl, alkoxy, amido, amino, acyl, acyloxy, alkoxycarbonyl, or sulfonamido, it is substituted by one or more of alkyl, heteroalkyl, alkenyl, alkynyl, cycloalkyl, heterocyclyl, aryl, heteroaryl, alkoxy, amido, amino, acyl, acyloxy, alkoxycarbonyl, sulfonamido, halo, cyano, hydroxyl or nitro, each of which alkyl, heteroalkyl, alkenyl, alkynyl, cycloalkyl, heterocyclyl, aryl, heteroaryl, alkoxy, amido, amino, acyl, acyloxy, alkoxycarbonyl, or sulfonamido can itself be substituted.

In some embodiments, there are no occurrences of $R^2$. In other embodiments, there is one occurrence of $R^2$. In still other embodiments, there are two occurrences of $R^2$. In yet other embodiments, there are three occurrences of $R^2$. In yet other embodiments, there are four occurrences of $R^2$. For example, in some embodiments B is aryl or heteroaryl and there are no occurrences of $R^2$. In other instances, B is aryl or heteroaryl and there is one occurrence of $R^2$ where $R^2$ is alkyl or halo.

In some embodiments, $R^{18}$ is hydrogen. In some embodiments, $R^{18}$ is unsubstituted or substituted alkyl, unsubstituted or substituted alkenyl, or unsubstituted or substituted alkynyl. In some embodiments, $R^{18}$ is unsubstituted or substituted aryl, unsubstituted or substituted heteroaryl, unsubstituted or substituted cycloalkyl, or unsubstituted or substituted heterocyclyl. In some embodiments, $R^{18}$ is unsubstituted or substituted alkoxy, unsubstituted or substituted amido, or unsubstituted or substituted amino. In some embodiments, $R^{18}$ is unsubstituted or substituted acyl, unsubstituted or substituted acyloxy, or unsubstituted or substituted sulfonamido. In some embodiments, $R^{18}$ is halo, selected from —I, —F, —Cl, and —Br. In some embodiments, $R^{18}$ is H, halo, alkyl, alkoxy, heteroaryl, or cycloalkyl. For example, $R^{18}$ is H, $CH_3$, $CH_2CH_3$, $CF_3$, Cl, or F. In some instances, $R^{18}$ is $CH_3$, $CF_3$, or Cl.

In some embodiments, $R^{18}$ is selected from cyano, hydroxyl, and nitro. In some embodiments, when $R^{18}$ is alkyl, $R^{18}$ is methyl, ethyl, propyl, isopropyl, n-butyl, tert-butyl, sec-butyl, pentyl, hexyl or heptyl. In some embodiments, $R^{18}$ is —$CF_3$, —$CH_2F$ or —$CHF_2$.

In some embodiments, when $R^{18}$ is alkyl, alkenyl, alkynyl, aryl, heteroaryl, cycloalkyl, heterocyclyl, alkoxy, amido, amino, acyl, acyloxy, or sulfonamido, it is substituted with one or more of alkyl, heteroalkyl, alkenyl, alkynyl, cycloalkyl, heterocyclyl, aryl, heteroaryl, alkoxy, amido, amino, acyl, acyloxy, alkoxycarbonyl, sulfonamido, halo, cyano, hydroxyl or nitro, each of which alkyl, heteroalkyl, alkenyl, alkynyl, cycloalkyl, heterocyclyl, aryl, heteroaryl, alkoxy, amido, amino, acyl, acyloxy, alkoxycarbonyl, or sulfonamido can itself be substituted.

In some embodiments, $R^{18}$ is a 5-membered heteroaryl group. Such groups include, for example, pyrrole, furan, thiophene, triazole, oxazole, pyrazole, and isoxazole. In other embodiments, $R^{18}$ is a 5-membered heterocycle, including, but not limited to, oxazoline and oxazolidinone. In still other embodiments, $R^{18}$ is a 6-membered heteroaryl group including, but not limited to, pyridine, pyrazine, pyrimidine and pyridazine. Alternatively, $R^{18}$ is a 6-membered heterocycle, including moieties such as morpholino or piperidino. In other embodiments, $R^{18}$ is a fused 5/6-bicyclic heteroaryl, for example, benzothiazole, benzoxazole, benzisoxazole, indazole, benzimidazole, benzothiophene, indole, isoindole, purine, or pyrazolopyrimidine. In yet other embodiments, $R^{18}$ is a fused 5/6-bicyclic heterocycle.

In some embodiments, $R^{18}$ is a $C_1$-$C_6$ alkyl group substituted with a 5-membered heteroaryl, a 5-membered heterocycle, a 6-membered heteroaryl, a 6-membered heterocycle, a fused 5/6-bicyclic heteroaryl, or a fused 5/6-bicyclic heterocycle. Alternatively, $R^{18}$ is amino, sulfonyl, sulfonyl, sulfoxide, sulfone, or alkoxy where the N, S or O heteroatom has a covalent bond either directly or through a $C_1$-$C_6$ alkyl group to a 5-membered heteroaryl, a 5-membered heterocycle, a 6-membered heteroaryl, a 6-membered heterocycle, a fused 5/6-bicyclic heteroaryl, or a fused 5/6-bicyclic nonaromatic heterocycle.

In other embodiments, $R^{18}$ is a $C_1$-$C_6$ alkyl group substituted with a fused polycyclic group, wherein the polycyclic group has greater than two rings and is carbocyclic or heterocyclic; $C_1$-$C_6$ alkyl group substituted with a bridged cycloalkyl or bridged heterocyclic group; $C_1$-$C_6$ alkyl group substituted with a spirocyclic cycloalkyl or spirocyclic heterocyclic group; or branched $C_4$-$C_{12}$ alkyl group, wherein said branched alkyl group contains at least one terminal t-butyl group.

Each of the embodiments named above for $R^{18}$ is unsubstituted or optionally additionally substituted with an alkyl, heteroalkyl, alkenyl, alkynyl, cycloalkyl, heterocyclyl, aryl, heteroaryl, alkoxy, amido, amino, acyl, acyloxy, alkoxycarbonyl, sulfonamido, halo, cyano, hydroxyl or nitro group.

In certain embodiments, $R^{18}$ is a substituted or unsubstituted heterocyclyl or heteroaryl group selected from pyridine, pyrazole, piperazine, and pyrrolidine, wherein the substituent can be a $C_1$-$C_6$ alkyl group or a halogen.

In some embodiments, a compound is provided wherein $R^{18}$ is selected from a 5-membered heteroaryl such as a pyrrole, a furan, or a thiophene group; 5-membered nonaromatic heterocyclyl such as a pyrrolidine, a tetrahydrofuran, or a tetrahydrothiophene group; 6-membered heteroaryl such as pyridine, pyrazine, pyrimidine, or pyridazine; 6-membered nonaromatic heterocyclyl such as piperidine, tetrahydropyran, or thiane; and fused 5/6-bicyclic heteroaryl such as indole, isoindole, benzofuran, isobenzofuran, benzothiophene, benzimidazole, indazole, benzoxazole, benzisoxazole, or purine. In certain embodiments, $R^{18}$ is a substituted or unsubstituted group such as pyridine, pyrazole, piperazine, or pyrrolidine. By way of non-limiting example, the $R^{18}$ group can be substituted with a $C_1$-$C_6$ alkyl group or a halogen. For example, the $R^{18}$ group can be substituted with a methyl group.

In some embodiments, a compound is provided wherein $R^{18}$ is selected from

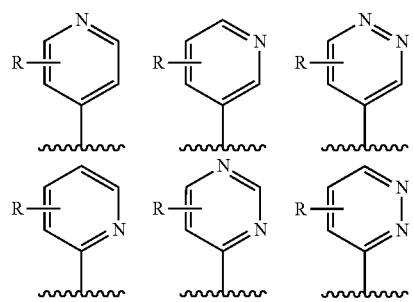

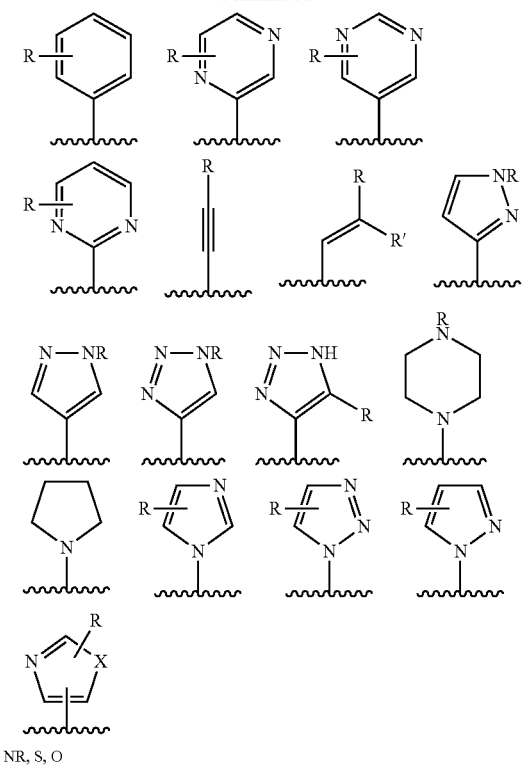

$X = NR, S, O$ wherein R is H, $C_1$-$C_6$ alkyl, $C_1$-$C_6$ alkoxy, halo, and haloalkyl. In certain embodiments, R is methyl. In other embodiments, a compound is provided wherein $R^{18}$ is selected from:

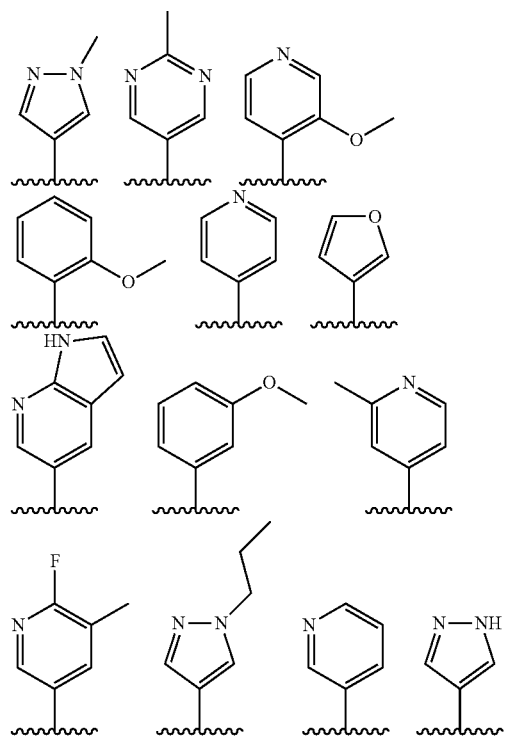

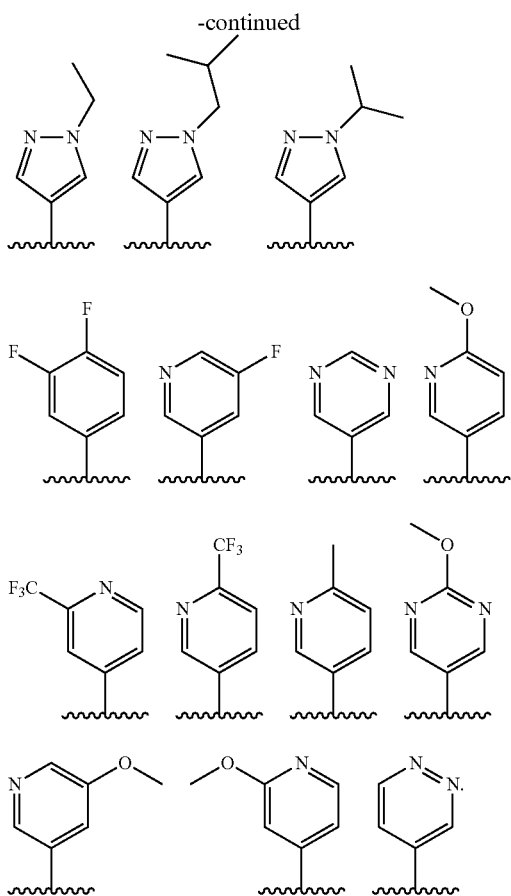

In some embodiments, X is absent. In some embodiments, X is —(CH($R^9$))$_z$, and z is an integer of 1, 2, 3 or 4.

In some embodiments, $R^9$ is unsubstituted or substituted alkyl including, but not limited to unsubstituted or substituted $C_1$-$C_{10}$alkyl. In some embodiments, $R^9$ is unsubstituted or substituted cycloalkyl including, but not limited to unsubstituted or substituted $C_3$-$C_7$ cycloalkyl. In some embodiments, $R^9$ is ethyl, methyl or hydrogen. In some embodiments, $R^9$ is unsubstituted or substituted heterocyclyl including, but not limited to, unsubstituted or substituted $C_2$-$C_{10}$heteroalkyl. In some embodiments, $R^9$ is unsubstituted or substituted heteroalkyl including, but not limited to, unsubstituted or substituted $C_2$-$C_{10}$heteroalkyl.

Also provided herein is a compound of Formula (XV) wherein $R^9$ is hydrogen, and X is —CH$_2$—, —CH$_2$CH$_2$—, —CH$_2$CH$_2$CH$_2$—, —CH(CH$_3$)—, or —CH(CH$_2$CH$_3$)—. In other embodiments, X is —(CH($R^9$))$_z$, $R^9$ is not hydrogen, and z is an integer of 1. When X is —CH($R^9$)— and $R^9$ is not hydrogen, then the compound can adopt either an (S)- or (R)-stereochemical configuration with respect to the CH carbon. In some embodiments, the compound is a racemic mixture of (S)- and (R) isomers with respect to the CH carbon. In other embodiments, provided herein is a mixture of compounds of Formula (XV) wherein individual compounds of the mixture exist predominately in an (S)- or (R)-isomeric configuration. For example, the compound mixture has an (S)-enantiomeric excess of greater than about 55%, about 60%, about 65%, about 70%, about 75%, about 80%, about 85%, about 90%, about 95%, about 96%, about 97%, about 98%, about 99%, about 99.5%, or more at the X carbon. In other embodiments, the compound mixture has an (S)-enantiomeric excess of greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5%, or more.

In other embodiments, the compound mixture has an (R)-enantiomeric excess of greater than about 55%, about 60%, about 65%, about 70%, about 75%, about 80%, about 85%, about 90%, about 95%, about 96%, about 97%, about 98%, about 99%, about 99.5%, or more at the CH carbon. In some other embodiments, the compound mixture has an (R)-enantiomeric excess of greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5%, or more.

In some embodiments, the compound of Formula (XV), X is —CH($R^9$)—, $R^9$ is methyl or ethyl, and the compound is the (S)-isomer.

In some embodiments of the compound of Formula (XV), Y is absent.

In some embodiments, Y is —O—, —S—, —S(=O)—, —S(=O)$_2$—, —C(=O)—, —N($R^9$)(C=O)—, —N($R^9$)(C=O)NH—, —N($R^9$)C($R^9$)$_2$— (such as —N($R^9$)CH$_2$—, including, but not limited to, —N(CH$_3$)CH$_2$—, N(CH(CH$_3$)$_2$)CH$_2$— or —N(CH$_2$CH$_3$)CH$_2$—), —N($R^9$)—, —N(CH$_3$)—, —N(CH$_2$CH$_3$)—, or —N(CH(CH$_3$)$_2$)—. In some embodiments, Y is —C(=O)—(CHR$^9$)$_z$— and z is an integer of 1, 2, 3, or 4.

In some embodiments, at least one of X and Y is present. In some embodiments of the compound of Formula I, —XY— is —CH$_2$—, —CH$_2$—N(CH$_3$), —CH$_2$—N(CH$_2$CH$_3$), —CH(CH$_3$)—NH—, (S)—CH(CH$_3$)—NH—, or (R)—CH(CH$_3$)—NH—. In other embodiments, X—Y is —N(CH$_3$)—CH$_2$—, N(CH$_2$CH$_3$) CH$_2$—, —N(CH(CH$_3$)$_2$)CH$_2$—, or —NHCH$_2$—.

In certain embodiments, the compound of Formula (XV) has a structure of Formula (XVI):

Formula (XVI)

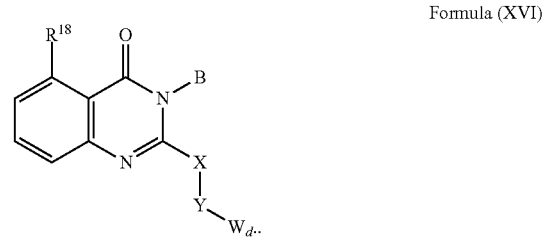

In some embodiments, the compound of Formula (XVI) has a structure of Formula (XVII):

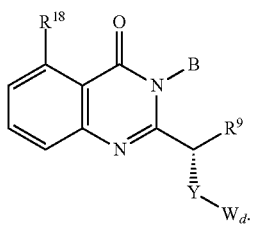
Formula (XVII)

In some embodiments of compounds of Formula (XVI) or (XVII), B is aryl substituted with 0-3 occurrences of $R^2$. For example, B is phenyl substituted with 0-3 occurrences of $R^2$. In some embodiments of compounds of Formula (XVI) or (XVII), B is unsubstituted phenyl. In other embodiments of compounds of Formula (XVI) or (XVII), B is phenyl substituted with 1 occurrence of $R^2$. $R^2$ is, in some instances, halo or alkyl. In other embodiments of compounds of Formula (XVI) or (XVII), B is cycloalkyl or heterocyclyl.

In still other embodiments, the compound of Formula (XV) has a structure selected from:

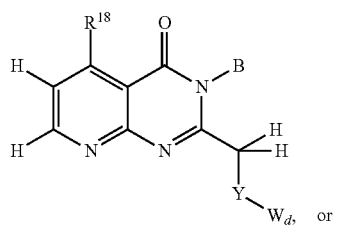

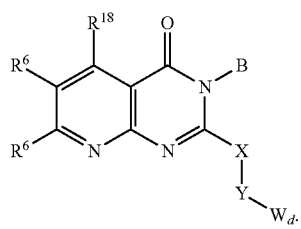

In certain embodiments, the compound of Formula (XV) has a structure of Formula (XVIII):

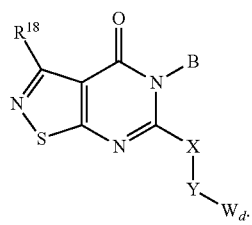
Formula (XVIII)

In some embodiments, the compound of Formula (XVIII) has a structure of Formula (XVIV):

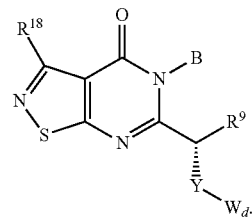
Formula (XVIV)

In certain embodiments, the compound of Formula (XV) has a structure of Formula (XX):

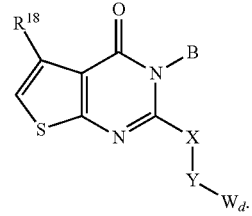
Formula (XX)

In certain embodiments, the compound of Formula (XX) has a structure of Formula (XXI):

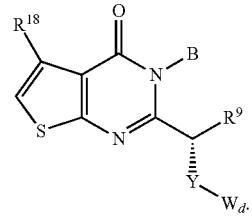
Formula (XXI)

In one aspect, B is selected from the moieties presented in Table 2.

TABLE 2

Illustrative B moieties of the compounds described herein.

| Sub-class # | B |
|---|---|
| B-1 | cyclopentyl |
| B-2 | 1-isopropylpiperidin-4-yl |
| B-3 | —CH(CH$_3$)$_2$ |

TABLE 2-continued
Illustrative B moieties of the compounds described herein.
| Subclass # | B |
|---|---|
| B-4 | 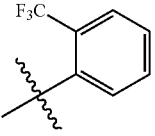 [SMILES: *c1ccccc1C(F)(F)F] |
| B-5 | 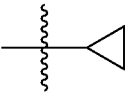 |
| B-6 | 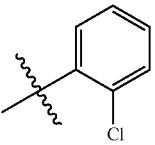 [SMILES: *c1ccccc1Cl] |
| B-7 | 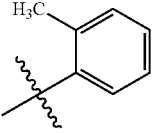 |
| B-8 | 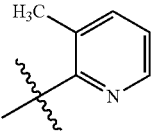 |
| B-9 | 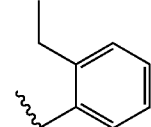 |
| B-10 | 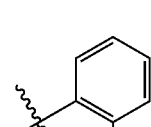 |
| B-11 | 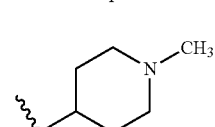 |
| B-12 | 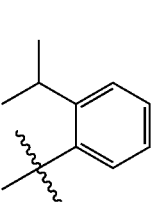 [SMILES: *c1ccccc1C(C)C] |
| B-13 | 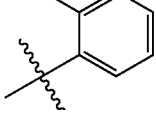 |
| B-14 | 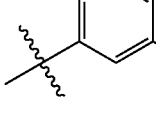 |
| B-15 | 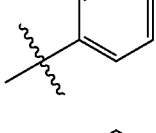 |
| B-16 | 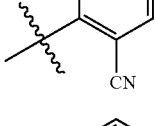 |
| B-17 | 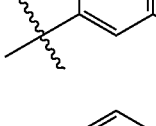 |
| B-18 | 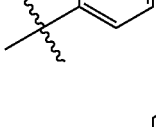 |
| B-19 | 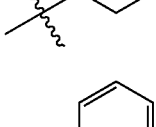 |
| B-20 | 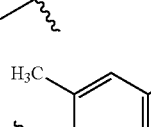 |
| B-21 | 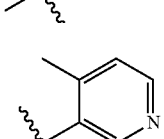 |
| B-22 |  |

TABLE 2-continued

Illustrative B moieties of the compounds described herein.

| Sub-class # | B |
|---|---|
| B-23 | 3-nitrophenyl |
| B-24 | 2-(2-morpholinoethoxy)phenyl |
| B-25 | tetrahydro-2H-pyran-4-yl |
| B-26 | 2-(4-methylpiperazin-1-yl)ethyl |
| B-27 | pyridin-2-yl |
| B-28 | 6-chloropyridin-2-yl |
| B-29 | 6-methylpyridin-2-yl |
| B-30 | 5-methylpyridin-2-yl |
| B-31 | 4-methylpyridin-2-yl |
| B-32 | 6-methoxypyridin-2-yl |
| B-33 | 6-(trifluoromethyl)pyridin-3-yl |
| B-34 | 1H-indazol-5-yl |
| B-35 | 1H-indazol-6-yl |
| B-36 | 5-aminopyridin-2-yl |
| B-37 | 6-aminopyridin-2-yl |
| B-38 | 6-cyanopyridin-2-yl |
| B-39 | methyl 6-substituted-nicotinate |
| B-40 | 5-chloropyrazin-2-yl |
| B-41 | methyl 6-substituted-picolinate |

TABLE 2-continued

Illustrative B moieties of the compounds described herein.

| Sub-class # | B |
|---|---|
| B-42 | (pyridine with methyl ester) |
| B-43 | (pyridine with CN) |
| B-44 | (methylpyridine) |
| B-45 | (pyridinone, NH) |
| B-46 | (hydroxypyridine) |
| B-47 | (fluoropyridine) |
| B-48 | (aminopyridine, NH₂) |
| B-49 | (methoxypyrazine) |
| B-50 | (aminopyrazine, NH₂) |
| B-51 | (methylpyrazine) |
| B-52 | (dimethylaminopyrazine) |
| B-53 | (N-methyl-N-ethylaminopyrazine) |
| B-54 | (diethylaminopyrazine) |
| B-55 | (4-methylpiperazinyl pyrazine) |
| B-56 | (pyrrolidinyl pyrazine) |
| B-57 | (piperidinyl pyrazine) |
| B-58 | (morpholinyl pyrazine) |

TABLE 2-continued
Illustrative B moieties of the compounds described herein.
| Sub-class # | B |
|---|---|
| B-59 | 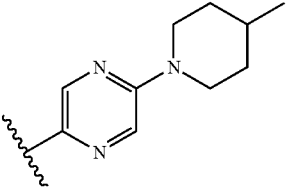 [SMILES: *c1cnc(N2CCC(C)CC2)cn1] |
| B-60 | 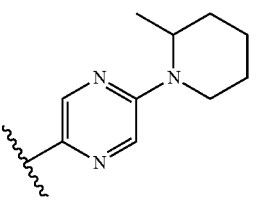 [SMILES: *c1cnc(N2CCCCC2C)cn1] |
| B-61 | 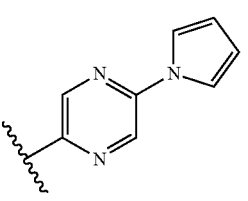 [SMILES: *c1cnc(-n2cccc2)cn1] |
| B-62 | 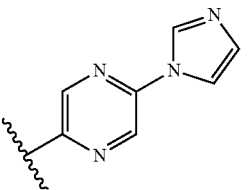 [SMILES: *c1cnc(-n2ccnc2)cn1] |
| B-63 | 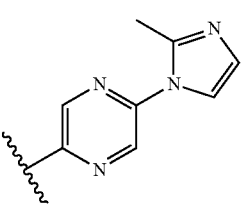 [SMILES: *c1cnc(-n2ccnc2C)cn1] |
| B-64 | 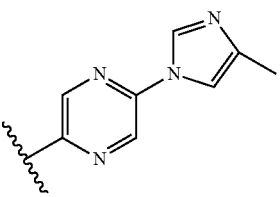 [SMILES: *c1cnc(-n2cnc(C)c2)cn1] |
| B-65 | 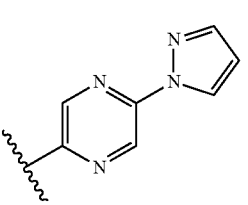 [SMILES: *c1cnc(-n2cccn2)cn1] |
| B-66 | 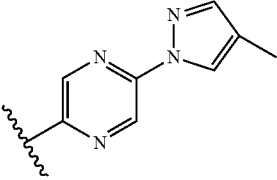 [SMILES: *c1cnc(-n2cc(C)cn2)cn1] |
| B-67 | 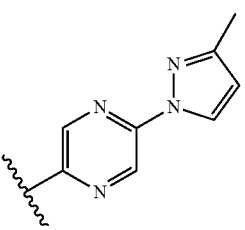 [SMILES: *c1cnc(-n2ccc(C)n2)cn1] |
| B-68 | 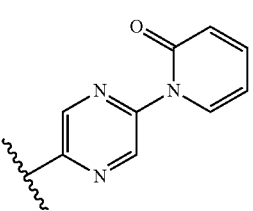 [SMILES: *c1cnc(-n2ccccc2=O)cn1] |
| B-69 | 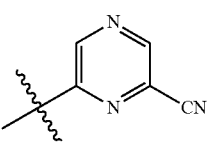 [SMILES: *c1cncc(C#N)n1] |
| B-70 | 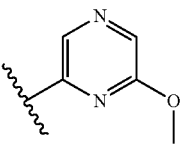 [SMILES: *c1cncc(OC)n1] |
| B-71 | 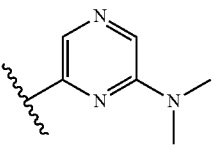 [SMILES: *c1cncc(N(C)C)n1] |
| B-72 | 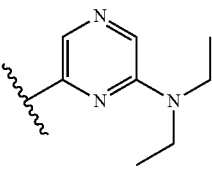 [SMILES: *c1cncc(N(CC)CC)n1] |
| B-73 | 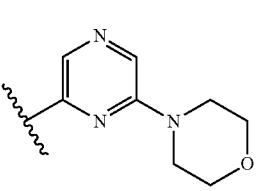 [SMILES: *c1cncc(N2CCOCC2)n1] |

TABLE 2-continued
Illustrative B moieties of the compounds described herein.
| Subclass # | B |
|---|---|
| B-74 | 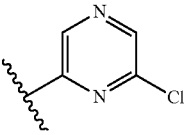 |
| B-75 | 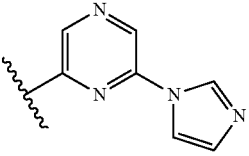 [SMILES: *c1cncc(-n2ccnc2)n1] |
| B-76 | 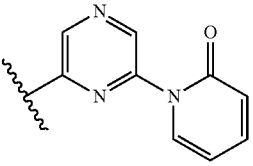 [SMILES: *c1cncc(-n2ccccc2=O)n1] |
| B-77 | 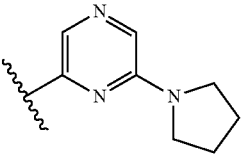 [SMILES: *c1cncc(N2CCCC2)n1] |
| B-78 | 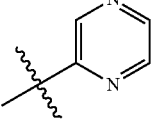 |
| B-79 | 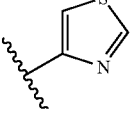 |
| B-80 | 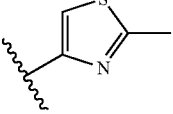 |
| B-81 | 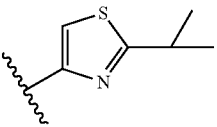 [SMILES: *c1csc(C(C)C)n1] |
| B-82 | 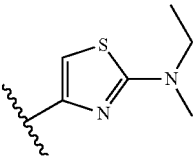 |
| B-83 | 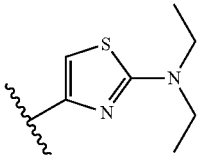 [SMILES: *c1csc(N(CC)CC)n1] |
| B-84 | 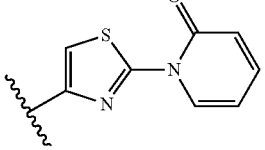 |
| B-85 | 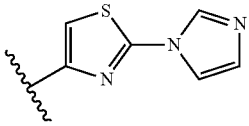 [SMILES: *c1csc(-n2ccnc2)n1] |
| B-86 | 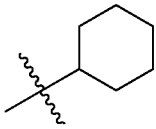 [SMILES: *C1CCCCC1] |
| B-87 | —CH$_3$ |
| B-88 | —CH$_2$CH$_3$ |
| B-89 | 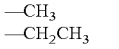 |
| B-90 |  |
| B-91 | 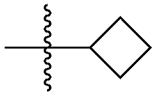 [SMILES: *C1CCC1] |
| B-92 | 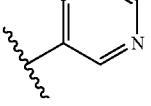 |
| B-93 | 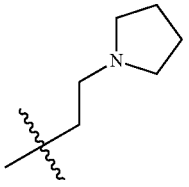 [SMILES: *CCN1CCCC1] |

TABLE 2-continued

Illustrative B moieties of the compounds described herein.

| Subclass # | B |
|---|---|
| B-94 | 2,6-dimethylphenyl |
| B-95 | 3,5-difluorophenyl |
| B-96 | 3-(4-ethylpiperazin-1-yl)propyl |
| B-97 | piperidin-4-yl |
| B-98 | 1-acetylpiperidin-4-yl |
| B-99 | 1-(2-hydroxyethyl)piperidin-4-yl |
| B-100 | 1-(2-(methylsulfonyl)ethyl)piperidin-4-yl |
| B-101 | 1-(2-cyanoethyl)piperidin-4-yl |
| B-102 | 4-fluorophenyl |

In some embodiments, the compound of Formula (XV) is selected from the following:

-continued

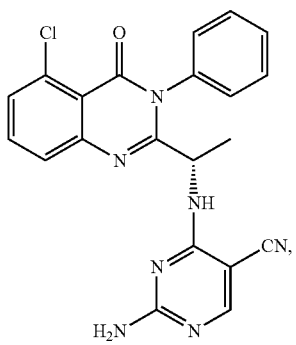

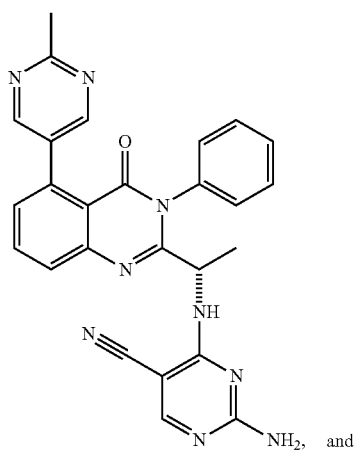

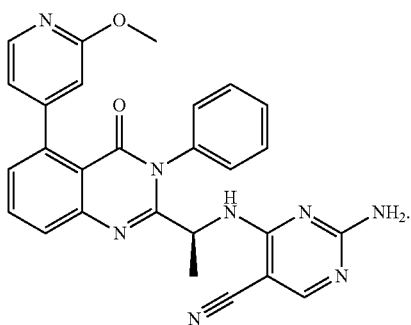

In another aspect, provided herein are compounds of Formula (X) or (XI):

In another aspect, provided herein are compounds of Formula (X) or (XI):

Formula (X)

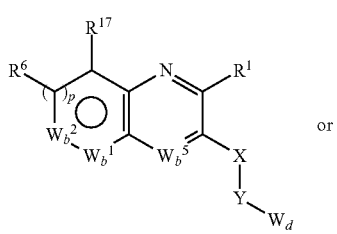

or

-continued

Formula (XI)

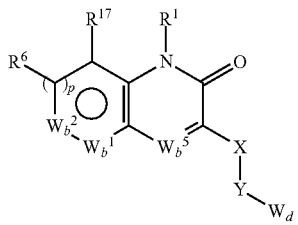

or an enantiomer, a mixture of enantiomers, or a mixture of two or more diastereomers thereof, or a pharmaceutically acceptable form thereof, wherein:

$W_b^1$ and $W_b^2$ are each independently $CR^6$, S, O, N or $NR^{14}$, wherein at least one of $W_b^1$ and $W_b^2$ is $CR^6$, N or $NR^{14}$;

each $R^6$ is independently hydrogen, alkyl, alkenyl, alkynyl, cycloalkyl, heterocyclyl, fluoroalkyl, heteroalkyl, alkoxy, amido, amino, acyl, acyloxy, sulfinyl, sulfonyl, sulfoxide, sulfone, sulfonamido, halo, cyano, heteroaryl, aryl, hydroxyl, or nitro;

each $R^{14}$ is independently hydrogen, alkyl, cycloalkyl, heterocyclyl or heteroalkyl;

$R^1$ is -(L)-$R^{1'}$;

L is a bond, —S—, —N($R^{15}$)—, —C($R^{15}$)$_2$—, —C(=O)—, or —O—;

$R^{1'}$ is hydrogen, alkyl, heteroalkyl, alkenyl, alkynyl, cycloalkyl, cycloalkylalkyl, heterocyclyl, heterocyclylalkyl, aryl, arylalkyl, heteroaryl, heteroarylalkyl, alkoxy, heterocyclyloxy, amido, amino, acyl, acyloxy, alkoxycarbonyl, sulfonamido, halo, cyano, hydroxyl, nitro, phosphate, urea, carbonate, substituted nitrogen, or NR'R" wherein R' and R" are taken together with nitrogen to form a cyclic moiety;

p is 0, 1, 2 or 3;

$W_b^5$ is $CR^8$ or N;

$R^8$ is alkyl, alkenyl, alkynyl, cycloalkyl, heteroalkyl, alkoxy, amido, amino, acyl, acyloxy, sulfonamido, halo, cyano, hydroxyl, or nitro;

$R^{17}$ is alkyl, haloalkyl, alkoxy, cycloalkyl, cycloalkylalkyl, aryl, heteroaryl, heterocyclyl, aralkyl, heteroaralkyl, heterocyclylalkyl, alkenyl, or alkynyl, or $R^{17}$ is a heteroatom selected from N, S, and O, wherein the heteroatom has a covalent bond either directly or through a $C_1$-$C_6$ alkyl group to an aryl, heteroaryl or heterocyclyl, or $R^{17}$ and $R^6$ are taken together with the carbons to which they are attached form a 5- or 6-membered ring; wherein each of the above substituents can be substituted with 0, 1, 2, or 3 $R^{13}$;

X is absent or is —(CH($R^{16}$))$_z$—;

Y is absent, —O—, —S—, —S(=O)—, —S(=O)$_2$—, —N($R^{16}$)—, —C(=O)—(CH$R^{16}$)$_z$—, —C(=O)—, —N($R^{16}$)—C(=O)—, or —N($R^{16}$)—C(=O)NH—, —N($R^{16}$)C($R^{16}$)$_2$—, —C(=O)—N($R^9$)$_2$, or —C(=O)—N($R^{16}$)—(CH$R^{16}$)$_z$—;

each z is an integer of 1, 2, 3, or 4;

each $R^{16}$ is independently hydrogen, alkyl, cycloalkyl, heterocyclyl, heteroalkyl, aryl, halo or heteroaryl;

$W_d$ is

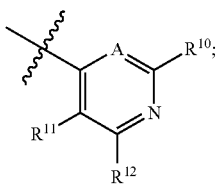

A is N or $CR^{19}$; and $R^{10}$, $R^{11}$, $R^{12}$, $R^{13}$, and $R^{19}$ are independently hydrogen, alkyl, heteroalkyl, alkenyl, alkynyl, cycloalkyl, heterocyclyl, aryl, arylalkyl, heteroaryl, heteroarylalkyl, alkoxy, heterocyclyloxy, amido, amino, acyl, acyloxy, alkoxycarbonyl, sulfonamido, halo, cyano, hydroxyl, nitro, phosphate, urea, carbonate, oxo, or NR'R" wherein R' and R" are taken together with nitrogen to form a cyclic moiety.

In certain embodiments, $W_b{}^1$ is $CR^6$ and $W_b{}^2$ is $CR^6$.

In certain embodiments, $W_b{}^5$ is CH.

In certain embodiments, L is a bond, —$N(R^{15})$— or —C(=O)—.

In certain embodiments, the compound of Formula (I) has a structure of Formula (XXII):

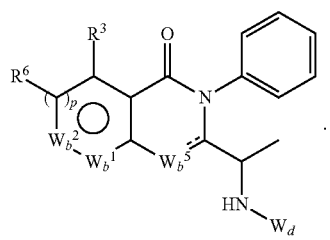

(XXII)

In certain embodiments, the compound of Formula (XXII) has a structure of Formula (XXIII):

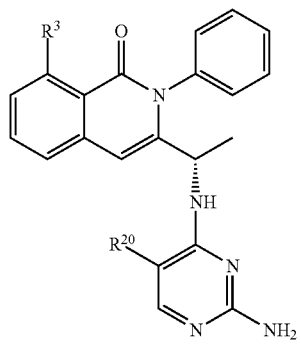

(XXIII)

wherein:
$R^3$ is aryl or heteroaryl; and
$R^{20}$ is amido or cyano.

In certain embodiments, $R^3$ is phenyl, pyrazolyl, or pyridyl, and $R^{20}$ is cyano. In certain embodiments, $R^3$ is substituted phenyl or substituted pyridyl. In some embodiments, the substitutions are selected from alkyl, (e.g., methyl), heteroalkyl (e.g., $CF_3$), alkoxy, halo, amino, hydroxyl, cyano, aryl, heteroaryl, and sulfonamido.

In certain embodiments, the compound of Formula (XXIII) is selected from the following:

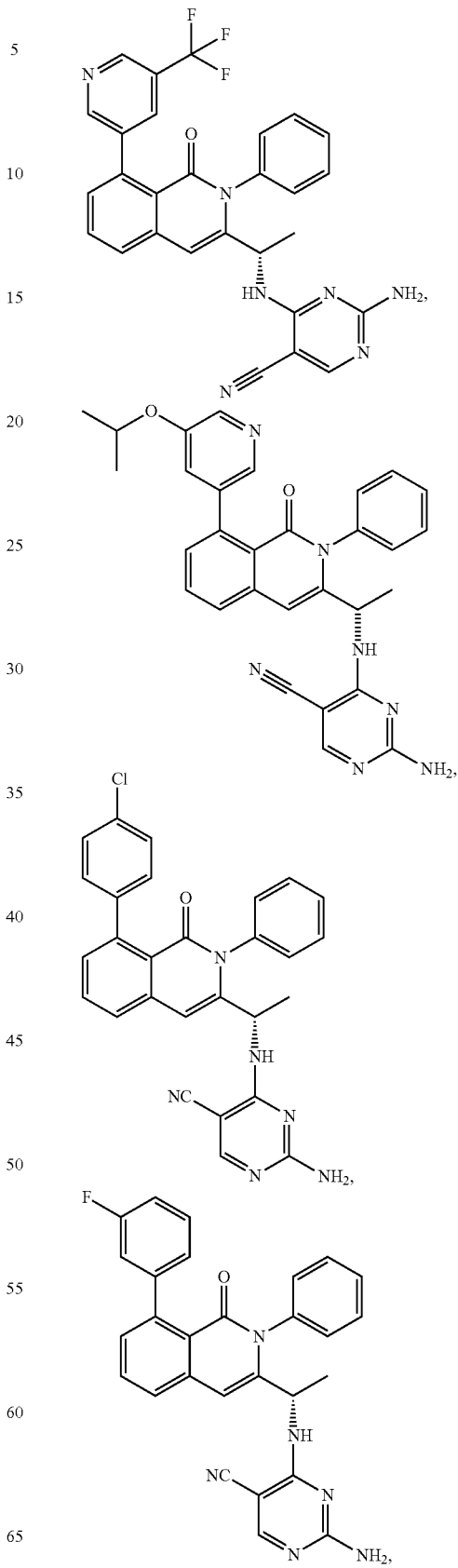

113
-continued
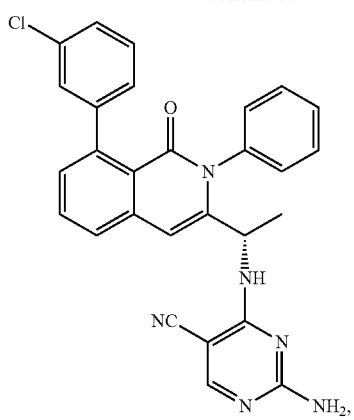
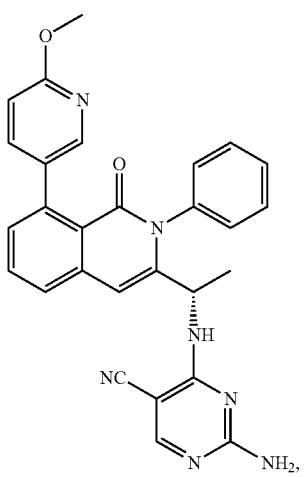
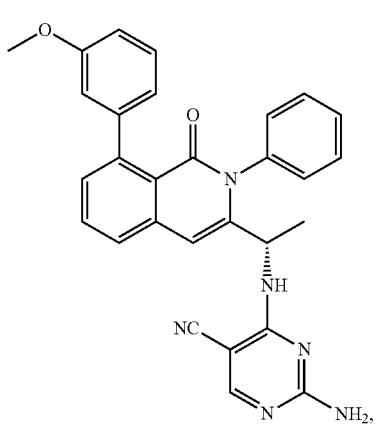
114
-continued
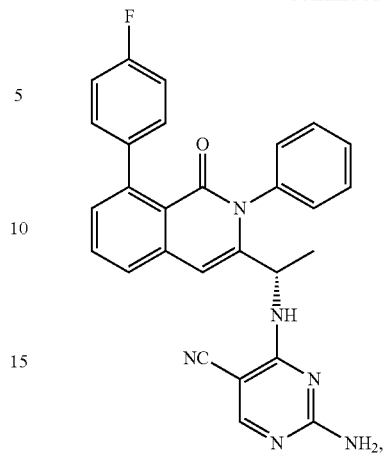
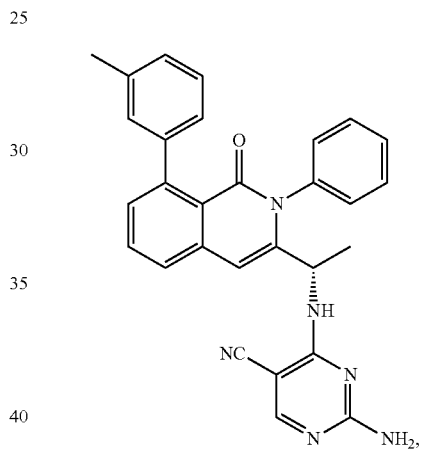
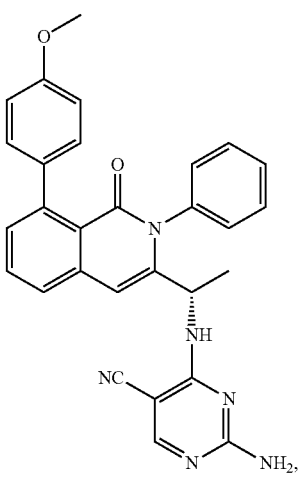

115
-continued
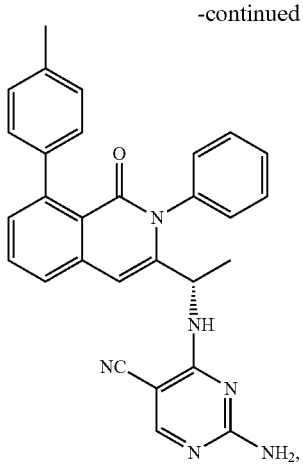
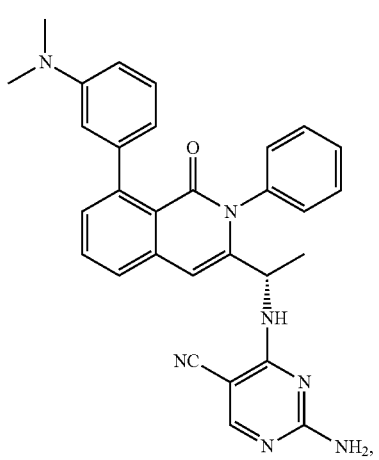
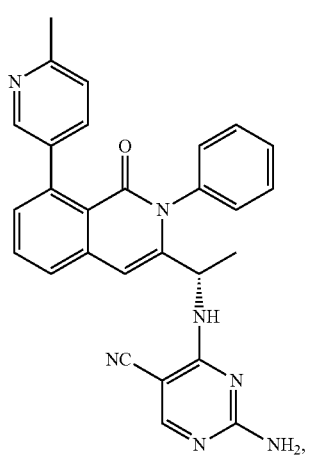
116
-continued
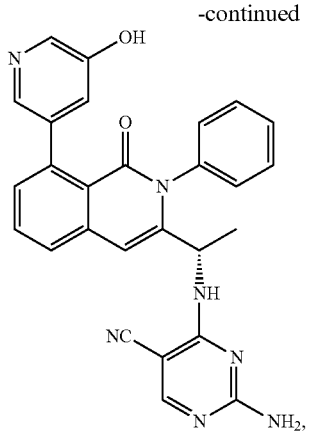
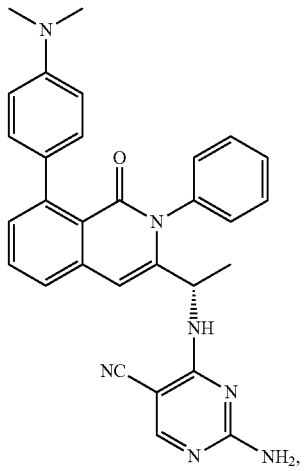
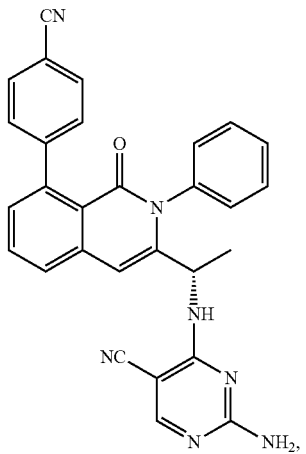

117
-continued
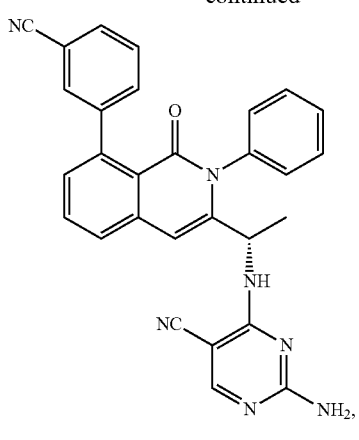
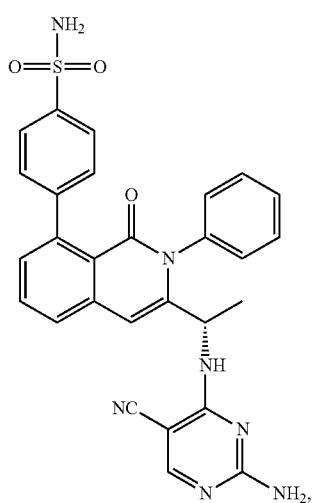
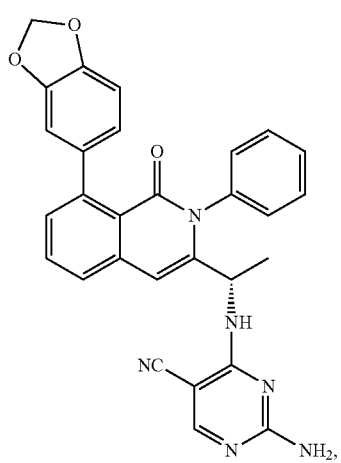
118
-continued
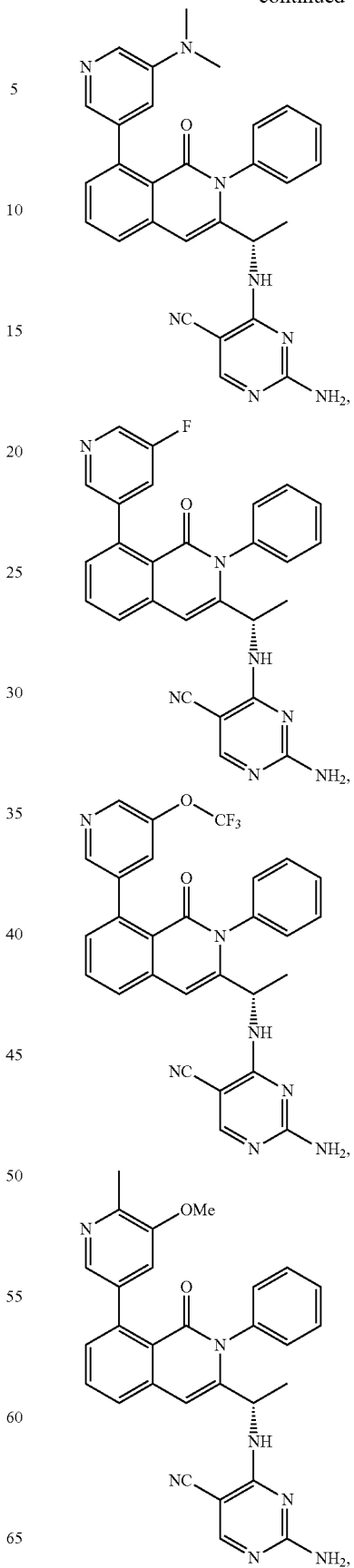

119
-continued
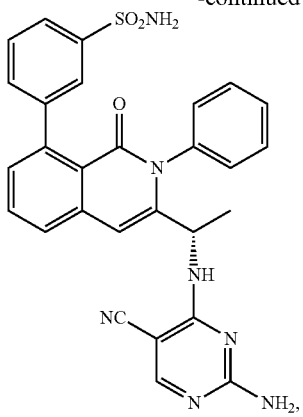
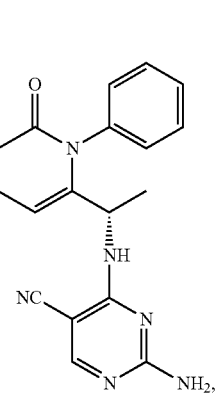
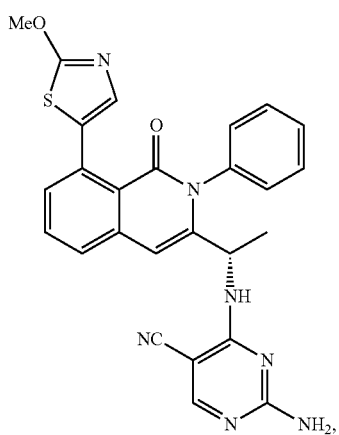
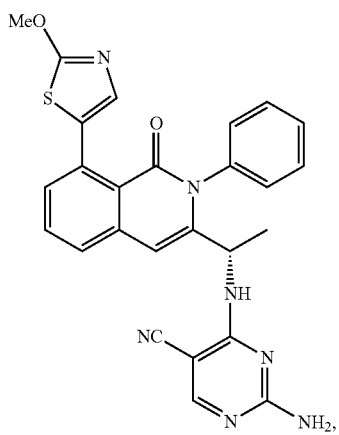
120
-continued
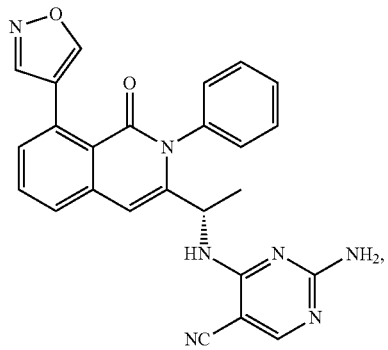
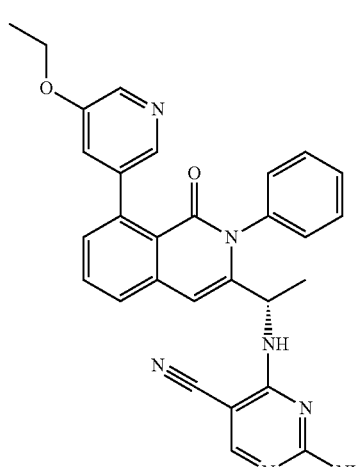
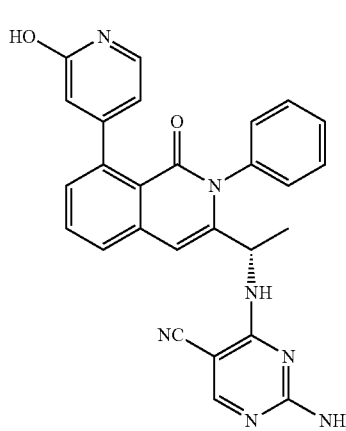
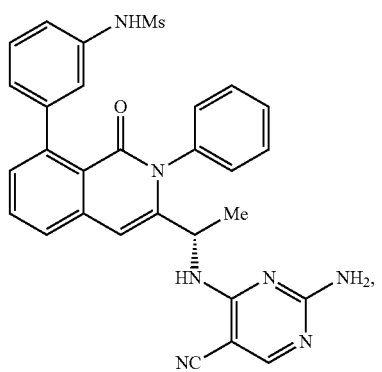

121
-continued
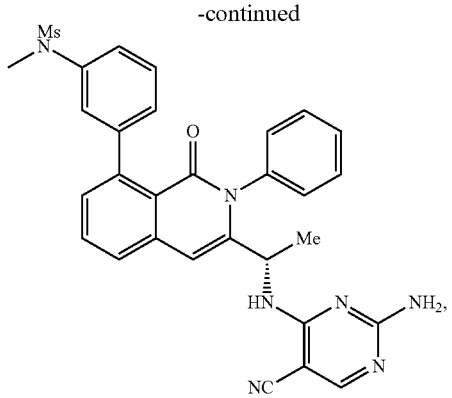
122
-continued
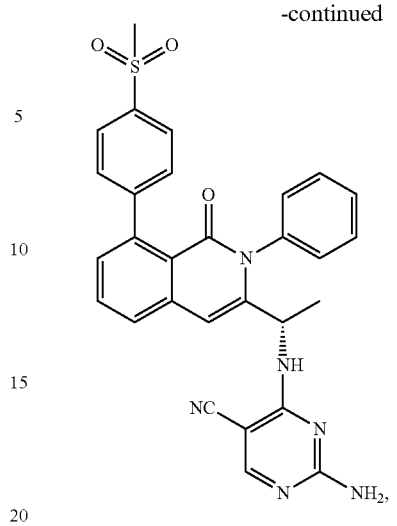
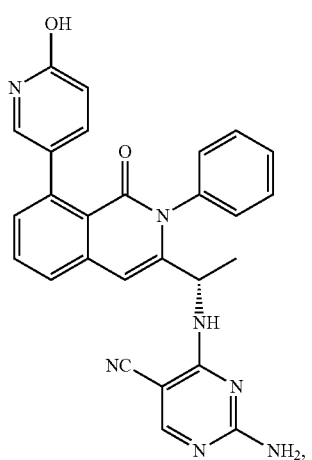
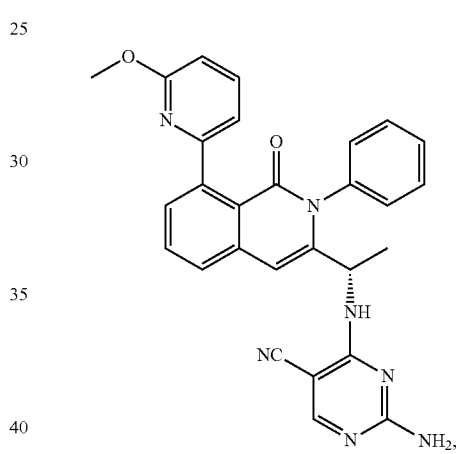
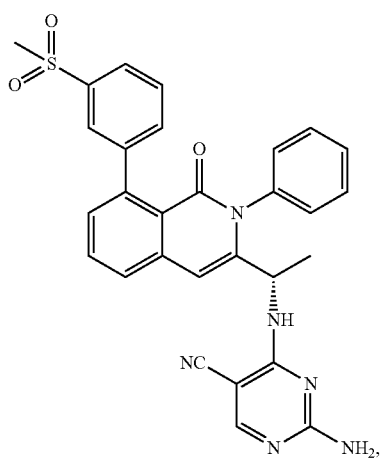
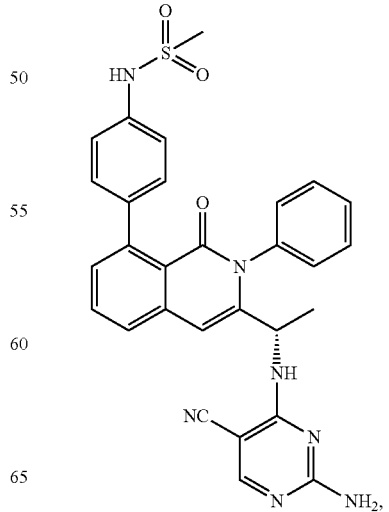

123
-continued
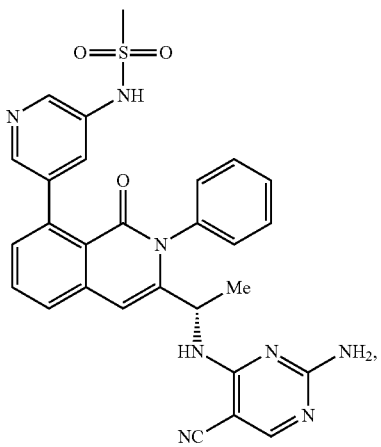
124
-continued
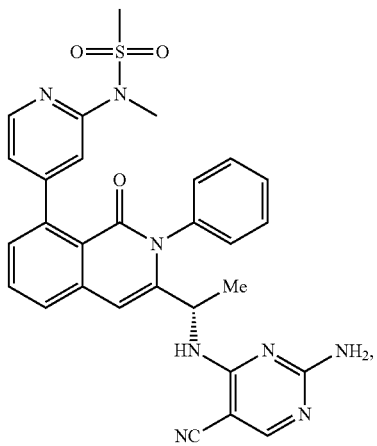
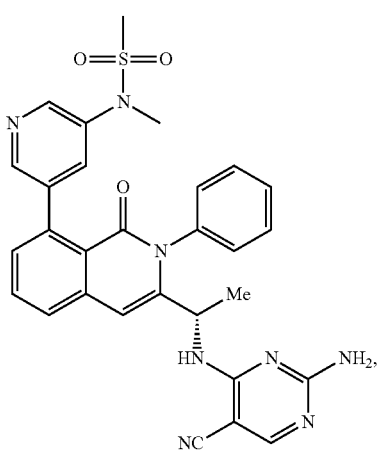
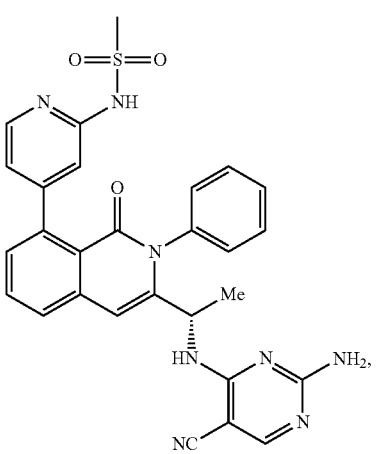
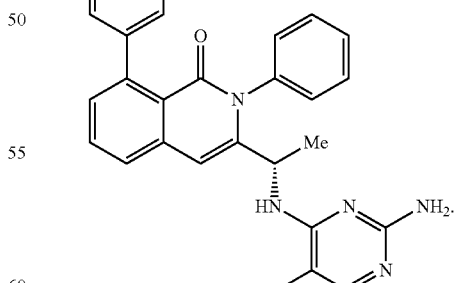
In certain embodiments, R³ is 2-pyridyl, 4-pyridyl, pyrazinyl, pyridazinyl, or pyrimidinyl.
In certain embodiments, the compound of Formula (XXIII) is selected from the following:

125
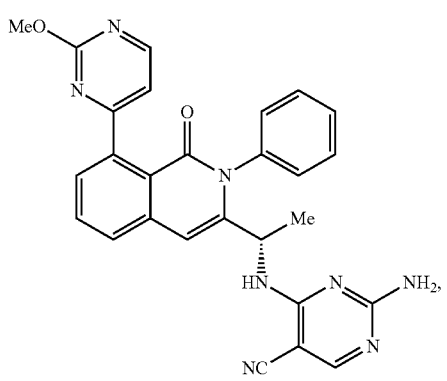
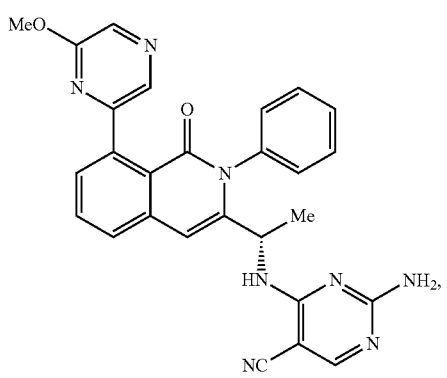
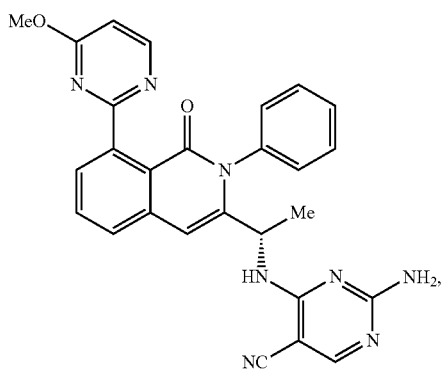
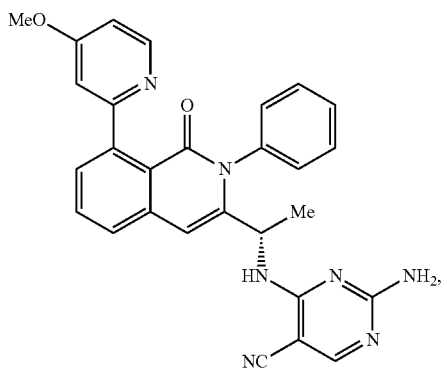
126
-continued
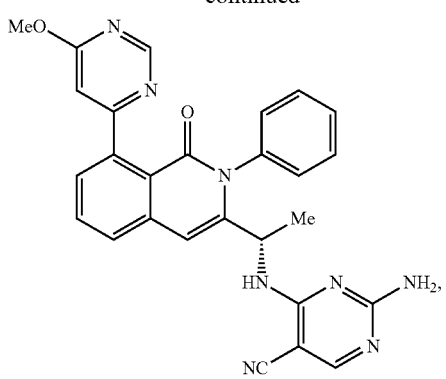
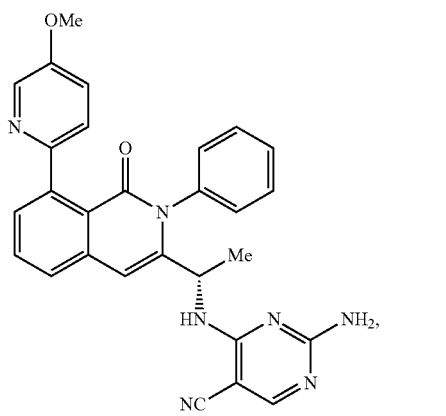
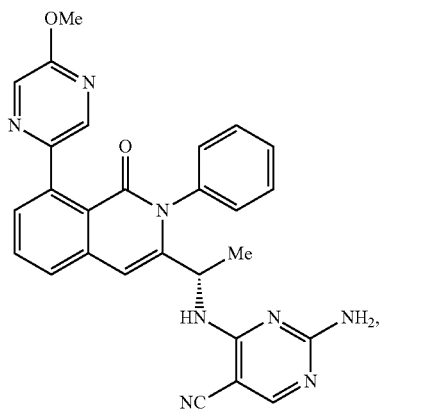
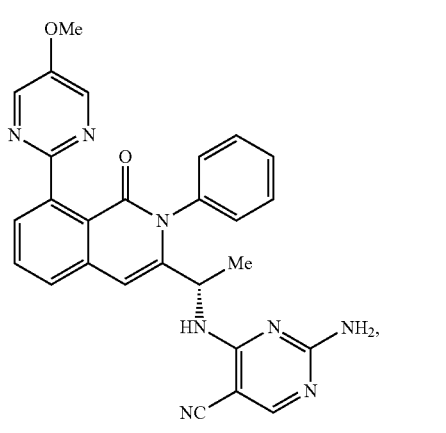

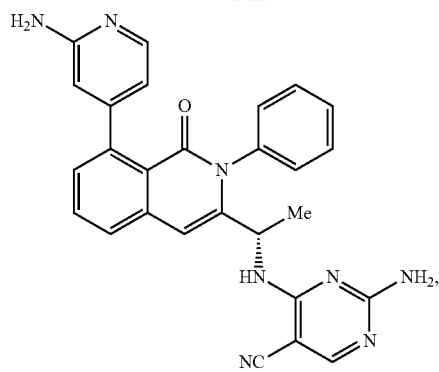
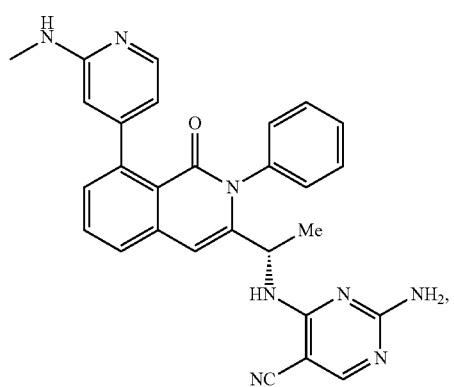
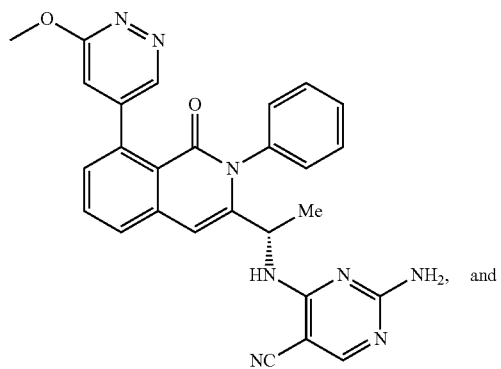
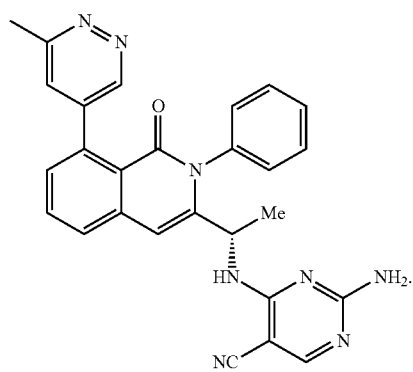
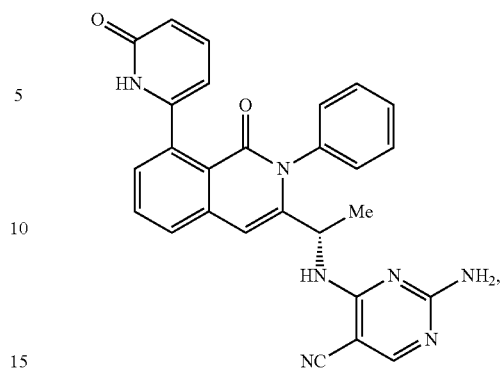
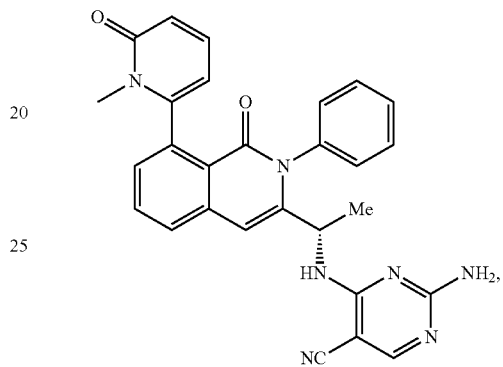
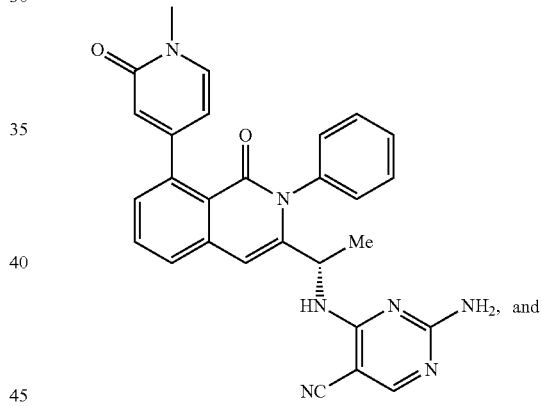
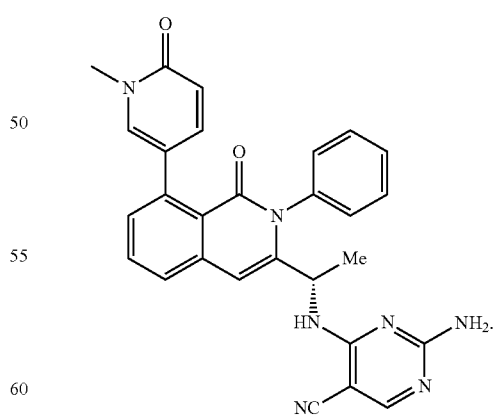
In certain embodiments, $R^3$ is pyridinone.
In certain embodiments, the compound of Formula (XXIII) is selected from the following:
In certain embodiments, $R^3$ is pyridyl and $R^{20}$ is amido. In certain embodiments, $R^3$ is pyridyl substituted with alkoxy.
In certain embodiments, the compound of Formula (XXIII) is selected from the following:

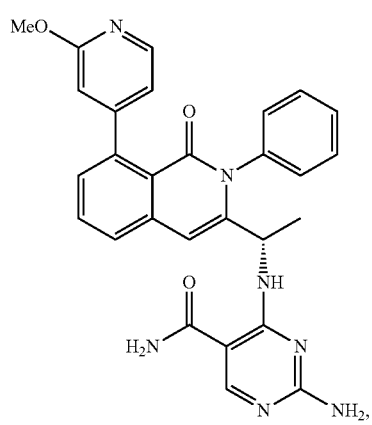
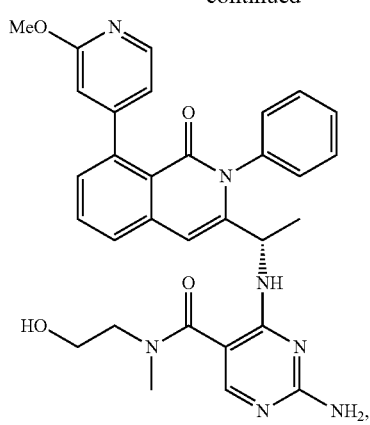
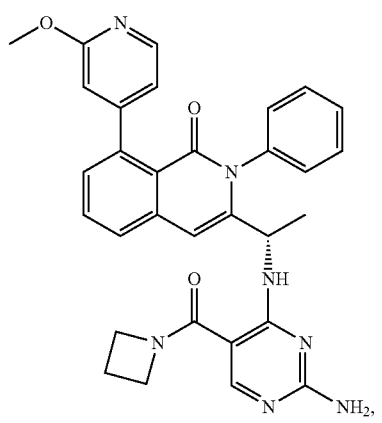
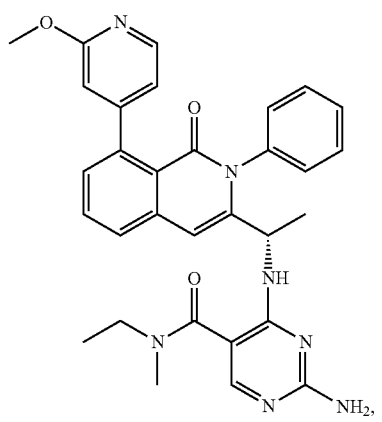
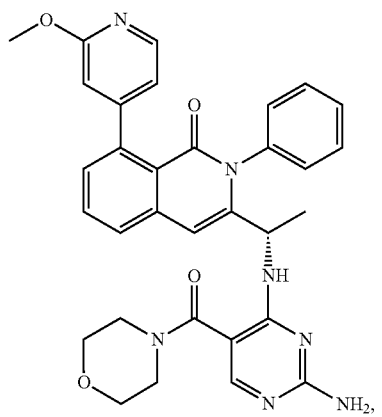

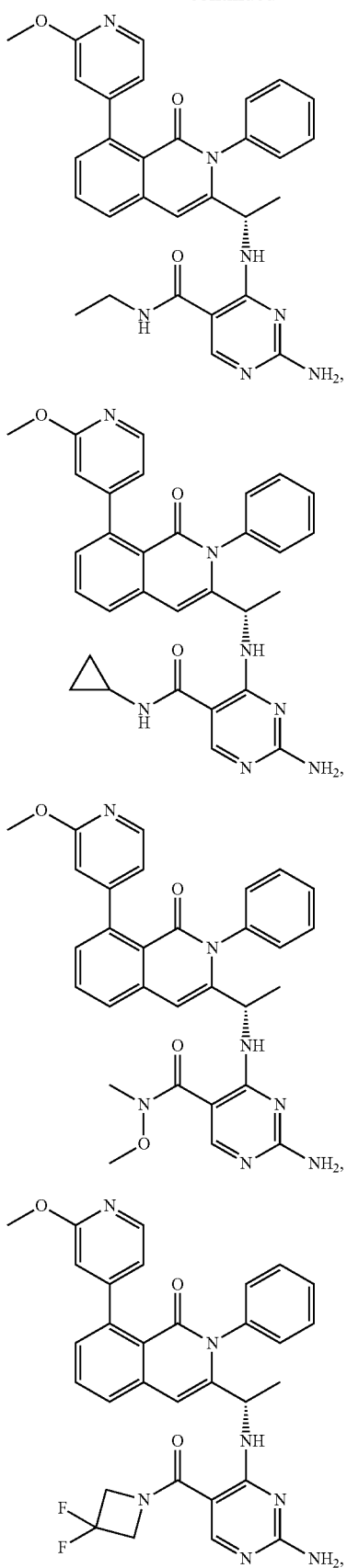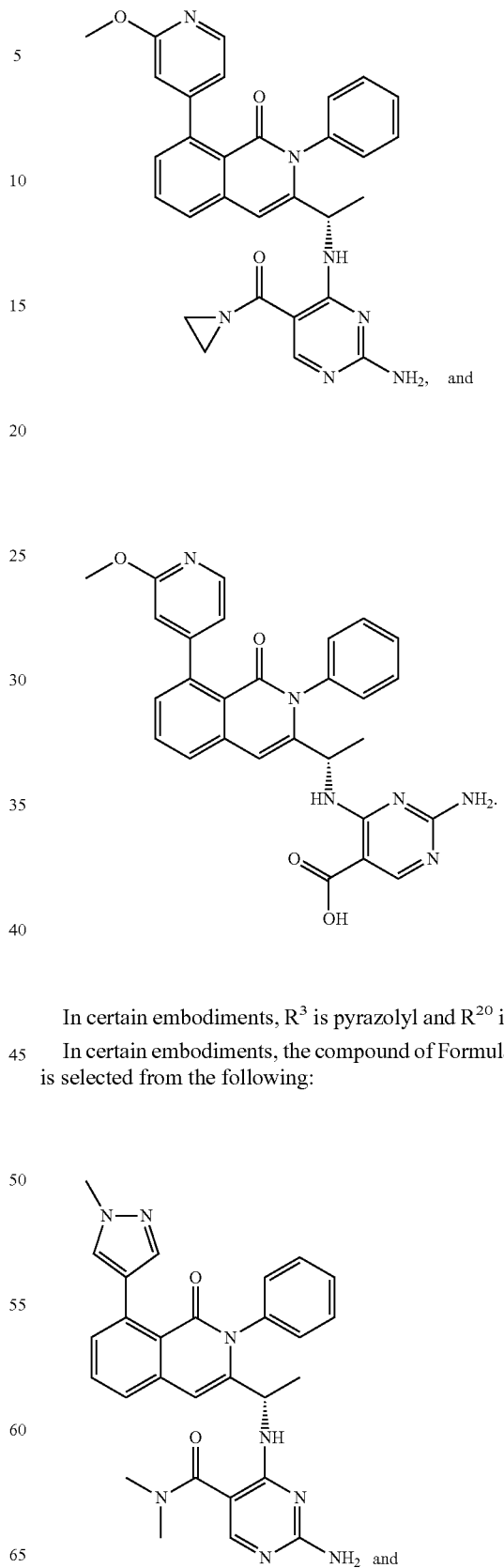
In certain embodiments, $R^3$ is pyrazolyl and $R^{20}$ is amido.
In certain embodiments, the compound of Formula (XXII) is selected from the following:

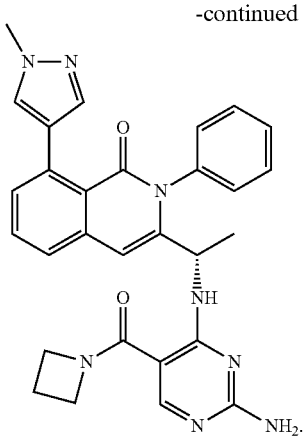

In certain embodiments, the compound of Formula (XXII) has a structure of Formula (XXIV):

(XXIV)

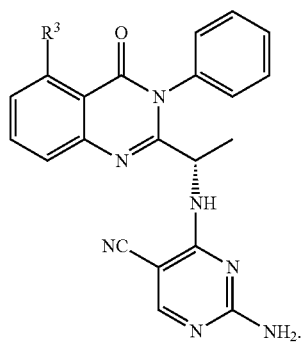

wherein $R^3$ is alkynyl, aryl, heteroaryl. In certain embodiments, $R^3$ is phenyl, triazole, or pyridyl. In some embodiments, $R^3$ is

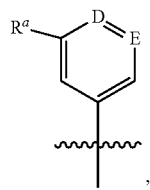

wherein Ra is amino, and either D is nitrogen and E is carbon, or D is carbon and E is nitrogen.

In certain embodiments, the compound of Formula (XXIV) is selected from the following:

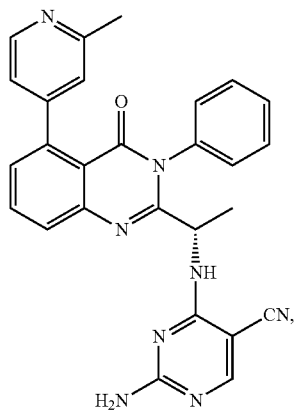

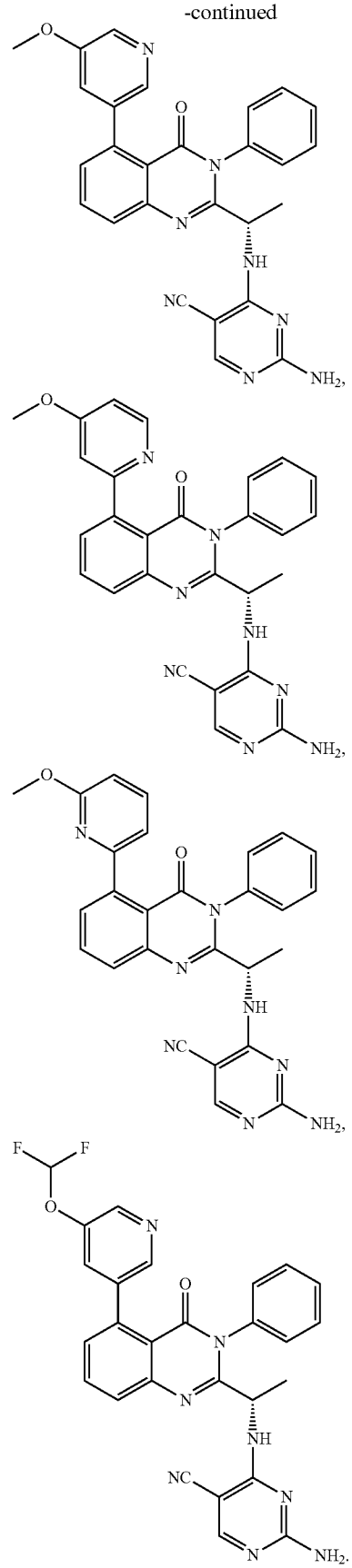

In certain embodiments, the compound of Formula (I) has a structure of Formula (XXV):
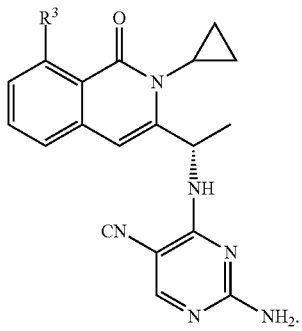
(XXV)
In certain embodiments, R³ is heteroaryl;
In certain embodiments, R³ is pyrimidinyl, pyridyl, or pyridanizyl;
In certain embodiments, the compound of Formula (XXV) is selected from the following:
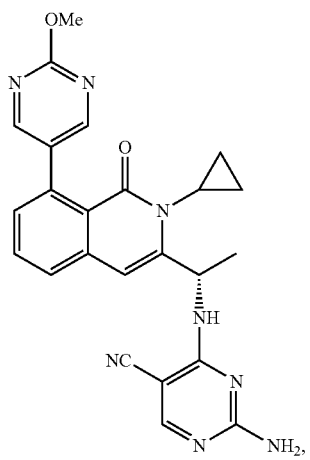
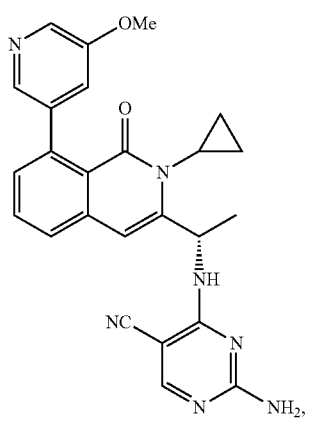
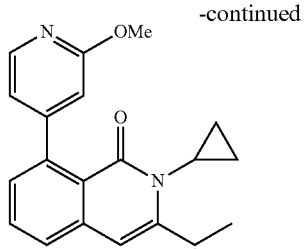
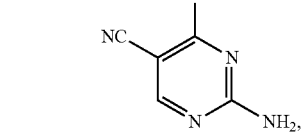
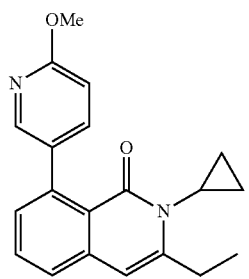
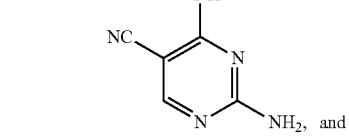
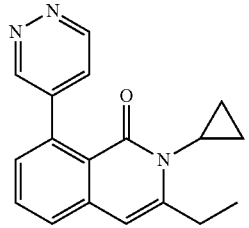
, and
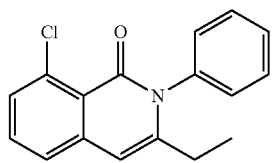
In another aspect, provided herein are compounds of Formula (XXVI):
(XXVI)
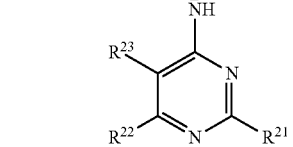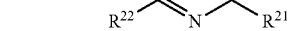

wherein:
R²¹ and R²² are each independently hydrogen, methyl, chloro, or amino;
R²³ is hydrogen, alkynyl, phenyl, cyano, methylsulfonyl or nitro; and
wherein when R²¹ is amino, then at least one of R²² and R²³ is not H.
In certain embodiments, the compound of Formula (XXVI) is selected from the following:
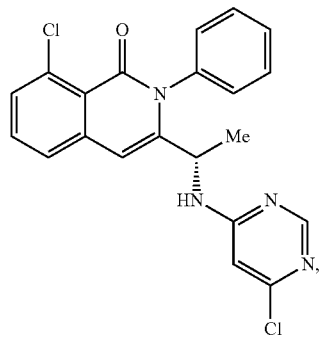
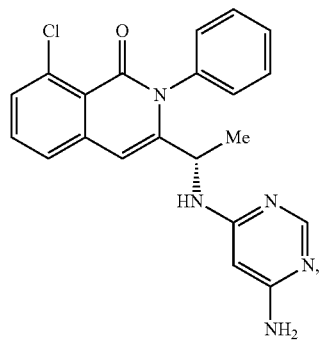
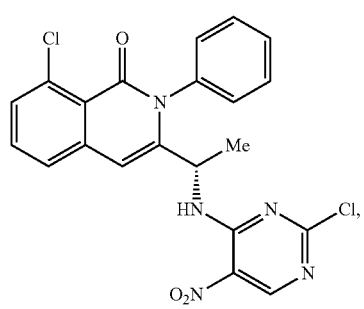
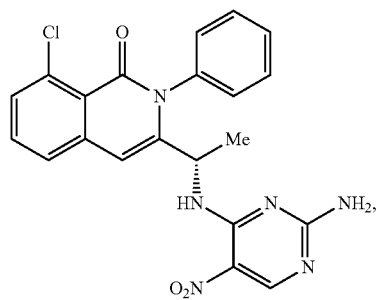
-continued
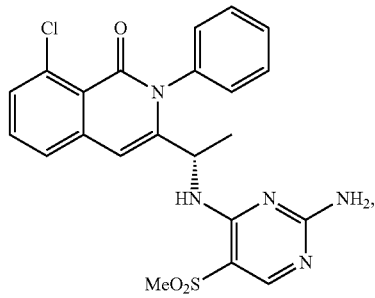
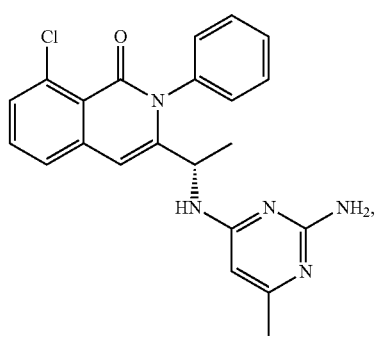
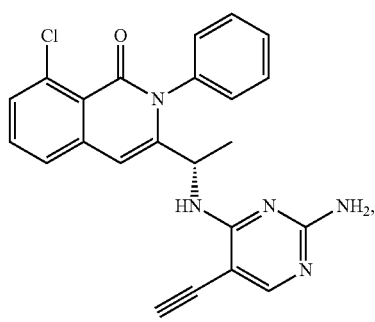
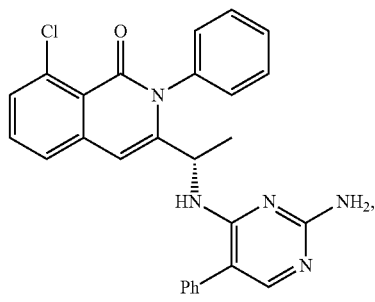
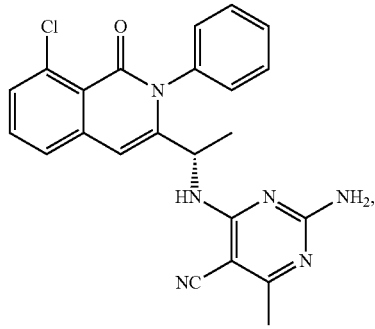

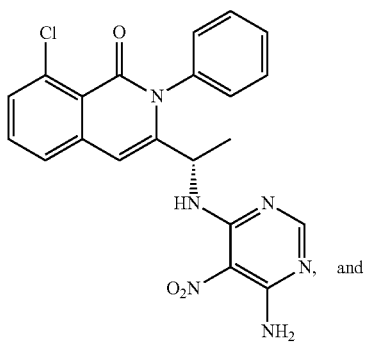

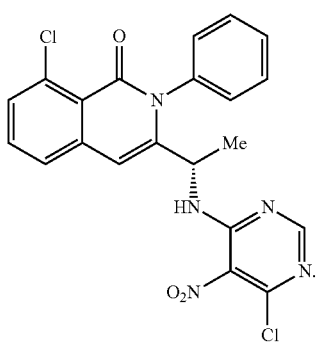 [SMILES: C[C@H](Nc1ncnc(Cl)c1[N+](=O)[O-])c1cc2cccc(Cl)c2c(=O)n1-c1ccccc1]

In another aspect, provided herein are compounds of Formula (XXVII):

(XXVII)

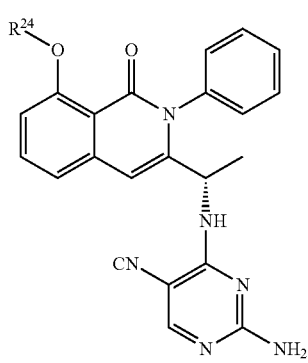

wherein $R^{24}$ is H, alkyl, or aryl.

In certain embodiments, the compound of Formula (XXVII) is selected from the following:

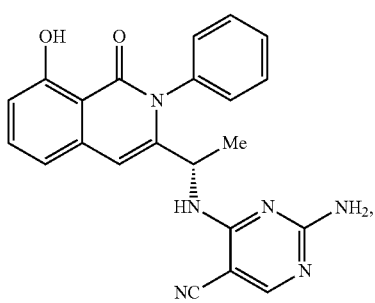

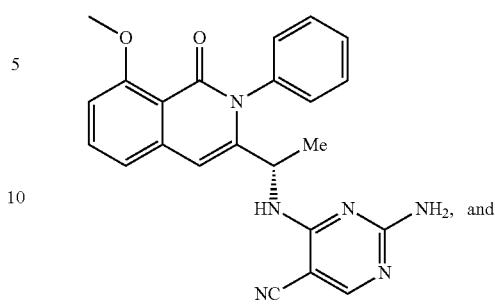

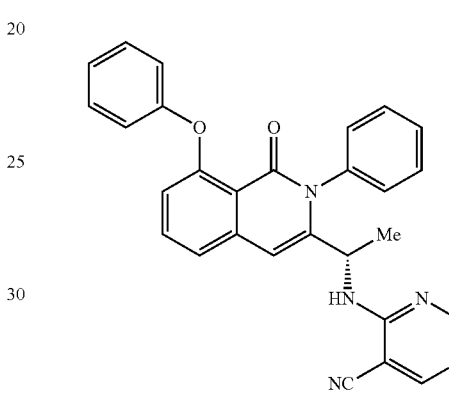

In another aspect, provided herein are compounds of Formula (XXVIII):

(XXVIII)

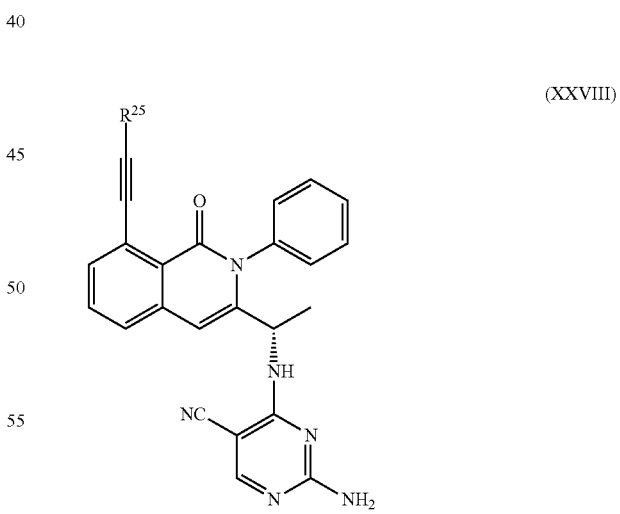

wherein $R^{25}$ is H or substituted alkyl (e.g., alkyl substituted with amide).

In certain embodiments, the compound of Formula (XXVIII) is selected from the following:

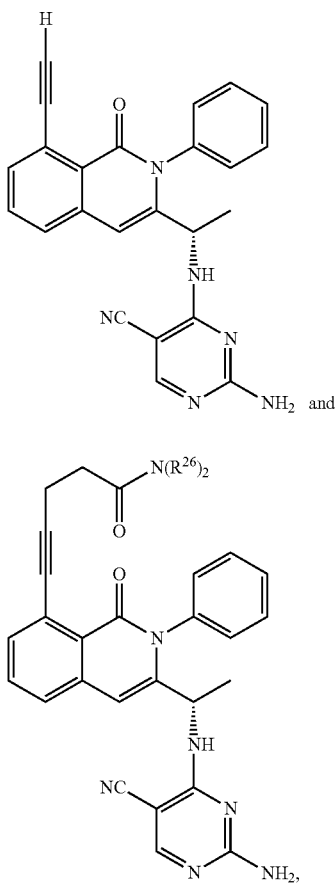

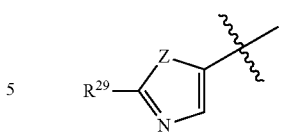

wherein Z is O, S, or NH; and $R^{29}$ is H, alkyl, or alkoxy.

In certain embodiments, the compound of Formula (XXIX) is selected from the following:

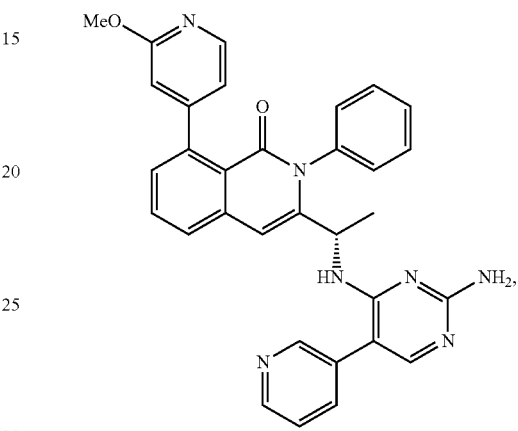

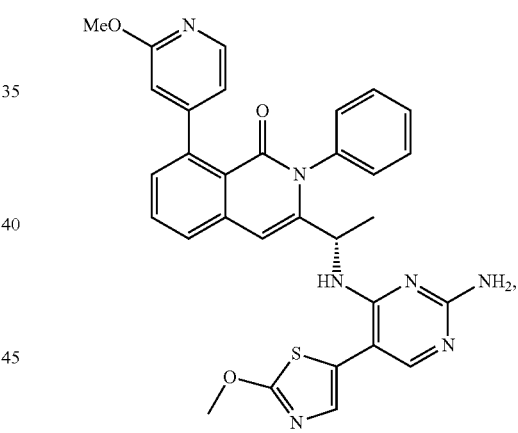

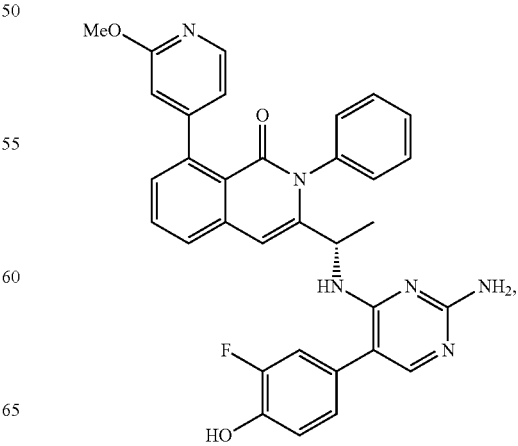

wherein $R^{26}$ is selected from H, alkyl, heteroalkyl, cycloalkyl, heterocyclyl, aryl or heteroaryl.

In another aspect, provided herein are compounds of Formula (XXIX):

(XXIX)

wherein $R^{27}$ is aryl, heteroaryl, —CO(NR$^{28}$R$^{28}$), or —N═C (O)R$^{28}$, and $R^{28}$ is selected from H, alkyl, heteroalkyl, cycloalkyl, heterocyclyl, aryl or heteroaryl. In certain embodiments, $R^{27}$ is substituted phenyl. In certain embodiments, $R^{27}$ is pyridinyl or substituted pyridinyl. In certain embodiments, $R^{27}$ is substituted phenyl. In certain embodiments, $R^{27}$ is -continued

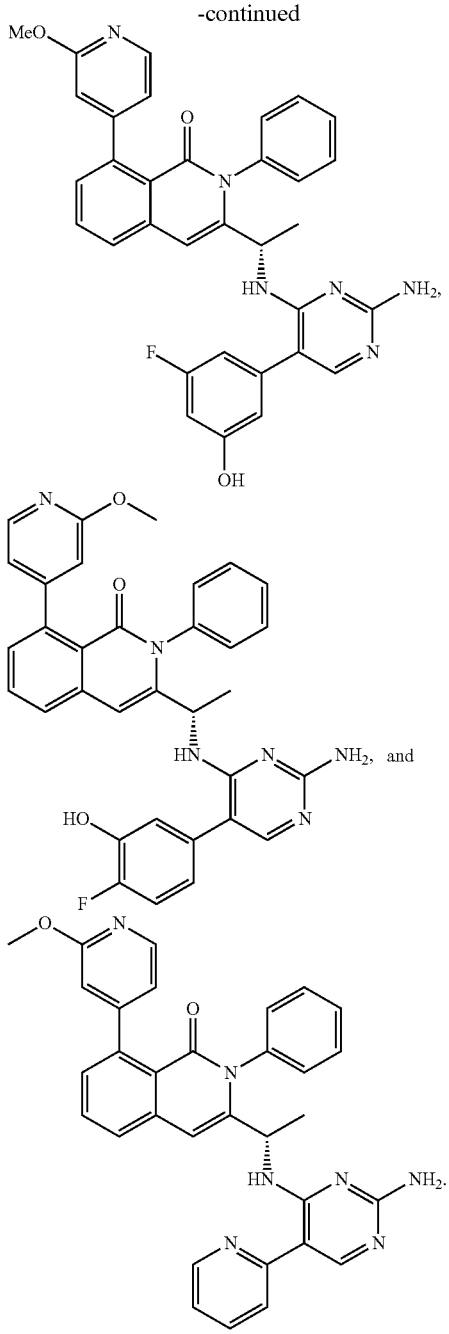

In some embodiments, one or more compounds described herein bind to a PI3 kinase (e.g., bind selectively). In some embodiments, one or more compounds described herein bind selectively to a γ or δ subtype of a PI3 kinase.

In some embodiments, the $IC_{50}$ of a subject compound for p110α, p110β, p110γ, or p110δ is less than about 1 μM, less than about 100 nM, less than about 50 nM, less than about 10 nM, less than 1 nM or even less than about 0.5 nM. In some embodiments, the $IC_{50}$ of a subject compound for mTor is less than about 1 μM, less than about 100 nM, less than about 50 nM, less than about 10 nM, less than 1 nM or even less than about 0.5 nM. In some other embodiments, one or more subject compounds exhibit dual binding specificity and are capable of inhibiting a PI3 kinase (e.g., a class I PI3 kinase) as well as a protein kinase (e.g., mTor) with an $IC_{50}$ value less than about 1 μM, less than about 100 nM, less than about 50 nM, less than about 10 nM, less than 1 nM or even less than about 0.5 nM. One or more subject compounds are capable of inhibiting tyrosine kinases including, for example, DNA-dependent protein kinase (Pubmed protein accession number (PPAN) AAA79184), Abl tyrosine kinase (CAA52387), Bcr-Abl, hemopoietic cell kinase (PPAN CAI19695), Src (PPAN CAA24495), vascular endothelial growth factor receptor 2 (PPAN ABB82619), vascular endothelial growth factor receptor-2 (PPAN ABB82619), epidermal growth factor receptor (PPAN AG43241), EPH receptor B4 (PPAN EAL23820), stem cell factor receptor (PPAN AAF22141), Tyrosine-protein kinase receptor TIE-2 (PPAN Q02858), fms-related tyrosine kinase 3 (PPAN NP_004110), platelet-derived growth factor receptor alpha (PPAN NP_990080), RET (PPAN CAA73131), and functional mutants thereof. In some embodiments, the tyrosine kinase is Abl, Bcr-Abl, EGFR, or Flt-3, and any other kinases listed in the Tables herein.

In some embodiments, non-limiting exemplary compounds exhibit one or more functional characteristics provided herein. For example, one or more subject compounds bind specifically to a PI3 kinase. In some embodiments, the $IC_{50}$ of a subject compound for p110α, p110β, p110γ, or p110δ is less than about 1 μM, less than about 100 nM, less than about 50 nM, less than about 10 nM, less than about 1 nM, less than about 0.5 nM, less than about 100 pM, or less than about 50 pM.

In some embodiments, one or more of the subject compounds can selectively inhibit one or more members of type I or class I phosphatidylinositol 3-kinases (PI3-kinase) with an $IC_{50}$ value of about 100 nM, 50 nM, 10 nM, 5 nM, 100 pM, 10 pM or 1 pM, or less as measured in an in vitro kinase assay.

In some embodiments, one or more of the subject compounds can selectively inhibit one or two members of type I or class I phosphatidylinositol 3-kinases (PI3-kinase) such as PI3-kinase α, PI3-kinase β, PI3-kinase γ, and PI3-kinase δ. In some aspects, some of the subject compounds selectively inhibit PI3-kinase δ as compared to all other type I PI3-kinases. In other aspects, some of the subject compounds selectively inhibit PI3-kinase δ and PI3-kinase γ as compared to the rest of the type I PI3-kinases. In yet other aspects, some of the subject compounds selectively inhibit PI3-kinase α and PI3-kinase β as compared to the rest of the type I PI3-kinases. In still yet some other aspects, some of the subject compounds selectively inhibit PI3-kinase δ and PI3-kinase α as compared to the rest of the type I PI3-kinases. In still yet some other aspects, some of the subject compounds selectively inhibit PI3-kinase δ and PI3-kinase β as compared to the rest of the type I PI3-kinases, or selectively inhibit PI3-kinase δ and PI3-kinase α as compared to the rest of the type I PI3-kinases, or selectively inhibit PI3-kinase α and PI3-kinase γ as compared to the rest of the type I PI3-kinases, or selectively inhibit PI3-kinase γ and PI3-kinase β as compared to the rest of the type I PI3-kinases.

In yet another aspect, an inhibitor that selectively inhibits one or more members of type I PI3-kinases, or an inhibitor that selectively inhibits one or more type I PI3-kinase mediated signaling pathways, alternatively can be understood to refer to a compound that exhibits a 50% inhibitory concentration ($IC_{50}$) with respect to a given type I PI3-kinase, that is at least about 10-fold, at least about 20-fold, at least about 50-fold, at least about 100-fold, at least about 1000-fold, at least about 10.000-fold, or lower, than the inhibitor's $IC_{50}$ with respect to the rest of the other type I PI3-kinases. In one embodiment, an inhibitor selectively inhibits PI3-kinase δ as compared to PI3-kinase β with at least about 10-fold lower $IC_{50}$ for PI3-kinase δ. In certain embodiments, the $IC_{50}$ for PI3-kinase δ is below about 100 nM, while the $IC_{50}$ for PI3-kinase β is above about 1000 nM. In certain embodiments, the $IC_{50}$ for PI3-kinase δ is below about 50 nM, while the $IC_{50}$ for PI3-kinase β is above about 5000 nM. In certain embodiments, the $IC_{50}$ for PI3-kinase δ is below about 10 nM, while the $IC_{50}$ for PI3-kinase β is above about 1000 nM, above about 5,000 nM, or above about 10,000 nM.

PHARMACEUTICAL COMPOSITIONS

In some embodiments, provided herein are pharmaceutical compositions comprising one or more compounds as provided herein, or a pharmaceutically acceptable form thereof (e.g., pharmaceutically acceptable salts, hydrates, solvates, isomers, prodrugs, and isotopically labeled derivatives), and one or more pharmaceutically acceptable excipients carriers, including inert solid diluents and fillers, diluents, including sterile aqueous solution and various organic solvents, permeation enhancers, solubilizers and adjuvants. In some embodiments, a pharmaceutical composition described herein includes a second active agent such as an additional therapeutic agent, (e.g., a chemotherapeutic).

1. FORMULATIONS

Pharmaceutical compositions can be specially formulated for administration in solid or liquid form, including those adapted for the following: oral administration, for example, drenches (aqueous or non-aqueous solutions or suspensions), tablets (e.g., those targeted for buccal, sublingual, and systemic absorption), capsules, boluses, powders, granules, pastes for application to the tongue, and intraduodenal routes; parenteral administration, including intravenous, intraarterial, subcutaneous, intramuscular, intravascular, intraperitoneal or infusion as, for example, a sterile solution or suspension, or sustained-release formulation; topical application, for example, as a cream, ointment, or a controlled-release patch or spray applied to the skin; intravaginally or intrarectally, for example, as a pessary, cream, stent or foam; sublingually; ocularly; pulmonarily; local delivery by catheter or stent; intrathecally, or nasally.

Examples of suitable aqueous and nonaqueous carriers which can be employed in pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions can also contain adjuvants such as preservatives, wetting agents, emulsifying agents, dispersing agents, lubricants, and/or antioxidants. Prevention of the action of microorganisms upon the compounds described herein can be ensured by the inclusion of various antibacterial and antifungal agents, for example, paraben, chlorobutanol, phenol sorbic acid, and the like. It can also be desirable to include isotonic agents, such as sugars, sodium chloride, and the like into the compositions. In addition, prolonged absorption of the injectable pharmaceutical form can be brought about by the inclusion of agents which delay absorption such as aluminum monostearate and gelatin.

Methods of preparing these formulations or compositions include the step of bringing into association a compound described herein and/or the chemotherapeutic with the carrier and, optionally, one or more accessory ingredients. In general, the formulations are prepared by uniformly and intimately bringing into association a compound as provided herein with liquid carriers, or finely divided solid carriers, or both, and then, if necessary, shaping the product.

Preparations for such pharmaceutical compositions are well-known in the art. See, e.g., Anderson, Philip O.; Knoben, James E.; Troutman, William G, eds., *Handbook of Clinical Drug Data*, Tenth Edition, McGraw-Hill, 2002; Pratt and Taylor, eds., *Principles of Drug Action*, Third Edition, Churchill Livingston, New York, 1990; Katzung, ed., *Basic and Clinical Pharmacology*, Ninth Edition, McGraw Hill, 20037ybg; Goodman and Gilman, eds., *The Pharmacological Basis of Therapeutics*, Tenth Edition, McGraw Hill, 2001; *Remingtons Pharmaceutical Sciences*, 20th Ed., Lippincott Williams & Wilkins, 2000; Martindale, *The Extra Pharmacopoeia*, Thirty-Second Edition (The Pharmaceutical Press, London, 1999); all of which are incorporated by reference herein in their entirety. Except insofar as any conventional excipient medium is incompatible with the compounds provided herein, such as by producing any undesirable biological effect or otherwise interacting in a deleterious manner with any other component(s) of the pharmaceutically acceptable composition, the excipient's use is contemplated to be within the scope of this disclosure.

In some embodiments, the concentration of one or more of the compounds provided in the disclosed pharmaceutical compositions is less than about 100%, about 90%, about 80%, about 70%, about 60%, about 50%, about 40%, about 30%, about 20%, about 19%, about 18%, about 17%, about 16%, about 15%, about 14%, about 13%, about 12%, about 11%, about 10%, about 9%, about 8%, about 7%, about 6%, about 5%, about 4%, about 3%, about 2%, about 1%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, about 0.009%, about 0.008%, about 0.007%, about 0.006%, about 0.005%, about 0.004%, about 0.003%, about 0.002%, about 0.001%, about 0.0009%, about 0.0008%, about 0.0007%, about 0.0006%, about 0.0005%, about 0.0004%, about 0.0003%, about 0.0002%, or about 0.0001% w/w, w/v or v/v.

In some embodiments, the concentration of one or more of the compounds as provided herein is greater than about 90%, about 80%, about 70%, about 60%, about 50%, about 40%, about 30%, about 20%, about 19.75%, about 19.50%, about 19.25% about 19%, about 18.75%, about 18.50%, about 18.25%, about 18%, about 17.75%, about 17.50%, about 17.25%, about 17%, about 16.75%, about 16.50%, about 16.25%, about 16%, about 15.75%, about 15.50%, about 15.25%, about 15%, about 14.75%, about 14.50%, about 14.25%, about 14%, about 13.75%, about 13.50%, about 13.25%, about 13%, about 12.75%, about 12.50%, about 12.25%, about 12%, about 11.75%, about 11.50%, about 11.25%, about 11%, about 10.75%, about 10.50%, about 10.25%, about 10%, about 9.75%, about 9.50%, about 9.25%, about 9%, about 8.75%, about 8.50%, about 8.25%, about 8%, about 7.75%, about 7.50%, about 7.25%, about 7%, about 6.75%, about 6.50%, about 6.25%, about 6%, about 5.75%, about 5.50%, about 5.25%, about 5%, about 4.75%, about 4.50%, about 4.25%, about 4%, about 3.75%, about 3.50%, about 3.25%, about 3%, about 2.75%, about 2.50%, about 2.25%, about 2%, about 1.75%, about 1.50%, about 1.25%, about 1%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, about 0.009%, about 0.008%, about 0.007%, about 0.006%, about 0.005%, about 0.004%, about 0.003%, about 0.002%, about 0.001%, about 0.0009%, about 0.0008%, about 0.0007%, about 0.0006%, about 0.0005%, about 0.0004%, about 0.0003%, about 0.0002%, or about 0.0001% w/w, w/v, or v/v.

In some embodiments, the concentration of one or more of the compounds as provided herein is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% w/w, w/v or v/v. v/v.

In some embodiments, the concentration of one or more of the compounds as provided herein is in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v or v/v.

In some embodiments, the amount of one or more of the compounds as provided herein is equal to or less than about 10 g, about 9.5 g, about 9.0 g, about 8.5 g, about 8.0 g, 7.5 g, about 7.0 g, about 6.5 g, about 6.0 g, about 5.5 g, about 5.0 g, about 4.5 g, about 4.0 g, about 3.5 g, about 3.0 g, about 2.5 g, about 2.0 g, about 1.5 g, about 1.0 g, about 0.95 g, about 0.9 g, about 0.85 g, about 0.8 g, about 0.75 g, about 0.7 g, about 0.65 g, about 0.6 g, about 0.55 g, about 0.5 g, about 0.45 g, about 0.4 g, about 0.35 g, about 0.3 g, about 0.25 g, about 0.2 g, about 0.15 g, about 0.1 g, about 0.09 g, about 0.08 g, about 0.07 g, about 0.06 g, about 0.05 g, about 0.04 g, about 0.03 g, about 0.02 g, about 0.01 g, about 0.009 g, about 0.008 g, about 0.007 g, about 0.006 g, about 0.005 g, about 0.004 g, about 0.003 g, about 0.002 g, about 0.001 g, about 0.0009 g, about 0.0008 g, about 0.0007 g, about 0.0006 g, about 0.0005 g, about 0.0004 g, about 0.0003 g, about 0.0002 g, or about 0.0001 g.

In some embodiments, the amount of one or more of the compounds as provided herein is more than about 0.0001 g, about 0.0002 g, about 0.0003 g, about 0.0004 g, about 0.0005 g, about 0.0006 g, about 0.0007 g, about 0.0008 g, about 0.0009 g, about 0.001 g, about 0.0015 g, about 0.002 g, about 0.0025 g, about 0.003 g, about 0.0035 g, about 0.004 g, about 0.0045 g, about 0.005 g, about 0.0055 g, about 0.006 g, about 0.0065 g, about 0.007 g, about 0.0075 g, about 0.008 g, about 0.0085 g, about 0.009 g, about 0.0095 g, about 0.01 g, about 0.015 g, about 0.02 g, about 0.025 g, about 0.03 g, about 0.035 g, about 0.04 g, about 0.045 g, about 0.05 g, about 0.055 g, about 0.06 g, about 0.065 g, about 0.07 g, about 0.075 g, about 0.08 g, about 0.085 g, about 0.09 g, about 0.095 g, about 0.1 g, about 0.15 g, about 0.2 g, about 0.25 g, about 0.3 g, about 0.35 g, about 0.4 g, about 0.45 g, about 0.5 g, about 0.55 g, about 0.6 g, about 0.65 g, about 0.7 g, about 0.75 g, about 0.8 g, about 0.85 g, about 0.9 g, about 0.95 g, about 1 g, about 1.5 g, about 2 g, about 2.5, about 3 g, about 3.5, about 4 g, about 4.5 g, about 5 g, about 5.5 g, about 6 g, about 6.5 g, about 7 g, about 7.5 g, about 8 g, about 8.5 g, about 9 g, about 9.5 g, or about 10 g.

In some embodiments, the amount of one or more of the compounds as provided herein is in the range of about 0.0001-about 10 g, about 0.0005-about 9 g, about 0.001-about 8 g, about 0.005-about 7 g, about 0.01-about 6 g, about 0.05-about 5 g, about 0.1-about 4 g, about 0.5-about 4 g, or about 1-about 3 g.

1A. FORMULATIONS FOR ORAL ADMINISTRATION

In some embodiments, provided herein are pharmaceutical compositions for oral administration containing a compound as provided herein, and a pharmaceutical excipient suitable for oral administration. In some embodiments, provided herein are pharmaceutical compositions for oral administration containing: (i) an effective amount of a disclosed compound; optionally (ii) an effective amount of one or more second agents; and (iii) one or more pharmaceutical excipients suitable for oral administration. In some embodiments, the pharmaceutical composition further contains: (iv) an effective amount of a third agent.

In some embodiments, the pharmaceutical composition can be a liquid pharmaceutical composition suitable for oral consumption. Pharmaceutical compositions suitable for oral administration can be presented as discrete dosage forms, such as capsules, cachets, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil liquid emulsion. Such dosage forms can be prepared by any of the methods of pharmacy, but all methods include the step of bringing the active ingredient into association with the carrier, which constitutes one or more ingredients. In general, the pharmaceutical compositions are prepared by uniformly and intimately admixing the active ingredient with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

The present disclosure further encompasses anhydrous pharmaceutical compositions and dosage forms comprising an active ingredient, since water can facilitate the degradation of some compounds. For example, water can be added (e.g., about 5%) in the pharmaceutical arts as a means of simulating long-term storage in order to determine characteristics such as shelf-life or the stability of formulations over time. Anhydrous pharmaceutical compositions and dosage forms can be prepared using anhydrous or low moisture containing ingredients and low moisture or low humidity conditions. For example, pharmaceutical compositions and dosage forms which contain lactose can be made anhydrous if substantial contact with moisture and/or humidity during manufacturing, packaging, and/or storage is expected. An anhydrous pharmaceutical composition can be prepared and stored such that its anhydrous nature is maintained. Accordingly, anhydrous pharmaceutical compositions can be packaged using materials known to prevent exposure to water such that they can be included in suitable formulary kits. Examples of suitable packaging include, but are not limited to, hermetically sealed foils, plastic or the like, unit dose containers, blister packs, and strip packs.

An active ingredient can be combined in an intimate admixture with a pharmaceutical carrier according to conventional pharmaceutical compounding techniques. The carrier can take a wide variety of forms depending on the form of preparation desired for administration. In preparing the pharmaceutical compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, microcrystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. In some embodiments, tablets can be coated by standard aqueous or nonaqueous techniques.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical compositions and dosage forms provided herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants can be used in the pharmaceutical compositions as provided herein to provide tablets that disintegrate when exposed to an aqueous environment. Too much of a disintegrant can produce tablets which can disintegrate in the bottle. Too little can be insufficient for disintegration to occur and can thus alter the rate and extent of release of the active ingredient(s) from the dosage form. Thus, a sufficient amount of disintegrant that is neither too little nor too much to detrimentally alter the release of the active ingredient(s) can be used to form the dosage forms of the compounds provided herein. The amount of disintegrant used can vary based upon the type of formulation and mode of administration, and can be readily discernible to those of ordinary skill in the art. About 0.5 to about 15 weight percent of disintegrant, or about 1 to about 5 weight percent of disintegrant, can be used in the pharmaceutical composition. Disintegrants that can be used to form pharmaceutical compositions and dosage forms include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethylaureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the pharmaceutical composition.

When aqueous suspensions and/or elixirs are desired for oral administration, the active ingredient therein can be combined with various sweetening or flavoring agents, coloring matter or dyes and, for example, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactant which can be used to form pharmaceutical compositions and dosage forms include, but are not limited to, hydrophilic surfactants, lipophilic surfactants, and mixtures thereof. That is, a mixture of hydrophilic surfactants can be employed, a mixture of lipophilic surfactants can be employed, or a mixture of at least one hydrophilic surfactant and at least one lipophilic surfactant can be employed.

A suitable hydrophilic surfactant can generally have an HLB value of at least about 10, while suitable lipophilic surfactants can generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants can be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Within the aforementioned group, ionic surfactants include, by way of example: lecithins, lysolecithin, phospholipids, lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Ionic surfactants can be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants can include, but are not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and mixtures thereof; polyethylene glycol sorbitan fatty acid esters and hydrophilic transesterification products of a polyol with at least one member of triglycerides, vegetable oils, and hydrogenated vegetable oils. The polyol can be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10oleate, Tween 40, Tween 60, sucrose monostearate, sucrose monolaurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of glycerides, vegetable oils, hydrogenated vegetable oils, fatty acids and sterols; oil-soluble vitamins/vitamin derivatives; and mixtures thereof. Within this group, non-limiting examples of lipophilic surfactants include glycerol fatty acid esters, propylene glycol fatty acid esters, and mixtures thereof, or are hydrophobic transesterification products of a polyol with at least one member of vegetable oils, hydrogenated vegetable oils, and triglycerides.

In one embodiment, the pharmaceutical composition can include a solubilizer to ensure good solubilization and/or dissolution of a compound as provided herein and to minimize precipitation of the compound. This can be especially important for pharmaceutical compositions for non-oral use, e.g., pharmaceutical compositions for injection. A solubilizer can also be added to increase the solubility of the hydrophilic drug and/or other components, such as surfactants, or to maintain the pharmaceutical composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, $\epsilon$-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, $\epsilon$-caprolactone and isomers thereof, $\delta$-valerolactone and isomers thereof, $\beta$-butyrolactone and isomers thereof; and other solubilizers known in the art, such as dimethyl acetamide, dimethyl isosorbide, N-methylpyrrolidones, monooctanoin, diethylene glycol monoethyl ether, and water.

Mixtures of solubilizers can also be used. Examples include, but not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. In some embodiments, solubilizers include sorbitol, glycerol, triacetin, ethyl alcohol, PEG-400, glycofurol and propylene glycol.

The amount of solubilizer that can be included is not particularly limited. The amount of a given solubilizer can be limited to a bioacceptable amount, which can be readily determined by one of skill in the art. In some circumstances, it can be advantageous to include amounts of solubilizers far in excess of bioacceptable amounts, for example to maximize the concentration of the drug, with excess solubilizer removed prior to providing the pharmaceutical composition to a subject using conventional techniques, such as distillation or evaporation. Thus, if present, the solubilizer can be in a weight ratio of about 10%, 25%, 50%, 100%, or up to about 200% by weight, based on the combined weight of the drug, and other excipients. If desired, very small amounts of solubilizer can also be used, such as about 5%, 2%, 1% or even less. Typically, the solubilizer can be present in an amount of about 1% to about 100%, more typically about 5% to about 25% by weight.

The pharmaceutical composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, oils, odorants, opacifiers, suspending agents, binders, fillers, plasticizers, lubricants, and mixtures thereof.

Exemplary preservatives can include antioxidants, chelating agents, antimicrobial preservatives, antifungal preservatives, alcohol preservatives, acidic preservatives, and other preservatives. Exemplary antioxidants include, but are not limited to, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfate, sodium metabisulfite, and sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and sorbic acid. Exemplary alcohol preservatives include, but are not limited to, ethanol, polyethylene glycol, phenol, phenolic compounds, bisphenol, chlorobutanol, hydroxybenzoate, and phenylethyl alcohol. Exemplary acidic preservatives include, but are not limited to, vitamin A, vitamin C, vitamin E, beta-carotene, citric acid, acetic acid, dehydroacetic acid, ascorbic acid, sorbic acid, and phytic acid. Other preservatives include, but are not limited to, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfate, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

In addition, an acid or a base can be incorporated into the pharmaceutical composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl)aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals, alkaline earth metals, and the like. Examples can include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid and the like.

1B. FORMULATIONS FOR PARENTERAL ADMINISTRATION

In some embodiments, provided herein are pharmaceutical compositions for parenteral administration containing a compound as provided herein, and a pharmaceutical excipient suitable for parenteral administration. In some embodiments, provided herein are pharmaceutical compositions for parenteral administration containing: (i) an effective amount of a disclosed compound; optionally (ii) an effective amount of one or more second agents; and (iii) one or more pharmaceutical excipients suitable for parenteral administration. In some embodiments, the pharmaceutical composition further contains: (iv) an effective amount of a third agent.

The forms in which the disclosed pharmaceutical compositions can be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol, liquid polyethylene glycol, and the like (and suitable mixtures thereof), cyclodextrin derivatives, and vegetable oils can also be employed.

Aqueous solutions in saline are also conventionally used for injection. Ethanol, glycerol, propylene glycol, liquid polyethylene glycol, and the like (and suitable mixtures thereof), cyclodextrin derivatives, and vegetable oils can also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating a compound as provided herein in the required amount in the appropriate solvent with various other ingredients as enumerated above, as appropriate, followed by filtered sterilization. Generally, dispersions are prepared by incorporating the various sterilized active ingredients into a sterile vehicle which contains the basic dispersion medium and the appropriate other ingredients from those enumerated above. In the case of sterile powders for the preparation of sterile injectable solutions, certain methods of preparation are vacuum-drying and freeze-drying techniques which yield a powder of the active ingredient plus any additional ingredient from a previously sterile-filtered solution thereof.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. Injectable compositions can contain from about 0.1 to about 5% w/w of a compound as disclosed herein.

1C. FORMULATIONS FOR TOPICAL ADMINISTRATION

In some embodiments, provided herein are pharmaceutical compositions for topical (e.g., transdermal) administration containing a compound as provided herein, and a pharmaceutical excipient suitable for topical administration. In some embodiments, provided herein are pharmaceutical compositions for topical administration containing: (i) an effective amount of a disclosed compound; optionally (ii) an effective amount of one or more second agents; and (iii) one or more pharmaceutical excipients suitable for topical administration. In some embodiments, the pharmaceutical composition further contains: (iv) an effective amount of a third agent.

Pharmaceutical compositions provided herein can be formulated into preparations in solid, semi-solid, or liquid forms suitable for local or topical administration, such as gels, water soluble jellies, creams, lotions, suspensions, foams, powders, slurries, ointments, solutions, oils, pastes, suppositories, sprays, emulsions, saline solutions, dimethylsulfoxide (DMSO)-based solutions. In general, carriers with higher densities are capable of providing an area with a prolonged exposure to the active ingredients. In contrast, a solution formulation can provide more immediate exposure of the active ingredient to the chosen area.

The pharmaceutical compositions also can comprise suitable solid or gel phase carriers or excipients, which are compounds that allow increased penetration of, or assist in the delivery of, therapeutic molecules across the stratum corneum permeability barrier of the skin. There are many of these penetration-enhancing molecules known to those trained in the art of topical formulation. Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

Another exemplary formulation for use in the disclosed methods employs transdermal delivery devices ("patches"). Such transdermal patches can be used to provide continuous or discontinuous infusion of a compound as provided herein in controlled amounts, either with or without another agent.

The construction and use of transdermal patches for the delivery of pharmaceutical agents is well known in the art. See, e.g., U.S. Pat. Nos. 5,023,252, 4,992,445 and 5,001,139. Such patches can be constructed for continuous, pulsatile, or on demand delivery of pharmaceutical agents.

Suitable devices for use in delivering intradermal pharmaceutically acceptable compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions can be administered by devices which limit the effective penetration length of a needle into the skin, such as those described in PCT publication WO 99/34850 and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate vaccine in powder form through the outer layers of the skin to the dermis are suitable. Alternatively or additionally, conventional syringes can be used in the classical mantoux method of intradermal administration.

Topically-administrable formulations can, for example, comprise from about 1% to about 10% (w/w) compound of formula (I), although the concentration of the compound of formula (I) can be as high as the solubility limit of the compound of formula (I) in the solvent. In some embodiments, topically-administrable formulations can, for example, comprise from about 1% to about 9% (w/w) compound of formula (I), such as from about 1% to about 8% (w/w), further such as from about 1% to about 7% (w/w), further such as from about 1% to about 6% (w/w), further such as from about 1% to about 5% (w/w), further such as from about 1% to about 4% (w/w), further such as from about 1% to about 3% (w/w), and further such as from about 1% to about 2% (w/w) compound of formula (I). Formulations for topical administration can further comprise one or more of the additional pharmaceutically acceptable excipients described herein.

1D. FORMULATIONS FOR INHALATION ADMINISTRATION

In some embodiments, provided herein are pharmaceutical compositions for inhalation administration containing a compound as provided herein, and a pharmaceutical excipient suitable for topical administration. In some embodiments, provided herein are pharmaceutical compositions for inhalation administration containing: (i) an effective amount of a disclosed compound; optionally (ii) an effective amount of one or more second agents; and (iii) one or more pharmaceutical excipients suitable for inhalation administration. In some embodiments, the pharmaceutical composition further contains: (iv) an effective amount of a third agent.

Pharmaceutical compositions for inhalation or insufflation include solutions and suspensions in pharmaceutically acceptable, aqueous or organic solvents, or mixtures thereof, and powders. The liquid or solid pharmaceutical compositions can contain suitable pharmaceutically acceptable excipients as described herein. In some embodiments, the pharmaceutical compositions are administered by the oral or nasal respiratory route for local or systemic effect. Pharmaceutical compositions in pharmaceutically acceptable solvents can be nebulized by use of inert gases. Nebulized solutions can be inhaled directly from the nebulizing device or the nebulizing device can be attached to a face mask tent, or intermittent positive pressure breathing machine. Solution, suspension, or powder pharmaceutical compositions can be administered, e.g., orally or nasally, from devices that deliver the formulation in an appropriate manner.

1E. FORMULATIONS FOR OCULAR ADMINISTRATION

In some embodiments, the disclosure provides a pharmaceutical composition for treating ophthalmic disorders. The pharmaceutical composition can contain an effective amount of a compound as provided herein and a pharmaceutical excipient suitable for ocular administration. Pharmaceutical compositions suitable for ocular administration can be presented as discrete dosage forms, such as drops or sprays each containing a predetermined amount of an active ingredient a solution, or a suspension in an aqueous or non-aqueous liquid, an oil-in-water emulsion, or a water-in-oil liquid emulsion. Other administration forms include intraocular injection, intravitreal injection, topically, or through the use of a drug eluting device, microcapsule, implant, or microfluidic device. In some cases, the compounds as provided herein are administered with a carrier or excipient that increases the intraocular penetrance of the compound such as an oil and water emulsion with colloid particles having an oily core surrounded by an interfacial film. It is contemplated that all local routes to the eye can be used including topical, subconjunctival, periocular, retrobulbar, subtenon, intracameral, intravitreal, intraocular, subretinal, juxtascleral and suprachoroidal administration. Systemic or parenteral administration can be feasible including, but not limited to intravenous, subcutaneous, and oral delivery. An exemplary method of administration will be intravitreal or subtenon injection of solutions or suspensions, or intravitreal or subtenon placement of bioerodible or non-bioerodible devices, or by topical ocular administration of solutions or suspensions, or posterior juxtascleral administration of a gel or cream formulation.

Eye drops can be prepared by dissolving the active ingredient in a sterile aqueous solution such as physiological saline, buffering solution, etc., or by combining powder compositions to be dissolved before use. Other vehicles can be chosen, as is known in the art, including, but not limited to: balance salt solution, saline solution, water soluble polyethers such as polyethyene glycol, polyvinyls, such as polyvinyl alcohol and povidone, cellulose derivatives such as methylcellulose and hydroxypropyl methylcellulose, petroleum derivatives such as mineral oil and white petrolatum, animal fats such as lanolin, polymers of acrylic acid such as carboxypolymethylene gel, vegetable fats such as peanut oil and polysaccharides such as dextrans, and glycosaminoglycans such as sodium hyaluronate. In some embodiments, additives ordinarily used in the eye drops can be added. Such additives include isotonizing agents (e.g., sodium chloride, etc.), buffer agent (e.g., boric acid, sodium monohydrogen phosphate, sodium dihydrogen phosphate, etc.), preservatives (e.g., benzalkonium chloride, benzethonium chloride, chlorobutanol, etc.), thickeners (e.g., saccharide such as lactose, mannitol, maltose, etc.; e.g., hyaluronic acid or its salt such as sodium hyaluronate, potassium hyaluronate, etc.; e.g., mucopolysaccharide such as chondroitin sulfate, etc.; e.g., sodium polyacrylate, carboxyvinyl polymer, crosslinked polyacrylate, polyvinyl alcohol, polyvinyl pyrrolidone, methyl cellulose, hydroxy propyl methylcellulose, hydroxyethyl cellulose, carboxymethyl cellulose, hydroxy propyl cellulose or other agents known to those skilled in the art).

In some cases, the colloid particles include at least one cationic agent and at least one non-ionic surfactant such as a poloxamer, tyloxapol, a polysorbate, a polyoxyethylene castor oil derivative, a sorbitan ester, or a polyoxyl stearate. In some cases, the cationic agent is an alkylamine, a tertiary alkyl amine, a quarternary ammonium compound, a cationic lipid, an amino alcohol, a biguanidine salt, a cationic compound or a mixture thereof. In some cases, the cationic agent is a biguanidine salt such as chlorhexidine, polyaminopropyl biguanidine, phenformin, alkylbiguanidine, or a mixture thereof. In some cases, the quaternary ammonium compound is a benzalkonium halide, lauralkonium halide, cetrimide, hexadecyltrimethylammonium halide, tetradecyltrimethylammonium halide, dodecyltrimethylammonium halide, cetrimonium halide, benzethonium halide, behenalkonium halide, cetalkonium halide, cetethyldimonium halide, cetylpyridinium halide, benzododecinium halide, chlorallyl methenamine halide, mnyristylalkonium halide, stearalkonium halide or a mixture of two or more thereof. In some cases, cationic agent is a benzalkonium chloride, lauralkonium chloride, benzododecinium bromide, benzethenium chloride, hexadecyltrimethylammonium bromide, tetradecyltrimethylammonium bromide, dodecyltrimethylammonium bromide or a mixture of two or more thereof. In some cases, the oil phase is mineral oil and light mineral oil, medium chain triglycerides (MCT), coconut oil; hydrogenated oils comprising hydrogenated cottonseed oil, hydrogenated palm oil, hydrogenate castor oil or hydrogenated soybean oil; polyoxyethylene hydrogenated castor oil derivatives comprising poluoxyl-40 hydrogenated castor oil, polyoxyl-60 hydrogenated castor oil or polyoxyl-100 hydrogenated castor oil.

1F. FORMULATIONS FOR CONTROLLED RELEASE ADMINISTRATION

In some embodiments, provided herein are pharmaceutical compositions for controlled release administration containing a compound as provided herein, and a pharmaceutical excipient suitable for controlled release administration. In some embodiments, provided herein are pharmaceutical compositions for controlled release administration containing: (i) an effective amount of a disclosed compound; optionally (ii) an effective amount of one or more second agents; and (iii) one or more pharmaceutical excipients suitable for controlled release administration. In some embodiments, the pharmaceutical composition further contains: (iv) an effective amount of a third agent.

Active agents such as the compounds provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; 6,699,500 each of which is incorporated herein by reference. Such dosage forms can be used to provide slow or controlled release of one or more active agents using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled release formulations known to those of ordinary skill in the art, including those described herein, can be readily selected for use with the active agents provided herein. Thus, the pharmaceutical compositions provided encompass single unit dosage forms suitable for oral administration such as, but not limited to, tablets, capsules, gelcaps, and caplets that are adapted for controlled release.

All controlled release pharmaceutical products have a common goal of improving drug therapy over that achieved by their non controlled counterparts. In some embodiments, the use of a controlled release preparation in medical treatment is characterized by a minimum of drug substance being employed to cure or control the disease, disorder, or condition in a minimum amount of time. Advantages of controlled release formulations include extended activity of the drug, reduced dosage frequency, and increased subject compliance. In addition, controlled release formulations can be used to affect the time of onset of action or other characteristics, such as blood levels of the drug, and can thus affect the occurrence of side (e.g., adverse) effects.

In some embodiments, controlled release formulations are designed to initially release an amount of a compound as provided herein that promptly produces the desired therapeutic effect, and gradually and continually release other amounts of the compound to maintain this level of therapeutic or prophylactic effect over an extended period of time. In order to maintain this constant level of the compound in the body, the compound should be released from the dosage form at a rate that will replace the amount of drug being metabolized and excreted from the body. Controlled release of an active agent can be stimulated by various conditions including, but not limited to, pH, temperature, enzymes, water, or other physiological conditions or compounds.

In certain embodiments, the pharmaceutical composition can be administered using intravenous infusion, an implantable osmotic pump, a transdermal patch, liposomes, or other modes of administration. In one embodiment, a pump can be used (see, Sefton, *CRC Crit. Ref. Biomed. Eng.* 14:201 (1987); Buchwald et al., *Surgery* 88:507 (1980); Saudek et al., *N. Engl. J. Med.* 321:574 (1989)). In another embodiment, polymeric materials can be used. In yet another embodiment, a controlled release system can be placed in a subject at an appropriate site determined by a practitioner of skill, i.e., thus requiring only a fraction of the systemic dose (see, e.g., Goodson, *Medical Applications of Controlled Release,* 115-138 (vol. 2, 1984). Other controlled release systems are discussed in the review by Langer, *Science* 249:1527-1533 (1990). The one or more active agents can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The one or more active agents then diffuse through the outer polymeric membrane in a release rate controlling step. The percentage of active agent in such parenteral compositions is highly dependent on the specific nature thereof, as well as the needs of the subject.

2. DOSAGE

A compound described herein can be delivered in the form of pharmaceutically acceptable compositions which comprise a therapeutically effective amount of one or more compounds described herein and/or one or more additional therapeutic agents such as a chemotherapeutic, formulated together with one or more pharmaceutically acceptable excipients. In some instances, the compound described herein and the additional therapeutic agent are administered in separate pharmaceutical compositions and can (e.g., because of different physical and/or chemical characteristics) be administered by different routes (e.g., one therapeutic is administered orally, while the other is administered intravenously). In other instances, the compound described herein and the additional therapeutic agent can be administered separately, but via the same route (e.g., both orally or both intravenously). In still other instances, the compound described herein and the additional therapeutic agent can be administered in the same pharmaceutical composition.

The selected dosage level will depend upon a variety of factors including, for example, the activity of the particular compound employed, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

In general, a suitable daily dose of a compound described herein and/or a chemotherapeutic will be that amount of the compound which, in some embodiments, can be the lowest dose effective to produce a therapeutic effect. Such an effective dose will generally depend upon the factors described above. Generally, doses of the compounds described herein for a patient, when used for the indicated effects, will range from about 0.0001 mg to about 100 mg per day, or about 0.001 mg to about 100 mg per day, or about 0.01 mg to about 100 mg per day, or about 0.1 mg to about 100 mg per day, or about 0.0001 mg to about 500 mg per day, or about 0.001 mg to about 500 mg per day, or about 0.01 mg to 1000 mg, or about 0.01 mg to about 500 mg per day, or about 0.1 mg to about 500 mg per day, or about 1 mg to 50 mg per day, or about 5 mg to 40 mg. An exemplary dosage is about 10 to 30 mg per day. In some embodiments, for a 70 kg human, a suitable dose would be about 0.05 to about 7 g/day, such as about 0.05 to about 2.5 g/day. Actual dosage levels of the active ingredients in the pharmaceutical compositions described herein can be varied so as to obtain an amount of the active ingredient which is effective to achieve the desired therapeutic response for a particular patient, composition, and mode of administration, without being toxic to the patient. In some instances, dosage levels below the lower limit of the aforesaid range can be more than adequate, while in other cases still larger doses can be employed without causing any harmful side effect, e.g., by dividing such larger doses into several small doses for administration throughout the day.

In some embodiments, the compounds can be administered daily, every other day, three times a week, twice a week, weekly, or bi-weekly. The dosing schedule can include a "drug holiday," i.e., the drug can be administered for two weeks on, one week off, or three weeks on, one week off, or four weeks on, one week off, etc., or continuously, without a drug holiday. The compounds can be administered orally, intravenously, intraperitoneally, topically, transdermally, intramuscularly, subcutaneously, intranasally, sublingually, or by any other route.

In some embodiments, a compound as provided herein is administered in multiple doses. Dosing can be about once, twice, three times, four times, five times, six times, or more than six times per day. Dosing can be about once a month, about once every two weeks, about once a week, or about once every other day. In another embodiment, a compound as provided herein and another agent are administered together about once per day to about 6 times per day. In another embodiment, the administration of a compound as provided herein and an agent continues for less than about 7 days. In yet another embodiment, the administration continues for more than about 6, about 10, about 14, about 28 days, about two months, about six months, or about one year. In some cases, continuous dosing is achieved and maintained as long as necessary.

Administration of the pharmaceutical compositions as provided herein can continue as long as necessary. In some embodiments, an agent as provided herein is administered for more than about 1, about 2, about 3, about 4, about 5, about 6, about 7, about 14, or about 28 days. In some embodiments, an agent as provided herein is administered for less than about 28, about 14, about 7, about 6, about 5, about 4, about 3, about 2, or about 1 day. In some embodiments, an agent as provided herein is administered chronically on an ongoing basis, e.g., for the treatment of chronic effects.

Since the compounds described herein can be administered in combination with other treatments (such as additional chemotherapeutics, radiation or surgery), the doses of each agent or therapy can be lower than the corresponding dose for single-agent therapy. The dose for single-agent therapy can range from, for example, about 0.0001 to about 200 mg, or about 0.001 to about 100 mg, or about 0.01 to about 100 mg, or about 0.1 to about 100 mg, or about 1 to about 50 mg per kilogram of body weight per day.

When a compound provided herein, is administered in a pharmaceutical composition that comprises one or more agents, and the agent has a shorter half-life than the compound provided herein unit dose forms of the agent and the compound provided herein can be adjusted accordingly.

3. KITS

In some embodiments, provided herein are kits. The kits can include a compound or pharmaceutical composition as described herein, in suitable packaging, and written material that can include instructions for use, discussion of clinical studies, listing of side effects, and the like. Such kits can also include information, such as scientific literature references, package insert materials, clinical trial results, and/or summaries of these and the like, which indicate or establish the activities and/or advantages of the pharmaceutical composition, and/or which describe dosing, administration, side effects, drug interactions, or other information useful to the health care provider. Such information can be based on the results of various studies, for example, studies using experimental animals involving in vivo models and studies based on human clinical trials.

In some embodiments, a memory aid is provided with the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. . . . Second Week, Monday, Tuesday, . . . " etc. Other variations of memory aids will be readily apparent. A "daily dose" can be a single tablet or capsule or several tablets or capsules to be taken on a given day.

The kit can further contain another agent. In some embodiments, the compound as provided herein and the agent are provided as separate pharmaceutical compositions in separate containers within the kit. In some embodiments, the compound as provided herein and the agent are provided as a single pharmaceutical composition within a container in the kit. Suitable packaging and additional articles for use (e.g., measuring cup for liquid preparations, foil wrapping to minimize exposure to air, and the like) are known in the art and can be included in the kit. In other embodiments, kits can further comprise devices that are used to administer the active agents. Examples of such devices include, but are not limited to, syringes, drip bags, patches, and inhalers. Kits described herein can be provided, marketed and/or promoted to health providers, including physicians, nurses, pharmacists, formulary officials, and the like. Kits can also, in some embodiments, be marketed directly to the consumer.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process, recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. The strength of the sheet is such that the tablets or capsules can be removed from the blister pack by manually applying pressure on the recesses whereby an opening is formed in the sheet at the place of the recess. The tablet or capsule can then be removed via said opening.

Kits can further comprise pharmaceutically acceptable vehicles that can be used to administer one or more active agents. For example, if an active agent is provided in a solid form that must be reconstituted for parenteral administration, the kit can comprise a sealed container of a suitable vehicle in which the active agent can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

The present disclosure further encompasses anhydrous pharmaceutical compositions and dosage forms comprising an active ingredient, since water can facilitate the degradation of some compounds. For example, water can be added (e.g., about 5%) in the pharmaceutical arts as a means of simulating long-term storage in order to determine characteristics such as shelf-life or the stability of formulations over time. Anhydrous pharmaceutical compositions and dosage forms can be prepared using anhydrous or low moisture containing ingredients and low moisture or low humidity conditions. For example, pharmaceutical compositions and dosage forms which contain lactose can be made anhydrous if substantial contact with moisture and/or humidity during manufacturing, packaging, and/or storage is expected. An anhydrous pharmaceutical composition can be prepared and stored such that its anhydrous nature is maintained. Accordingly, anhydrous pharmaceutical compositions can be packaged using materials known to prevent exposure to water such that they can be included in suitable formulary kits. Examples of suitable packaging include, but are not limited to, hermetically sealed foils, plastic or the like, unit dose containers, blister packs, and strip packs.

THERAPEUTIC METHODS

Phosphoinositide 3-kinases (PI3Ks) are members of a conserved family of lipid kinases that regulate numerous cell functions, including proliferation, differentiation, cell survival and metabolism. Several classes of PI3Ks exist in mammalian cells, including Class IA subgroup (e.g., PI3K-α, β, δ), which are generally activated by receptor tyrosine kinases (RTKs); Class IB (e.g., PI3K-γ), which is activated by G-protein coupled receptors (GPCRs), among others. PI3Ks exert their biological activities via a "PI3K-mediated signaling pathway" that includes several components that directly and/or indirectly transduce a signal triggered by a PI3K, including the generation of second messenger phophotidylinositol, 3,4,5-triphosphate (PIP3) at the plasma membrane, activation of heterotrimeric G protein signaling, and generation of further second messengers such as cAMP, DAG, and IP3, all of which leads to an extensive cascade of protein kinase activation (reviewed in Vanhaesebroeck, B. et al. (2001) *Annu Rev Biochem.* 70:535-602). For example, PI3K-δ is activated by cellular receptors through interaction between the PI3K regulatory subunit (p85) SH2 domains, or through direct interaction with RAS. PIP3 produced by PI3K activates effector pathways downstream through interaction with plextrin homology (PH) domain containing enzymes (e.g., PDK-1 and AKT [PKB]). (Fung-Leung W P. (2011) *Cell Signal.* 23(4):603-8). Unlike PI3K-δ, PI3K-γ is not associated with a regulatory subunit of the p85 family, but rather with a regulatory subunit in the p101 family. PI3K-γ is associated with GPCRs, and is responsible for the very rapid induction of PIP3. PI3K-γ can be also activated by RAS.

In some embodiments, provided herein are methods of modulating a PI3K kinase activity (e.g., selectively modulating) by contacting the kinase with an effective amount of a compound, or a pharmaceutically acceptable form (e.g., pharmaceutically acceptable salts, hydrates, solvates, isomers, prodrugs, and isotopically labeled derivatives) thereof, or pharmaceutical compositions as provided herein. Modulation can be inhibition (e.g., reduction) or activation (e.g., enhancement) of kinase activity. In some embodiments, provided herein are methods of inhibiting kinase activity by contacting the kinase with an effective amount of a compound as provided herein in solution. In some embodiments, provided herein are methods of inhibiting the kinase activity by contacting a cell, tissue, organ that express the kinase of interest with a compound provided herein. In some embodiments, provided herein are methods of inhibiting kinase activity in a subject by administering into the subject an effective amount of a compound as provided herein. In some embodiments, the kinase activity is inhibited (e.g., reduced) by more than about 25%, 30%, 40%, 50%, 60%, 70%, 80%, or 90% when contacted with a compound provided herein as compared to the kinase activity without such contact. In some embodiments, provided herein are methods of inhibiting PI3 kinase activity in a subject (including mammals such as humans) by contacting said subject with an amount of a compound as provided herein sufficient to inhibit or reduce the activity of the PI3 kinase in said subject.

In some embodiments, the kinase is a lipid kinase or a protein kinase. In some embodiments, the kinase is selected from a PI3 kinase including different isoforms such as PI3 kinase α, PI3 kinase β, PI3 kinase γ, PI3 kinase δ; DNA-PK; mTor; Abl, VEGFR, Ephrin receptor B4 (EphB4); TEK receptor tyrosine kinase (TIE2); FMS-related tyrosine kinase 3 (FLT-3); Platelet derived growth factor receptor (PDGFR); RET; ATM; ATR; hSmg-1; Hck; Src; Epidermal growth factor receptor (EGFR); KIT; Insulin Receptor (IR); and IGFR.

As used herein, a "PI3K-mediated disorder" refers to a disease or condition involving aberrant PI3K-mediated signaling pathway. In one embodiment, provided herein is a method of treating a PI3K mediated disorder in a subject, the method comprising administering a therapeutically effective amount of a compound or a pharmaceutical composition as provided herein. In some embodiments, provided herein is a method of treating a PI3K-δ or PI3K-γ mediated disorder in a subject, the method comprising administering a therapeutically effective amount of a compound or a pharmaceutical composition as provided herein. In some embodiments, provided herein is a method for inhibiting at least one of PI3K-δ and PI3K-γ, the method comprising contacting a cell expressing PI3K in vitro or in vivo with an effective amount of the compound or composition provided herein. PI3Ks have been associated with a wide range of conditions, including immunity, cancer and thrombosis (reviewed in Vanhaesebroeck, B. et al. (2010) *Current Topics in Microbiology and Immunology*, DOI 10.1007/82_2010_65). For example, Class I PI3Ks, particularly PI3K-γ and PI3K-δ isoforms, are highly expressed in leukocytes and have been associated with adaptive and innate immunity; thus, these PI3Ks are believed to be important mediators in inflammatory disorders and hematologic malignancies (reviewed in Harris, S J et al. (2009) *Curr Opin Investig Drugs* 10(11):1151-62); Rommel C. et al. (2007) *Nat Rev Immunol* 7(3):191-201; Durand C A et al. (2009) *J. Immunol.* 183(9):5673-84; Dil N, Marshall A J. (2009) *Mol. Immunol.* 46(10):1970-8; Al-Alwan M M et al. (2007) J. Immunol. 178(4):2328-35; Zhang T T, et al. (2008) *J Allergy Clin Immunol.* 2008; 122(4):811-819.e2; Srinivasan L, et al. (2009) *Cell* 139(3):573-86).

Numerous publications support roles of PI3K-δ, PI3K-γ, and PI3K-β in the differentiation, maintenance, and activation of immune and malignant cells, as described in more detail below.

The importance of PI3K-δ in the development and function of B-cells is supported from inhibitor studies and genetic models. PI3K-δ is an important mediator of B-cell receptor (BCR) signaling, and is upstream of AKT, calcium flux, PLCγ, MAP kinase, P70S6k, and FOXO3a activation. PI3K-δ is also important in IL4R, S1P, and CXCR5 signaling, and has been shown to modulate responses to toll-like receptors 4 and 9 Inhibitors of PI3K-δ have shown the importance of PI3K-δ in B-cell development (Marginal zone and B1 cells), B-cell activation, chemotaxis, migration and homing to lymphoid tissue, and in the control of immunoglobulin class switching leading to the production of IgE. Clayton E et al. (2002) *J Exp Med.* 196(6):753-63; Bilancio A, et al. (2006) *Blood* 107(2):642-50; Okkenhaug K. et al. (2002) *Science* 297(5583):1031-4; Al-Alwan M M et al. (2007) *J Immunol.* 178(4):2328-35; Zhang T T, et al. (2008) *J Allergy Clin Immunol.* 2008; 122(4):811-819.e2; Srinivasan L, et al. (2009) *Cell* 139(3):573-86)

In T-cells, PI3K-δ has been demonstrated to have a role in T-cell receptor and cytokine signaling, and is upstream of AKT, PLCγ, and GSK3b. In PI3K-δ deletion or kinase-dead knock-in mice, or in inhibitor studies, T-cell defects including proliferation, activation, and differentiation have been observed, leading to reduced T helper cell 2 (TH2) response, memory T-cell specific defects (DTH reduction), defects in antigen dependent cellular trafficking, and defects in chemotaxis/migration to chemokines (e.g., S1P, CCR7, CD62L). (Garçon F. et al. (2008) *Blood* 111(3):1464-71; Okkenhaug K et al. (2006). *J Immunol.* 177(8):5122-8; Soond D R, et al. (2010) *Blood* 115(11):2203-13; Reif K, (2004). *J Immunol* 2004; 173(4):2236-40; Ji H. et al. (2007) *Blood* 110(8):2940-7; Webb L M, et al. (2005) *J Immunol.* 175(5):2783-7; Liu D, et al. (2010) *J Immunol.* 184(6):3098-105; Haylock-Jacobs S, et al. (2011) *J Autoimmun.* 2011; 36(3-4):278-87; Jarmin S J, et al. (2008) *J Clin Invest.* 118(3):1154-64).

In neutrophils, PI3K-δ along with PI3K-γ, and PI3K-β, contribute to the responses to immune complexes, FCγRII signaling, including migration and neutrophil respiratory burst. Human neutrophils undergo rapid induction of PIP3 in response to formyl peptide receptor (FMLP) or complement component C5a (C5a) in a PI3K-γ dependent manner, followed by a longer PIP3 production period that is PI3K-δ dependent, and is essential for respiratory burst. The response to immune complexes is contributed by PI3K-δ, PI3K-γ, and PI3K-β, and is an important mediator of tissue damage in models of autoimmune disease (Randis T M et al. (2008) *Eur J. Immunol.* 38(5):1215-24; Pinho V, (2007) *J Immunol.* 179 (11):7891-8; Sadhu C. et al. (2003) *J Immunol.* 170(5):2647-54; Condliffe A M et al. (2005) *Blood* 106(4):1432-40). It has been reported that in certain autoimmune diseases, perfrential activation of PI3Kβ may be involved. (Kulkarni et al., *Immunology* (2011) 4(168) ra23: 1-11). It was also reported that PI3Kβ-deficient mice were highly protected in an FcγR-dependent model of autoantibody-induced skin blistering and partially protected in an FcγR-dependent model of inflammatory arthritis, whereas combined deficiency of PI3Kβ and PI3Kδ resulted in near complete protection in inflammatory arthritis. (Id.).

In macrophages collected from patients with chronic obstructive pulmonary disease (COPD), glucocorticoid responsiveness can be restored by treatment of the cells with inhibitors of PI3K-δ. Macrophages also rely on PI3K-δ and PI3K-γ for responses to immune complexes through the arthus reaction (FCgR and C5a signaling) (Randis T M, et al. (2008) *Eur J Immunol.* 38(5):1215-24; Marwick J A et al. (2009) *Am J Respir Crit. Care Med.* 179(7):542-8; Konrad S, et al. (2008) *J Biol. Chem.* 283(48):33296-303).

In mast cells, stem cell factor—(SCF) and IL3-dependent proliferation, differentiation and function are PI3K-δ dependent, as is chemotaxis. The allergen/IgE crosslinking of FCgR1 resulting in cytokine release and degranulation of the mast cells is severely inhibited by treatment with PI3K-δ inhibitors, suggesting a role for PI3K-δ in allergic disease (Ali K et al. (2004) *Nature* 431(7011):1007-11; Lee K S, et al. (2006) *FASEB J.* 20(3):455-65; Kim M S, et al. (2008) *Trends Immunol.* 29(10):493-501).

Natural killer (NK) cells are dependent on both PI3K-δ and PI3K-γ for efficient migration towards chemokines including CXCL10, CCL3, S1P and CXCL12, or in response to LPS in the peritoneum (Guo H, et al. (2008) *J Exp Med.* 205(10): 2419-35; Tassi I, et al. (2007) *Immunity* 27(2):214-27; Saudemont A, (2009) *Proc Natl Acad Sci USA.* 106(14):5795-800; Kim N, et al. (2007) *Blood* 110(9):3202-8).

The roles of PI3K-δ, PI3K-γ, and PI3K-β in the differentiation, maintenance, and activation of immune cells support a role for these enzymes in inflammatory disorders ranging from autoimmune diseases (e.g., rheumatoid arthritis, multiple sclerosis) to allergic inflammatory disorders, such as asthma, and inflammatory respiratory disease such as COPD. Extensive evidence is available in experimental animal models, or can be evaluated using art-recognized animal models. In an embodiment, described herein is a method of treating inflammatory disorders ranging from autoimmune diseases (e.g., rheumatoid arthritis, multiple sclerosis) to allergic inflammatory disorders, such as asthma and COPD using a compound described herein.

For example, inhibitors of PI3K-δ and/or -γ have been shown to have anti-inflammatory activity in several autoimmune animal models for rheumatoid arthritis (Williams, O. et al. (2010) *Chem Biol,* 17(2):123-34; WO 2009/088986; WO2009/088880; WO 2011/008302). PI3K-δ is expressed in the RA synovial tissue (especially in the synovial lining which contains fibroblast-like synoviocytes (FLS), and selective PI3K-δ inhibitors have been shown to be effective in inhibiting synoviocyte growth and survival (Bartok et al. (2010) *Arthritis Rheum* 62 Suppl 10:362). Several PI3K-δ and -γ inhibitors have been shown to ameliorate arthritic symptoms (e.g., swelling of joints, reduction of serum-induced collagen levels, reduction of joint pathology and/or inflammation), in art-recognized models for RA, such as collagen-induced arthritis and adjuvant induced arthritis (WO 2009/088986; WO2009/088880; WO 2011/008302).

The role of PI3K-δ has also been shown in models of T-cell dependent response, including the DTH model. In the murine experimental autoimmune encephalomyelitis (EAE) model of multiple sclerosis, the PI3K-γ/δ-double mutant mice are resistant. PI3K-δ inhibitors have also been shown to block EAE disease induction and development of TH-17 cells both in vitro and in vivo (Haylock-Jacobs, S. et al. (2011) *J. Autoimmunity* 36(3-4):278-87).

Systemic lupus erythematosus (SLE) is a complex disease that at different stages requires memory T-cells, B-cell polyclonal expansion and differentiation into plasma cells, and the innate immune response to endogenous damage associated molecular pattern molecules (DAMPS), and the inflammatory responses to immune complexes through the complement system as well as the $F_C$ receptors. The role of PI3K-δ and PI3K-γ together in these pathways and cell types suggest that blockade with an inhibitor would be effective in these diseases. A role for PI3K in lupus is also predicted by two genetic models of lupus. The deletion of phosphatase and tensin homolog (PTEN) leads to a lupus-like phenotype, as does a transgenic activation of Class1A PI3Ks, which includes PI3K-δ. The deletion of PI3K-γ in the transgenically activated class 1A lupus model is protective, and treatment with a PI3K-γ selective inhibitor in the murine MLR/lpr model of lupus improves symptoms (Barber, D F et al. (2006) *J. Immunol.* 176(1): 589-93).

In allergic disease, PI3K-δ has been shown by genetic models and by inhibitor treatment to be essential for mast-cell activation in a passive cutaneous anaphalaxis assay (Ali K et al. (2008) *J. Immunol.* 180(4):2538-44; Ali K, (2004) *Nature* 431(7011):1007-11). In a pulmonary measure of response to immune complexes (Arthus reaction) a PI3K-δ knockout is resistant, showing a defect in macrophage activation and C5a production. Knockout studies and studies with inhibitors for both PI3K-δ and PI3K-γ support a role for both of these enzymes in the ovalbumin induced allergic airway inflammation and hyper-responsiveness model (Lee K S et al. (2006) *FASEB J.* 20(3):455-65). Reductions of infiltration of eosinophils, neutrophils, and lymphocytes as well as TH2 cytokines (IL4, IL5, and IL13) were seen with both PI3K-δ specific and dual PI3K-δ and PI3K-γ inhibitors in the Ova induced asthma model (Lee K S et al. (2006) *J Allergy Clin Immunol* 118(2): 403-9).

PI3K-δ and PI3K-γ inhibition can be used in treating COPD. In the smoked mouse model of COPD, the PI3K-δ knockout does not develop smoke induced glucocorticoid resistance, while wild-type and PI3K-γ knockout mice do. An inhaled formulation of dual PI3K-δ and PI3K-γ inhibitor blocked inflammation in a LPS or smoke COPD models as measured by neutrophilia and glucocorticoid resistance (Doukas J, et al. (2009) *J Pharmacol Exp Ther.* 328(3):758-65).

Class I PI3Ks, particularly PI3K-δ and PI3K-γ isoforms, are also associated with cancers (reviewed, e.g., in Vogt, P K et al. (2010) Curr Top Microbiol Immunol 347:79-104; Fresno Vara, J A et al. (2004) *Cancer Treat Rev.* 30(2):193-204; Zhao, L and Vogt, P K. (2008) *Oncogene* 27(41):5486-96) Inhibitors of PI3K, e.g., PI3K-δ and/or -γ, have been shown to have anti-cancer activity (e.g., Courtney, K D et al. (2010) *J Clin Oncol.* 28(6):1075-1083); Markman, B et al. (2010) Ann Oncol. 21(4):683-91; Kong, D and Yamori, T (2009) Curr Med. Chem. 16(22):2839-54; Jimeno, A et al. (2009) J Clin Oncol. 27:156s (suppl; abstr 3542); Flinn, I W et al. (2009) *J Clin Oncol.* 27:156s (suppl; abstr 3543); Shapiro, G et al. (2009) *J Clin Oncol.* 27:146s (suppl; abstr 3500); Wagner, A J et al. (2009) *J Clin Oncol.* 27:146s (suppl; abstr 3501); Vogt, P K et al. (2006) Virology 344(1):131-8; Ward, S et al. (2003) *Chem. Biol.* 10(3):207-13; WO 2011/041399; US 2010/0029693; US 2010/0305096; US 2010/0305084). In an embodiment, described herein is a method of treating cancer.

Types of cancer that can be treated with an inhibitor of PI3K (particularly, PI3K-δ and/or -γ) include, e.g., leukemia, chronic lymphocytic leukemia, acute myeloid leukemia, chronic myeloid leukemia (e.g., Salmena, L et al. (2008) *Cell* 133:403-414; Chapuis, N et al. (2010) *Clin Cancer Res.* 16(22):5424-35; Khwaja, A (2010) *Curr Top Microbiol Immunol.* 347:169-88); lymphoma, e.g., non-Hodgkin's lymphoma (e.g., Salmena, L et al. (2008) *Cell* 133:403-414); lung cancer, e.g., non-small cell lung cancer, small cell lung cancer (e.g., Herrera, V A et al. (2011) *Anticancer Res.* 31(3):849-54); melanoma (e.g., Haluska, F et al. (2007) *Semin Oncol.* 34(6):546-54); prostate cancer (e.g., Sarker, D et al. (2009) *Clin Cancer Res.* 15(15):4799-805); glioblastoma (e.g., Chen, J S et al. (2008) Mol Cancer Ther. 7:841-850); endometrial cancer (e.g., Bansal, N et al. (2009) Cancer Control. 16(1):8-13); pancreatic cancer (e.g., Furukawa, T (2008) *J. Gastroenterol.* 43(12):905-11); renal cell carcinoma (e.g., Porta, C and Figlin, R A (2009) *J. Urol.* 182(6):2569-77); colorectal cancer (e.g., Saif, M W and Chu, E (2010) Cancer J. 16(3):196-201); breast cancer (e.g., Torbett, N E et al. (2008) *Biochem J.* 415:97-100); thyroid cancer (e.g., Brzezianska, E and Pastuszak-Lewandoska, D (2011) *Front Biosci.* 16:422-39); and ovarian cancer (e.g., Mazzoletti, M and Broggini, M (2010) *Curr Med. Chem.* 17(36):4433-47).

Numerous publications support a role of PI3K-δ and PI3K-γ in treating hematological cancers. PI3K-δ and PI3K-γ are highly expressed in the heme compartment, and some solid tumors, including prostate, breast and glioblastomas (Chen J. S. et al. (2008) *Mol Cancer Ther.* 7(4):841-50; Ikeda H. et al. (2010) *Blood* 116(9): 1460-8).

In hematological cancers including acute myeloid leukemia (AML), multiple myeloma (MM), and chronic lymphocytic leukemia (CLL), overexpression and constitutive activation of PI3K-δ supports the model that PI3K-δ inhibition would be therapeutic Billottet C, et al. (2006) *Oncogene* 25(50):6648-59; Billottet C, et al. (2009) *Cancer Res.* 69(3): 1027-36; Meadows, S A, 52nd Annual ASH Meeting and Exposition; 2010 Dec. 4-7; Orlando, Fla.; Ikeda H, et al. (2010) *Blood* 116(9):1460-8; Herman S E et al. (2010) *Blood* 116(12):2078-88; Herman S E et al. (2011). *Blood* 117(16): 4323-7. In an embodiment, described herein is a method of treating hematological cancers including, but not limited to acute myeloid leukemia (AML), multiple myeloma (MM), and chronic lymphocytic leukemia (CLL).

A PI3K-δ inhibitor (CAL-101) has been evaluated in a phase 1 trial in patients with haematological malignancies, and showed activity in CLL in patients with poor prognostic characteristics. In CLL, inhibition of PI3K-δ not only affects tumor cells directly, but it also affects the ability of the tumor cells to interact with their microenvironment. This microenvironment includes contact with and factors from stromal cells, T-cells, nurse like cells, as well as other tumor cells. CAL-101 suppresses the expression of stromal and T-cell derived factors including CCL3, CCL4, and CXCL13, as well as the CLL tumor cells' ability to respond to these factors. CAL-101 treatment in CLL patients induces rapid lymph node reduction and redistribution of lymphocytes into the circulation, and affects tonic survival signals through the BCR, leading to reduced cell viability, and an increase in apoptosis. Single agent CAL-101 treatment was also active in mantle cell lymphoma and refractory non Hodgkin's lymphoma (Furman, R R, et al. 52nd Annual ASH Meeting and Exposition; 2010 Dec. 4-7; Orlando, Fla.; Hoellenriegel, J, et al. 52nd Annual ASH Meeting and Exposition; 2010 Dec. 4-7; Orlando, Fla.; Webb, H K, et al. 52nd Annual ASH Meeting and Exposition; 2010 Dec. 4-7; Orlando, Fla.; Meadows, et al. 52nd Annual ASH Meeting and Exposition; 2010 Dec. 4-7; Orlando, Fla.; Kahl, B, et al. 52nd Annual ASH Meeting and Exposition; 2010 Dec. 4-7; Orlando, Fla.; Lannutti B J, et al. (2011) *Blood* 117(2):591-4).

PI3K-δ inhibitors have shown activity against PI3K-δ positive gliomas in vitro (Kashishian A, et al. Poster presented at: The American Association of Cancer Research 102nd Annual Meeting; 2011 Apr. 2-6; Orlando, Fla.). PI3K-δ is the PI3K isoform that is most commonly activated in tumors where the PTEN tumor suppressor is mutated (Ward S, et al. (2003) *Chem. Biol.* 10(3):207-13). In this subset of tumors, treatment with the PI3K-δ inhibitor either alone or in combination with a cytotoxic agent can be effective.

Another mechanism for PI3K-δ inhibitors to have an affect in solid tumors involves the tumor cells' interaction with their micro-environment. PI3K-δ, PI3K-γ, and PI3K-β are expressed in the immune cells that infiltrate tumors, including tumor infiltrating lymphocytes, macrophages, and neutrophils. PI3K-δ inhibitors can modify the function of these tumor-associated immune cells and how they respond to signals from the stroma, the tumor, and each other, and in this way affect tumor cells and metastasis (Hoellenriegel, J, et al. 52$^{nd}$ Annual ASH Meeting and Exposition; 2010 Dec. 4-7; Orlando, Fla.).

PI3K-δ is also expressed in endothelial cells. It has been shown that tumors in mice treated with PI3K-δ selective inhibitors are killed more readily by radiation therapy. In this same study, capillary network formation is impaired by the PI3K inhibitor, and it is postulated that this defect contributes to the greater killing with radiation. PI3K-δ inhibitors can affect the way in which tumors interact with their microenviroment, including stromal cells, immune cells, and endothelial cells and be therapeutic either on its own or in conjunction with another therapy (Meadows, SA, et al. Paper presented at: 52$^{nd}$ Annual ASH Meeting and Exposition; 2010 Dec. 4-7; Orlando, Fla.; Geng L, et al. (2004) *Cancer Res.* 64(14):4893-9).

In other embodiments, inhibition of PI3K (such as PI3K-δ and/or -γ) can be used to treat a neuropsychiatric disorder, e.g., an autoimmune brain disorder. Infectious and immune factors have been implicated in the pathogenesis of several neuropsychiatric disorders, including, but not limited to, Sydenham's chorea (SC) (Garvey, M. A. et al. (2005) *J. Child Neurol.* 20:424-429), Tourette's syndrome (TS), obsessive compulsive disorder (OCD) (Asbahr, F. R. et al. (1998) *Am. J. Psychiatry* 155:1122-1124), attention deficit/hyperactivity disorder (AD/HD) (Hirschtritt, M. E. et al. (2008) *Child Neuropsychol.* 1:1-16; Peterson, B. S. et al. (2000) *Arch. Gen. Psychiatry* 57:364-372), anorexia nervosa (Sokol, M. S. (2000) *J. Child Adolesc. Psychopharmacol.* 10:133-145; Sokol, M. S. et al. (2002) *Am. J. Psychiatry* 159:1430-1432), depression (Leslie, D. L. et al. (2008) *J. Am. Acad. Child Adolesc. Psychiatry* 47:1166-1172), and autism spectrum disorders (ASD) (Hollander, E. et al. (1999) *Am. J. Psychiatry* 156:317-320; Margutti, P. et al. (2006) *Curr. Neurovasc. Res.* 3:149-157). A subset of childhood obsessive compulsive disorders and tic disorders has been grouped as Pediatric Autoimmune Neuropsychiatric Disorders Associated with Streptococci (PANDAS). PANDAS disorders provide an example of disorders where the onset and exacerbation of neuropsychiatric symptoms is preceded by a streptococcal infection (Kurlan, R., Kaplan, E. L. (2004) *Pediatrics* 113: 883-886; Garvey, M. A. et al. (1998) *J. Clin. Neurol.* 13:413-423). Many of the PANDAS disorders share a common mechanism of action resulting from antibody responses against streptococcal associated epitopes, such as GlcNAc, which produces neurological effects (Kirvan. C. A. et al. (2006) *J. Neuroimmunol.* 179:173-179). Autoantibodies recognizing central nervous system (CNS) epitopes are also found in sera of most PANDAS subjects (Yaddanapudi, K. et al. (2010) *Mol. Psychiatry.* 15:712-726). Thus, several neuropsychiatric disorders have been associated with immune and autoimmune components, making them suitable for therapies that include PI3K-δ and/or -γ inhibition.

In certain embodiments, a method of treating (e.g., reducing or ameliorating one or more symptoms of) a neuropsychiatric disorder, (e.g., an autoimmune brain disorder), using a PI3K-δ and/or -γ inhibitor is described, alone or in combination therapy. For example, one or more PI3K-δ and/or -γ inhibitors described herein can be used alone or in combination with any suitable therapeutic agent and/or modalities, e.g., dietary supplement, for treatment of neuropsychiatric disorders. Exemplary neuropsychiatric disorders that can be treated with the PI3K-δ and/or -γ inhibitors described herein include, but are not limited to, PANDAS disorders, Sydenham's chorea, Tourette's syndrome, obsessive compulsive disorder, attention deficit/hyperactivity disorder, anorexia nervosa, depression, and autism spectrum disorders. Pervasive Developmental Disorder (PDD) is an exemplary class of autism spectrum disorders that includes Autistic Disorder, Asperger's Disorder, Childhood Disintegrative Disorder (CDD), Rett's Disorder and PDD-Not Otherwise Specified (PDD-NOS) Animal models for evaluating the activity of the PI3K-δ and/or -γ inhibitor are known in the art. For example, a mouse model of PANDAS disorders is described in, e.g., Yaddanapudi, K. et al. (2010) supra; and Hoffman, K. I. et al. (2004) *J. Neurosci.* 24:1780-1791.

In some embodiments, provided herein are methods of using the compounds, or a pharmaceutically acceptable form (e.g., pharmaceutically acceptable salts, hydrates, solvates, isomers, prodrugs, and isotopically labeled derivatives) thereof, or pharmaceutical compositions as provided herein to treat disease conditions, including, but not limited to, diseases associated with malfunctioning of one or more types of PI3 kinase. A detailed description of conditions and disorders mediated by p110δ kinase activity is set forth in Sadu et al., WO 01/81346, which is incorporated herein by reference in its entirety for all purposes.

In some embodiments, the disclosure relates to a method of treating a hyperproliferative disorder in a subject that comprises administering to said subject a therapeutically effective amount of a compound, or a pharmaceutically acceptable form (e.g., pharmaceutically acceptable salts, hydrates, solvates, isomers, prodrugs, and isotopically labeled derivatives) thereof, or pharmaceutical compositions as provided herein. In some embodiments, said method relates to the treatment of cancer such as acute myeloid leukemia, thymus, brain, lung, squamous cell, skin, eye, retinoblastoma, intraocular melanoma, oral cavity and oropharyngeal, bladder, gastric, stomach, pancreatic, bladder, breast, cervical, head, neck, renal, kidney, liver, ovarian, prostate, colorectal, esophageal, testicular, gynecological, thyroid, CNS, PNS, AIDS-related (e.g., Lymphoma and Kaposi's Sarcoma) or viral-induced cancer. In some embodiments, said method relates to the treatment of a non-cancerous hyperproliferative disorder such as benign hyperplasia of the skin (e.g., psoriasis), restenosis, or prostate (e.g., benign prostatic hypertrophy (BPH)).

Patients that can be treated with compounds, or a pharmaceutically acceptable form (e.g., pharmaceutically acceptable salts, hydrates, solvates, isomers, prodrugs, and isotopically labeled derivatives) thereof, or pharmaceutical compositions as provided herein, according to the methods as provided herein include, for example, but not limited to, patients that have been diagnosed as having psoriasis; restenosis; atherosclerosis; BPH; breast cancer such as a ductal carcinoma in duct tissue in a mammary gland, medullary carcinomas, colloid carcinomas, tubular carcinomas, and inflammatory breast cancer; ovarian cancer, including epithelial ovarian tumors such as adenocarcinoma in the ovary and an adenocarcinoma that has migrated from the ovary into the abdominal cavity; uterine cancer; cervical cancer such as adenocarcinoma in the cervix epithelial including squamous cell carcinoma and adenocarcinomas; prostate cancer, such as a prostate cancer selected from the following: an adenocarcinoma or an adenocarinoma that has migrated to the bone; pancreatic cancer such as epitheliod carcinoma in the pancreatic duct tissue and an adenocarcinoma in a pancreatic duct; bladder cancer such as a transitional cell carcinoma in urinary bladder, urothelial carcinomas (transitional cell carcinomas), tumors in the urothelial cells that line the bladder, squamous cell carcinomas, adenocarcinomas, and small cell cancers; leukemia such as acute myeloid leukemia (AML), acute lymphocytic leukemia, chronic lymphocytic leukemia, chronic myeloid leukemia, hairy cell leukemia, myelodysplasia, myeloproliferative disorders, NK cell leukemia (e.g., blastic plasmacytoid dendritic cell neoplasm), acute myelogenous leukemia (AML), chronic myelogenous leukemia (CML), mastocytosis, chronic lymphocytic leukemia (CLL), multiple myeloma (MM), and myelodysplastic syndrome (MDS); bone cancer; lung cancer such as non-small cell lung cancer (NSCLC), which is divided into squamous cell carcinomas, adenocarcinomas, and large cell undifferentiated carcinomas, and small cell lung cancer; skin cancer such as basal cell carcinoma, melanoma, squamous cell carcinoma and actinic keratosis, which is a skin condition that sometimes develops into squamous cell carcinoma; eye retinoblastoma; cutaneous or intraocular (eye) melanoma; primary liver cancer (cancer that begins in the liver); kidney cancer; thyroid cancer such as papillary, follicular, medullary and anaplastic; lymphoma such as diffuse large B-cell lymphoma, B-cell immunoblastic lymphoma, NK cell lymphoma (e.g., blastic plasmacytoid dendritic cell neoplasm), and small non-cleaved cell lymphoma; Kaposi's Sarcoma; viral-induced cancers including hepatitis B virus (HBV), hepatitis C virus (HCV), and hepatocellular carcinoma; human lymphotropic virus-type 1 (HTLV-1) and adult T-cell leukemia/lymphoma; and human papilloma virus (HPV) and cervical cancer; central nervous system cancers (CNS) such as primary brain tumor, which includes gliomas (astrocytoma, anaplastic astrocytoma, or glioblastoma multiforme), Oligodendroglioma, Ependymoma, Meningioma, Lymphoma, Schwannoma, and Medulloblastoma; peripheral nervous system (PNS) cancers such as acoustic neuromas and malignant peripheral nerve sheath tumor (MPNST) including neurofibromas and schwannomas, malignant fibrous cytoma, malignant fibrous histiocytoma, malignant meningioma, malignant mesothelioma, and malignant mixed Müllerian tumor; oral cavity and oropharyngeal cancer such as, hypopharyngeal cancer, laryngeal cancer, nasopharyngeal cancer, and oropharyngeal cancer; stomach cancer such as lymphomas, gastric stromal tumors, and carcinoid tumors; testicular cancer such as germ cell tumors (GCTs), which include seminomas and nonseminomas, and gonadal stromal tumors, which include Leydig cell tumors and Sertoli cell tumors; thymus cancer such as to thymomas, thymic carcinomas, Hodgkin disease, non-Hodgkin lymphomas carcinoids or carcinoid tumors; rectal cancer; and colon cancer.

In one embodiment, provided herein is a method of treating an inflammation disorder, including autoimmune diseases in a subject. The method comprises administering to said subject a therapeutically effective amount of a compound, or a pharmaceutically acceptable form (e.g., pharmaceutically acceptable salts, hydrates, solvates, isomers, prodrugs, and isotopically labeled derivatives) thereof, or pharmaceutical compositions as provided herein. Examples of autoimmune diseases includes but is not limited to acute disseminated encephalomyelitis (ADEM), Addison's disease, antiphospholipid antibody syndrome (APS), aplastic anemia, autoimmune hepatitis, autoimmune skin disease, coeliac disease, Crohn's disease, Diabetes mellitus (type 1), Goodpasture's syndrome, Graves' disease, Guillain-Barré syndrome (GBS), Hashimoto's disease, lupus erythematosus, multiple sclerosis, myasthenia gravis, opsoclonus myoclonus syndrome (OMS), optic neuritis, Ord's thyroiditis, oemphigus, polyarthritis, primary biliary cirrhosis, psoriasis, rheumatoid arthritis, Reiter's syndrome, Takayasu's arteritis, temporal arteritis (also known as "giant cell arteritis"), warm autoimmune hemolytic anemia, Wegener's granulomatosis, alopecia universalis (e.g., inflammatory alopecia), Chagas disease, chronic fatigue syndrome, dysautonomia, endometriosis, hidradenitis suppurativa, interstitial cystitis, neuromyotonia, sarcoidosis, scleroderma, ulcerative colitis, vitiligo, and vulvodynia. Other disorders include bone-resorption disorders and thrombosis.

Inflammation takes on many forms and includes, but is not limited to, acute, adhesive, atrophic, catarrhal, chronic, cirrhotic, diffuse, disseminated, exudative, fibrinous, fibrosing, focal, granulomatous, hyperplastic, hypertrophic, interstitial, metastatic, necrotic, obliterative, parenchymatous, plastic, productive, proliferous, pseudomembranous, purulent, sclerosing, seroplastic, serous, simple, specific, subacute, suppurative, toxic, traumatic, and/or ulcerative inflammation.

Exemplary inflammatory conditions include, but are not limited to, inflammation associated with acne, anemia (e.g., aplastic anemia, haemolytic autoimmune anaemia), asthma, arteritis (e.g., polyarteritis, temporal arteritis, periarteritis nodosa, Takayasu's arteritis), arthritis (e.g., crystalline arthritis, osteoarthritis, psoriatic arthritis, gout flare, gouty arthritis, reactive arthritis, rheumatoid arthritis and Reiter's arthritis), ankylosing spondylitis, amylosis, amyotrophic lateral sclerosis, autoimmune diseases, allergies or allergic reactions, atherosclerosis, bronchitis, bursitis, chronic prostatitis, conjunctivitis, Chagas disease, chronic obstructive pulmonary disease, cermatomyositis, diverticulitis, diabetes (e.g., type I diabetes mellitus, type 2 diabetes mellitus), a skin condition (e.g., psoriasis, eczema, burns, dermatitis, pruritus (itch)), endometriosis, Guillain-Barre syndrome, infection, ischaemic heart disease, Kawasaki disease, glomerulonephritis, gingivitis, hypersensitivity, headaches (e.g., migraine headaches, tension headaches), ileus (e.g., postoperative ileus and ileus during sepsis), idiopathic thrombocytopenic purpura, interstitial cystitis (painful bladder syndrome), gastrointestinal disorder (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GORD, or its synonym GERD), inflammatory bowel disease (IBD) (e.g., Crohn's disease, ulcerative colitis, collagenous colitis, lymphocytic colitis, ischaemic colitis, diversion colitis, Behcet's syndrome, indeterminate colitis) and inflammatory bowel syndrome (IBS)), lupus, multiple sclerosis, morphea, myeasthenia gravis, myocardial ischemia, nephrotic syndrome, pemphigus vulgaris, pernicious aneaemia, peptic ulcers, polymyositis, primary biliary cirrhosis, neuroinflammation associated with brain disorders (e.g., Parkinson's disease, Huntington's disease, and Alzheimer's disease), prostatitis, chronic inflammation associated with cranial radiation injury, pelvic inflammatory disease, polymyalgia rheumatic, reperfusion injury, regional enteritis, rheumatic fever, systemic lupus erythematosus, scleroderma, scleroderma, sarcoidosis, spondyloarthopathies, Sjogren's syndrome, thyroiditis, transplantation rejection, tendonitis, trauma or injury (e.g., frostbite, chemical irritants, toxins, scarring, burns, physical injury), vasculitis, vitiligo and Wegener's granulomatosis. In certain embodiments, the inflammatory disorder is selected from arthritis (e.g., rheumatoid arthritis), inflammatory bowel disease, inflammatory bowel syndrome, asthma, psoriasis, endometriosis, interstitial cystitis and prostatistis. In certain embodiments, the inflammatory condition is an acute inflammatory condition (e.g., for example, inflammation resulting from infection). In certain embodiments, the inflammatory condition is a chronic inflammatory condition (e.g., conditions resulting from asthma, arthritis and inflammatory bowel disease). The compounds can also be useful in treating inflammation associated with trauma and non-inflammatory myalgia.

Immune disorders, such as auto-immune disorders, include, but are not limited to, arthritis (including rheumatoid arthritis, spondyloarthopathies, gouty arthritis, degenerative joint diseases such as osteoarthritis, systemic lupus erythematosus, Sjogren's syndrome, ankylosing spondylitis, undifferentiated spondylitis, Behcet's disease, haemolytic autoimmune anaemias, multiple sclerosis, amyotrophic lateral sclerosis, amylosis, acute painful shoulder, psoriatic, and juvenile arthritis), asthma, atherosclerosis, osteoporosis, bronchitis, tendonitis, bursitis, skin condition (e.g., psoriasis, eczema, burns, dermatitis, pruritus (itch)), enuresis, eosinophilic disease, gastrointestinal disorder (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GORD, or its synonym GERD), inflammatory bowel disease (IBD) (e.g., Crohn's disease, ulcerative colitis, collagenous colitis, lymphocytic colitis, ischaemic colitis, diversion colitis, Behcet's syndrome, indeterminate colitis) and inflammatory bowel syndrome (IBS)), relapsing polychondritis (e.g., atrophic polychondritis and systemic polychondromalacia), and disorders ameliorated by a gastroprokinetic agent (e.g., ileus, postoperative ileus and ileus during sepsis; gastroesophageal reflux disease (GORD, or its synonym GERD); eosinophilic esophagitis, gastroparesis such as diabetic gastroparesis; food intolerances and food allergies and other functional bowel disorders, such as non-ulcerative dyspepsia (NUD) and non-cardiac chest pain (NCCP, including costo-chondritis)). In certain embodiments, a method of treating inflammatory or autoimmune diseases is provided comprising administering to a subject (e.g., a mammal) a therapeutically effective amount of a compound, or a pharmaceutically acceptable form (e.g., pharmaceutically acceptable salts, hydrates, solvates, isomers, prodrugs, and isotopically labeled derivatives) thereof, or pharmaceutical compositions as provided herein, that selectively inhibit PI3K-δ and/or PI3K-γ as compared to all other type I PI3 kinases.

Such selective inhibition of PI3K-δ and/or PI3K-γ can be advantageous for treating any of the diseases or conditions described herein. For example, selective inhibition of PI3K-δ can inhibit inflammatory responses associated with inflammatory diseases, autoimmune disease, or diseases related to an undesirable immune response including, but not limited to asthma, emphysema, allergy, dermatitis, rheumatoid arthritis, psoriasis, lupus erythematosus, anaphylaxsis, or graft versus host disease. Selective inhibition of PI3K-δ can further provide for a reduction in the inflammatory or undesirable immune response without a concomittant reduction in the ability to reduce a bacterial, viral, and/or fungal infection. Selective inhibition of both PI3K-δ and PI3K-γ can be advantageous for inhibiting the inflammatory response in the subject to a greater degree than that would be provided for by inhibitors that selectively inhibit PI3K-δ or PI3K-γ alone. In one aspect, one or more of the subject methods are effective in reducing antigen specific antibody production in vivo by about 2-fold, 3-fold, 4-fold, 5-fold, 7.5-fold, 10-fold, 25-fold, 50-fold, 100-fold, 250-fold, 500-fold, 750-fold, or about 1000-fold or more. In another aspect, one or more of the subject methods are effective in reducing antigen specific IgG3 and/or IgGM production in vivo by about 2-fold, 3-fold, 4-fold, 5-fold, 7.5-fold, 10-fold, 25-fold, 50-fold, 100-fold, 250-fold, 500-fold, 750-fold, or about 1000-fold or more.

In one aspect, one of more of the subject methods are effective in ameliorating symptoms associated with rheumatoid arthritis including, but not limited to a reduction in the swelling of joints, a reduction in serum anti-collagen levels, and/or a reduction in joint pathology such as bone resorption, cartilage damage, pannus, and/or inflammation. In another aspect, the subject methods are effective in reducing ankle inflammation by at least about 2%, 5%, 10%, 15%, 20%, 25%, 30%, 50%, 60%, or about 75% to 90%. In another aspect, the subject methods are effective in reducing knee inflammation by at least about 2%, 5%, 10%, 15%, 20%, 25%, 30%, 50%, 60%, or about 75% to 90% or more. In still another aspect, the subject methods are effective in reducing serum anti-type II collagen levels by at least about 10%, 12%, 15%, 20%, 24%, 25%, 30%, 35%, 50%, 60%, 75%, 80%, 86%, 87%, or about 90% or more. In another aspect, the subject methods are effective in reducing ankle histopathology scores by about 5%, 10%, 15%, 20%, 25%, 30%, 40%, 50%, 60%, 75%, 80%, 90% or more. In still another aspect, the subject methods are effective in reducing knee histopathology scores by about 5%, 10%, 15%, 20%, 25%, 30%, 40%, 50%, 60%, 75%, 80%, 90% or more.

In some embodiments, provided herein are methods for treating disorders or conditions in which the δ isoform of PI3K is implicated to a greater extent than other PI3K isoforms such as PI3K-α and/or -β. Selective inhibition of PI3K-δ and/or PI3K-γ can provide advantages over using less selective compounds which inhibit PI3K-α and/or -β, such as an improved side effects profile or lessened reduction in the ability to reduce a bacterial, viral, and/or fungal infection.

In other embodiments, provided herein are methods of using a compound, or a pharmaceutically acceptable form (e.g., pharmaceutically acceptable salts, hydrates, solvates, isomers, prodrugs, and isotopically labeled derivatives) thereof, or pharmaceutical compositions as provided herein, to treat respiratory diseases including, but not limited to diseases affecting the lobes of lung, pleural cavity, bronchial tubes, trachea, upper respiratory tract, or the nerves and muscle for breathing. For example, methods are provided to treat obstructive pulmonary disease. Chronic obstructive pulmonary disease (COPD) is an umbrella term for a group of respiratory tract diseases that are characterized by airflow obstruction or limitation. Conditions included in this umbrella term include, but are not limited to: chronic bronchitis, emphysema, and bronchiectasis.

In another embodiment, the compounds, or a pharmaceutically acceptable form (e.g., pharmaceutically acceptable salts, hydrates, solvates, isomers, prodrugs, and isotopically labeled derivatives) thereof, or pharmaceutical compositions as provided herein are used for the treatment of asthma. Also, the compounds or pharmaceutical compositions described herein can be used for the treatment of endotoxemia and sepsis. In one embodiment, the compounds or pharmaceutical compositions described herein are used to for the treatment of rheumatoid arthritis (RA). In yet another embodiment, the compounds or pharmaceutical compositions described herein is used for the treatment of contact or atopic dermatitis. Contact dermatitis includes irritant dermatitis, phototoxic dermatitis, allergic dermatitis, photoallergic dermatitis, contact urticaria, systemic contact-type dermatitis and the like. Irritant dermatitis can occur when too much of a substance is used on the skin of when the skin is sensitive to certain substance. Atopic dermatitis, sometimes called eczema, is a kind of dermatitis, an atopic skin disease.

In some embodiments, the disclosure provides a method of treating diseases related to vasculogenesis or angiogenesis in a subject that comprises administering to said subject a therapeutically effective amount of a compound, or a pharmaceutically acceptable form (e.g., pharmaceutically acceptable salts, hydrates, solvates, isomers, prodrugs, and isotopically labeled derivatives) thereof, or pharmaceutical compositions as provided herein. In some embodiments, said method is for treating a disease selected from tumor angiogenesis, chronic inflammatory disease such as rheumatoid arthritis and chronic inflammatory demyelinating polyneuropathy, atherosclerosis, inflammatory bowel disease, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

In addition, the compounds described herein can be used for the treatment of arteriosclerosis, including atherosclerosis. Arteriosclerosis is a general term describing any hardening of medium or large arteries. Atherosclerosis is a hardening of an artery specifically due to an atheromatous plaque.

In some embodiments, provided herein is a method of treating a cardiovascular disease in a subject that comprises administering to said subject a therapeutically effective amount of a compound as provided herein, or a pharmaceutically acceptable form (e.g., pharmaceutically acceptable salts, hydrates, solvates, isomers, prodrugs, and isotopically labeled derivatives) thereof. Examples of cardiovascular conditions include, but are not limited to, atherosclerosis, restenosis, vascular occlusion and carotid obstructive disease.

In some embodiments, the disclosure relates to a method of treating diabetes in a subject that comprises administering to said subject a therapeutically effective amount of a compound as provided herein, or a pharmaceutically acceptable form (e.g., pharmaceutically acceptable salts, hydrates, solvates, isomers, prodrugs, and isotopically labeled derivatives) thereof, or pharmaceutical compositions as provided herein.

In addition, the compounds, or a pharmaceutically acceptable form (e.g., pharmaceutically acceptable salts, hydrates, solvates, isomers, prodrugs, and isotopically labeled derivatives) thereof, or pharmaceutical compositions as provided herein, can be used to treat acne. In certain embodiments, the inflammatory condition and/or immune disorder is a skin condition. In some embodiments, the skin condition is pruritus (itch), psoriasis, eczema, burns or dermatitis. In certain embodiments, the skin condition is psoriasis. In certain embodiments, the skin condition is pruritis.

In certain embodiments, the inflammatory disorder and/or the immune disorder is a gastrointestinal disorder. In some embodiments, the gastrointestinal disorder is selected from gastrointestinal disorder (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GORD, or its synonym GERD), inflammatory bowel disease (IBD) (e.g., Crohn's disease, ulcerative colitis, collagenous colitis, lymphocytic colitis, ischaemic colitis, diversion colitis, Behcet's syndrome, indeterminate colitis) and inflammatory bowel syndrome (IBS)). In certain embodiments, the gastrointestinal disorder is inflammatory bowel disease (IBD).

Further, the compounds, or a pharmaceutically acceptable form (e.g., pharmaceutically acceptable salts, hydrates, solvates, isomers, prodrugs, and isotopically labeled derivatives) thereof, or pharmaceutical compositions as provided herein, can be used for the treatment of glomerulonephritis. Glomerulonephritis is a primary or secondary autoimmune renal disease characterized by inflammation of the glomeruli. It can be asymptomatic, or present with hematuria and/or proteinuria. There are many recognized types, divided in acute, subacute or chronic glomerulonephritis. Causes are infectious (bacterial, viral or parasitic pathogens), autoimmune or paraneoplastic.

In some embodiments, provided herein are compounds, or a pharmaceutically acceptable form (e.g., pharmaceutically acceptable salts, hydrates, solvates, isomers, prodrugs, and isotopically labeled derivatives) thereof, or pharmaceutical compositions as provided herein, for the treatment of multiorgan failure. Also provided herein are compounds, or a pharmaceutically acceptable form (e.g., pharmaceutically acceptable salts, hydrates, solvates, isomers, prodrugs, and isotopically labeled derivatives) thereof, or pharmaceutical compositions as provided herein, for the treatment of liver diseases (including diabetes), gall bladder disease (including gallstones), pancreatitis or kidney disease (including proliferative glomerulonephritis and diabetes-induced renal disease) or pain in a subject.

In some embodiments, provided herein are compounds, or a pharmaceutically acceptable form (e.g., pharmaceutically acceptable salts, hydrates, solvates, isomers, prodrugs, and isotopically labeled derivatives) thereof, or pharmaceutical compositions as provided herein, for the prevention of blastocyte implantation in a subject.

In some embodiments, provided herein are compounds, or a pharmaceutically acceptable form (e.g., pharmaceutically acceptable salts, hydrates, solvates, isomers, prodrugs, and isotopically labeled derivatives) thereof, or pharmaceutical compositions as provided herein, for the treatment of disorders involving platelet aggregation or platelet adhesion, including, but not limited to Idiopathic thrombocytopenic purpura, Bernard-Soulier syndrome, Glanzmann's thrombasthenia, Scott's syndrome, von Willebrand disease, Hermansky-Pudlak Syndrome, and Gray platelet syndrome.

In some embodiments, compounds, or a pharmaceutically acceptable form (e.g., pharmaceutically acceptable salts, hydrates, solvates, isomers, prodrugs, and isotopically labeled derivatives) thereof, or pharmaceutical compositions as provided herein, are provided for treating a disease which is skeletal muscle atrophy, skeletal or muscle hypertrophy. In some embodiments, provided herein are compounds, or a pharmaceutically acceptable form (e.g., pharmaceutically acceptable salts, hydrates, solvates, isomers, prodrugs, and isotopically labeled derivatives) thereof, or pharmaceutical compositions as provided herein, for the treatment of disorders that include, but are not limited to, cancers as discussed herein, transplantation-related disorders (e.g., lowering rejection rates, graft-versus-host disease, etc.), muscular sclerosis (MS), allergic disorders (e.g., arthritis, allergic encephalomyelitis) and other immunosuppressive-related disorders, metabolic disorders (e.g., diabetes), reducing intimal thickening following vascular injury, and misfolded protein disorders (e.g., Alzheimer's Disease, Gaucher's Disease, Parkinson's Disease, Huntington's Disease, cystic fibrosis, macular degeneration, retinitis pigmentosa, and prion disorders) (as mTOR inhibition can alleviate the effects of misfolded protein aggregates). The disorders also include hamartoma syndromes, such as tuberous sclerosis and Cowden Disease (also termed Cowden syndrome and multiple hamartoma syndrome).

Additionally, the compounds, or a pharmaceutically acceptable form (e.g., pharmaceutically acceptable salts, hydrates, solvates, isomers, prodrugs, and isotopically labeled derivatives) thereof, or pharmaceutical compositions as provided herein, can be used for the treatment of bursitis, lupus, acute disseminated encephalomyelitis (ADEM), Addison's disease, antiphospholipid antibody syndrome (APS), amyloidosis (including systemic and localized amyloidosis; and primary and secondary amyloidosis), aplastic anemia, autoimmune hepatitis, coeliac disease, crohn's disease, diabetes mellitus (type 1), eosinophilic gastroenterides, goodpasture's syndrome, graves' disease, guillain-barré syndrome (GBS), hashimoto's disease, inflammatory bowel disease, lupus erythematosus (including cutaneous lupus erythematosus and systemic lupus erythematosus), myasthenia gravis, opsoclonus myoclonus syndrome (OMS), optic neuritis, ord's thyroiditis, ostheoarthritis, uveoretinitis, pemphigus, polyarthritis, primary biliary cirrhosis, reiter's syndrome, takayasu's arteritis, temporal arteritis, warm autoimmune hemolytic anemia, wegener's granulomatosis, alopecia universalis, chagas' disease, chronic fatigue syndrome, dysautonomia, endometriosis, hidradenitis suppurativa, interstitial cystitis, neuromyotonia, sarcoidosis, scleroderma, ulcerative colitis, vitiligo, vulvodynia, appendicitis, arteritis, arthritis, blepharitis, bronchiolitis, bronchitis, cervicitis, cholangitis, cholecystitis, chorioamnionitis, colitis, conjunctivitis, cystitis, dacryoadenitis, dermatomyositis, endocarditis, endometritis, enteritis, enterocolitis, epicondylitis, epididymitis, fasciitis, fibrositis, gastritis, gastroenteritis, gingivitis, hepatitis, hidradenitis, ileitis, iritis, laryngitis, mastitis, meningitis, myelitis, myocarditis, myositis, nephritis, omphalitis, oophoritis, orchitis, osteitis, otitis, pancreatitis, parotitis, pericarditis, peritonitis, pharyngitis, pleuritis, phlebitis, pneumonitis, proctitis, prostatitis, pyelonephritis, rhinitis, salpingitis, sinusitis, stomatitis, synovitis, tendonitis, tonsillitis, uveitis (e.g., ocular uveitis), vaginitis, vasculitis, or vulvitis.

In another aspect, provided herein are methods of disrupting the function of a leukocyte or disrupting a function of an osteoclast. The method includes contacting the leukocyte or the osteoclast with a function disrupting amount of a compound as provided herein.

In another aspect, methods are provided for treating ophthalmic disease by administering one or more of the subject compounds or pharmaceutical compositions to the eye of a subject.

In certain embodiments, provided herein are methods of treating, preventing and/or managing a disease or a disorder using a compound, or a pharmaceutically acceptable form (e.g., pharmaceutically acceptable salts, hydrates, solvates, isomers, prodrugs, and isotopically labeled derivatives) thereof, or pharmaceutical compositions as provided herein, wherein the disease or disorder is: Crohn's disease; cutaneous lupus; multiple sclerosis; rheumatoid arthritis; and systemic lupus erythematosus.

In other embodiments, provided herein are methods of treating, preventing and/or managing a disease or a disorder using a compound, or a pharmaceutically acceptable form (e.g., pharmaceutically acceptable salts, hydrates, solvates, isomers, prodrugs, and isotopically labeled derivatives) thereof, or pharmaceutical compositions as provided herein, wherein the disease or disorder is: ankylosing spondylitis; chronic obstructive pulmonary disease; myasthenia gravis; ocular uveitis, psoriasis; and psoriatic arthritis.

In other embodiments, provided herein are methods of treating, preventing and/or managing a disease or a disorder using a compound, or a pharmaceutically acceptable form (e.g., pharmaceutically acceptable salts, hydrates, solvates, isomers, prodrugs, and isotopically labeled derivatives) thereof, or pharmaceutical compositions as provided herein, wherein the disease or disorder is: adult-onset Still's disease; inflammatory alopecia; amyloidosis; antiphospholipid syndrome; autoimmune hepatitis; autoimmune skin disease, Behcet's disease; chronic inflammatory demyelinating polyneuropathy; eosinophilic gastroenteritis; inflammatory myopathies, pemphigus, polymyalgia rheumatica; relapsing polychondritis; Sjorgen's syndrome; temporal arthritis; ulcerative colitis; vasculis; vitiligo, and Wegner's granulomatosis.

In other embodiments, provided herein are methods of treating, preventing and/or managing a disease or a disorder using a compound, or a pharmaceutically acceptable form (e.g., pharmaceutically acceptable salts, hydrates, solvates, isomers, prodrugs, and isotopically labeled derivatives) thereof, or pharmaceutical compositions as provided herein, wherein the disease or disorder is: gout flare; sacoidosis; and systemic sclerosis.

In certain embodiments, provided herein are methods of treating, preventing and/or managing a disease or a disorder using a compound, or a pharmaceutically acceptable form (e.g., pharmaceutically acceptable salts, hydrates, solvates, isomers, prodrugs, and isotopically labeled derivatives) thereof, or pharmaceutical compositions as provided herein, wherein the disease or disorder is: asthma; arthritis (e.g., rheumatoid arthritis and psoriatic arthritis); psoriasis; scleroderma; myositis (e.g., dermatomyositis); lupus (e.g., cutaneous lupus erythematosus ("CLE") or systemic lupus erythematosus ("SLE")); or Sjögren's syndrome.

Efficacy of a compound provided herein in treating, preventing and/or managing the disease or disorder can be tested using various animal models known in the art. For example: efficacy in treating, preventing and/or managing asthma can be assessed using ova induced asthma model described, for example, in Lee et al. (2006) *J Allergy Clin Immunol* 118(2): 403-9; efficacy in treating, preventing and/or managing arthritis (e.g., rheumatoid or psoriatic arthritis) can be assessed using autoimmune animal models described, for example, in Williams et al. (2010) *Chem Biol,* 17(2):123-34, WO 2009/088986, WO2009/088880, and WO 2011/008302; efficacy in treating, preventing and/or managing psoriasis can be assessed using transgenic or knockout mouse model with targeted mutations in epidermis, vasculature or immune cells, mouse model resulting from spontaneous mutations, and immunodeficient mouse model with xenotransplantation of human skin or immune cells, all of which are described, for example, in Boehncke et al. (2007) *Clinics in Dermatology,* 25: 596-605; efficacy in treating, preventing and/or managing fibrosis or fibrotic condition can be assessed using the unilateral ureteral obstruction model of renal fibrosis (see Chevalier et al., *Kidney International* (2009) 75:1145-1152), the bleomycin induced model of pulmonary fibrosis (see Moore and Hogaboam, *Am. J. Physiol. Lung. Cell. Mol. Physiol.* (2008) 294:L152-L160), a variety of liver/biliary fibrosis models (see Chuang et al., *Clin Liver Dis* (2008) 12:333-347 and Omenetti, A. et al. (2007) *Laboratory Investigation* 87:499-514 (biliary duct-ligated model)), or a number of myelofibrosis mouse models (see Varicchio, L. et al. (2009) *Expert Rev. Hematol.* 2(3):315-334); efficacy in treating, preventing and/or managing scleroderma can be assessed using mouse model induced by repeated local injections of bleomycin ("BLM")

described, for example, in Yamamoto et al. (1999) *J Invest Dermatol* 112: 456-462; efficacy in treating, preventing and/or managing dermatomyositis can be assessed using myositis mouse model induced by immunization with rabbit myosin described, for example, in Phyanagi et al. (2009) *Arthritis & Rheumatism*, 60(10): 3118-3127; efficacy in treating, preventing and/or managing lupus (e.g., CLE or SLE) can be assessed using various animal models described, for example, in Ghoreishi et al. (2009) *Lupus*, 19: 1029-1035, Ohl et al. (2011) *Journal of Biomedicine and Biotechnology, Article ID* 432595 (14 pages), Xia et al. (2011) *Rheumatology*, 50:2187-2196, Pau et al. (2012) *PLoS ONE*, 7(5):e36761 (15 pages), Mustafa et al. (2011) *Toxicology*, 290:156-168, Ichikawa et al. (2012) *Arthritis and Rheumatism*, 62(2): 493-503, Ouyang et al. (2012) *J Mol Med*, DOI 10.1007/s00109-012-0866-3 (10 pages), Rankin et al. (2012) *Journal of Immunology*, 188:1656-1667; and efficacy in treating, preventing and/or managing Sjögren's syndrome can be assessed using various mouse models described, for example, in Chiorini et al. (2009) *Journal of Autoimmunity*, 33: 190-196.

In one embodiment, provided herein is a method of treating, preventing and/or managing asthma. As used herein, "asthma" encompasses airway constriction regardless of the cause. Common triggers of asthma include, but are not limited to, exposure to an environmental stimulants (e.g., allergens), cold air, warm air, perfume, moist air, exercise or exertion, and emotional stress. Also provided herein is a method of treating, preventing and/or managing one or more symptoms associated with asthma. Examples of the symptoms include, but are not limited to, severe coughing, airway constriction and mucus production.

In one embodiment, provided herein is a method of treating, preventing and/or managing arthritis. As used herein, "arthritis" encompasses all types and manifestations of arthritis. Examples include, but are not limited to, crystalline arthritis, osteoarthritis, psoriatic arthritis, gouty arthritis, reactive arthritis, rheumatoid arthritis and Reiter's arthritis. In one embodiment, the disease or disorder is rheumatoid arthritis. In another embodiment, the disease or disorder is psoriatic arthritis. Also provided herein is a method of treating, preventing and/or managing one or more symptoms associated with arthritis. Examples of the symptoms include, but are not limited to, joint pain, which progresses into joint deformation, or damages in body organs such as in blood vessels, heart, lungs, skin, and muscles.

In one embodiment, provided herein is a method of treating, preventing and/or managing psoriasis. As used herein, "psoriasis" encompasses all types and manifestations of psoriasis. Examples include, but are not limited to, plaque psoriasis (e.g., chronic plaque psoriasis, moderate plaque psoriasis and severe plaque psoriasis), guttate psoriasis, inverse psoriasis, pustular psoriasis, pemphigus vulgaris, erythrodermic psoriasis, psoriasis associated with inflammatory bowel disease (IBD), and psoriasis associated with rheumatoid arthritis (RA). Also provided herein is a method of treating, preventing and/or managing one or more symptoms associated with psoriasis. Examples of the symptoms include, but are not limited to: red patches of skin covered with silvery scales; small scaling spots; dry, cracked skin that may bleed; itching; burning; soreness; thickened, pitted or ridged nails; and swollen and stiff joints.

In one embodiment, provided herein is a method of treating, preventing and/or managing fibrosis and fibrotic condition. As used herein, "fibrosis" or "fibrotic condition encompasses all types and manifestations of fibrosis or fibrotic condition. Examples include, but are not limited to, formation or deposition of tissue fibrosis; reducing the size, cellularity (e.g., fibroblast or immune cell numbers), composition; or cellular content, of a fibrotic lesion; reducing the collagen or hydroxyproline content, of a fibrotic lesion; reducing expression or activity of a fibrogenic protein; reducing fibrosis associated with an inflammatory response; decreasing weight loss associated with fibrosis; or increasing survival.

In certain embodiments, the fibrotic condition is primary fibrosis. In one embodiment, the fibrotic condition is idiopathic. In other embodiments, the fibrotic condition is associated with (e.g., is secondary to) a disease (e.g., an infectious disease, an inflammatory disease, an autoimmune disease, a malignant or cancerous disease, and/or a connective disease); a toxin; an insult (e.g., an environmental hazard (e.g., asbestos, coal dust, polycyclic aromatic hydrocarbons), cigarette smoking, a wound); a medical treatment (e.g., surgical incision, chemotherapy or radiation), or a combination thereof.

In some embodiments, the fibrotic condition is associated with an autoimmune disease selected from scleroderma or lupus, e.g., systemic lupus erythematosus. In some embodiments, the fibrotic condition is systemic. In some embodiments, the fibrotic condition is systemic sclerosis (e.g., limited systemic sclerosis, diffuse systemic sclerosis, or systemic sclerosis sine scleroderma), nephrogenic systemic fibrosis, cystic fibrosis, chronic graft vs. host disease, or atherosclerosis.

In certain embodiments, the fibrotic condition is a fibrotic condition of the lung, a fibrotic condition of the liver, a fibrotic condition of the heart or vasculature, a fibrotic condition of the kidney, a fibrotic condition of the skin, a fibrotic condition of the gastrointestinal tract, a fibrotic condition of the bone marrow or a hematopoietic tissue, a fibrotic condition of the nervous system, a fibrotic condition of the eye, or a combination thereof.

In other embodiment, the fibrotic condition affects a tissue chosen from one or more of: muscle, tendon, cartilage, skin (e.g., skin epidermis or endodermis), cardiac tissue, vascular tissue (e.g., artery, vein), pancreatic tissue, lung tissue, liver tissue, kidney tissue, uterine tissue, ovarian tissue, neural tissue, testicular tissue, peritoneal tissue, colon, small intestine, biliary tract, gut, bone marrow, hematopoietic tissue, or eye (e.g., retinal) tissue.

In some embodiments, the fibrotic condition is a fibrotic condition of the eye. In some embodiments, the fibrotic condition is glaucoma, macular degeneration (e.g., age-related macular degeneration), macular edema (e.g., diabetic macular edema), retinopathy (e.g., diabetic retinopathy), or dry eye disease.

In certain embodiments, the fibrotic condition is a fibrotic condition of the lung. In certain embodiments, the fibrotic condition of the lung is chosen from one or more of: pulmonary fibrosis, idiopathic pulmonary fibrosis (IPF), usual interstitial pneumonitis (UIP), interstitial lung disease, cryptogenic fibrosing alveolitis (CFA), bronchiectasis, and scleroderma lung disease. In one embodiment, the fibrosis of the lung is secondary to a disease, a toxin, an insult, a medical treatment, or a combination thereof. For example, the fibrosis of the lung can be associated with (e.g., secondary to) one or more of: a disease process such as asbestosis and silicosis; an occupational hazard; an environmental pollutant; cigarette smoking; an autoimmune connective tissue disorders (e.g., rheumatoid arthritis, scleroderma and systemic lupus erythematosus (SLE)); a connective tissue disorder such as sarcoidosis; an infectious disease, e.g., infection, particularly chronic infection; a medical treatment, including but not limited to, radiation therapy, and drug therapy, e.g., chemotherapy (e.g., treatment with as bleomycin, methotrexate, amiodarone, busulfan, and/or nitrofurantoin). In one embodiment, the fibrotic condition of the lung treated with the methods of the invention is associated with (e.g., secondary to) a cancer treatment, e.g., treatment of a cancer (e.g., squamous cell carcinoma, testicular cancer, Hodgkin's disease with bleomycin). In one embodiment, the fibrotic condition of the lung is associated with an autoimmune connective tissue disorder (e.g., scleroderma or lupus, e.g., SLE).

In certain embodiments, the fibrotic condition is a fibrotic condition of the liver. In certain embodiments, the fibrotic condition of the liver is chosen from one or more of: fatty liver disease, steatosis (e.g., nonalcoholic steatohepatitis (NASH), cholestatic liver disease (e.g., primary biliary cirrhosis (PBC)), cirrhosis, alcohol induced liver fibrosis, biliary duct injury, biliary fibrosis, or cholangiopathies. In other embodiments, hepatic or liver fibrosis includes, but is not limited to, hepatic fibrosis associated with alcoholism, viral infection, e.g., hepatitis (e.g., hepatitis C, B or D), autoimmune hepatitis, non-alcoholic fatty liver disease (NAFLD), progressive massive fibrosis, exposure to toxins or irritants (e.g., alcohol, pharmaceutical drugs and environmental toxins).

In certain embodiments, the fibrotic condition is a fibrotic condition of the heart. In certain embodiments, the fibrotic condition of the heart is myocardial fibrosis (e.g., myocardial fibrosis associated with radiation myocarditis, a surgical procedure complication (e.g., myocardial post-operative fibrosis), infectious diseases (e.g., Chagas disease, bacterial, trichinosis or fungal myocarditis)); granulomatous, metabolic storage disorders (e.g., cardiomyopathy, hemochromatosis); developmental disorders (e.g, endocardial fibroelastosis); arteriosclerotic, or exposure to toxins or irritants (e.g., drug induced cardiomyopathy, drug induced cardiotoxicity, alcoholic cardiomyopathy, cobalt poisoning or exposure). In certain embodiments, the myocardial fibrosis is associated with an inflammatory disorder of cardiac tissue (e.g., myocardial sarcoidosis). In some embodiments, the fibrotic condition is a fibrotic condition associated with a myocardial infarction. In some embodiments, the fibrotic condition is a fibrotic condition associated with congestive heart failure.

In certain embodiments, the fibrotic condition is a fibrotic condition of the kidney. In certain embodiments, the fibrotic condition of the kidney is chosen from one or more of: renal fibrosis (e.g., chronic kidney fibrosis), nephropathies associated with injury/fibrosis (e.g., chronic nephropathies associated with diabetes (e.g., diabetic nephropathy)), lupus, scleroderma of the kidney, glomerular nephritis, focal segmental glomerular sclerosis, IgA nephropathyrenal fibrosis associated with human chronic kidney disease (CKD), chronic progressive nephropathy (CPN), tubulointerstitial fibrosis, ureteral obstruction, chronic uremia, chronic interstitial nephritis, radiation nephropathy, glomerulosclerosis, progressive glomerulonephrosis (PGN), endothelial/thrombotic microangiopathy injury, HIV-associated nephropathy, or fibrosis associated with exposure to a toxin, an irritant, or a chemotherapeutic agent. In one embodiment, the fibrotic condition of the kidney is scleroderma of the kidney. In some embodiments, the fibrotic condition of the kidney is transplant nephropathy, diabetic nephropathy, lupus nephritis, or focal segmental glomerulosclerosis (FSGS).

In certain embodiments, the fibrotic condition is a fibrotic condition of the skin. In certain embodiments, the fibrotic condition of the skin is chosen from one or more of: skin fibrosis (e.g., hypertrophic scarring, keloid), scleroderma, nephrogenic systemic fibrosis (e.g., resulting after exposure to gadolinium (which is frequently used as a contrast substance for MRIs) in patients with severe kidney failure), and keloid.

In certain embodiments, the fibrotic condition is a fibrotic condition of the gastrointestinal tract. In certain embodiments, the fibrotic condition is chosen from one or more of: fibrosis associated with scleroderma; radiation induced gut fibrosis; fibrosis associated with a foregut inflammatory disorder such as Barrett's esophagus and chronic gastritis, and/or fibrosis associated with a hindgut inflammatory disorder, such as inflammatory bowel disease (IBD), ulcerative colitis and Crohn's disease. In some embodiments, the fibrotic condition of the gastrointestinal tract is fibrosis associated with scleroderma.

In certain embodiments, the fibrotic condition is a fibrotic condition of the bone marrow or a hematopoietic tissue. In certain embodiments, the fibrotic condition of the bone marrow is an intrinsic feature of a chronic myeloproliferative neoplasm of the bone marrow, such as primary myelofibrosis (also referred to herein as agnogenic myeloid metaplasia or chronic idiopathic myelofibrosis). In other embodiments, the bone marrow fibrosis is associated with (e.g., is secondary to) a malignant condition or a condition caused by a clonal proliferative disease. In other embodiments, the bone marrow fibrosis is associated with a hematologic disorder (e.g., a hematologic disorder chosen from one or more of polycythemia vera, essential thrombocythemia, myelodysplasia, hairy cell leukemia, lymphoma (e.g., Hodgkin or non-Hodgkin lymphoma), multiple myeloma or chronic myelogeneous leukemia (CML)). In yet other embodiments, the bone marrow fibrosis is associated with (e.g., secondary to) a non-hematologic disorder (e.g., a non-hematologic disorder chosen from solid tumor metastasis to bone marrow, an autoimmune disorder (e.g., systemic lupus erythematosus, scleroderma, mixed connective tissue disorder, or polymyositis), an infection (e.g., tuberculosis), or secondary hyperparathyroidism associated with vitamin D deficiency. In some embodiments, the fibrotic condition is idiopathic or drug-induced myelofibrosis. In some embodiments, the fibrotic condition of the bone marrow or hematopoietic tissue is associated with systemic lupus erythematosus or scleroderma.

In one embodiment, provided herein is a method of treating, preventing and/or managing scleroderma. Scleroderma is a group of diseases that involve hardening and tightening of the skin and/or other connective tissues. Scleroderma may be localized (e.g., affecting only the skin) or systemic (e.g., affecting other systems such as, e.g., blood vessels and/or internal organs). Common symptoms of scleroderma include Raynaud's phenomenon, gastroesophageal reflux disease, and skin changes (e.g., swollen fingers and hands, or thickened patches of skin). In some embodiments, the scleroderma is localized, e.g., morphea or linear scleroderma. In some embodiments, the condition is a systemic sclerosis, e.g., limited systemic sclerosis, diffuse systemic sclerosis, or systemic sclerosis sine scleroderma.

Localized scleroderma (localized cutaneous fibrosis) includes morphea and linear scleroderma. Morphea is typically characterized by oval-shaped thickened patches of skin that are white in the middle, with a purple border. Linear scleroderma is more common in children. Symptoms of linear scleroderma may appear mostly on one side of the body. In linear scleroderma, bands or streaks of hardened skin may develop on one or both arms or legs or on the forehead. En coup de sabre (frontal linear scleroderma or morphea en coup de sabre) is a type of localized scleroderma typically characterized by linear lesions of the scalp or face.

Systemic scleroderma (systemic sclerosis) includes, e.g., limited systemic sclerosis (also known as limited cutaneous systemic sclerosis, or CREST syndrome), diffuse systemic sclerosis (also known as diffuse cutaneous systemic sclerosis), and systemic sclerosis sine scleroderma. CREST stands for the following complications that may accompany limited scleroderma: calcinosis (e.g., of the digits), Raynaud's phenomenon, esophageal dysfunction, sclerodactyl), and telangiectasias. Typically, limited scleroderma involves cutaneous manifestations that mainly affect the hands, arms, and face. Limited and diffuse subtypes are distinguished based on the extent of skin involvement, with sparing of the proximal limbs and trunk in limited disease. See, e.g., Denton, C. P. et al. (2006), *Nature Clinical Practice Rheumatology*, 2(3):134-143. The limited subtype also typically involves a long previous history of Raynaud's phenomenon, whereas in the diffuse subtype, onset of Raynaud's phenomenon can be simultaneous with other manifestations or might occur later. Both limited and diffuse subtypes may involve internal organs. Typical visceral manifestations of limited systemic sclerosis include isolated pulmonary hypertension, severe bowel involvement, and pulmonary fibrosis. Typical visceral manifestations of diffuse systemic sclerosis include renal crisis, lung fibrosis, and cardiac disease. Diffuse systemic sclerosis typically progresses rapidly and affects a large area of the skin and one or more internal organs (e.g., kidneys, esophagus, heart, or lungs). Systemic sclerosis sine scleroderma is a rare disorder in which patients develop vascular and fibrotic damage to internal organs in the absence of cutaneous sclerosis.

In one embodiment, provided herein is a method of treating, preventing and/or managing inflammatory myopathies. As used herein, "inflammatory myopathies" encompass all types and manifestations of inflammatory myopathies. Examples include, but are not limited to, muscle weakness (e.g., proximal muscle weakness), skin rash, fatigue after walking or standing, tripping or falling, dysphagia, dysphonia, difficulty breathing, muscle pain, tender muscles, weight loss, low-grade fever, inflamed lungs, light sensitivity, calcium deposits (calcinosis) under the skin or in the muscle, as well as biological concomitants of inflammatory myopathies as disclosed herein or as known in the art. Biological concomitants of inflammatory myopathies (e.g., dermatomyositis) include, e.g., altered (e.g., increased) levels of cytokines (e.g., Type I interferons (e.g., IFN-α and/or IFN-β, interleukins (e.g., IL-6, IL-10, IL-15, IL-17 and IL-18), and TNF-α), TGF-β, B-cell activating factor (BAFF), overexpression of IFN inducible genes (e.g., Type I IFN inducible genes). Other biological concomitants of inflammatory myopathies can include, e.g., an increased erythrocyte sedimentation rate (ESR) and/or elevated level of creatine kinase. Further biological concomitants of inflammatory myopathies can include autoantibodies, e.g., anti-synthetase autoantibodies (e.g., anti-Jo 1 antibodies), anti-signal recognition particle antibodies (anti-SRP), anti-Mi-2 antibodies, anti-p155 antibodies, anti-PM/Sci antibodies, and anti-RNP antibodies.

The inflammatory myopathy can be an acute inflammatory myopathy or a chronic inflammatory myopathy. In some embodiments, the inflammatory myopathy is a chronic inflammatory myopathy (e.g., dermatomyositis, polymyositis, or inclusion body myositis). In some embodiments, the inflammatory myopathy is caused by an allergic reaction, another disease (e.g., cancer or a connective tissue disease), exposure to a toxic substance, a medicine, or an infectious agent (e.g., a virus). In some embodiments, the inflammatory myopathy is associated with lupus, rheumatoid arthritis, or systemic sclerosis. In some embodiments, the inflammatory myopathy is idiopathic. In some embodiments, the inflammatory myopathy is selected from polymyositis, dermatomyositis, inclusion body myositis, and immune-mediated necrotizing myopathy. In some embodiments, the inflammatory myopathy is dermatomyositis.

In another embodiment, provided herein is a method of treating, preventing and/or managing a skin condition (e.g., a dermatitis). In some embodiments, the methods provided herein can reduce symptoms associated with a skin condition (e.g., itchiness and/or inflammation). In some such embodiments, the compound provided herein is administered topically (e.g., as a topical cream, eyedrop, nose drop or nasal spray). In some such embodiments, the compound is a PI3K delta inhibitor (e.g., a PI3K inhibitor that demonstrates greater inhibition of PI3K delta than of other PI3K isoforms). In some embodiments, the PI3K delta inhibitor prevents mast cell degranulation.

As used herein, "skin condition" includes any inflammatory condition of the skin (e.g., eczema or dermatitis, e.g., contact dermatitis, atopic dermatitis, dermatitis herpetiformis, seborrheic dermatitis, nummular dermatitis, stasis dermatitis, perioral dermatitis), as well as accompanying symptoms (e.g., skin rash, itchiness (pruritis), swelling (edema), hay fever, anaphalaxis). Frequently, such skin conditions are caused by an allergen. As used herein, a "skin condition" also includes, e.g., skin rashes (e.g., allergic rashes, e.g., rashes resulting from exposure to allergens such as poison ivy, poison oak, or poison sumac, or rashes caused by other diseases or conditions), insect bites, minor burns, sunburn, minor cuts, and scrapes. In some embodiments, the symptom associated with inflammatory myopathy, or the skin condition or symptom associated with the skin condition, is a skin rash or itchiness (pruritis) caused by a skin rash.

The skin condition (e.g., the skin rash) may be spontaneous, or it may be induced, e.g., by exposure to an allergen (e.g., poison ivy, poison oak, or poison sumac), drugs, food, insect bite, inhalants, emotional stress, exposure to heat, exposure to cold, or exercise. In some embodiments, the skin condition is a skin rash (e.g., a pruritic rash, e.g., utricaria). In some embodiments, the skin condition is an insect bite. In some embodiments, the skin condition is associated with another disease (e.g., an inflammatory myopathy, e.g., dermatomyositis).

In some embodiments, the subject (e.g., the subject in need of treatment for an inflammatory myopathy and/or a skin condition) exhibits an elevated level or elevated activity of IFN-α TNF-α, IL-6, IL-8, IL-1, or a combination thereof. In certain embodiments, the subject exhibits an elevated level of IFN-α. In some embodiments, treating (e.g., decreasing or inhibiting) the inflammatory myopathy, or the skin condition, comprises inhibiting (e.g., decreasing a level of, or decreasing a biological activity of) one or more of IFN-α, TNF-α, IL-6, IL-8, or IL-1 in the subject or in a sample derived from the subject. In some embodiments, the method decreases a level of IFN-α, TNF-α, IL-6, IL-8, or IL-1 in the subject or in a sample derived from the subject. In some embodiments, the method decreases a level of IFN-α in the subject or in a sample derived from the subject. In some embodiments, the level of IFN-α, TNF-α, IL-6, IL-8, or IL-1 is the level assessed in a sample of whole blood or PBMCs. In some embodiments, the level of IFN-α, TNF-α, IL-6, IL-8, or IL-1 is the level assessed in a sample obtained by a skin biopsy or a muscle biopsy. In some embodiments, the sample is obtained by a skin biopsy.

In one embodiment, provided herein is a method of treating, preventing and/or managing myositis. As used herein, "myositis" encompasses all types and manifestations of myositis. Examples include, but are not limited to, myositis ossificans, fibromyositis, idiopathic inflammatory myopathies, dermatomyositis, juvenile dermatomyositis, polymyositis, inclusion body myositis and pyomyositis. In one embodiment, the disease or disorder is dermatomyositis. Also provided herein is a method of treating, preventing and/or managing one or more symptoms associated with myositis. Examples of the symptoms include, but are not limited to: muscle weakness; trouble lifting arms; trouble swallowing or breathing; muscle pain; muscle tenderness; fatigue; fever; lung problems; gastrointestinal ulcers; intestinal perforations; calcinosis under the skin; soreness; arthritis; weight loss; and rashes.

In one embodiment, provided herein is a method of treating, preventing and/or managing lupus. As used herein, "lupus" refers to all types and manifestations of lupus. Examples include, but are not limited to, systemic lupus erythematosus; lupus nephritis; cutaneous manifestations (e.g., manifestations seen in cutaneous lupus erythematosus, e.g., a skin lesion or rash); CNS lupus; cardiovascular, pulmonary, hepatic, hematological, gastrointestinal and musculoskeletal manifestations; neonatal lupus erythematosus; childhood systemic lupus erythematosus; drug-induced lupus erythematosus; anti-phospholipid syndrome; and complement deficiency syndromes resulting in lupus manifestations. In one embodiment, the lupus is systemic lupus erythematosus (SLE), cutaneous lupus erythematosus (CLE), drug-induced lupus, or neonatal lupus. In another embodiment, the lupus is a CLE, e.g., acute cutaneous lupus erythematosus (ACLE), subacute cutaneous lupus erythematosus (SCLE), intermittent cutaneous lupus erythematosus (also known as lupus erythematosus tumidus (LET)), or chronic cutaneous lupus. In some embodiments, the intermittent CLE is chronic discloid lupus erythematosus (CDLE) or lupus erythematosus profundus (LEP) (also known as lupus erythematosus panniculitis). Types, symptoms, and pathogenesis of CLE are described, for example, in Wenzel et al. (2010), *Lupus*, 19, 1020-1028.

In one embodiment, provided herein is a method of treating, preventing and/or managing Sjögren's syndrome. As used herein, "Sjögren's syndrome" refers to all types and manifestations of Sjögren's syndrome. Examples include, but are not limited to, primary and secondary Sjögren's syndrome. Also provided herein is a method of treating, preventing and/or managing one or more symptoms associated with Sjögren's syndrome. Examples of the symptoms include, but are not limited to: dry eyes; dry mouth; joint pain; swelling; stiffness; swollen salivary glands; skin rashes; dry skin; vaginal dryness; persistent dry cough; and prolonged fatigue.

In some embodiments, a symptom associated with the disease or disorder provided herein is reduced by at least 10%, at least 20%, at least 30%, at least 40%, at least 50%, at least 60%, at least 70%, at least 80%, at least 90%, or at least 95% relative to a control level. The control level includes any appropriate control as known in the art. For example, the control level can be the pre-treatment level in the sample or subject treated, or it can be the level in a control population (e.g., the level in subjects who do not have the disease or disorder or the level in samples derived from subjects who do not have the disease or disorder). In some embodiments, the decrease is statistically significant, for example, as assessed using an appropriate parametric or non-parametric statistical comparison.

COMBINATION THERAPY

In some embodiments, provided herein are methods for combination therapies in which an agent known to modulate other pathways, or other components of the same pathway, or even overlapping sets of target enzymes are used in combination with a compound as provided herein, or a pharmaceutically acceptable form (e.g., pharmaceutically acceptable salts, hydrates, solvates, isomers, prodrugs, and isotopically labeled derivatives) thereof. In one aspect, such therapy includes, but is not limited to, the combination of the subject compound with chemotherapeutic agents, therapeutic antibodies, and radiation treatment, to provide a synergistic or additive therapeutic effect.

In one aspect, a compound as provided herein, or a pharmaceutically acceptable form (e.g., pharmaceutically acceptable salts, hydrates, solvates, isomers, prodrugs, and isotopically labeled derivatives) thereof, or pharmaceutical compositions as provided herein, can present synergistic or additive efficacy when administered in combination with agents that inhibit IgE production or activity. Such combination can reduce the undesired effect of high level of IgE associated with the use of one or more PI3K-δ inhibitors, if such effect occurs. This can be particularly useful in treatment of autoimmune and inflammatory disorders (AIID) such as rheumatoid arthritis. Additionally, the administration of PI3K-δ or PI3K-δ/γ inhibitors as provided herein in combination with inhibitors of mTOR can also exhibit synergy through enhanced inhibition of the PI3K pathway.

In a separate but related aspect, provided herein is a combination treatment of a disease associated with PI3K-δ comprising administering to a PI3K-δ inhibitor and an agent that inhibits IgE production or activity. Other exemplary PI3K-δ inhibitors are applicable for this combination and they are described, e.g., U.S. Pat. No. 6,800,620. Such combination treatment is particularly useful for treating autoimmune and inflammatory diseases (AIID) including, but not limited to rheumatoid arthritis.

Agents that inhibit IgE production are known in the art and they include, but are not limited to, one or more of TEI-9874, 2-(4-(6-cyclohexyloxy-2-naphtyloxy)phenylacetamide)benzoic acid, rapamycin, rapamycin analogs (i.e., rapalogs), TORC1 inhibitors, TORC2 inhibitors, and any other compounds that inhibit mTORC1 and mTORC2. Agents that inhibit IgE activity include, for example, anti-IgE antibodies such as for example Omalizumab and TNX-901.

For treatment of autoimmune diseases, a compound as provided herein, or a pharmaceutically acceptable form (e.g., pharmaceutically acceptable salts, hydrates, solvates, isomers, prodrugs, and isotopically labeled derivatives) thereof, or pharmaceutical compositions as provided herein, can be used in combination with commonly prescribed drugs including, but not limited to Enbrel®, Remicade®, Humira®, Avonex®, and Rebif®. For treatment of respiratory diseases, the subject compounds or pharmaceutical compositions can be administered in combination with commonly prescribed drugs including, but not limited to Xolair®, Advair®, Singulair®, and Spiriva®.

The compounds as provided herein, or a pharmaceutically acceptable form (e.g., pharmaceutically acceptable salts, hydrates, solvates, isomers, prodrugs, and isotopically labeled derivatives) thereof, or pharmaceutical compositions as provided herein, can be formulated or administered in conjunction with other agents that act to relieve the symptoms of inflammatory conditions such as encephalomyelitis, asthma, and the other diseases described herein. These agents include non-steroidal anti-inflammatory drugs (NSAIDs), e.g., acetylsalicylic acid; ibuprofen; naproxen; indomethacin; nabumetone; tolmetin; etc. Corticosteroids are used to reduce inflammation and suppress activity of the immune system. An exemplary drug of this type is Prednisone. Chloroquine (Aralen) or hydroxychloroquine (Plaquenil) can also be used in some individuals with lupus. They can be prescribed for skin and joint symptoms of lupus. Azathioprine (Imuran) and cyclophosphamide (Cytoxan) suppress inflammation and tend to suppress the immune system. Other agents, e.g., methotrexate and cyclosporin are used to control the symptoms of lupus. Anticoagulants are employed to prevent blood from clotting rapidly. They range from aspirin at very low dose which prevents platelets from sticking, to heparin/coumadin. Other compounds used in the treatment of lupus include belimumab (Benlysta®).

In another aspect, provided herein is a pharmaceutical composition for inhibiting abnormal cell growth in a subject which comprises an amount of a compound as provided herein, or a pharmaceutically acceptable form (e.g., pharmaceutically acceptable salts, hydrates, solvates, isomers, prodrugs, and isotopically labeled derivatives) thereof, in combination with an amount of an anti-cancer agent (e.g., a chemotherapeutic agent). Many chemotherapeutics are presently known in the art and can be used in combination with the compounds as provided herein.

In some embodiments, the chemotherapeutic is selected from mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens. Non-limiting examples are chemotherapeutic agents, cytotoxic agents, and non-peptide small molecules such as Gleevec® (Imatinib Mesylate), Velcade® (bortezomib), Casodex (bicalutamide), Iressa®, and Adriamycin as well as a host of chemotherapeutic agents. Non-limiting examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; BTK inhibitors such as ibrutinib (PCI-32765) and AVL-292; HDAC inhibitors usch as vorinostat, romidepsin, panobinostat, valproic acid, belinostat, mocetinostat, abrexinostat, entinostat, SB939, resminostat, givinostat, CUDC-101, AR-42, CHR-2845, CHR-3996, 4SC-202, CG200745, ACY-1215 and kevetrin; JAK/STAT inhibitors such as lestaurtinib, tofacitinib, ruxolitinib, pacritinib, CYT387, baricitinib, fostamatinib, GLPG0636, TG101348, INCB16562 and AZD1480; nitrogen mustards such as bedamustine, chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, Casodex™, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pralatrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK.R™; razoxane; sizofiran; spirogermanium; tenuazonic acid; triaziquone; 2,2',2"-trichlorotriethyla-mine; urethan; vindesine; dacarbazine; mannomustine; mitobronitol; mitolactol; pipobroman; gacytosine; arabinoside ("Ara-C"); cyclophosphamide; thiotepa; taxanes, e.g., paclitaxel (TAXOL™, Bristol-Myers Squibb Oncology, Princeton, N.J.) and docetaxel (TAXOTERE™, Rhone-Poulenc Rorer, Antony, France) and ABRAXANE® (paclitaxel protein-bound particles); retinoic acid; esperamicins; capecitabine; and pharmaceutically acceptable forms (e.g., pharmaceutically acceptable salts, hydrates, solvates, isomers, prodrugs, and isotopically labeled derivatives) of any of the above. Also included as suitable chemotherapeutic cell conditioners are anti-hormonal agents that act to regulate or inhibit hormone action on tumors such as anti-estrogens including for example tamoxifen (Nolvadex™), raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; camptothecin-11 (CPT-11); topoisomerase inhibitor RFS 2000; difluoromethylornithine (DMFO). Where desired, the compounds or pharmaceutical composition as provided herein can be used in combination with commonly prescribed anti-cancer drugs such as Herceptin®, Avastin®, Erbitux®, Rituxan®, Taxol®, Arimidex®, Taxotere®, ABVD, AVICINE, Abagovomab, Acridine carboxamide, Adecatumumab, 17-N-Allylamino-17-demethoxygeldanamycin, Alpharadin, Alvocidib, 3-Aminopyridine-2-carboxaldehyde thiosemicarbazone, Amonafide, Anthracenedione, Anti-CD22 immunotoxins, Antineoplastic, Antitumorigenic herbs, Apaziquone, Atiprimod, Azathioprine, Belotecan, Bendamustine, BIBW 2992, Biricodar, Brostallicin, Bryostatin, Buthionine sulfoximine, CBV (chemotherapy), Calyculin, Crizotinib, cell-cycle nonspecific antineoplastic agents, Dichloroacetic acid, Discodermolide, Elsamitrucin, Enocitabine, Epothilone, Eribulin, Everolimus, Exatecan, Exisulind, Ferruginol, Forodesine, Fosfestrol, ICE chemotherapy regimen, IT-101, Imexon, Imiquimod, Indolocarbazole, Irofulven, Laniquidar, Larotaxel, Lenalidomide, Lucanthone, Lurtotecan, Mafosfamide, Mitozolomide, Nafoxidine, Nedaplatin, Olaparib, Ortataxel, PAC-1, Pawpaw, Pixantrone, Proteasome inhibitor, Rebeccamycin, Resiquimod, Rubitecan, SN-38, Salinosporamide A, Sapacitabine, Stanford V, Swainsonine, Talaporfin, Tariquidar, Tegafur-uracil, Temodar, Tesetaxel, Triplatin tetranitrate, Tris (2-chloroethyl)amine, Troxacitabine, Uramustine, Vadimezan, Vinflunine, ZD6126, and Zosuquidar.

In some embodiments, the chemotherapeutic is selected from hedgehog inhibitors including, but not limited to IPI-926 (See U.S. Pat. No. 7,812,164). Other suitable hedgehog inhibitors include, for example, those described and provided in U.S. Pat. No. 7,230,004, U.S. Patent Application Publication No. 2008/0293754, U.S. Patent Application Publication No. 2008/0287420, and U.S. Patent Application Publication No. 2008/0293755, the entire disclosures of which are incorporated by reference herein. Examples of other suitable hedgehog inhibitors include those described in U.S. Patent Application Publication Nos. US 2002/0006931, US 2007/0021493 and US 2007/0060546, and International Application Publication Nos. WO 2001/19800, WO 2001/26644, WO 2001/27135, WO 2001/49279, WO 2001/74344, WO 2003/011219, WO 2003/088970, WO 2004/020599, WO 2005/013800, WO 2005/033288, WO 2005/032343, WO 2005/042700, WO 2006/028958, WO 2006/050351, WO 2006/078283, WO 2007/054623, WO 2007/059157, WO 2007/120827, WO 2007/131201, WO 2008/070357, WO 2008/110611, WO 2008/112913, and WO 2008/131354. Additional examples of hedgehog inhibitors include, but are not limited to, GDC-0449 (also known as RG3616 or vismodegib) described in, e.g., Von Hoff D. et al., *N Engl. J. Med.* 2009; 361(12):1164-72; Robarge K. D. et al., *Bioorg Med Chem. Lett.* 2009; 19(19):5576-81; Yauch, R. L. et al. (2009) *Science* 326: 572-574; Sciencexpress: 1-3 (10.1126/science.1179386); Rudin, C. et al. (2009) *New England J of Medicine* 361-366 (10.1056/nejma0902903); BMS-833923 (also known as XL139) described in, e.g., in Siu L. et al., *J. Clin. Oncol.* 2010; 28:15s (suppl; abstr 2501); and National Institute of Health Clinical Trial Identifier No. NCT006701891; LDE-225 described, e.g., in Pan S. et al., *ACS Med. Chem. Lett.,* 2010; 1(3): 130-134; LEQ-506 described, e.g., in National Institute of Health Clinical Trial Identifier No. NCT01106508; PF-04449913 described, e.g., in National Institute of Health Clinical Trial Identifier No. NCT00953758; Hedgehog pathway antagonists provided in U.S. Patent Application Publication No. 2010/0286114; SMOi2-17 described, e.g., U.S. Patent Application Publication No. 2010/0093625; SANT-1 and SANT-2 described, e.g., in Rominger C. M. et al., *J. Pharmacol. Exp. Ther.* 2009; 329(3):995-1005; 1-piperazinyl-4-arylphthalazines or analogues thereof, described in Lucas B. S. et al., *Bioorg. Med. Chem. Lett.* 2010; 20(12):3618-22.

Other chemotherapeutic agents include, but are not limited to, anti-estrogens (e.g. tamoxifen, raloxifene, and megestrol), LHRH agonists (e.g. goscrelin and leuprolide), anti-androgens (e.g. flutamide and bicalutamide), photodynamic therapies (e.g. vertoporfin (BPD-MA), phthalocyanine, photosensitizer Pc4, and demethoxy-hypocrellin A (2BA-2-DMHA)), nitrogen mustards (e.g. cyclophosphamide, ifosfamide, trofosfamide, chlorambucil, estramustine, and melphalan), nitrosoureas (e.g. carmustine (BCNU) and lomustine (CCNU)), alkylsulphonates (e.g. busulfan and treosulfan), triazenes (e.g. dacarbazine, temozolomide), platinum containing compounds (e.g. cisplatin, carboplatin, oxaliplatin), vinca alkaloids (e.g. vincristine, vinblastine, vindesine, and vinorelbine), taxoids (e.g. paclitaxel or a paclitaxel equivalent such as nanoparticle albumin-bound paclitaxel (Abraxane), docosahexaenoic acid bound-paclitaxel (DHA-paclitaxel, Taxoprexin), polyglutamate bound-paclitaxel (PG-paclitaxel, paclitaxel poliglumex, CT-2103, XYOTAX), the tumor-activated prodrug (TAP) ANG1005 (Angiopep-2 bound to three molecules of paclitaxel), paclitaxel-EC-1 (paclitaxel bound to the erbB2-recognizing peptide EC-1), and glucose-conjugated paclitaxel, e.g., 2'-paclitaxel methyl 2-glucopyranosyl succinate; docetaxel, taxol), epipodophyllins (e.g. etoposide, etoposide phosphate, teniposide, topotecan, 9-aminocamptothecin, camptoirinotecan, irinotecan, crisnatol, mytomycin C), anti-metabolites, DHFR inhibitors (e.g. methotrexate, dichloromethotrexate, trimetrexate, edatrexate), IMP dehydrogenase inhibitors (e.g. mycophenolic acid, tiazofurin, ribavirin, and EICAR), ribonucleotide reductase inhibitors (e.g. hydroxyurea and deferoxamine), uracil analogs (e.g. 5-fluorouracil (5-FU), floxuridine, doxifluridine, ratitrexed, tegafur-uracil, capecitabine), cytosine analogs (e.g. cytarabine (ara C), cytosine arabinoside, and fludarabine), purine analogs (e.g. mercaptopurine and Thioguanine), Vitamin D3 analogs (e.g. EB 1089, CB 1093, and KH 1060), isoprenylation inhibitors (e.g. lovastatin), dopaminergic neurotoxins (e.g. 1-methyl-4-phenylpyridinium ion), cell cycle inhibitors (e.g. staurosporine), actinomycin (e.g. actinomycin D, dactinomycin), bleomycin (e.g. bleomycin A2, bleomycin B2, peplomycin), anthracycline (e.g. daunorubicin, doxorubicin, pegylated liposomal doxorubicin, idarubicin, epirubicin, pirarubicin, zorubicin, mitoxantrone), MDR inhibitors (e.g. verapamil), $Ca^{2+}$ ATPase inhibitors (e.g. thapsigargin), imatinib, thalidomide, lenalidomide, tyrosine kinase inhibitors (e.g., axitinib (AG013736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR®), everolimus (AFINITOR®), alemtuzumab (CAMPATH®), gemtuzumab ozogamicin (MYLOTARG®), temsirolimus (TORISEL®), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (Velcade)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe) and OSI-027 (OSI)), oblimersen, gemcitabine, caminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, caminomycin, aminopterin, and hexamethyl melamine.

Exemplary biotherapeutic agents include, but are not limited to, interferons, cytokines (e.g., tumor necrosis factor, interferon α, interferon γ), vaccines, hematopoietic growth factors, monoclonal serotherapy, immunostimulants and/or immunodulatory agents (e.g., IL-1,2,4,6, or 12), immune cell growth factors (e.g., GM-CSF) and antibodies (e.g. Herceptin (trastuzumab), T-DM1, AVASTIN (bevacizumab), ERBITUX (cetuximab), Vectibix (panitumumab), Rituxan (rituximab), Bexxar (tositumomab)).

In some embodiments, the chemotherapeutic is selected from HSP90 inhibitors. The HSP90 inhibitor can be a geldanamycin derivative, e.g., a benzoquinone or hygroquinone ansamycin HSP90 inhibitor (e.g., IPI-493 and/or IPI-504). Non-limiting examples of HSP90 inhibitors include IPI-493, IPI-504, 17-AAG (also known as tanespimycin or CNF-1010), BIIB-021 (CNF-2024), BIIB-028, AUY-922

(also known as VER-49009), SNX-5422, STA-9090, AT-13387, XL-888, MPC-3100, CU-0305, 17-DMAG, CNF-1010, Macbecin (e.g., Macbecin I, Macbecin II), CCT-018159, CCT-129397, PU-H71, or PF-04928473 (SNX-2112).

In some embodiments, the chemotherapeutic is selected from PI3K inhibitors (e.g., including those PI3K inhibitors provided herein and those PI3K inhibitors not provided herein). In some embodiment, the PI3K inhibitor is an inhibitor of delta and gamma isoforms of PI3K. In some embodiments, the PI3K inhibitor is an inhibitor of alpha isoforms of PI3K. In other embodiments, the PI3K inhibitor is an inhibitor of one or more alpha, beta, delta and gamma isoforms of PI3K. Exemplary PI3K inhibitors that can be used in combination are described in, e.g., WO 09/088,990, WO 09/088,086, WO 2011/008302, WO 2010/036380, WO 2010/006086, WO 09/114,870, WO 05/113556; US 2009/0312310, and US 2011/0046165. Additional PI3K inhibitors that can be used in combination with the pharmaceutical compositions, include but are not limited to, AMG-319, GSK 2126458, GDC-0980, GDC-0941, Sanofi XL147, XL499, XL756, XL147, PF-46915032, BKM 120, CAL-101 (GS-1101), CAL 263, SF1126, PX-886, and a dual PI3K inhibitor (e.g., Novartis BEZ235). In one embodiment, the PI3K inhibitor is an isoquinolinone.

In some embodiments, provided herein is a method for using the a compound as provided herein, or a pharmaceutically acceptable form (e.g., pharmaceutically acceptable salts, hydrates, solvates, isomers, prodrugs, and isotopically labeled derivatives) thereof, or pharmaceutical compositions as provided herein, in combination with radiation therapy in inhibiting abnormal cell growth or treating the hyperproliferative disorder in the subject. Techniques for administering radiation therapy are known in the art, and these techniques can be used in the combination therapy described herein. The administration of the compound as provided herein in this combination therapy can be determined as described herein.

Radiation therapy can be administered through one of several methods, or a combination of methods, including without limitation external-beam therapy, internal radiation therapy, implant radiation, stereotactic radiosurgery, systemic radiation therapy, radiotherapy and permanent or temporary interstitial brachytherapy. The term "brachytherapy," as used herein, refers to radiation therapy delivered by a spatially confined radioactive material inserted into the body at or near a tumor or other proliferative tissue disease site. The term is intended without limitation to include exposure to radioactive isotopes (e.g., At-211, I-131, I-125, Y-90, Re-186, Re-188, Sm-153, Bi-212, P-32, and radioactive isotopes of Lu). Suitable radiation sources for use as a cell conditioner as provided herein include both solids and liquids. By way of non-limiting example, the radiation source can be a radionuclide, such as I-125, I-131, Yb-169, Ir-192 as a solid source, I-125 as a solid source, or other radionuclides that emit photons, beta particles, gamma radiation, or other therapeutic rays. The radioactive material can also be a fluid made from any solution of radionuclide(s), e.g., a solution of I-125 or I-131, or a radioactive fluid can be produced using a slurry of a suitable fluid containing small particles of solid radionuclides, such as Au-198, Y-90. Moreover, the radionuclide(s) can be embodied in a gel or radioactive micro spheres.

Without being limited by any theory, the compounds as provided herein, or a pharmaceutically acceptable form (e.g., pharmaceutically acceptable salts, hydrates, solvates, isomers, prodrugs, and isotopically labeled derivatives) thereof, or pharmaceutical compositions as provided herein, can render abnormal cells more sensitive to treatment with radiation for purposes of killing and/or inhibiting the growth of such cells. Accordingly, provided herein is a method for sensitizing abnormal cells in a subject to treatment with radiation which comprises administering to the subject an amount of a compound as provided herein or pharmaceutically acceptable forms (e.g., pharmaceutically acceptable salts, hydrates, solvates, isomers, prodrugs, and isotopically labeled derivatives) thereof, which amount is effective is sensitizing abnormal cells to treatment with radiation. The amount of the compound used in this method can be determined according to the means for ascertaining effective amounts of such compounds described herein.

The compounds as provided herein, or a pharmaceutically acceptable form (e.g., pharmaceutically acceptable salts, hydrates, solvates, isomers, prodrugs, and isotopically labeled derivatives) thereof, or pharmaceutical compositions as provided herein, can be used in combination with an amount of one or more substances selected from anti-angiogenesis agents, signal transduction inhibitors, and antiproliferative agents, glycolysis inhibitors, or autophagy inhibitors.

Anti-angiogenesis agents, such as MMP-2 (matrix-metalloproteinase 2) inhibitors, MMP-9 (matrix-metalloprotienase 9) inhibitors, and COX-11 (cyclooxygenase 11) inhibitors, can be used in conjunction with a compound as provided herein and pharmaceutical compositions described herein. Anti-angiogenesis agents include, for example, rapamycin, temsirolimus (CCI-779), everolimus (RAD001), sorafenib, sunitinib, and bevacizumab. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931,788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain Patent Application No. 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are incorporated herein in their entireties by reference. In some embodiments, MMP-2 and MMP-9 inhibitors are those that have little or no activity inhibiting MMP-1. Other embodiments include those that selectively inhibit MMP-2 and/or AMP-9 relative to the other matrix-metalloproteinases (i.e., MAP-1, MMP-3, MMP-4, MMP-5, MMP-6, MMP-7, MMP-8, MMP-10, MMP-11, MMP-12, and MMP-13). Some non-limiting examples of MMP inhibitors are AG-3340, RO 32-3555, and RS 13-0830.

Autophagy inhibitors include, but are not limited to, chloroquine, 3-methyladenine, hydroxychloroquine (Plaquenil™), bafilomycin A1, 5-amino-4-imidazole carboxamide riboside (AICAR), okadaic acid, autophagy-suppressive algal toxins which inhibit protein phosphatases of type 2A or type 1, analogues of cAMP, and drugs which elevate cAMP levels such as adenosine, LY204002, N6-mercaptopurine riboside, and vinblastine. In addition, antisense or siRNA that inhibits expression of proteins including, but not limited to ATG5 (which are implicated in autophagy), can also be used.

In some embodiments, provided herein is a method of and/or a pharmaceutical composition for treating a cardiovascular disease in a subject which comprises an amount of a compound as provided herein, or a pharmaceutically acceptable form (e.g., pharmaceutically acceptable salts, hydrates, solvates, isomers, prodrugs, and isotopically labeled derivatives) thereof, and an amount of one or more therapeutic agents use for the treatment of cardiovascular diseases.

Exemplary agents for use in cardiovascular disease applications are anti-thrombotic agents, e.g., prostacyclin and salicylates, thrombolytic agents, e.g., streptokinase, urokinase, tissue plasminogen activator (TPA) and anisoylated plasminogen-streptokinase activator complex (APSAC), anti-platelets agents, e.g., acetylsalicylic acid (ASA) and clopidrogel, vasodilating agents, e.g., nitrates, calcium channel blocking drugs, antiproliferative agents, e.g., colchicine and alkylating agents, intercalating agents, growth modulating factors such as interleukins, transformation growth factor-beta and congeners of platelet derived growth factor, monoclonal antibodies directed against growth factors, anti-inflammatory agents, both steroidal and non-steroidal, and other agents that can modulate vessel tone, function, arteriosclerosis, and the healing response to vessel or organ injury post intervention. Antibiotics can also be included in combinations or coatings. Moreover, a coating can be used to effect therapeutic delivery focally within the vessel wall. By incorporation of the active agent in a swellable polymer, the active agent will be released upon swelling of the polymer.

The compounds as provided herein, or a pharmaceutically acceptable form (e.g., pharmaceutically acceptable salts, hydrates, solvates, isomers, prodrugs, and isotopically labeled derivatives) thereof, or pharmaceutical compositions as provided herein, can be formulated or administered in conjunction with liquid or solid tissue barriers also known as lubricants. Examples of tissue barriers include, but are not limited to, polysaccharides, polyglycans, seprafilm, interceed and hyaluronic acid.

Medicaments which can be administered in conjunction with the compounds as provided herein, or a pharmaceutically acceptable form (e.g., pharmaceutically acceptable salts, hydrates, solvates, isomers, prodrugs, and isotopically labeled derivatives) thereof, include any suitable drugs usefully delivered by inhalation for example, analgesics, e.g., codeine, dihydromorphine, ergotamine, fentanyl or morphine; anginal preparations, e.g., diltiazem; antiallergics, e.g. cromoglycate, ketotifen or nedocromil; anti-infectives, e.g., cephalosporins, penicillins, streptomycin, sulphonamides, tetracyclines or pentamidine; antihistamines, e.g., methapyrilene; anti-inflammatories, e.g., beclomethasone, flunisolide, budesonide, tipredane, triamcinolone acetonide or fluticasone; antitussives, e.g., noscapine; bronchodilators, e.g., ephedrine, adrenaline, fenoterol, formoterol, isoprenaline, metaproterenol, phenylephrine, phenylpropanolamine, pirbuterol, reproterol, rimiterol, salbutamol, salmeterol, terbutalin, isoetharine, tulobuterol, orciprenaline or (−)-4-amino-3,5-dichloro-α-[[[6-[2-(2-pyridinyl)ethoxy]hexyl]-amino]methyl]benzenemethanol; diuretics, e.g., amiloride; anticholinergics e.g., ipratropium, atropine or oxitropium; hormones, e.g., cortisone, hydrocortisone or prednisolone; xanthines e.g., aminophylline, choline theophyllinate, lysine theophyllinate or theophylline; and therapeutic proteins and peptides, e.g., insulin or glucagon. It will be clear to a person skilled in the art that, where appropriate, the medicaments can be used in the form of salts (e.g., as alkali metal or amine salts or as acid addition salts) or as esters (e.g., lower alkyl esters) to optimize the activity and/or stability of the medicament.

Other exemplary therapeutic agents useful for a combination therapy include, but are not limited to, agents as described above, radiation therapy, hormone antagonists, hormones and their releasing factors, thyroid and antithyroid drugs, estrogens and progestins, androgens, adrenocorticotropic hormone; adrenocortical steroids and their synthetic analogs; inhibitors of the synthesis and actions of adrenocortical hormones, insulin, oral hypoglycemic agents, and the pharmacology of the endocrine pancreas, agents affecting calcification and bone turnover: calcium, phosphate, parathyroid hormone, vitamin D, calcitonin, vitamins such as water-soluble vitamins, vitamin B complex, ascorbic acid, fat-soluble vitamins, vitamins A, K, and E, growth factors, cytokines, chemokines, muscarinic receptor agonists and antagonists; anticholinesterase agents; agents acting at the neuromuscular junction and/or autonomic ganglia; catecholamines, sympathomimetic drugs, and adrenergic receptor agonists or antagonists; and 5-hydroxytryptamine (5-HT, serotonin) receptor agonists and antagonists.

Therapeutic agents can also include agents for pain and inflammation such as histamine and histamine antagonists, bradykinin and bradykinin antagonists, 5-hydroxytryptamine (serotonin), lipid substances that are generated by biotransformation of the products of the selective hydrolysis of membrane phospholipids, eicosanoids, prostaglandins, thromboxanes, leukotrienes, aspirin, nonsteroidal anti-inflammatory agents, analgesic-antipyretic agents, agents that inhibit the synthesis of prostaglandins and thromboxanes, selective inhibitors of the inducible cyclooxygenase, selective inhibitors of the inducible cyclooxygenase-2, autacoids, paracrine hormones, somatostatin, gastrin, cytokines that mediate interactions involved in humoral and cellular immune responses, lipid-derived autacoids, eicosanoids, β-adrenergic agonists, ipratropium, glucocorticoids, methylxanthines, sodium channel blockers, opioid receptor agonists, calcium channel blockers, membrane stabilizers and leukotriene inhibitors.

Additional therapeutic agents contemplated herein include diuretics, vasopressin, agents affecting the renal conservation of water, rennin, angiotensin, agents useful in the treatment of myocardial ischemia, anti-hypertensive agents, angiotensin converting enzyme inhibitors, β-adrenergic receptor antagonists, agents for the treatment of hypercholesterolemia, and agents for the treatment of dyslipidemia.

Other therapeutic agents contemplated herein include drugs used for control of gastric acidity, agents for the treatment of peptic ulcers, agents for the treatment of gastroesophageal reflux disease, prokinetic agents, antiemetics, agents used in irritable bowel syndrome, agents used for diarrhea, agents used for constipation, agents used for inflammatory bowel disease, agents used for biliary disease, agents used for pancreatic disease. Therapeutic agents include, but are not limited to, those used to treat protozoan infections, drugs used to treat Malaria, Amebiasis, Giardiasis, Trichomoniasis, Trypanosomiasis, and/or Leishmaniasis, and/or drugs used in the chemotherapy of helminthiasis. Other therapeutic agents include, but are not limited to, antimicrobial agents, sulfonamides, trimethoprim-sulfamethoxazole quinolones, and agents for urinary tract infections, penicillins, cephalosporins, and other, β-Lactam antibiotics, an agent containing an aminoglycoside, protein synthesis inhibitors, drugs used in the chemotherapy of tuberculosis, *mycobacterium avium* complex disease, and leprosy, antifungal agents, antiviral agents including nonretroviral agents and antiretroviral agents.

Examples of therapeutic antibodies that can be combined with a subject compound include but are not limited to anti-receptor tyrosine kinase antibodies (cetuximab, panitumumab, trastuzumab), anti CD20 antibodies (rituximab, tositumomab), and other antibodies such as alemtuzumab, bevacizumab, and gemtuzumab.

Moreover, therapeutic agents used for immunomodulation, such as immunomodulators, immunosuppressive agents, tolerogens, and immunostimulants are contemplated by the methods herein. In addition, therapeutic agents acting on the blood and the blood-forming organs, hematopoietic agents, growth factors, minerals, and vitamins, anticoagulant, thrombolytic, and antiplatelet drugs.

For treating renal carcinoma, one can combine a a compound as provided herein, or a pharmaceutically acceptable form (e.g., pharmaceutically acceptable salts, hydrates, solvates, isomers, prodrugs, and isotopically labeled derivatives) thereof, or pharmaceutical compositions as provided herein, with sorafenib and/or avastin. For treating an endometrial disorder, one can combine a compound as provided herein with doxorubincin, taxotere (taxol), and/or cisplatin (carboplatin). For treating ovarian cancer, one can combine a compound as provided herein with cisplatin (carboplatin), taxotere, doxorubincin, topotecan, and/or tamoxifen. For treating breast cancer, one can combine a compound as provided herein with taxotere (taxol), gemcitabine (capecitabine), tamoxifen, letrozole, tarceva, lapatinib, PD0325901, avastin, herceptin, OSI-906, and/or OSI-930. For treating lung cancer, one can combine a compound as provided herein with taxotere (taxol), gemcitabine, cisplatin, pemetrexed, Tarceva, PD0325901, and/or avastin.

In some embodiments, the disorder to be treated, prevented and/or managed is hematological cancer, e.g., lymphoma (e.g., T-cell lymphoma; NHL), myeloma (e.g., multiple myeloma), and leukemia (e.g., CLL), and a compound provided herein is used in combination with: HDAC inhibitors such as vorinostat and romidepsin; mTOR inhibitors such as everolmus; anti-folates such as pralatrexate; nitrogen mustard such as bendamustine; gemcitabine, optionally in further combination with oxaliplatin; rituximab.cyclophosphamide combination; PI3K inhibitors such as GS-1101, XL 499, GDC-0941, and AMG-319; or BTK inhibitors such as ibrutinib and AVL-292.

In certain embodiments, wherein inflammation (e.g., arthritis, asthma) is treated, prevented and/or managed, a compound provided herein can be combined with, for example: PI3K inhibitors such as GS-1101, XL 499, GDC-0941, and AMG-319; BTK inhibitors such as ibrutinib and AVL-292; JAK inhibitors such as tofacitinib, fostamatinib, and GLPG0636.

In certain embodiments wherein asthma is treated, prevented and/or managed, a compound provided herein can be combined with, for example: beta 2-agonists such as, but not limited to, albuterol (Proventil®, or Ventolin®), salmeterol (Serevent®), formoterol (Foradil®), metaproterenol (Alupent®), pirbuterol (MaxAir®), and terbutaline sulfate; corticosteroids such as, but not limited to, budesonide (e.g., Pulmicort®), flunisolide (e.g., AeroBid Oral Aerosol Inhaler® or Nasalide Nasal Aerosol®), fluticasone (e.g., Flonase® or Flovent®) and triamcinolone (e.g., Azmacort®); mast cell stabilizers such as cromolyn sodium (e.g., Intal® or Nasalcrom®) and nedocromil (e.g., Tilade®); xanthine derivatives such as, but not limited to, theophylline (e.g., Aminophyllin®, Theo-24® or Theolair®); leukotriene receptor antagonists such as, but are not limited to, zafirlukast (Accolate®), montelukast (Singulair®), and zileuton (Zyflo®); and adrenergic agonists such as, but are not limited to, epinephrine (Adrenalin®, Bronitin®, EpiPen® or Primatene Mist®).

In certain embodiments wherein arthritis is treated, prevented and/or managed, a compound provided herein can be combined with, for example: TNF antagonist (e.g., a TNF antibody or fragment, a soluble TNF receptor or fragment, fusion proteins thereof, or a small molecule TNF antagonist); an antirheumatic (e.g., methotrexate, auranofin, aurothioglucose, azathioprine, etanercept, gold sodium thiomalate, hydroxychloroquine sulfate, leflunomide, sulfasalzine); a muscle relaxant; a narcotic; a non-steroid anti-inflammatory drug (NSAID); an analgesic; an anesthetic; a sedative; a local anesthetic; a neuromuscular blocker; an antimicrobial (e.g., an aminoglycoside, an antifungal, an antiparasitic, an antiviral, a carbapenem, cephalosporin, a fluoroquinolone, a macrolide, a penicillin, a sulfonamide, a tetracycline, another antimicrobial); an antipsoriatic; a corticosteroid; an anabolic steroid; a cytokine or a cytokine antagonist.

In certain embodiments wherein psoriasis is treated, prevented and/or managed, a compound provided herein can be combined with, for example: budesonide, epidermal growth factor, corticosteroids, cyclosporine, sulfasalazine, aminosalicylates, 6-mercaptopurine, azathioprine, metronidazole, lipoxygenase inhibitors, mesalamine, olsalazine, balsalazide, antioxidants, thromboxane inhibitors, IL-1 receptor antagonists, anti-IL-1β monoclonal antibodies, anti-IL-6 monoclonal antibodies, growth factors, elastase inhibitors, pyridinyl-imidazole compounds, antibodies or agonists of TNF, LT, IL-1, IL-2, IL-6, IL-7, IL-8, IL-15, IL-16, IL-18, EMAP-II, GM-CSF, FGF, and PDGF, antibodies of CD2, CD3, CD4, CD8, CD25, CD28, CD30, CD40, CD45, CD69, CD90 or their ligands, methotrexate, cyclosporine, FK506, rapamycin, mycophenolate mofetil, leflunomide, NSAIDs, ibuprofen, corticosteroids, prednisolone, phosphodiesterase inhibitors, adenosine agonists, antithrombotic agents, complement inhibitors, adrenergic agents, IRAK, NIK, IKK, p38, MAP kinase inhibitors, IL-1β converting enzyme inhibitors, TNFα converting enzyme inhibitors, T-cell signaling inhibitors, metalloproteinase inhibitors, sulfasalazine, azathioprine, 6-mercaptopurines, angiotensin converting enzyme inhibitors, soluble cytokine receptors, soluble p55 TNF receptor, soluble p75 TNF receptor, sIL-1RI, sIL-1RI, sIL-6R, anti-inflammatory cytokines, IL-4, IL-10, IL-11, IL-13 and TGFβ.

In certain embodiments wherein fibrosis or fibrotic condition of the bone marrow is treated, prevented and/or managed, a compound provided herein can be combined with, for example, a Jak2 inhibitor (including, but not limited to, INCB018424, XL019, TG101348, or TG101209), an immunomodulator, e.g., an IMID® (including, but not limited to thalidomide, lenalidomide, or panolinomide), hydroxyurea, an androgen, erythropoietic stimulating agents, prednisone, danazol, HDAC inhibitors, or other agents or therapeutic modalities (e.g., stem cell transplants, or radiation).

In certain embodiments wherein fibrosis or fibrotic condition of the heart is treated, prevented and/or managed, a compound provided herein can be combined with, for example, eplerenone, furosemide, pycnogenol, spironolactone, TcNC100692, torasemide (e.g., prolonged release form of torasemide), or combinations thereof.

In certain embodiments wherein fibrosis or fibrotic condition of the kidney is treated, prevented and/or managed, a compound provided herein can be combined with, for example, cyclosporine, cyclosporine A, daclizumab, everolimus, gadofoveset trisodium (ABLAVAR®), imatinib mesylate (GLEEVEC®), matinib mesylate, methotrexate, mycophenolate mofetil, prednisone, sirolimus, spironolactone, STX-100, tamoxifen, TheraCLEC™, or combinations thereof.

In certain embodiments wherein fibrosis or fibrotic condition of the skin is treated, prevented and/or managed, a compound provided herein can be combined with, for example, Bosentan (Tracleer), p144, pentoxifylline; pirfenidone; pravastatin, STI571, Vitamin E, or combinations thereof.

In certain embodiments wherein fibrosis or fibrotic condition of the gastrointestinal system is treated, prevented and/or managed, a compound provided herein can be combined with, for example, ALTU-135, bucelipase alfa (INN), DCI1020, EUR-1008 (ZENPEP™), ibuprofen, Lym-X-Sorb powder, pancrease MT, pancrelipase (e.g., pancrelipase delayed release), pentade canoic acid (PA), repaglinide, TheraCLECT™, triheptadecanoin (THA), ULTRASE MT20, ursodiol, or combinations thereof.

In certain embodiments wherein fibrosis or fibrotic condition of the lung is treated, prevented and/or managed, a compound provided herein can be combined with, for example, 18-FDG, AB0024, ACT-064992 (macitentan), aerosol interferon-gamma, aerosolized human plasma-derived alpha-1 antitrypsin, alpha1-proteinase inhibitor, ambrisentan, amikacin, amiloride, amitriptyline, anti-pseudomonas IgY gargle, ARIKACE™ AUREXIS® (tefibazumab), AZAPRED, azathioprine, azithromycin, azithromycin, AZLI, aztreonam lysine, BIBF1120, Bio-25 probiotic, bosentan, Bramitob®, calfactant aerosol, captopril, CC-930, ceftazidime, ceftazidime, cholecalciferol (Vitamin D3), ciprofloxacin (CIPRO®, BAYQ3939), CNTO 888, colistin CF, combined Plasma Exchange (PEX), rituximab, and corticosteroids, cyclophosphamide, dapsone, dasatinib, denufosol tetrasodium (INS37217), dornase alfa (PULMOZYME®), EPI-hNE4, erythromycin, etanercept, FG-3019, fluticasone, FTI, GC1008, GS-9411, hypertonic saline, ibuprofen, iloprost inhalation, imatinib mesylate (GLEEVEC®), inhaled sodium bicarbonate, inhaled sodium pyruvate, interferon gamma-1b, interferon-alpha lozenges, isotonic saline, IW001, KB001, losartan, lucinactant, mannitol, meropenem, meropenem infusion, miglustat, minocycline, Moli1901, MP-376 (levofloxacin solution for inhalation), mucoid exopolysaccharide *P. aeruginosa* immune globulin IV, mycophenolate mofetil, n-acetylcysteine, N-acetylcysteine (NAC), NaCl 6%, nitric oxide for inhalation, obramycin, octreotide, oligoG CF-5/20, Omalizumab, pioglitazone, piperacillin-tazobactam, pirfenidone, pomalidomide (CC-4047), prednisone, prevastatin, PRM-151, QAX576, rhDNAse, SB 656933, SB-656933-AAA, sildenafil, tamoxifen, technetium [Tc-99 m]sulfur colloid and Indium [In-111] DTPA, tetrathiomolybdate, thalidomide, ticarcillin-clavulanate, tiotropium bromide, tiotropium RESPIMAT® inhaler, tobramycin (GERNEBCIN®), treprostinil, uridine, valganciclovir (VALCYTE®), vardenafil, vitamin D3, xylitol, zileuton, or combinations thereof.

In certain embodiments wherein fibrosis or fibrotic condition of the liver is treated, prevented and/or managed, a compound provided herein can be combined with, for example, adefovir dipivoxil, candesartan, colchicine, combined ATG, mycophenolate mofetil, and tacrolimus, combined cyclosporine microemulsion and tacrolimus, elastometry, everolimus, FG-3019, Fuzheng Huayu, GI262570, glycyrrhizin (monoammonium glycyrrhizinate, glycine, L-cysteine monohydrochloride), interferon gamma-1b, irbesartan, losartan, oltipraz, ORAL IMPACT®, peginterferon alfa-2a, combined peginterferon alfa-2a and ribavirin, peginterferon alfa-2b (SCH 54031), combined peginterferon alpha-2b and ribavirin, praziquantel, prazosin, raltegravir, ribavirin (REBETOL®, SCH 18908), ritonavir-boosted protease inhibitor, pentoxyphilline, tacrolimus, tauroursodeoxycholic acid, tocopherol, ursodiol, warfarin, or combinations thereof.

In certain embodiments wherein cystic fibrosis is treated, prevented and/or managed, a compound provided herein can be combined with, for example, 552-02, 5-methyltetrahydrofolate and vitamin B12, Ad5-CB-CFTR, Adeno-associated virus-CFTR vector, albuterol, alendronate, alpha tocopherol plus ascorbic acid, amiloride HCl, aquADEKTM, ataluren (PTC124), AZD1236, AZD9668, azithromycin, bevacizumab, biaxin (clarithromycin), BIIL 283 BS (amelubent), buprofen, calcium carbonate, ceftazidime, cholecalciferol, choline supplementation, CPX, cystic fibrosis transmembrane conductance regulator, DHA-rich supplement, digitoxin, cocosahexaenoic acid (DHA), doxycycline, ECGC, ecombinant human IGF-1, educed glutathione sodium salt, ergocalciferol (vitamin D2), fluorometholone, gadobutrol (GADOVIST®, BAY86-4875), gentamicin, ghrelin, glargine, glutamine, growth hormone, GS-9411, H5.001CBCFTR, human recombinant growth hormone, hydroxychloroquine, hyperbaric oxygen, hypertonic saline, IH636 grape seed proanthocyanidin extract, insulin, interferon gamma-1b, IoGen (molecular iodine), iosartan potassium, isotonic saline, itraconazole, IV gallium nitrate (GANITE®) infusion, ketorolac acetate, lansoprazole, L-arginine, linezolid, lubiprostone, meropenem, miglustat, MP-376 (levofloxacin solution for inhalation), normal saline IV, Nutropin AQ, omega-3 triglycerides, pGM169/GL67A, pGT-1 gene lipid complex, pioglitazone, PTC124, QAU145, salmeterol, SB656933, SB656933, simvastatin, sitagliptin, sodium 4-phenylbutyrate, standardized turmeric root extract, tgAAVCF, TNF blocker, TOBI, tobramycin, tocotrienol, unconjugated Isoflavones 100, vitamin: choline bitartrate (2-hydroxyethyl) trimethylammonium salt 1:1, VX-770, VX-809, Zinc acetate, or combinations thereof.

In some embodiments, a compound provided herein is administered in combination with an agent that inhibits IgE production or activity. In some embodiments, the PI3K inhibitor (e.g., PI3Kδ inhibitor) is administered in combination with an inhibitor of mTOR. Agents that inhibit IgE production are known in the art and they include but are not limited to one or more of TEI-9874, 2-(4-(6-cyclohexyloxy-2-naphtyloxy)phenylacetamide)benzoic acid, rapamycin, rapamycin analogs (i.e. rapalogs), TORC1 inhibitors, TORC2 inhibitors, and any other compounds that inhibit mTORC1 and mTORC2. Agents that inhibit IgE activity include, for example, anti-IgE antibodies such as for example Omalizumab and TNX-901.

In certain embodiments wherein scleroderma is treated, prevented and/or managed, a compound provided herein can be combined with, for example: an immunosuppressant (e.g., methotrexate, azathioprine (Imuran®), cyclosporine, mycophenolate mofetil (Cellcept®), and cyclophosphamide (Cytoxan®)); T-cell-directed therapy (e.g., halofuginone, basiliximab, alemtuzumab, abatacept, rapamycin); B-cell directed therapy (e.g., rituximab); autologous hematopoietic stem cell transplantation; a chemokine ligand receptor antagonist (e.g., an agent that targets the CXCL12/CSCR4 axis (e.g., AMD3100)); a DNA methylation inhibitor (e.g., 5-azacytidine); a histone dactylase inhibitor (e.g., trichostatin A); a statin (e.g., atorvastatin, simvastatin, pravastatin); an endothelin receptor antagonist (e.g., Bosentan®); a phosphodiesterase type V inhibitor (e.g., Sildenafil®); a prostacyclin analog (e.g., trepostinil); an inhibitor of cytokine synthesis and/or signaling (e.g., Imatinib mesylate, Rosiglitazone, rapamycin, antitransforming growth factor β1 (anti-TGFβ1) antibody, mycophenolate mofetil, an anti-IL-6 antibody (e.g., tocilizumab)); corticosteroids; nonsteroidal anti-inflammatory drugs; light therapy; and blood pressure medications (e.g., ACE inhibitors).

In certain embodiments wherein inflammatory myopathies are treated, prevented and/or managed, a compound provided herein can be combined with, for example: topical creams or ointments (e.g., topical corticosteroids, tacrolimus, pimecrolimus); cyclosporine (e.g., topical cyclosporine); an anti-interferon therapy, e.g., AGS-009, Rontalizumab (rhuMAb IFNalpha), Vitamin D3, Sifalimumab (MEDI-545), AMG 811, IFNα Kinoid, or CEP33457. In some embodiments, the other therapy is an IFN-α therapy, e.g., AGS-009, Rontalizumab, Vitamin D3, Sifalimumab (MEDI-545) or IFNα Kinoid; corticosteroids such as prednisone (e.g., oral prednisone); immunosuppressive therapies such as methotrexate (Trexall®, Methotrexate®, Rheumatrex®), azathioprine (Azasan®, Imuran®), intravenous immunoglobulin, tacrolimus (Prograf®), pimecrolimus, cyclophosphamide (Cytoxan®), and cyclosporine (Gengraf®, Neoral®, Sandimmune®); anti-malarial agents such as hydroxychloroquine (Plaquenil®) and chloroquine (Aralen®); total body irradiation; rituximab (Rituxan®); TNF inhibitors (e.g., etanercept (Enbrel®), infliximab (Remicade®)); AGS-009; Rontalizumab (rhuMAb IFNαalpha); Vitamin D3; Sifalimumab (MEDI-545); AMG 811; IFNα Kinoid; CEP33457; agents that inhibit IgE production such as TEI-9874, 2-(4-(6-cyclohexyloxy-2-naphtyloxy)phenylacetamide)benzoic acid, rapamycin, rapamycin analogs (i.e. rapalogs), TORC1 inhibitors, TORC2 inhibitors, and any other compounds that inhibit mTORC1 and mTORC2; agents that inhibit IgE activity such as anti-IgE antibodies (e.g., Omalizumab and TNX-90); and additional therapies such as physical therapy, exercise, rest, speech therapy, sun avoidance, heat therapy, and surgery.

In certain embodiments wherein myositis (e.g., dermatomysitis) is treated, prevented and/or managed, a compound provided herein can be combined with, for example: corticosteroids; corticosteroid sparing agents such as, but not limited to, azathioprine and methotrexate; intravenous immunoglobulin; immunosuppressive agents such as, but not limited to, tacrolimus, cyclophosphamide and cyclosporine; rituximab; TNFα inhibitors such as, but not limited to, etanercept and infliximab; growth hormone; growth hormone secretagogues such as, but not limited to, MK-0677, L-162752, L-163022, NN703 ipamorelin, hexarelin, GPA-748 (KP102, GHRP-2), and LY444711 (Eli Lilly); other growth hormone release stimulators such as, but not limited to, Geref, GHRH (1-44), Somatorelin (GRF 1-44), ThGRF genotropin, L-DOPA, glucagon, and vasopressin; and insulin-like growth factor.

In certain embodiments wherein Sjögren's syndrome is treated, prevented and/or managed, a compound provided herein can be combined with, for example: pilocarpine; cevimeline; nonsteroidal anti-inflammatory drugs; arthritis medications; antifungal agents; cyclosporine; hydroxychloroquine; prednisone; azathioprine; and cyclophamide.

Further therapeutic agents that can be combined with a subject compound can be found in Goodman and Gilman's "*The Pharmacological Basis of Therapeutics*" Tenth Edition edited by Hardman, Limbird and Gilman or the Physician's Desk Reference, both of which are incorporated herein by reference in their entirety.

The compounds described herein can be used in combination with the agents provided herein or other suitable agents, depending on the condition being treated. Hence, in some embodiments, the compounds as provided herein will be co-administered with other agents as described above. When used in combination therapy, the compounds described herein can be administered with the second agent simultaneously or separately. This administration in combination can include simultaneous administration of the two agents in the same dosage form, simultaneous administration in separate dosage forms, and separate administration. That is, a compound described herein and any of the agents described above can be formulated together in the same dosage form and administered simultaneously. Alternatively, a compound as provided herein and any of the agents described above can be simultaneously administered, wherein both the agents are present in separate formulations. In another alternative, a compound as provided herein can be administered just followed by and any of the agents described above, or vice versa. In the separate administration protocol, a compound as provided herein and any of the agents described above can be administered a few minutes apart, or a few hours apart, or a few days apart.

Administration of the compounds as provided herein can be effected by any method that enables delivery of the compounds to the site of action. An effective amount of a compound as provided herein can be administered in either single or multiple doses by any of the accepted modes of administration of agents having similar utilities, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

When a compound as provided herein is administered in a pharmaceutical composition that comprises one or more agents, and the agent has a shorter half-life than the compound as provided herein, unit dose forms of the agent and the compound as provided herein can be adjusted accordingly.

The examples and preparations provided below further illustrate and exemplify the compounds as provided herein and methods of preparing such compounds. It is to be understood that the scope of the present disclosure is not limited in any way by the scope of the following examples and preparations. In the following examples molecules with a single chiral center, unless otherwise noted, exist as a racemic mixture. Those molecules with two or more chiral centers, unless otherwise noted, exist as a racemic mixture of diastereomers. Single enantiomers/diastereomers can be obtained by methods known to those skilled in the art.

EXAMPLES

Chemical Examples

The chemical entities described herein can be synthesized according to one or more illustrative schemes herein and/or techniques well known in the art.

Unless specified to the contrary, the reactions described herein take place at atmospheric pressure, generally within a temperature range from −10° C. to 200° C. Further, except as otherwise specified, reaction times and conditions are intended to be approximate, e.g., taking place at about atmospheric pressure within a temperature range of about −10° C. to about 110° C. over a period that is, for example, about 1 to about 24 hours; reactions left to run overnight in some embodiments can average a period of about 16 hours.

The terms "solvent," "organic solvent," or "inert solvent" each mean a solvent inert under the conditions of the reaction being described in conjunction therewith including, but not limited to, benzene, toluene, acetonitrile, tetrahydrofuran ("THF"), dimethylformamide ("DMF"), chloroform, methylene chloride (or dichloromethane), diethyl ether, methanol, N-methylpyrrolidone ("NMP"), pyridine and the like. Unless specified to the contrary, the solvents used in the reactions described herein are inert organic solvents. Unless specified to the contrary, for each gram of the limiting reagent, one cc (or mL) of solvent constitutes a volume equivalent.

Isolation and purification of the chemical entities and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures are given by reference to the examples hereinbelow. However, other equivalent separation or isolation procedures can also be used.

When desired, the (R)- and (S)-isomers of the non-limiting exemplary compounds, if present, can be resolved by methods known to those skilled in the art, for example by formation of diastereoisomeric salts or complexes which can be separated, for example, by crystallization; via formation of diastereoisomeric derivatives which can be separated, for example, by crystallization, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. Alternatively, a specific enantiomer can be synthesized by asymmetric synthesis using optically active reagents, substrates, catalysts or solvents, or by converting one enantiomer to the other by asymmetric transformation.

The compounds described herein can be optionally contacted with a pharmaceutically acceptable acid to form the corresponding acid addition salts. Also, the compounds described herein can be optionally contacted with a pharmaceutically acceptable base to form the corresponding basic addition salts.

In some embodiments, disclosed compounds can generally be synthesized by an appropriate combination of generally well known synthetic methods. Techniques useful in synthesizing these chemical entities are both readily apparent and accessible to those of skill in the relevant art, based on the instant disclosure. Many of the optionally substituted starting compounds and other reactants are commercially available, e.g., from Aldrich Chemical Company (Milwaukee, Wis.) or can be readily prepared by those skilled in the art using commonly employed synthetic methodology.

The discussion below is offered to illustrate certain of the diverse methods available for use in making the disclosed compounds and is not intended to limit the scope of reactions or reaction sequences that can be used in preparing the compounds provided herein.

GENERAL SYNTHETIC METHODS

The compounds described, it will be more readily understood by reference to the following examples, which are included merely for purposes of illustration of certain aspects and embodiments described herein, and are not intended to limit these aspects and embodiments.

(i) General Method for the Synthesis of Amine Cores:

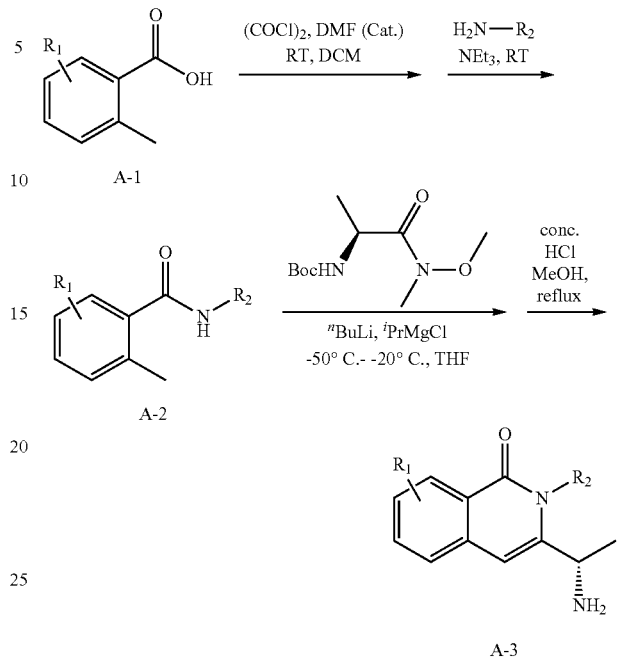

Method A

General conditions for the preparation of (S)-3-(1-aminoethyl)-isoquinolin-1(2H)-ones:

To a stirred mixture of a given o-methylbenzoic acid (A-1) (1.5 mol, 1 eq) and DMF (2 mL) in DCM (1275 mL) at RT, oxalyl chloride (1.65 mol, 1.1 eq) is added over 5 min and the resulting mixture is stirred at RT for 2 h. The mixture is then concentrated in vacuo. The residue is dissolved in DCM (150 mL) and the resulting solution (solution A) is used directly in the next step.

To a stirred mixture of a given amine $R_2$—$NH_2$ (1.58 mol, 1.05 eq) and triethylamine (3.15 mol, 2.1 eq) in DCM (1350 mL), the above solution A (150 mL) is added dropwise while the reaction temperature is maintained between 25° C. to 40° C. by an ice-water bath. The resulting mixture is stirred at RT for 2 h and then water (1000 mL) is added. The organic layer is separated, washed with water (2×1000 mL), dried over $Na_2SO_4$ and filtered. The filtrate is concentrated in vacuo. The product is suspended in heptane (1000 mL) and stirred at RT for 30 min. The precipitate is collected by filtration, rinsed with heptane (500 mL) and further dried in vacuo to afford the amide (A-2).

To a stirred mixture of amide (A-2) (173 mmol, 1 eq) in anhydrous THF (250 mL) at −30° C. under argon, a solution of n-butyllithium in hexanes (432 mol, 2.5 eq) is added dropwise over 30 min while keeping inner temperature between −30° C. and −10° C. The resulting mixture B is then stirred at −30° C. for 30 min. To a stirred mixture of (S)-tert-butyl 1-(methoxy(methyl)amino)-1-oxopropan-2-ylcarbamate (260 mmol, 1.5 eq) in anhydrous THF (250 mL) at −30° C. under argon, a solution of isopropylmagnesium chloride in THF (286 mmol, 1.65 eq) is added dropwise over 30 min while keeping inner temperature between −30° C. and −10° C. The resulting mixture is stirred at −30° C. for 30 min. This mixture is then slowly added to above reaction mixture B while keeping the inner temperature between −30° C. and −10° C. The resulting mixture is stirred at −15° C. for 1 h. The reaction mixture is quenched with water (50 mL) and then acidified with conc. HCl at −10° C.-0° C. to adjust the pH to 1-3. The mixture is allowed to warm to RT and concentrated in vacuo. The residue is dissolved in MeOH (480 mL), and then conc. HCl (240 mL) is added at RT. The resulting mixture is stirred at reflux for 1 h. The reaction mixture is cooled to RT and concentrated in vacuo to reduce the volume to about 450 mL. The residue is extracted with a 2:1 mixture of heptane and ethyl acetate (2×500 mL). The aqueous layer is basified with concentrated ammonium hydroxide to adjust the pH to 9-10 while keeping the inner temperature between −10° C. and 0° C. The mixture is then extracted with DCM (3×300 mL), washed with brine, dried over $MgSO_4$ and filtered. The filtrate is concentrated in vacuo and the residue is dissolved in MeOH (1200 mL) at RT. To this solution, D-(−)-tartaric acid (21 g, 140 mmol, 0.8 eq) is added in one portion at RT. After stirring at RT for 30 min, a solid precipitate forms and the mixture is slurried at RT for 10 h. The solid is collected by filtration and rinsed with MeOH (50 mL×3). The collected solid is suspended in water (500 mL) and then neutralized with concentrated ammonium hydroxide solution at RT to adjust the pH to 9-10. The mixture is extracted with DCM (200 mL×3). The combined organic layers are washed with brine, dried over $MgSO_4$ and filtered. The filtrate is concentrated in vacuo to afford (S)-3-(1-aminoethyl)-isoquinolin-1 (2H)-ones (A-3).

Method A'

General conditions for the preparation of (S)-3-(1-aminoethyl)-isoquinolin-1(2H)-ones:

In one embodiment, an amino compound (A-3') may be prepared following Method A', wherein the intermediate (A-1') may be prepared following procedures known in the art or the procedure as described in Method A. In one embodiment, intermediate (A-2') may be prepared from intermediate (A-1') by contacting intermediate (A-1') with a base (e.g., "BuLi) followed by (S)-benzyl (1-(methoxy(methyl)amino)-1-oxopropan-2-yl)carbamate. In one embodiment, the amino compound (A-3') may be prepared from intermediate (A-2') by cyclizing intermediate (A-2') in the presence of an acid. In one embodiment, the acid is $H_2SO_4$. In another embodiment, the acid is HCl. In one embodiment, the amount of the acid is about 1 to 20 equivalents relative to the amount of the intermediate (A-2'). In one embodiment, the acid is about 5 equivalents of $H_2SO_4$. In one embodiment, the cyclization occurs at about room temperature to 65° C. In one embodiment, the cyclization occurs at about 65° C. for about 1 to 5 hours.

In one embodiment, the cyclization provides the amino compound (A-3') with a ratio of (S)-enantiomer to (R)-enantiomer of about 1:1 to 20:1. In one embodiment, the cyclization provides the amino compound (A-3') with a ratio of (S)-enantiomer to (R)-enantiomer of about 1:1 to 10:1. In one embodiment, the cyclization provides the amino compound (A-3') with a ratio of (S)-enantiomer to (R)-enantiomer of about 1:1 to 4:1. It is to be understood that the methods provided herein are also suitable for the preparation of (R)-enantiomer of the amino compound (A-3') when (R)-benzyl (1-(methoxy(methyl)amino)-1-oxopropan-2-yl)carbamate is used in place of (S)-benzyl (1-(methoxy(methyl)amino)-1-oxopropan-2-yl)carbamate.

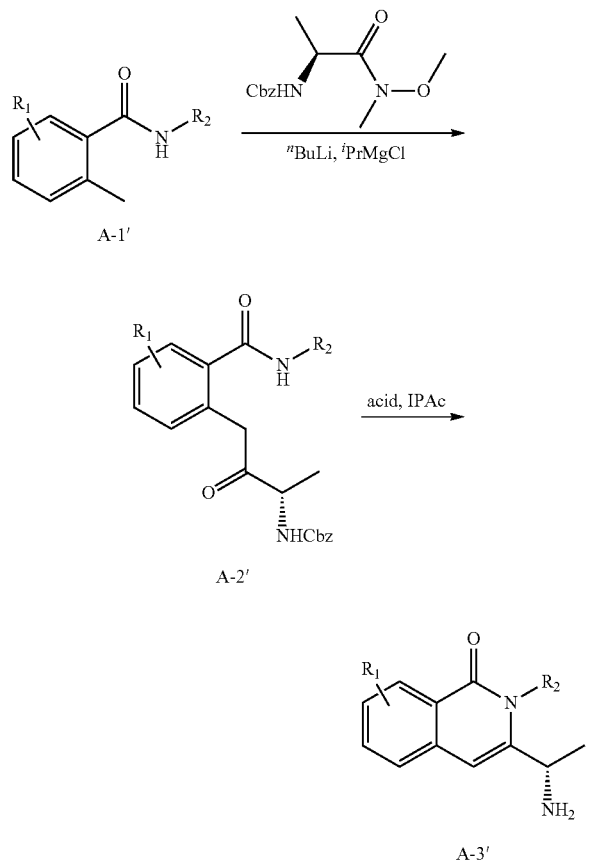

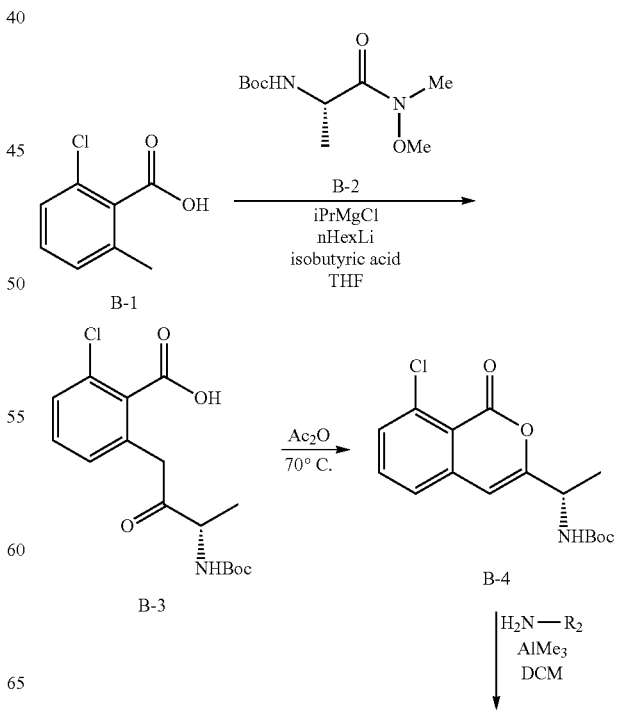

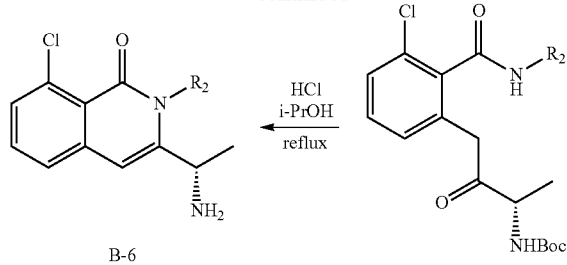

Method B

General conditions for the preparation of (S)-3-(1-aminoethyl)-isoquinolin-1(2H)-ones:

To 2-chloro-6-methylbenzoic acid (B-1) (8.00 g, 46.9 mmol) in a dry round bottom flask under $N_2$ is added 50 mL of dry THF. The resulting mixture is cooled to −25° C. Then, n-hexyllithium (88 mL, 202 mmol) (2.3 M in hexanes) is added, and the reaction is stirred at −20° C. for about 20 min.

To compound (B-2) (14.16 g, 61.0 mmol) in a second dry round bottom flask under $N_2$ is added 70 mL of dry THF. The mixture is cooled to about −10° C. To the cold mixture is slowly added isopropyl magnesium chloride (63.3 ml, 2 M, 127 mmol). The resulting mixture is then stirred at −10° C. for about 20 min. Then, this mixture is slowly cannulated drop wise into the flask containing the (B-1) reaction while maintaining the temperature at −20° C. After addition is complete, the reaction is slowly warmed to RT and stirred at RT for about 1.6 hours. The reaction mixture is then cooled to −10° C. and quickly cannulated to another flask containing 15 mL of ethyl acetate and 10 mL of isobutyric acid at −10° C. under $N_2$. After stirring for about 5 minutes, 10 mL of water is rapidly added. The cooling bath is removed, and the reaction mixture is stirred for 10 minutes at RT. The mixture is transferred to a separation funnel, and water (200 mL) is added. The water layer is extracted with EtOAc (3×400 mL). The aqueous layer is then acidified with HCl (2M) to pH 3, and is extracted with EtOAc (3×500 mL), dried over sodium sulfate and concentrated in vacuo. The resulting material is purified by silica gel column chromatography using 0-10% MeOH in DCM to afford benzoic acid (B-3).

A mixture of benzoic acid (B-3) (5.00 g, 14.63 mmol) in acetic anhydride (10 mL) is stirred in a round bottom flask at 70° C. for about 2.5 hours. Then, the remaining acetic anhydride is removed in vacuo. The residue is purified using silica gel column chromatography using EtOAc/hexanes to afford lactone (B-4).

To a mixture of $R_2$—$NH_2$ (197 mg, 1.54 mmol) in 2 mL of DCM is added $AlMe_3$ (0.772 ml, 1.54 mmol). The mixture is stirred for about 15 min. Then, a solution of lactone (B-4) (100 mg, 0.309 mmol) in 2 mL of DCM is added, and the reaction is stirred at RT for about 3 hours. The reaction mixture is then quenched with addition of 10 mL of Rochelle's salt and stirring for about 2 hours. The mixture is diluted with DCM, washed with brine, dried with $Na_2SO_4$ and concentrated in vacuo to afford the amide (B-5) which is carried directly to the next reaction.

To the amide (B-5) in 5 mL of isopropanol is added 3 mL of concentrated HCl. The reaction is heated at 65° C. for about 3 hours. After cooling to RT, the mixture is concentrated in vacuo. The solid is suspended in 15 mL of DCM, followed by the addition of 10 mL of sat. $NaHCO_3$. This mixture is then stirred at RT for about 30 min, then 50 mL of DCM is added. The layers are separated and the organic layer is dried with $Na_2SO_4$ and concentrated in vacuo to afford isoquinolinone (B-6).

The following isoquinolinone compounds (B-6) given in Table 3 were made in analogous fashion to Method B using the following $R_2$—$NH_2$ reagents.

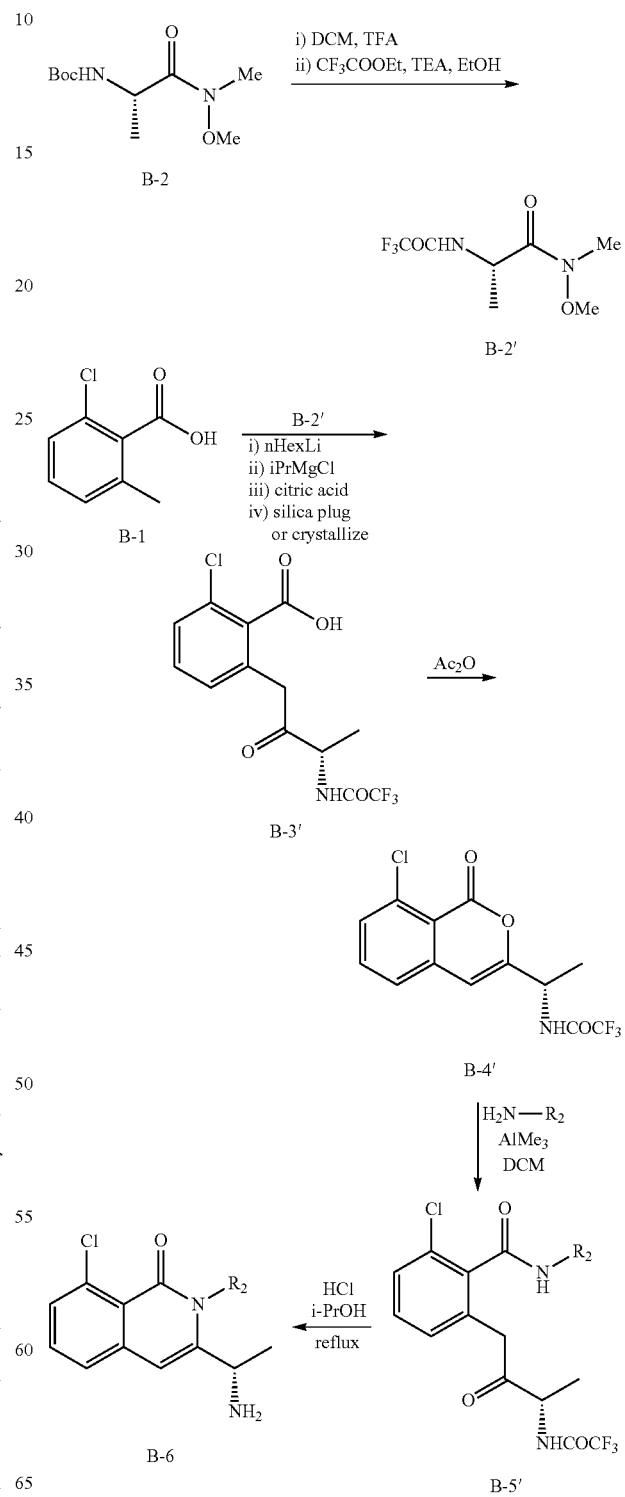

Method B'

General conditions for the preparation of (S)-3-(1-aminoethyl)-isoquinolin-1(2H)-ones:

In some embodiments, isoquinolinone (B-6) may be prepared by following the procedures exemplified in Method B'. In one embodiment, intermediate (B-2') is prepared by contacting intermediate (B-2) with TFA followed by CF$_3$COOEt. In one embodiment, benzoic acid (B-3') is prepared by contacting o-methylbenzoic acid (B-1) with a base (e.g., nHexLi), followed by intermediate (B-2'), and followed by purification by silica plug or crystallization. In one embodiment, lactone (B-4') is prepared by contacting benzoic acid (B-3') with Ac$_2$O under conditions suitable for cyclization. In one embodiment, amide (B-5') is prepared by contacting lactone (B-4') with corresponding amine or aniline in the presence of AlMe$_3$. In one embodiment, isoquinolinone (B-6) is prepared by contacting amide (B-5') with an acid under conditions suitable for cyclization and deprotection. In one embodiment, the acid is HCl.

In one embodiment, the cyclization provides the amino compound (B-6) with a ratio of (S)-enantiomer to (R)-enantiomer of about 1:1 to 20:1. In one embodiment, the cyclization provides the amino compound (B-6) with a ratio of (S)-enantiomer to (R)-enantiomer of about 1:1 to 10:1. In one embodiment, the cyclization provides the amino compound (B-6) with a ratio of (S)-enantiomer to (R)-enantiomer of about 1:1 to 4:1. It is to be understood that the methods provided herein are also suitable for the preparation of (R)-enantiomer of the amino compound (B-6) when (R)-enantiomer of intermediate (B-2) is used in place of (S)-enantiomer of (B-2).

TABLE 3

Compounds (B-6)

| R$_2$—NH$_2$ | Compound (B-6) | ESI-MS m/z: [M + H]$^+$ |
|---|---|---|
| H$_2$N-phenyl | 8-Cl-2-phenyl isoquinolinone with NH$_2$-ethyl | 299.10 |
| H$_2$N-(4-Cl-phenyl) | 8-Cl-2-(4-Cl-phenyl) isoquinolinone with NH$_2$-ethyl | 335 |
| H$_2$N-(4-CN-phenyl) | 8-Cl-2-(4-CN-phenyl) isoquinolinone with NH$_2$-ethyl | 324.12 |
| H$_2$N-(4-Me-phenyl) | 8-Cl-2-(4-Me-phenyl) isoquinolinone with NH$_2$-ethyl | 313.10 |
| H$_2$N-(4-OMe-phenyl) | 8-Cl-2-(4-OMe-phenyl) isoquinolinone with NH$_2$-ethyl | 329.09 |

TABLE 3-continued

Compounds (B-6)

| R₂—NH₂ | Compound (B-6) | ESI-MS m/z: [M + H]⁺ |
|---|---|---|
| 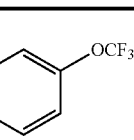 | 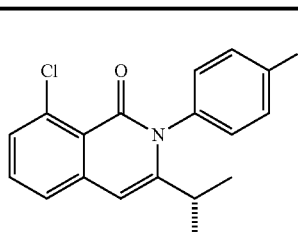 | 383.13 |
|  | 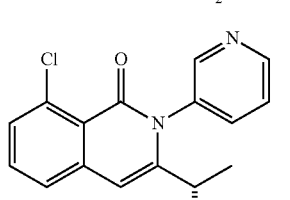 | 300.09 |
|  | 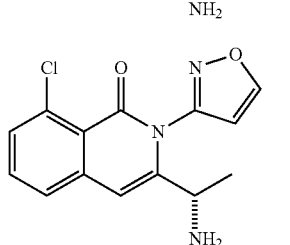 | 290.06 |

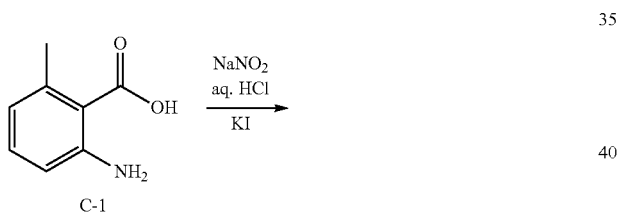

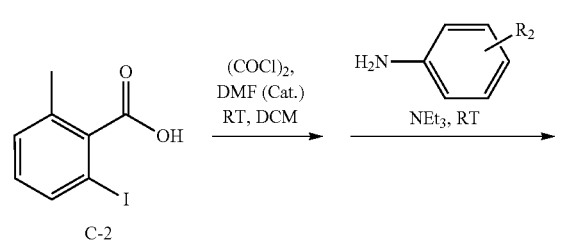

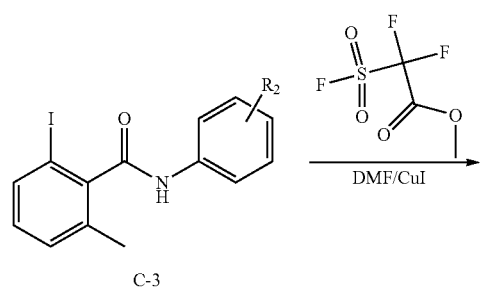

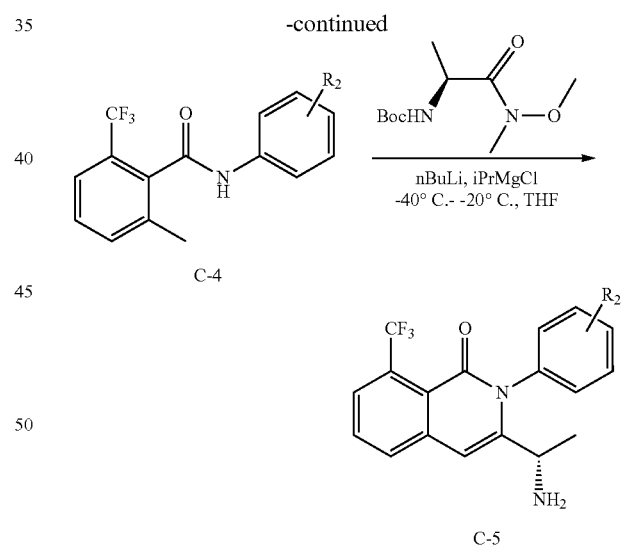

Method C

To a suspension of 2-amino-6-methylbenzoic acid (C-1) (20.0 g, 132.0 mmol, 1.0 eq) in H₂O (55 mL) at 0-5° C., conc. HCl (36.5%, 64 mL, 749 mmol, 5.7 eq) is added slowly. After stirring for 15 min, the mixture is added dropwise to a solution of sodium nitrite (12.02 g, 174.0 mmol, 1.32 eq) in H₂O (36 mL) at 0-5° C., and the resulting mixture is stirred for 1 h. The resulting solution is then added to a solution of KI (60.5 g, 364.5 mmol, 2.76 eq) in H2O (150 mL) at 0-5° C. The reaction mixture is allowed to warm to RT and stirred at RT overnight. The mixture is extracted with ethyl acetate (3×100 mL). The combined organic layers are washed with water (2×100 mL), dried over anhydrous Na$_2$SO$_4$ and filtered. The filtrate is concentrated in vacuo and the residue is purified by flash column chromatography on silica gel (0-20% ethyl acetate-petro ether) to afford the product, 2-iodo-6-methylbenzoic acid (C-2).

To a stirred mixture of 2-iodo-6-methylbenzoic acid (C-2) (305.3 mmol, 1.0 eq) and DMF (0.3 mL) in DCM (350 mL) at RT, oxalyl chloride (466.4 mmol, 1.5 eq) is added dropwise. The resulting mixture is stirred at RT for 3 h and then concentrated in vacuo. The residue is dissolved in DCM (50 mL) and the resulting solution (solution A) is used directly in the next step. To a stirred mixture of R$^3$-substituted aniline (335.7 mmol, 1.1 eq) and triethylamine (915.0 mmol, 3.0 eq) in DCM (350 mL), solution A (150 mL) is added dropwise while the reaction temperature is controlled below 30° C. by an ice-water bath. The reaction mixture is stirred at RT for 1 h and then quenched with water (200 mL). The organic layer is separated, washed with water (2×200 mL), dried over anhydrous Na$_2$SO$_4$ and filtered. The filtrate is concentrated in vacuo. The product is rinsed with isopropyl ether and dried in vacuo to afford the product amide (C-3).

A mixture of amide (C-3) (18.0 mmol, 1.0 eq), methyl 2,2-difluoro-2-(fluorosulfonyl)acetate (72.9 mmol, 4.0 eq) and CuI (3.63 mmol, 0.2 eq) in DMF (130 mL) is stirred at 70° C. under an argon atmosphere overnight. The mixture is allowed to cool to RT and then concentrated in vacuo to remove the solvent. The resulting residue is partitioned between ethyl acetate (60 mL) and water (60 mL), and the aqueous layer is extracted with ethyl acetate (2×60 mL). The combined organic layers are washed with water (2×60 mL), dried over anhydrous Na$_2$SO$_4$ and filtered. The filtrate is concentrated in vacuo and the residue is purified by flash column chromatography on silica gel to afford the product, trifluoromethyl amide (C-4).

To a stirred mixture of amide (C-4) (10.1 mmol, 1.0 eq) in anhydrous THF (25 mL) at −40° C. under an argon atmosphere, a solution of n-butyllithium in THF (2.5M, 25.3 mmol, 2.5 eq) is added dropwise (over 15 min) and the inner temperature is controlled between −30° C. and −20° C. during the addition. The resulting mixture is stirred at −30° C. for an additional 1 h. To a stirred mixture of (S)-tert-butyl 1-(methoxy(methyl)amino)-1-oxopropan-2-ylcarbamate (11.1 mmol, 1.1 eq) in anhydrous THF (20 mL) at −30° C. under an argon atmosphere, a solution of isopropylmagnesium chloride in THF (12.6 mmol, 1.25 eq) is added dropwise (over 15 min) and the inner temperature is controlled below −20° C. during the addition. The resulting mixture is stirred at −15° C. for 1 h. This solution is then slowly added to the above reaction mixture at −30° C. (over 10 min), and the resulting mixture is stirred at −30° C. for an additional 30 min. The reaction mixture is quenched with water (50 mL) and then acidified with conc. HCl at −5° C. to adjust the pH to 5. The mixture is allowed to warm to RT and concentrated in vacuo. The residue is dissolved in MeOH (10 mL), and then conc. HCl (10 mL) is added quickly at RT. The resulting mixture is stirred at reflux for 2 h, cooled to RT and then concentrated in vacuo. The residue is suspended in water (15 mL), basified with concentrated ammonium hydroxide to adjust the pH to 9-10 while keeping the inner temperature below 5° C. and then extracted with DCM (3×15 mL). The combined organic layers are washed with brine, dried over MgSO$_4$ and filtered. The filtrate is concentrated in vacuo and the residue is dissolved in MeOH (70 mL).

To this solution, D-(−)-tartaric acid (8.1 mmol, 0.8 eq) is added in one portion at RT. After stirring at RT for 30 min, a solid precipitates and the mixture is slurried at RT for 10 h. The precipitate is collected by filtration and rinsed with MeOH (3×4.0 mL). The collected solid is suspended in water (30 mL) and then neutralized with concentrated ammonium hydroxide solution at RT to adjust the pH to 9-10. The mixture is extracted with DCM (3×15 mL). The combined organic layers are washed with brine, dried over anhydrous MgSO$_4$ and filtered. The filtrate is concentrated in vacuo to afford the product, (S)-3-(1-aminoethyl)-8-(trifluoromethyl)isoquinolin-1(2H)-one (C-5).

(ii) General Method for Synthesis of (S)-2-(1-aminoethyl)-quinazolin-4($^3$H)-one amine core

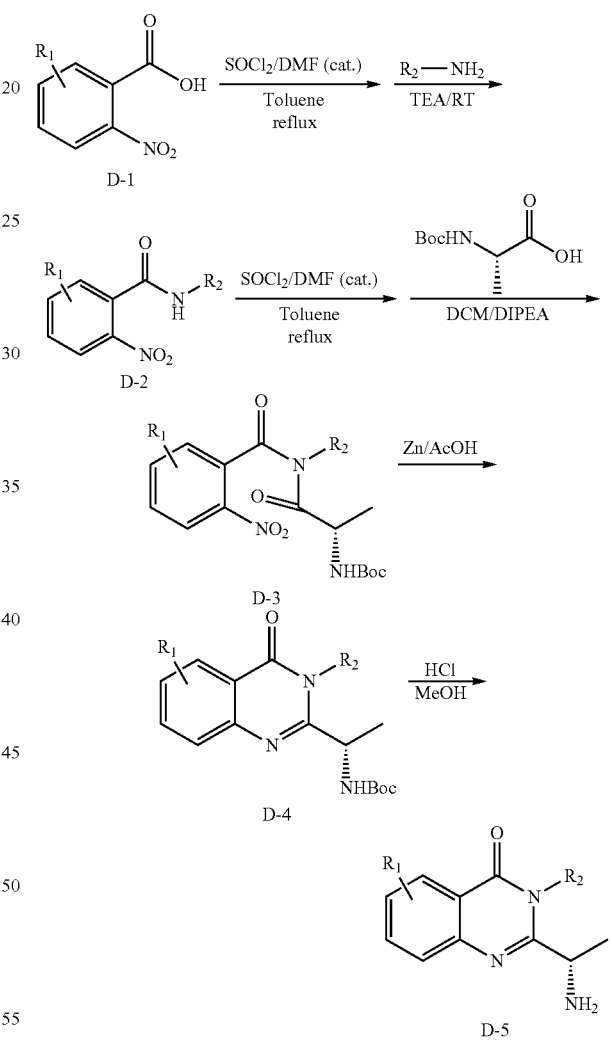

Method D

General conditions for the preparation of (S)-2-(1-aminoethyl)-quinazolin-4(3H)-ones:

To a stirred mixture of nitrobenzoic acid (D-1) (1.0 mol, 1.0 eq) and DMF (2.0 mL) in toluene (800 mL), thionyl chloride (1.0 mol, 4.0 eq) is added dropwise (over 15 min) and the resulting mixture is stirred at reflux for 1.5 h. The mixture is allowed to cool to RT and then concentrated in vacuo. The residue is dissolved in DCM (100 mL) to form solution A, which is used directly in the next step.

To a stirred mixture of a given amine R$_2$—NH$_2$ (1.1 mol, 1.1 eq) and triethylamine (2.0 mol, 2.0 eq) in DCM (700 mL), solution A is added dropwise while the reaction temperature is maintained below 10° C. The resulting mixture is allowed to warm to RT and stirred at RT overnight. The reaction mixture is diluted with ice-water (1.0 L) and stirred for 15 min. The solid is collected by filtration, rinsed with isopropyl ether (3×100 mL) and petroleum ether (3×100 mL), and then dried in vacuo to afford amide (D-2).

To a mixture of amide (D-2) (20.0 mmol, 1.0 eq) and DMF (catalytic amount) in toluene (60 mL) at RT, thionyl chloride (164 mmol, 8.2 eq) is added dropwise (over 5 min) The resulting mixture is stirred at reflux for 2 h. The mixture is allowed to cool to RT and concentrated in vacuo. The residue is dissolved in DCM (10 mL) to form solution B, which is used directly in the next step.

To a mixture of N-(tert-butoxycarbonyl)-L-alanine (16.0 mmol, 0.8 eq) and N,N-diisopropylethylamine (31.0 mol, 1.5 eq) in DCM (20 mL), above solution B is added dropwise while the reaction temperature is maintained at 10° C. The resulting mixture is stirred for an additional 1 h at this temperature and then stirred at RT overnight. The reaction mixture is quenched with ice-water (100 mL). The organic layer is separated and the aqueous layer is extracted with DCM (2×80 mL). The combined organic layers are washed with brine, dried over Na$_2$SO$_4$ and filtered. The filtrate is concentrated in vacuo and the residue is slurried in isopropyl ether (100 mL) for 15 min. The precipitate is collected by filtration and then dried in vacuo to afford product (D-3).

To a suspension of zinc dust (110 mmol, 10.0 eq) in glacial acetic acid (40 mL) at 15° C., a mixture of (D-3) (11.0 mmol, 1.0 eq) in glacial acetic acid (40 mL) is added and the resulting mixture is stirred at RT for 4 h. The mixture is poured into ice-water (200 mL) and neutralized with saturated aqueous NaHCO$_3$ solution to adjust the pH value to 8. The resulting mixture is extracted with DCM (3×150 mL). The combined organic layers are washed with brine, dried over Na$_2$SO$_4$ and filtered. The filtrate is concentrated in vacuo and the residue is purified by flash chromatography on silica gel eluting with 7% ethyl acetate/petroleum ether to afford product (D-4).

A mixture of (D-4) (0.5 mmol, 1.0 eq) in HCl methanol solution (2 N, 20 mL) is stirred at RT for 2 h. The mixture is concentrated in vacuo. The residue is diluted with water (30 mL) and then neutralized with saturated aqueous NaHCO$_3$ to adjust the pH value to 8 while the temperature is maintained below 5° C. The resulting mixture is extracted with DCM (3×30 mL). The combined organic layers are washed with brine, dried over Na$_2$SO$_4$ and filtered. The filtrate is concentrated in vacuo and the residue is slurried in petroleum ether (10 mL). The solid is collected by filtration and dried in vacuo to afford product (D-5).

(iii) General Method for the Synthesis of Cl-Wd:

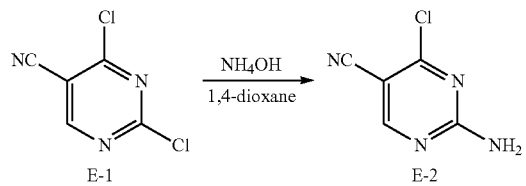

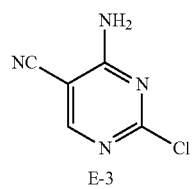

Method E

General conditions for the preparation of 2-amino-4-chloropyrimidine-5-carbonitrile:

To a solution of 2,4-dichloropyrimidine-5-carbonitrile (E-1) (2.0 g, 11.5 mmol) in 1,4-dioxane (20 mL) at 0° C., ammonium hydroxide (28-30%, 4.4 mL, 34.5 mmol) is added dropwise, and the resulting mixture is stirred while warming from 0° C. to RT for 2 h. Then, the mixture is partitioned between ethyl acetate (200 mL) and water (50 mL). The organic layer is washed with brine, dried over Na$_2$SO$_4$ and filtered. The filtrate is mixed with silica gel and then concentrated in vacuo. The residue is purified by silica gel chromatography eluting with 0-100% ethyl acetate/hexanes to afford the product (E-2) (917 mg) and a mixture of (E-2) and (E-3). Additional (E-3) can be obtained from this mixture by a second column chromatographic purification.

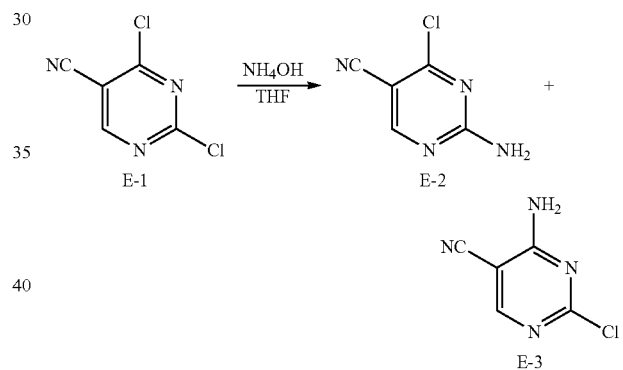

Method E'

In one embodiment, 2-amino-4-chloropyrimidine-5-carbonitrile (E-2) may be prepared following procedures exemplified in Method E'. In one embodiment, compound (E-2) may be prepared by contacting 2,4-dichloropyrimidine-5-carbonitrile (E-1) with ammonium hydroxide in a solvent of THF. In one embodiment, the reaction temperature is about −50° C. In one embodiment, the reaction provides a mixture of compounds (E-2) and (E-3) with a ratio of (E-2) to (E-3) of about 4:1. In one embodiment, compound (E-2) is further purified by crystallization from THF.

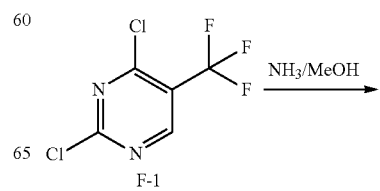

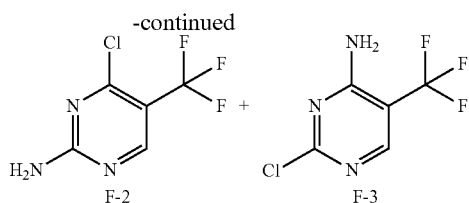

reaction can occur under other conditions known in the art that are suitable for $S_NAr$ displacement reaction. In one embodiment, the reaction solvent is NMP.

(v) Methods for Synthesis of Substituted Quinazolin-4(3H)-One Cores

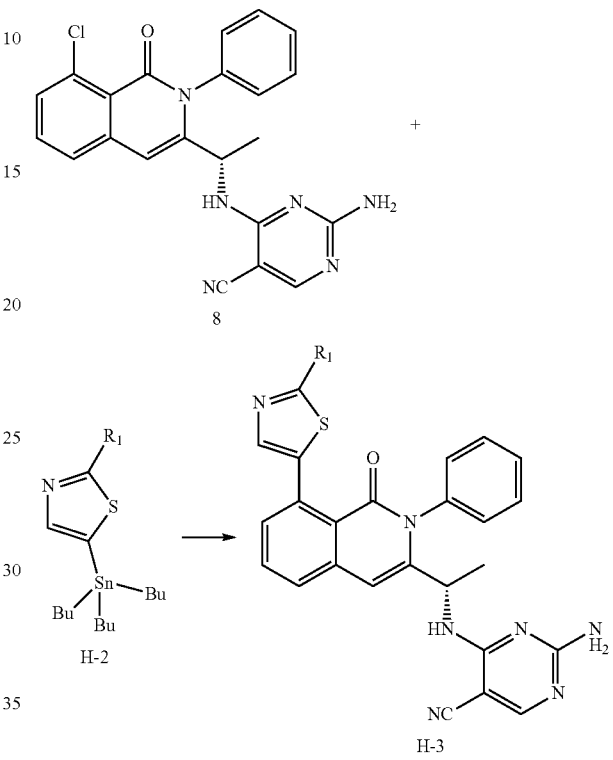

Method F

General conditions for the preparation of 4-chloro-5-(trifluoromethyl)pyrimidin-2-amine:

To stirred neat 2,4-dichloro-5-(trifluoromethyl)pyrimidine (F-1) (5.0 g, 23.04 mmol) under argon, ammonia in methanol (7N solution, 15 mL) is added dropwise and the resulting mixture is stirred at RT for 2 h. The reaction mixture is quenched with water and then extracted with ethyl acetate (200 mL×2). The combined organic layers are washed with brine, dried over $Na_2SO_4$ and filtered. The filtrate is concentrated in vacuo and the residue is purified by flash chromatography on silica gel eluting with 0-20% ethyl acetate/hexanes to afford the product, 4-chloro-5-(trifluoromethyl)pyrimidin-2-amine (F-2) (1.03 g, 22.6% yield). The other regio-isomer, 2-chloro-5-(trifluoromethyl)pyrimidin-4-amine (F-3), can also be isolated.

(iv) General Conditions for Attachment of $W_d$ Substituents:

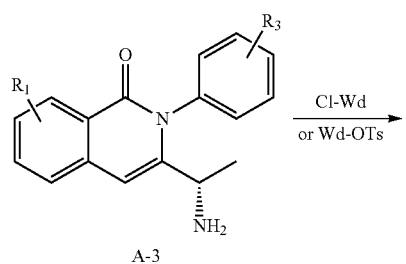

Method G (S)-3-(1-Aminoethyl)-isoquinolin-1(2H)-one (A-3) (115 mmol, 1.0 eq), Cl-Wd or Wd-OTs (173 mmol, 1.5 eq) and triethylamine (344 mmol, 3.0 eq) are dissolved in n-BuOH (350 mL) and the mixture is stirred at reflux for 16 h. The reaction mixture is cooled to RT and concentrated in vacuo. The residue is suspended in a mixture of $H_2O$ (200 mL) and ethyl acetate (100 mL) and stirred at RT for 30 min. The solid is then collected by filtration, rinsed with ethyl acetate (25 mL) and dried in vacuo to afford the product (G-1). The

Method H

A mixture of compound 8 (0.12 mmol, 1.0 equiv.), 2-(R1)-5-(tributylstannyl)thiazole (H-2) (0.24 mmol, 2.0 equiv.), and Pd(0) catalyst (0.024 mmol, 0.2 equiv.) in 1 ml degassed DMF is heated for 3 h. before partitioning between EtOAc and water. The organic layer is collected, the aqueous layer is extracted with EtOAc, and the combined EtOAc layers are washed with brine. The solvent is removed and the residue purified on silica gel to provide (H-3).

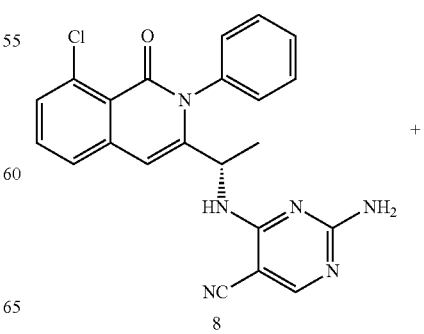

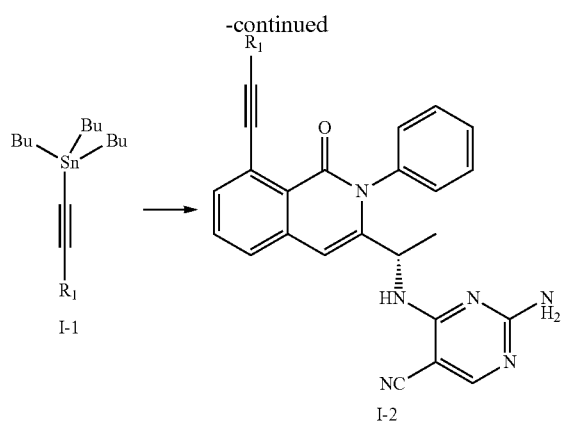

Method I

A mixture of compound 8 (0.4 mmol, 1.0 equiv.), (1-R1) Ethynyl tributylstannane (I-1) (0.8 mmol, 2.0 equiv.), and Pd(0) catalyst (0.08 mmol, 0.2 equiv.) in 3 ml degassed DMF is heated for 5 h. before partitioning between EtOAc and water. The organic layer is collected, the aqueous layer is extracted with EtOAc, and the combined EtOAc layers are washed with brine. The solvent is removed and the residue is purified on silica gel to provide (I-2).

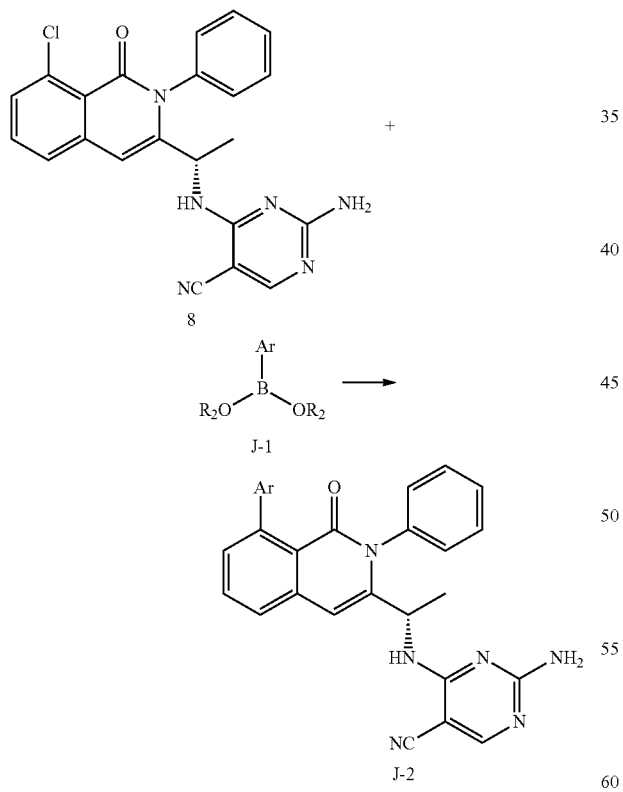

Method J

A mixture of compound 8 (0.17 mmol, 1.0 equiv.), boronic acid or boronate (J-1) (0.34 mmol, 2.0 equiv.), base (0.85 mol, 5 equiv.) and Pd(0) catalyst (0.034 mmol, 0.2 equiv.) in 1.5 ml degassed 4:1 dioxane-water is heated for 1 h. before partitioning between EtOAc and water. The organic layer is collected, the aqueous layer is extracted with EtOAc, and the combined EtOAc layers are washed with brine. The solvent is removed and the residue is purified on silica gel to provide (J-2).

A compound of Formula (I) (e.g., H-3, 1-2, and J-2) may contain one or more chiral center. Conventional techniques for the preparation/isolation of individual enantiomers include synthesis from a suitable optically pure precursor, asymmetric synthesis from achiral starting materials, or resolution of an enantiomeric mixture, for example, by chiral chromatography, recrystallization, resolution, diastereomeric salt formation, or derivatization into diastereomeric adducts followed by separation. In one embodiment, the enantiopurity of a compound of Formula (I) may be improved by contacting the compound of Formula (I) with a suitable solvent or mixture thereof, followed by filtration. In one embodiment, the solvent is a mixture of water and dichloromethane.

In another embodiment, the solvent is a mixture of dichloromethane and methanol.

(vi) Methods for Synthesis of N-Methylpyridinone Boronic Esters

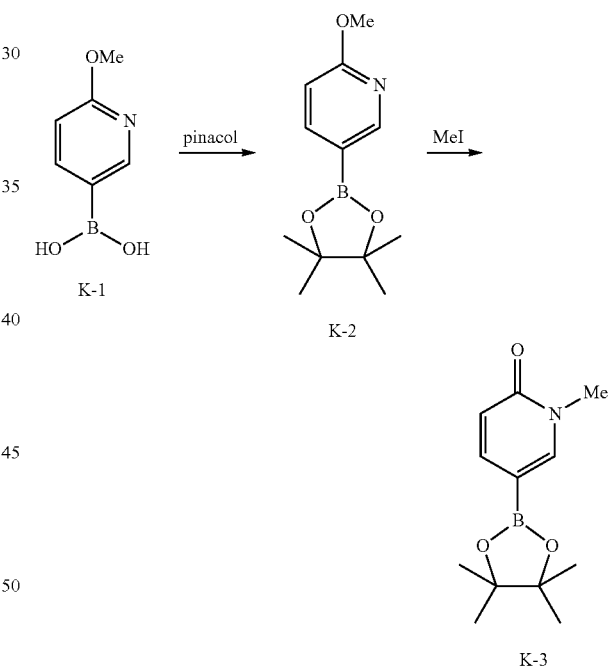

Method K

In one embodiment, the N-methylpyridinone boronic ester (K-3) may be prepared following procedures exemplified in Method K. In one embodiment, pyridyl boronic ester (K-2) may be prepared by contacting pyridyl boronic acid (K-1) with pinacol under conditions suitable for the formation of boronic esters. In one embodiment, the N-methylpyridinone boronic ester (K-3) may be prepared by contacting pyridyl boronic ester (K-2) with MeI under conditions suitable for O-methyl-to-N-methyl shifting.

Example 1

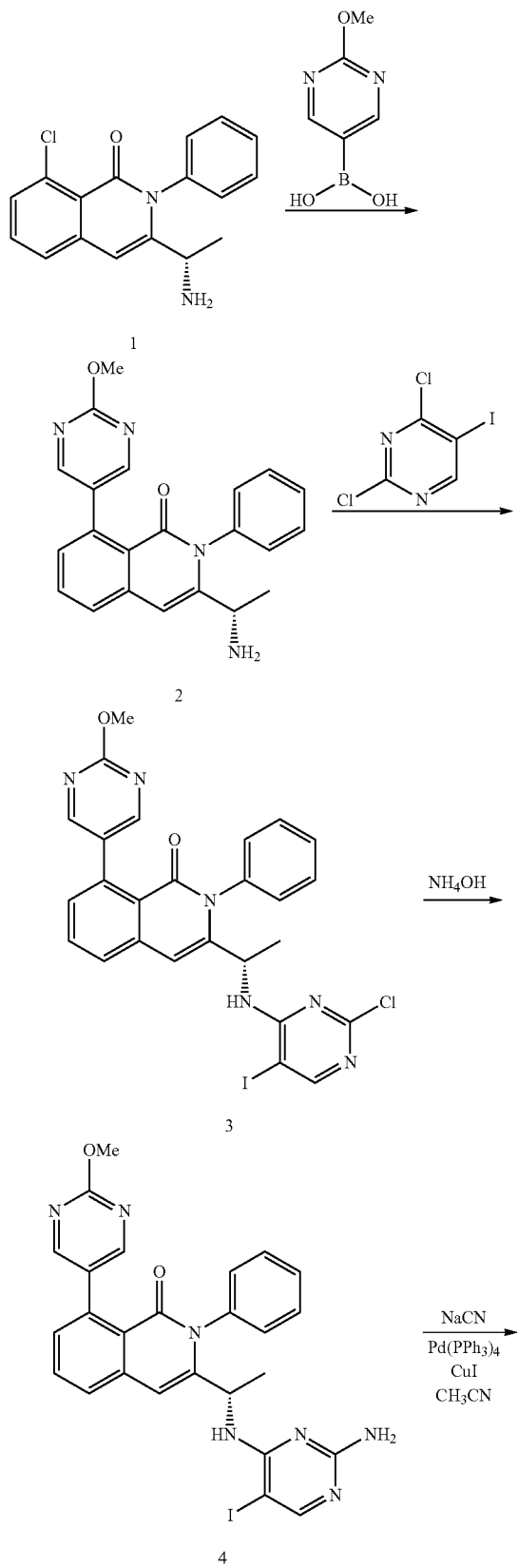

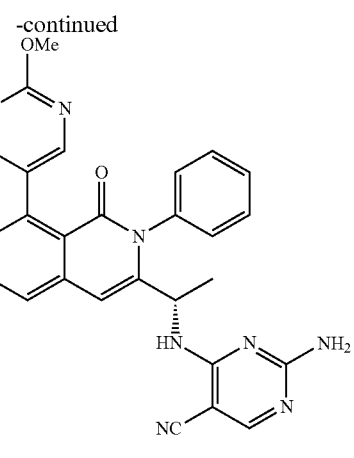

Amine 1 was prepared from commercially available 2-chloro-6-methylbenzoic acid according to Method A. Amine 1 was then converted to compound 2 according to the following procedure:

To a mixture of (S)-3-(1-aminoethyl)-8-chloro-2-phenyl-isoquinolin-1(2H)-one 1 (1.41 g, 4.72 mmol) and (2-methoxypyrimidin-5-yl)boronic acid (1.09 g, 7.08 mmol) in anhydrous DMA (20 mL) in a sealed tube, $PdCl_2$(dppf) (309 mg, 0.38 mmol) and aqueous $Na_2CO_3$ solution (1 M, 14.2 mL, 14.2 mmol) were added and the resulting mixture was stirred at 120° C. for 16 h. The reaction mixture was allowed to cool to RT, quenched with water, and then extracted with ethyl acetate. The combined organic layers were washed with brine, dried over $Na_2SO_4$ and filtered. The filtrate was concentrated in vacuo and the residue was slurried in ether for 10 min. The solid was collected by filtration, rinsed with ether and dried in vacuo to afford a first amount of product 2. The filtrate was concentrated in vacuo and the residue was further purified by ISCO column chromatography using a silica gel cartridge and eluting with 0-8% MeOH-DCM to afford a second amount of product 2.

Compound 2 was coupled to 2,4-dichloro-5-iodopyrimidine to afford compound 3 according to Method G. Compound 3 was then converted to compound 5 according to the following procedures:

To a solution of (S)-3-(1-((2-chloro-5-iodopyrimidin-4-yl)amino)ethyl)-8-(2-methoxypyrimidin-5-yl)-2-phenylisoquinolin-1 (2H)-one 3 (800 mg, 1.31 mmol) in anhydrous 1,4-dioxane (4 mL) in a sealed tube, ammonium hydroxide (7 mL) was added and the resulting mixture was stirred at 110° C. for 20 h. The mixture was allowed to cool to RT, quenched with water and extracted with ethyl acetate. The combined organic layers were washed with brine, dried over $Na_2SO_4$ and filtered. The filtrate was concentrated in vacuo and the residue was purified by ISCO column chromatography using a silica gel cartridge and eluting with 0-8% MeOH-DCM to afford the product, (S)-3-(1-((2-amino-5-iodopyrimidin-4-yl)amino)ethyl)-8-(2-methoxypyrimidin-5-yl)-2-phenylisoquinolin-1(2H)-one 4.

To a solution of (S)-3-(1-((2-amino-5-iodopyrimidin-4-yl)amino)ethyl)-8-(2-methoxypyrimidin-5-yl)-2-phenylisoquinolin-1(2H)-one 4 (352 mg, 0.60 mmol) in anhydrous acetonitrile (20 mL) in a sealed tube, sodium cyanide (292 mg, 5.95 mmol), tetrakis(triphenylphosphine) palladium(0) (344 mg, 0.30 mmol), and copper iodide (80 mg, 0.42 mmol) were added, and the resulting mixture was stirred at 80° C. for 16 h. The mixture was allowed to cool to RT, quenched with water and extracted with ethyl acetate. The combined organic layers were washed with brine, dried over Na₂SO₄ and filtered. The filtrate was concentrated in vacuo and the residue was purified by ISCO column chromatography using a silica gel cartridge and eluting with 0-8.5% MeOH-DCM to afford the product, (S)-2-chloro-4-((1-(8-(2-methoxypyrimidin-5-yl)-1-oxo-2-phenyl-1,2-dihydroisoquinolin-3-yl)ethyl)amino)pyrimidine-5-carbonitrile 5. ESI-MS m/z: 491.2 [M+H]

Example 2

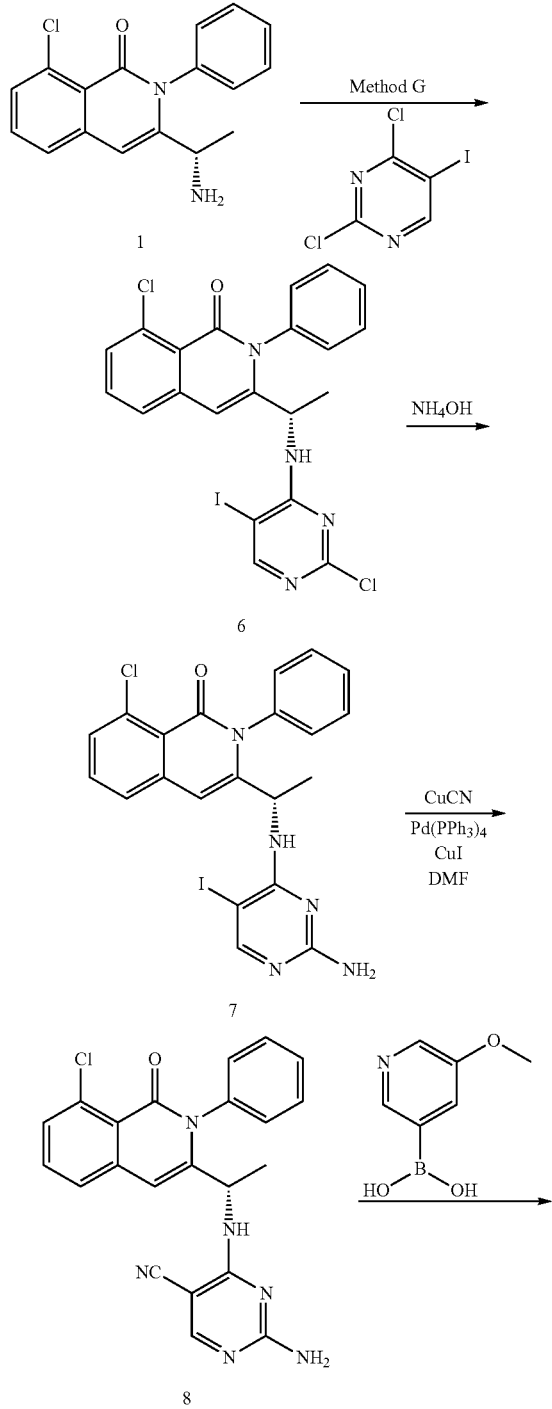

Compound 1 was coupled to 2,4-dichloro-5-iodopyrimidine to afford compound 6 according to Method G. Compound 6 was then converted to 7 in analogous fashion to compound 4 in Example 1.

Compound 7 was then converted to 9 in 2 steps according to the following procedures:

To a solution of (S)-3-(1-((2-amino-5-iodopyrimidin-4-yl)amino)ethyl)-8-chloro-2-phenylisoquinolin-1(2H)-one 7 (700 mg, 1.35 mmol) in DMF (40 mL), cyanocopper (243 mg, 2.7 mmol), tetrakis(triphenylphosphine) palladium(0) (779 mg, 0.68 mmol), and copper iodide (180 mg, 0.95 mmol) were added and the resulting mixture was stirred at 80° C. for 16 h. The mixture was allowed to cool to RT, quenched with water and extracted with ethyl acetate (2×50 mL). The combined organic layers were washed with brine, dried over Na₂SO₄ and filtered. The filtrate was concentrated in vacuo and the residue was purified by flash column chromatography on silica gel eluting with 0-10% MeOH-DCM to afford the product, (S)-2-amino-4-((1-(8-chloro-1-oxo-2-phenyl-1,2-dihydroisoquinolin-3-yl)ethyl)amino)pyrimidine-5-carbonitrile 8.

To a mixture of (S)-2-amino-4-((1-(8-chloro-1-oxo-2-phenyl-1,2-dihydroisoquinolin-3-yl)ethyl)amino)pyrimidine-5-carbonitrile 8 (50 mg, 0.12 mmol) and (5-methoxypyridin-3-yl)boronic acid (37 mg, 0.24 mmol) in anhydrous 1,4-dioxane (4 mL), PdCl₂(dppf) (9.8 mg, 0.012 mmol) and aqueous Na₂CO₃ solution (1 M, 0.6 mL, 0.6 mmol) were added and the resulting mixture was stirred at 120° C. for 3 h. The reaction mixture was allowed to cool to RT, quenched with water, and then extracted with ethyl acetate (3×50 mL). The combined organic layers were washed with brine, dried over Na$_2$SO$_4$ and filtered. The filtrate was concentrated in vacuo and the residue was purified by flash column chromatography on silica gel eluting with 0-10% MeOH-DCM to afford the product, (S)-2-amino-4-((1-(8-(5-methoxypyridin-3-yl)-1-oxo-2-phenyl-1,2-dihydroisoquinolin-3-yl)ethyl)amino)pyrimidine-5-carbonitrile 9. ESI-MS m/z: 490.2 [M+H]$^+$. Compound 2-amino-4-((S)-1-(8-(5-methoxypyridin-3-yl)-1-oxo-2-phenyl-1,2-dihydroisoquinolin-3-yl)ethylamino)pyrimidine-5-carboxamide 10 was also formed in the above reaction and it was isolated by column chromatography. ESI-MS m/z: 508.2 [M+H]$^+$.

Example 3

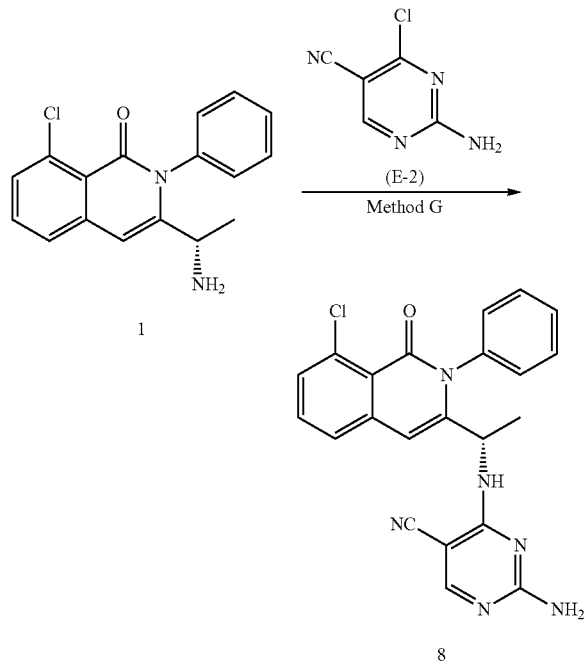

Compound 8 was prepared from compound 1 and (E-2) using Method G. ESI-MS m/z: 417.2 [M+H]$^+$.

Example 4

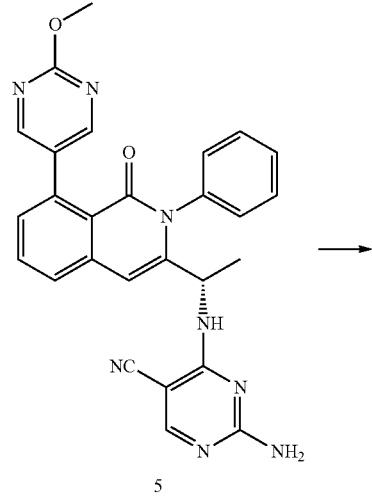

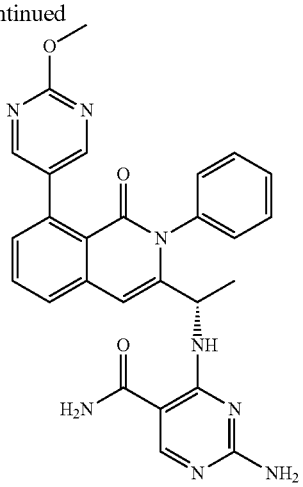

Compound 11 was prepared from compound 5 according to the following procedure:

To a solution of (S)-2-amino-4-((1-(8-(2-methoxypyrimidin-5-yl)-1-oxo-2-phenyl-1,2-dihydroisoquinolin-3-yl)ethyl)amino)pyrimidine-5-carbonitrile 5 (34 mg, 0.070 mmol) in anhydrous toluene (4 mL) under argon, acetaldoxime (13 μL, 0.21 mmol), palladium(II) acetate (5 mg, 0.01 mmol) and triphenyl phosphine (5 mg, 0.017 mmol) were added and the resulting mixture was stirred at 80° C. for 3 h. The mixture was allowed to cool to RT and partitioned between water and ethyl acetate. The organic layer was washed with brine, dried with Na$_2$SO$_4$ and filtered. The filtrate was concentrated in vacuo and the residue was purified by ISCO column chromatography (silica gel cartridge, 0-10% MeOH/DCM) to afford the product, (S)-2-amino-4-((1-(8-(2-methoxypyrimidin-5-yl)-1-oxo-2-phenyl-1,2-dihydroisoquinolin-3-yl)ethyl)amino)pyrimidine-5-carboxamide 11. ESI-MS m/z: 509.2 [M+H]$^+$.

Example 5

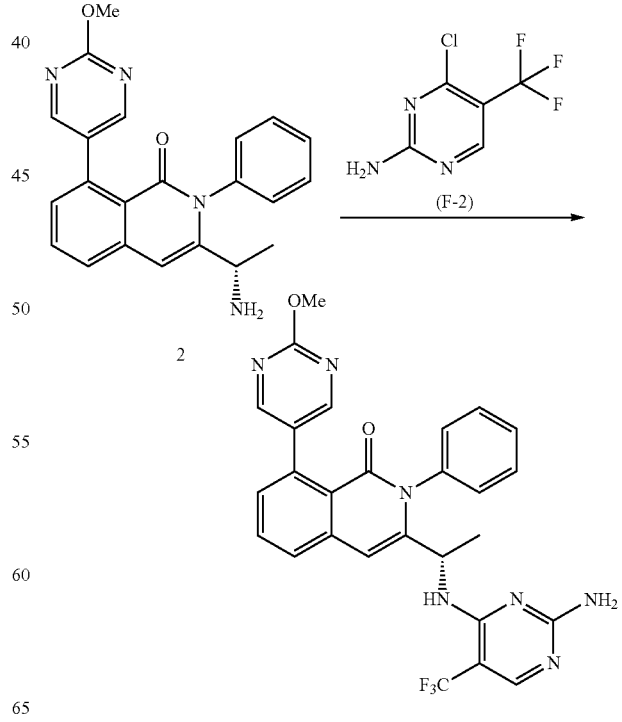

Compound 12 was prepared by coupling compound 2 with 4-chloro-5-(trifluoromethyl)pyrimidin-2-amine (F-2), prepared by Method F, according to Method G. ESI-MS m/z: 534.2 [M+H]+.

Example 6

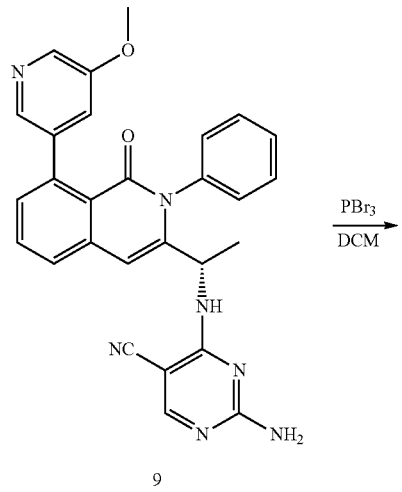

9

13

Compound 13 was prepared from compound 9 according to the following procedure:

To a stirred mixture of (S)-2-amino-4-((1-(8-(5-methoxypyridin-3-yl)-1-oxo-2-phenyl-1,2-dihydroisoquinolin-3-yl)ethyl)amino)pyrimidine-5-carbonitrile 9 (15 mg, 0.031 mmol) in DCM (5 mL) at −78° C. under argon, PBr₃ (77 mg, 0.31 mmol) was added and the resulting mixture was stirred from −78° C. to RT overnight. The reaction mixture was poured into ice-water (10 mL) and then neutralized with saturated aqueous NaHCO₃ to adjust the pH value to 8-9. The mixture was extracted with a mixture of methanol in DCM (5%, 5×10 mL). The organic layer was dried over Na₂SO₄ and filtered. The filtrate was concentrated in vacuo and the residue was purified by flash column chromatography on silica gel eluting with 1-3% MeOH/DCM to afford 2-amino-4-((S)-1-(8-(5-hydroxypyridin-3-yl)-1-oxo-2-phenyl-1,2-dihydroisoquinolin-3-yl)ethylamino)pyrimidine-5-carbonitrile 13. ESI-MS m/z: 476.0 [M+H]+.

Example 7

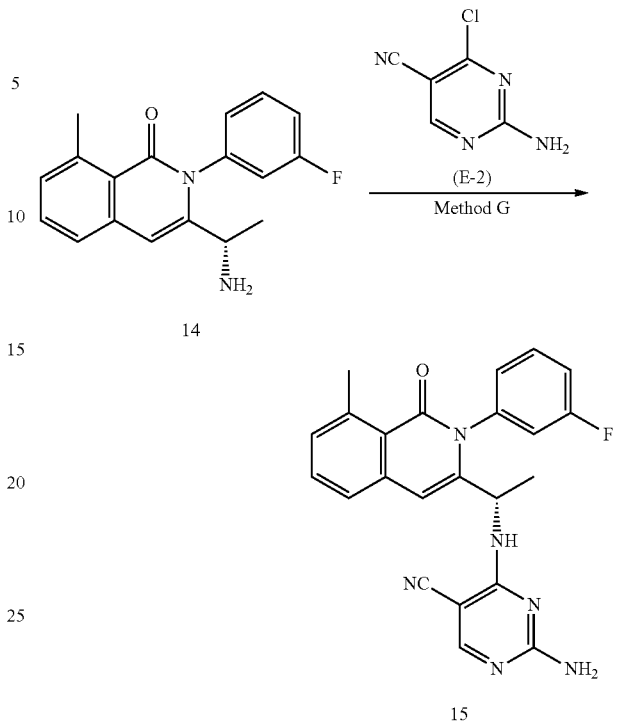

Amine 14 was prepared from commercially available 2,6-dimethylbenzoic acid according to Method A. Compound 14 was coupled to 2-amino-4-chloropyrimidine-5-carbonitrile (E-2) according to Method G to afford compound 15. ESI-MS m/z: 415.2 [M+H]+.

Example 8

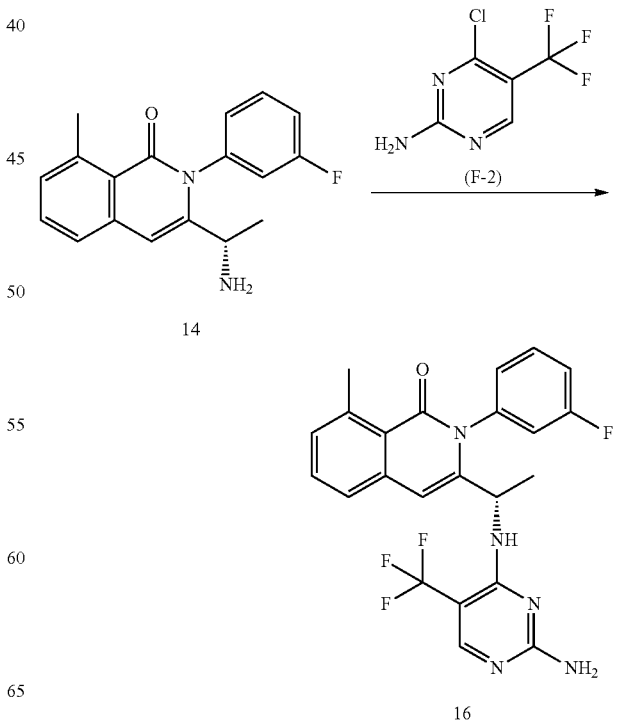

Compound 16 was prepared from compound 14 by coupling with 4-chloro-5-(trifluoromethyl)pyrimidin-2-amine (F-2) according to Method G. ESI-MS m/z: 458.0 [M+H]⁺.

Example 9

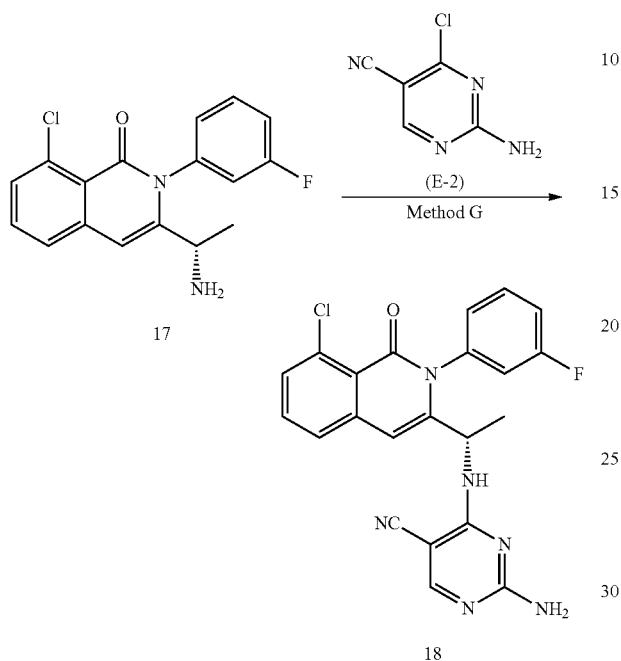

17

18

Amine 17 was prepared from commercially available 2-chloro-6-methylbenzoic acid according to Method A. Compound 17 was coupled to 2-amino-4-chloropyrimidine-5-carbonitrile (E-2) according to Method G to afford compound 18. ESI-MS m/z: 435.0 [M+H]⁺.

Example 10

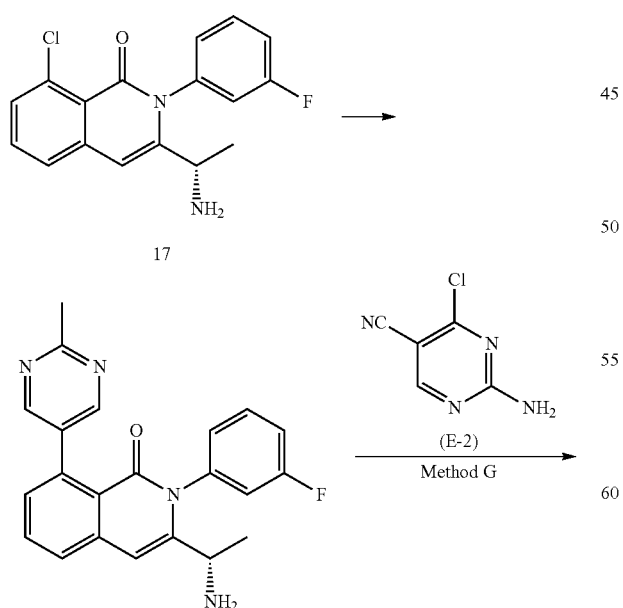

17

19

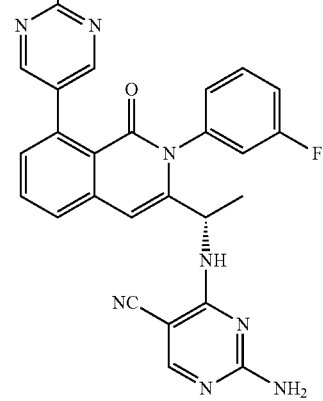

20

Compound 19 was prepared from amine 17 in analogous fashion to compound 2 in Example 1. Compound 19 was coupled to 2-amino-4-chloropyrimidine-5-carbonitrile (E-2) according to Method G to afford compound 20. ESI-MS m/z: 493.2 [M+H]⁺.

Example 11

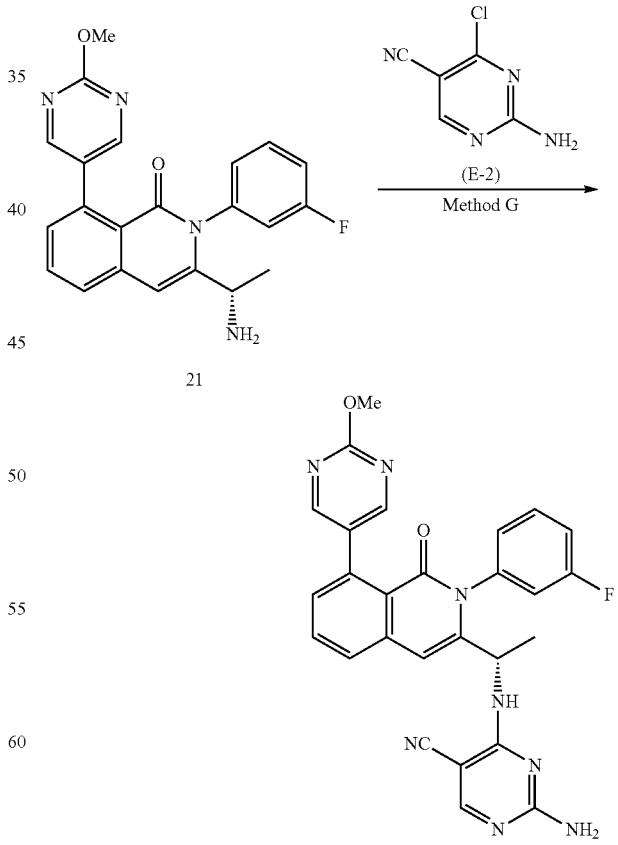

21

22

Compound 21 was prepared in analogous fashion to compound 2 in Example 1. Compound 22 was prepared by coupling compound 21 with 2-amino-4-chloropyrimidine-5-carbonitrile (E-2) according to Method G. ESI-MS m/z: 509.2 [M+H]⁺.

Example 12

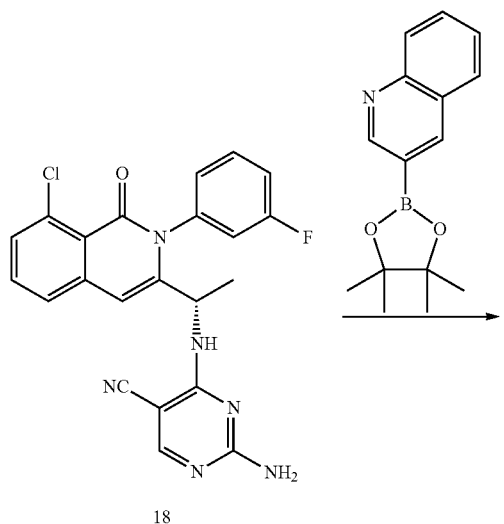

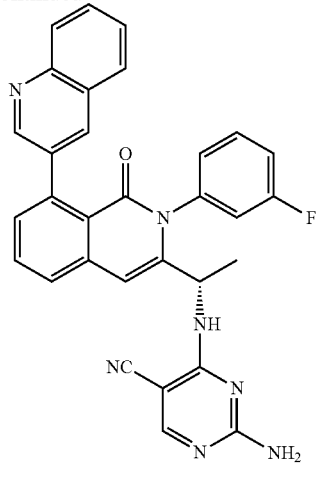

Compound 23 was prepared from compound 28 in analogous fashion to compound 2 in Example 1. ESI-MS m/z: 528.2 [M+H]⁺.

The following compounds were also prepared from compound 18 by Suzuki coupling with various commercially available or self-prepared heterocyclic aryl boronic acid/boronates in analogous fashion to compound 23 in Example 12.

| Example | Compound | Boronic acid/pinacol ester | ESI-MS m/z |
|---|---|---|---|
| 13 | 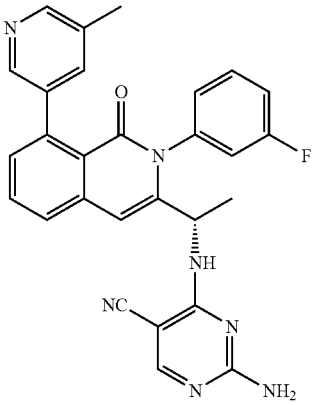 [SMILES: Cc1cncc(-c2cccc3cc([C@H](C)Nc4nc(N)ncc4C#N)n(-c4cccc(F)c4)c(=O)c23)c1] 24 | 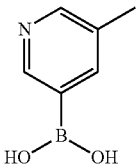 | 492.2 [M + H]⁺ |
| 14 | 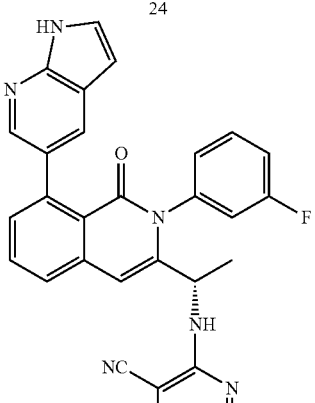 25 | 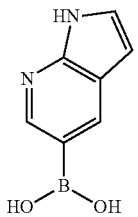 [SMILES: OB(O)c1cnc2[nH]ccc2c1] | 517.2 [M + H]⁺ |

-continued
| Example | Compound | Boronic acid/pinacol ester | ESI-MS m/z |
|---|---|---|---|
| 15 | 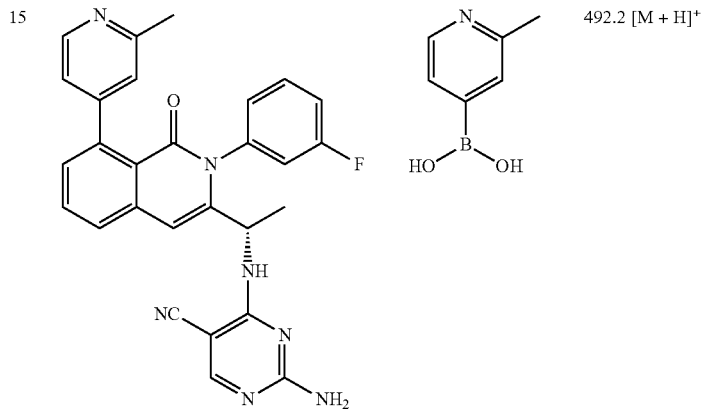  26 | | 492.2 [M + H]+ |
| 16 | 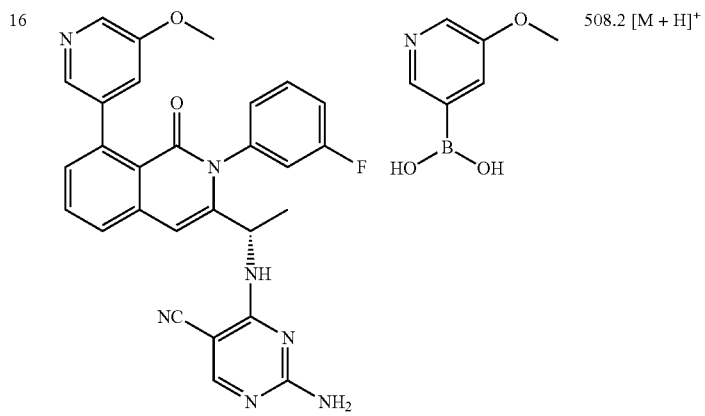  27 | | 508.2 [M + H]+ |
| 17 | 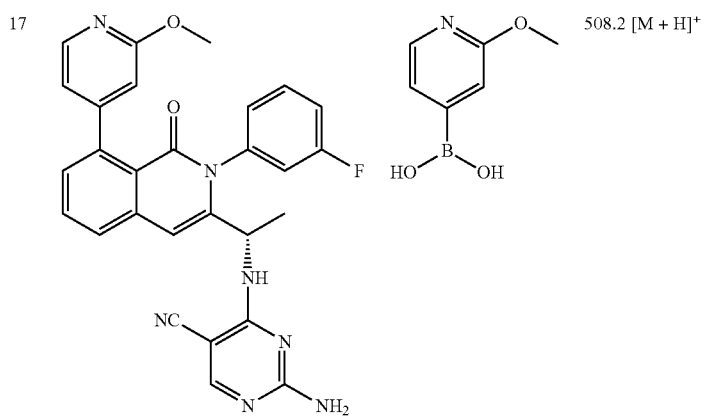  28 | | 508.2 [M + H]+ |

Example 18

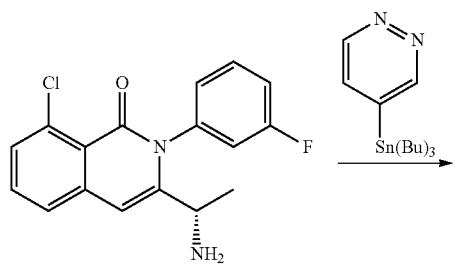

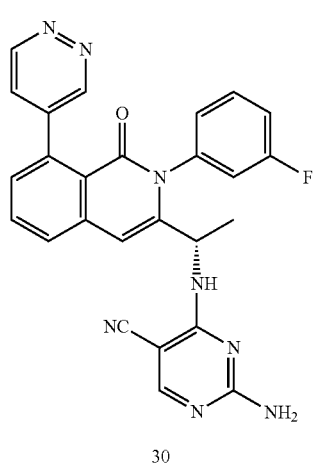

Compound 29 was prepared from amine 17 in analogous fashion to compound 2 in Example 1 except that 4-(tributylstannyl)pyridazine was used in place of (2-methoxypyrimidin-5-yl)boronic acid. Compound 29 was coupled to 2-amino-4-chloropyrimidine-5-carbonitrile (E-2) according to Method G to afford compound 30. ESI-MS m/z: 479.2 [M+H]+.

Example 19

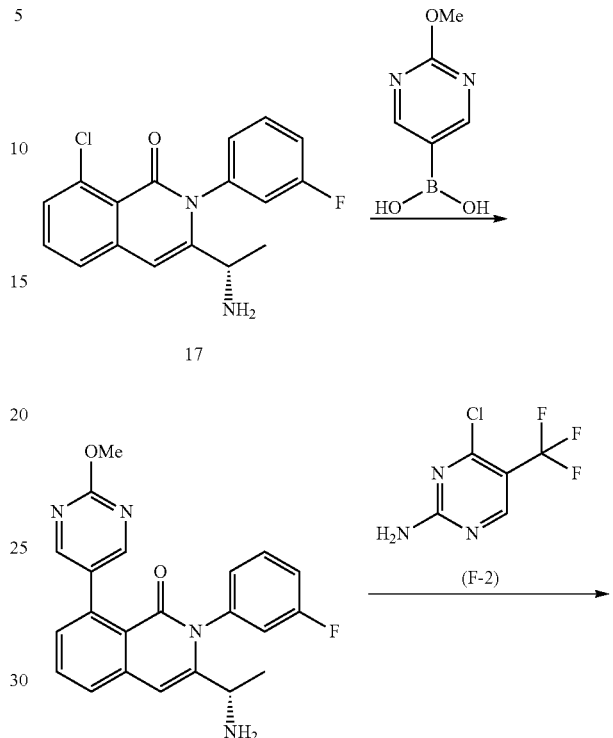

Compound 21 was prepared from amine 17 in analogous fashion to compound 2 in Example 1. Compound 21 was coupled to 4-chloro-5-(trifluoromethyl)pyrimidin-2-amine (F-2) according to Method G to afford compound 31. ESI-MS m/z: 552.0 [M+H]+.

The following compounds were prepared from compound 1 in two steps by Suzuki coupling with an aryl or heteroaryl boronic acid/pinacol ester (commercially purchased or self-prepared) in analogous fashion to compound 2 in Example 1, followed by coupling to 2-amino-4-chloropyrimidine-5-carbonitrile (E-2) (prepared by Method E) according to Method G.

| Example | Compound | Boronic acid/pinacol ester | ESI-MS m/z |
|---|---|---|---|
| 20 | 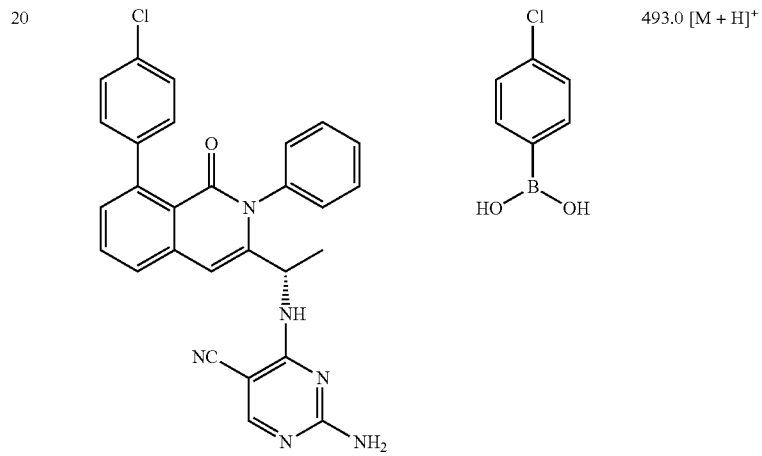 32 | | 493.0 [M + H]+ |
| 21 | 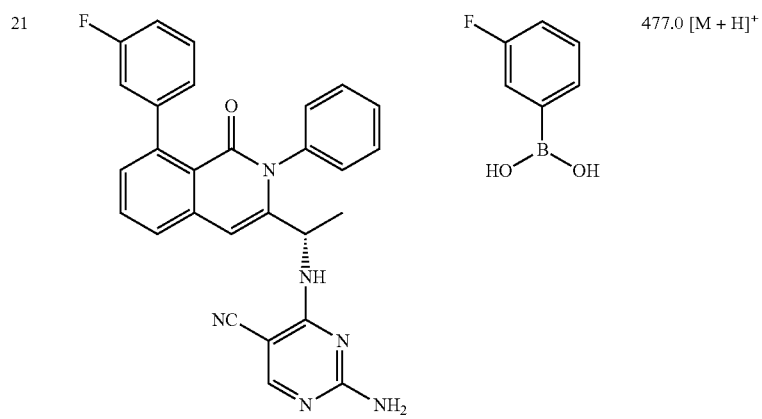 33 | | 477.0 [M + H]+ |
| 22 | 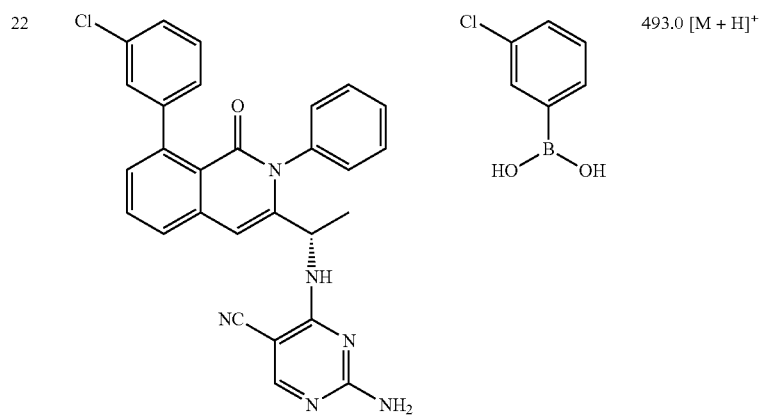 34 | | 493.0 [M + H]+ |

-continued
| Example | Compound | Boronic acid/pinacol ester | ESI-MS m/z |
|---|---|---|---|
| 23 | 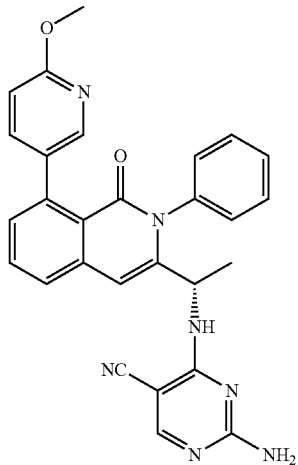 35 | 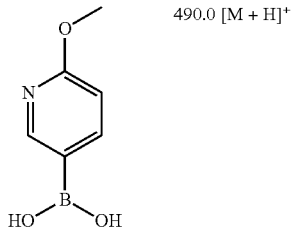 | 490.0 [M + H]+ |
| 24 | 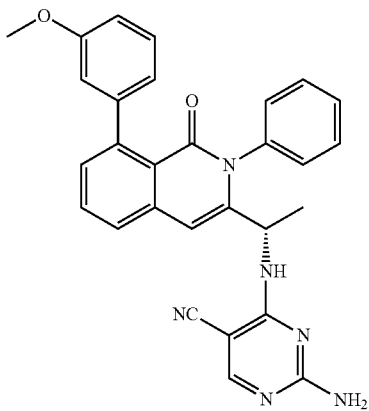 36 | 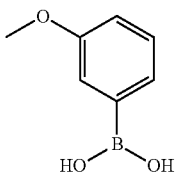 | 489.0 [M + H]+ |
| 25 | 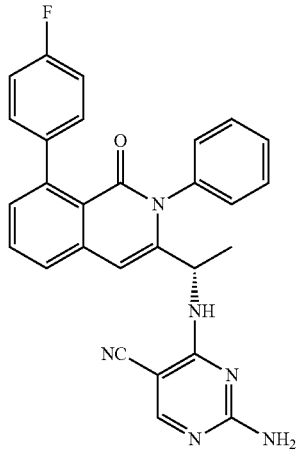 37 | 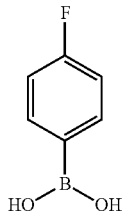 | 477.0 [M + H]+ |

-continued

| Example | Compound | Boronic acid/pinacol ester | ESI-MS m/z |
|---------|----------|---------------------------|------------|
| 26 | 38 | | 489.2 [M + H]⁺ |
| 27 | 39 | | 473.0 [M + H]⁺ |
| 28 | 40 | | 502.0 [M + H]⁺ |

-continued

| Example | Compound | Boronic acid/pinacol ester | ESI-MS m/z |
|---|---|---|---|
| 29 | 41 | | 474.0 [M + H]+ |
| 30 | 42 | | 502.0 [M + H]+ |
| 31 | 43 | | 484.0 [M + H]+ |

| Example | Compound | Boronic acid/pinacol ester | ESI-MS m/z |
|---|---|---|---|
| 32 | 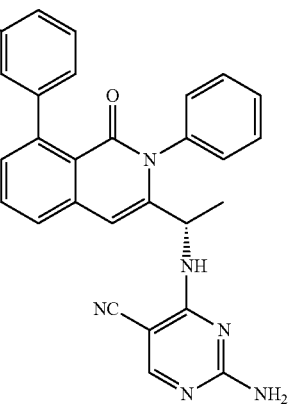 44 | 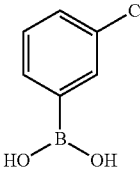 | 484.0 [M + H]⁺ |
| 33 | 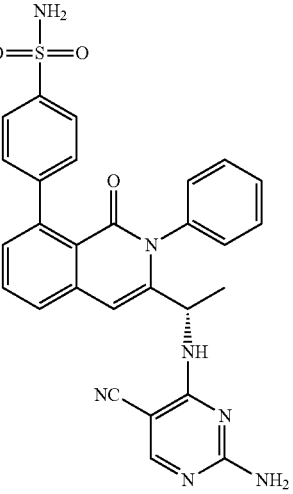 45 | 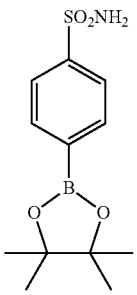 | 538.0 [M + H]⁺ |
| 34 | 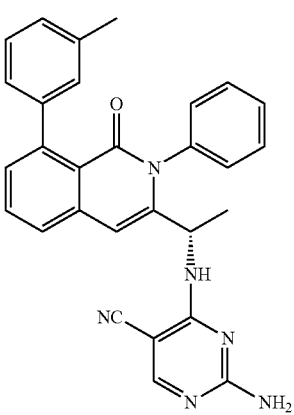 [SMILES: Cc1cccc(-c2cccc3cc([C@H](C)Nc4nc(N)ncc4C#N)n(-c4ccccc4)c(=O)c23)c1] 46 | 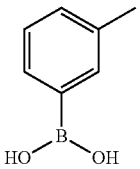 | 473.2 [M + H]⁺ |
The following compounds were prepared from compound 8 (Example 3) by Suzuki coupling with various heterocyclic aryl/heteroaryl boronic acid or pinacol ester according to the coupling conditions in Example 2

| Example | Compound | Boronic Acid | ESI-MS m/z |
|---|---|---|---|
| 35 | 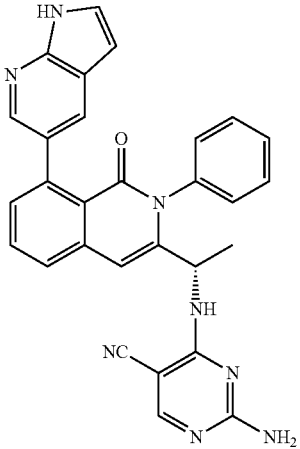 [SMILES: C[C@H](Nc1nc(N)ncc1C#N)c1cc2cccc(-c3cnc4[nH]ccc4c3)c2c(=O)n1-c1ccccc1]<br>47 | 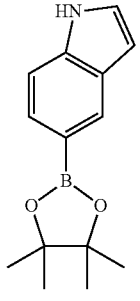 | 499.2 [M + H]+ |
| 36 | 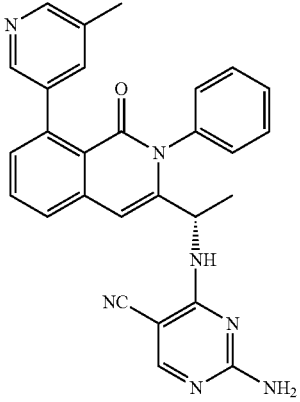 [SMILES: Cc1cncc(-c2cccc3cc([C@H](C)Nc4nc(N)ncc4C#N)n(-c4ccccc4)c(=O)c23)c1]<br>48 | 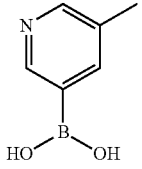 | 474.2 [M + H]+ |
| 37 | 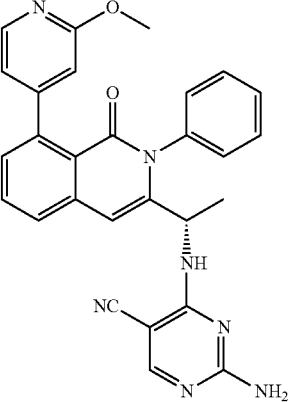 [SMILES: COc1cc(-c2cccc3cc([C@H](C)Nc4nc(N)ncc4C#N)n(-c4ccccc4)c(=O)c23)ccn1]<br>49 | 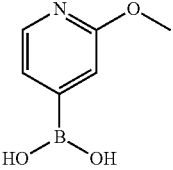 | 490.2 [M + H]+ |

| Example | Compound | Boronic Acid | ESI-MS m/z |
|---------|----------|--------------|------------|
| 38 | 50 | (quinolin-3-yl pinacol boronate) | 510.22 [M + H]+ |
| 39 | 51 | (2-methylpyridin-4-yl boronic acid) | 474.2 [M + H]+ |
| 40 | 52 | (5-(trifluoromethyl)pyridin-3-yl boronic acid) | 528.0 [M + H]+ |

-continued
| Example | Compound | Boronic Acid | ESI-MS m/z |
|---|---|---|---|
| 41 | 53 | | 518.0 [M + H]+ |
Example 42
Compound 55 was prepared from compound 1 in two steps in an analogous fashion to compound 30 in Example 18. ESI-MS m/z: 475.2 [M+H]+.
Example 43
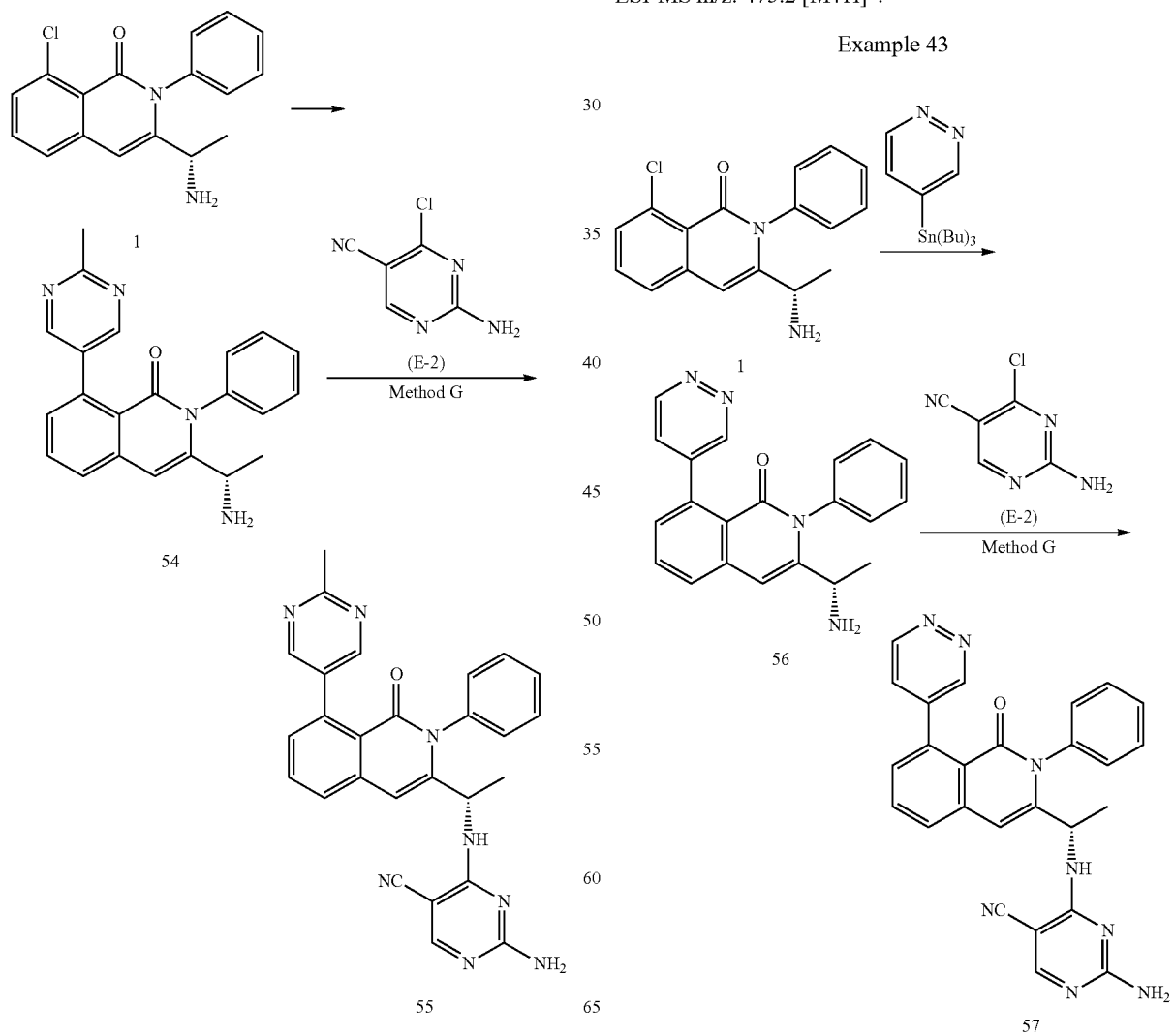

Compound 57 was prepared from compound 1 in two steps in an analogous fashion to compound 30 in Example 18. ESI-MS m/z: 461.2 [M+H]+.

Example 44

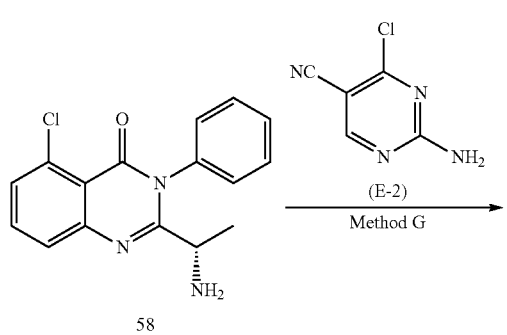

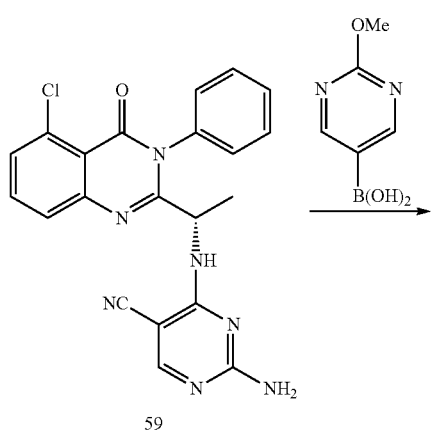

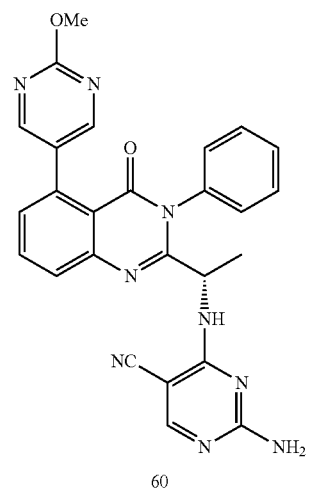

Compound 58 was prepared from 2-chloro-6-nitrobenzoic acid according to Method D. Compound 58 was coupled to (E-2) according to Method G to afford compound 59. Compound 59 was converted to compound 60 by Suzuki coupling with (2-methoxypyrimidin-5-yl)boronic acid in analogous fashion to compound 2 in Example 1. ESI-MS m/z: 492.2 [M+H]+.

The following compounds were also prepared from compound 59 by Suzuki coupling with heteroaryl boronic acid or pinacol ester in analogous fashion to compound 60 in Example 44.

| Example | Compound | Boronic Acid | ESI-MS m/z |
|---|---|---|---|
| 45 | (61) | | 464.2 [M + H]+ |

| Example | Compound | Boronic Acid | ESI-MS m/z |
|---|---|---|---|
| 46 | 62 | | 475.2 [M + H]⁺ |

Example 47

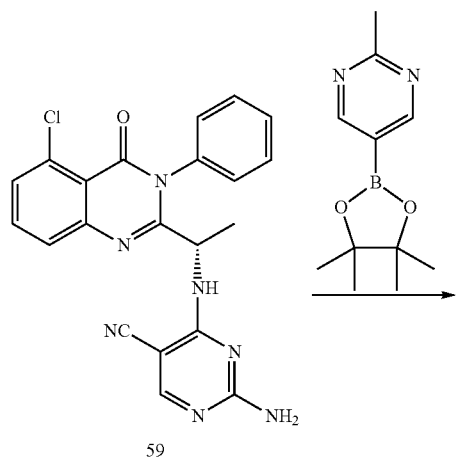

59 carbonitrile 59 (50 mg, 0.12 mmol) and 2-methyl-5-(4,4,5,5-tetramethyl-1,3,2-dioxaborolan-2-yl)pyrimidine (40 mg, 0.18 mmol) in a 4:1 mixture of 1,4-dioxane and water (4 mL) in a sealed tube, $Na_2CO_3$ (38 mg, 0.36 mmol), RuPhos (28 mg, 0.06 mmol) and $Pd(OAc)_2$ (6.8 mg, 0.03 mmol) were added. The mixture was degassed and back-filled with argon (three cycles) and then stirred at 120° C. for 1 h. The reaction mixture was allowed to cool to RT, and then partitioned between ethyl acetate and water. The organic layer was washed with brine, dried over $Na_2SO_4$ and filtered. The filtrate was concentrated in vacuo and the residue was purified by ISCO column chromatography (silica gel cartridge, 0-10% MeOH-DCM) to afford the product, (S)-2-amino-4-((1-(5-(2-methylpyrimidin-5-yl)-4-oxo-3-phenyl-3,4-dihydroquinazolin-2-yl)ethyl)amino)pyrimidine-5-carbonitrile 63. ESI-MS m/z: 476.2 [M+H]⁺.

Example 48

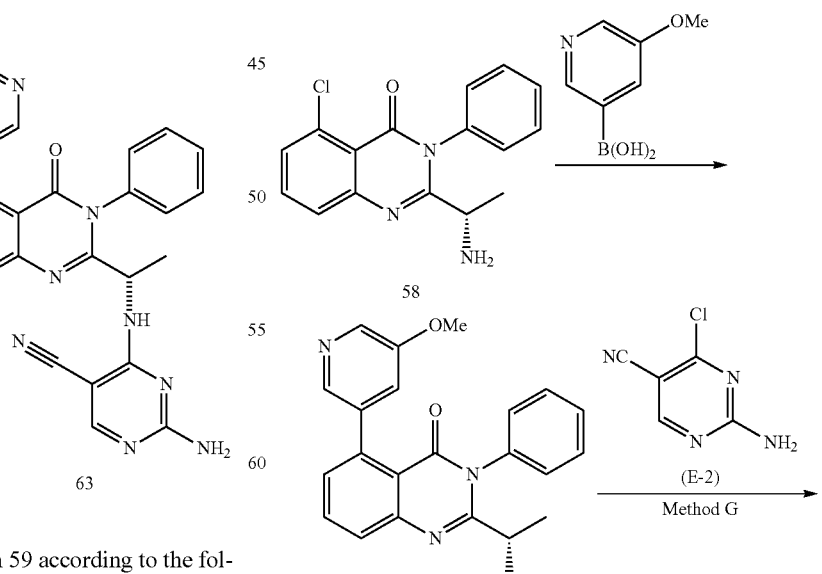

Compound 63 was prepared from 59 according to the following procedure:

To a mixture of (S)-2-amino-4-((1-(5-chloro-4-oxo-3-phenyl-3,4-dihydroquinazolin-2-yl)ethyl)amino)pyrimidine-5-

-continued

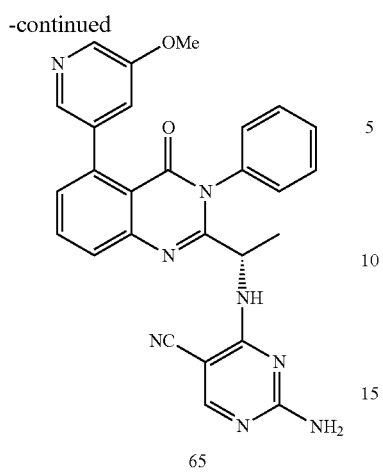
65

Compound 64 was prepared from amine 58 in analogous fashion to compound 2 in Example 1. Compound 64 was coupled to (E-2) according to Method G to afford compound 65. ESI-MS m/z: 491.2 [M+H]⁺

Example 49

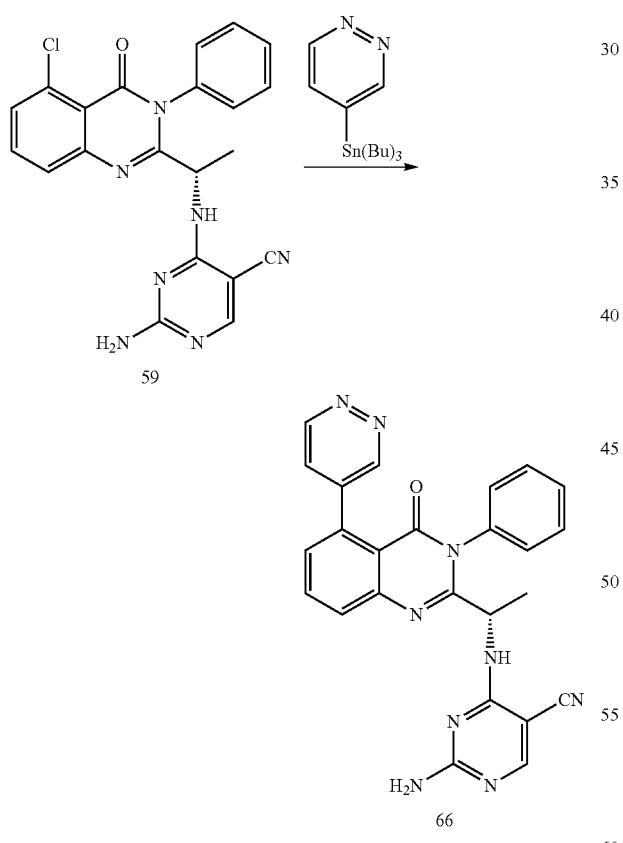

Compound 66 was prepared from 59 according to the following procedure:

A mixture of (S)-2-amino-4-(1-(5-chloro-4-oxo-3-phenyl-3,4-dihydroquinazolin-2-yl)ethylamino)pyrimidine-5-carbonitrile 59 (50 mg, 0.12 mmol), 4-(tributylstannyl)pyridazine (89 mg, 0.24 mmol) and PdCl₂(dppf) (9.7 mg, 0.012 mmol) in 1,4-dioxane (5 mL) was stirred at reflux under argon for 16 h. The mixture was allowed to cool to RT, poured into water (20 mL) and extracted with ethyl acetate (2×15 mL). The combined organic layers were washed with brine, dried over Na₂SO₄ and filtered. The filtrate was concentrated in vacuo and the residue was purified by flash column chromatography on silica gel eluting with 3% MeOH-DCM to afford the product, (S)-2-amino-4-((1-(4-oxo-3-phenyl-5-(pyridazin-4-yl)-3,4-dihydroquinazolin-2-yl)ethyl)amino)pyrimidine-5-carbonitrile 66. ESI-MS m/z: 462.2 [M+H]⁺.

Example 50

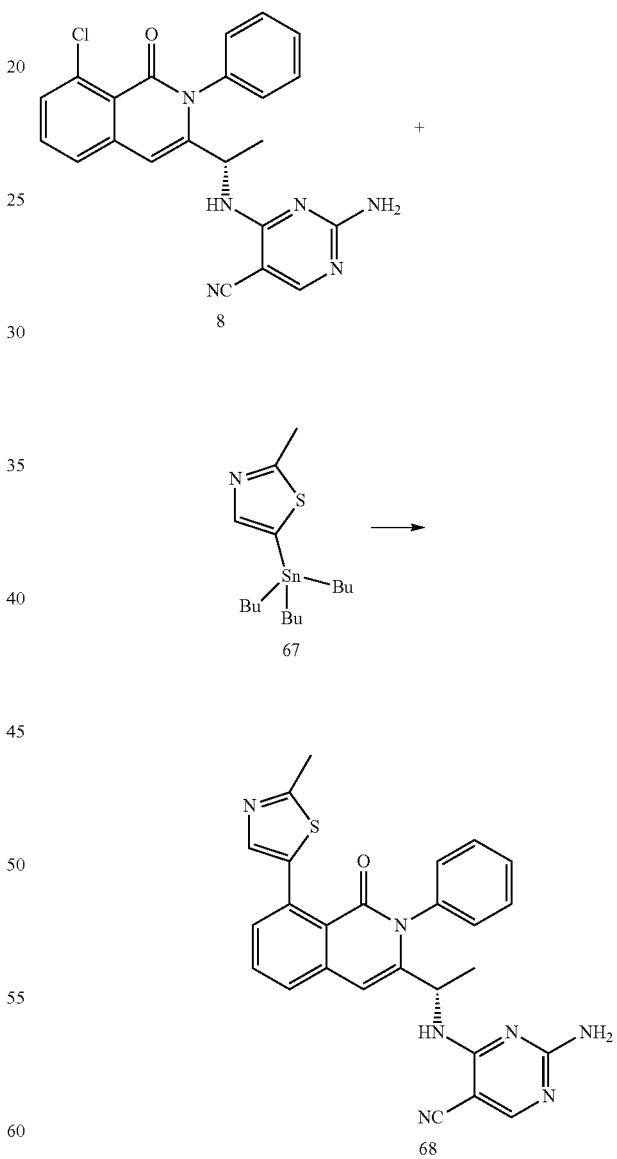

Compound 68 was prepared from compound 8 in analogous fashion to Method H. ESI-MS m/z: 480.3 [M+H]⁺.

Example 51
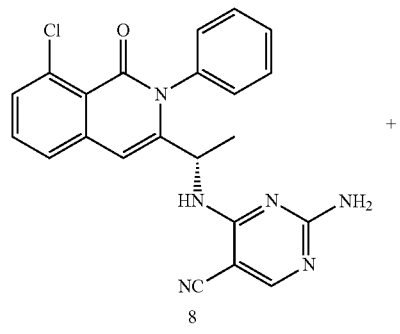
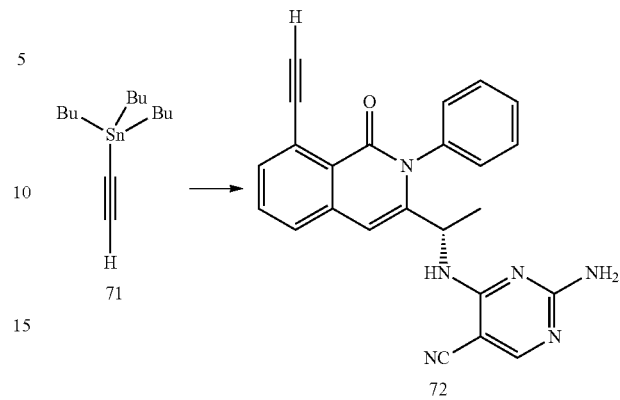
Compound 72 was prepared from compound 8 in analogous fashion to Method I. ESI-MS m/z: 407.23 [M+H]$^+$.
Example 53
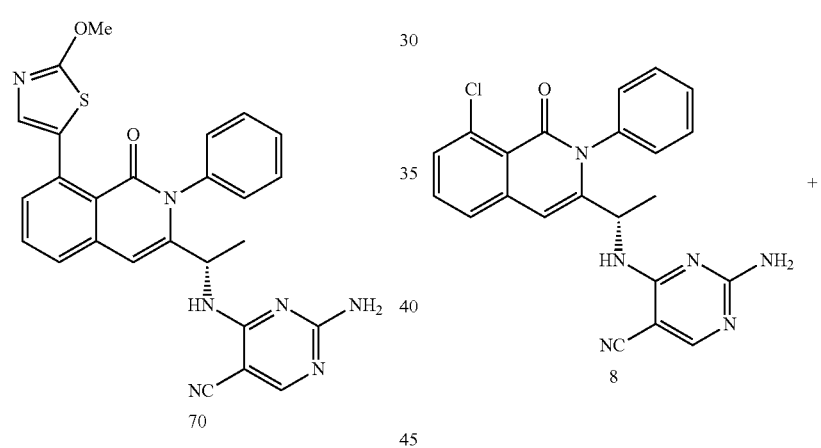
Compound 70 was prepared from compound 8 in analogous fashion to Method H. ESI-MS m/z: 496.3 [M+H]$^+$.
Example 52
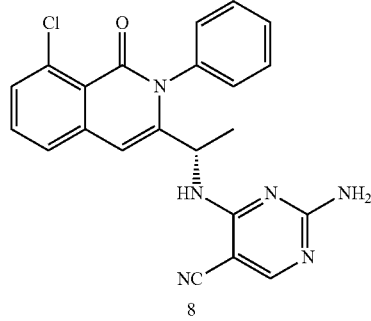
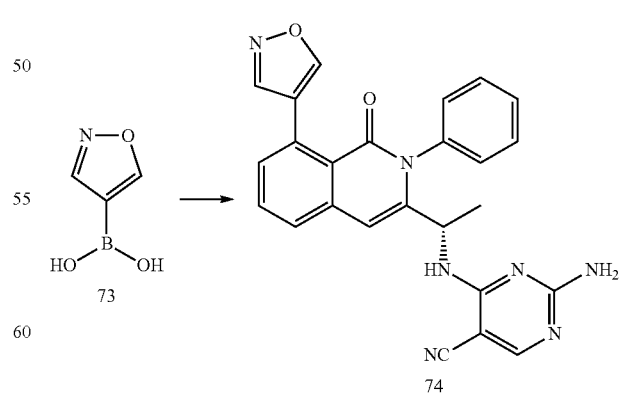
Compound 74 was prepared from compound 8 in analogous fashion to Method H. ESI-MS m/z: 450.2 [M+H]$^+$.

Example 54

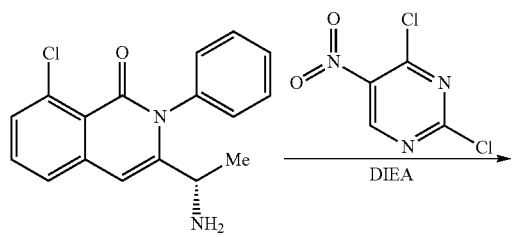

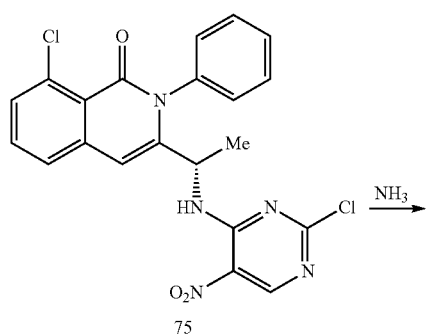

A solution of 2,4-dichloro-5-nitropyrimidine (250 mg, 1.29 mmol, 1.15 eq.) in THF (2 mL) was chilled in a −78° C. bath. To this solution was slowly added over 40 mins a mixture of compound 1 (335 mg, 1.12 mmol, 1.0 eq.) and DIEA (450 µL, 2.58 mmol, 2.3 eq.) in THF (4 mL). After addition was complete, the reaction was stirred at −78° C. during 30-40 mins, then allowed to warm slowly to 15° C. over 1 h. The reaction mixture was diluted with DCM (40 mL), washed with water and brine (15 mL each), dried over Na₂SO₄, and concentrated. This residue was purified by flash chromatography eluting with 300 mL each 10/20/30/40% EtOAc/hexanes to give (S)-8-chloro-3-(1-(2-chloro-5-nitropyrimidin-4-ylamino)ethyl)-2-phenylisoquinolin-1(2H)-one 75. ESI-MS m/z: 456.15 [M+H]⁺.

Example 55

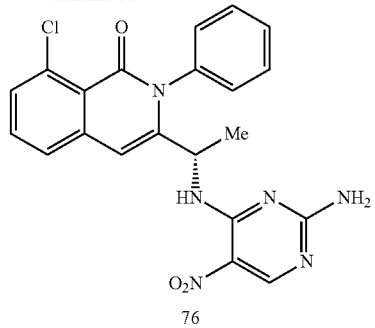

Compound 75 (450 mg, 0.99 mmol) was dissolved in THF (45 mL), treated with concentrated ammonium hydroxide solution (9 mL), and stirred at ambient temperature for 16 h. The solvent was evaporated in vacuo and the residue suspended in water (50 mL) and brine (20 mL), and extracted with DCM (3×35 mL). The combined organic layers were washed with brine (15 mL each), dried over Na₂SO₄, and concentrated to afford (S)-3-(1-(2-amino-5-nitropyrimidin-4-ylamino)ethyl)-8-chloro-2-phenylisoquinolin-1(2H)-one 76, 430 mg (0.99 mmol, quant.). ESI-MS m/z: 437.16 [M+H]⁺.

Example 56

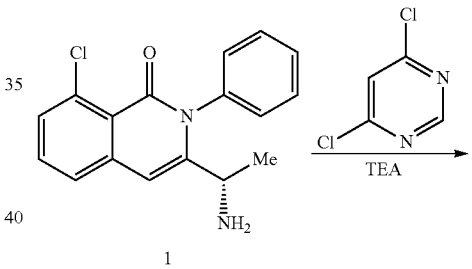

A mixture of 4,6-dichloropyrimidine (200 mg, 1.34 mmol, 1.6 eq.), compound 1 (250 mg, 0.84 mmol, 1.0 eq.), and TEA (350 µL, 2.5 mmol, 3.0 eq.) in 1,4-dioxane (7.5 mL) was heated at 60° C. for 3 days. The reaction was charged with *additional* 4,6-dichloropyrimidine (100 mg, 0.67 mmol, 0.8 eq.) and TEA (175 µL, 1.3 mmol, 1.5 eq.) and heated at 80° C. for 16 h. The reaction mixture was diluted with DCM, 5% aqueous acetic acid, and brine (50 mL each), separated, and the organic phase was washed with 0.1 M NaOH and brine (15 mL each), dried on Na₂SO₄, and concentrated. The residue was purified by flash chromatography eluting with 300 mL each 10/20/30/40/50% EtOAc/hexanes to give (S)-8-chloro-3-(1-(6-chloropyrimidin-4-ylamino)ethyl)-2-phenylisoquinolin-1(2H)-one 77. ESI-MS m/z: 411.14 [M+H]$^+$.

Example 57

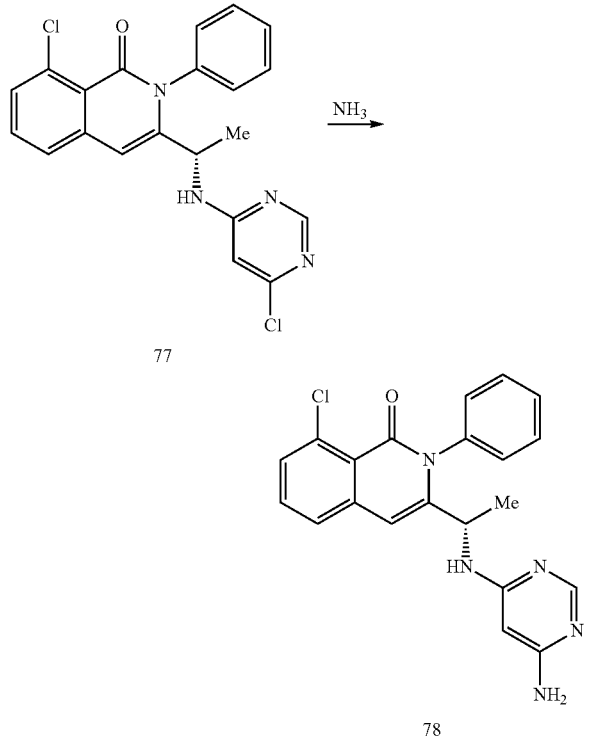

A heavy-wall glass tube with stir bar and FEP-encapsulated-silicone O-ring seal was charged with 77 (ca. 300 mg, 0.73 mmol) in 1,4-dioxane (12 mL) and concentrated ammonium hydroxide solution (10 mL), then sealed tightly and heated at 120° C. After 16 h, more ammonium hydroxide (6 mL) was added and heating continued at 150° C. during 6 h, then 160° C. during 24 h. A third portion of ammonium hydroxide (8 mL) was added and heating continued at 150° C. during 3 days. The reaction mixture was poured into a mixture of water and brine (35 mL each), stirred about 1 h at 0° C., and the resulting precipitate collected by filtration and washed with ice-water. This material was dried in vacuo to give (S)-3-(1-(6-aminopyrimidin-4-ylamino)ethyl)-8-chloro-2-phenylisoquinolin-1(2H)-one 78. ESI-MS m/z: 392.15 [M+H]$^+$.

Example 58

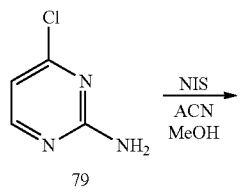

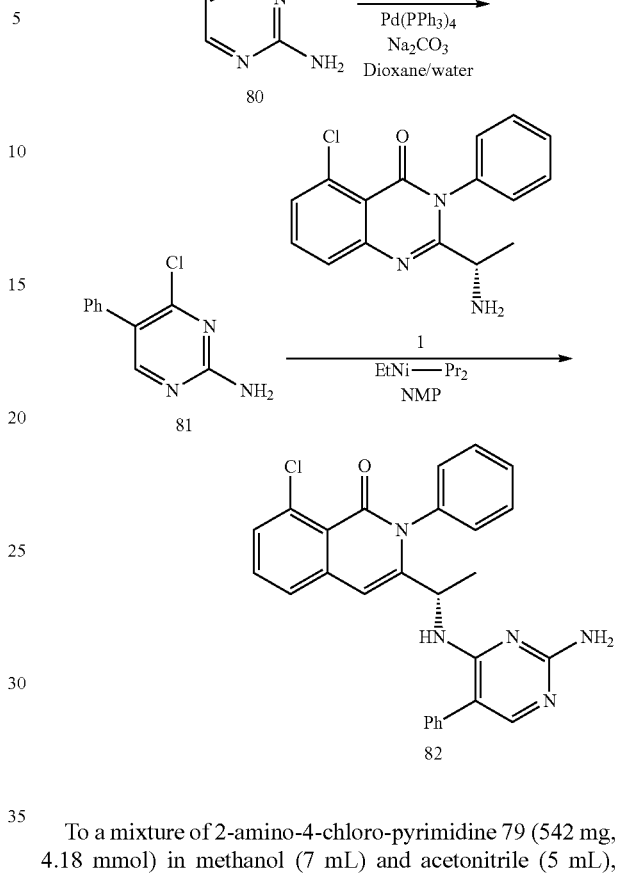

To a mixture of 2-amino-4-chloro-pyrimidine 79 (542 mg, 4.18 mmol) in methanol (7 mL) and acetonitrile (5 mL), N-iodosuccinimide (941 mg, 4.18 mmol) was added and the resulting mixture was stirred at 60° C. for 1.5 h. The reaction mixture was allowed to cool to room temperature, treated with Et$_2$O (10 mL) and filtered to afford product 80.

To a mixture of compound 80 (250 mg, 0.979 mmol) and phenyl boronic acid (239 mg, 1.957 mmol) in anhydrous dioxane (5 mL) in a sealed tube, Pd(PPh$_3$)$_4$ (226 mg, 0.196 mmol) and aqueous Na$_2$CO$_3$ solution (1.5 M, 1.30 mL, 1.95 mmol) were added and the resulting mixture was stirred at 120° C. for 1.5 h. The reaction mixture was allowed to cool to room temperature, quenched with water, and then extracted with ethyl acetate. The combined organic layers were washed with brine, dried over Na$_2$SO$_4$ and filtered. The filtrate was concentrated in vacuo and the residue was further purified by ISCO column chromatography (silica gel cartridge, 10-50% EtOAc-Hexanes) to afford product 81.

To a mixture of compound 81 (69 mg, 0.335 mmol) and compound 1 (100 mg, 0.335 mmol) in anhydrous NMP (3 mL) in a sealed tube, diisopropylethylamine (0.234 mL, 1.34 mmol) was added and the resulting mixture was stirred at 160° C. for 20 h. The mixture was allowed to cool to room temperature, quenched with water and extracted with ethyl acetate. The combined organic layers were washed with brine, dried over Na$_2$SO$_4$ and filtered. The filtrate was concentrated in vacuo and the residue was purified by ISCO column chromatography (silica gel cartridge, 0-8% MeOH in 1/1 EtOAc/DCM) to afford the product (S)-3-(1-(2-amino-5-phenylpyrimidin-4-ylamino)ethyl)-8-chloro-2-phenylisoquinolin-1(2H)-one 82. ESI-MS m/z: 468.2 [M+H]$^+$.

Example 59

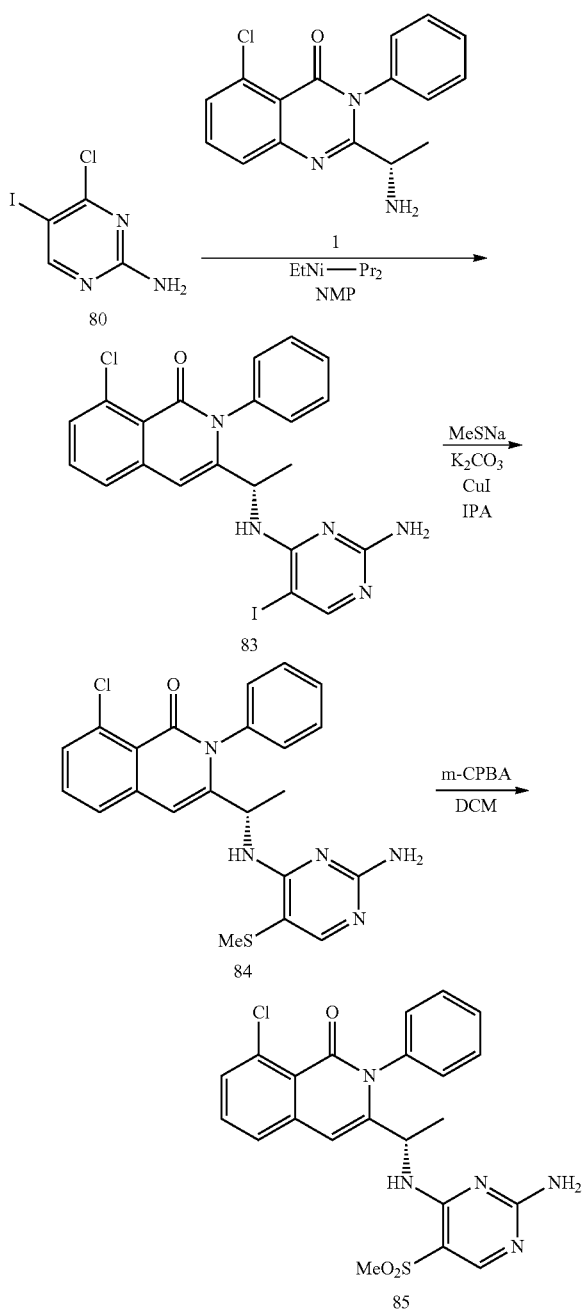

To a mixture of compound 80 (128 mg, 0.502 mmol) and compound 1 (100 mg, 0.335 mmol) in anhydrous NMP (3 mL) in a sealed tube, diisopropylethylamine (0.234 mL, 1.34 mmol) was added and the resulting mixture was stirred at 120° C. for 16 h. The mixture was allowed to cool to room temperature, quenched with water and extracted with ethyl acetate. The combined organic layers were washed with brine, dried over Na$_2$SO$_4$ and filtered. The filtrate was concentrated in vacuo and the residue was purified by ISCO column chromatography (silica gel cartridge, 10-75% EtOAc/Hexanes) to afford the product 83.

A mixture of compound 83 (40 mg, 0.077 mmol), sodium thiomethoxide (11 mg, 0.155 mmol), sodium carbonate (21 mg, 0.155 mmol) and copper iodide (0.7 mg, 0.007 mmol) in IPA (2 mL) in a sealed tube was stirred at 80° C. for 24 h. The reaction mixture was allowed to cool to room temperature, quenched with water, and then extracted with ethyl acetate. The combined organic layers were washed with brine, dried over Na$_2$SO$_4$ and filtered. The filtrate was concentrated in vacuo and the residue was further purified by ISCO column chromatography (silica gel cartridge, 10-75% EtOAc-Hexanes) to afford product 84.

To a solution of compound 84 (10 mg, 0.023 mmol) in anhydrous DCM (3 mL), m-chloroperbenzoic acid (11 mg, 0.069 mmol) was added and the resulting mixture was stirred at room temperature for 0.5 h. The mixture was allowed to cool to room temperature, quenched with water and extracted with ethyl acetate. The combined organic layers were washed with brine, dried over Na$_2$SO$_4$ and filtered. The filtrate was concentrated in vacuo and the residue was purified by ISCO column chromatography (silica gel cartridge, 0-80% EtOAc/Hexanes) to afford the product (S)-3-(1-(2-amino-5-(methylsulfonyl)pyrimidin-4-ylamino)ethyl)-8-chloro-2-phenylisoquinolin-1(2H)-one 85. ESI-MS m/z: 470.2 [M+H]$^+$.

Example 60

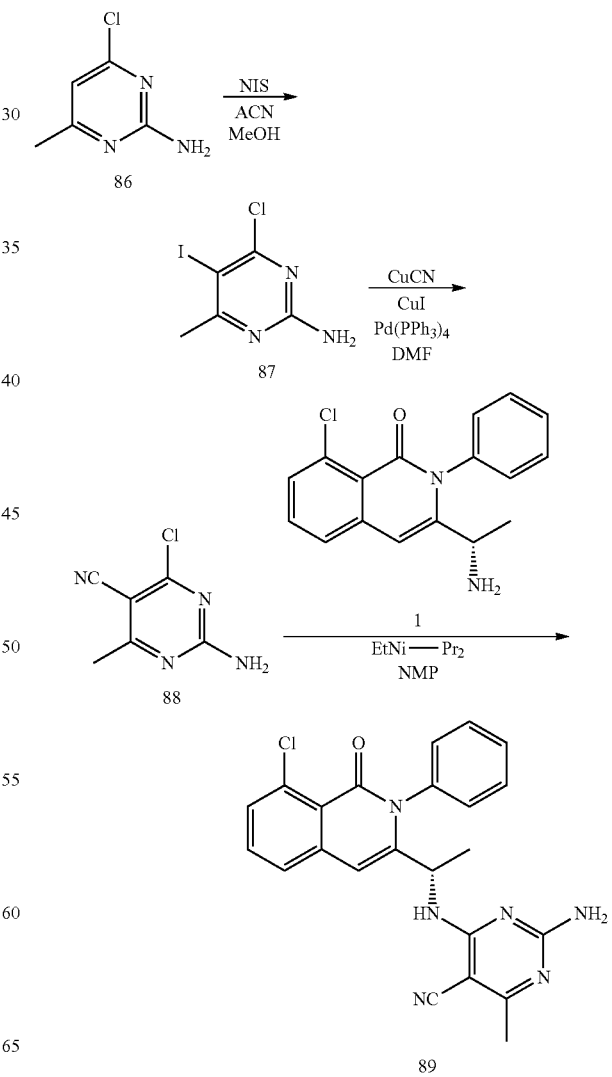

265

To a mixture of 2-amino-4-chloro-6-methylpyrimidine 86 (5.0 g, 34.8 mmol) in methanol (70 mL) and acetonitrile (50 mL), N-iodosuccinimide (11.8 g, 52.2 mmol) was added and the resulting mixture was stirred at 60° C. for 5 h. The reaction mixture was allowed to cool to room temperature, treated with Et$_2$O (100 mL) and filtered to afford product 87.

To a mixture of compound 87 (250 mg, 0.979 mmol) in anhydrous DMF (40 mL), copper cyanide (332 mg, 3.71 mmol), copper iodide (247 mg, 1.30 mmol) and Pd(PPh$_3$)$_4$ (1.07 g, 0.928 mmol) were added and the resulting mixture was stirred at 80° C. for 1.5 h. The reaction mixture was allowed to cool to room temperature, quenched with water, and treated with ethyl acetate. The biphasic mixture was filtered on celite and extracted with ethyl acetate. The combined organic layers were washed with brine, dried over Na$_2$SO$_4$ and filtered. The filtrate was concentrated in vacuo and the residue was further purified by ISCO column chromatography (silica gel cartridge, 10-50% EtOAc-Hexanes) to afford product 88.

To a mixture of compound 88 (42 mg, 0.250 mmol) and compound 1 (50 mg, 0.167 mmol) in anhydrous DMF (3 mL) in a sealed tube, diisopropylethylamine (0.117 mL, 0.669 mmol) was added and the resulting mixture was stirred at 120° C. for 20 h. The mixture was allowed to cool to room temperature, quenched with water and extracted with ethyl acetate. The combined organic layers were washed with brine, dried over Na$_2$SO$_4$ and filtered. The filtrate was concentrated in vacuo and the residue was purified by ISCO column chromatography (silica gel cartridge, 20-100 EtOAc/Hexanes) to afford the product (S)-2-amino-4-(1-(8-chloro-1-oxo-2-phenyl-1,2-dihydroisoquinolin-3-yl)ethylamino)-6-methylpyrimidine-5-carbonitrile 89. ESI-MS m/z: 431.2 [M+H]$^+$.

Example 61

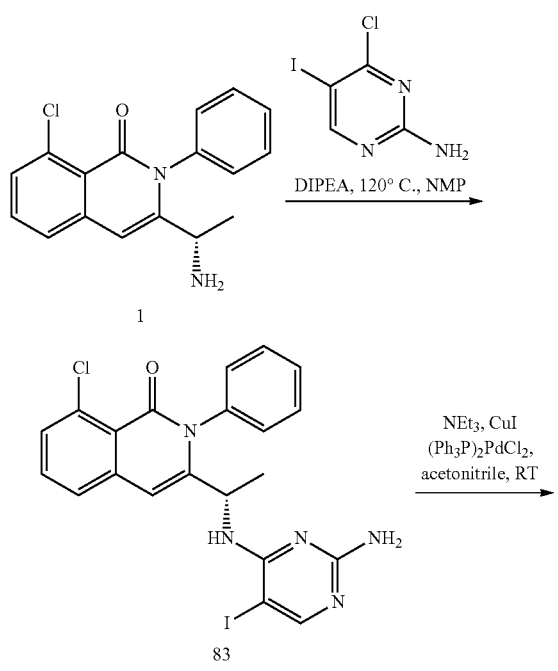

266

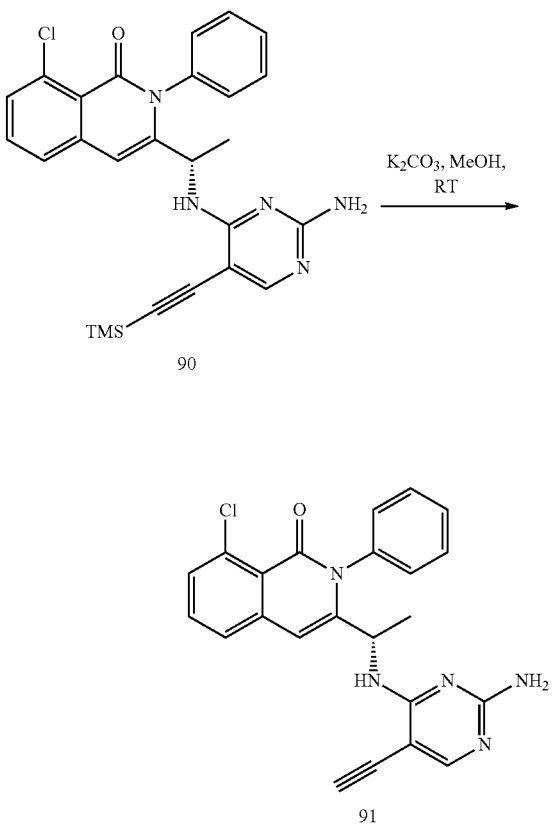

To a stirred mixture of compound 1 (0.335 mmol, 1 eq) and 4-chloro-5-iodopyrimidin-2-amine (0.502 mmol, 1.5 eq) in NMP (3 mL) at 120° C., DIPEA was added and the resulting mixture was stirred at 120° C. overnight and then cooled to room temperature. The mixture was partitioned between ethyl acetate and brine, washed several times with brine, dried and concentrated. The product was purified by silica gel column chromatography eluting with ethyl acetate/hexanes to give product 83.

To a stirred mixture of 83 (0.044 mmol, 1 eq) and copper(I) iodine (4.44 μmol, 0.1 eq) in triethylamine, dichlorobis(triphenylphosphine) palladium (4.44 μmol, 0.1 eq) and TMS-acetylene (0.049 mmol, 6.91 μl) were added. The mixture was degassed for 15 minutes and then stirred for 1 h at room temperature. The mixture was extracted with ethyl acetate and washed with brine, and the organic layers were concentrated to give product 90.

To a stirred mixture of 90 in methanol (2 mL), potassium carbonate (10.66 μmol, 0.15 eq) was added. The mixture was stirred under argon at room temperature for 40 minutes. The mixture was then extracted with ethyl acetate and washed with brine. The organic layers were separated and concentrated under vacuum. The product was purified by silica gel column chromatography eluting with ethyl acetate (from 10 to 100%)/hexanes to give product 91. ESI-MS m/z: 416.2 [M+H]$^+$.

Example 62

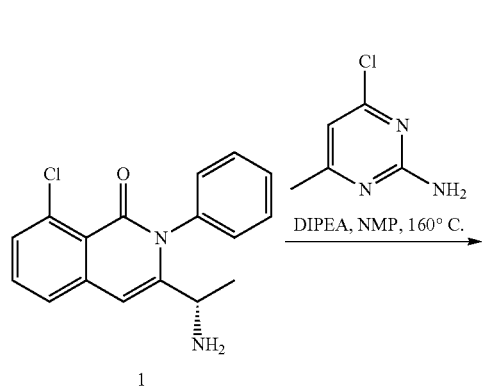

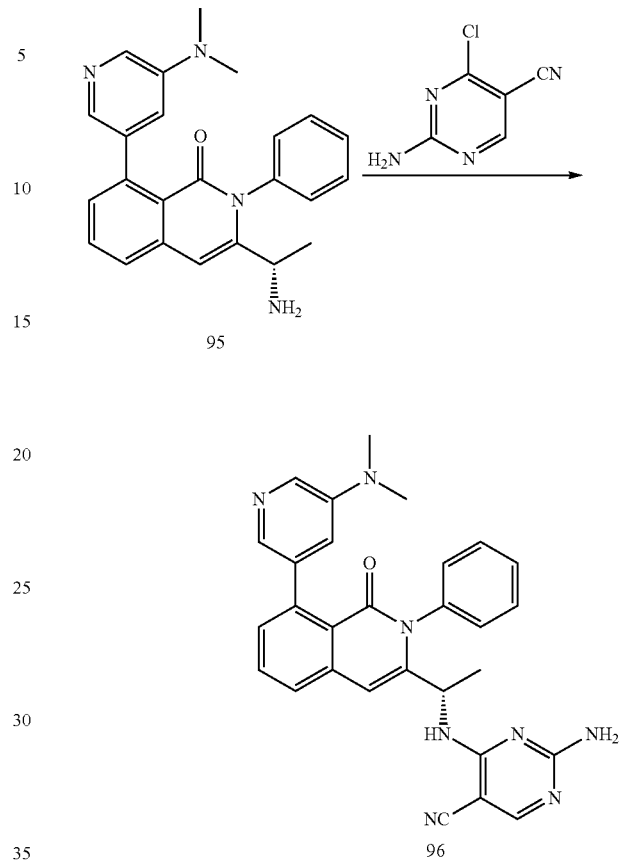

To a stirred mixture of 2-amino-4-chloro-6-methylpyrimidine (0.266 mmol, 1.62 eq) and compound 1 (0.164 mmol, 0.164 mmol, 1 eq) in NMP (1.5 ml), DIPEA (0.656 mmol, 4 eq) was added. The mixture was heated to 160° C. for 12 hours. Then the mixture was extracted with ethyl acetate and washed with water and brine. The product was purified by silica gel column chromatography eluting with DCM/methanol (from 0 to 10%) to afford the product (S)-3-(1-((2-amino-6-methylpyrimidin-4-yl)amino)ethyl)-8-chloro-2-phenyl-isoquinolin-1(2H)-one 92. ESI-MS m/z: 406.2 [M+H]$^+$.

Compound 94 was prepared from compound 1 in two steps by Suzuki coupling with benzo[d][1,3]dioxol-5-ylboronic acid in analogous fashion to compound 2 in Example 1 to afford compound 93, then coupling to 2-amino-4-chloropyrimidine-5-carbonitrile (E-2) (prepared by Method E) according to Method G. ESI-MS m/z: 503.0 [M+H]$^+$.

Example 63

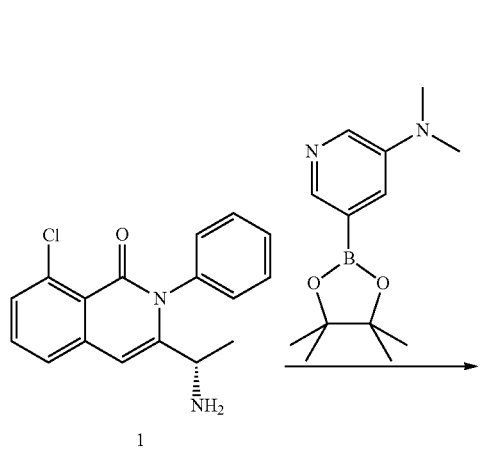

Example 64

-continued

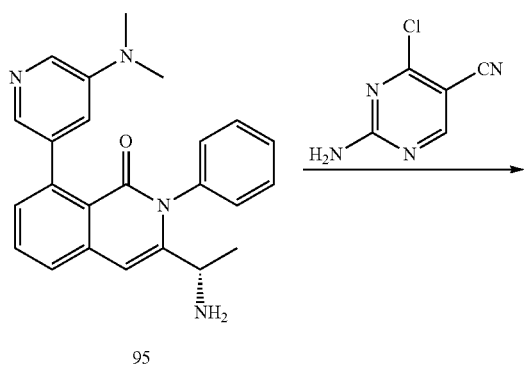

95

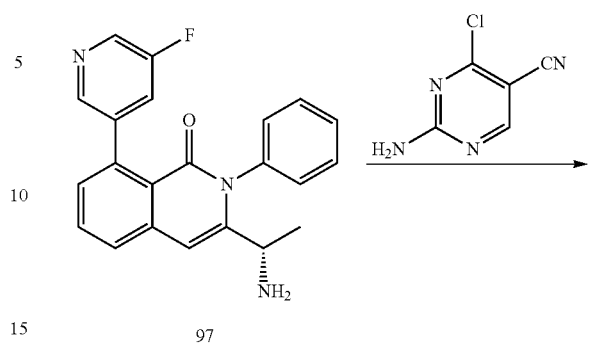

97

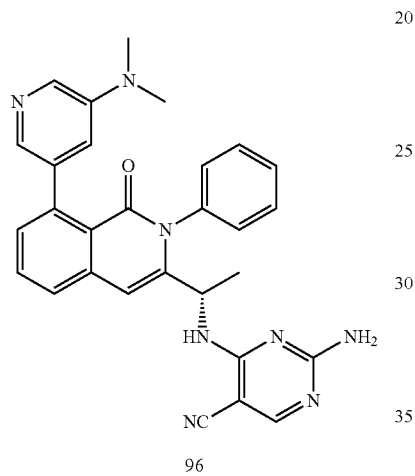

96

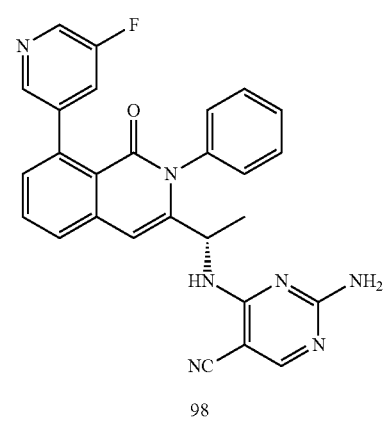

98

Compound 96 was prepared from compound 1 in two steps by Suzuki coupling with N,N-dimethyl-5-(4,4,5,5-tetramethyl-1,3,2-dioxaborolan-2-yl)pyridin-3-amine in analogous fashion to compound 2 in Example 1 to afford compound 95, then coupling to 2-amino-4-chloropyrimidine-5-carbonitrile (E-2) (prepared by Method E) according to Method G. ESI-MS m/z: 503.2 [M+H]$^+$.

Example 65

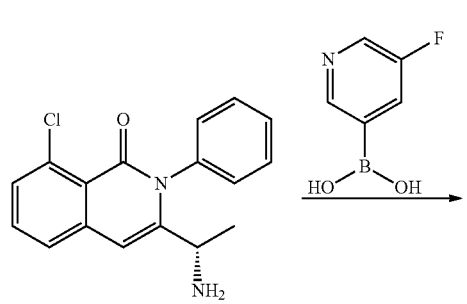

1

Compound 98 was prepared from compound 1 in two steps by Suzuki coupling with (5-fluoropyridin-3-yl)boronic acid in analogous fashion to compound 2 in Example 1 to afford compound 97, then coupling to 2-amino-4-chloropyrimidine-5-carbonitrile (E-2) (prepared by Method E) according to Method G. ESI-MS m/z: 478.2 [M+H]$^+$.

Example 66

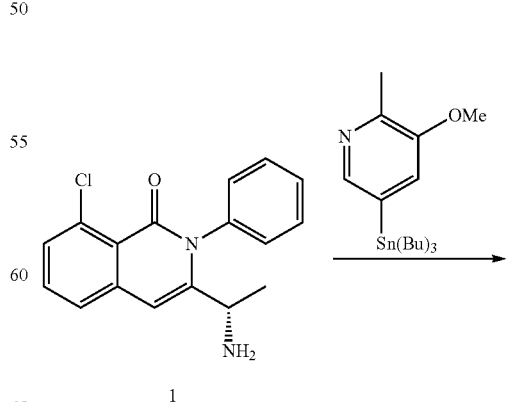

1

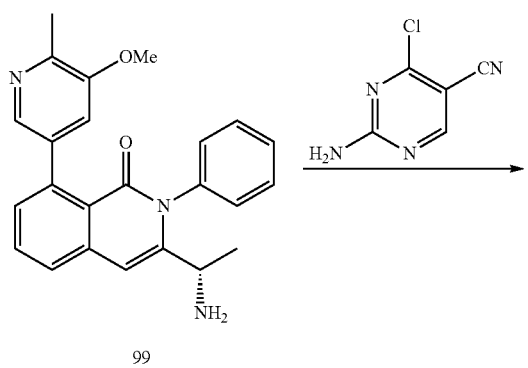

99

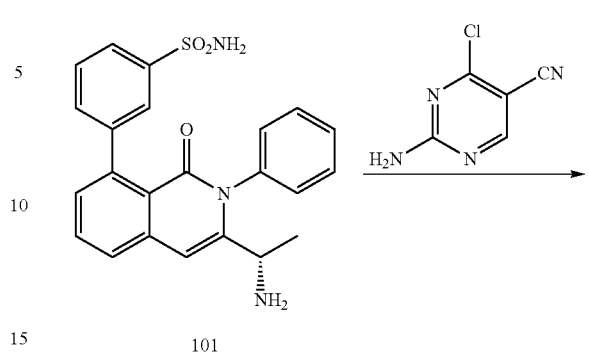

101

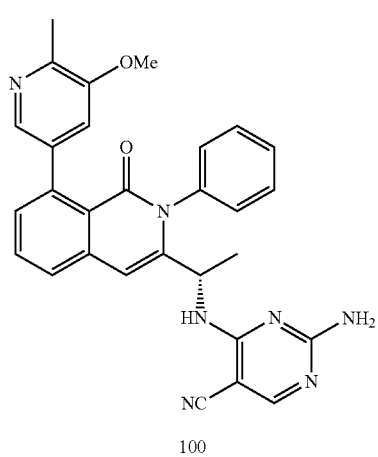

100

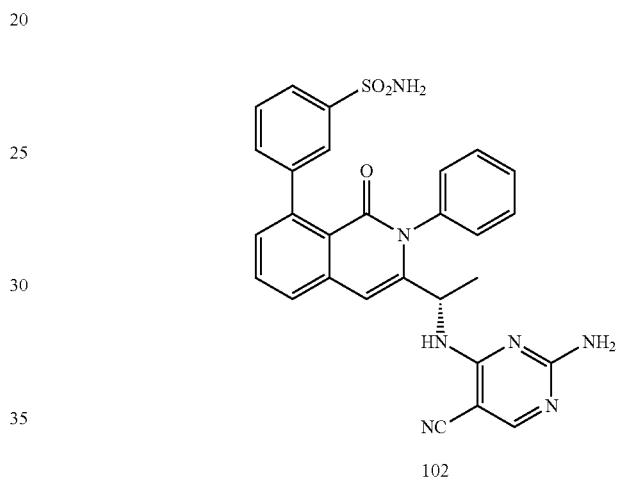

102

Compound 100 was prepared from compound 1 in two steps by Stille coupling with 3-methoxy-2-methyl-5-(tributylstannyl)pyridine in analogous fashion to compound 66 in Example 49 to afford compound 99, then coupling to 2-amino-4-chloropyrimidine-5-carbonitrile (E-2) (prepared by Method E) according to Method G. ESI-MS m/z: 504.2 [M+H]$^+$.

Example 67

Compound 102 was prepared from compound 1 in two steps by Suzuki coupling with 3-(4,4,5,5-tetramethyl-1,3,2-dioxaborolan-2-yl)benzenesulfonamide in analogous fashion to compound 2 in Example 1 to afford compound 101, then coupling to 2-amino-4-chloropyrimidine-5-carbonitrile (E-2) (prepared by Method E) according to Method G. ESI-MS m/z: 538.0 [M+H]$^+$.

Example 68

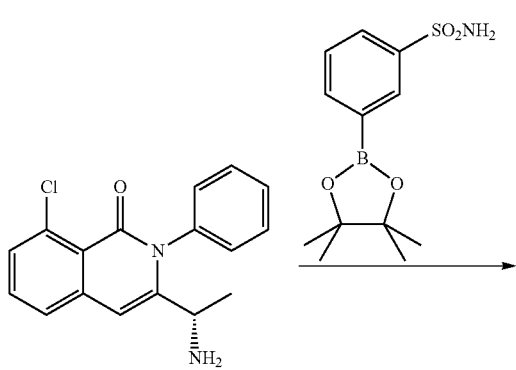

1

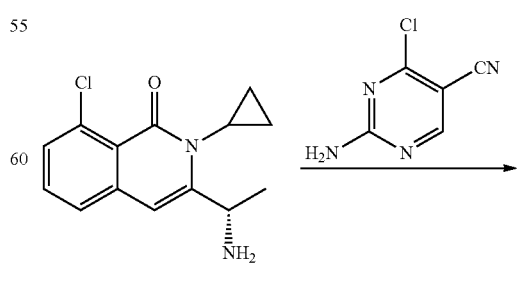

103

-continued

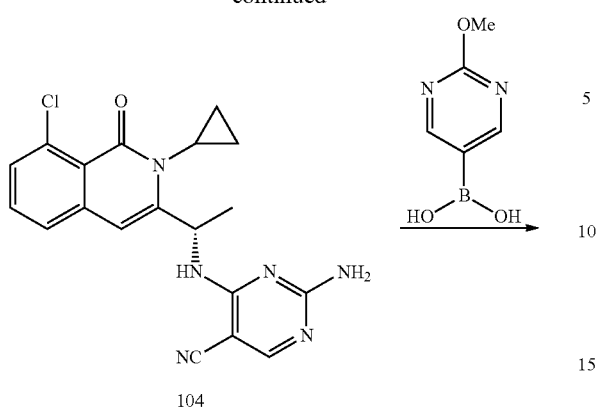

104

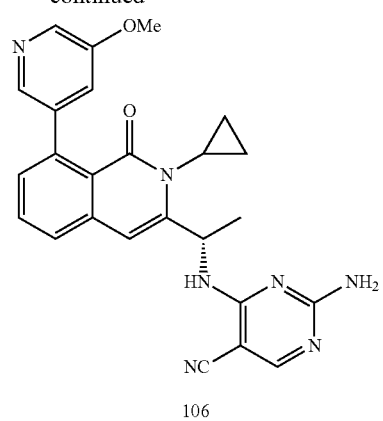

106

Compound 104 was prepared as described in Example 68. Suzuki coupling of compound 104 with (5-methoxypyridin-3-yl)boronic acid was in analogous fashion to compound 9 in Example 2 to afford compound 106. ESI-MS m/z: 454.2 [M+H]$^+$.

Example 70

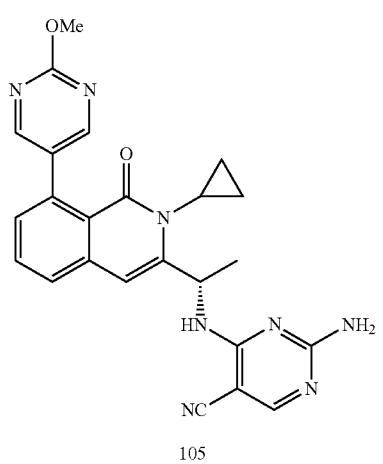

105

Amine 103 was prepared from commercially available 2-chloro-6-methylbenzoic acid according to Method A. Compound 103 was then coupled to 2-amino-4-chloropyrimidine-5-carbonitrile (E-2) according to Method G to afford compound 104. The following Suzuki coupling with (2-methoxypyrimidin-5-yl)boronic acid was in analogous fashion to compound 9 in Example 2 to afford compound 105. ESI-MS m/z: 455.2 [M+H]$^+$.

Example 69

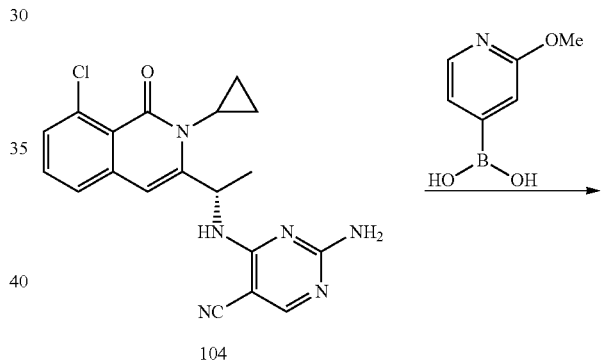

104

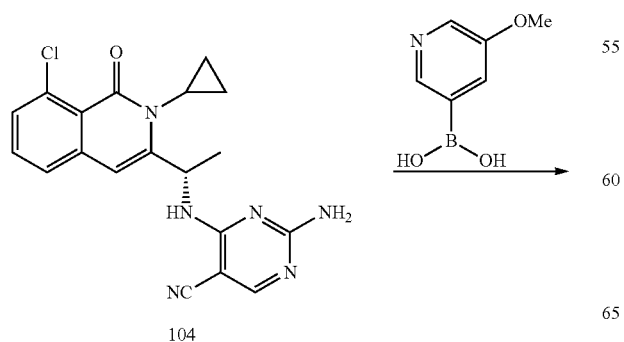

104

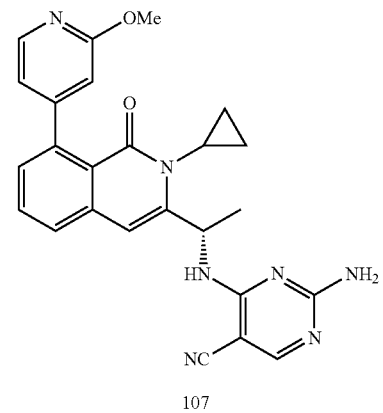

107

Compound 104 was prepared as described in Example 68. Suzuki coupling of compound 104 with ((2-methoxypyridin-4-yl)boronic acid was in analogous fashion to compound 9 in Example 2 to afford compound 107. ESI-MS m/z: 454.2 [M+H]$^+$.

Example 71

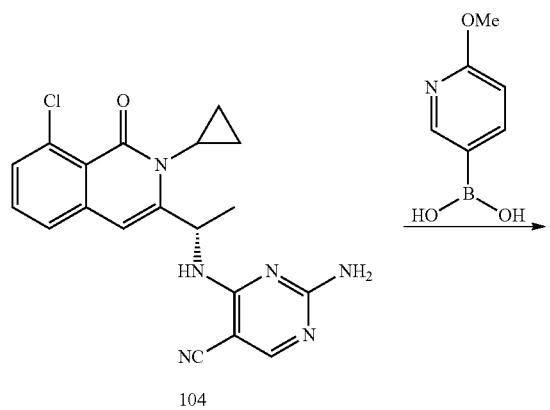

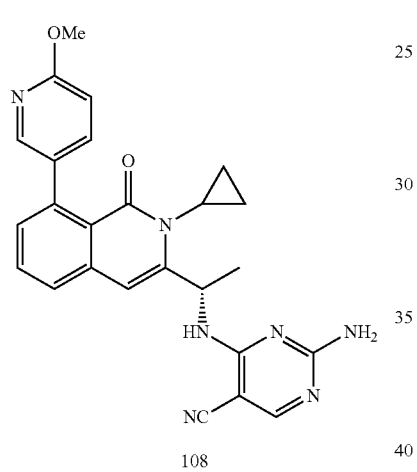

Compound 108 was prepared as described in Example 68. Suzuki coupling of compound 104 with (6-methoxypyridin-3-yl)boronic acid was in analogous fashion to compound 9 in Example 2 to afford compound 108. ESI-MS m/z: 454.0 [M+H]+.

Example 72

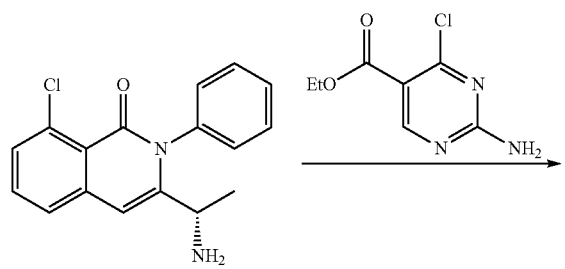

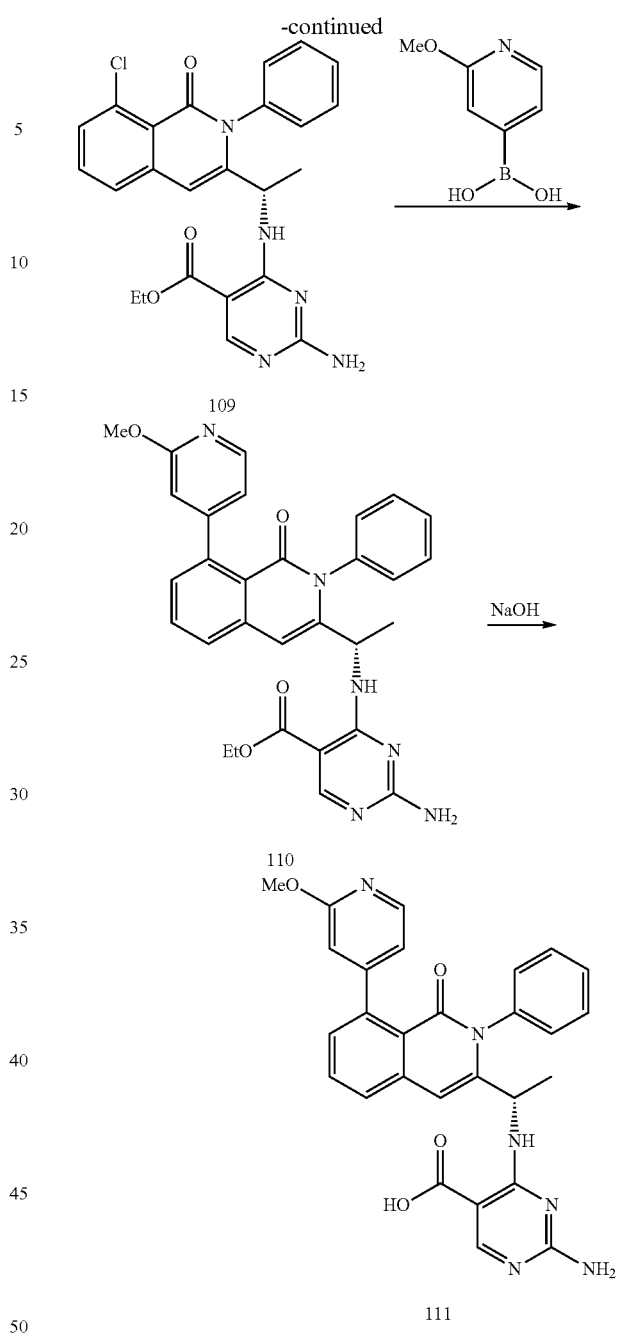

Compound 109 was prepared from compound 8 according to Method G. Compound 109 was then converted to compound 110 according to the following procedure: The mixture of (S)-ethyl 2-amino-4-((1-(8-chloro-1-oxo-2-phenyl-1,2-dihydroisoquinolin-3-yl)ethyl)amino)pyrimidine-5-carboxylate (300 mg, 0.65 mmol) and 2-methoxypyridin-4-yl)boronic acid (149 mg, 0.98 mmol) in 1,4-dioxane:water (3:1, 12 mL) was degassed and backfilled with argon (three cycles). To this mixture, 2-dicyclohexylphosphino-2',6'-diisopropoxybiphenyl (121 mg, 0.26 mmol), palladium(II) acetate (29 mg, 0.13 mmol), and Na$_2$CO$_3$ (207 mg, 1.95 mmol) were added sequentially. The resulting mixture was degassed and backfilled with argon (three cycles), and then stirred at 120° C. for 3 h. The mixture was allowed to cool to RT, and then partitioned between ethyl acetate and water. The organic layer was washed with brine, dried over Na$_2$SO$_4$ and filtered. The filtrate was concentrated in vacuo and the residue was purified by ISCO column chromatography (silica gel cartridge, 0-10% MeOH/DCM) to afford the product 110, (S)—ethyl 2-amino-4-((1-(8-(2-methoxypyridin-4-yl)-1-oxo-2-phenyl-1,2-dihydroisoquinolin-3-yl)ethyl)amino)pyrimidine-5-carboxylate.

To a solution of compound 110 (196 mg, 0.37 mmol) in 1,4-dioxane-water (3:1, 8 mL), sodium hydroxide (73 mg, 1.83 mmol) was added and the resulting mixture was stirred at 50° C. for 1 h. Sodium hydroxide (18 mg, 0.46 mmol) was added to the mixture and stirring was continued for 16 h. The reaction was allowed to cool to RT, and then concentrated in vacuo. The residue was diluted with water and acidified with aqueous HCl (2.0 M) to adjust the pH to 3-4. The mixture was extracted with 10% MeOH-DCM. The organic layer was washed with brine, dried over $Na_2SO_4$ and filtered. The filtrate was concentrated in vacuo to afford product 111, (S)-2-amino-4-((1-(8-(2-methoxypyridin-4-yl)-1-oxo-2-phenyl-1,2-dihydroisoquinolin-3-yl)ethyl)amino)pyrimidine-5-carboxylic acid. ESI-MS m/z: 509.2 $[M+H]^+$.

Example 73

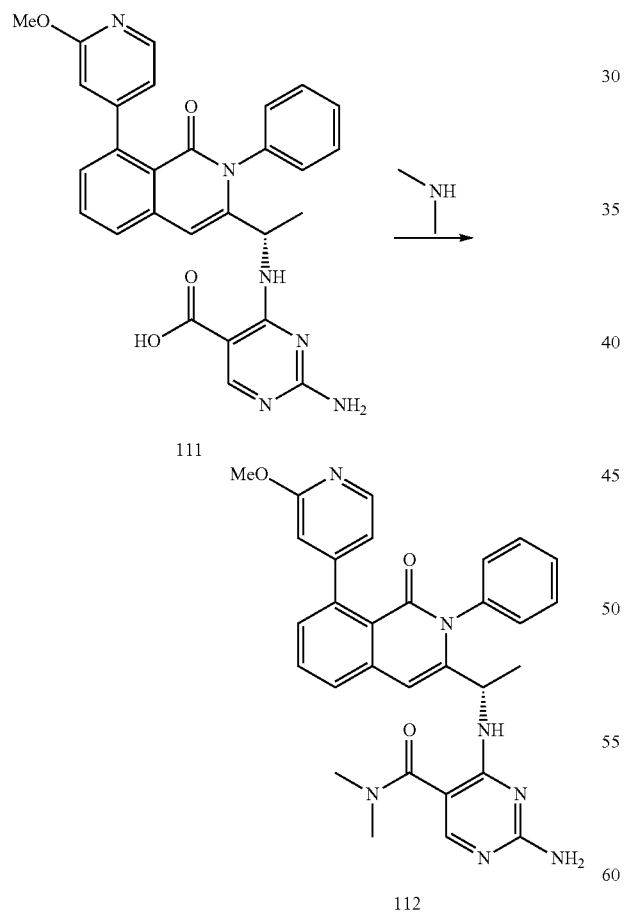

To a solution of (S)-2-amino-4-((1-(8-(2-methoxypyridin-4-yl)-1-oxo-2-phenyl-1,2-dihydroisoquinolin-3-yl)ethyl)amino)-pyrimidine-5-carboxylic acid (44 mg, 0.087 mmol) in anhydrous N,N-dimethylmethanamide (3 mL), 1-ethyl-3-(3-dimethylaminopropyl)carbodiimide (25 mg, 0.13 mmol) and hydroxybenzotriazole (18 mg, 0.13 mmol) were added and the resulting mixture was stirred at RT for 30 min. To this mixture, dimethylamine (2M in THF, 0.065 mL, 0.13 mmol) and N,N-diisopropylethylamine (0.040 mL, 0.19 mmol) were added and the reaction mixture was stirred at RT for 3 h. The mixture was partitioned between water and ethyl acetate. The organic layer was washed with brine, dried over $Na_2SO_4$ and filtered. The filtrate was concentrated in vacuo to afford the product 112, (S)-2-amino-4-((1-(8-(2-methoxypyridin-4-yl)-1-oxo-2-phenyl-1,2-dihydroisoquinolin-3-yl)ethyl)amino)-N,N-dimethylpyrimidine-5-carboxamide. ESI-MS m/z: 533.8 [M−H]

Example 74

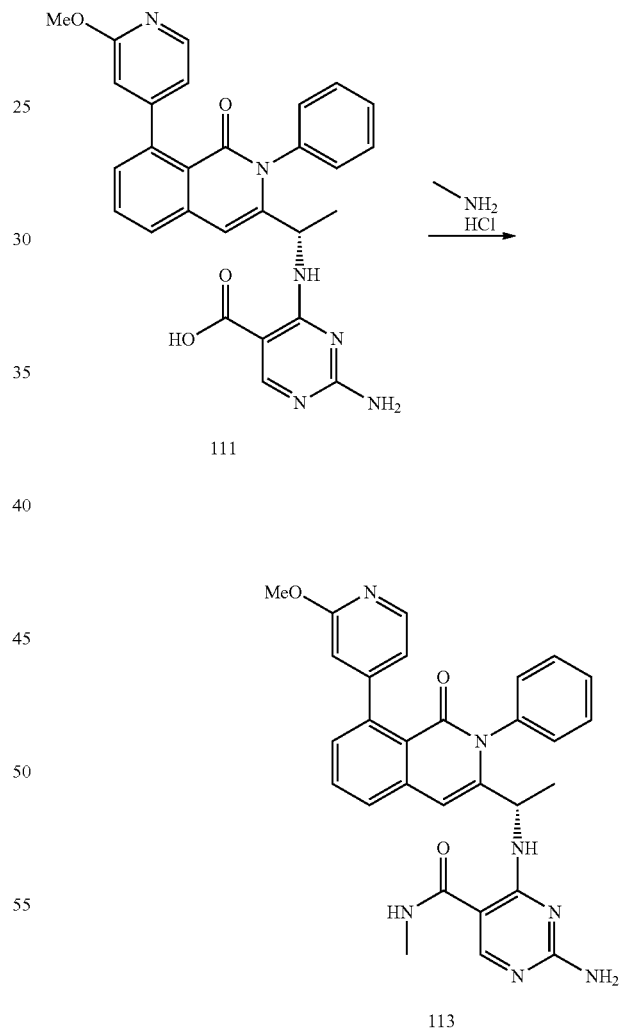

Compound 113 was prepared from compound III in analogous fashion to compound 112 except that methylamine hydrochloride was used in place of dimethylamine. ESI-MS m/z: 522.2.0 $[M+H]^+$.

Example 75

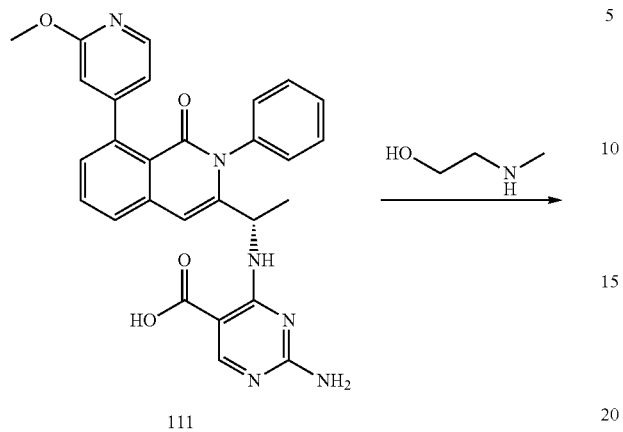

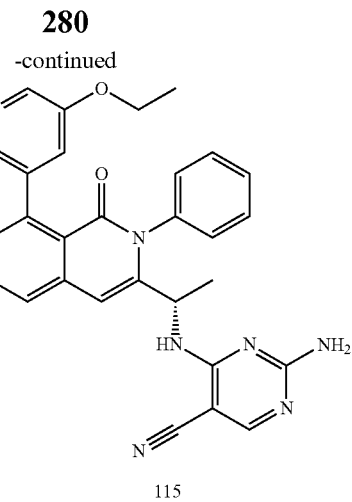

Compound 115 was prepared by Suzuki coupling of compound 8 and (5-ethoxypyridin-3-yl)boronic acid according to Example 2. ESI-MS m/z: 504.2 [M+H]$^+$.

Example 77

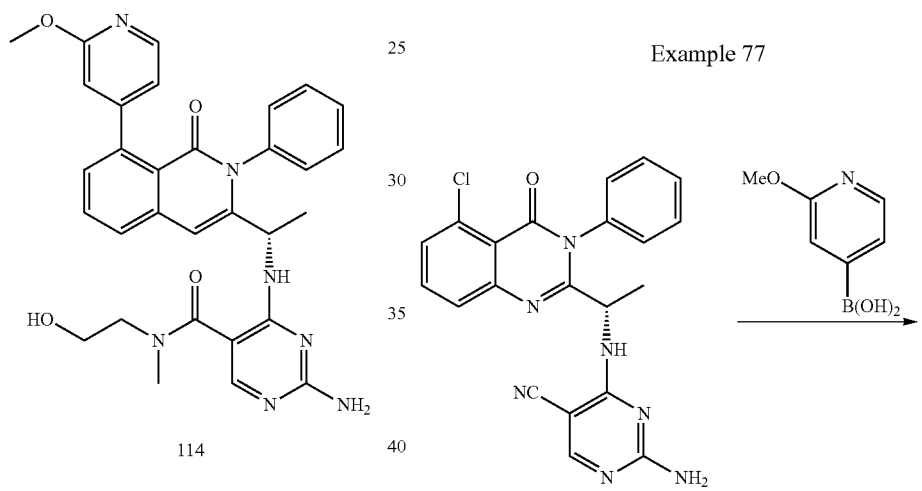

Compound 114 was prepared from compound III in analogous fashion to compound 112 except that 2-dimethylaminoethanol was used in place of dimethylamine. ESI-MS m/z: 565.8 [M+H]$^+$.

Example 76

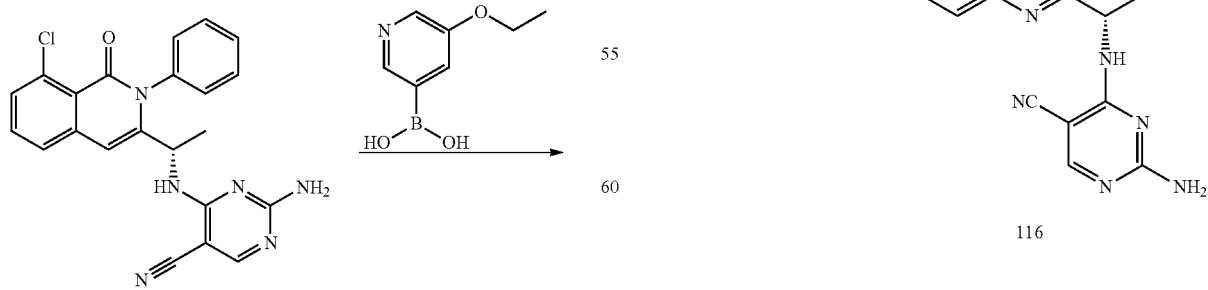

Compound 116 was prepared from compound 62 in analogous fashion to compound 66 in Example 49. ESI-MS m/z: 491.2 [M+H]$^+$.

Example 78

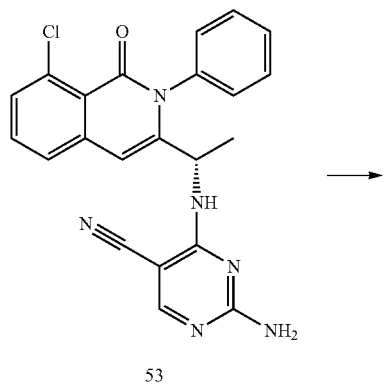

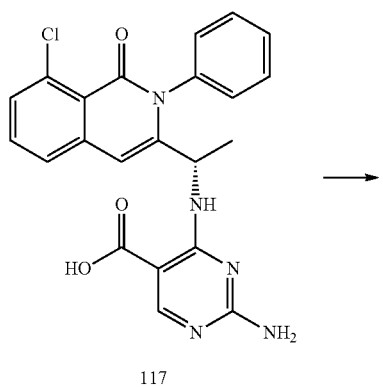

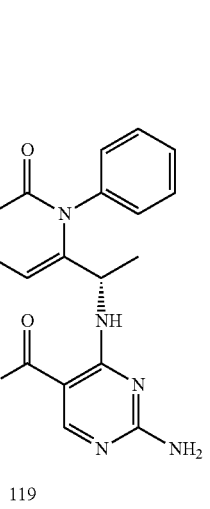

To a solution of (S)-2-amino-4-((1-(8-chloro-1-oxo-2-phenyl-1,2-dihydroisoquinolin-3-yl)ethyl)amino)pyrimidine-5-carbonitrile (53) (495 mg, 1.19 mmol) in anhydrous 1,4-dioxane (20 mL), sulfuric acid/water (1:1, 7 mL) was added dropwise. The reaction mixture was stirred at 90° C. for 60 h. The mixture was allowed to cool to RT and basified with NaHCO$_3$. The precipitate was collected by filtration and then dissolved in water. The resulting mixture was extracted with ethyl acetate. The combined organic layers were washed with brine, dried over Na$_2$SO$_4$ and filtered. The filtrate was concentrated in vacuo to afford the product 117, (S)-2-amino-4-((1-(8-chloro-1-oxo-2-phenyl-1,2-dihydroisoquinolin-3-yl)ethyl)amino)pyrimidine-5-carboxylic acid. The material was used directly in the next step.

Compound 117 was converted to compound 118 in analogous fashion to compound 112 in Example 73. Compound 118 was then converted to 119 by Suzuki coupling with (2-methoxypyridin-4-yl)boronic acid in analogous fashion to compound 8 in Example 2. ESI-MS m/z: 575.9 [M−H]⁻.

Example 79

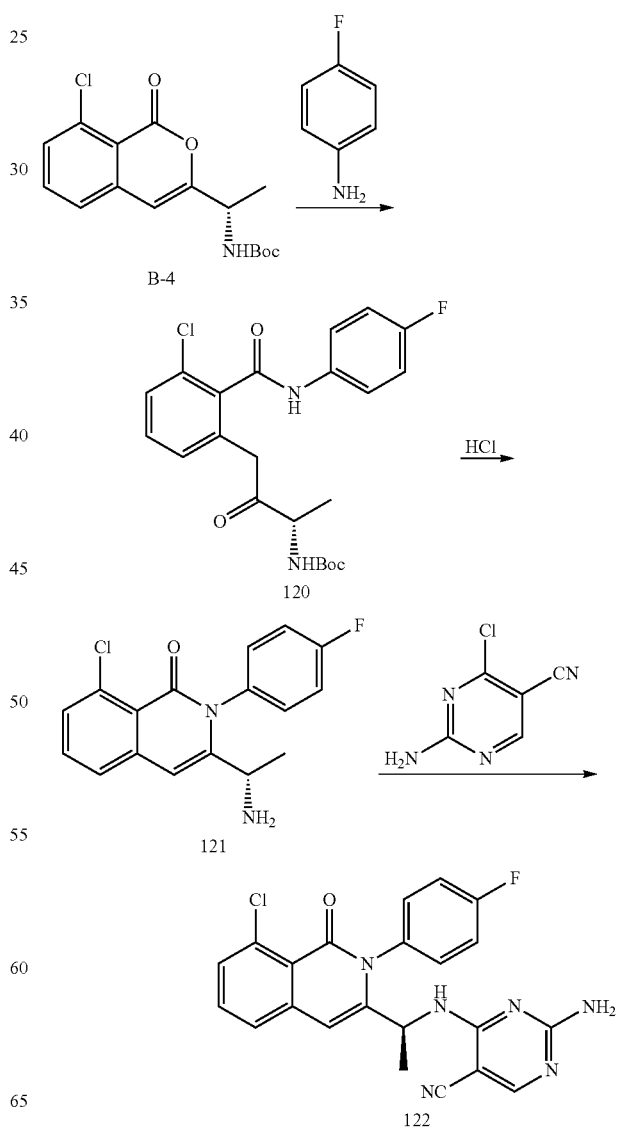

Compound 121 was synthesized in analogous fashion to B-6 using Method B and 4-fluoroaniline as the amine coupling partner. Compound 121 was then coupled with 2-amino-4-chloropyrimidine-5-carbonitrile according to Method G to afford the product 122. ESI-MS m/z: 435.2 [M−H]+.

Example 80

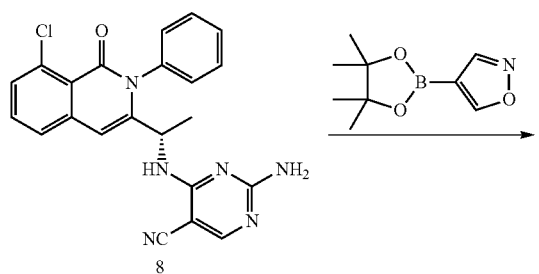

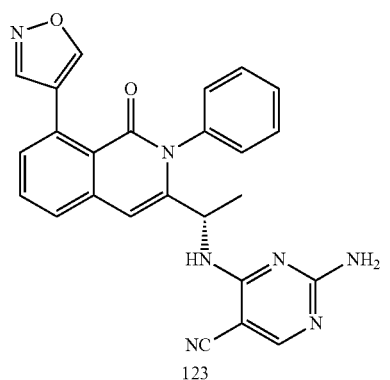

123

+

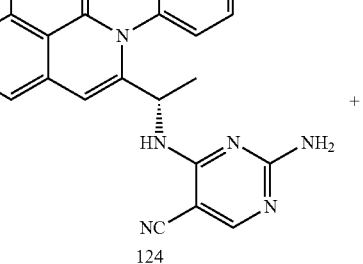

124

+

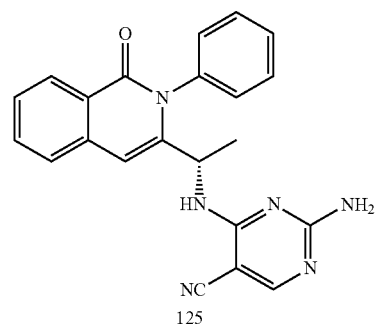

125

A mixture of compound 8 (71.1 mg, 0.17 mmol, 1.0 equiv.), 4-isoxazole pinacol boronate (66.5 mg, 0.34 mmol, 2.0 equiv.), sodium carbonate (90 mg, 0.85 mol, 5 equiv.) and Pd-AMPHOS catalyst (24.1 mg, 0.034 mmol, 0.2 equiv.) in 1.5 ml degassed 4:1 dioxane-water was heated for 1 h. before partitioning between EtOAc and water. The organic layer was collected, the aqueous layer was extracted with EtOAc, and the combined EtOAc layers were washed with brine. The solvent was removed and the residue was purified on silica gel to provide 124 (ESI-MS m/z: 422.2 [M−H]+) and a mixture of 123 and 125. The mixture was then purified by HPLC to give 123 (ESI-MS m/z: 450.2 [M−H]+) and 125 (ESI-MS m/z: 383.2 [M−H]+).

Example 81

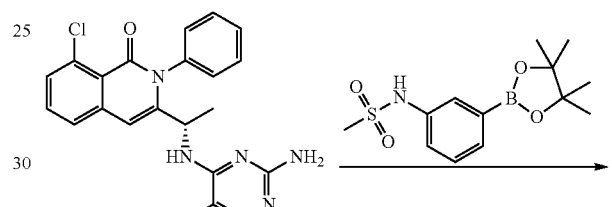

8

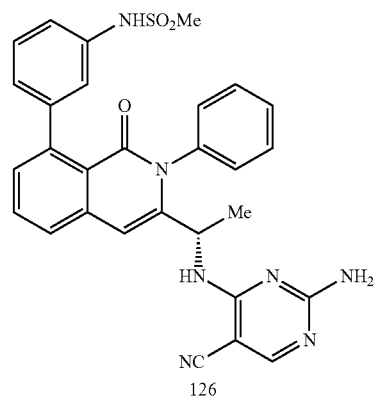

126

Compound 126 was prepared from compound 8 using N-(3-(4,4,5,5-tetramethyl-1,3,2-dioxaborolan-2-yl)phenyl) methanesulfonamide in the Suzuki reaction according to Method J. ESI-MS m/z: 552.2 [M−H]+.

Example 82
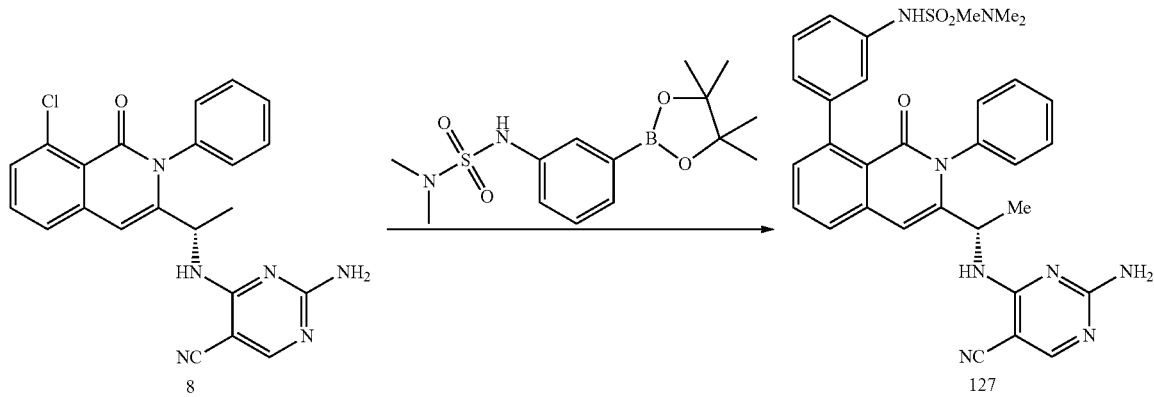
Compound 127 was prepared from compound 8 using 3-(N,N-dimethylsulfamoylamino)phenylboronic acid in the Suzuki reaction according to Method J. ESI-MS m/z: 552.2 [M−H]+.
Example 83
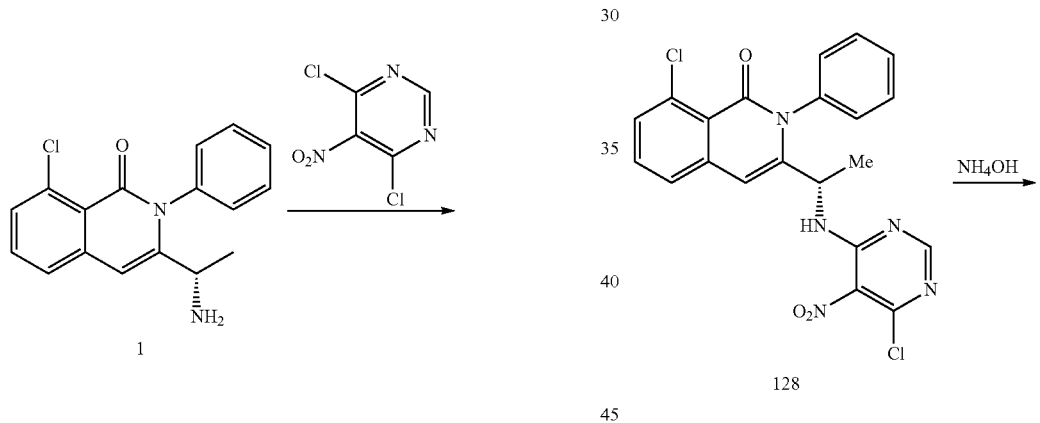
Compound 128 was prepared from compound 1 using 4,6-dichloro-5-nitropyrimidine according to Method G. ESI-MS m/z: 456.1 [M−H]+.
Example 84
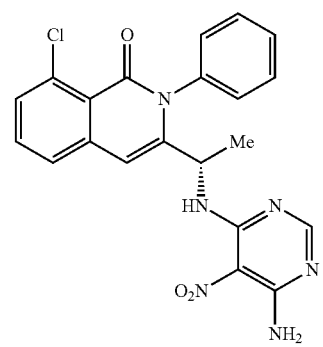

Compound 129 was prepared from compound 128 using the procedure to convert compound 3 to compound 4 in Example 1. ESI-MS m/z: 456.1 [M−H]+.
Example 85
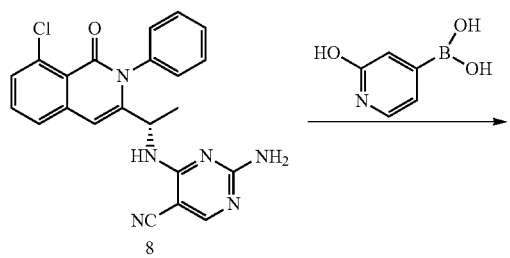
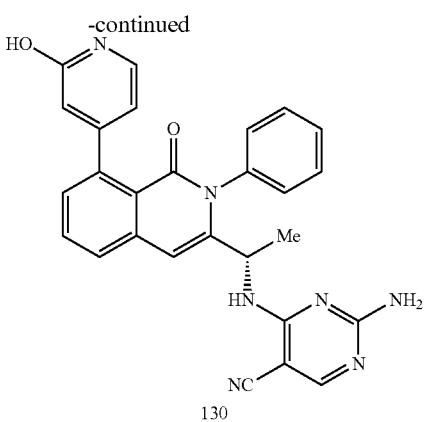
Compound 130 was prepared from compound 8 using 2-hydroxypyridin-4-ylboronic acid in the Suzuki reaction according to Method J. ESI-MS m/z: 476.2 [M−H]+.
Example 86
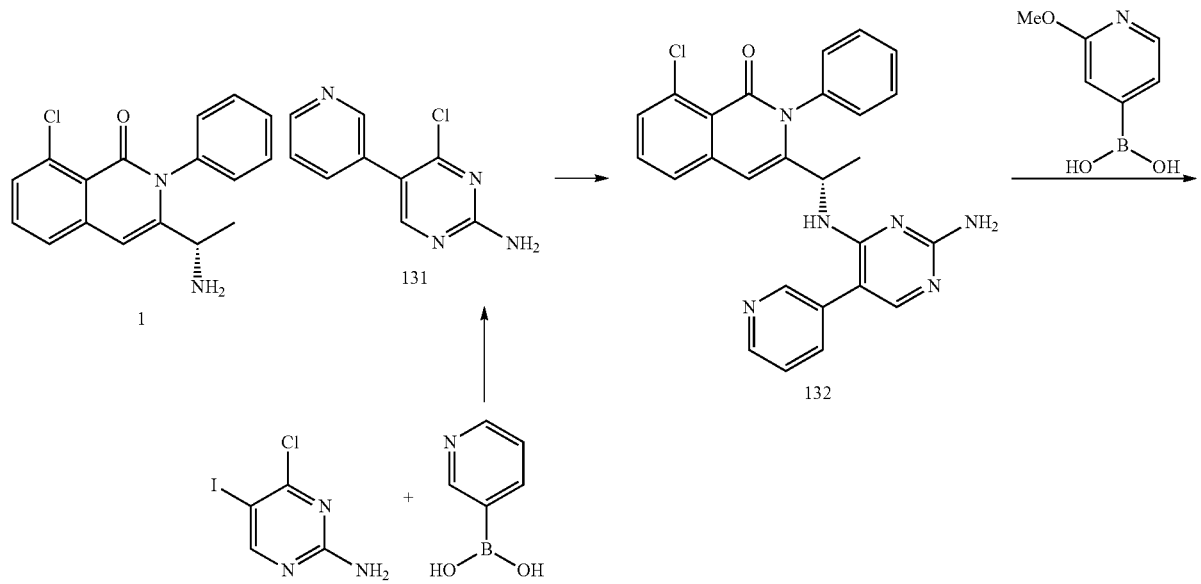
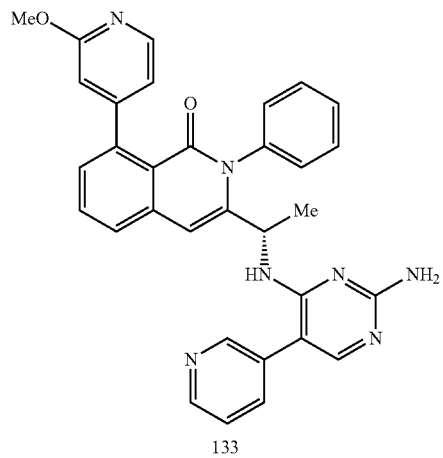

4-Chloro-5-(pyridin-3-yl)pyrimidin-2-amine 131 was prepared from the coupling of 4-chloro-5-iodopyrimidin-2-amine with pyridin-3-ylboronic acid as follows: the amine (150 mg, 0.587 mmol), and the boronic acid (144 mg, 1.174 mmol) were suspended in dioxane (2.5 mL) and Na₂CO₃ (783 µA, 1.174 mmol) The mixture was bubbled with Ar for 5 min then charged with Pd(Ph₃P)₄ (136 mg, 0.117 mmol). The mixture was stirred at 90° C. for 2 h, then cooled to room temperature. The mixture was partitioned between EtOAc and water. The organic layer was dried, filtered, and concentrated to give a residue which was purified by silica gel column chromatography to give 4-chloro-5-(pyridin-3-yl)pyrimidin-2-amine 131.

Compound 132 was prepared from 1 using 4-chloro-5-(pyridin-3-yl)pyrimidin-2-amine in the coupling reaction according to Method G. Compound 133 was prepared from 132 using 2-methoxypyridin-4-ylboronic acid in the Suzuki reaction according to Method J.

Example 87

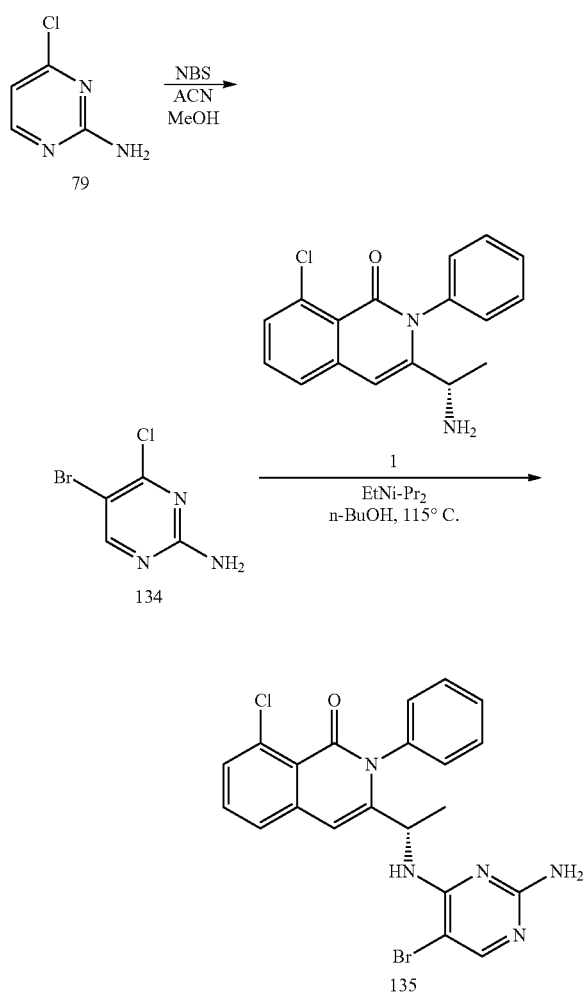

To a mixture of 2-amino-4-chloro-pyrimidine 79 (10.2 g, 79 mmol) in methanol (140 mL) and acetonitrile (100 mL), N-bromosuccinimide (14.01 g, 79 mmol) was added, and the resulting mixture was stirred at RT for about 0.5 h. The reaction mixture was treated with Et₂O (200 mL), then cooled to about 5° C. and stirred for about 1 h. The mixture was filtered and the product air dried to afford compound 134.

To a mixture of compound 134 (4.83 g, 23.23 mmol) and compound 1 (5.34 g, 17.87 mmol) in anhydrous n-butanol (80 mL), diisopropylethylamine (6.93 g, 053.6 mmol) was added, and the resulting mixture was stirred at about 115° C. for about 36 hrs. The mixture was allowed to cool to RT and concentrated in vacuo. The residue was suspended in toluene (100 mL) and concentrated in vacuo. The resulting product was suspended in toluene and heated to reflux, then cooled to about 5° C. over about 2 hrs. The resulting suspension was filtered, the solids washed with cold toluene, then air dried to afford the product 135. ESI-MS m/z: 470.0 [M+H]⁺.

Example 88

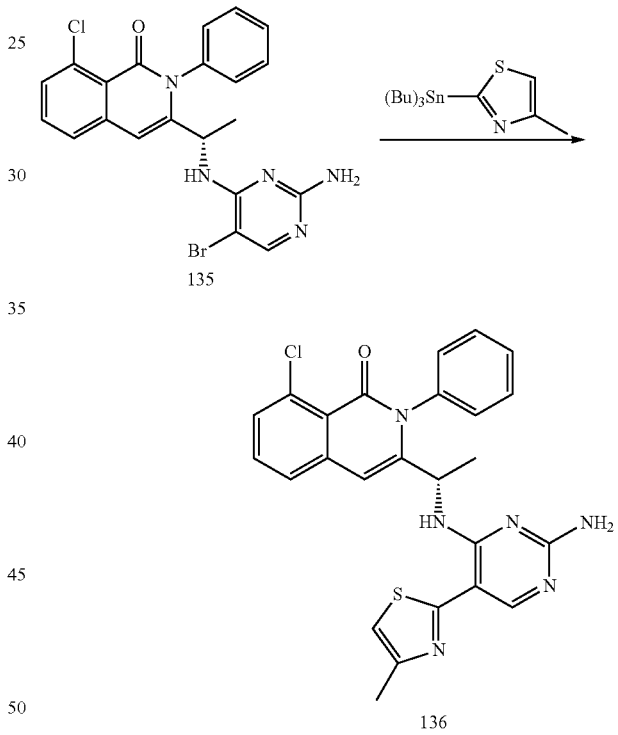

A mixture of compound 135 (125 mg, 0.266 mmol) and 4-methyl-2-(tribyulstannyl)thiazole (129 mg, 0.332 mmol) in anhydrous toluene (2 mL) in a sealed tube was degassed by bubbling Ar for 5 min. The mixture was charged with Pd(PPh₃)₄ (31 mg, 0.027 mmol) and the resulting mixture was stirred at 90° C. for 15 hrs. The reaction mixture was allowed to cool to room temperature, filtered, washed with toluene and the filtrate was concentrated in vacuo. The residue was purified by column chromatography (silica gel cartridge, 0-10% MeOH in 1/1 EtOAc-DCM). The residue was further purified by semi-prep HPLC (ACN/water/ammonium bicarbonate) to affort product 136. ESI-MS m/z: 489.1 [M+H]⁺.

Example 89

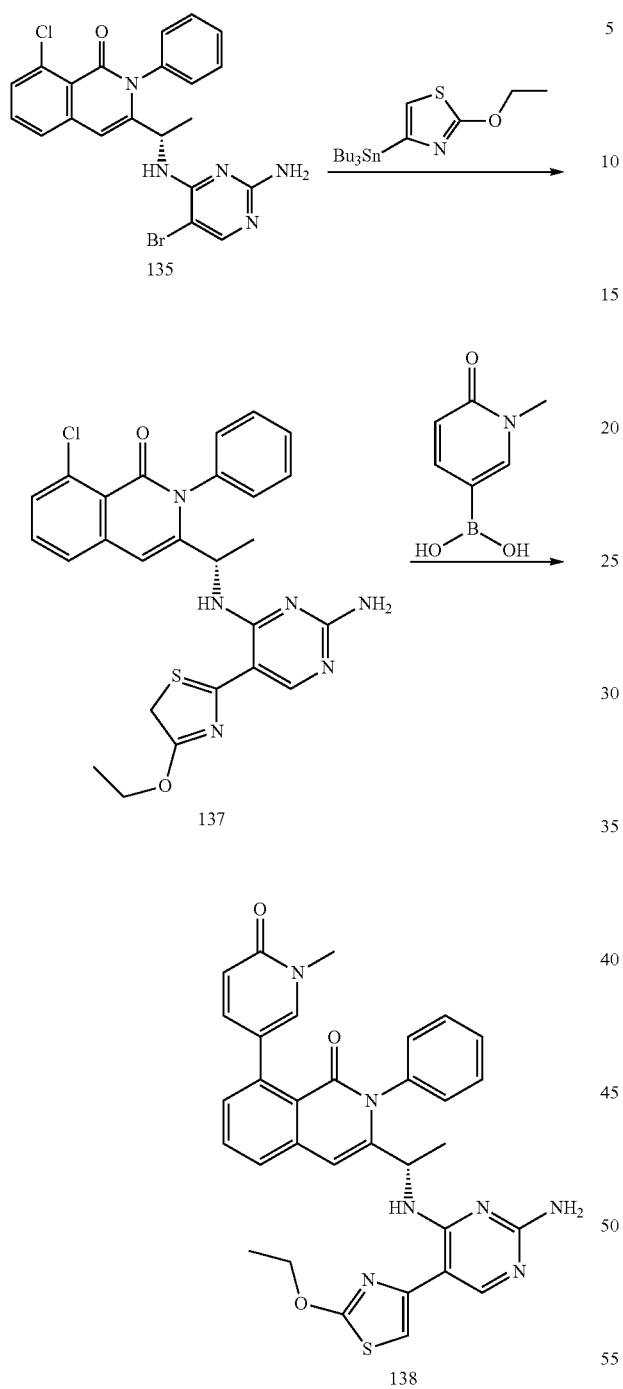

Example 90 temperature and poured into a saturated sodium bicarbonate/EtOAc mixture. The layers were separated and the organic layer was dried over Na$_2$SO$_4$, filtered and concentrated. The residue was purified by HPLC to give the product 138. ESI-MS m/z: 592.3 [M+H]$^+$.

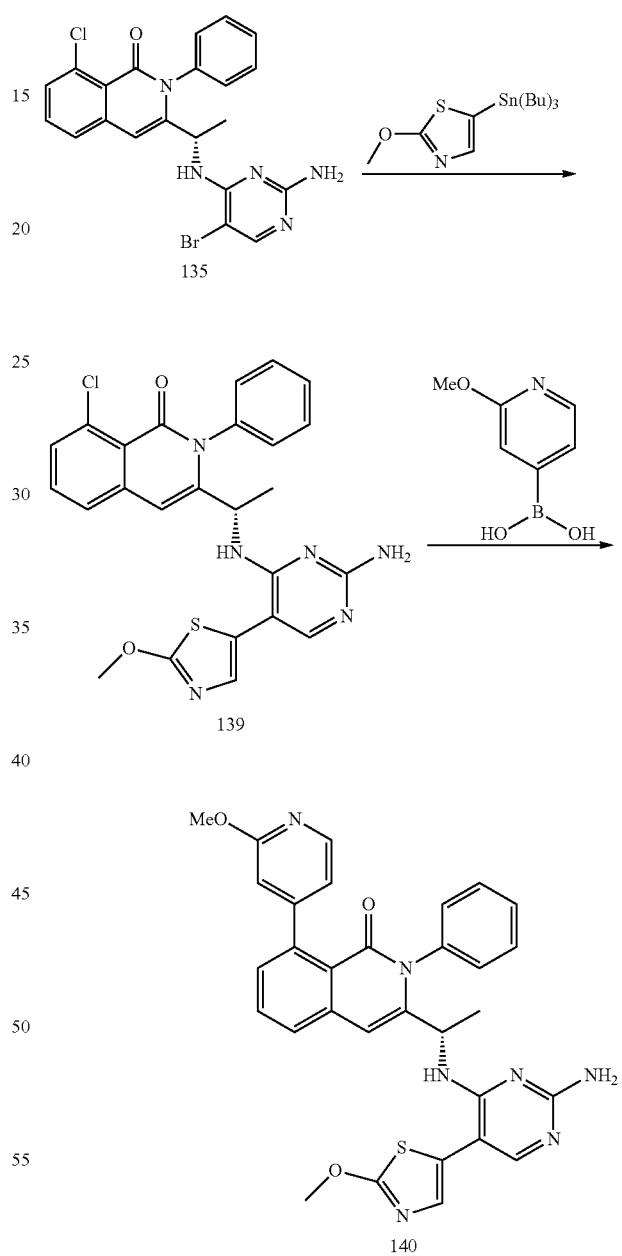

Compound 137 was prepared from compound 135 using 2-ethoxy-4-(tributylstannyl)thiazole in analogous fashion to compound 136 in Example 88. Compound 137 (60.5 mg, 0.117 mmol) and 1-methyl-6-oxo-1,6-dihydropyridin-3-yl-boronic acid (54.8 mg, 0.233 mmol) were dissolved in dioxane (2 mL) and Na$_2$CO$_3$ aq. (0.155 ml, 0.233 mmol). The mixture was bubbled with Ar for 5 min then charged with PdCl$_2$(amphos)$_2$ (20.63 mg, 0.029 mmol). The mixture was heated to 80° C. for 2 h. The reaction was cooled to room Compound 139 was prepared from compound 135 using 2-methoxy-5-(tributylstannyl)thiazole in analogous fashion to compound 136 in Example 88. Compound 140 was prepared from compound 139 using 2-methoxypyridin-4-ylboronic acid in analogous fashion to compound 138 in Example 89. ESI-MS m/z: 578.3 [M+H]$^+$.

Example 91

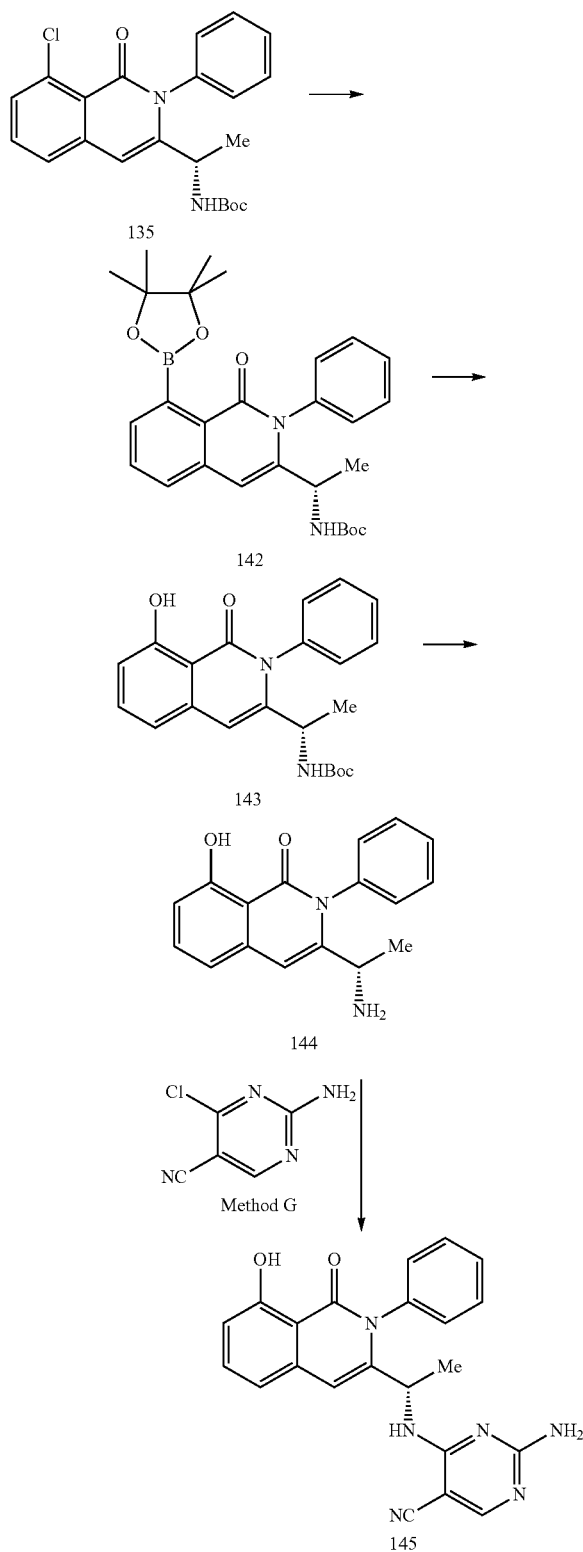

A flask was charged with compound 141 (350 mg, 0.88 mmol), bis(pinacolato)diboron (668 mg, 2.6 mmol), Pd₂(dba)₃ (24 mg, 0.026 mmol), X-phos (25 mg, 0.06 mmol) and potassium acetate (258 mg, 2.6 mmol). The flask was evacuated and filled with Ar. 4 mL of degassed dioxane (bubbling N₂ for 15 min) was added, and the reaction was stirred at 110° C. for 8 h, then cooled to room temperature. The mixture was diluted with ethyl acetate (50 ml) and washed with water (15 ml) and brine and dried. The material was purified with a combiflash silica gel column to give 320 mg of pinacol boronate ester 142.

To a mixture of compound 142 (320 mg, 0.65 mmol) in THF (10 mL) was added 1M NaOH (2 mL, 2.0 mmol), followed by 30% H₂O₂/H₂O (0.67 mL, 6.5 mmol), and the mixture was stirred for 2 h. The mixture was then diluted (EtOAc, 50 mL), washed with H₂O (20 mL), brine, dried and concentrated. Combiflash purification (30% EtOAc) gave phenol 143 (105 mg).

To phenol 143 (40 mg, 0.1 mmol) was added 1.25 M HCl (2.52 mL, 3.15 mmol) and the mixture stirred for 4 h at 50 C. The mixture was cooled to room temperature, MeOH was removed by evaporation, and the residue was diluted with 20 ml DCM. Saturated sodium bicarbonate (5 mL) was added, and the mixture was stirred at room temperature for 1 h. The organic layer was separated from the aqueous layer, and the aqueous layer was extracted with DCM (20 ml). The combined organic layers were dried, filtered, and concentrated to give the amine 144 (26 mg), which was directly used in next step without purification. The amine 144 was treated with 2-amino-4-chloropyrimidine-5-carbonitrile in analogous fashion to Method G to afford product 145. ESI-MS m/z: 399.3 [M+11]⁺.

Example 92

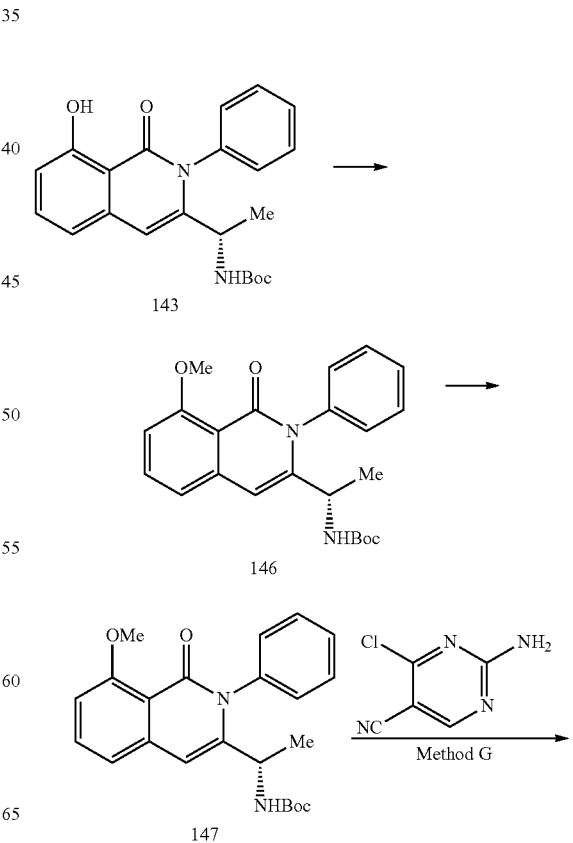

-continued

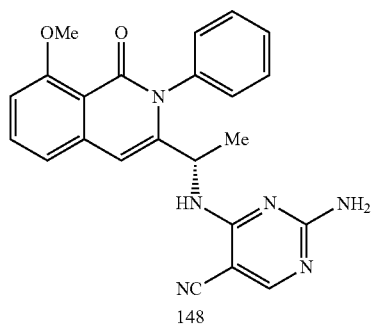

148

To a de-oxygenated suspension of potassium carbonate (65 mg, 0.47 mmol) and dimethyl sulfate (60 mg, 0.47 mmol) in acetone (5 ml) under nitrogen was added compound 143 (30 mg. 0.07 mmol) in de-oxygenated acetone (4 ml). The mixture was heated at reflux under nitrogen for 5 h, then methanol (10 ml) was added and the mixture was refluxed for a further hour. The mixture was filtered and concentrated, and flash chromatography on silica gel gave 26 mg of ether 146. Compound 146 was converted to compound 147 in a similar manner as compound 143 in Example 91 to give amine 146, which was coupled to 2-amino-4-chloropyrimidine-5-carbonitrile using Method G to give product 148. ESI-MS m/z: 413.3 [M+H]$^+$.

Example 93

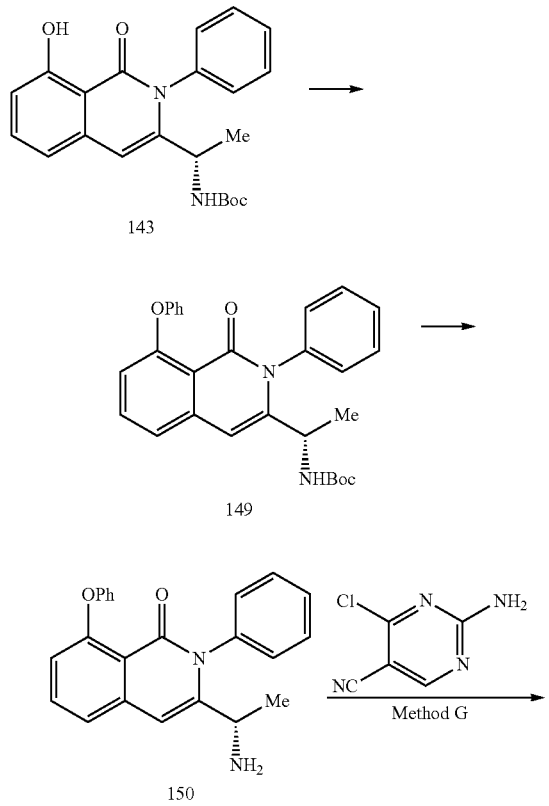

-continued

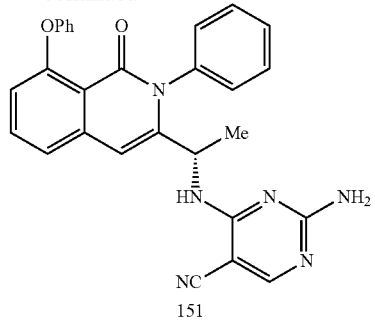

151

A flask was charged with compound 143 (30 mg, 1 equiv), Cu(OAc)$_2$ (29 mg, 2 equiv), phenylboronic acid (20 mg, 2 equiv), and powdered 4 Å MS (15 mg). The mixture was diluted with DCM (8 ml) and Et$_3$N (33 μl, 3 equiv) was added. The reaction was stirred at room temperature for 3 days. The mixture was filtered through a bed of celite/silica. The combined filtrate was concentrated to give product 149 (25 mg), which was used directly in next step. Compound 149 was converted in a similar manner as 143 in Example 91 to give amine 150, which was coupled to 2-amino-4-chloropyrimidine-5-carbonitrile using Method G to give product 151. ESI-MS m/z: 475.3 [M+H]$^+$.

Example 94

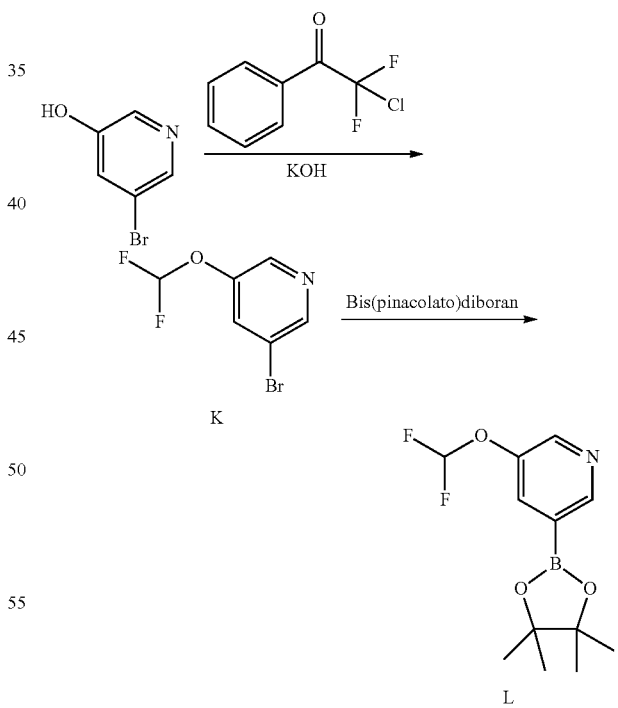

To a mixture of 3-bromopyridol (870 mg, 5 mmol, 1 equiv.), aqueous KOH (21 mL, 30% solution, 105 mmol, 21 equiv.) in 20 mL acetonitrile in a pressure vessel at −78° C. was added 2-chloro-2,2-difluoroacetophenone. The vessel was sealed and heated at 80° C. for 4 h before cooling and diluting with 50 mL MTBE. The organic layer was collected, the aqueous layer was extracted with MTBE (2×50 mL), and the combined organic layers were washed with water (50 mL), brine (50 mL), and dried over sodium sulfate. Then, the solvents were removed in vacuo and the residue was purified on silica gel (12 g, ISCO) using 0→20% EtOAc-hexanes to give K (488 mg).

A mixture of K (475 mg, 2.12 mmol), bis(pinacolato)diboron (808 mg, 3.18 mmol, 1.5 equiv.) and PdCl$_2$(dppf) DCM adduct (87 mg, 0.106 mmol 0.05 equiv.) and potassium acetate (666 mg, 6.8 mmol, 3.2 equiv.) in 10 mL dioxane was heated for 1 h. The mixture was cooled, concentrated in vacuo, diluted with DCM and filtered through a pad of celite. The filter cake was washed with 4×10 mL DCM, and the combined DCM layers were concentrated in vacuo. The residue was purified on silica gel (12 g, ISCO) using 0→50% acetone-DCM to give 312 mg of product L.

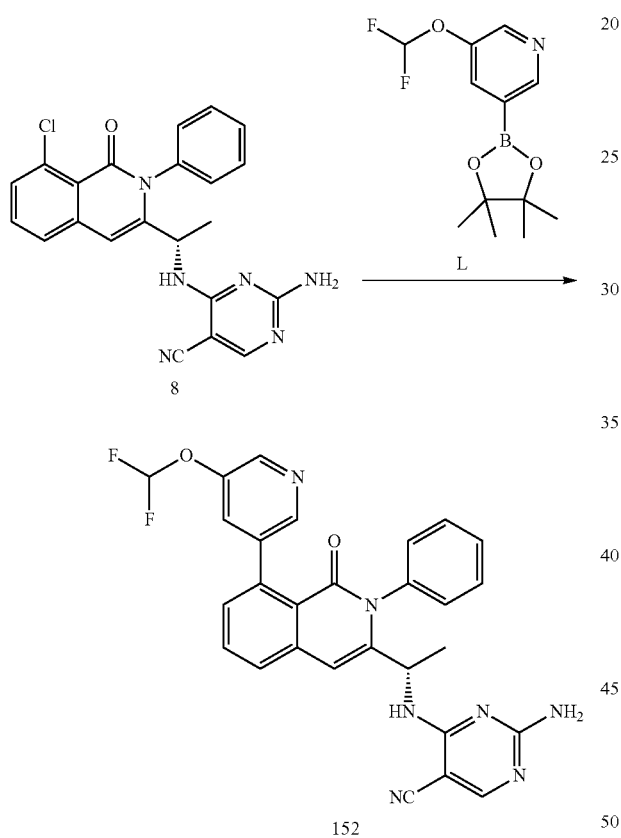

A mixture of compound 8 (70 mg, 0.219 mmol, 1 equiv.), compound L (150 mg, 60%, 0.332 mmol, 2 equiv.) sodium carbonate (89 mg, 0.84 mmol, 5 equiv.) and Pd-AMPHOS catalyst (17.8 mg, 0.025 mmol, 0.15 equiv.) in 1.8 mL of degassed 4:1 dioxane-water was sparged with argon for 2 min. The mixture was sealed and heated at 100° C. for 1 h, cooled, and diluted with 10 mL each EtOAc and water. The organic layer was collected, the aqueous layer was extracted with EtOAc (3×10 mL), the combined EtOAc layers were washed with water (10 mL), brine (10 mL), dried over sodium sulfate and the solvents were removed in vacuo. The residue was purified on silica gel using 0-70% acetone in DCM to give compound 152. ESI-MS m/z: 526.3 [M+H]$^+$.

Example 95

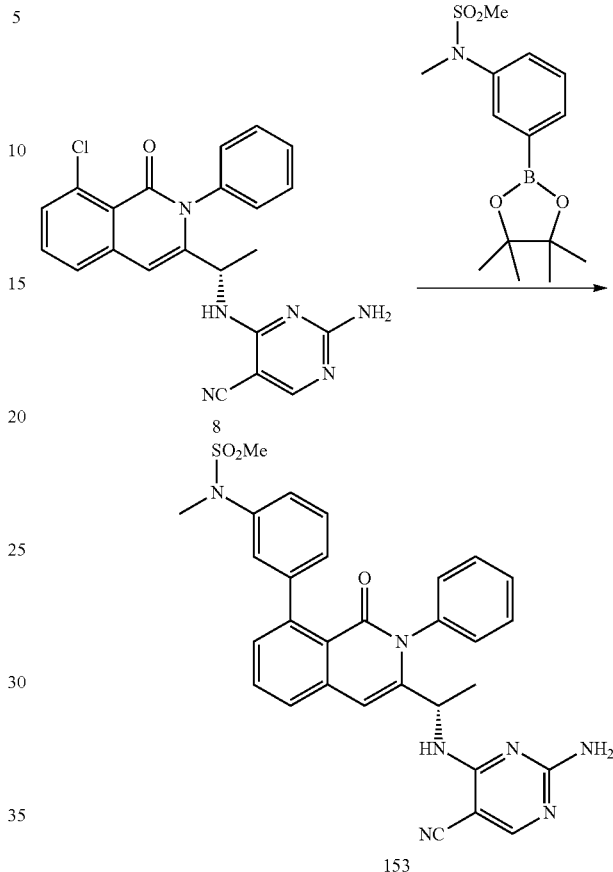

Compound 153 was prepared from compound 8 using Method J as described in Example 94 with N-methyl-N-(3-(4,4,5,5-tetramethyl-1,3,2-dioxaborolan-2-yl)phenyl)methanesulfonamide in the Suzuki reaction. ESI-MS m/z: 566.3 [M+H]$^+$.

Example 96

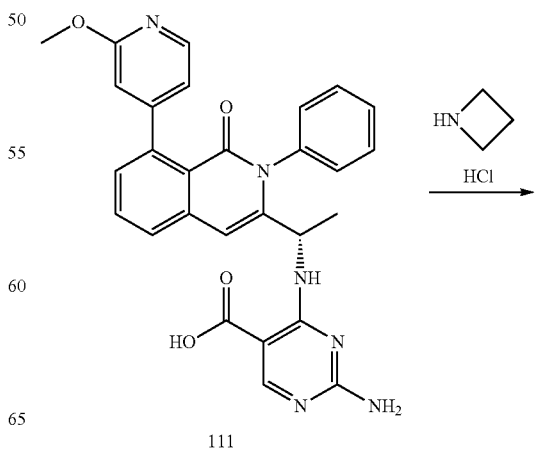

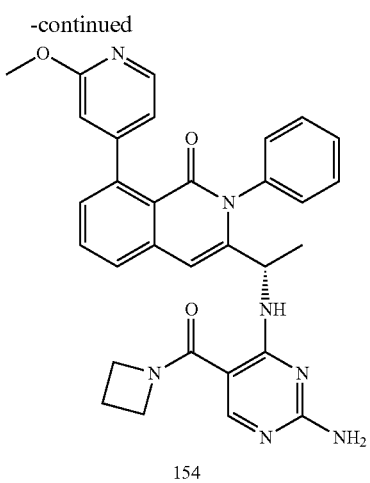

154

Compound 154 was prepared from compound III in analogous fashion to compound 112 in Example 73, where azetidine hydrochloride was used in place of dimethylamine. ESI-MS m/z: 547.8 [M+H]$^+$.

Example 97

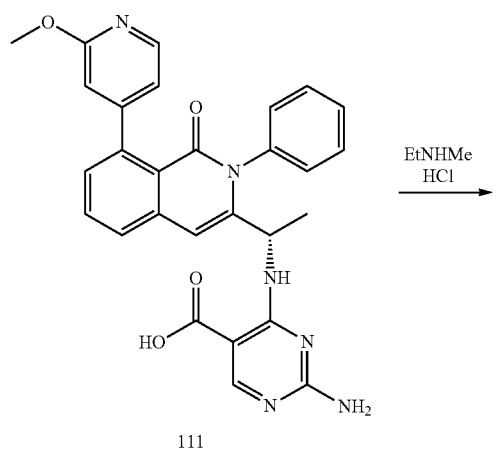

111

Compound 155 was prepared from compound III in analogous fashion to compound 112 in Example 73, where ethylmethylamine was used in place of dimethylamine. ESI-MS m/z: 549.8 [M+H]$^+$.

Example 98

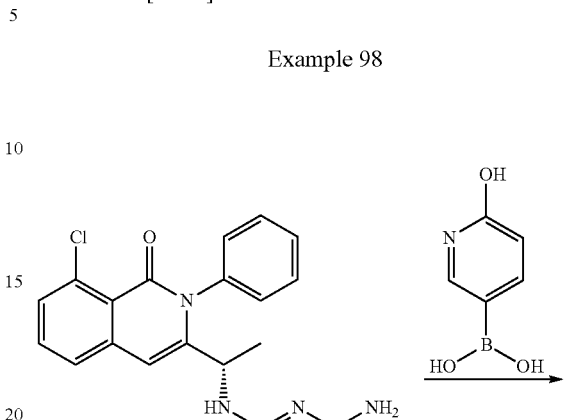

8

156

Compound 156 was prepared from compound 8 using 6-hydroxypyridin-3-ylboronic acid according to Method J. ESI-MS m/z: 549.8 [M+H]$^+$.

Example 99

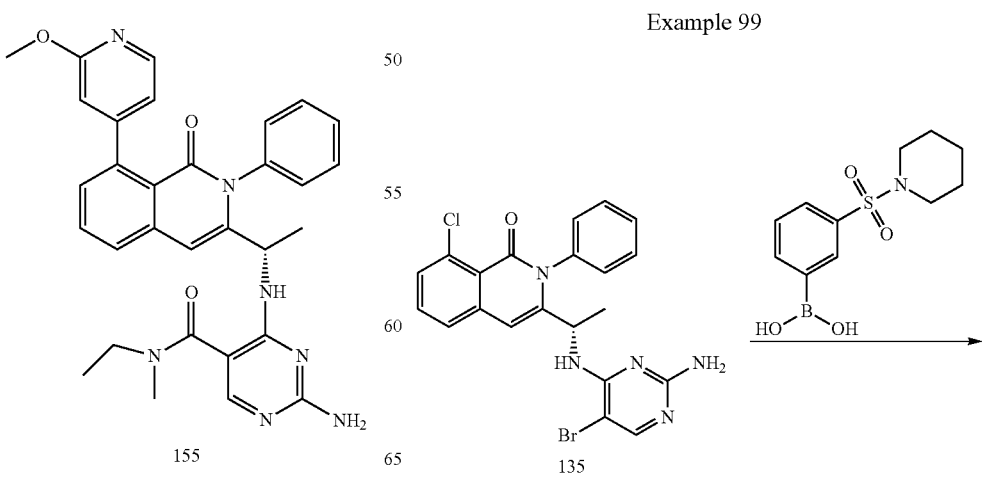

155

135

301
-continued

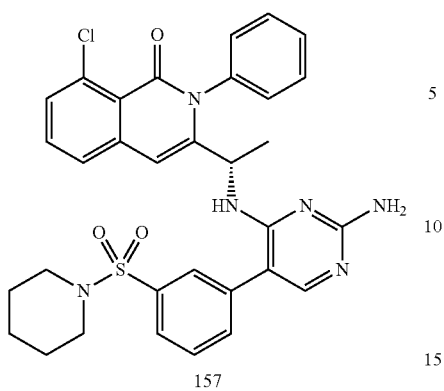

157

Bromide 135 (100 mg, 0.212 mmol) and 3-(piperidin-1-ylsulfonyl)phenylboronic acid (86 mg, 0.319 mmol) were dissolved in dioxane (2 mL) and $Na_2CO_3$ aq. (283 μl, 0.425 mmol). The mixture was bubbled with Ar for 5 min then charged with $Pd(Ph_3P)_4$ (12 mg, 10.6 μmol). The mixture was heated to 90° C. for 3 h. The reaction was cooled to room temperature, and poured into a saturated bicarbonate/EtOAc mixture. The phases were split and the organic layer was dried, filtered and pre-adsorbed on $SiO_2$. The residue was purified on $SiO_2$ (0-90 Acetone/DCM) to give the sulfonamide 157. ESI-MS m/z: 615.3 $[M+H]^+$.

Example 100

302
-continued

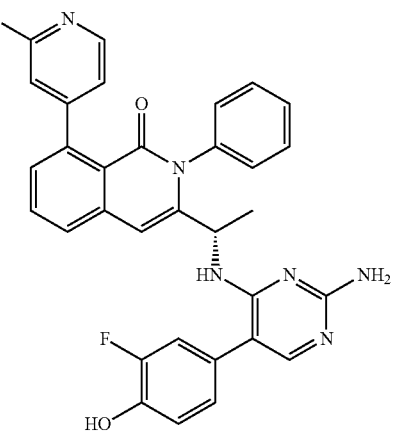

159

Compound 158 was prepared from compound 135 using 3-fluoro-4-hydroxyphenylboronic acid according to Example 99. Compound 159 was prepared from compound 158 using 2-methoxypyridin-4-ylboronic acid according to Example 89. ESI-MS m/z: 475.3 $[M+H]^+$.

Example 101

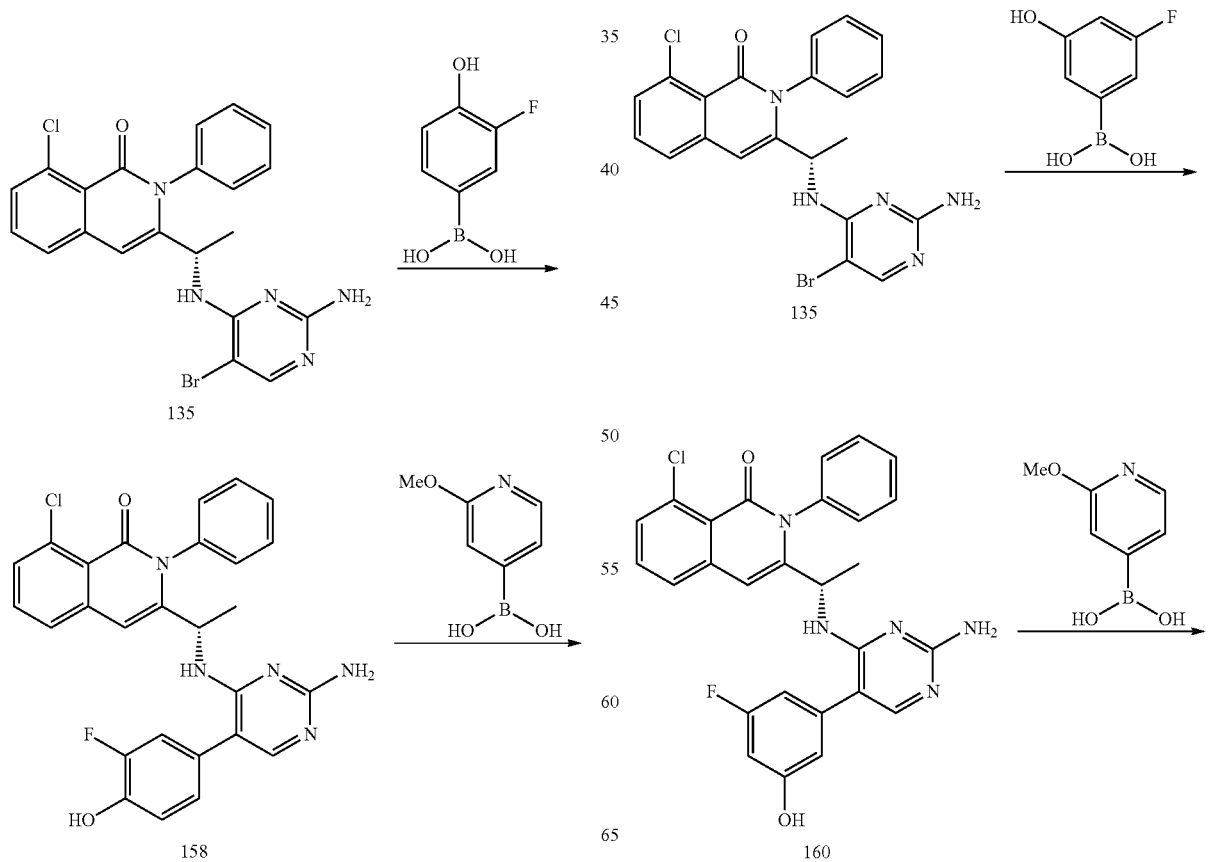

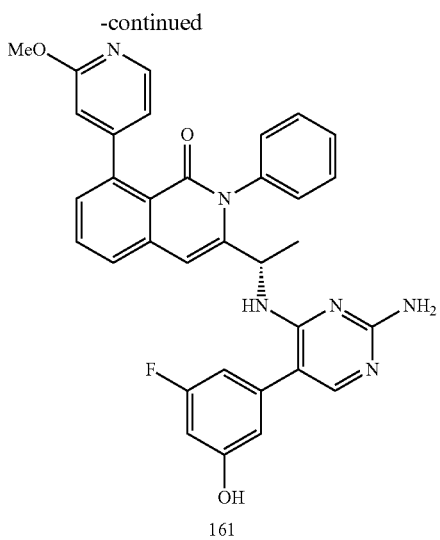

161

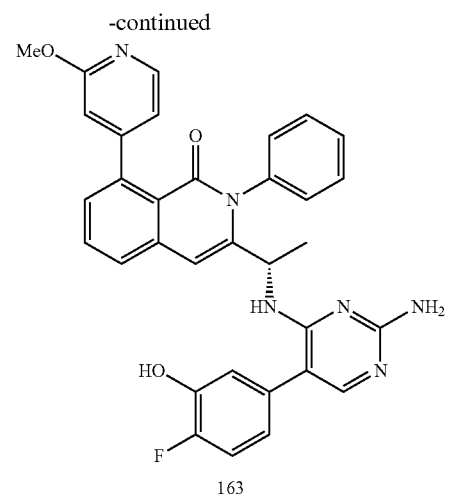

163

Compound 160 was prepared from compound 135 using 3-fluoro-5-hydroxyphenylboronic acid according to Example 99. Compound 161 was prepared from compound 160 using 2-methoxypyridin-4-ylboronic acid according to Example 89. ESI-MS m/z: 475.3 [M+H]$^+$.

Compound 162 was prepared from compound 135 using 4-fluoro-3-hydroxyphenylboronic acid according to Example 99. Compound 163 was prepared from compound 162 using 2-methoxypyridin-4-ylboronic acid according to Example 89. ESI-MS m/z: 475.2 [M+H]$^+$.

Example 102

Example 103

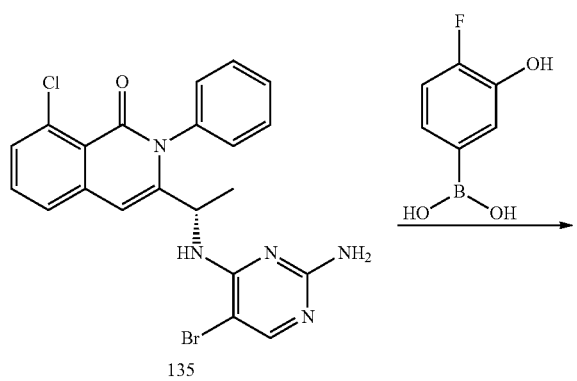

135

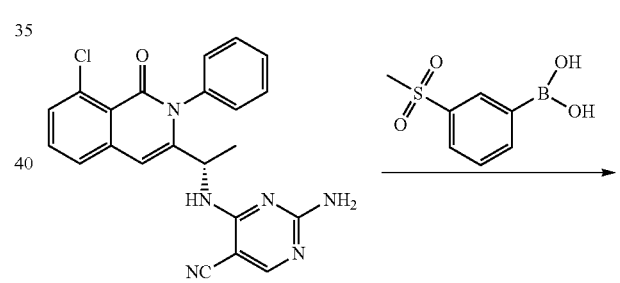

8

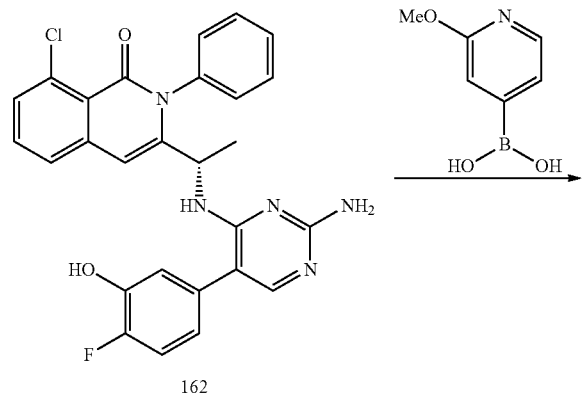

162

164

Compound 164 was prepared from compound 8 using 3-(methylsulfonyl)phenylboronic acid according to Method J. ESI-MS m/z: 535.2 [M+H]+.

Example 104

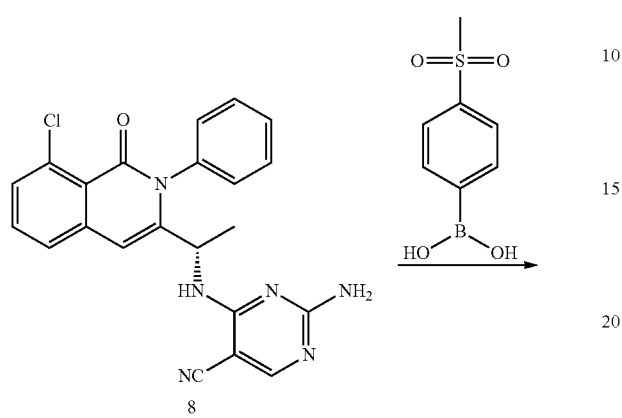

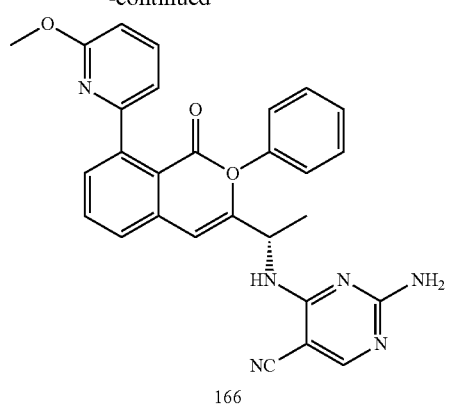

Compound 166 was prepared from compound 8 using 2-methoxy-6-(4,4,5,5-tetramethyl-1,3,2-dioxaborolan-2-yl)pyridine according to Method J. ESI-MS m/z: 490.2 [M+H]+.

Example 106

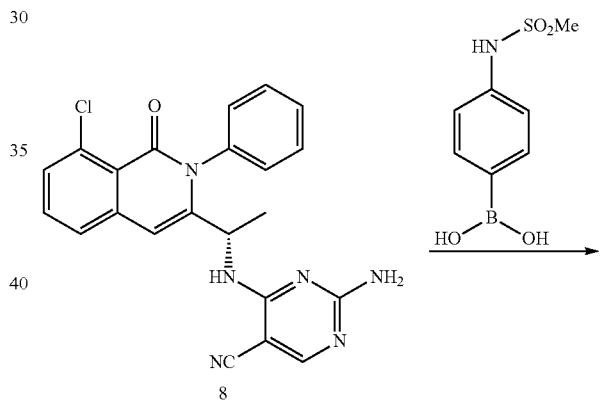

Compound 165 was prepared from compound 8 using 3-(methylsulfonyl)phenylboronic acid according to Method J. ESI-MS m/z: 535.2 [M+H]+.

Example 105

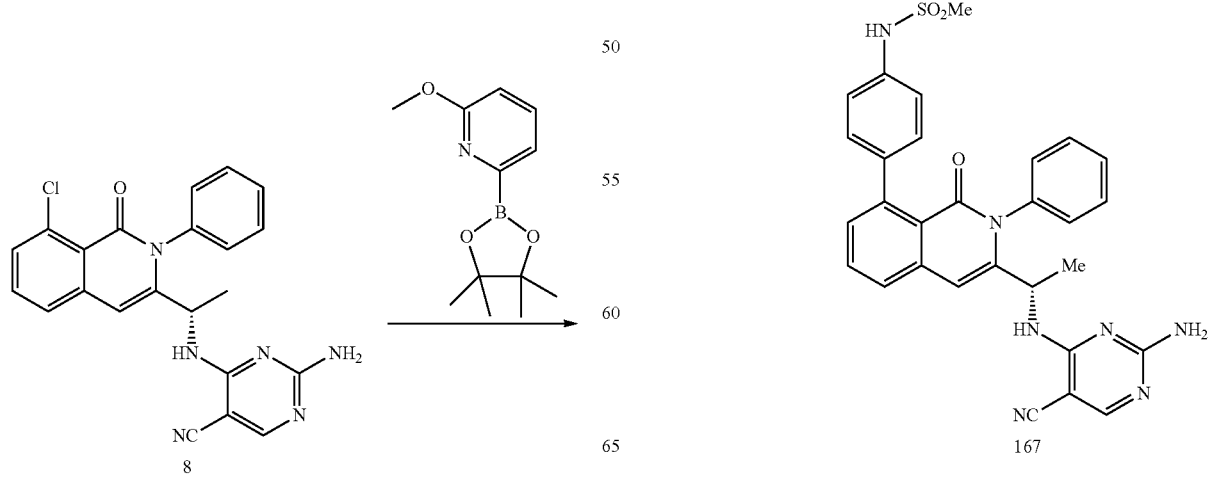

Compound 167 was prepared from compound 8 using 4-(methylsulfonamido)phenylboronic acid according to Method J. ESI-MS m/z: 552.2 [M+H]+.

Example 107

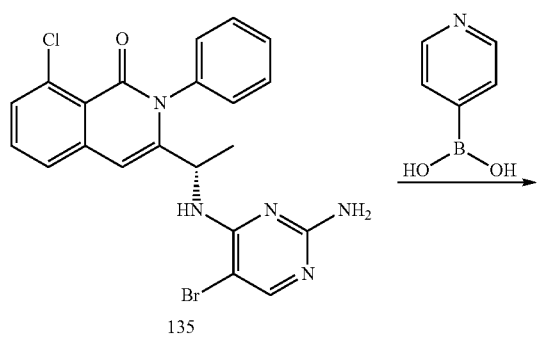

pound 169 was prepared from compound 168 using 2-methoxypyridin-4-ylboronic acid according to Example 89. ESI-MS m/z: 542.3 [M+H]+.

Example 108

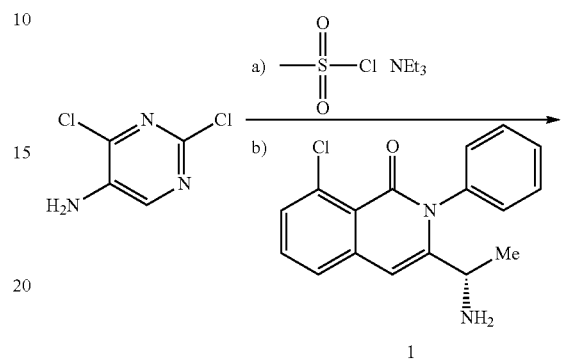

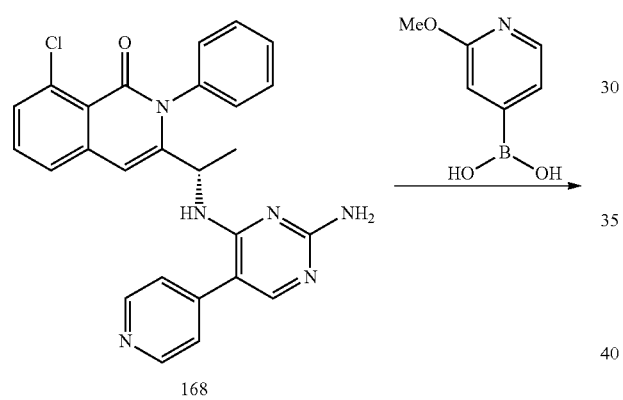

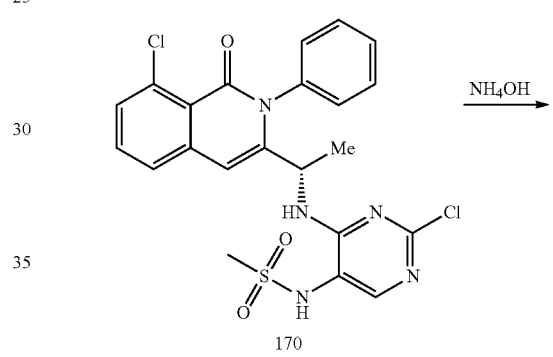

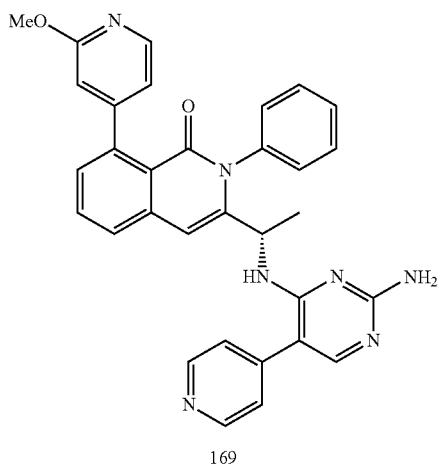

Compound 168 was prepared from compound 135 using pyridin-4-ylboronic acid according to Example 99. Com- 5-amino-2,4-dichloropyrimidine (100 mg, 0.7 mmol) was dissolved in 10 mL of DCM at 0° C. The cooled solution was treated with triethylamine (340 µl, 4 equiv) followed by slow addition of methylsulfonyl chloride (80 µl, 1.7 equiv). The mixture was stirred for 4 h at room temperature. Then the mixture was concentrated in vacuo, and compound 1 (182 mg) was added. NMP (6 mL) was added and the reaction was heated to 120° C. overnight. The reaction was diluted in EtOAc (50 ml), washed with water (4×30 ml), brine, and the organic layer was dried over anhydrous $Na_2SO_4$, filtered and concentrated. The resulting compound 170 was subjected to aminolysis according to Method E to afford the product 171. ESI-MS m/z: 485.1 [M+H]$^+$.

Example 109

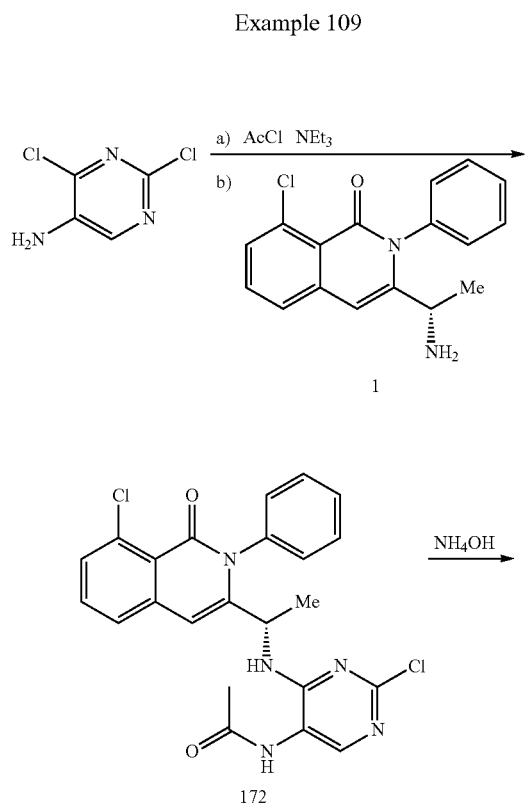

Example 110

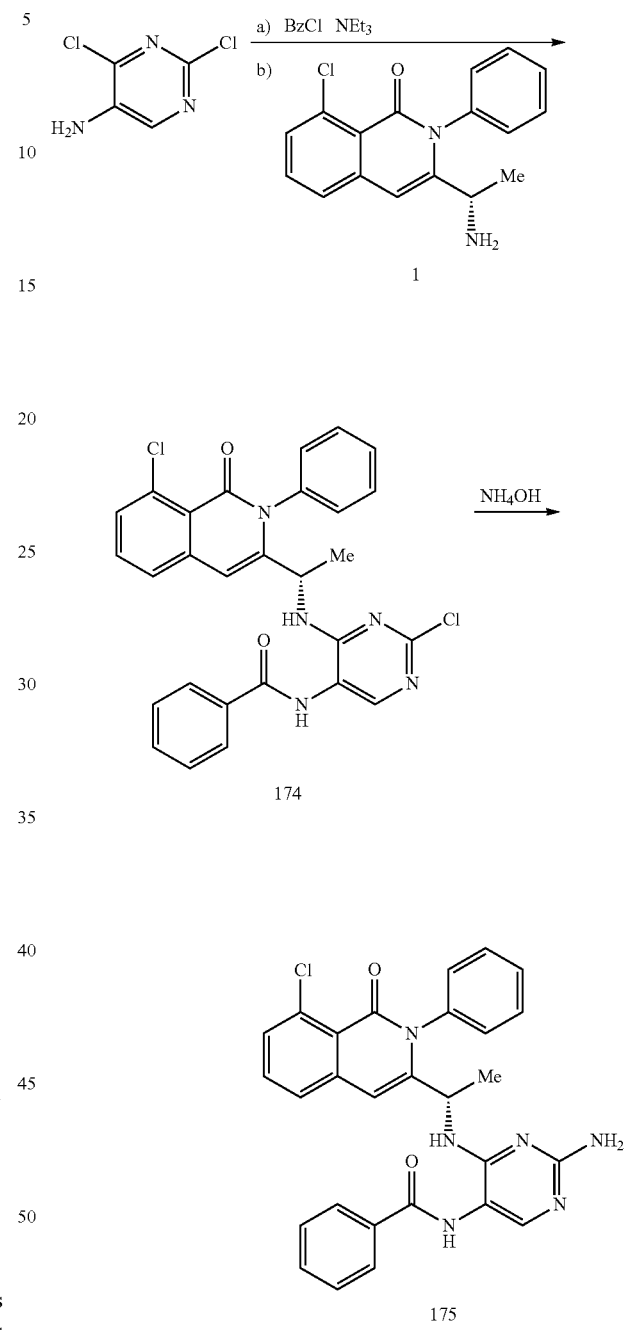

5-amino-2,4-dichloropyrimidine (100 mg, 0.7 mmol) was dissolved in 10 mL of DCM at 0° C. The cooled solution was treated with triethylamine (340 µl, 4 equiv) followed with slow addition of acetyl chloride (45 µl, 1 equiv). The mixture was stirred for 4 h at room temperature. Then the solvent was evaporated under reduced pressure, and compound 1 (182 mg) was added. NMP (6 mL) was added and the reaction was heated to 120° C. overnight. The reaction was diluted in EtOAc (50 ml), washed with water (4×30 ml), brine, and the organic layer was dried over anhydrous Na$_2$SO$_4$, filtered and concentrated. The resulting compound 172 was subjected to aminolysis according to Method E to give the product 173. ESI-MS m/z: 449.1 [M+H]$^+$.

5-amino-2,4-dichloropyrimidine (85 mg, 0.6 mmol) was dissolved in 10 mL of DCM at 0° C. The cooled solution was treated with triethylamine (108 µl, 1.5 equiv) followed with slow addition of benzoyl chloride (60 µl, 1 equiv). The mixture was stirred for 4 h at room temperature. Then the solvent was evaporated under reduced pressure, and compound 1 (155 mg) was added. NMP (6 mL) was added and the reaction was heated to 120° C. overnight. The reaction was diluted in EtOAc (50 ml), washed with water (4×30 ml), brine, and the organic layer was dried over anhydrous Na$_2$SO$_4$, filtered and concentrated. The resulting compound 174 was subjected to aminolysis according to Method E to give the product 175. ESI-MS m/z: 511.2 [M+H]$^+$.

Example 111

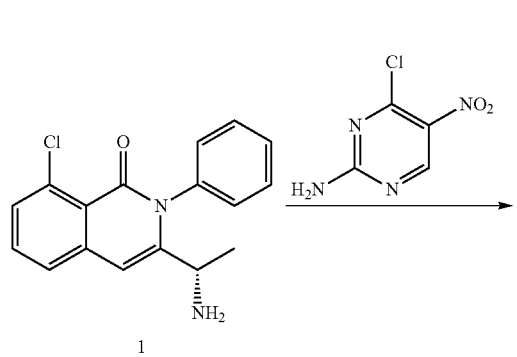

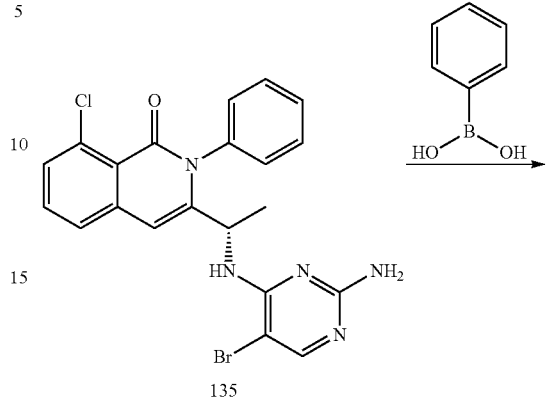

Example 112

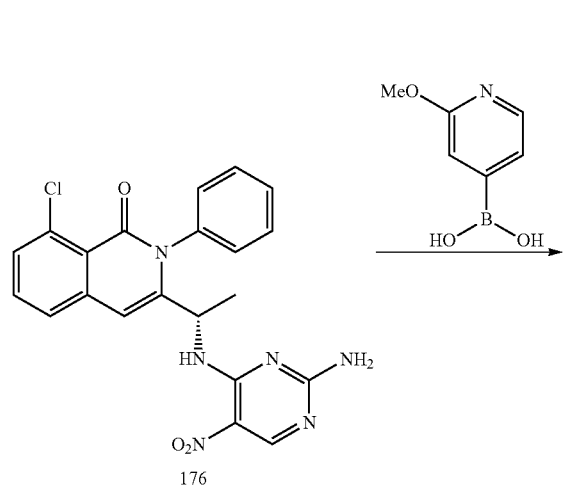

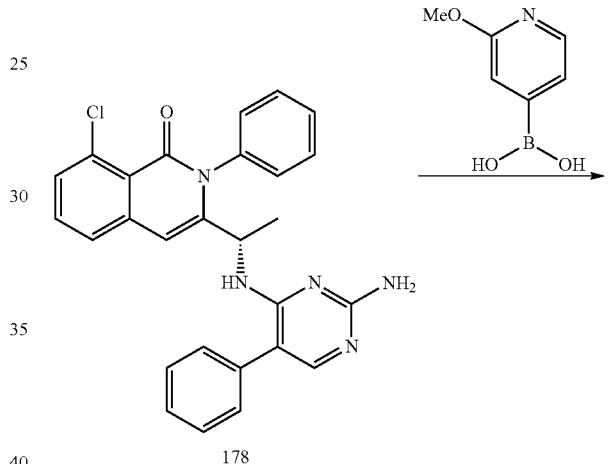

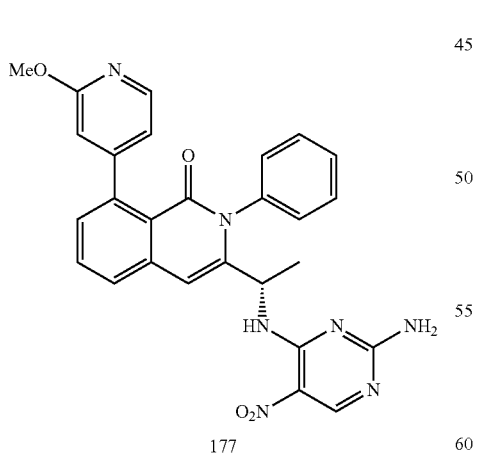

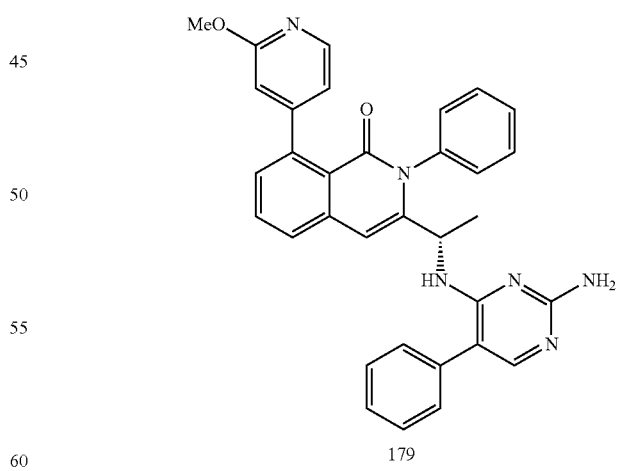

Compound 176 was prepared from compound 1 using 4-chloro-5-nitropyrimidin-2-amine according to Method G. Compound 177 was prepared from compound 176 using 2-methoxypyridin-4-ylboronic acid in a Suzuki reaction according to Method J. ESI-MS m/z: 510.2 [M+H]$^+$.

Compound 178 was prepared from compound 135 using phenylboronic acid according to Example 99. Compound 179 was prepared from compound 158 using 2-methoxypyridin-4-ylboronic acid according to Method J. ESI-MS m/z: 541.2 [M+H]$^+$.

Example 113

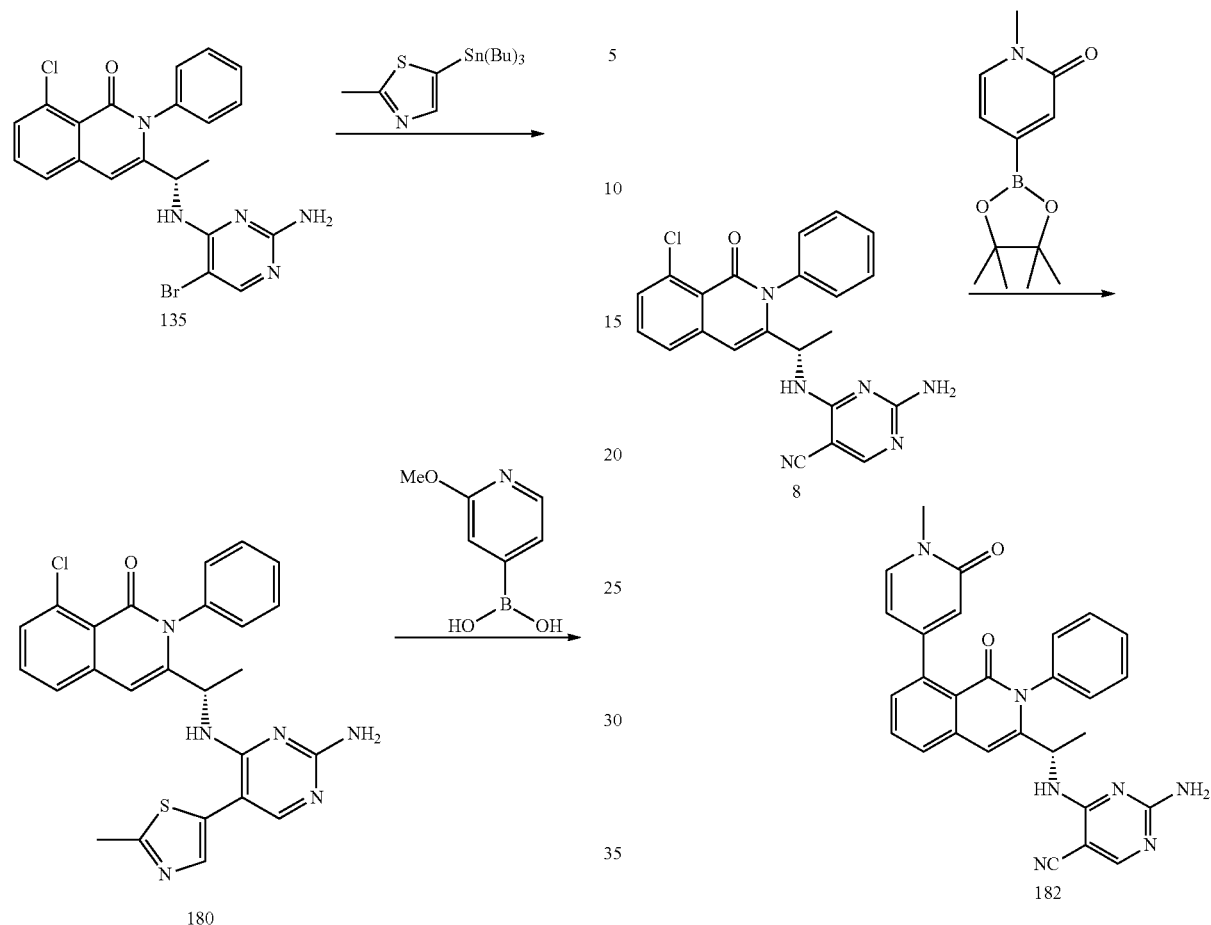

Example 114

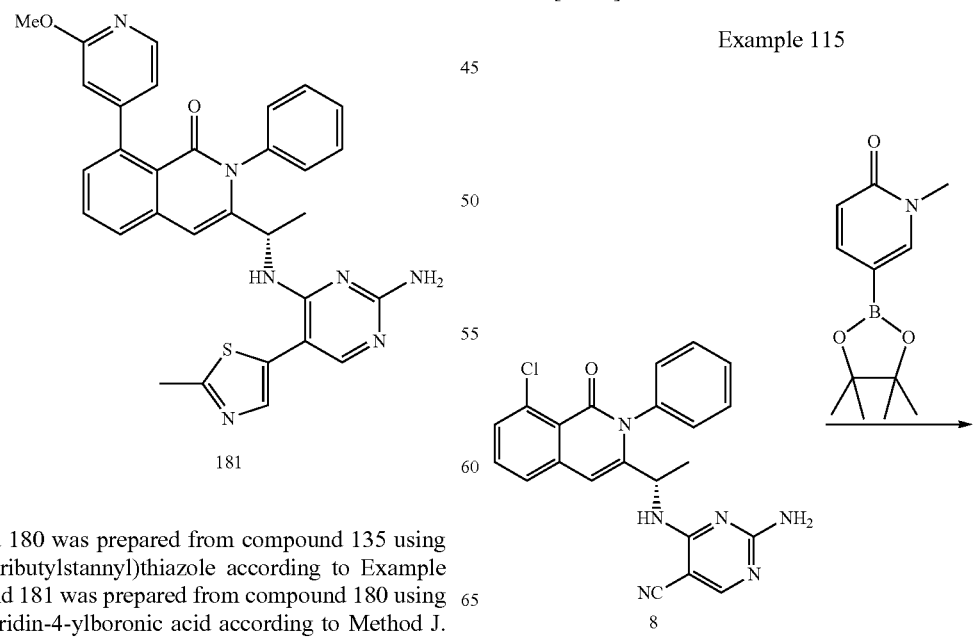

Compound 182 was prepared from compound 8 using 1-methyl-4-(4,4,5,5-tetramethyl-1,3,2-dioxaborolan-2-yl)pyridin-2(1H)-one according to Method J. ESI-MS m/z: 490.2 [M+H]$^+$.

Example 115

Compound 180 was prepared from compound 135 using 2-methyl-5-(tributylstannyl)thiazole according to Example 88. Compound 181 was prepared from compound 180 using 2-methoxypyridin-4-ylboronic acid according to Method J. ESI-MS m/z: 562.3 [M+H]$^+$.

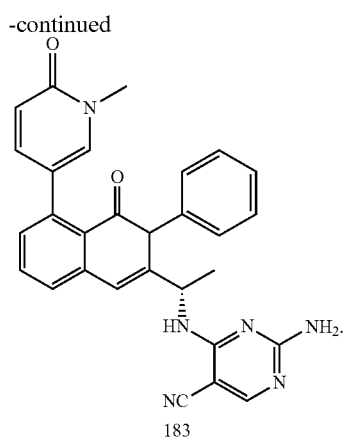

183

Compound 183 was prepared from compound 8 using 1-methyl-5-(4,4,5,5-tetramethyl-1,3,2-dioxaborolan-2-yl)pyridin-2(1H)-one according to Method J. ESI-MS m/z: 490.2 [M+H]$^+$.

Example 116

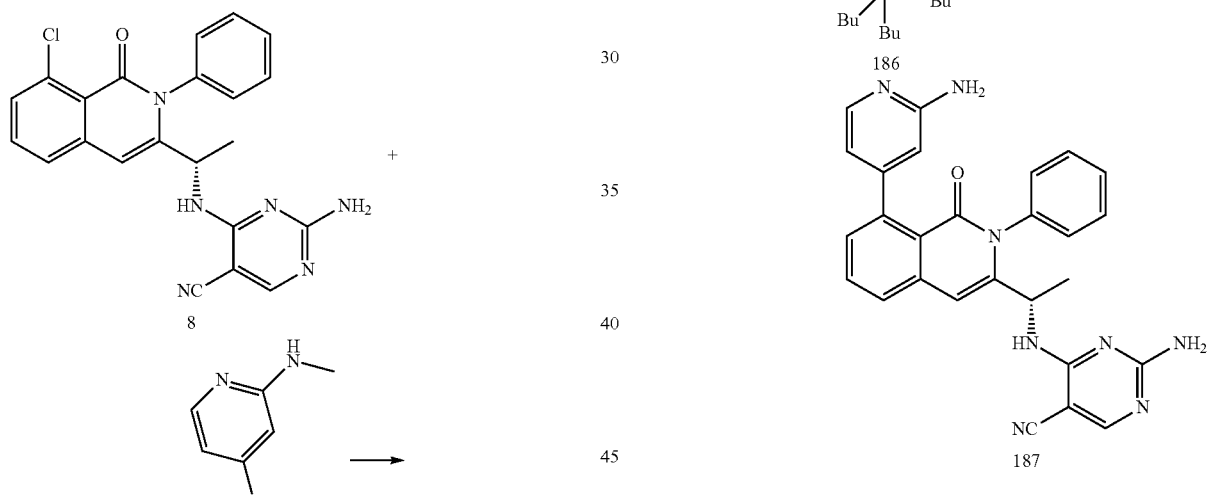

Compound 185 was prepared from compound 8 using N-methyl-4-(tributylstannyl)pyridin-2-amine in analogous fashion to preparation of compound 69 from compound 62 in Example 51. ESI-MS m/z: 489.2 [M+H]$^+$.

Example 117

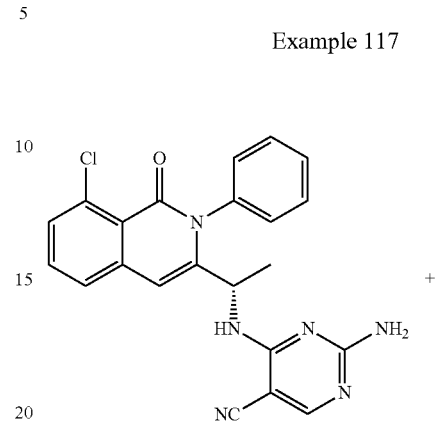

Compound 187 was prepared from compound 8 using 4-(tributylstannyl)pyridin-2-amine in analogous fashion to preparation of compound 69 from compound 62 in Example 51. ESI-MS m/z: 475.2 [M+H]$^+$.

Example 118

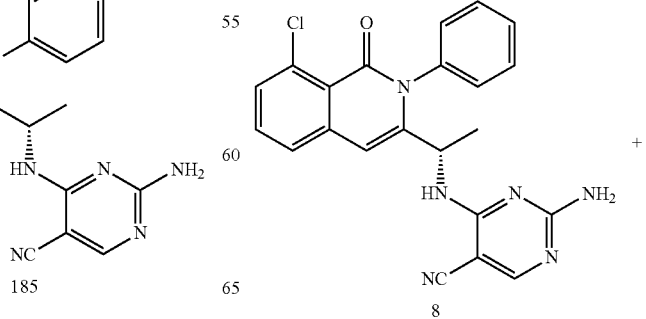

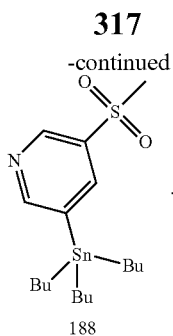

188

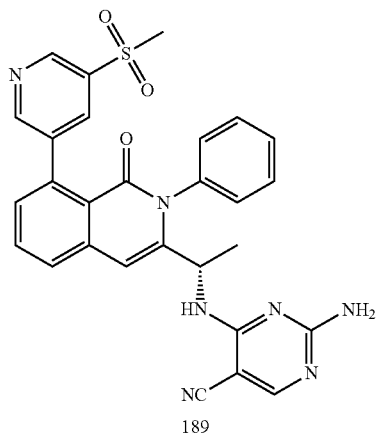

189

Compound 189 was prepared from compound 8 using 2,3-dimethoxy-5-(4,4,5,5-tetramethyl-1,3,2-dioxaborolan-2-yl)pyridine according to Method J. ESI-MS m/z: 538.2 [M+H]$^+$.

Example 119

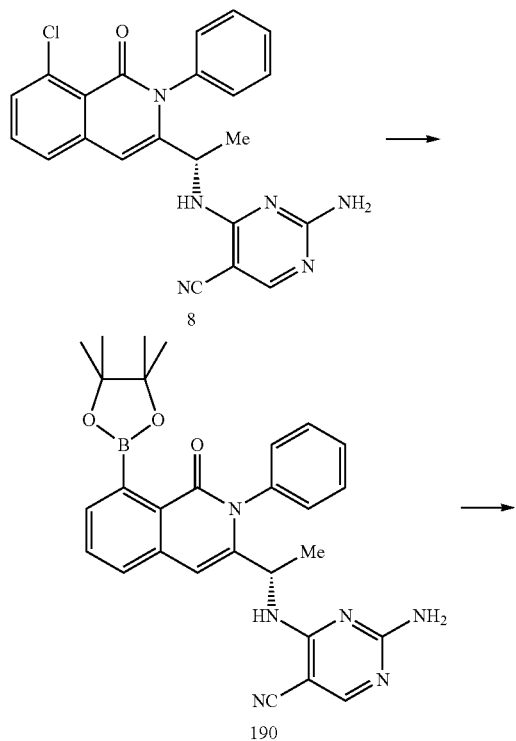

191

A mixture of 8 (50 mg), Pd$_2$(dba)$_3$ (4 mg), X-Phos (4 mg), KOAc (40 mg), and bis(pinacolato)diboron (100 mg) in degassed 1,4-dioxane (2 mL) was stirred at 90° C. overnight. The mixture was cooled to room temperature and diluted with EtOAc (50 mL) and washed 2×25 mL water. The organic layer was washed with brine, dried over Na$_2$SO$_4$, filtered and concentrated to give a residue that was purified by normal phase column to give compound 190. Compound 190 was coupled with N-(5-bromopyridin-3-yl)methanesulfonamide according to Method J to give Compound 191. ESI-MS m/z: 553.2 [M+H]$^+$.

Example 120

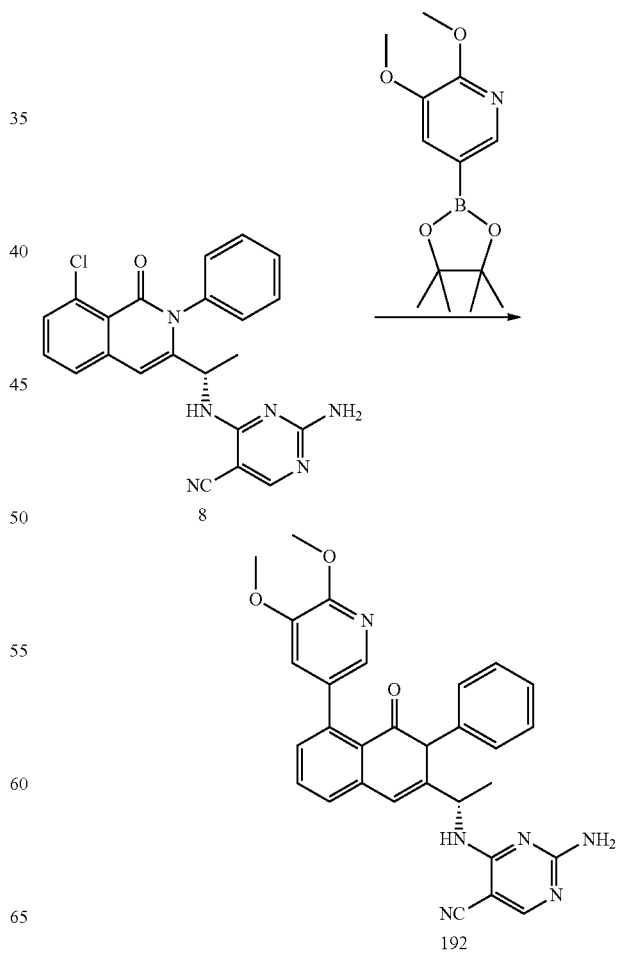

Compound 192 was prepared from compound 8 using 2,3-dimethoxy-5-(4,4,5,5-tetramethyl-1,3,2-dioxaborolan-2-yl)pyridine according to Method J. ESI-MS m/z: 520.3 [M+H]$^+$.

Example 121

Example 122

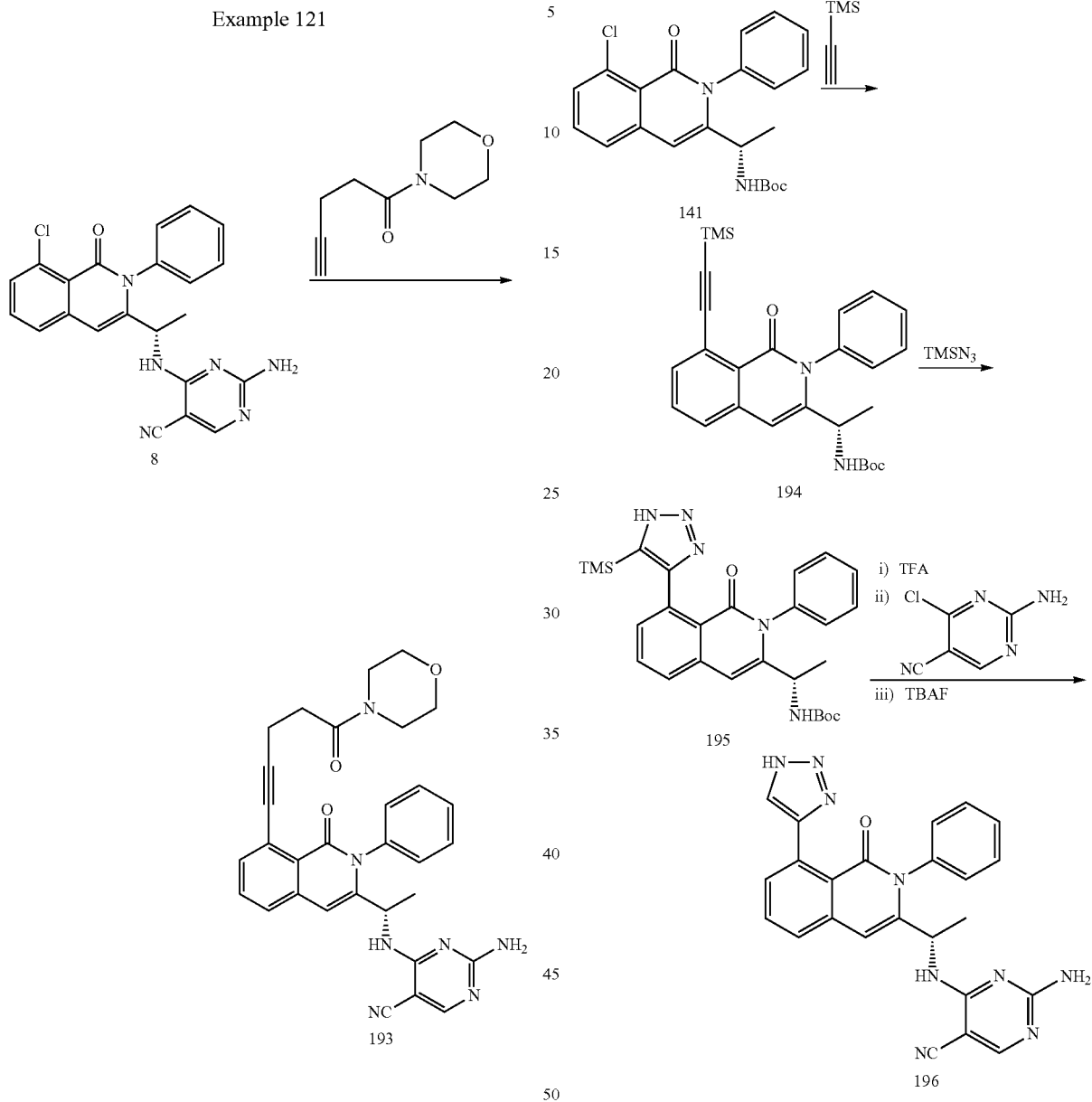

A mixture of dichlorobis(acetonitrile) Pd (9.0 mg, 0.035 mmol, 0.185 equiv.), X-Phos (51.1 mg, 0.11 mmol, 0.57 equiv.) and cesium carbonate (159 mg, 0.49 mmol, 2.6 equiv.) under argon was added 2 mL propionitrile. Compound 8 (78 mg, 0.187 mmol, 1 equiv.) was added followed by N-(4-pentynoyl)morpholine in 2 mL propionitrile (0.18 mL, 1.18 mmol, 6 equiv.). 2 mL propionitrile was added to the mixture which was stirred for 0.5 h at room temp. before heating at 100° C. for 1 h. The mixture was cooled, diluted with EtOAc (10 mL) and water (10 mL). The aqueous layer was extracted with EtOAc (3×10 mL), the combined organic layers were washed with water (2×10 mL), brine (10 mL), dried over sodium sulfate and the solvents were evaporated in vacuo. The residue was purified on silica gel using 0→5% methanol in DCM to give compound 193. ESI-MS m/z: 548.3 [M+H]$^+$.

To a mixture of dichlorobis(acetonitrile) Pd (13.8 mg, 0.053 mmol, 0.05 equiv.), X-Phos (76.2 mg, 0.16 mmol, 0.15 equiv.) and cesium carbonate (901 mg, 2.77 mmol, 2.5 equiv.) under argon was added 2 mL acetonitrile. Compound 141 (441 mg, 1.1 mmol, 1 equiv.) was added followed by trimethylsilyl acetylene in 1 mL acetonitrile (0.184 mL, 1.3 mmol, 1.2 equiv.). 2 mL of acetonitrile was added to the mixture and was stirred for 5 min at room temp. before heating at 90° C. for 2 h. The mixture was cooled, diluted with 25 mL EtOAc, 5 mL water, and filtered through a pad of celite. The organic layer was collected, the aqueous layer was extracted with EtOAc (2×25 mL), the combined filtrates were washed with water (2×20 mL), brine (10 mL), dried over sodium sulfate and the solvents were evaporated in vacuo. The residue was purified on silica gel using 10→85% EtOAc-Hexanes to give 201 mg of compound 195.

A mixture of compound 195 (110 mg, 0.24 mmol, 1 equiv.), azidotrimethylsilane (138 mg, 1.2 mmol, 5 equiv.), sodium ascorbate (0.5 mL, 0.02 M in water), and CuSO$_4$ (0.1 mL, 0.5 M in water) in 3 mL DMSO was heated at 80° C. for 17 h. The mixture was cooled, partitioned between 5 mL 10% citric acid and 10 mL DCM, and the aqueous layer was extracted with DCM (4×10 mL). The combined organic layers were washed with 10 mL 5% ammonia, 10 mL water, 10 mL brine, dried over sodium sulfate and the solvents were evaporated in vacuo. The residue was purified on silica gel using 0→50% acetone in DCM to give 29 mg of compound 195.

A solution of compound 195 (25 mg, 0.05 mmol, 1 equiv.) in 2 mL DCM at 22° C. was treated with two portions of TFA (2×80 µL, 2×1 mmol, 40 equiv) for one hour each. The mixture was concentrated in vacuo, co-evaporated with 10 mL DCM and then 10 mL hexanes. The residue was dissolved in 1 mL NMP, and N,N-diisopropylethylamine (20 µL, 2 equiv.) was added followed by 2-amino-4-chloro-5-cyanopyrimidine. The mixture was heated in a sealed tube at 110° C. for 15 h, cooled and treated with TBAF (2×200 µL, 1.0 M in THF, 0.4 mmol, 8 equiv.) and stirred for 4.5 h. The mixture was diluted with water (10 mL), and extracted with DCM (5×5 mL). The combined organic layers were washed with 10 mL brine, dried over sodium sulfate, filtered, and the solvent was removed in vacuo. The residue was purified by preparative HPLC to give compound 196. ESI-MS m/z: 450.2 [M+H]$^+$.

Example 123

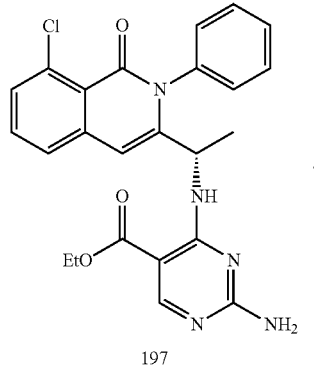

197

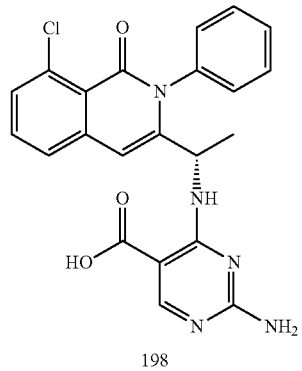

198

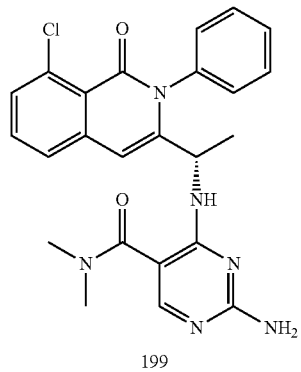

199

Compound 198 was prepared from compound 197 by ester hydrolysis in analogous fashion to Example 72. Compound 199 was prepared from compound 198 using dimethylamine in analogous fashion to Example 73. ESI-MS m/z: 463.0 [M−H]$^+$.

Example 124

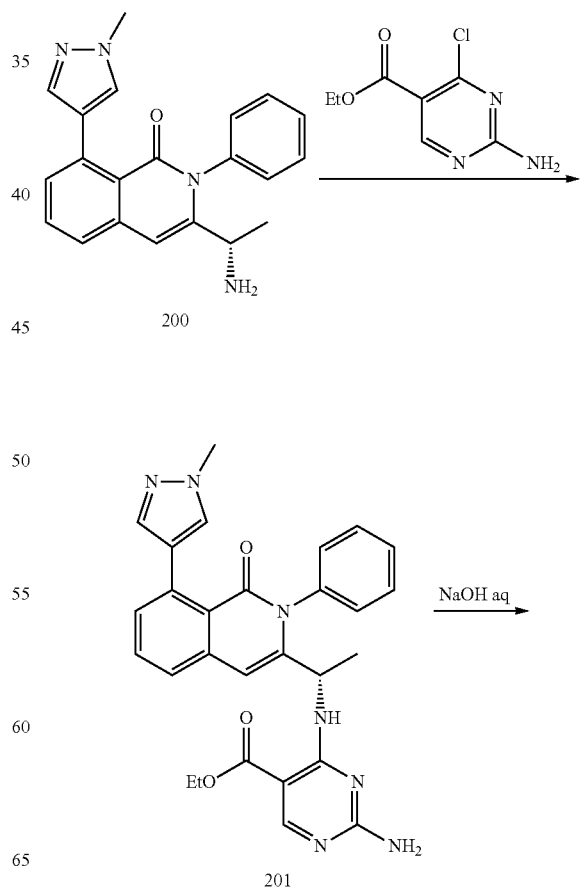

200

201

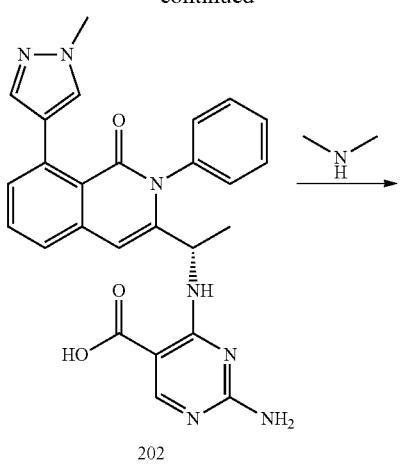
202
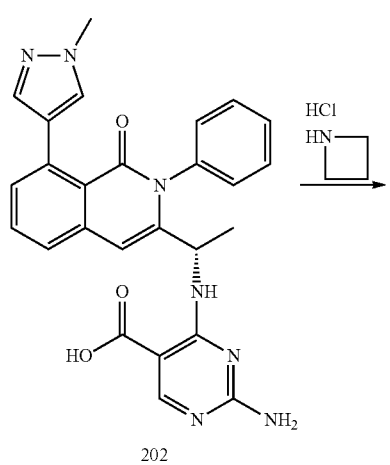
202
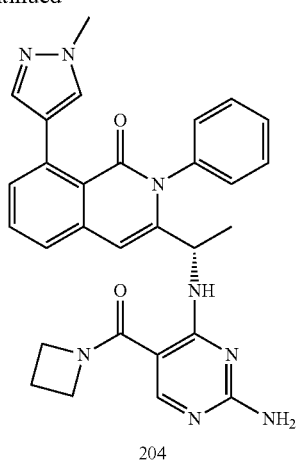
204
Compound 204 was prepared from compound 202 in analogous fashion to Example 124 except that azetidine hydrochloride was used in place of dimethylamine. ESI-MS m/z: 521.2 [M+H]$^+$.
Example 126
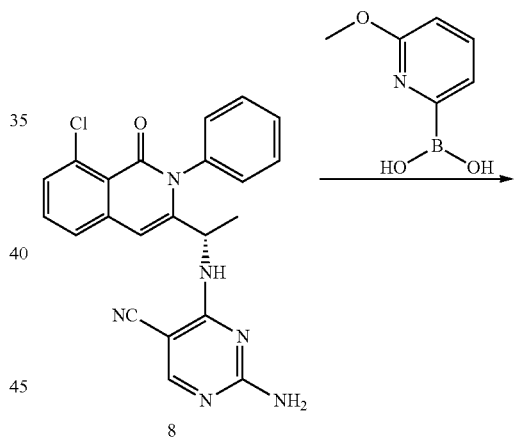
8
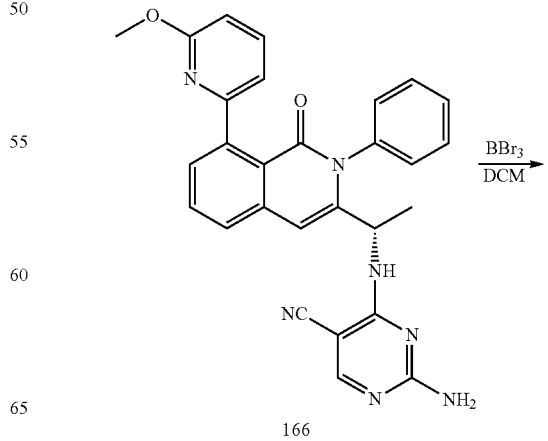
166
203
Compound 201 was prepared from compound 200 according to Method G. Compound 201 was then converted to 203 in 2 steps in analogous fashion to Example 123. ESI-MS m/z: 509.2 [M+H]$^+$.
Example 125

-continued

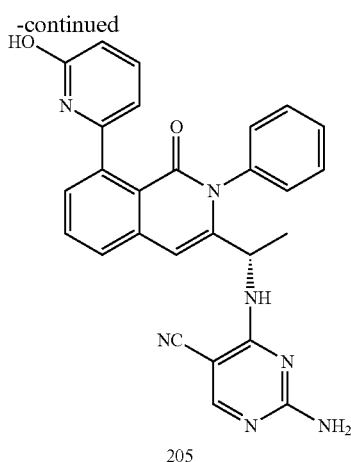

205

Compound 166 was prepared from compound 8 using 2-methoxypyridyl-6-boronic acid according to Method J. Compound 205 was prepared from Compound 166 in analogous fashion to Example 6, except BBr₃ was used in place of PBr₃. ESI-MS m/z: 476.2 [M+H]⁺.

Example 127

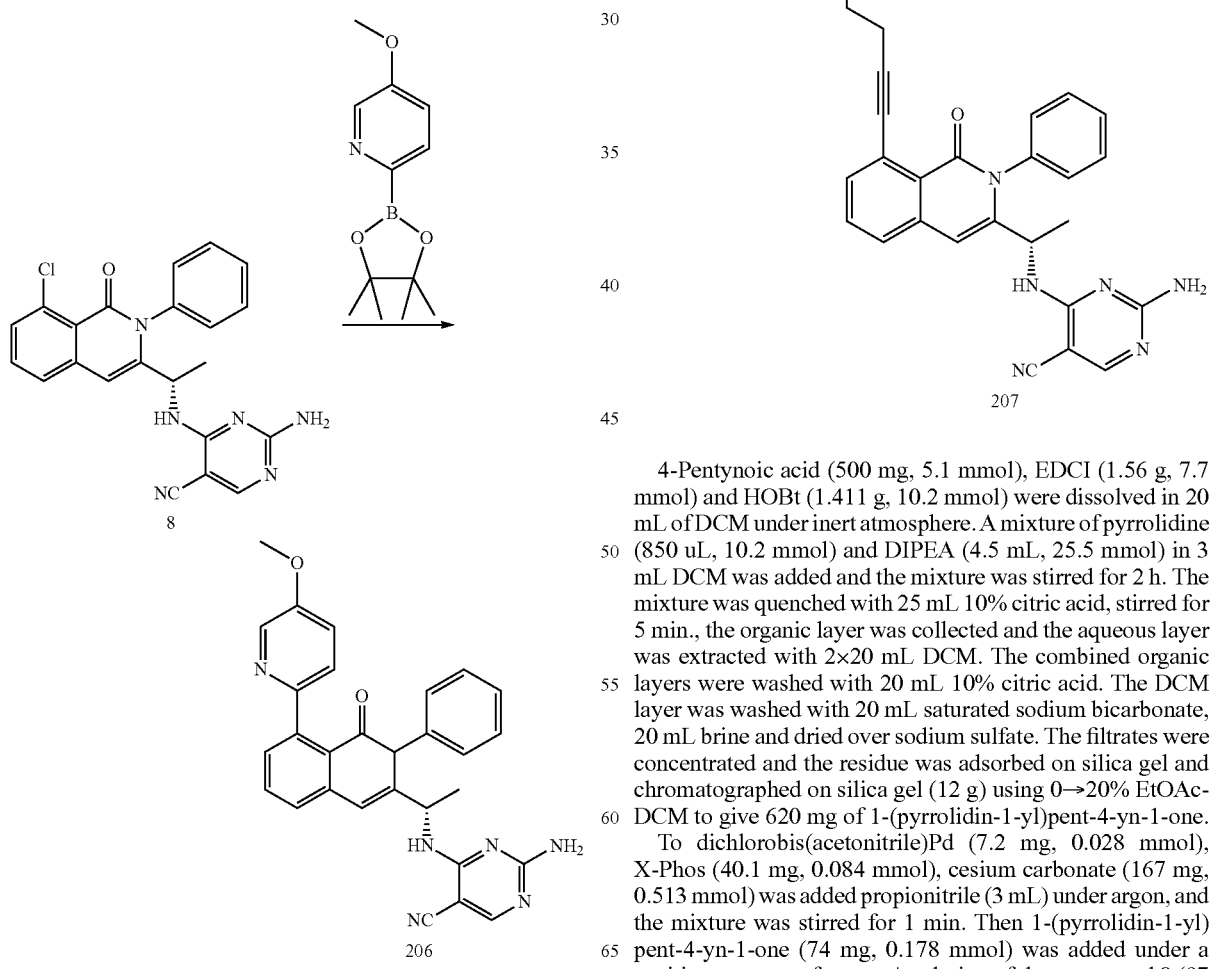

Compound 206 was prepared from compound 8 using 5-methoxy-2-(4,4,5,5-tetramethyl-1,3,2-dioxaborolan-2-yl)pyridine according to Method J. ESI-MS m/z: 490.2 [M+H]⁺.

Example 128

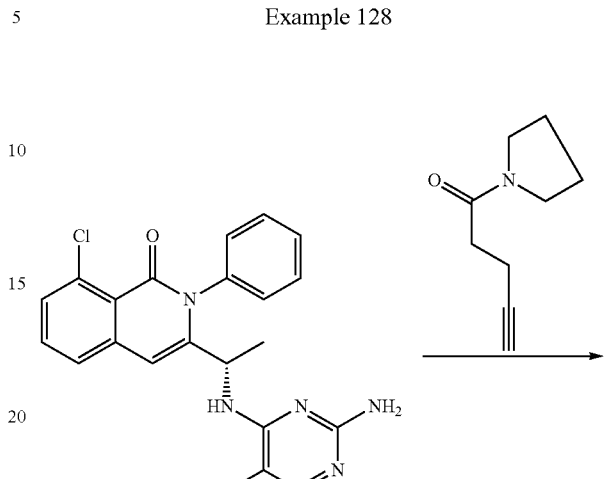

4-Pentynoic acid (500 mg, 5.1 mmol), EDCI (1.56 g, 7.7 mmol) and HOBt (1.411 g, 10.2 mmol) were dissolved in 20 mL of DCM under inert atmosphere. A mixture of pyrrolidine (850 uL, 10.2 mmol) and DIPEA (4.5 mL, 25.5 mmol) in 3 mL DCM was added and the mixture was stirred for 2 h. The mixture was quenched with 25 mL 10% citric acid, stirred for 5 min., the organic layer was collected and the aqueous layer was extracted with 2×20 mL DCM. The combined organic layers were washed with 20 mL 10% citric acid. The DCM layer was washed with 20 mL saturated sodium bicarbonate, 20 mL brine and dried over sodium sulfate. The filtrates were concentrated and the residue was adsorbed on silica gel and chromatographed on silica gel (12 g) using 0→20% EtOAc-DCM to give 620 mg of 1-(pyrrolidin-1-yl)pent-4-yn-1-one.

To dichlorobis(acetonitrile)Pd (7.2 mg, 0.028 mmol), X-Phos (40.1 mg, 0.084 mmol), cesium carbonate (167 mg, 0.513 mmol) was added propionitrile (3 mL) under argon, and the mixture was stirred for 1 min. Then 1-(pyrrolidin-1-yl)pent-4-yn-1-one (74 mg, 0.178 mmol) was added under a positive pressure of argon. A solution of the compound 8 (97 mg, 0.642 mmol) in 1 mL propionitrile was added dropwise, then the mixture was stirred at 100-105° C. for 3 h. The mixture was cooled to room temperature, diluted with 20 mL ethyl acetate, filtered through a pad of celite and the filter pad was washed with ethylacetate (3×20 mL). The combined filtrates were washed with water (20 mL) and brine (10 mL), then dried over sodium sulfate, filtered, and the filtrates were concentrated under reduced pressure. The residue was purified on silica gel (12 g) using 0→10% Methanol-DCM) to give compound 207. ESI-MS m/z: 532.3 [M+H]$^+$.

Example 129

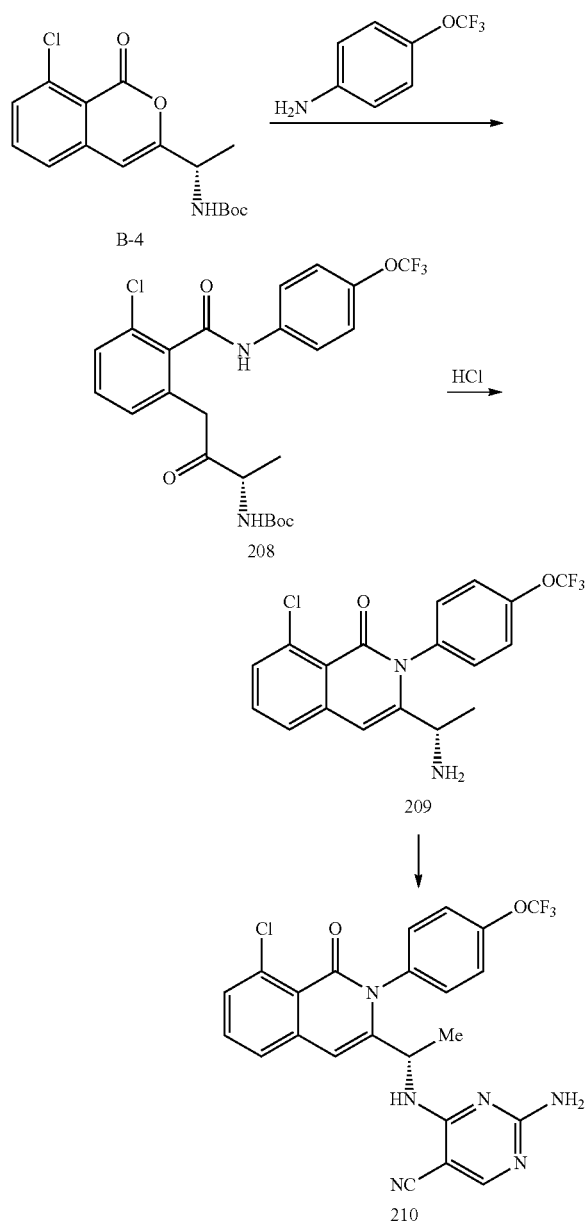

Compound 209 was synthesized from compound B-4 according to Method B using 4-trifluoromethoxyaniline. Compound 210 was prepared from compound 209 according to Method G. ESI-MS m/z: 501.2 [M+H]$^+$.

Example 130

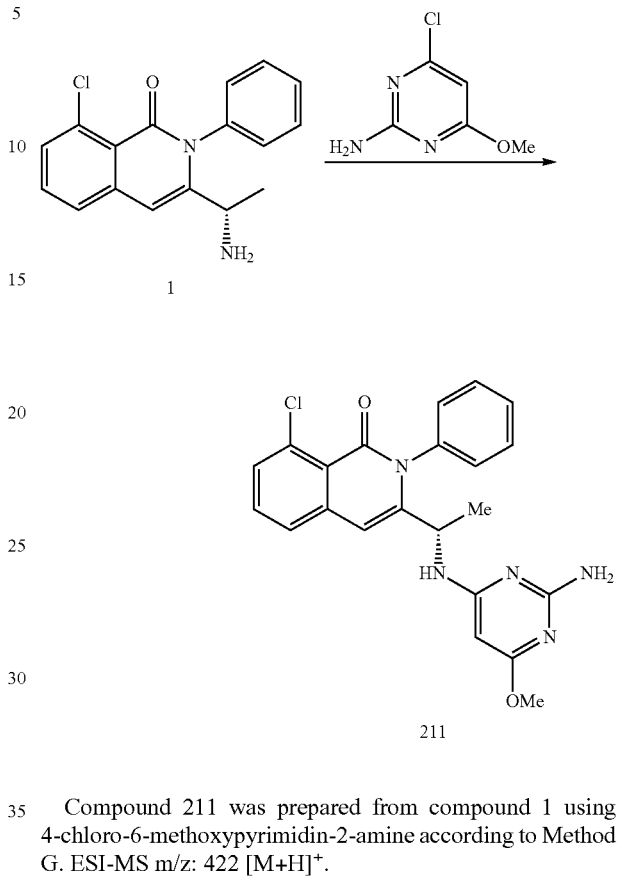

Compound 211 was prepared from compound 1 using 4-chloro-6-methoxypyrimidin-2-amine according to Method G. ESI-MS m/z: 422 [M+H]$^+$.

Example 131

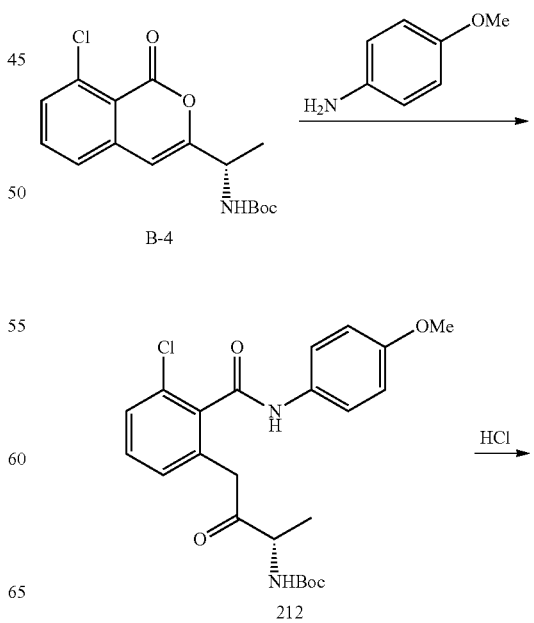

329

-continued

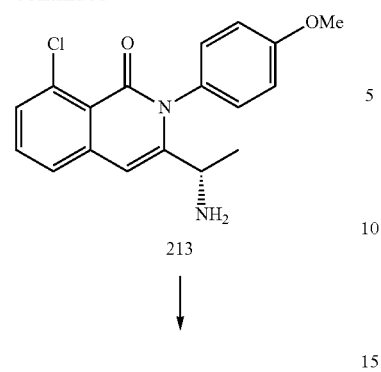
213

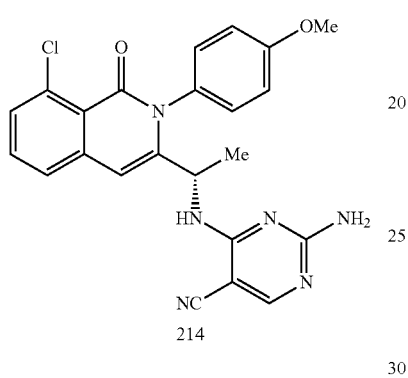
214

Compound 214 was prepared from compound B-4 in analogous fashion to Example 129 except that 4-methoxyaniline was used in place of 4-trifluoromethoxyaniline. ESI-MS m/z: 447.1 [M+H]$^+$.

Example 132

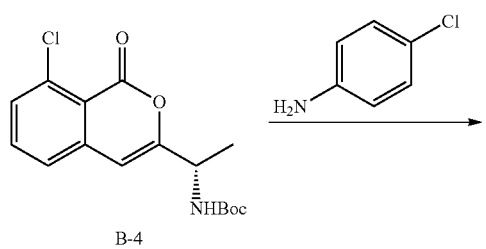
B-4

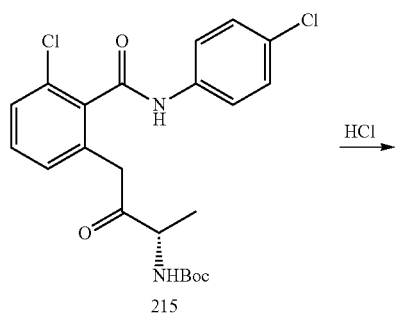
215

330

-continued

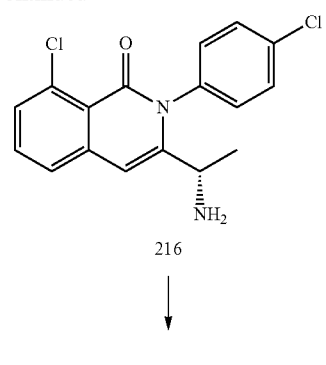
216

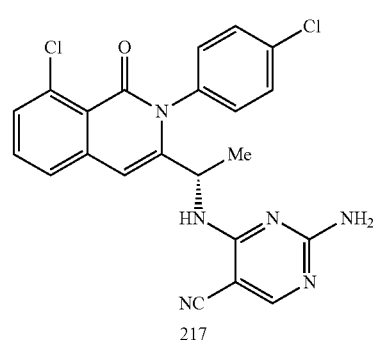
217

Compound 217 was prepared from compound B-4 in analogous fashion to Example 129 except that 4-chloroaniline was used in place of 4-trifluoromethoxyaniline. ESI-MS m/z: 453.0 [M+H]$^+$.

Example 133

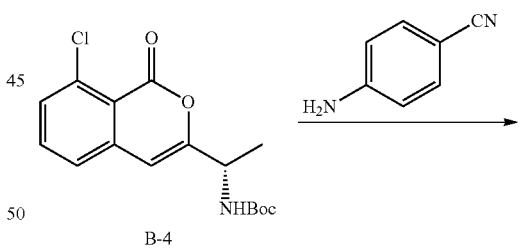
B-4

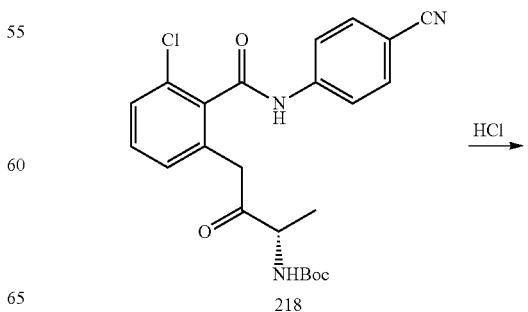
218

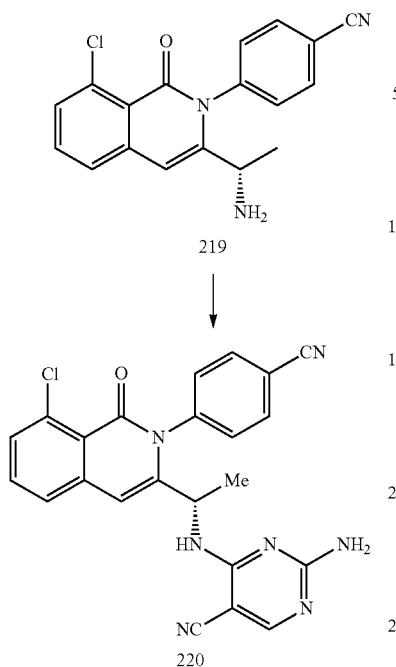

Compound 220 was prepared from compound B-4 in analogous fashion to Example 129 except that 4-cyanoaniline was used in place of 4-trifluoromethoxyaniline. ESI-MS m/z: 442.1 [M+H]$^+$.

Example 134

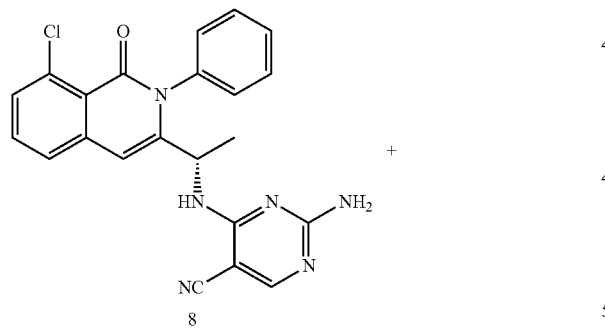

Compound 222 was prepared from compound 8 using tributyl(1-propynyl)tin according to Method I. ESI-MS m/z: 421.6 [M+H]$^+$.

Example 135

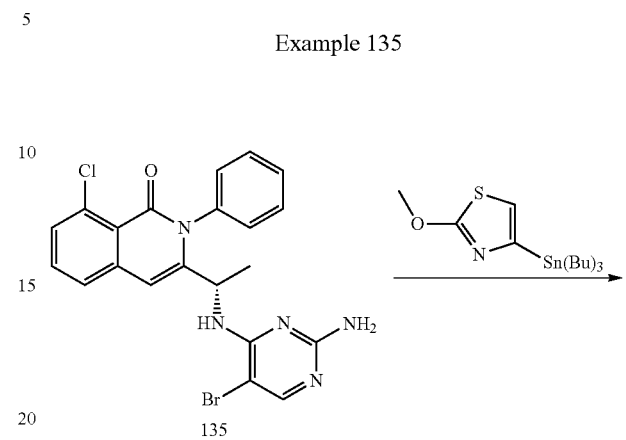

Compound 223 was prepared from compound 135 in analogous fashion to Example 88 except 2-methoxy-4-(tributylstannyl)thiazole was used in place of 4-methyl-2-(tribyulstannyl)thiazole. ESI-MS m/z: 505.2 [M+H]$^+$.

Example 136

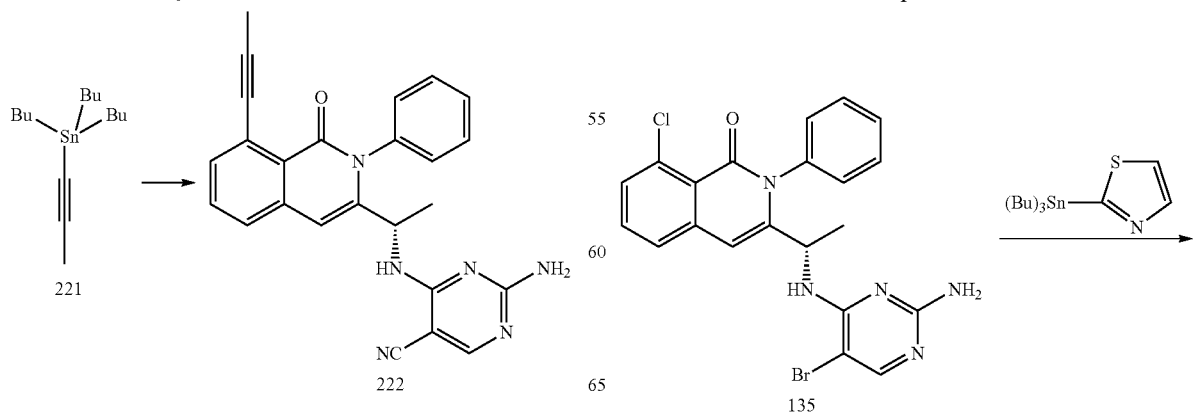

-continued

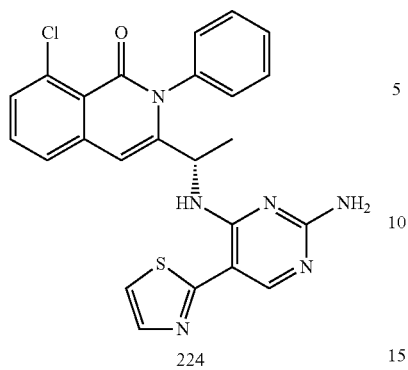

224

Compound 223 was prepared from compound 135 in analogous fashion to Example 88 except 2-(tributylstannyl)thiazole was used in place of 4-methyl-2-(tribyulstannyl)thiazole. ESI-MS m/z: 475.1 [M+H]$^+$.

Example 137

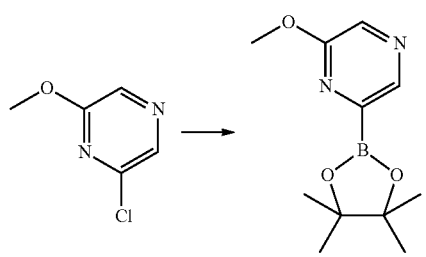

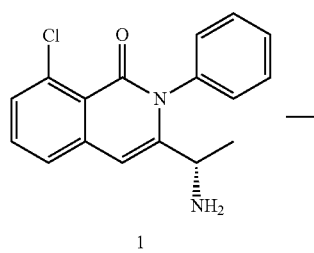

1

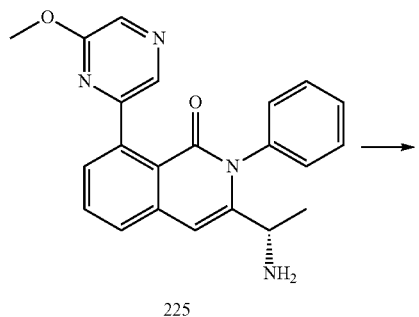

225

-continued

226

A mixture of 2-chloro-6-methoxypyrazine (500 mg, 3.46 mmol, 1.0 eq), bis(pinacolato)diboron (1.05 g, 4.13 mmol, 1.2 eq), Pd$_2$(dba)$_3$ (95 mg, 0.1 mmol, 0.029 eq), P(Cy)$_3$ (120 mg, 0.43 mmol, 0.13 eq), and potassium acetate (600 mg, 6.11 mmol, 1.77 eq) in 1,2-dimethoxyethane (10 mL) was irradiated under argon at 150° C. in a microwave oven for 3 h. The mixture was allowed to cool to RT, quenched with water and extracted with ethyl acetate. The combined organic layers were washed with brine, dried over Na$_2$SO$_4$ and filtered. The filtrate was concentrated in vacuo to afford the pinacol ester (600 mg). Compound 1 was prepared from commercially available 2-chloro-6-methylbenzoic acid according to Method A.

To a mixture of compound 1 (200 mg, 0.67 mmol) and the pinacol ester (300 mg, 1.27 mmol) in 1,4-dioxane and water (15 mL and 5 mL), PdCl$_2$(dppf) (50 mg, 0.068 mmol, 0.1 eq) and Na$_2$CO$_3$ (300 mg, 2.83 mmol, 4.21 eq) were added and the resulting mixture was stirred at 120° C. for 16 h. The reaction mixture was allowed to cool to RT, quenched with water, and then extracted with ethyl acetate. The combined organic layers were washed with brine, dried over Na$_2$SO$_4$ and filtered. The filtrate was concentrated in vacuo and the residue was purified by flash chromatography on silica gel (0-5% MeOH-DCM) to afford compound 225.

Compound 225 was coupled to 2-amino-4-chloropyrimidine-5-carbonitrile (E-2) to afford compound 226 according to Method G. ESI-MS m/z: 490.8 [M+H]$^+$.

Example 138

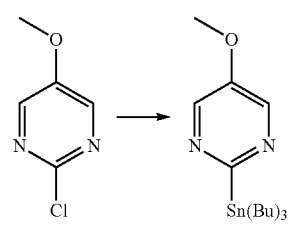

-continued

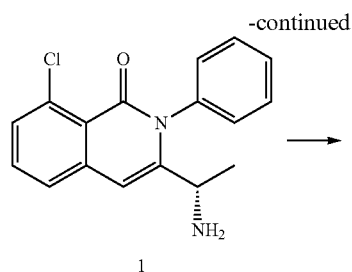
1

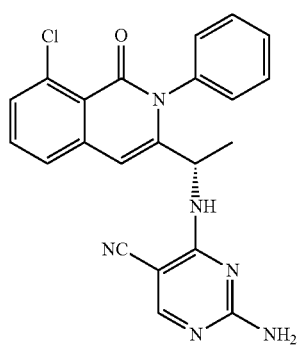
8

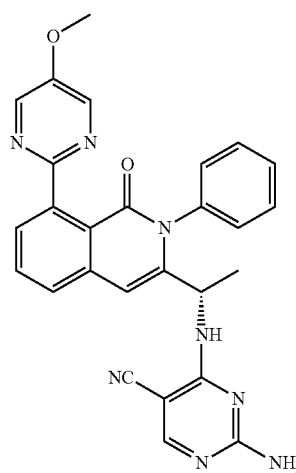
228

A mixture of 2-chloro-5-methoxypyrimidine (1.5 g, 6.38 mmol, 1.0 eq), bis(tri-butyltin) (4.07 g, 7.01 mmol, 1.1 eq), Pd(PPh$_3$)$_4$ (368 mg, 0.319 mmol, 0.05 eq) in toluene (20 mL) was stirred under argon at reflux for 15 h. The mixture was allowed to cool to RT and then filtered. The filtrate was concentrated in vacuo and the residue was purified by flash chromatography on silica gel (0-5% MeOH-DCM) to afford the tri-butylstannane. Compound 8 was prepared from compound 1 and (E-2) using Method G.

A mixture of compound 8 (100 mg, 0.24 mmol), 2-(tributylstannyl)-5-methoxypyrimidine (200 mg, 0.50 mmol, 2.08 eq), bis(tri-t-butylphosphine)palladium(0) (30 mg, 0.059 mmol, 0.25 eq) and CsF (100 mg, 0.66 mmol, 2.74 eq) in 1,4-dioxane (10 mL) was stirred under argon at reflux for 16 h. The mixture was allowed to cool to RT, poured into water (20 mL) and extracted with ethyl acetate (15 mL×2). The combined organic layers were washed with brine, dried over Na$_2$SO$_4$ and filtered. The filtrate was concentrated in vacuo and the residue was purified by flash column chromatography on silica gel (0-5% MeOH-DCM) to afford compound 228. ESI-MS m/z: 491.3[M+H]$^+$.

Example 139

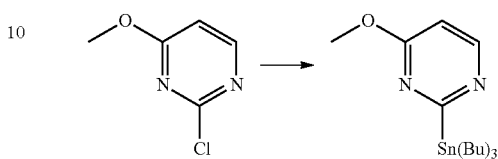

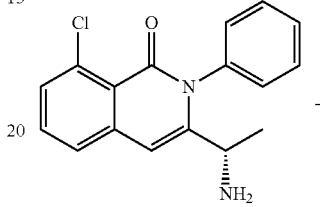
1

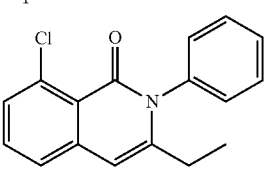

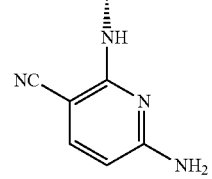
8

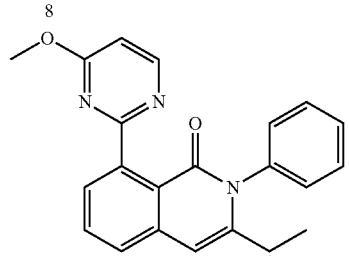
229

A mixture of 2-chloro-4-methoxypyrimidine (1.0 g, 6.92 mmol, 1.0 eq), bis(tri-butyltin) (5.0 g, 8.62 mmol, 1.24 eq), Pd(PPh$_3$)$_4$ (200 mg, 0.17 mmol, 0.025 eq) and Pd(dppf)Cl$_2$ (50 mg, 0.068 mmol, 0.01 eq) in toluene (20 mL) under argon was stirred at reflux for 15 h. The mixture was allowed to cool to RT and filtered. The filtrate was concentrated in vacuo and the residue was purified by flash chromatography on silica gel (0-5% MeOH-DCM) to afford the tri-butylstannane. Compound 8 was prepared from compound 1 and (E-2) using Method G.

Compound 8 was coupled to the tri-butylstannane in analogous fashion to Example 138 to afford the product 229. ESI-MS m/z: 491.3[M+H]$^+$.

Example 140

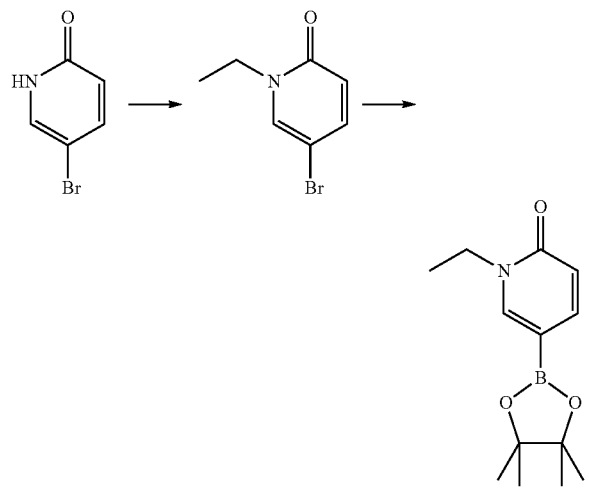

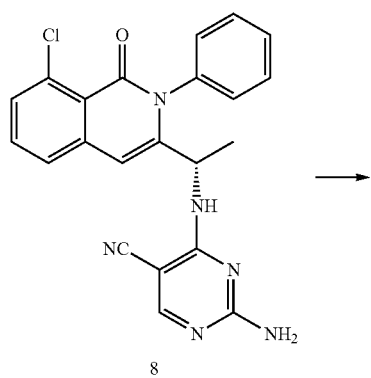

8

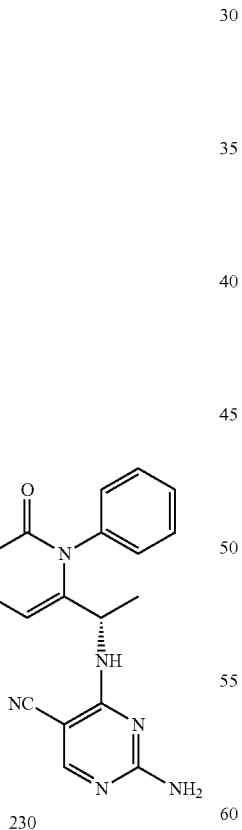

230

To a suspension of NaH (60% dispersion in mineral oil, 1.34 g, 0.056 mol) in THF (10 mL), a solution of 5-bromopyridin-2-ol (2.5 g, 0.014 mol) in THF (50 mL) was added and the resulting mixture was stirred at RT for 1 h. To this mixture, iodoethane (10.9 g, 0.07 mol) was added and the mixture was stirred at RT overnight. The mixture was quenched with water and washed with NH$_4$Cl solution. The organic phase was separated, then concentrated in vacuo and the residue was purified by flash chromatography on silica gel (50-100% PE-AE) to afford 5-bromo-1-ethylpyridin-2(1H)-one.

To a suspension of 5-bromo-1-ethylpyridin-2(1H)-one (250 mg, 1.23 mmol) in 1,4-dioxane (15 mL), 4,4,4',4',5,5,5',5'-octamethyl-2,2'-bi(1,3,2-dioxaborolane (346.4 mg, 1.35 mmol), 1,1'-bis(diphenyl phosphino)ferrocene]dichloropalladium(II) (100 mg, 0.12 mmol) and potassium acetate (301.4 mg, 3.08 mmol) were added. The reaction mixture was stirred at reflux for 3 h. The resulting mixture was concentrated in vacuo, and the residue was purified by column chromatography on silica gel (10-100% PE-AE) to afford 1-ethyl-5-(4,4,5,5-tetramethyl-1,3,2-dioxaborolan-2-yl)pyridin-2(1H)-one.

Compound 8 (100 mg, 0.24 mmol), 1-ethyl-5-(4,4,5,5-tetramethyl-1,3,2-dioxaborolan-2-yl)pyridin-2(1H)-one (89.7 mg, 0.361 mmol), 1,1'-Bis(diphenylphosphino)ferrocene]dichloropalladium(II) (19.58 mg, 0.024 mmol) and sodium carbonate (127.2 mg, 1.2 mmol) were suspended in 1,4-dioxane (5 mL) and water (1 mL) under argon, and the resulting mixture was stirred at reflux overnight. The resulting mixture was concentrated in vacuo, and the residue was purified by column chromatography on silica gel (0-5% MeOH-DCM) to afford compound 230. ESI-MS m/z: 504.3 [M+H]$^+$.

Example 141

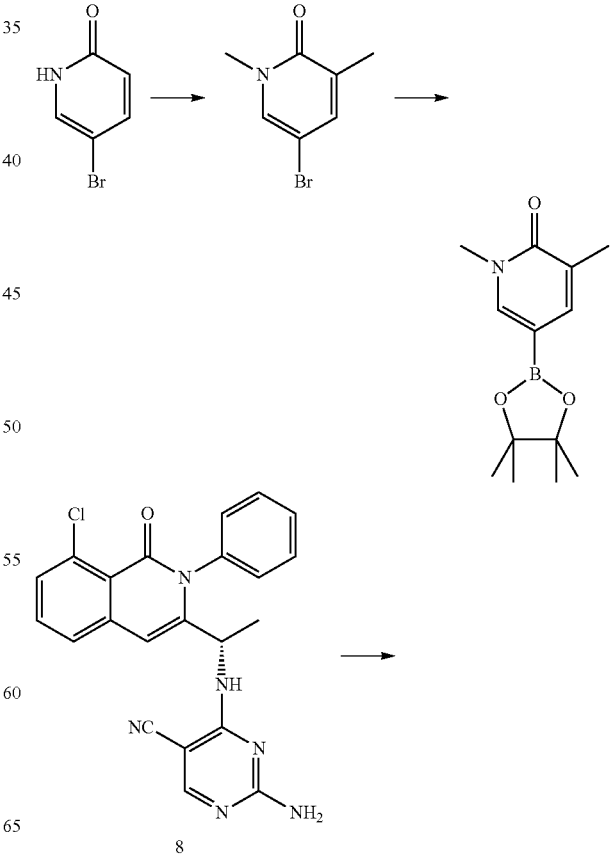

8

-continued

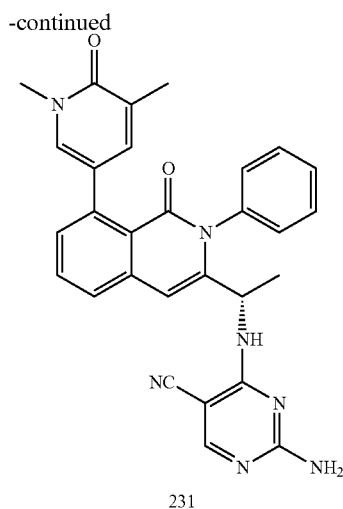

231

To a suspension of NaH (60% dispersion in mineral oil, 1.02 g, 42.4 mmol) in THF (10 mL), a solution of 5-bromopyridin-2-ol (2.0 g, 10.6 mmol) in THF (50 mL) was added, and the resulting mixture was stirred at RT for 1 h. To this mixture, iodomethane (7.5 g, 53.2 mmol) was added and the resulting mixture was stirred at RT overnight. The mixture was quenched with water and extracted with ethyl acetate (200 mL). The organic layer was washed with aqueous NH$_4$Cl solution and dried over anhydrous MgSO$_4$ and filtered. The filtrate was concentrated to dryness to afford 5-bromo-1,3-dimethylpyridin-2(1H)-one.

The pinacol ester was prepared in analogous fashion to Example 140, except 5-bromo-1,3-dimethylpyridin-2(1H)-one was used in place of 5-bromo-1-ethylpyridin-2(1H)-one. Compound 231 was prepared from compound 8 in analogous fashion to Example 140, except 1,3-dimethyl-5-(4,4,5,5-tetramethyl-1,3,2-dioxaborolan-2-yl)pyridin-2(1H)-one was used in place of 1-ethyl-5-(4,4,5,5-tetramethyl-1,3,2-dioxaborolan-2-yl)pyridin-2(1H)-one. ESI-MS m/z: 504.3 [M+H]$^+$.

Example 142

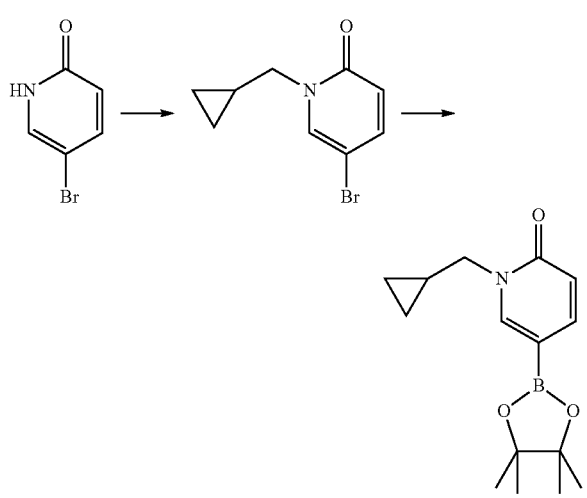

-continued

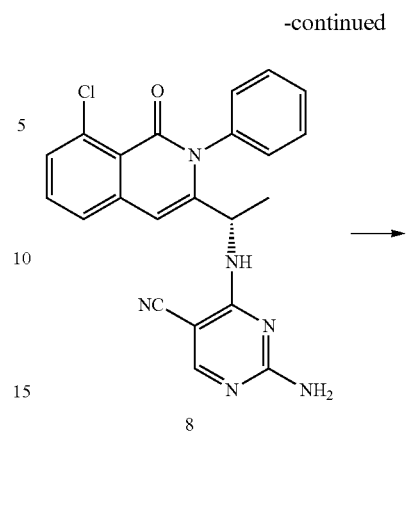

8

232

To a solution of 5-bromopyridin-2-ol (1.0 g, 5.75 mmol) in DMF (10 mL) at RT, potassium tert-butoxide (0.68 g, 6.07 mmol) was added and the mixture was stirred for 30 min. To this mixture, (bromomethyl)cyclopropane (1.03 g, 8.62 mmol) was added, and the resulting mixture was stirred at 70° C. for 2 h. The mixture was allowed to cool to RT, diluted with EtOAc (50 mL) and quenched with water (20 mL). The organic layer was washed with water (2×20 mL) and brine (20 mL), dried over anhydrous MgSO$_4$ and filtered. The filtrate was concentrated in vacuo to afford 5-bromo-1-(cyclopropylmethyl)pyridin-2(1H)-one.

1-(Cyclopropylmethyl)-5-(4,4,5,5-tetramethyl-1,3,2-dioxaborolan-2-yl)pyridin-2(1H)-one was prepared in analogous fashion to Example 140, except 5-bromo-1-(cyclopropylmethyl)pyridin-2(1H)-one was used in place of 5-bromo-1-ethylpyridin-2(1H)-one. Compound 232 was prepared from compound 8 in analogous fashion to Example 140, except 1-(cyclopropylmethyl)-5-(4,4,5,5-tetramethyl-1,3,2-dioxaborolan-2-yl)pyridin-2(1H)-one was used in place of 1-ethyl-5-(4,4,5,5-tetramethyl-1,3,2-dioxaborolan-2-yl)pyridin-2(1H)-one. ESI-MS m/z: 530.3 [M+H]$^+$.

Example 143

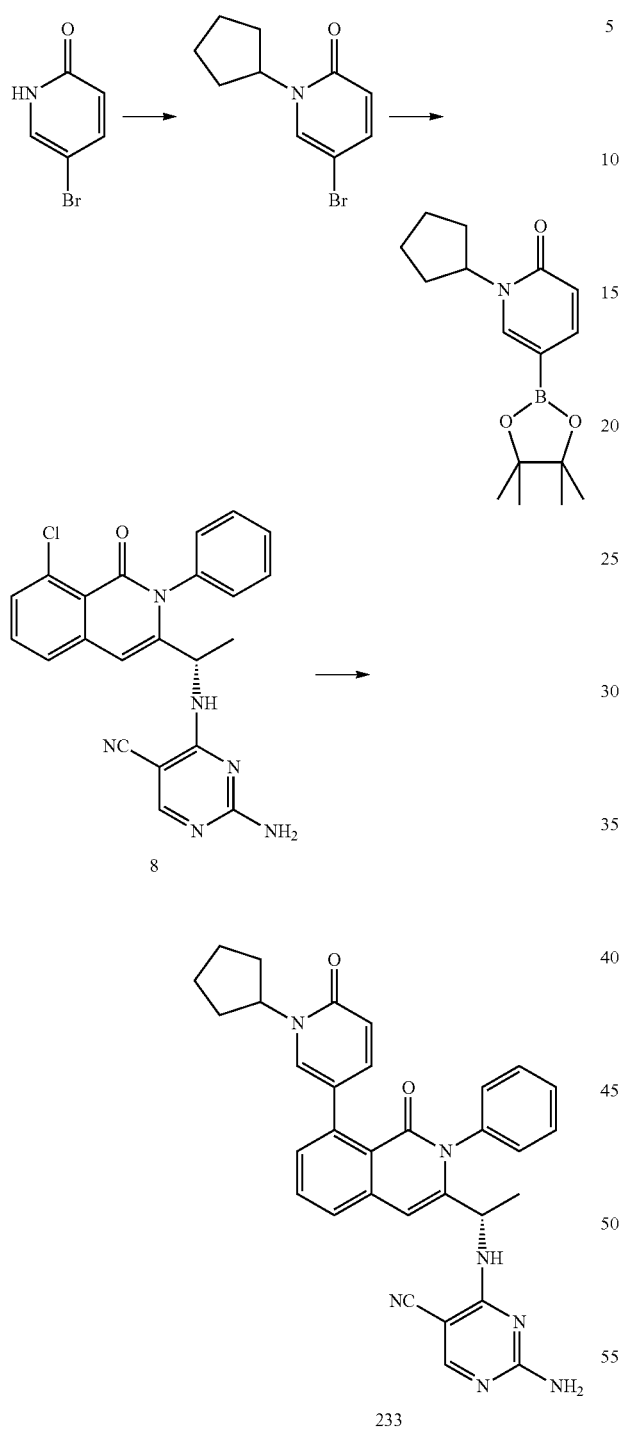

5-Bromo-1-cyclopentylpyridin-2(1H)-one was prepared from 5-bromopyridin-2(1H)-one in analogous fashion to Example 142, except 1-bromocyclopentpane was used in place of (bromomethyl)cyclopropane. 1-Cyclopentyl-5-(4,4,5,5-tetramethyl-1,3,2-dioxaborolan-2-yl)pyridin-2(1H)-one was prepared from 5-bromo-1-cyclopentylpyridin-2(1H)-one according to Example 140. Coupling of compound 8 with 1-cyclopentyl-5-(4,4,5,5-tetramethyl-1,3,2-dioxaborolan-2-yl)pyridin-2(1H)-one was performed according to Example 40 to afford product 233. ESI-MS m/z: 544.4 [M+H]⁺.

Example 144

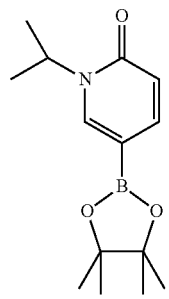

Compound 234 was prepared in analogous fashion to Example 143, except that 5-bromo-1-isopropylpyridin-2(1H)-one was used in place of 5-bromo-1-cyclopentylpyridin-2(1H)-one. ESI-MS m/z: 518.3 [M+H]⁺.

343
Example 145

344
Example 146

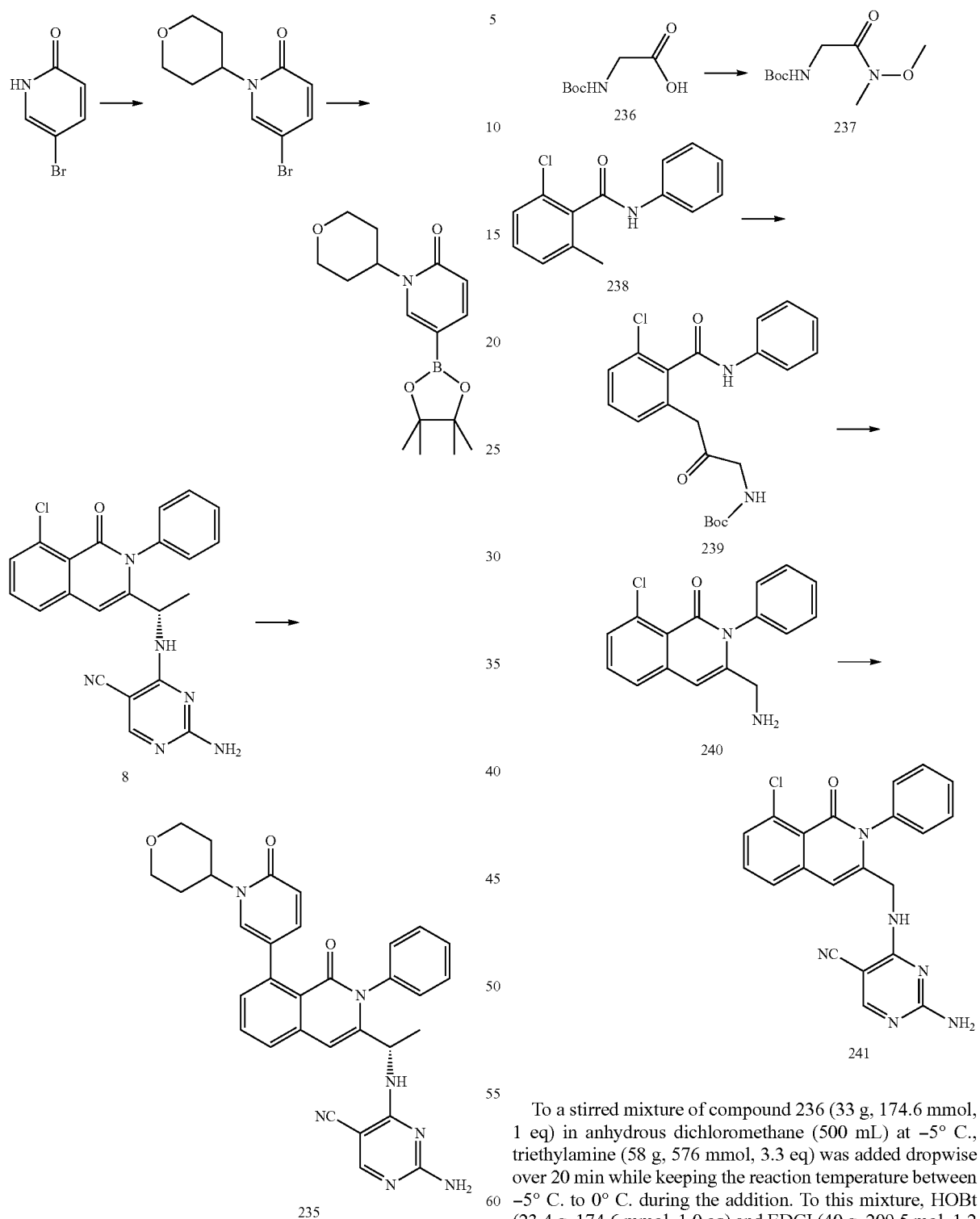

Compound 234 was prepared in analogous fashion to Example 143, except that 5-bromo-1-(tetrahydro-2H-pyran-4-yl)pyridin-2(1H)-one was used in place of 5-bromo-1-cyclopentylpyridin-2(1H)-one. ESI-MS m/z: 560.4 [M+H]$^+$.

To a stirred mixture of compound 236 (33 g, 174.6 mmol, 1 eq) in anhydrous dichloromethane (500 mL) at −5° C., triethylamine (58 g, 576 mmol, 3.3 eq) was added dropwise over 20 min while keeping the reaction temperature between −5° C. to 0° C. during the addition. To this mixture, HOBt (23.4 g, 174.6 mmol, 1.0 eq) and EDCI (40 g, 209.5 mol, 1.2 eq) were added sequentially while keeping the reaction temperature between −5° C. to 0° C. The resulting mixture was stirred at −5° C. for 30 min. N,O-Dimethylhydroxylamine hydrochloride (19 g, 192.1 mmol, 1.1 eq) was added in portions while keeping the reaction temperature between −5° C. to 0° C. After stirring at −5° C. for 30 min., the reaction mixture was allowed to warm to RT and stirred at RT for 16 h, and then quenched with water (200 mL). The organic layer was separated, washed with water (2×200 mL) and brine (150 mL), dried over anhydrous Na₂SO₄ and filtered. The filtrate was concentrated in vacuo. The product was slurried in PE (500 mL) and stirred at RT for 30 min. The solid was collected by filtration and further dried in vacuo to afford tert-butyl 2-(methoxy(methyl)amino)-2-oxoethylcarbamate (compound 237).

Compound 238 was prepared from 2-chloro-6-methylbenzoic acid in analogous fashion to compound A-2 in Method A.

To a solution of compound 238 (40 g, 163 mmol, 1.0 eq) in THF (200 mL) at −30° C. under an argon atmosphere, a solution of n-butyllithium in THF (2.5 M, 140 mL, 408 mmol, 2.5 eq) was added dropwise over 30 min while keeping the inner temperature between −30° C. and −10° C. The resulting mixture was stirred at −30° C. for an additional 30 min. To a solution of compound 237 (35 g, 198 mmol, 1.2 eq) in THF (200 mL) at −30° C. under an argon atmosphere, a solution of isopropylmagnesium chloride in THF (2 M, 115 mL, 268 mmol. 1.65 eq) was added dropwise over 30 min while keeping inner temperature between −30° C. and −10° C. The resulting mixture was stirred at −30° C. for 30 min. This solution was added slowly to above reaction mixture while keeping the inner temperature between −30° C. and −10° C. The resulting mixture was stirred at −15° C. for an additional 1 h. The reaction mixture was quenched with water (50 mL) and then acidified with 6 N HCl (160 mL) at −10° C. to 0° C. to adjust the pH to 1-3. The mixture was allowed to warm to RT and concentrated in vacuo to afford compound 239. The residue was dissolved in MeOH (400 mL), and then conc. HCl (200 mL) was added quickly at RT. The resulting mixture was stirred at reflux for 1 h. The reaction mixture was concentrated in vacuo to reduce the volume to about 450 mL. The residue was extracted with about a 2:1 mixture of PE and EA (2×500 mL). The aqueous layer was basified with concentrated ammonium hydroxide to adjust the pH to 9-10 while keeping the inner temperature between −10° C. and 0° C. The mixture was extracted with DCM (3×100 mL), washed with brine, dried over Na₂SO₄ and filtered. The filtrate was purified by flash column chromatography on silica gel (2-30% ethyl acetate—petroleum ether) to afford compound 240.

Compound 241 was prepared from compound 240 and (E-2) using Method G. ESI-MS m/z: 403.2 [M+H]⁺.

Example 147

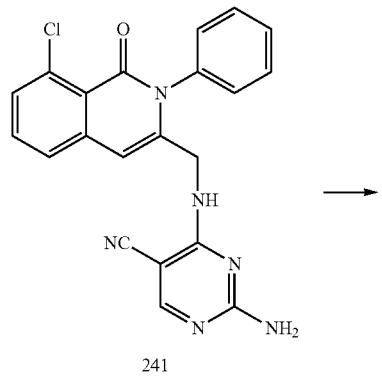

241

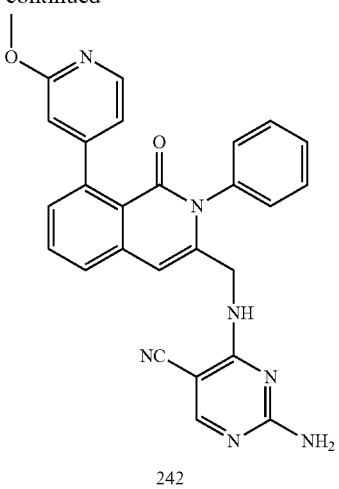

242

Compound 242 was prepared from compound 241 through coupling to 2-methoxypyridin-4-ylboronic acid according to Method J. ESI-MS m/z: 476.2 [M+H]⁺.

Example 148

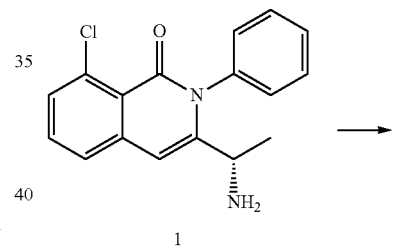

1

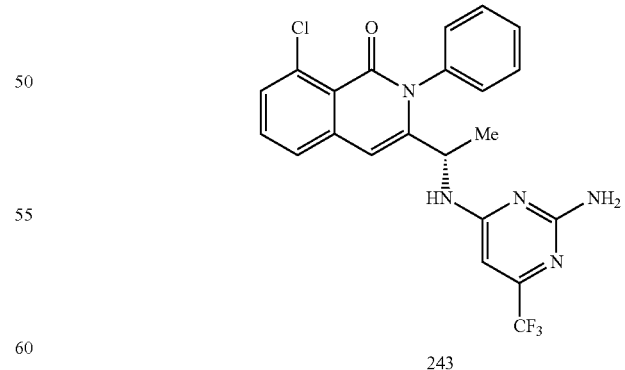

243

Compound 243 was prepared from compound 1 through coupling with 4-chloro-6-(trifluoromethyl)pyrimidin-2-amine according to Method G. ESI-MS m/z: 460.2 [M+H]⁺.

Example 149

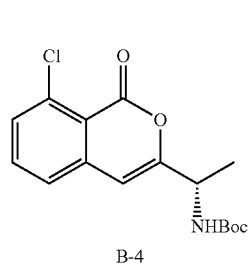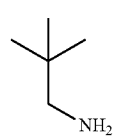

B-4

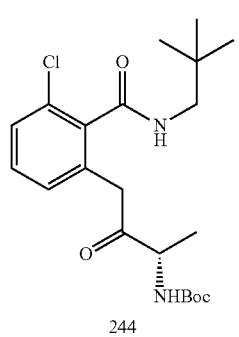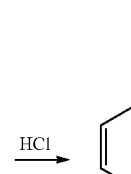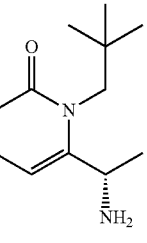

244    245

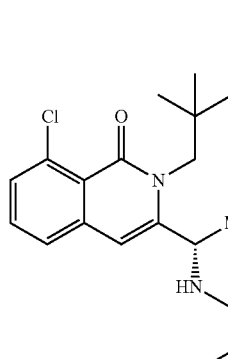

246

Compound 245 was synthesized from compound B-4 according to Method B using neopentylamine. Compound 246 was prepared from compound 245 according to Method G using 2-amino-4-chloropyrimidine-5-carbonitrile. ESI-MS m/z: 411.2 [M+H]⁺.

Example 150

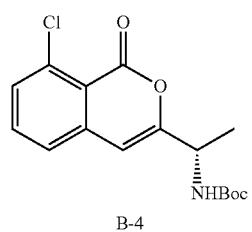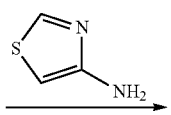

B-4

-continued

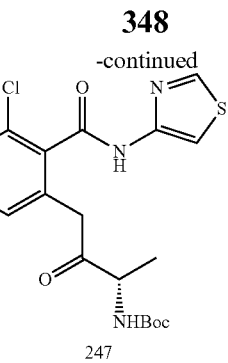

247

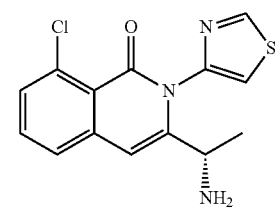

248

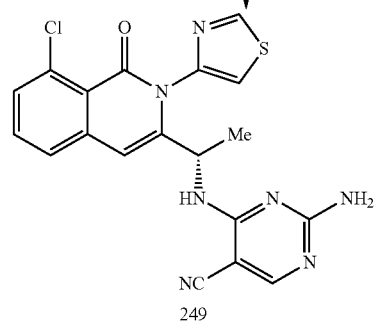

249

Compound 248 was synthesized from compound B-4 according to Method B using thiazol-4-amine. Compound 249 was prepared from compound 248 according to Method G using 2-amino-4-chloropyrimidine-5-carbonitrile. ESI-MS m/z: 424.1 [M+H]⁺.

Example 151

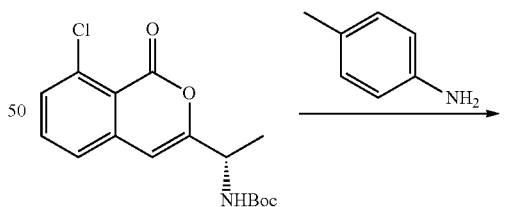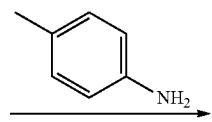

B-4

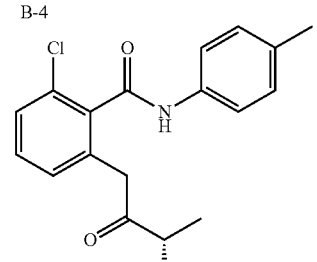

250

349

-continued

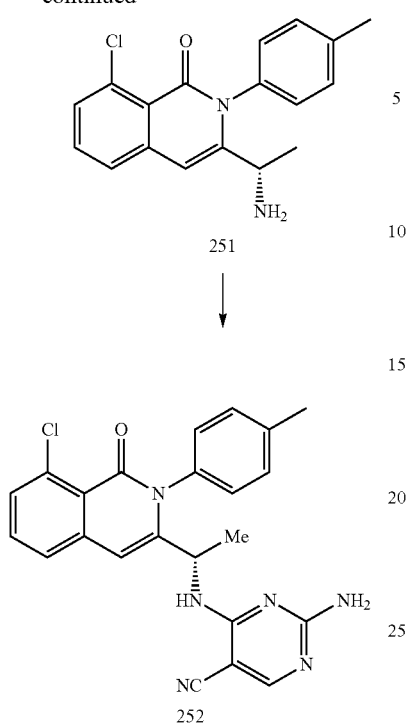

251

252

Compound 251 was synthesized from compound B-4 according to Method B using p-toluidine. Compound 252 was prepared from compound 251 according to Method G using 2-amino-4-chloropyrimidine-5-carbonitrile. ESI-MS m/z: 431.1 [M+H]⁺.

Example 152

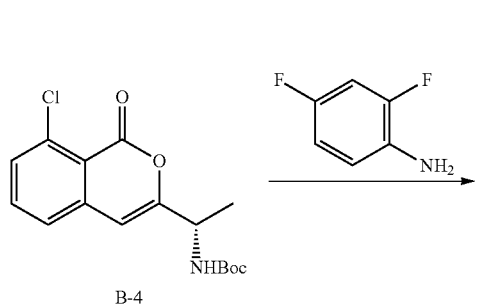

B-4

253

350

-continued

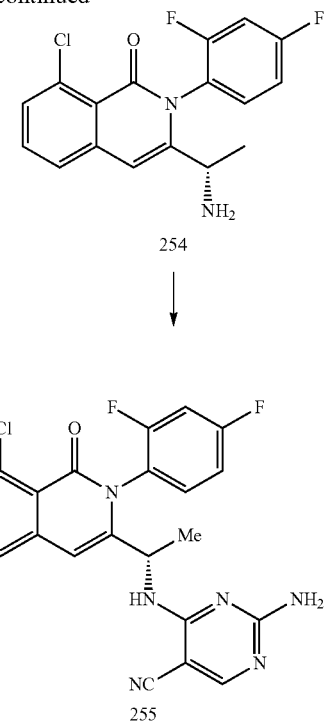

254

255

Compound 254 was synthesized from compound B-4 according to Method B using 2,4-difluoroaniline. Compound 255 was prepared from compound 254 according to Method G using 2-amino-4-chloropyrimidine-5-carbonitrile. ESI-MS m/z: 453.1 [M+H]⁺.

Example 153

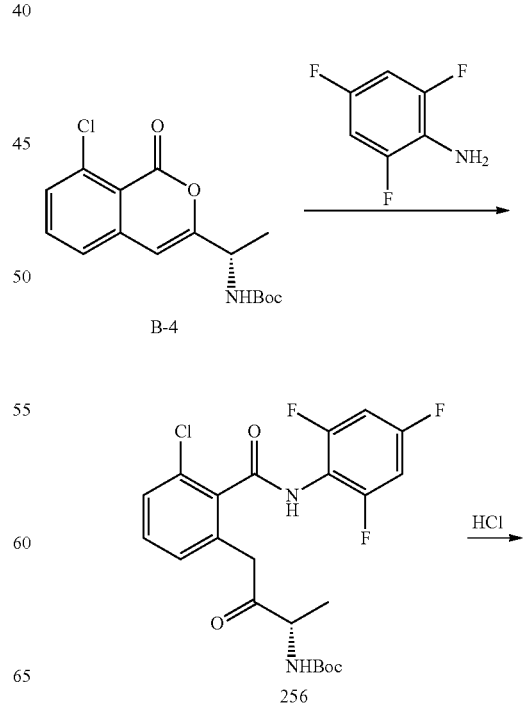

B-4

256

351

-continued

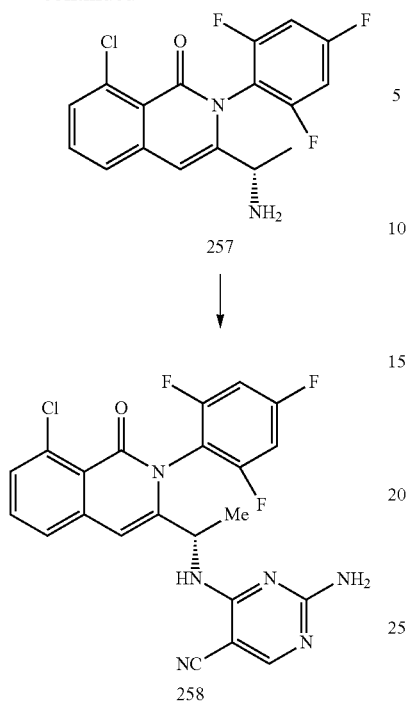

Compound 257 was synthesized from compound B-4 according to Method B using 2,4,6-trifluoroaniline. Compound 258 was prepared from compound 257 according to Method G using 2-amino-4-chloropyrimidine-5-carbonitrile. ESI-MS m/z: 471.0 [M+H]$^+$.

Example 154

352

-continued

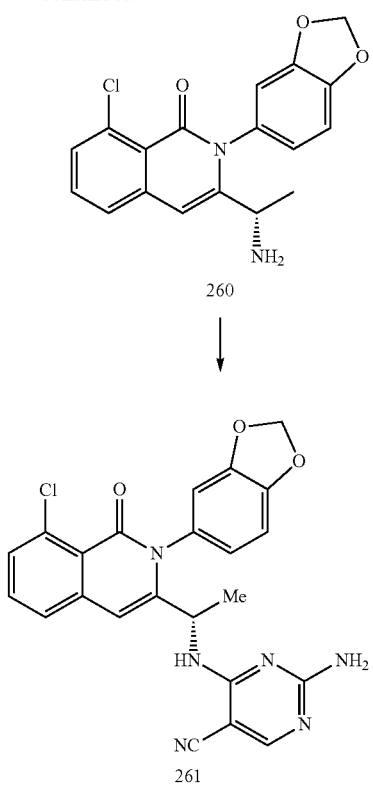

Compound 260 was synthesized from compound B-4 according to Method B using benzo[d][1,3]dioxol-5-amine. Compound 261 was prepared from compound 260 according to Method G using 2-amino-4-chloropyrimidine-5-carbonitrile. ESI-MS m/z: 461.1 [M+H]$^+$.

Example 155

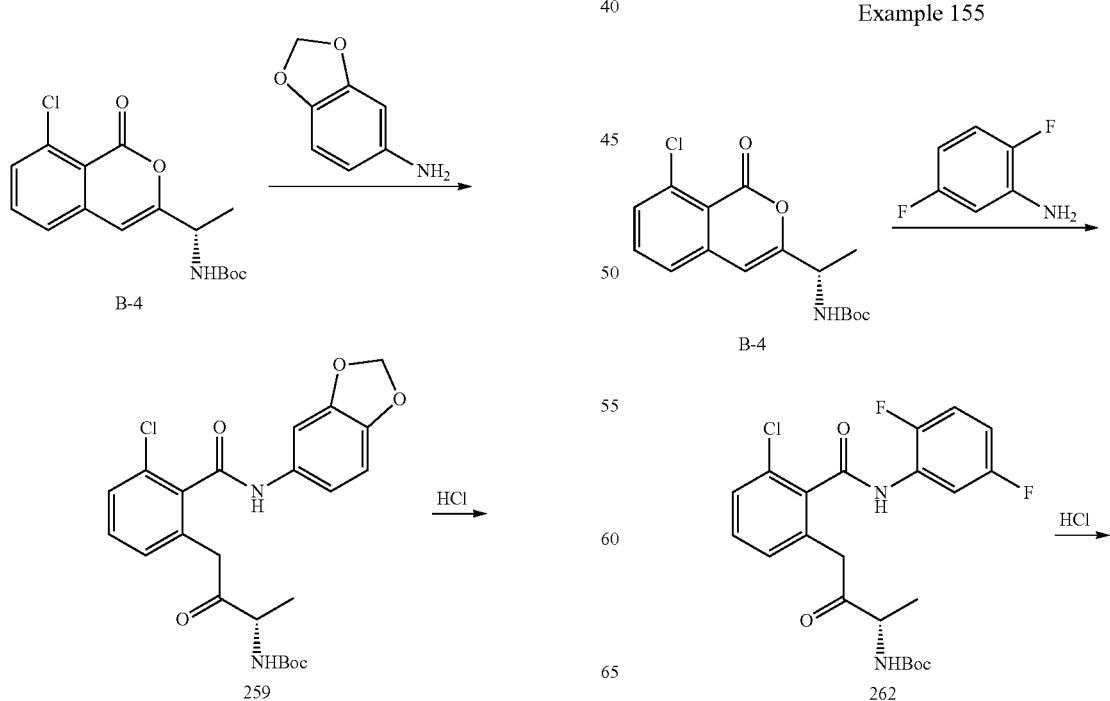

353

-continued

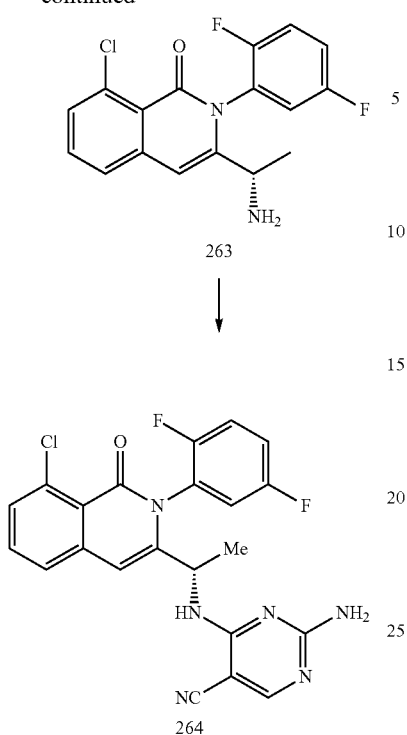

Compound 263 was synthesized from compound B-4 according to Method B using 2,5-difluoroaniline. Compound 264 was prepared from compound 263 according to Method G using 2-amino-4-chloropyrimidine-5-carbonitrile. ESI-MS m/z: 453.1 [M+H]+.

Example 156

354

-continued

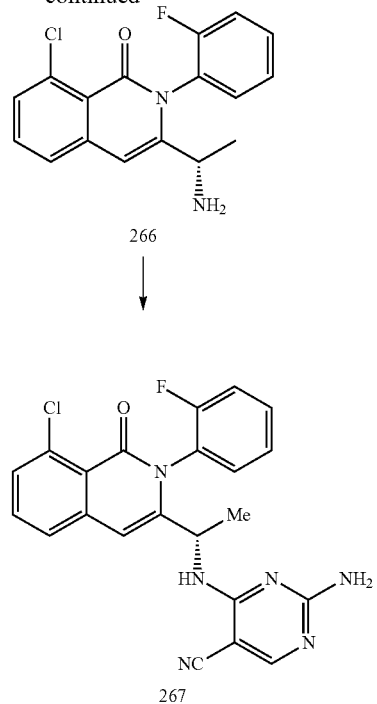

Compound 266 was synthesized from compound B-4 according to Method B using 2-fluoroaniline. Compound 267 was prepared from compound 266 according to Method G using 2-amino-4-chloropyrimidine-5-carbonitrile. ESI-MS m/z: 435.1 [M+H]+.

Example 157

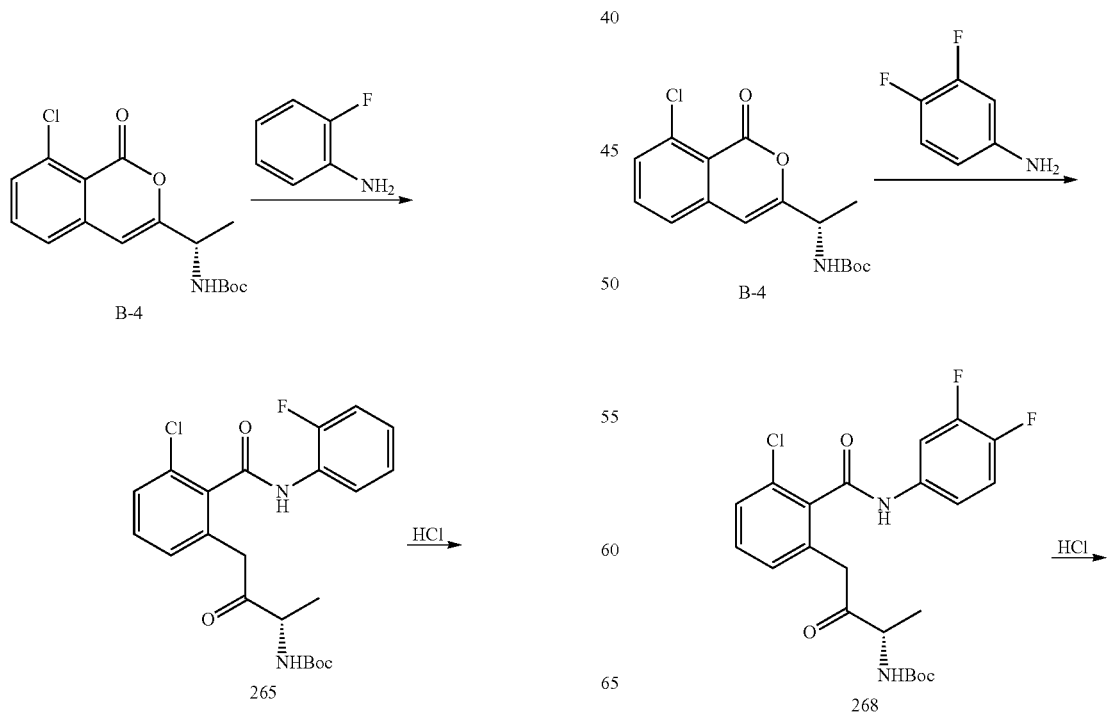

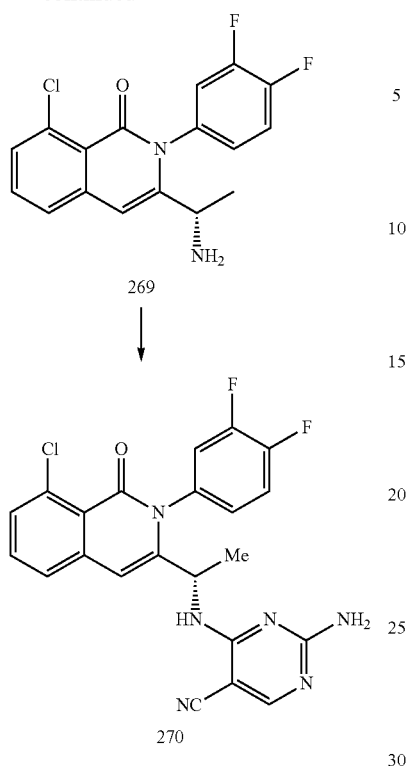

269

270

Compound 269 was synthesized from compound B-4 according to Method B using 3,4-difluoroaniline. Compound 270 was prepared from compound 269 according to Method G using 2-amino-4-chloropyrimidine-5-carbonitrile. ESI-MS m/z: 453.0 [M+H]⁺.

Example 158

272

273

Compound 272 was synthesized from compound B-4 according to Method B using 3,5-difluoroaniline. Compound 273 was prepared from compound 272 according to Method G using 2-amino-4-chloropyrimidine-5-carbonitrile. ESI-MS m/z: 453.1 [M+H]⁺.

Example 159

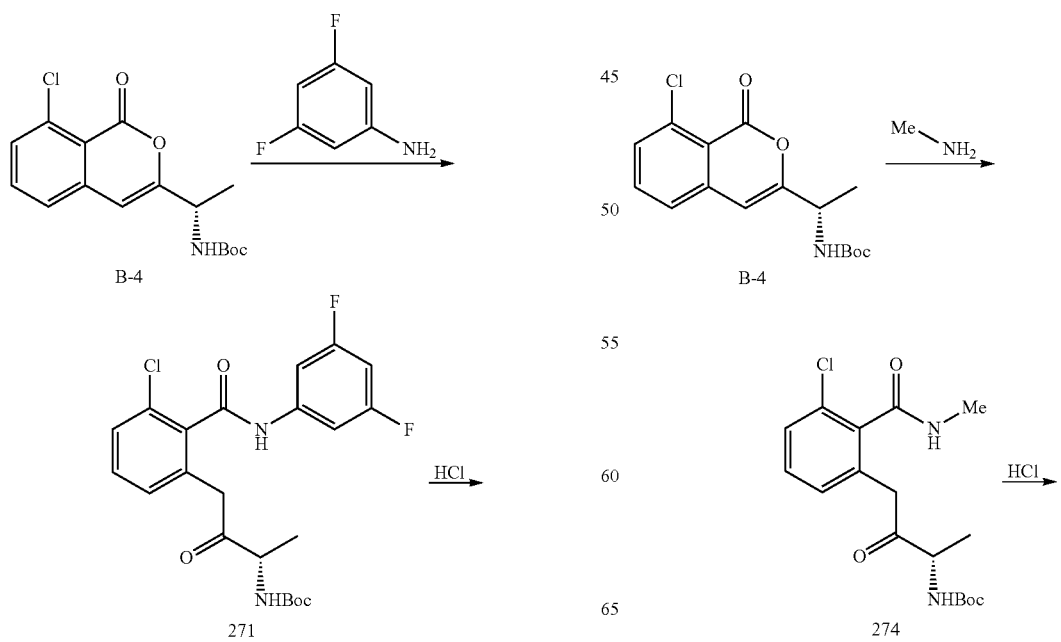

B-4

B-4

271

274

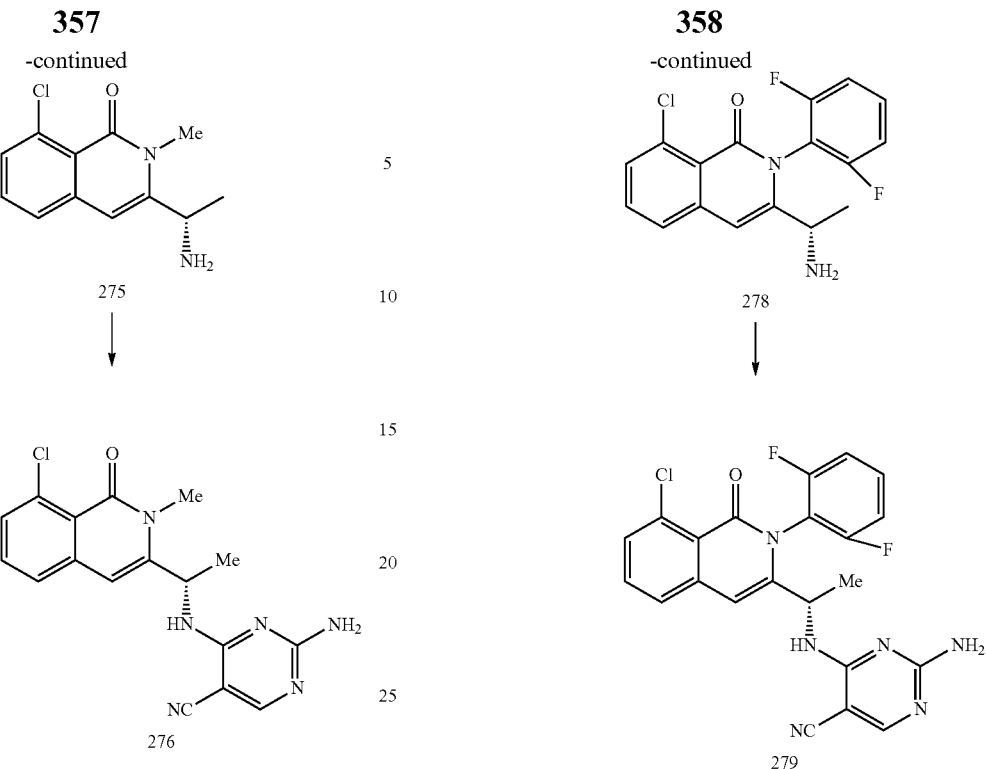

Compound 276 was synthesized from compound B-4 according to Method B using methylamine. Compound 276 was prepared from compound 275 according to Method G using 2-amino-4-chloropyrimidine-5-carbonitrile. ESI-MS m/z: 355.1 [M+H]+.

Compound 278 was synthesized from compound B-4 according to Method B using 2,6-difluoroaniline. Compound 279 was prepared from compound 278 according to Method G using 2-amino-4-chloropyrimidine-5-carbonitrile. ESI-MS m/z: 453.1 [M+H]+.

Example 160

Example 161

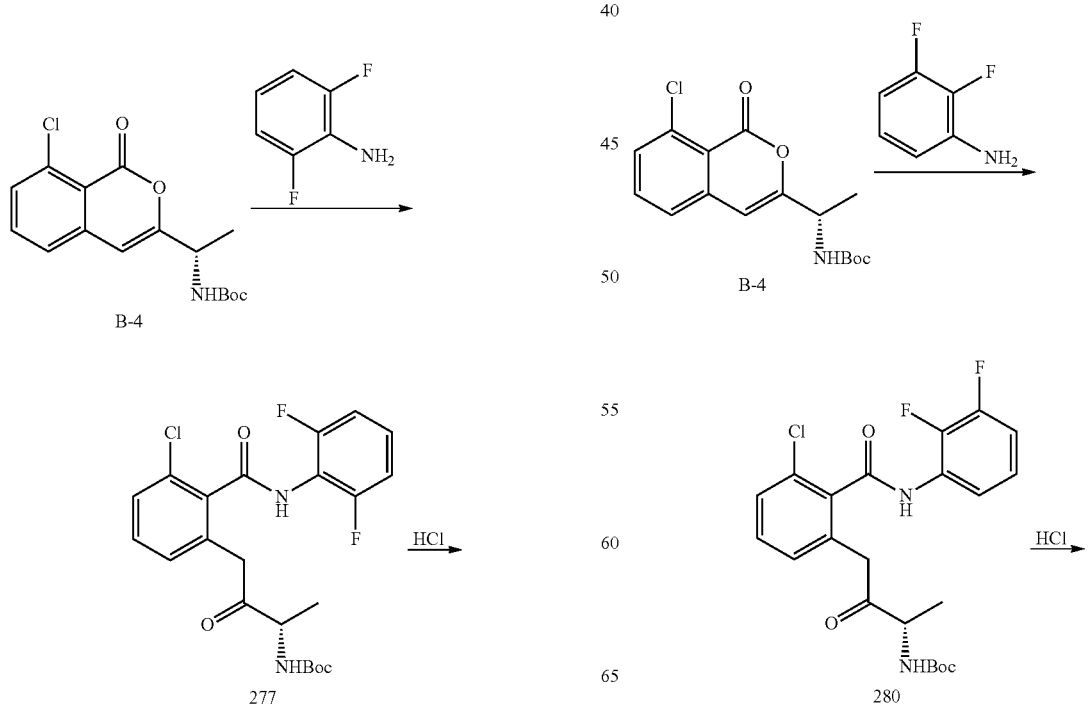

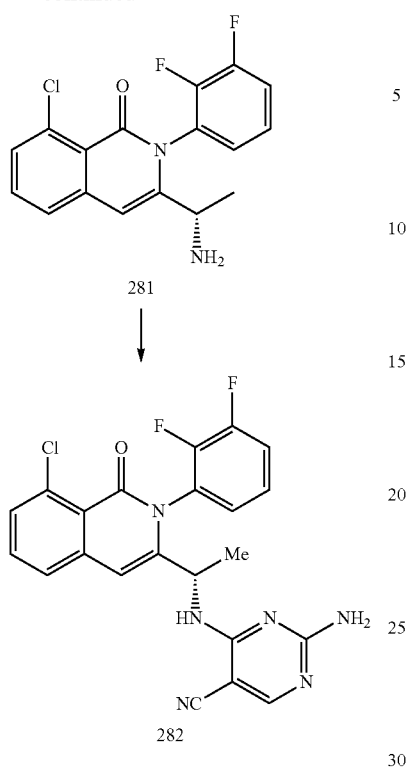

281

282

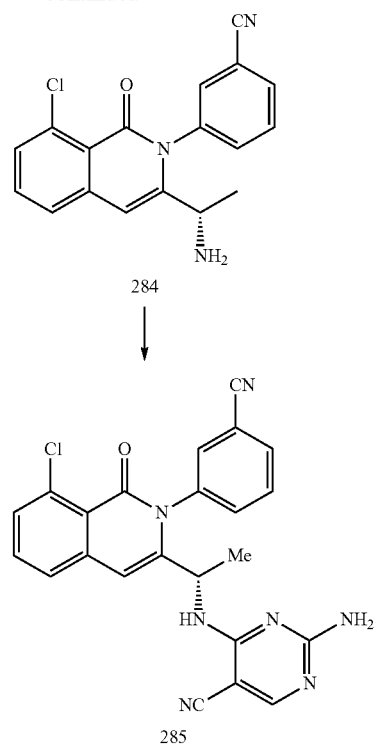

284

285

Compound 281 was synthesized from compound B-4 according to Method B using 2,3-difluoroaniline. Compound 282 was prepared from compound 281 according to Method G using 2-amino-4-chloropyrimidine-5-carbonitrile. ESI-MS m/z: 453.1 [M+H]⁺.

Compound 284 was synthesized from compound B-4 according to Method B using 3-aminobenzonitrile. Compound 285 was prepared from compound 284 according to Method G using 2-amino-4-chloropyrimidine-5-carbonitrile. ESI-MS m/z: 442.1 [M+H]⁺.

Example 162

Example 163

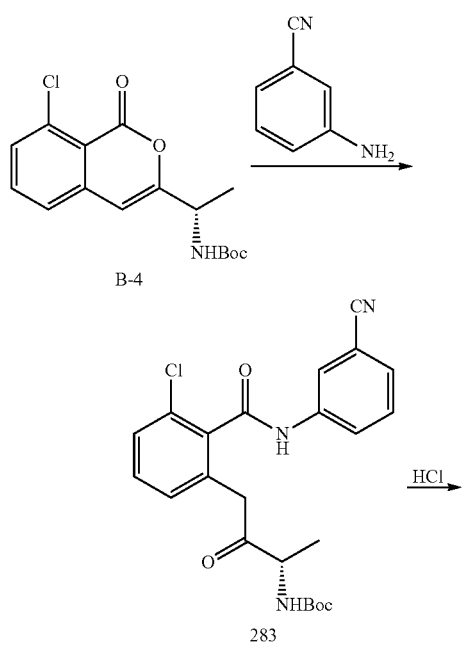

B-4

283

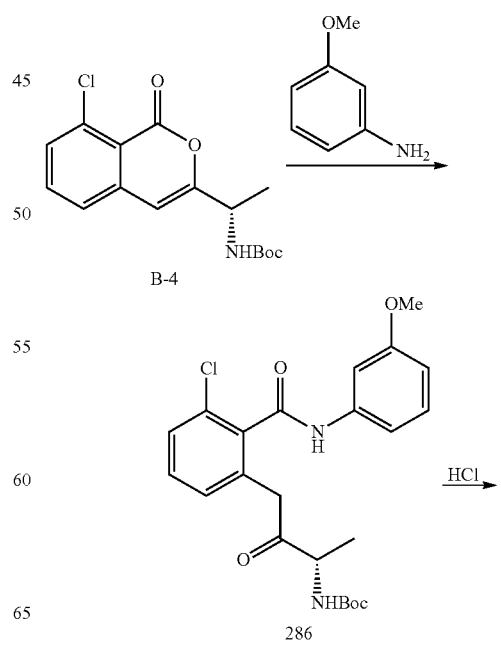

B-4

286

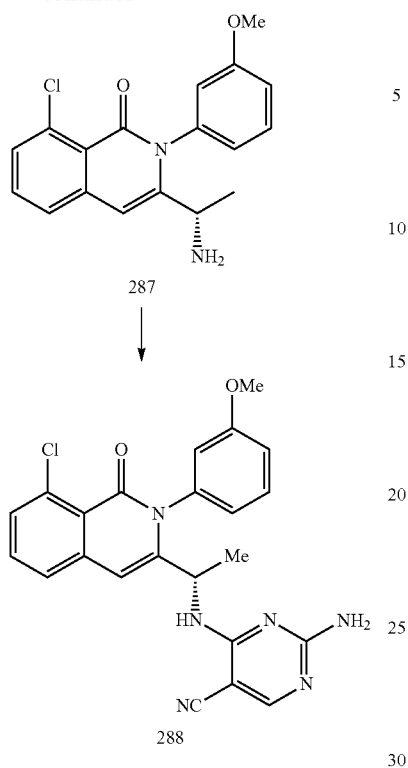

287

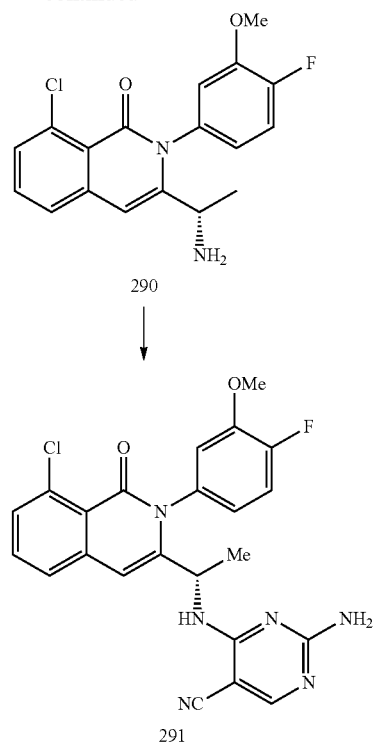

290

288

291

Compound 287 was synthesized from compound B-4 according to Method B using 3-methoxyaniline. Compound 288 was prepared from compound 287 according to Method G using 2-amino-4-chloropyrimidine-5-carbonitrile. ESI-MS m/z: 447.1 [M+H]+.

Compound 290 was synthesized from compound B-4 according to Method B using 4-fluoro-3-methoxyaniline. Compound 291 was prepared from compound 290 according to Method G using 2-amino-4-chloropyrimidine-5-carbonitrile. ESI-MS m/z: 465.1 [M+H]+.

Example 164

Example 165

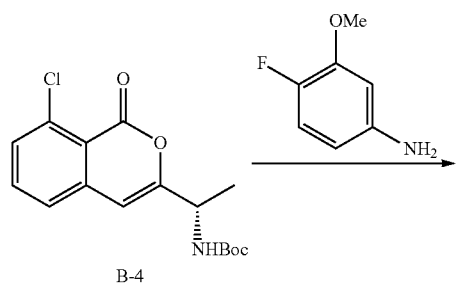

B-4

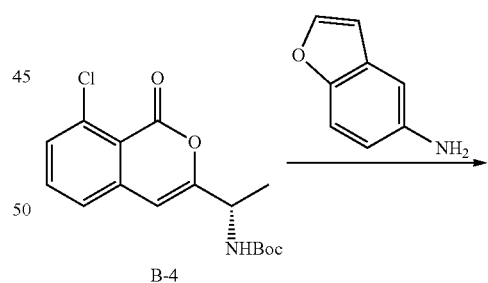

B-4

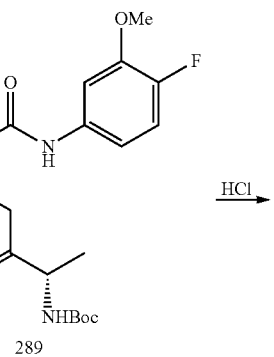

289

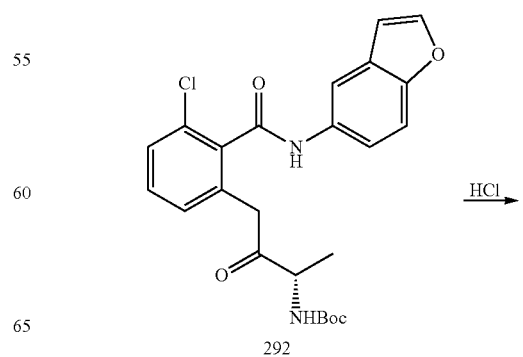

292

363
-continued

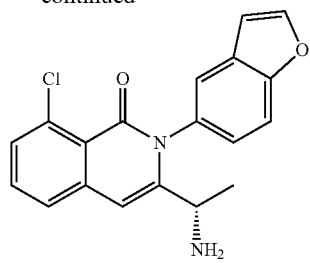
293

↓

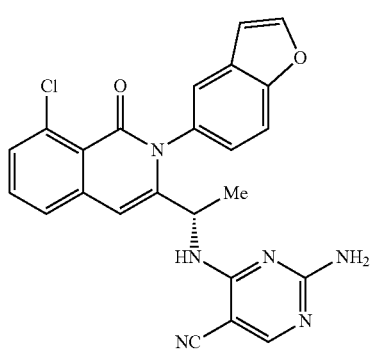
294

Compound 293 was synthesized from compound B-4 according to Method B using benzofuran-5-amine. Compound 294 was prepared from compound 293 according to Method G using 2-amino-4-chloropyrimidine-5-carbonitrile. ESI-MS m/z: 457.1 [M+H]⁺.

Example 166

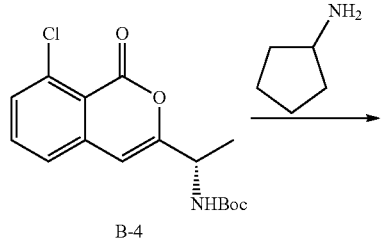
B-4

↓

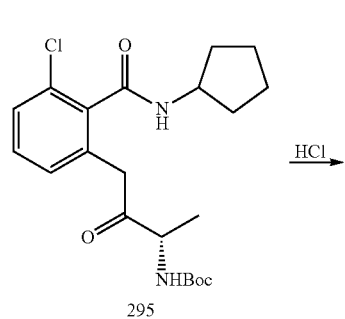
295

HCl→

364
-continued

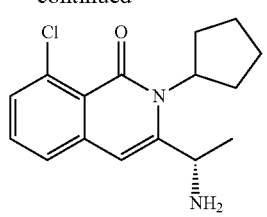
296

↓

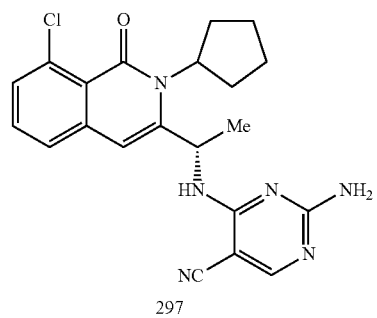
297

Compound 296 was synthesized from compound B-4 according to Method B using cyclopentylamine. Compound 297 was prepared from compound 296 according to Method G using 2-amino-4-chloropyrimidine-5-carbonitrile. ESI-MS m/z: 409.1 [M+H]⁺.

Example 167

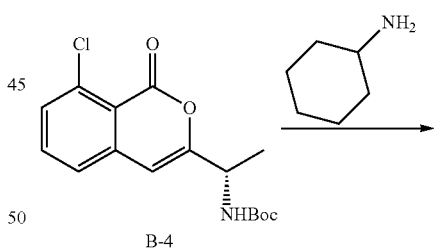
B-4

↓

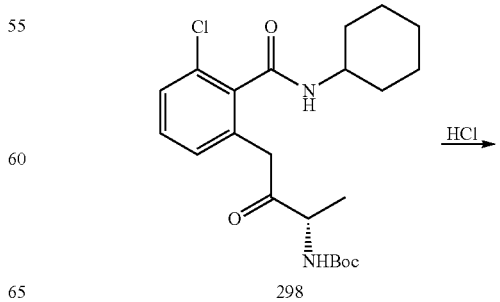
298

HCl→

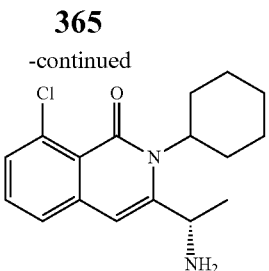

299

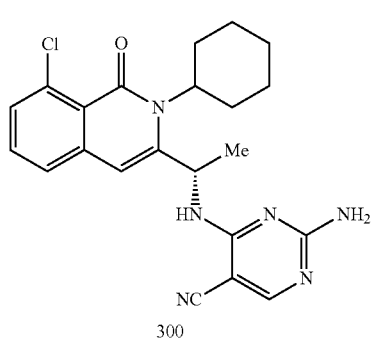

300

Compound 299 was synthesized from compound B-4 according to Method B using cyclohexylamine. Compound 300 was prepared from compound 299 according to Method G using 2-amino-4-chloropyrimidine-5-carbonitrile. ESI-MS m/z: 423.2 [M+H]$^+$.

Example 168

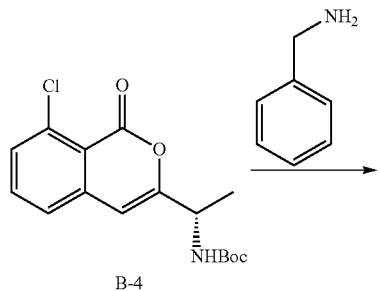

B-4

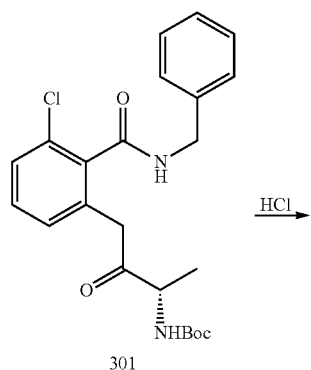

301

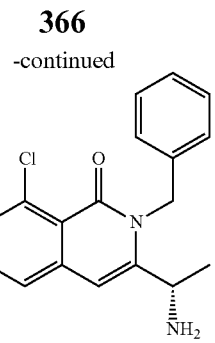

302

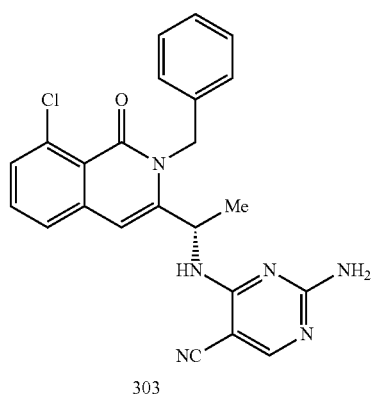

303

Compound 302 was synthesized from compound B-4 according to Method B using benzylamine. Compound 303 was prepared from compound 301 according to Method G using 2-amino-4-chloropyrimidine-5-carbonitrile. ESI-MS m/z: 431.1 [M+H]$^+$.

Example 169

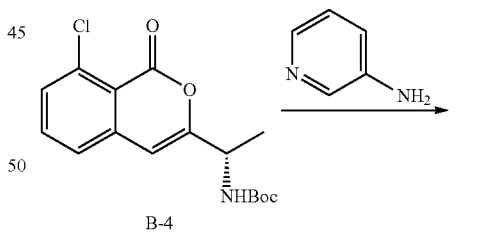

B-4

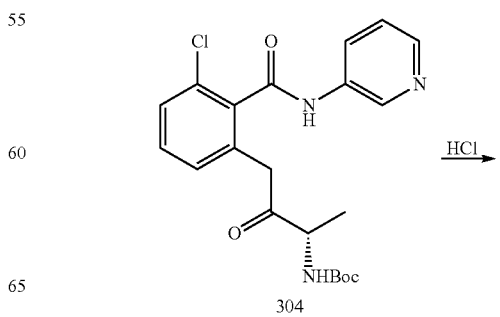

304

367
-continued

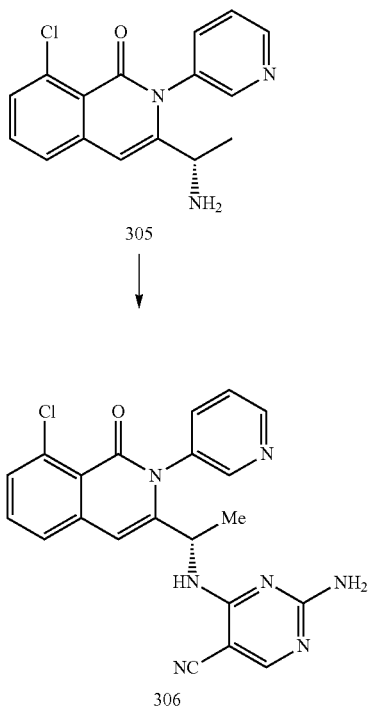

Compound 305 was synthesized from compound B-4 according to Method B using pyridin-3-amine. Compound 306 was prepared from compound 305 according to Method G using 2-amino-4-chloropyrimidine-5-carbonitrile. ESI-MS m/z: 418.1 [M+H]⁺.

368
-continued

Compound 308 was synthesized from compound B-4 according to Method B using ethylamine. Compound 309 was prepared from compound 308 according to Method G using 2-amino-4-chloropyrimidine-5-carbonitrile. ESI-MS m/z: 369.1 [M+H]⁺.

Example 171

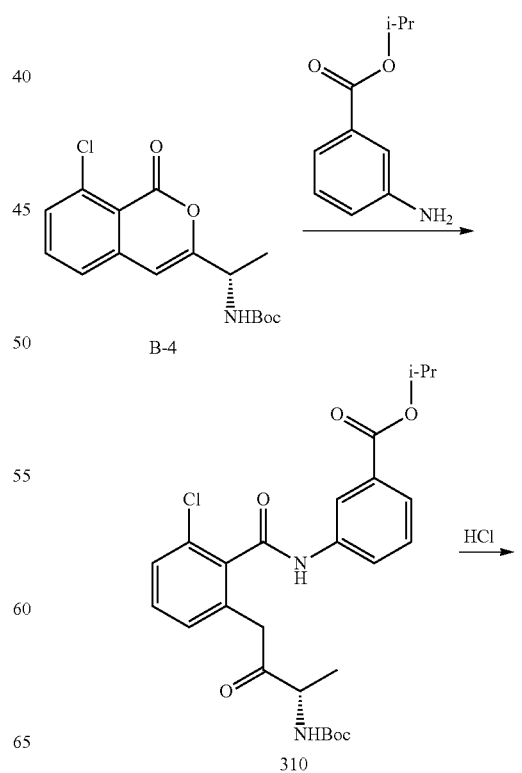

Example 170

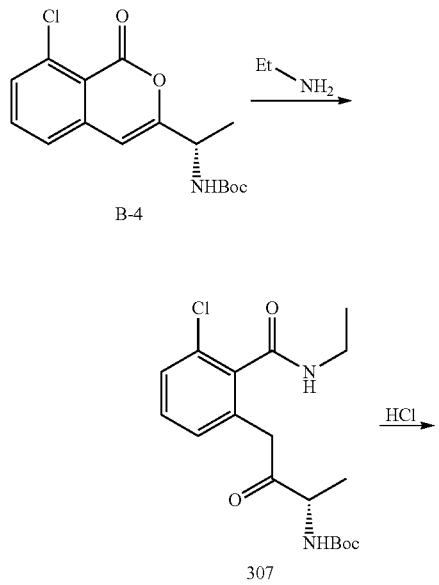

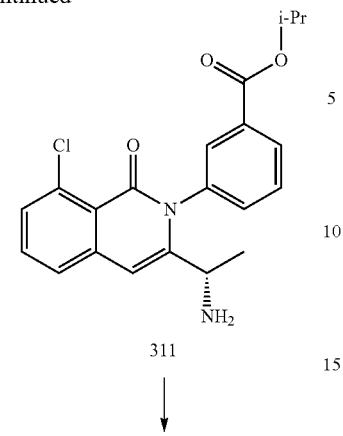

311

↓

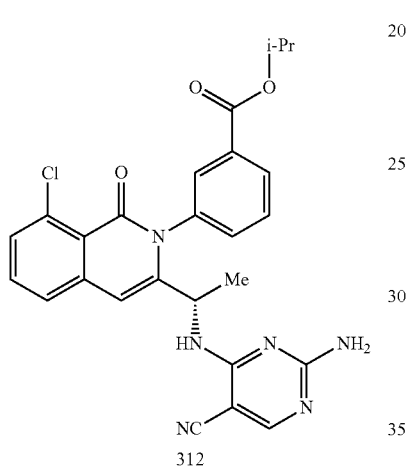

312

Compound 311 was synthesized from compound B-4 according to Method B using isopropyl 3-aminobenzoate. Compound 312 was prepared from compound 311 according to Method G using 2-amino-4-chloropyrimidine-5-carbonitrile. ESI-MS m/z: 503.1 [M+H]$^+$.

Example 172

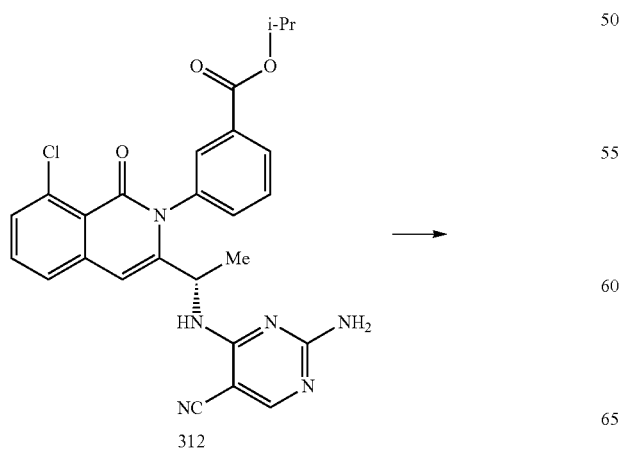

312

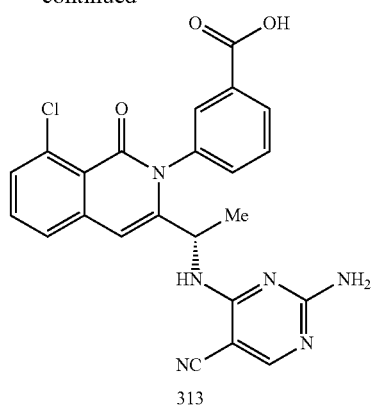

313

Compound 312 (8 mg, 0.016 mmol) dissolved in MeOH (2 ml) was treated with LiOH (4 mg, 0.16 mmol) in 1 ml water. This mixture was stirred at room temperature for 2 h. The solution was then directly purified by HPLC to give compound 313. ESI-MS m/z: 461.1 [M+H]$^+$.

Example 173

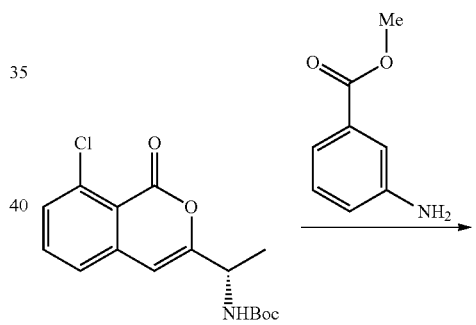

B-4

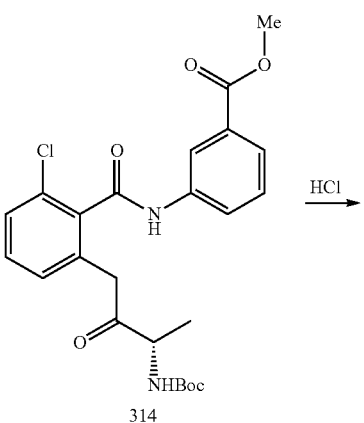

314

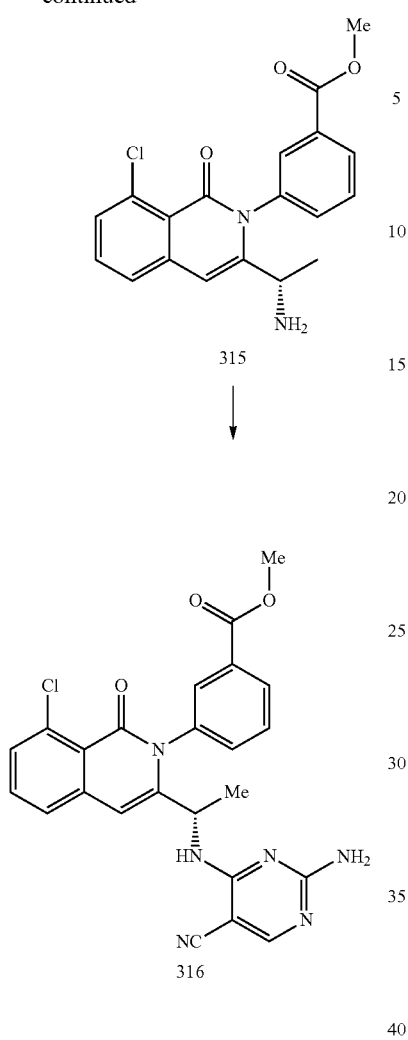

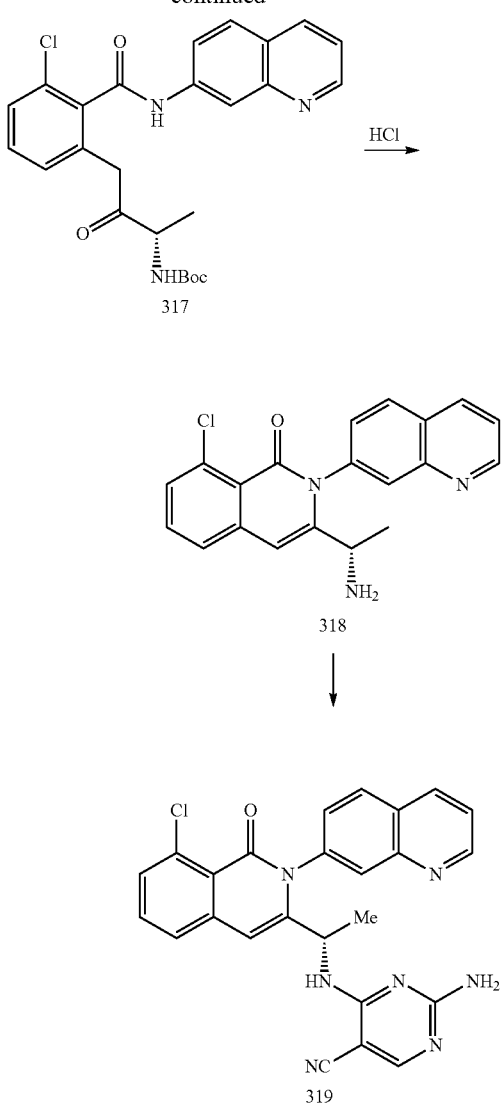

Compound 315 was synthesized from compound B-4 according to Method B using methyl 3-aminobenzoate. Compound 316 was prepared from compound 315 according to Method G using 2-amino-4-chloropyrimidine-5-carbonitrile. ESI-MS m/z: 475.1 [M+H]+.

Example 174

Compound 318 was synthesized from compound B-4 according to Method B using quinolin-7-amine. Compound 319 was prepared from compound 318 according to Method G using 2-amino-4-chloropyrimidine-5-carbonitrile. ESI-MS m/z: 467.1 [M+H]+.

Example 175

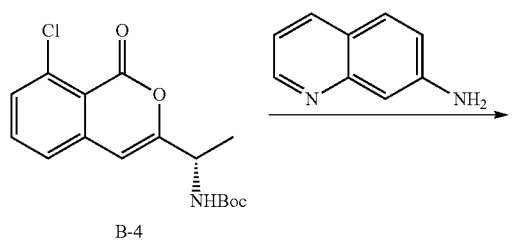

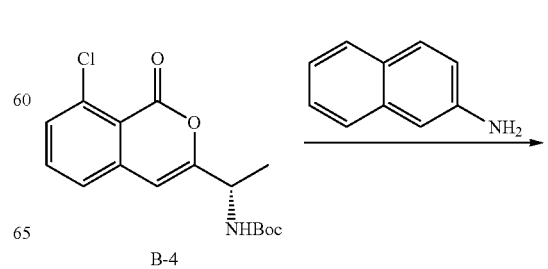

373
-continued
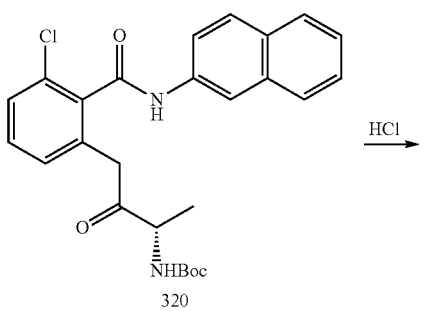
320
HCl →
321
374
-continued
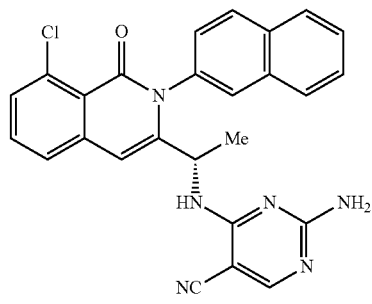
322
Compound 321 was synthesized from compound B-4 according to Method B using naphthalen-2-amine. Compound 322 was prepared from compound 321 according to Method G using 2-amino-4-chloropyrimidine-5-carbonitrile. ESI-MS m/z: 468.1 [M+H]$^+$.
Example 176
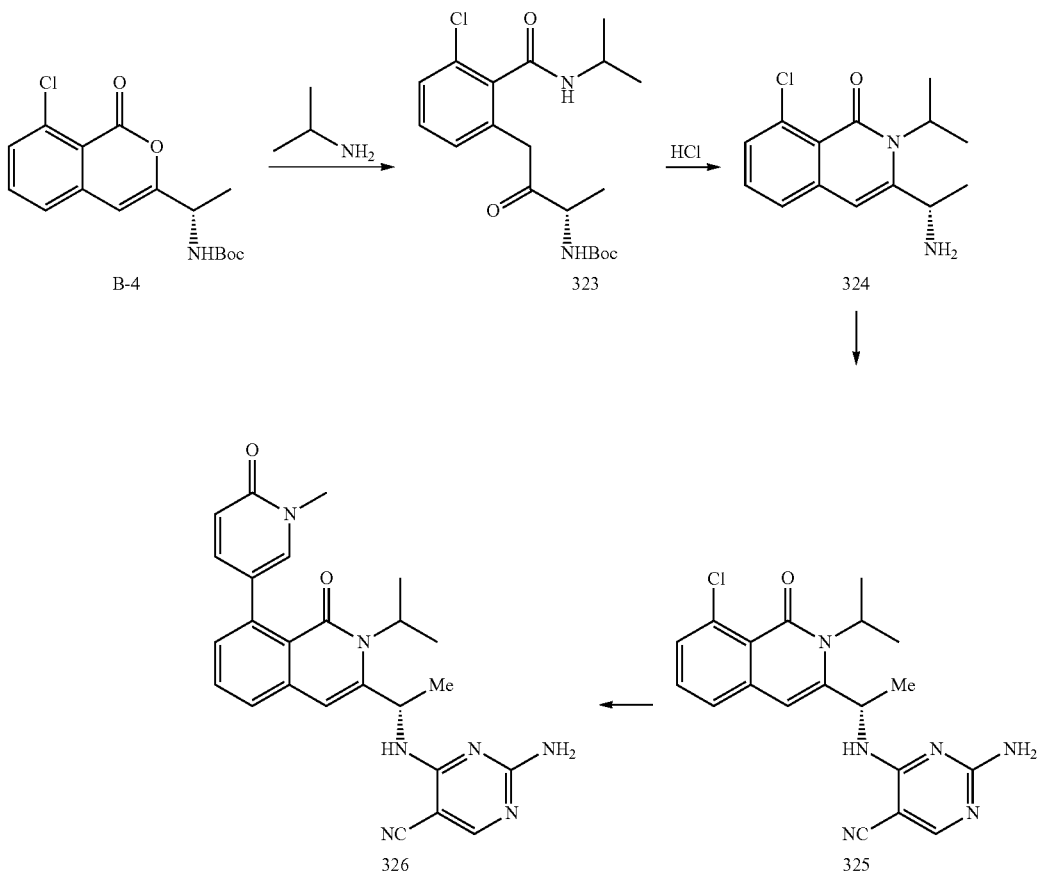

Compound 324 was synthesized from compound B-4 according to Method B using isopropylamine. Compound 325 was prepared from compound 324 according to Method G using 2-amino-4-chloropyrimidine-5-carbonitrile. Compound 326 was prepared from compound 325 according to Method J using 1-methyl-5-(4,4,5,5-tetramethyl-1,3,2-dioxaborolan-2-yl)pyridin-2(1H)-one. ESI-MS m/z: 456.2 [M+H]⁺.

Example 177

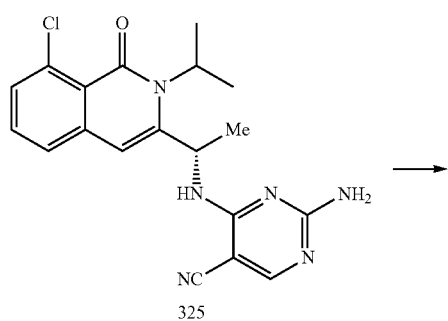

325

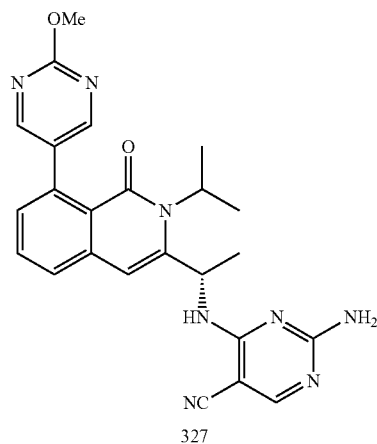

327

Compound 325 was prepared according to Example 176. Compound 327 was prepared from compound 325 according to Method J using 2-methoxypyrimidin-5-ylboronic acid. ESI-MS m/z: 457.2 [M+H]⁺.

Example 178

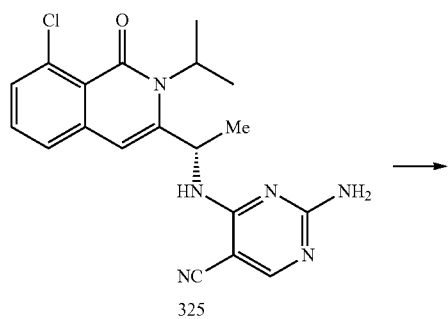

325

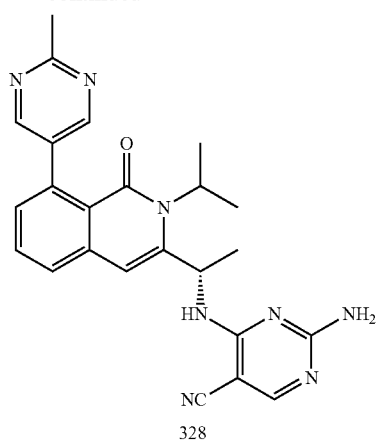

328

Compound 325 was prepared according to Example 176. Compound 328 was prepared from compound 325 according to Method J using 2-methyl-5-(4,4,5,5-tetramethyl-1,3,2-dioxaborolan-2-yl)pyrimidine. ESI-MS m/z: 457.2 [M+H]⁺.

Example 179

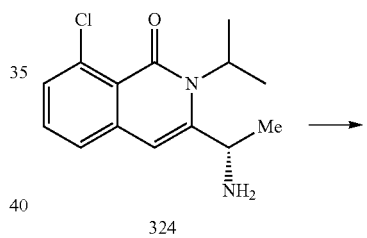

324

329

Compound 324 was prepared according to Example 176. Compound 329 was prepared from compound 324 according to Method G using 4-amino-6-chloropyrimidine-5-carbonitrile. ESI-MS m/z: 383.1 [M+H]⁺.

Example 180

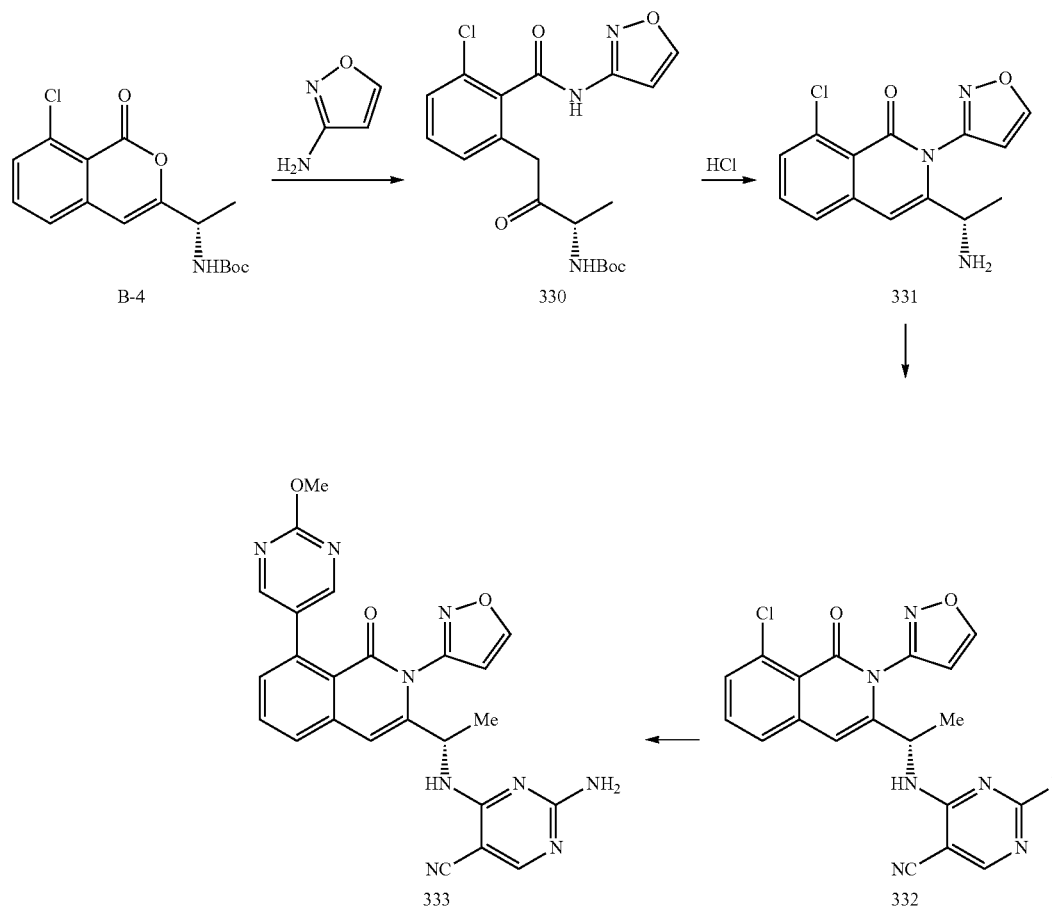

Compound 331 was synthesized from compound B-4 according to Method B using isoxazol-3-amine. Compound 332 was prepared from compound 321 according to Method G using 2-amino-4-chloropyrimidine-5-carbonitrile. Compound 333 was prepared from compound 332 according to Method J using 2-methoxypyrimidin-5-ylboronic acid. ESI-MS m/z: 482.2 [M+H]⁺.

Example 181

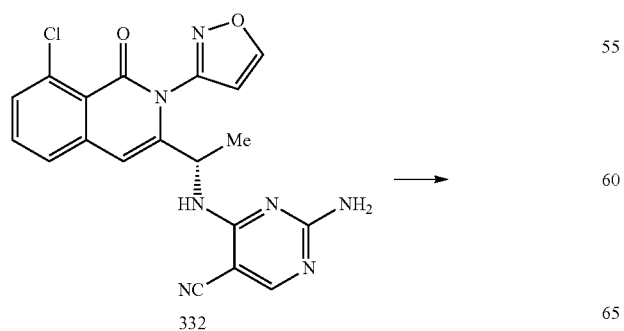

-continued

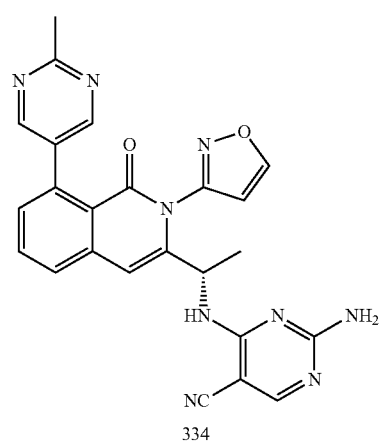

Compound 332 was prepared according to Example 180. Compound 334 was prepared from compound 332 according to Method J using 2-methylpyrimidin-5-ylboronic acid. ESI-MS m/z: 466.2 [M+H]⁺.

379
Example 182

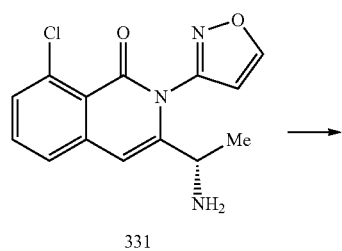

331

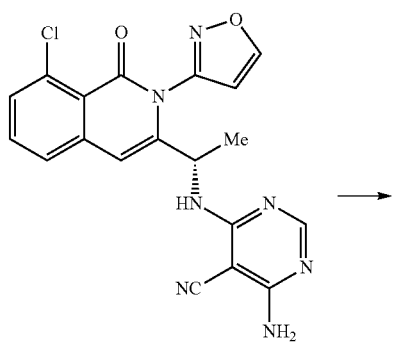

335

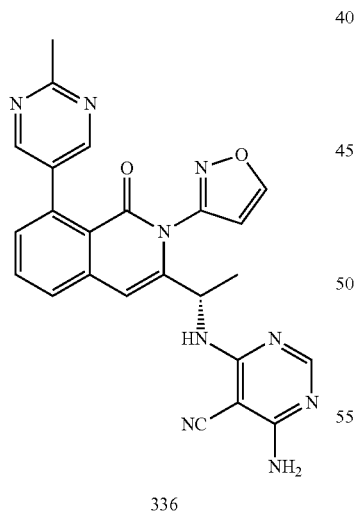

336

380
Example 183

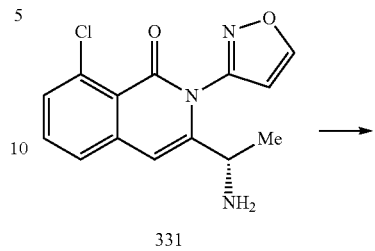

331

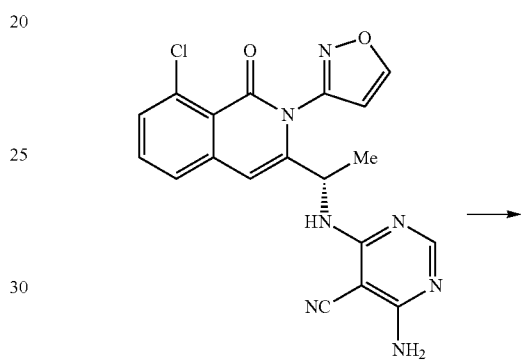

335

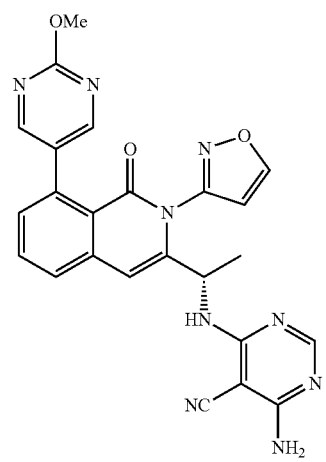

337

Compound 331 was prepared according to Example 180. Compound 335 was prepared from compound 331 according to Method G using 4-amino-6-chloropyrimidine-5-carbonitrile. Compound 336 was prepared from compound 335 according to Method J using 2-methylpyrimidin-5-ylboronic acid. ESI-MS m/z: 466.2 [M+H]$^+$.

Compound 331 was prepared according to Example 180. Compound 335 was prepared from compound 331 according to Method G using 4-amino-6-chloropyrimidine-5-carbonitrile. Compound 336 was prepared from compound 335 according to Method J using 2-methoxypyrimidin-5-ylboronic acid. ESI-MS m/z: 482.1 [M+H]$^+$.

Example 184
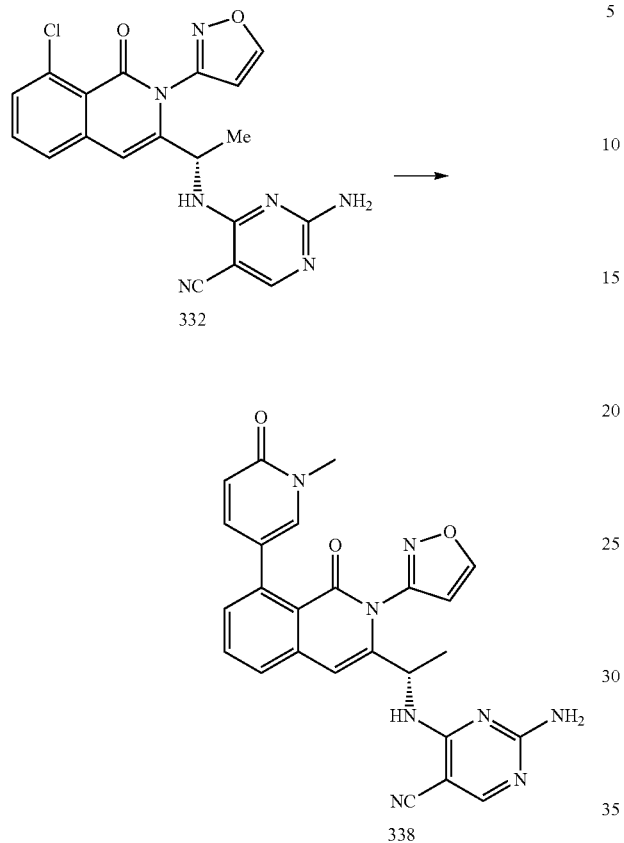
Compound 332 was prepared according to Example 180. Compound 338 was prepared from compound 332 according to Method J using 1-methyl-5-(4,4,5,5-tetramethyl-1,3,2-dioxaborolan-2-yl)pyridin-2(1H)-one. ESI-MS m/z: 481.2 [M+H]$^+$.
Example 185
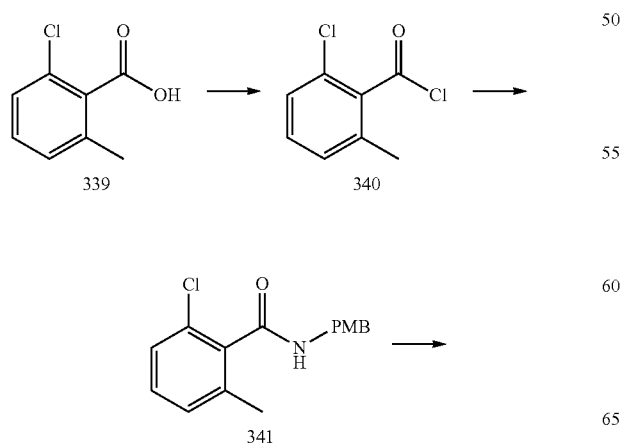
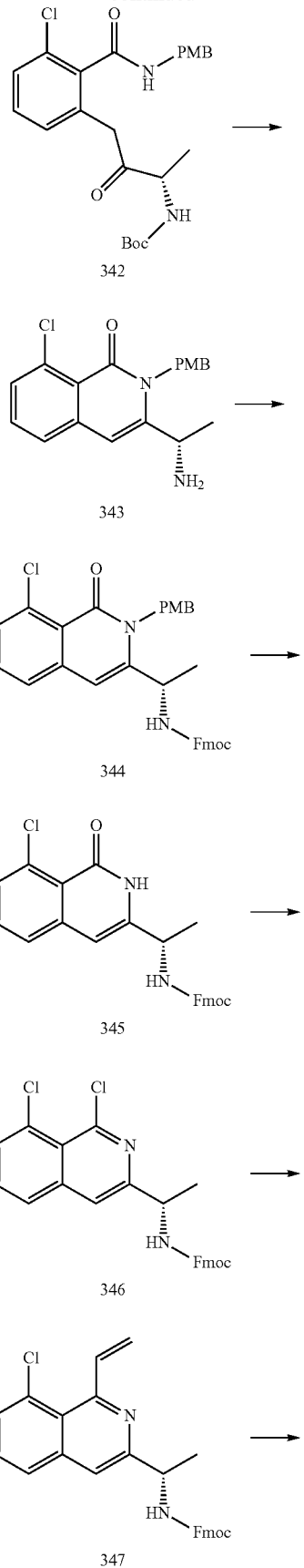

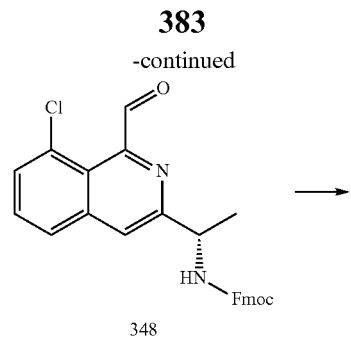

348

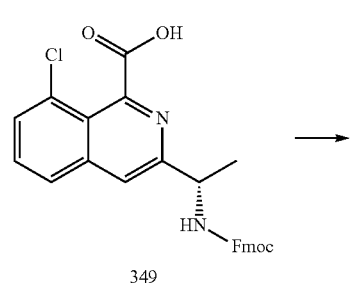

349

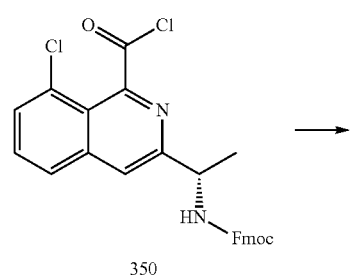

350

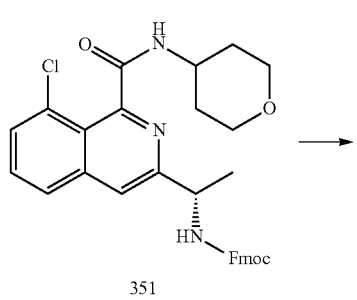

351

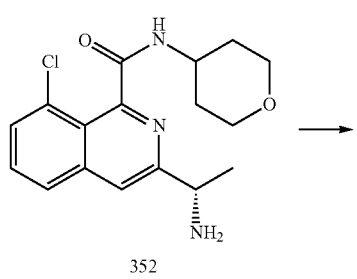

352

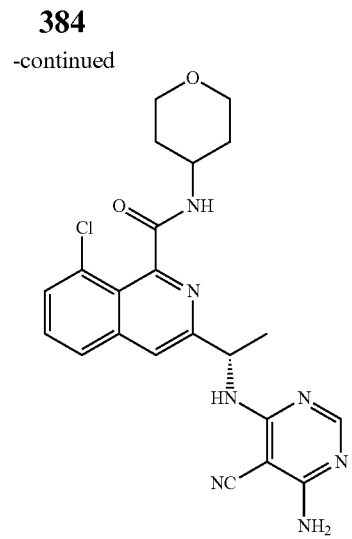

353

To a solution of 2-chloro-6-methylbenzoicacid (339) (300 g, 1.76 mol, 1.0 eq) and DMF (0.5 mL) in DCM (500 mL) at RT, oxalyl chloride (249 g, 1.92 mol, 1.1 eq) was added slowly (over 5 min) The resulting mixture was stirred at RT for 2 h and then concentrated in vacuo to afford 2-chloro-6-methylbenzoyl chloride (340) which was used directly in the next step.

To a solution of (4-methoxyphenyl)methanamine (264 g, 2.4 mol, 1.eq) in DCM (1800 mL), a solution of 2-chloro-6-methylbenzoyl chloride (340) in DCM (150 mL) was added dropwise while keeping the reaction temperature between 25° C. to 40° C. The resulting mixture was stirred at RT for 2 h, and then water (600 mL) was added. The organic layer was separated, washed with water (2×300 mL), dried over $Na_2SO_4$ and filtered. The filtrate was concentrated in vacuo and the residue was slurried in petroleum ether (300 mL) and stirred at RT for 30 min. The solid was collected by filtration and further dried in vacuo to afford N-(4-methoxybenzyl)-2-chloro-6-methylbenzamide (341).

To a solution of N-(4-methoxybenzyl)-2-chloro-6-methylbenzamide (341) (40 g, 138 mmol, 1.0 eq) in THF (200 mL) at −30° C. under an argon atmosphere, a solution of n-butyllithium in hexanes (2.5M, 139 mL, 346 mmol, 2.5 eq) was added dropwise over 30 min while keeping the inner temperature between −30° C. and −10° C. The resulting mixture was stirred at −30° C. for 30 min.

To a solution of (S)-tert-butyl 1-(methoxy(methyl)amino)-1-oxopropan-2-ylcarbamate (48 g, 165 mmol, 1.2 eq) in THF (200 mL) at −30° C. under an argon atmosphere, a solution of isopropylmagnesium chloride in THF (2 M, 115 mL, 207 mmol, 1.65 eq) was added dropwise over 30 min while keeping the inner temperature between −30° C. and −10° C. The resulting mixture was stirred at −30° C. for 30 min. This solution was slowly added to the above reaction mixture while keeping the inner temperature between −30° C. and −10° C. The resulting mixture was stirred at −15° C. for 1 h. The reaction mixture was quenched with water (50 mL) and then acidified with 6N HCl (160 mL) at −10° C.-0° C. to adjust the pH to 1-3. The mixture was allowed to warm to RT and concentrated in vacuo to afford (S)-tert-butyl 4-(2-((4-methoxybenzyl)carbamoyl)-3-chlorophenyl)-3-oxobutan-2-ylcarbamate (342). The residue was dissolved in MeOH (400 mL), and then conc. HCl (200 mL) was added quickly at RT. The resulting mixture was stirred at reflux for 1 h. The reaction mixture was concentrated in vacuo to reduce the volume to about 450 mL. The residue was extracted with a mixture of petroleum ether and EtOAc (2:1, v/v, 2×500 mL), and then separated. The aqueous layer was basified with concentrated ammonium hydroxide to adjust the pH to 9-10 while keeping the inner temperature between −10° C. and 0° C. The mixture was extracted with DCM (3×100 mL), washed with brine, dried over $Na_2SO_4$ and filtered. The filtrate was concentrated in vacuo and the residue was dissolved in MeOH (600 mL) at RT. D-(−)-Tartaric acid (17 g, 110.4 mmol, 0.8 eq) was added in one portion at RT. The resulting mixture was stirred at RT for 10 h. The solid was collected by filtration and washed with ethyl acetate (3×50 mL). The solid was suspended in water (300 mL) and neutralized with concentrated ammonium hydroxide to adjust the pH to 9-10 at RT. The mixture was extracted with DCM (3×100 mL). The organic layer was washed with brine, dried over $Na_2SO_4$, and filtered. The filtrate was concentrated in vacuo to afford (S)-2-(4-methoxybenzyl)-3-(1-aminoethyl)-8-chloroisoquinolin-1 (2H)-one (343).

To a solution of (S)-2-(4-methoxybenzyl)-3-(1-aminoethyl)-8-chloroisoquinolin-1(2H)-one (343) (20 g, 58.3 mmol, 1.0 eq) and $NaHCO_3$ (12.7 g, 291.51 mmol, 5.0 eq) in DCM (120 mL) and water (60 mL) at RT, Fmoc-Cl (15.7 g, 61.22 mmol, 1.05 eq) was slowly added and the resulting mixture was stirred at RT for 1 h. The reaction mixture was poured into water (200 mL) and extracted with DCM (3×100 mL). The combined organic layers were washed with brine, dried over $Na_2SO_4$ and filtered. The filtrate was concentrated in vacuo to afford (S)-(9H-fluoren-9-yl)methyl 1-(2-(4-methoxybenzyl)-8-chloro-1-oxo-1,2-dihydroisoquinolin-3-yl)ethylcarbamate (344).

(S)-(9H-fluoren-9-yl)methyl 1-(8-chloro-2-(4-methoxybenzyl)-1-oxo-1,2-dihydroisoquinolin-3-yl)ethylcarbamate (344) (80 g, 142 mmol, 1.0 eq) was dissolved in 2,2,2-trifluoroacetic acid (300 mL) and the resulting mixture was stirred at reflux for 2 h. The mixture was allowed to cool to RT and then concentrated in vacuo. The residue was poured into water and then neutralized with $NH_3.H_2O$ to adjust the pH value to 6-7 under 0° C. The resulting mixture was stirred at RT for 30 min. The solid was collected by filtration, rinsed with water (2×50 mL) and dried in vacuo to afford (S)-(9H-fluoren-9-yl)methyl 1-(8-chloro-1-oxo-1,2-dihydroisoquinolin-3-yl)ethylcarbamate (345).

To a solution of (S)-(9H-fluoren-9-yl)methyl 1-(8-chloro-1-oxo-1,2-dihydroisoquinolin-3-yl)ethylcarbamate (345) (58 g, 130 mmol, 1.0 eq) and DMF (0.5 mL) in toluene (300 mL), sulfurous dichloride (78 g, 0.65 mol, 5.0 eq) was added slowly, and the resulting mixture was stirred at reflux for 2.5 h. The mixture was allowed to cool to RT and then concentrated in vacuo. The residue was poured into water (200 mL) and extracted with ethyl acetate (3×100 mL). The organic layer was washed with water (2×100 mL) and brine (100 mL), dried over anhydrous $Na_2SO_4$ and filtered. The filtrate was concentrated in vacuo and the residue was purified by flash column chromatography on silica gel (5-20% ethyl acetate-petroleum ether) to afford (S)-(9H-fluoren-9-yl)methyl 1-(1,8-dichloroisoquinolin-3-yl)ethylcarbamate (346).

To a solution of (S)-(9H-fluoren-9-yl)methyl-1-(1,8-dichloroisoquinolin-3-yl)ethylcarbamate (346) (36 g, 77.7 mmol, 1.0 eq) in THF (300 mL) under argon, tributyl(vinyl)stannane (27 g, 85.5 mmol, 1.1 eq), $Pd(OAc)_2$ (5.23 g, 23.3 mmol, 0.3 eq) and $PPh_3$ (12.2 g, 46.6 mmol, 0.6 eq) were added, and the resulting mixture was stirred at reflux for 16 h. The mixture was allowed to cool to RT and then concentrated in vacuo. The residue was purified by flash column chromatography on silica gel (2-30% ethyl acetate-petroleum ether) to afford (S)-(9H-fluoren-9-yl)methyl 1-(8-chloro-1-vinylisoquinolin-3-yl)ethylcarbamate (347).

To a suspension of (S)-(9H-fluoren-9-yl)methyl 1-(8-chloro-1-vinylisoquinolin-3-yl)ethylcarbamate (347) (10.6 g, 23.3 mmol, 1.0 eq) in 1,4-dioxane (200 mL) and water (100 mL), $OsO_4$ (50 mg) was added and the resulting mixture was stirred at RT for 30 min. To this mixture, $NaIO_4$ (15 g, 69.9 mmol, 3.0 eq) was added, and then the mixture was stirred at RT for 16 h. The mixture reaction was poured into water (200 mL) and extracted with ethyl acetate (3×100 mL). The organic layer was washed with water (2×100 mL) and brine (100 mL), dried over anhydrous $Na_2SO_4$ and filtered. The filtrate was concentrated in vacuo. The residue was purified by flash column chromatography on silica gel (5-20% ethyl acetate-petro ether) to afford (S)-(9H-fluoren-9-yl)methyl 1-(8-chloro-1-formylisoquinolin-3-yl)ethylcarbamate (348).

To a solution of (S)-(9H-fluoren-9-yl)methyl 1-(8-chloro-1-formylisoquinolin-3-yl)ethylcarbamate (348) (12.0 g, 26.3 mmol, 1.0 eq) in DMF (150 mL), OXONE (30 g, 48.78 mmol, 1.85 eq) was added and the resulting mixture was stirred at RT over night. The mixture was poured into water (600 mL) and then filtered. The solid was dissolved in ethyl acetate (100 mL), and then PE (300 mL) was added dropwise to this solution. The precipitate was collected by filtration to afford (S)-3-(1-(((9H-fluoren-9-yl)methoxy)carbonylamino)ethyl)-8-chloroisoquinoline-1-carboxylic acid (349).

To a solution of (S)-3-(1-(((9H-fluoren-9-yl)methoxy)carbonylamino)ethyl)-8-chloroisoquinoline-1-carboxylic acid (349) (25.5 g, 54.0 mmol, 1.0 eq) and DMF (1.5 mL, 19.3 mmol, 0.35 eq) in $CH_2Cl_2$ (200 mL), oxalyl chloride (30 mL, 177.7 mmol, 3.29 eq) was added dropwise slowly. The resulting mixture was stirred at RT for 1 h. The reaction mixture was concentrated in vacuo and the residue was dissolved in $CH_2Cl_2$ (100 mL). This solution was added dropwise to a solution of tetrahydro-2H-pyran-4-amine (15 mL, 133 mmol, 2.46 eq) and $Et_3N$ (30 mL, 210.9 mmol, 3.90 eq) in $CH_2Cl_2$ (200 mL) at 0° C. The mixture was warmed to RT and stirred for 30 min. 5% Hydrochloric acid aqueous solution was added to the reaction mixture until the pH=1~2. The mixture was poured into water (400 mL), extracted with $CH_2Cl_2$ (150 mL×2). The organic layer was dried over anhydrous $Na_2SO_4$ and filtered. The filtrate was concentrated in vacuo. The residue was purified by flash column chromatography on silica gel (5-10% MeOH-DCM) to afford (S)-(9H-fluoren-9-yl)methyl 1-(8-chloro-1-(tetrahydro-2H-pyran-4-ylcarbamoyl)isoquinolin-3-yl)ethylcarbamate (351).

(S)-(9H-fluoren-9-yl)methyl 1-(8-chloro-1-(tetrahydro-2H-pyran-4-ylcarbamoyl)isoquinolin-3-yl)ethylcarbamate (351) (20.0 g, 36.0 mmol, 1.0 eq) was suspended in morpholine (200 mL), and then stirred at 40-50° C. for 1 h. The reaction mixture was concentrated in vacuo and then 1,4-dioxane (200 mL) was added to the residue. The mixture was concentrated in vacuo. The operation was repeated for 3-4 times. The residue was purified by flash column chromatography on silica gel (2-10% MeOH-DCM) to afford (S)-3-(1-aminoethyl)-8-chloro-N-(tetrahydro-2H-pyran-4-yl)isoquinoline-1-carboxamide (352).

The amine 352 was coupled to 4-amino-6-chloropyrimidine-5-carbonitrile in the SnAr according to Method G to give compound 353. ESI-MS m/z: 452.2 [M+H]+.

Example 186

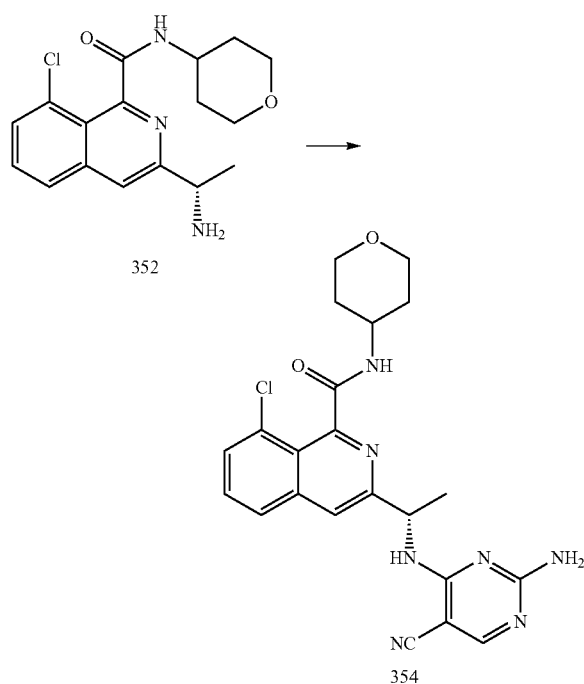

The amine 352 was prepared according to Example 185. Compound 352 was coupled to 4-amino-6-chloropyrimidine-5-carbonitrile according to Method G to give compound 354. ESI-MS m/z: 452.2 [M+H]$^+$.

Example 187

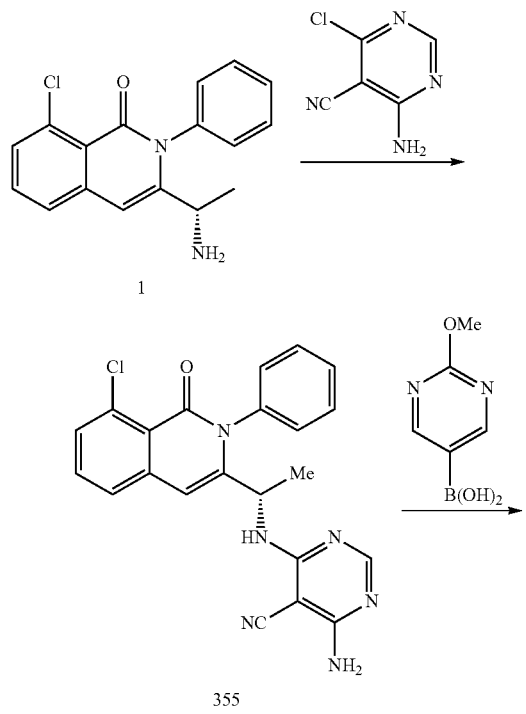

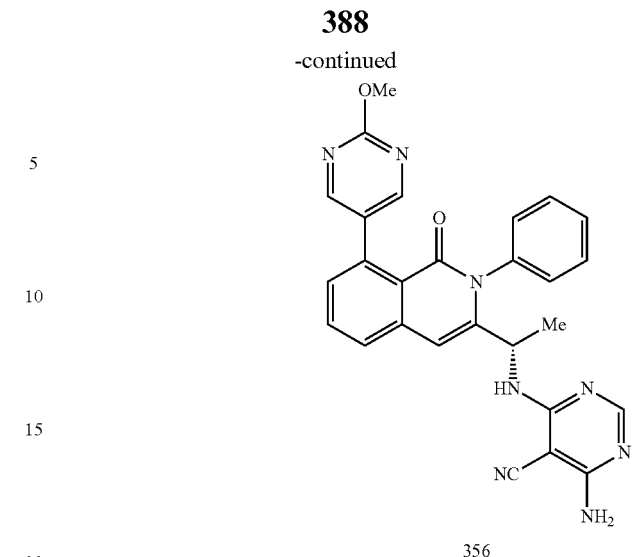

Compound 355 was prepared from compound 1 according to Method G using 4-amino-6-chloropyrimidine-5-carbonitrile. Compound 356 was prepared from compound 355 according to Method J using 2-methoxy-pyrimidin-5-ylboronic acid. ESI-MS m/z: 491.2 [M+H]$^+$.

Example 188

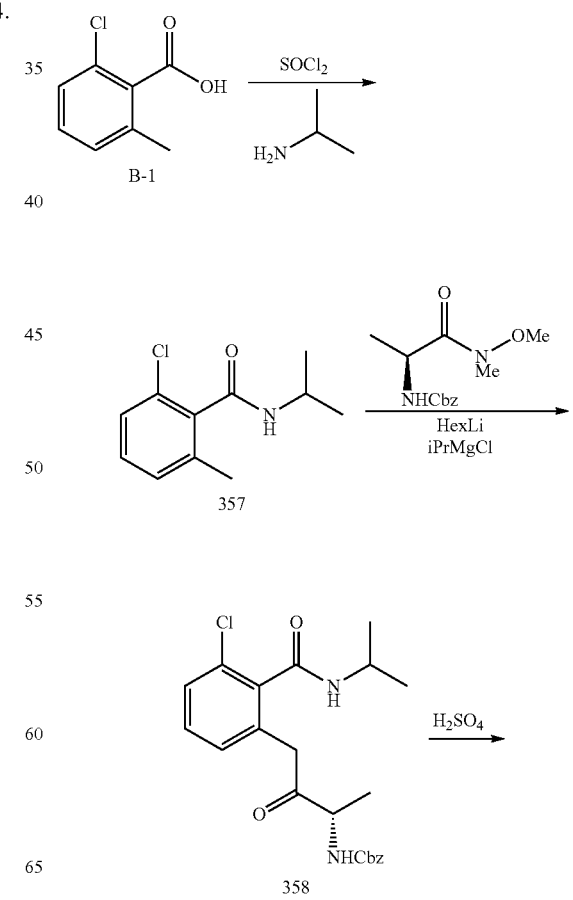

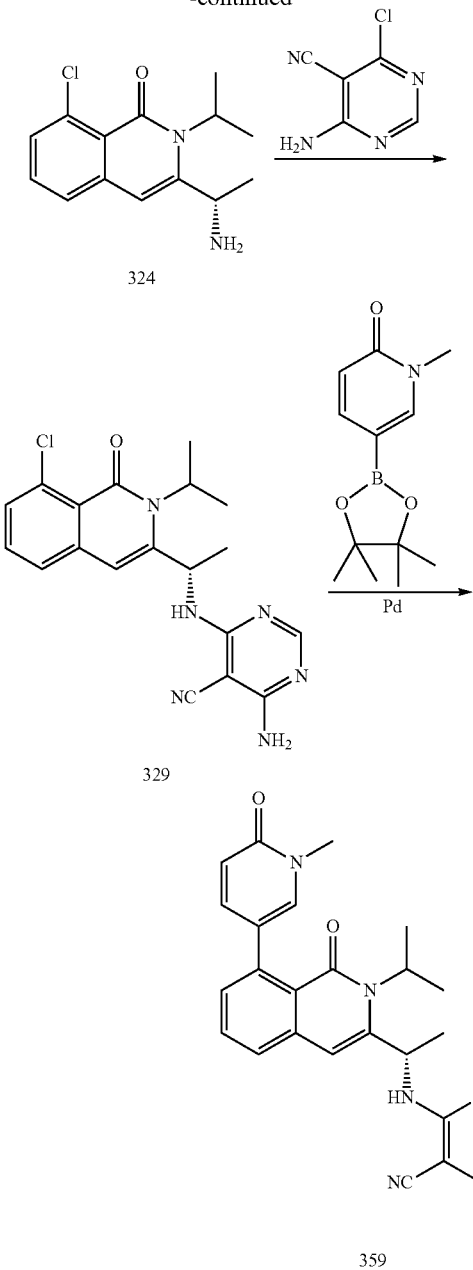

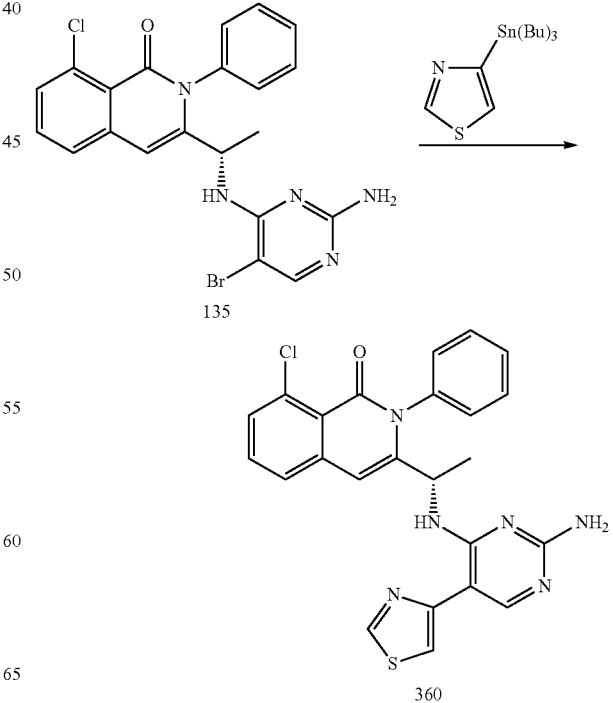

was treated with i-PrMgCl (168 ml, 338 mmol). After 15 min, the latter solution was cannulated into the former over 30 min. The reaction was stirred for 1 h at room temperature. The mixture was cannulated into a cooled solution (0-5° C.) of isobutyric acid (94 ml, 1032 mmol) in MTBE (625 mL). The mixture was warmed to room temperature and 3% brine (650 mL) was added. The phases were separated and the organic layer washed with water (650 mL). The organic layer was dried with $Na_2SO_4$ and concentrated until solid formed. The product was filtered to give the ketone 358.

A mixture of the ketone 358 (25.00 g, 60.0 mmol) in i-PrOAc (450 mL) was treated with $H_2SO_4$ (15.98 ml, 300 mmol) and heated to 70° C. After 1 h, the reaction was cooled to 50° C. and $H_2SO_4$ (38.4 ml, 720 mmol) was added. The resulting mixture was stirred at 70° C. for 5 h. After cooling to room temperature, $NH_4OH$ (284 ml, 2039 mmol) was added. The organic phase was separated and the aqueous layer was extracted with i-PrOAc (100 mL). The combined organic layers were dried over $Na_2SO_4$, filtered and concentrated. The resulting amine 324 was used directly in the next step.

A solution of the amine 324 (15.00 g, 56.7 mmol) in n-BuOH (225 mL) and Hunig's base (19.79 ml, 113 mmol) was treated with 4-amino-6-chloropyrimidine-5-carbonitrile (8.76 g, 56.7 mmol). The mixture was stirred at reflux for 5 h, then cooled to room temperature. The solid was filtered to give product 329.

A mixture of compound 329 (10.40 g, 27.2 mmol), 1-methyl-5-(4,4,5,5-tetramethyl-1,3,2-dioxaborolan-2-yl)pyridin-2(1H)-one (9.58 g, 40.7 mmol), sodium carbonate (5.76 g, 54.3 mmol) and $PdCl_2(Amphos)_2$ (0.962 g, 1.358 mmol)) in dioxane/water (4:1, 208 mL)) was heated to reflux for 4 h. The mixture was cooled to room temperature and water (200 mL) was added. The solid was filtered, washed with water, and dried overnight. The solid was purified by column chromatography eluting with 0-10% MeOH/dichloromethane to give compound 359. ESI-MS m/z: 456.2 $[M+H]^+$.

Example 189

To benzoic acid B-1 (10.00 g, 58.6 mmol) was added dichloromethane (63 ml) and DMF (0.227 ml, 2.93 mmol). Thionyl chloride (4.24 ml, 58.0 mmol) was added over 10 min, and the resulting mixture was stirred for 2 h. The reaction was cooled to 0-5° C. and i-$PrNH_2$ (15.73 ml, 185 mmol) was slowly added. The resulting mixture was stirred at room temperature for 0.5 h. The mixture was diluted with dichloromethane (63 ml) and water. The phases were separated and the organic layer was concentrated. The product was precipitated by addition of heptane to give the amide 357.

The amide 357 (50.0 g, 236 mmol) and THF (250 mL) were charged in a flask equipped with magnetic stirrer and thermocouple. The mixture was cooled to 0-5° C. and a solution of 2.3M hexyllithium in hexanes (232 ml, 534 mmol) was added. The mixture was stirred for 15 min. In a separate flask, a cooled solution (S)-benzyl 1-(methoxy(methyl)amino)-1-oxopropan-2-ylcarbamate (85 g, 319 mmol) in THF (500 mL)

Compound 135 was prepared according to Example 87. Compound 360 was prepared according to Example 88 using 4-(tributylstannyl)thiazole. ESI-MS m/z: 475.1 [M+H]+.

Example 190

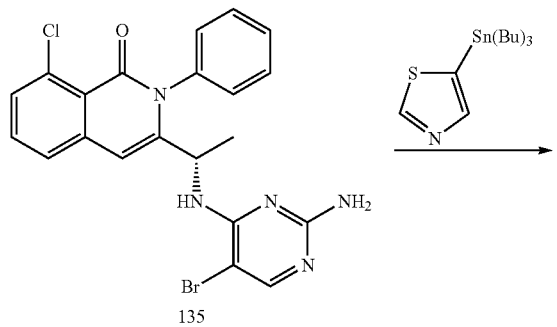

Compound 135 was prepared according to Example 87. Compound 361 was prepared according to Example 88 using 5-(tributylstannyl)thiazole. ESI-MS m/z: 475.1 [M+H]+.

Example 191

Compound 362 was prepared from compound 1 and 2-methoxypyridin-4-ylboronic acid in analogous fashion to Example 2. Compound 363 was prepared as follows: 2-amino-4-chloro-6-methylpyrimidine (5.00 g, 34.8 mmol) was suspended in ACN (50 mL) and MeOH (70 mL). The mixture was charged with NIS (11.75 g, 52.2 mmol) at room temperature and the mixture was heated to 60° C. for 5 h. The mixture was cooled to room temperature and 80% of the volatiles were removed. The suspension was diluted with Et$_2$O (100 mL) and the solids were filtered to obtain 10 g of 4-chloro-5-iodo-6-methylpyrimidin-2-amine. A solution of iodide (500 mg, 1.855 mmol) in DMF (40 mL) was charged with CuCN (332 mg, 3.71 mmol), Pd(PPh$_3$)$_4$ (1072 mg, 0.928 mmol) and CuI (247 mg, 1.299 mmol). The mixture was degassed for 10 min, then heated to 80° C. for 90 min. The mixture was cooled to room temperature and the material was partitioned between water and EA, then filtered on celite. The organic layer of the filtrate was washed several times with brine, dried and concentrated. The filtrate was pre-adsorbed on SiO$_2$ and purified on ISCO 40 g (EA/hex) to give 2-amino-4-chloro-6-methylpyrimidine-5-carbonitrile 363. Compound 363 was coupled to compound 362 according to Method G to afford compound 364. ESI-MS m/z: 504.3 [M+H]+.

Example 192

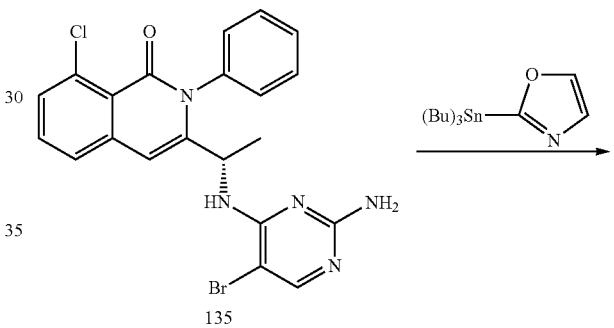

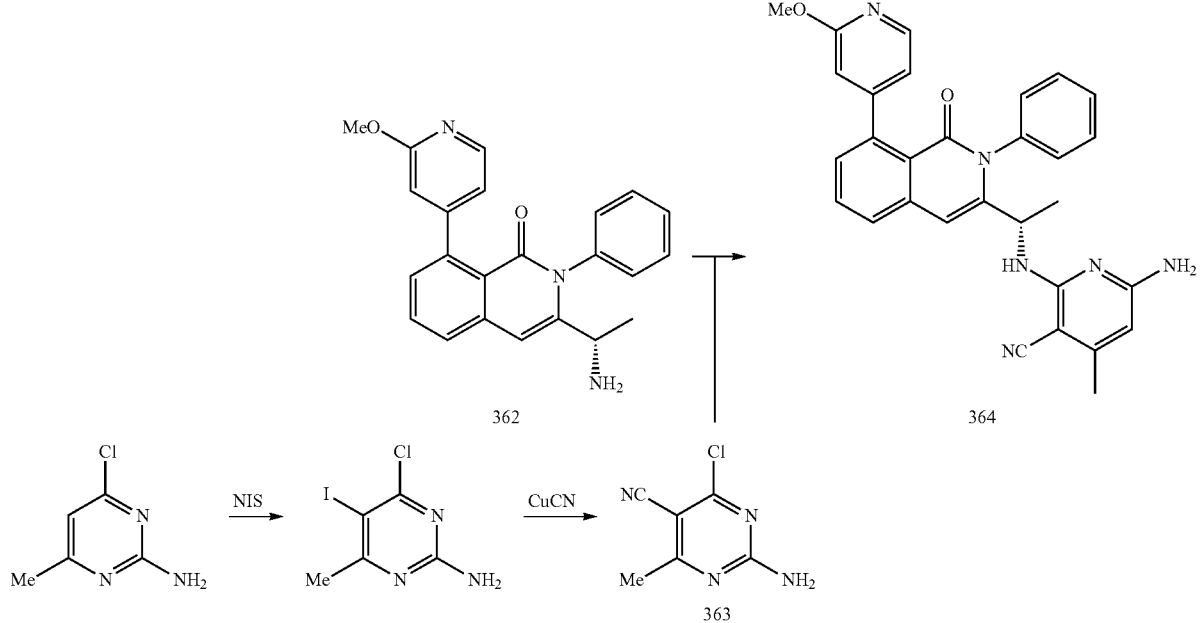

-continued

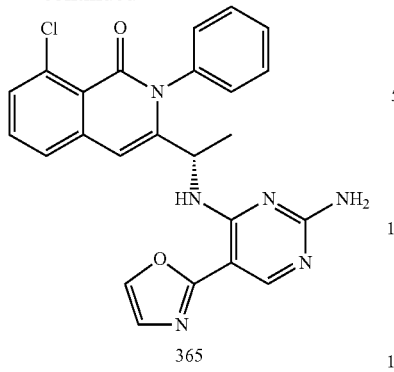

365

Compound 135 was prepared according to Example 87. Compound 365 was prepared according to Example 88 using 2-(tributylstannyl)oxazole. ESI-MS m/z: 459.1 [M+H]$^+$.

Example 193

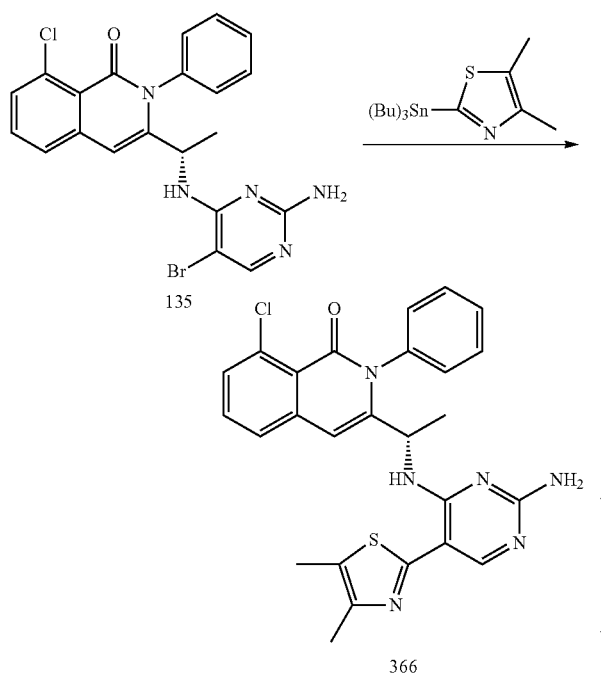

366

Compound 135 was prepared according to Example 87. Compound 366 was prepared according to Example 88 using 4,5-dimethyl-2-(tributylstannyl)thiazole. ESI-MS m/z: 503.2 [M+H]$^+$.

Example 194

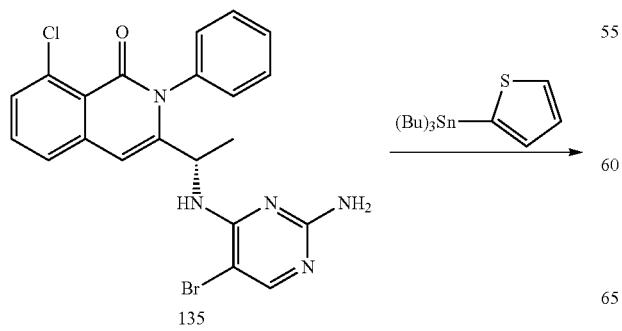

-continued

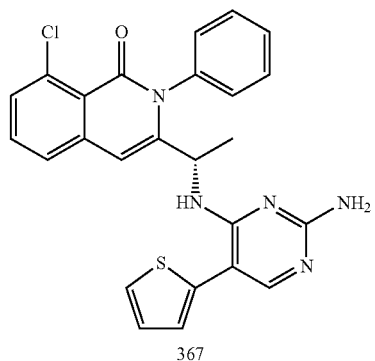

367

Compound 135 was prepared according to Example 87. Compound 367 was prepared according to Example 88 using tributyl(thiophen-2-yl)stannane. ESI-MS m/z: 474.1 [M+H]$^+$.

Example 195

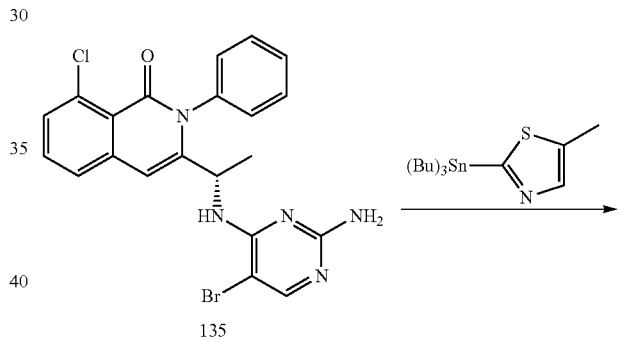

368

Compound 135 was prepared according to Example 87. Compound 368 was prepared according to Example 88 using 5-methyl-2-(tributylstannyl)thiazole. ESI-MS m/z: 489.1 [M+H]$^+$.

Example 196

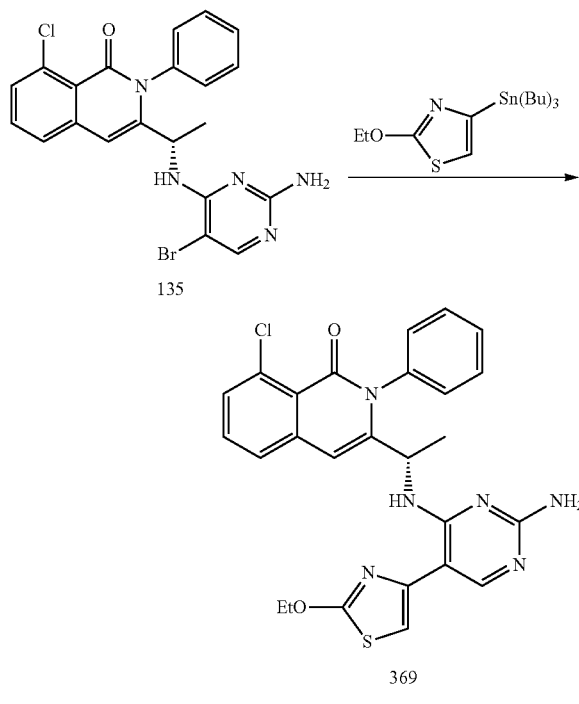

Compound 135 was prepared according to Example 87. Compound 369 was prepared according to Example 88 using 2-ethoxy-4-(tributylstannyl)thiazole. ESI-MS m/z: 519.1 [M+H]$^+$.

Example 197

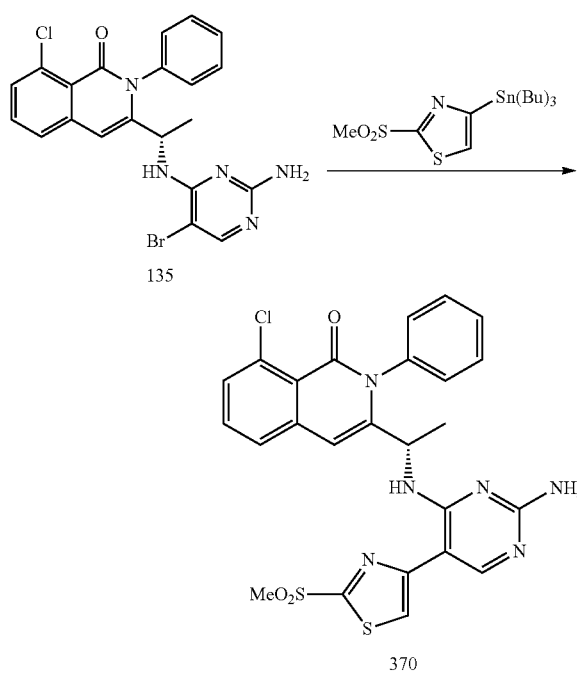

Compound 135 was prepared according to Example 87. Compound 370 was prepared according to Example 88 using 2-(methylsulfonyl)-4-(tributylstannyl)thiazole. ESI-MS m/z: 553.1 [M+H]$^+$.

Example 198

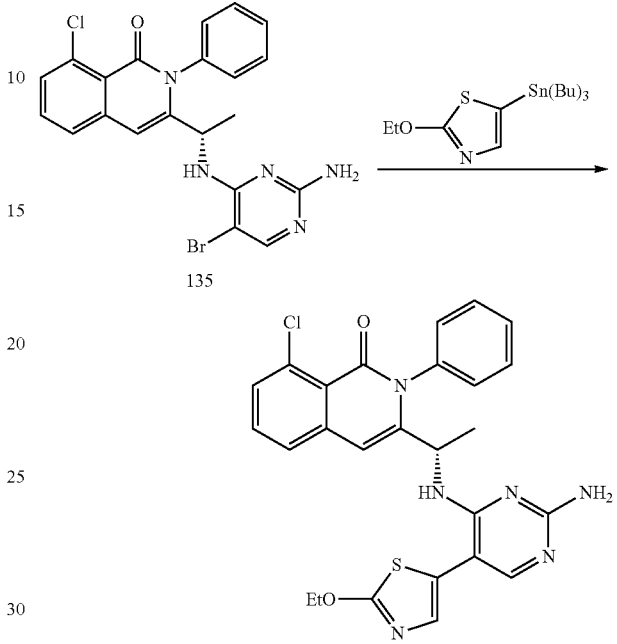

Compound 135 was prepared according to Example 87. Compound 371 was prepared according to Example 88 using 2-ethoxy-5-(tributylstannyl)thiazole. ESI-MS m/z: 519.2 [M+H]$^+$.

Example 199

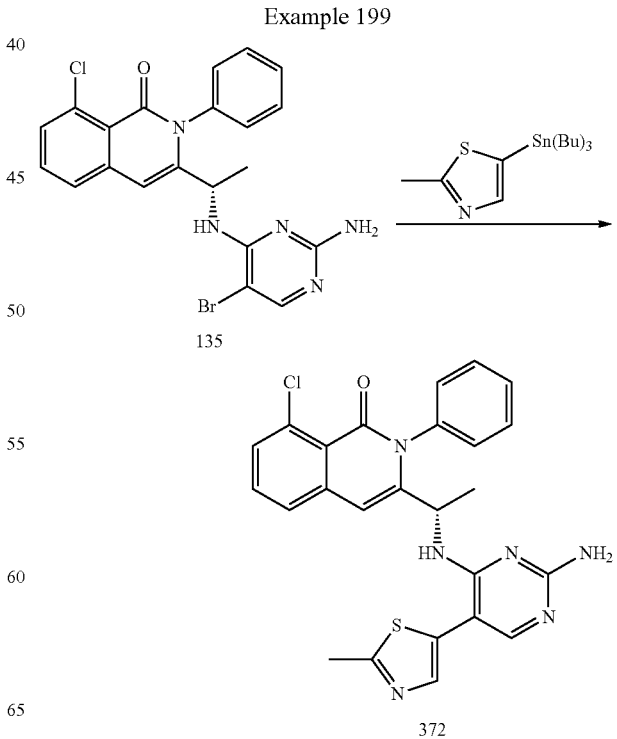

Compound 135 was prepared according to Example 87. Compound 372 was prepared according to Example 88 using 2-methyl-5-(tributylstannyl)thiazole. ESI-MS m/z: 489.1 [M+H]$^+$.

Example 200

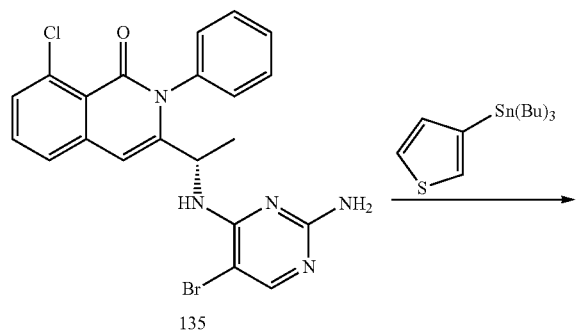

135

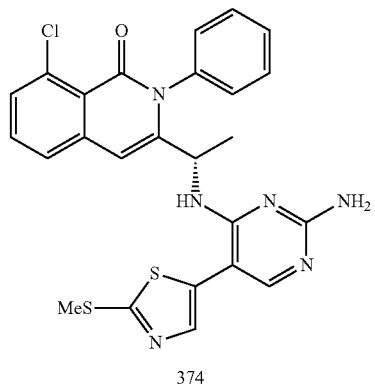

374

Compound 135 was prepared according to Example 87. Compound 374 was prepared according to Example 88 using 2-(methylthio)-5-(tributylstannyl)thiazole. ESI-MS m/z: 521.1 [M+H]$^+$.

Example 202

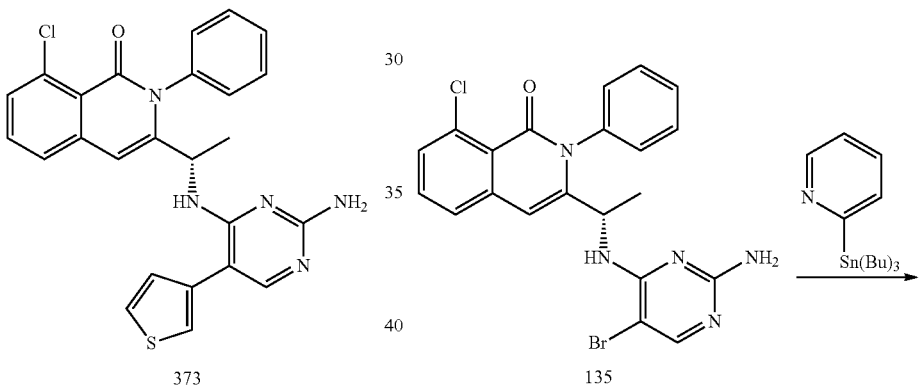

135

373

Compound 135 was prepared according to Example 87. Compound 373 was prepared according to Example 99 using thiophen-3-ylboronic acid. ESI-MS m/z: 489.1 [M+H]$^+$.

Example 201

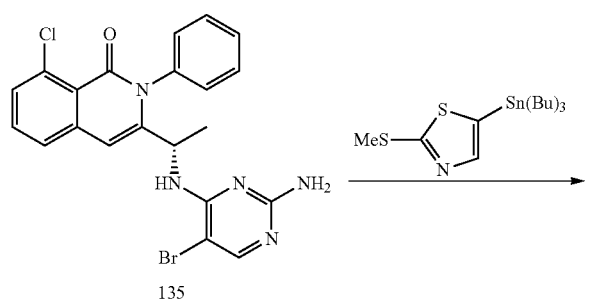

135

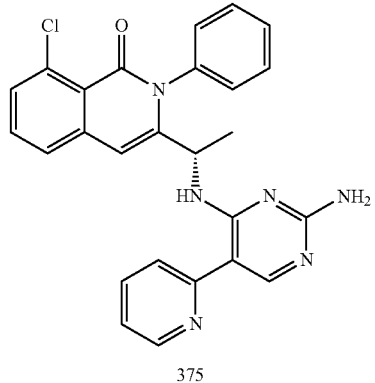

375

Compound 135 was prepared according to Example 87. Compound 375 was prepared according to Example 88 using 2-(tributylstannyl)pyridine. ESI-MS m/z: 521.1 [M+H]$^+$.

399
Example 203

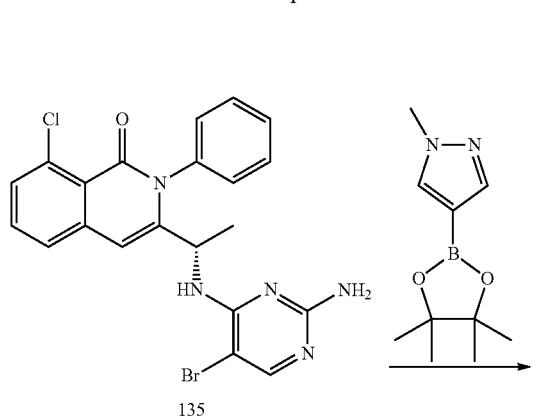

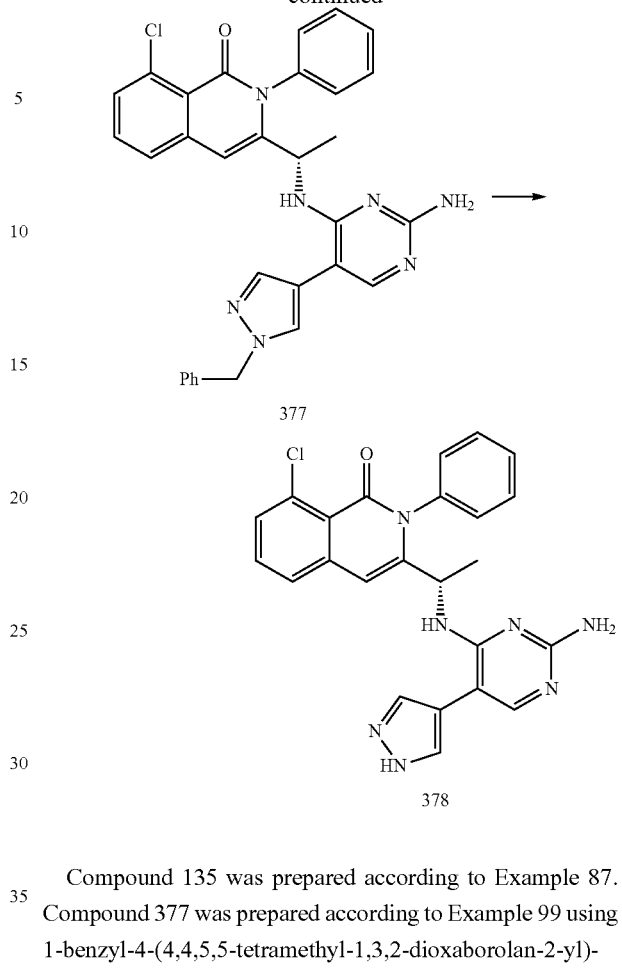

Compound 135 was prepared according to Example 87. Compound 376 was prepared according to Example 99 using 1-methyl-4-(4,4,5,5-tetramethyl-1,3,2-dioxaborolan-2-yl)-1H-pyrazole instead of 3-(piperidin-1-ylsulfonyl)phenylboronic acid. ESI-MS m/z: 472.2 [M+H]$^+$.

Example 204

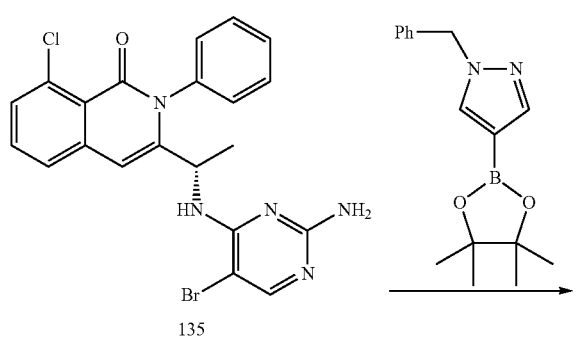

Compound 135 was prepared according to Example 87. Compound 377 was prepared according to Example 99 using 1-benzyl-4-(4,4,5,5-tetramethyl-1,3,2-dioxaborolan-2-yl)-1H-pyrazole instead of 3-(piperidin-1-ylsulfonyl)phenylboronic acid. Benzylated intermediate 377 (51 mg, 0.093 mmol) was dissolved in 8 mL of (EtOAc/MeOH, 5:3) and 150 µL of 6N HCl and placed under 1 atmosphere of hydrogen in presence of Pd/C (10%) for 4 h. After removal of the catalyst by filtration, the volatiles were removed and compound purified by HPLC to give the pyrazole 378. ESI-MS m/z: 458.2 [M+H]$^+$.

Example 205

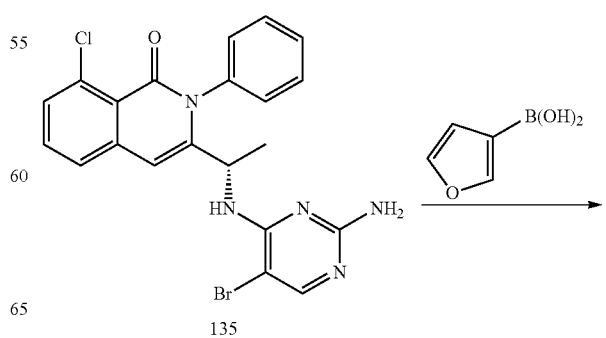

-continued

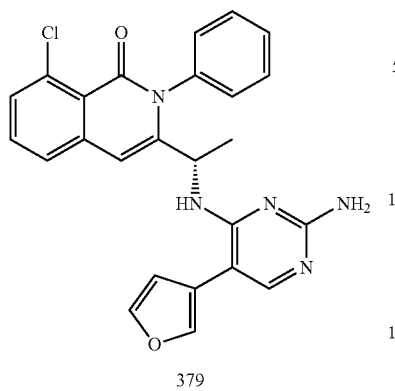

379

Compound 135 was prepared according to Example 87. Compound 379 was prepared according to Example 99 using furan-3-ylboronic acid. ESI-MS m/z: 458.1 [M+H]$^+$.

Example 207

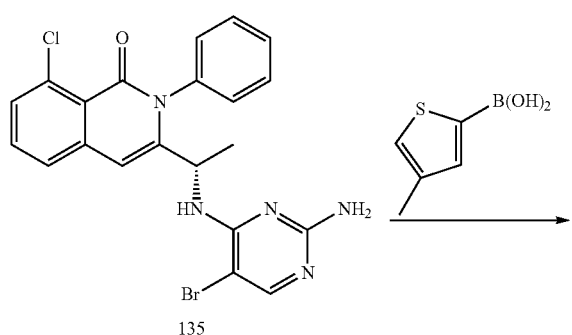

135

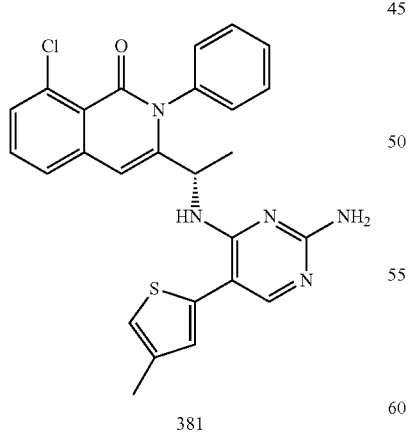

381

Compound 135 was prepared according to Example 87. Compound 381 was prepared according to Example 99 using 4-methylthiophen-2-ylboronic acid. ESI-MS m/z: 488.1 [M+H]$^+$.

Example 208

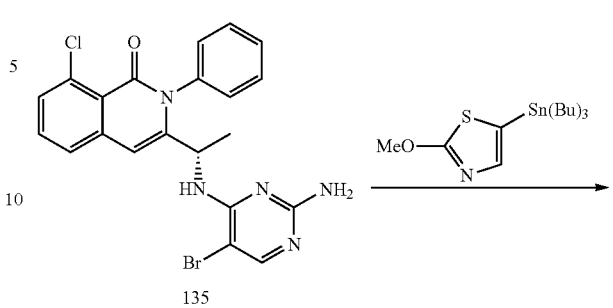

135

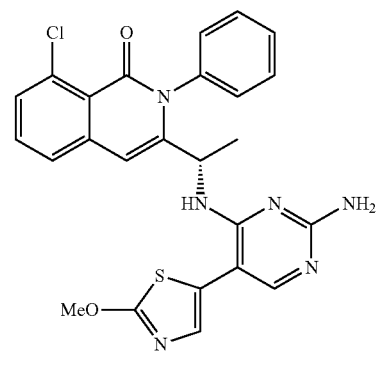

382

Compound 135 was prepared according to Example 87. Compound 382 was prepared according to Example 88 using 2-methoxy-5-(tributylstannyl)thiazole. ESI-MS m/z: 505.1 [M+H]$^+$.

Example 209

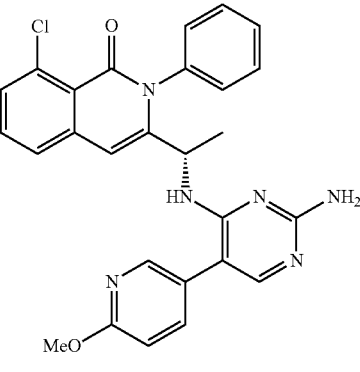

383

Compound 135 was prepared according to Example 87. Compound 383 was prepared according to Example 99 using 6-methoxypyridin-3-ylboronic acid. ESI-MS m/z: 499.1 [M+H]+.

Example 210

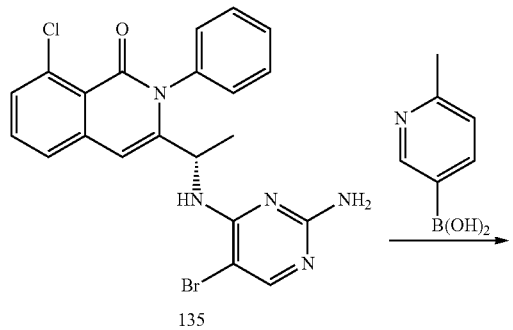

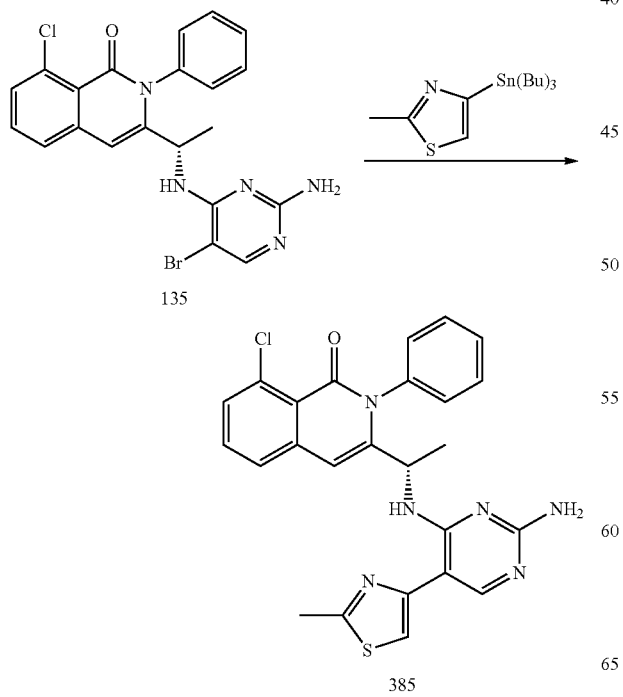

Compound 135 was prepared according to Example 87. Compound 384 was prepared according to Example 99 using 6-methylpyridin-3-ylboronic acid. ESI-MS m/z: 483.1 [M+H]+.

Example 211

Compound 135 was prepared according to Example 87. Compound 385 was prepared according to Example 88 using 2-methyl-4-(tributylstannyl)thiazole. ESI-MS m/z: 489.1 [M+H]+.

Example 212

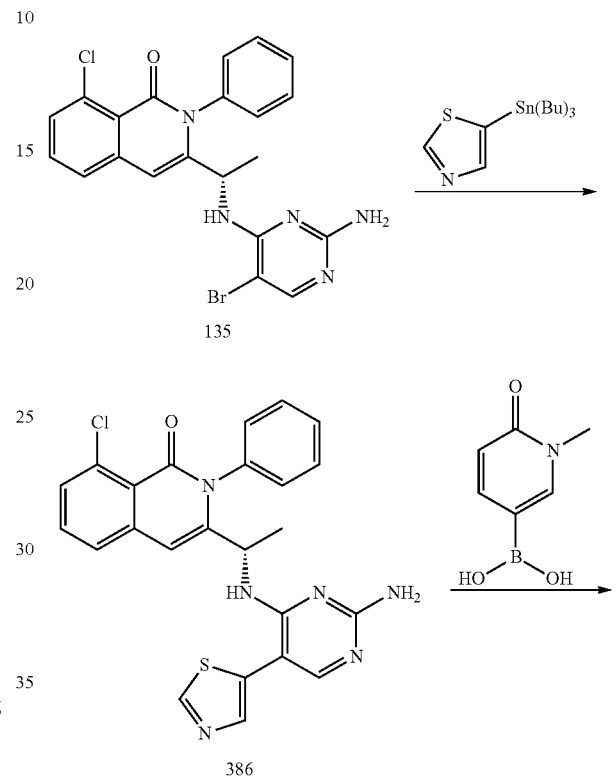

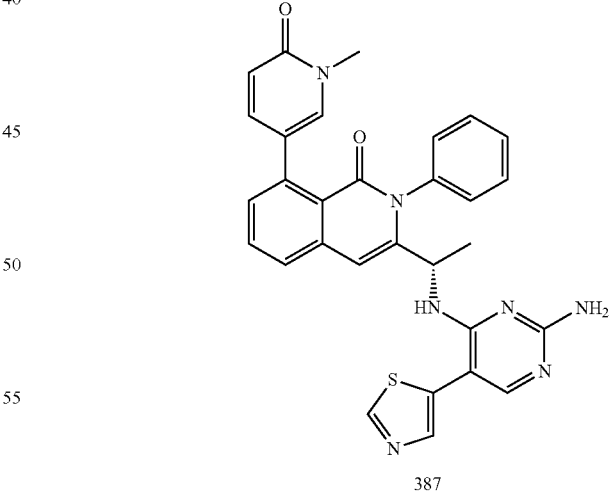

Compound 135 was prepared according to Example 87. Compound 386 was prepared from compound 135 according to Example 88 using 5-(tributylstannyl)thiazole. Compound 387 was prepared from compound 386 in analogous fashion to Example 89 using 1-methyl-6-oxo-1,6-dihydropyridin-3-ylboronic acid. ESI-MS m/z: 548.3 [M+H]+.

Example 213

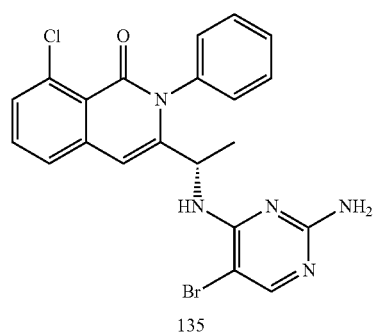 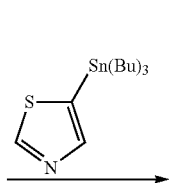 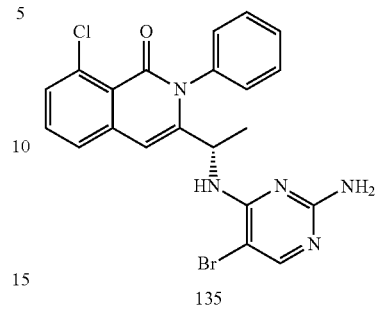

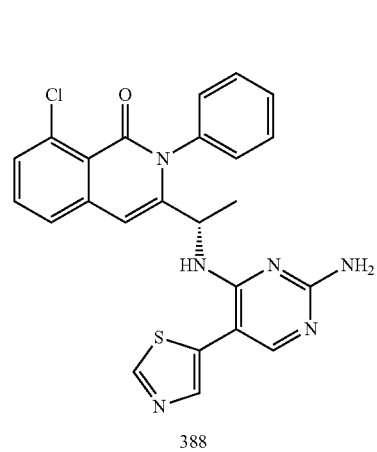 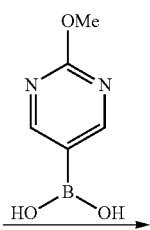

388

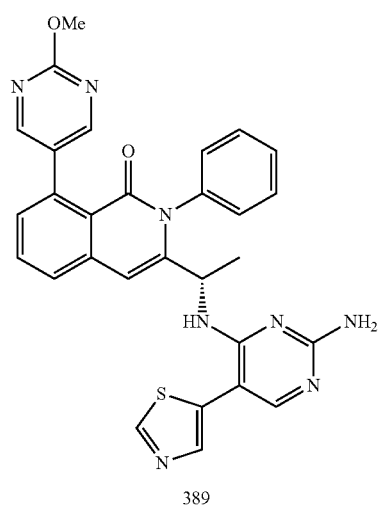

389

Compound 135 was prepared according to Example 87. Compound 388 was prepared from compound 135 according to Example 88 using 5-(tributylstannyl)thiazole. Compound 387 was prepared from compound 386 in analogous fashion to Example 89 using 2-methoxypyrimidin-5-ylboronic acid. ESI-MS m/z: 549.2 [M+H]$^+$.

Example 214

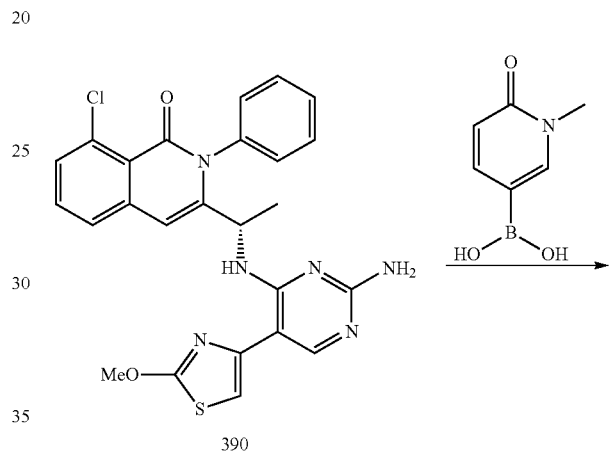

390

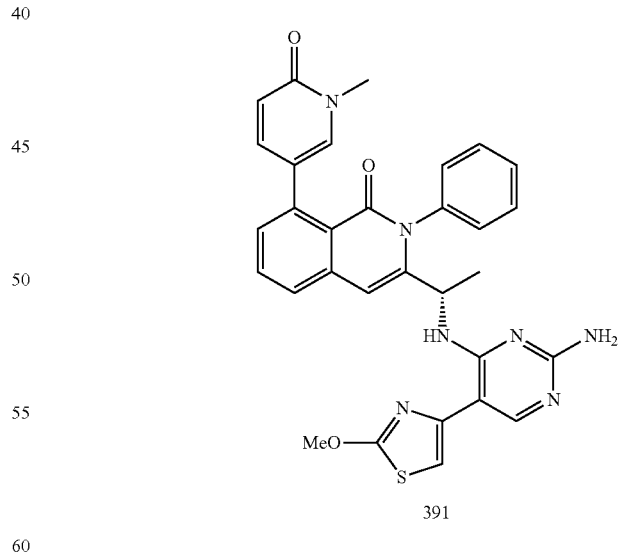

391

Compound 135 was prepared according to Example 87. Compound 390 was prepared from compound 135 according to Example 88 using 2-methoxy-4-(tributylstannyl)thiazole. Compound 391 was prepared from compound 390 in analogous fashion to Example 89 using 1-methyl-6-oxo-1,6-dihydropyridin-3-ylboronic acid. ESI-MS m/z: 578.3 [M+H]$^+$.

407
Example 215

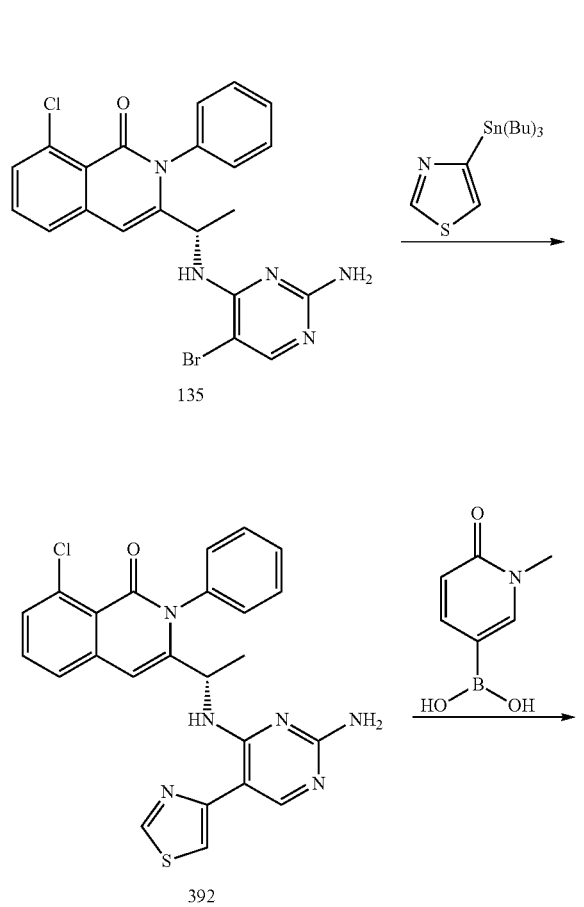

408
Example 216

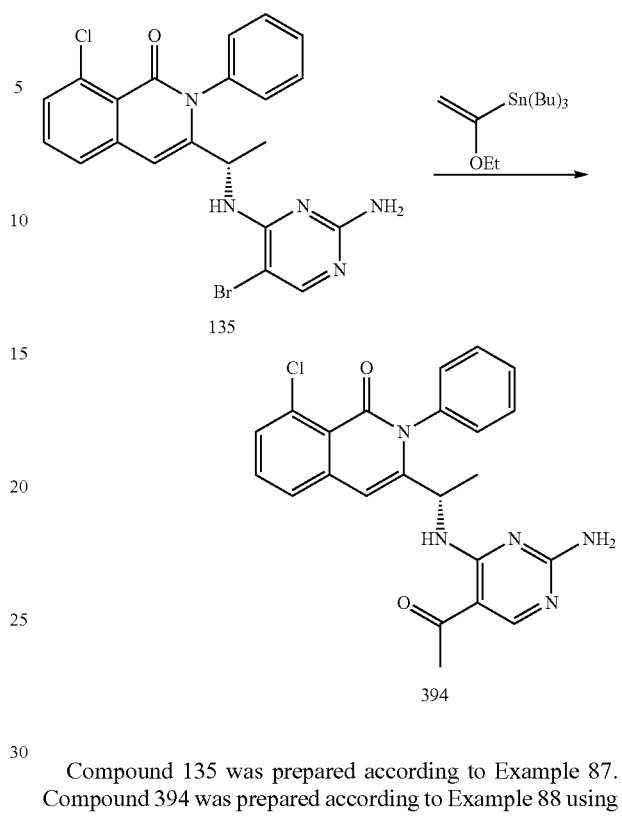

Compound 135 was prepared according to Example 87. Compound 394 was prepared according to Example 88 using tributyl(1-ethoxyvinyl)stannane. ESI-MS m/z: 434.1 [M+H]⁺.

Example 217

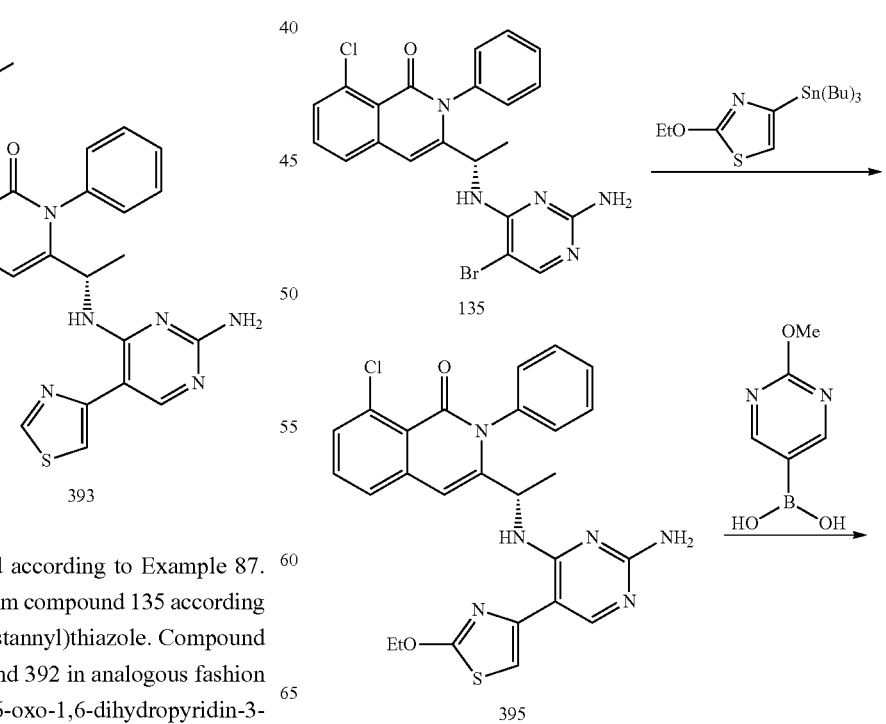

Compound 135 was prepared according to Example 87. Compound 392 was prepared from compound 135 according to Example 88 using 4-(tributylstannyl)thiazole. Compound 393 was prepared from compound 392 in analogous fashion to Example 89 using 1-methyl-6-oxo-1,6-dihydropyridin-3-ylboronic acid. ESI-MS m/z: 548.2 [M+H]⁺.

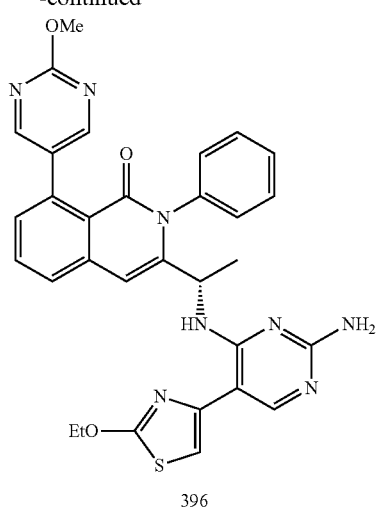

396

Compound 135 was prepared according to Example 87. Compound 395 was prepared from compound 135 according to Example 88 using 2-ethoxy-4-(tributylstannyl)thiazole. Compound 396 was prepared from compound 395 in analogous fashion to Example 89 using 2-methoxypyrimidin-5-ylboronic acid. ESI-MS m/z: 593.3 [M+H]+.

Example 218

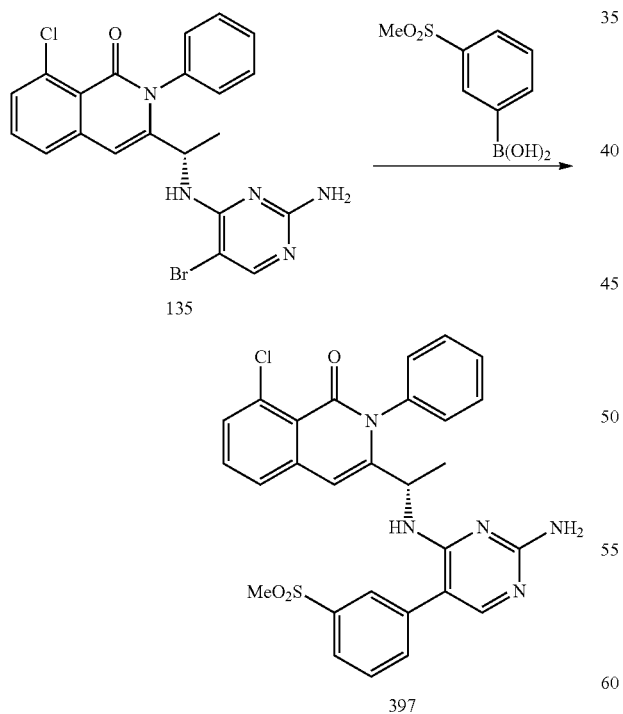

397

Compound 135 was prepared according to Example 87. Compound 397 was prepared according to Example 99 using 3-(methylsulfonyl)phenylboronic acid. ESI-MS m/z: 546.1 [M+H]+.

Example 219

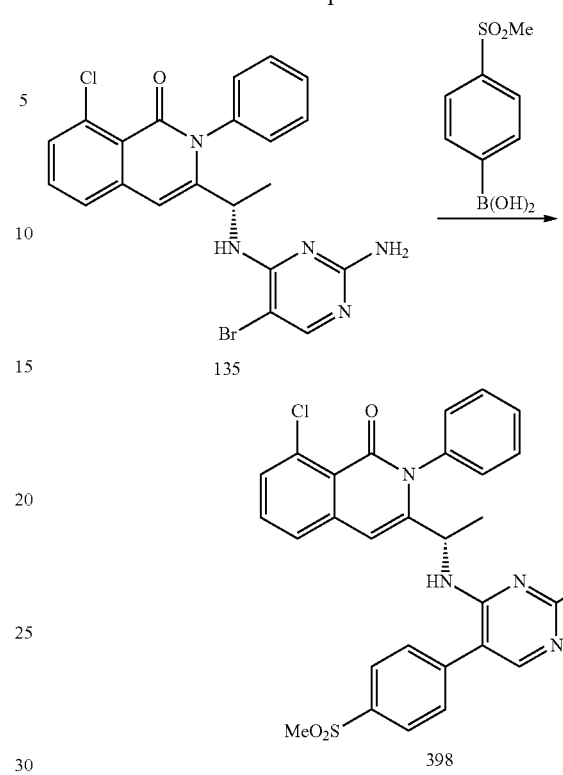

398

Compound 135 was prepared according to Example 87. Compound 398 was prepared according to Example 99 using 4-(methylsulfonyl)phenylboronic acid. ESI-MS m/z: 546.1 [M+H]+.

Example 220

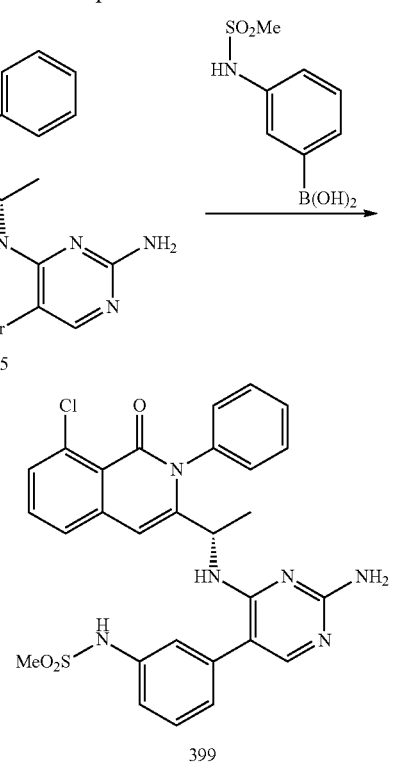

399

Compound 135 was prepared according to Example 87. Compound 399 was prepared according to Example 99 using 3-(methylsulfonamido)phenylboronic acid. ESI-MS m/z: 561.1 [M+H]⁺.

Example 221

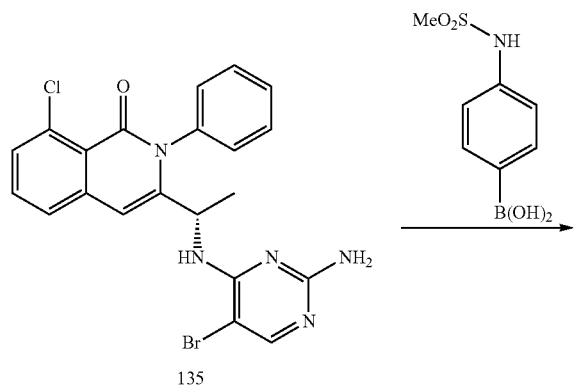

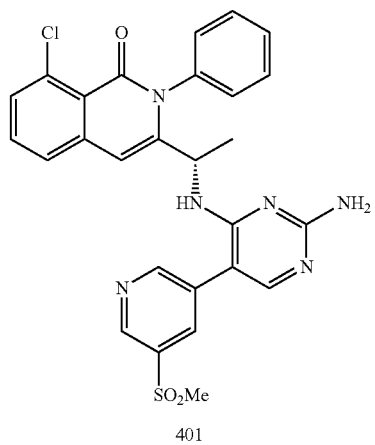

401

Compound 135 was prepared according to Example 87. Compound 401 was prepared according to Example 99 using 5-(methylsulfonyl)pyridin-3-ylboronic acid. ESI-MS m/z: 547.1 [M+H]⁺.

Example 223

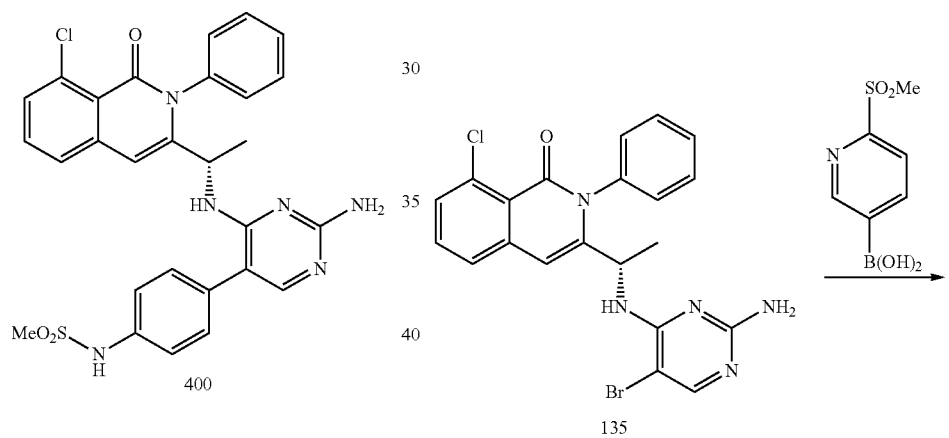

400

Compound 135 was prepared according to Example 87. Compound 400 was prepared according to Example 99 using 4-(methylsulfonamido)phenylboronic acid. ESI-MS m/z: 561.1 [M+H]⁺.

Example 222

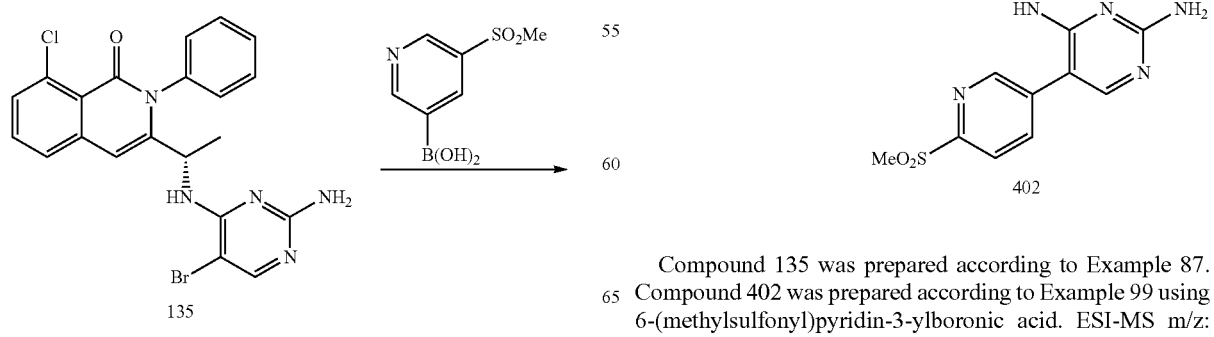

402

Compound 135 was prepared according to Example 87. Compound 402 was prepared according to Example 99 using 6-(methylsulfonyl)pyridin-3-ylboronic acid. ESI-MS m/z: 547.1 [M+H]⁺.

Example 224

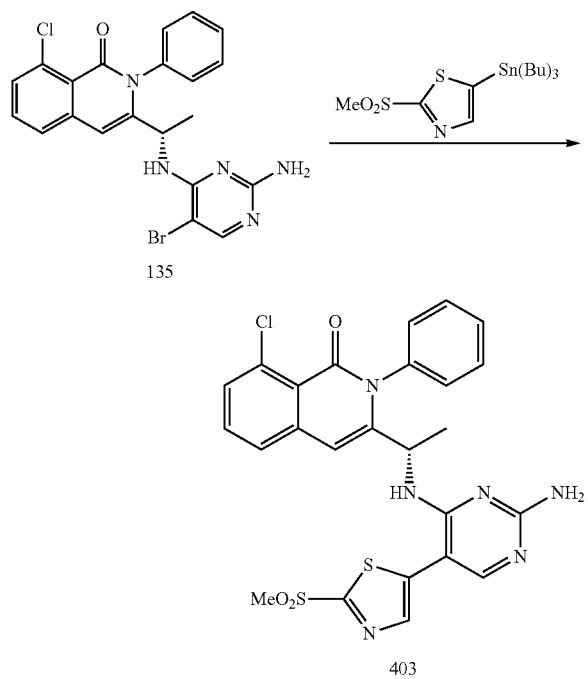

Compound 135 was prepared according to Example 87. Compound 403 was prepared according to Example 88 using 2-(methylsulfonyl)-5-(tributylstannyl)thiazole. ESI-MS m/z: 553.1 [M+H]⁺.

Example 225

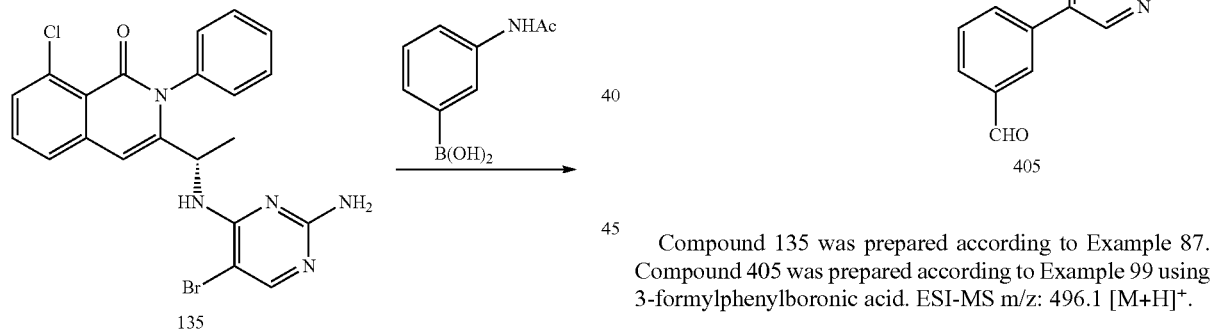

Compound 135 was prepared according to Example 87. Compound 404 was prepared according to Example 99 using 3-acetamidophenylboronic acid. ESI-MS m/z: 525.2 [M+H]⁺.

Example 226

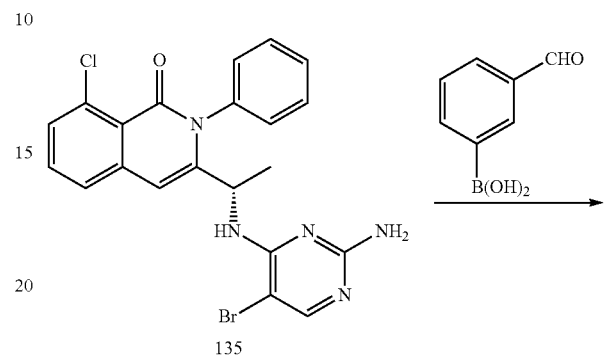

Compound 135 was prepared according to Example 87. Compound 405 was prepared according to Example 99 using 3-formylphenylboronic acid. ESI-MS m/z: 496.1 [M+H]⁺.

Example 227

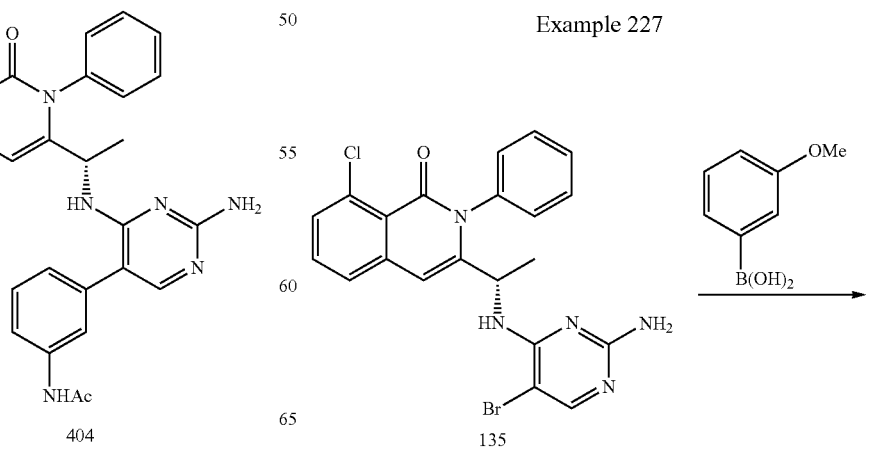

415
-continued

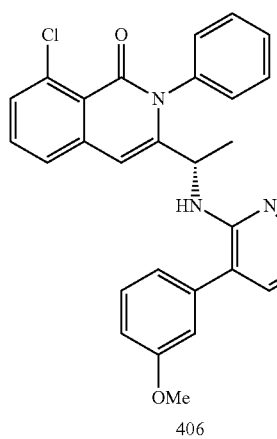

406

Compound 135 was prepared according to Example 87. Compound 406 was prepared according to Example 99 using 3-methoxyphenylboronic acid. ESI-MS m/z: 498.2 [M+H]+.

Example 228

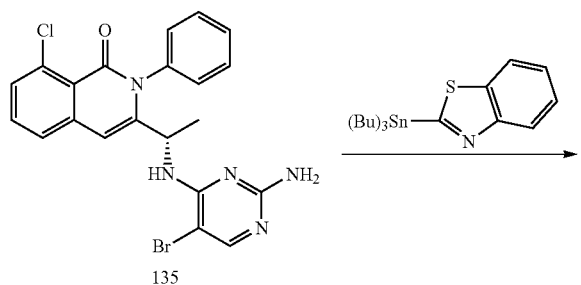

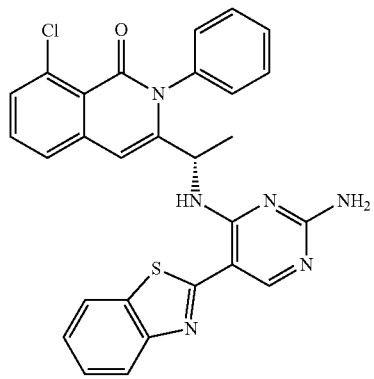

407

Compound 135 was prepared according to Example 87. Compound 407 was prepared according to Example 88 using 2-(tributylstannyl)benzo[d]thiazole. ESI-MS m/z: 525.2 [M+H]+.

416

Example 229

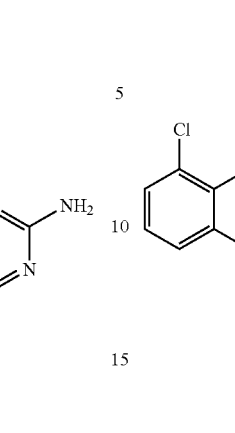 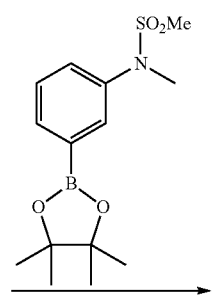

135

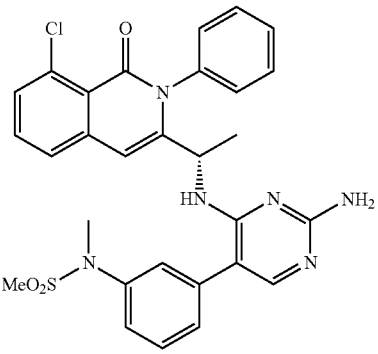

408

Compound 135 was prepared according to Example 87. Compound 408 was prepared according to Example 99 using N-methyl-N-[3-(4,4,5,5-tetramethyl-1,3,2-dioxaborolan-2-yl)-phenyl]-methanesulfonamide instead of 3-(piperidin-1-ylsulfonyl)phenylboronic acid. ESI-MS m/z: 575.2 [M+H]+.

Example 230

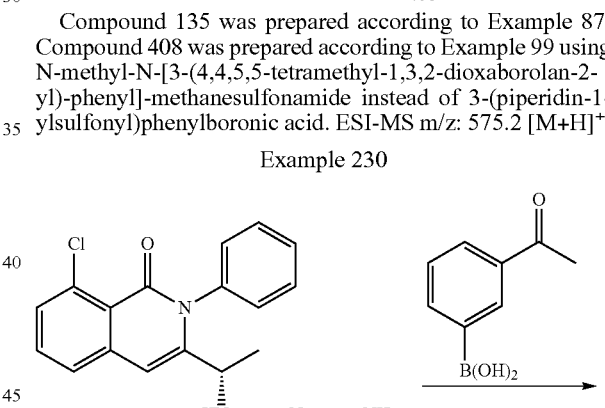 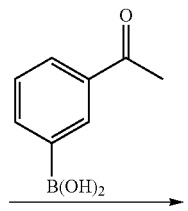

135

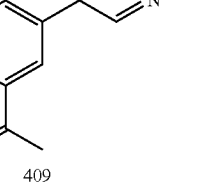

409

Compound 135 was prepared according to Example 87. Compound 409 was prepared according to Example 99 using 3-acetylphenylboronic acid. ESI-MS m/z: 510.2 [M+H]⁺.
Example 231
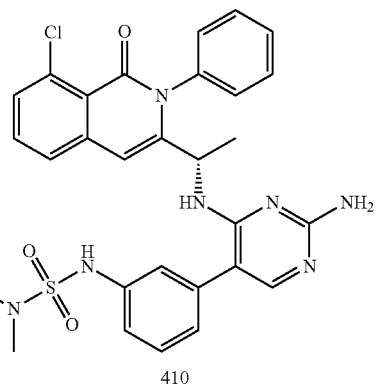
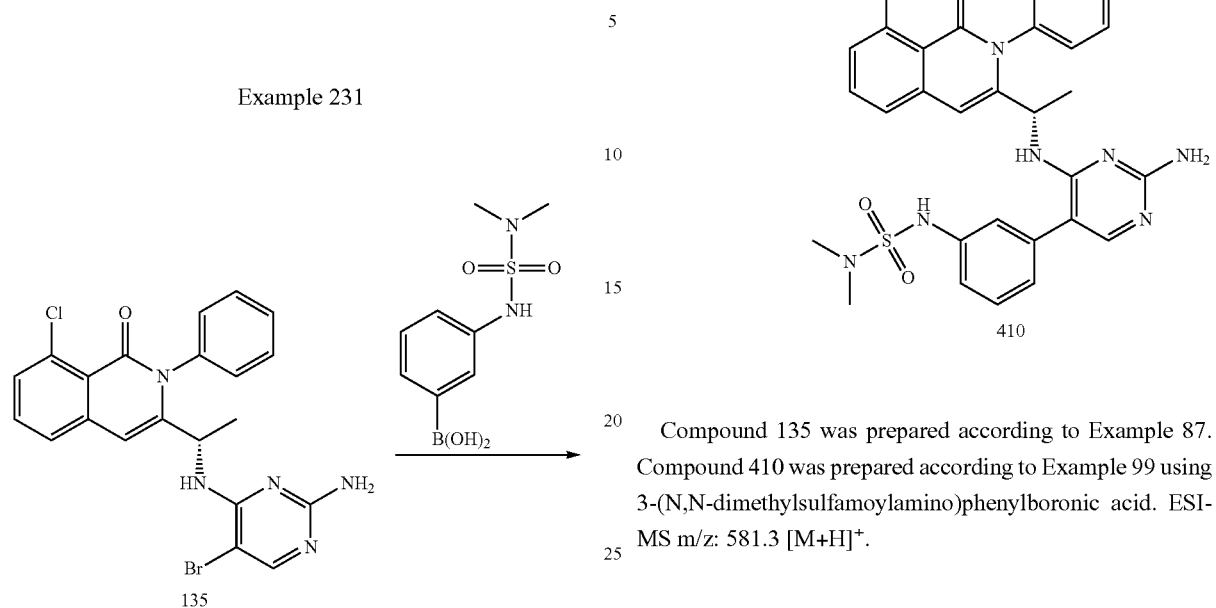
Compound 135 was prepared according to Example 87. Compound 410 was prepared according to Example 99 using 3-(N,N-dimethylsulfamoylamino)phenylboronic acid. ESI-MS m/z: 581.3 [M+H]⁺.
Example 232
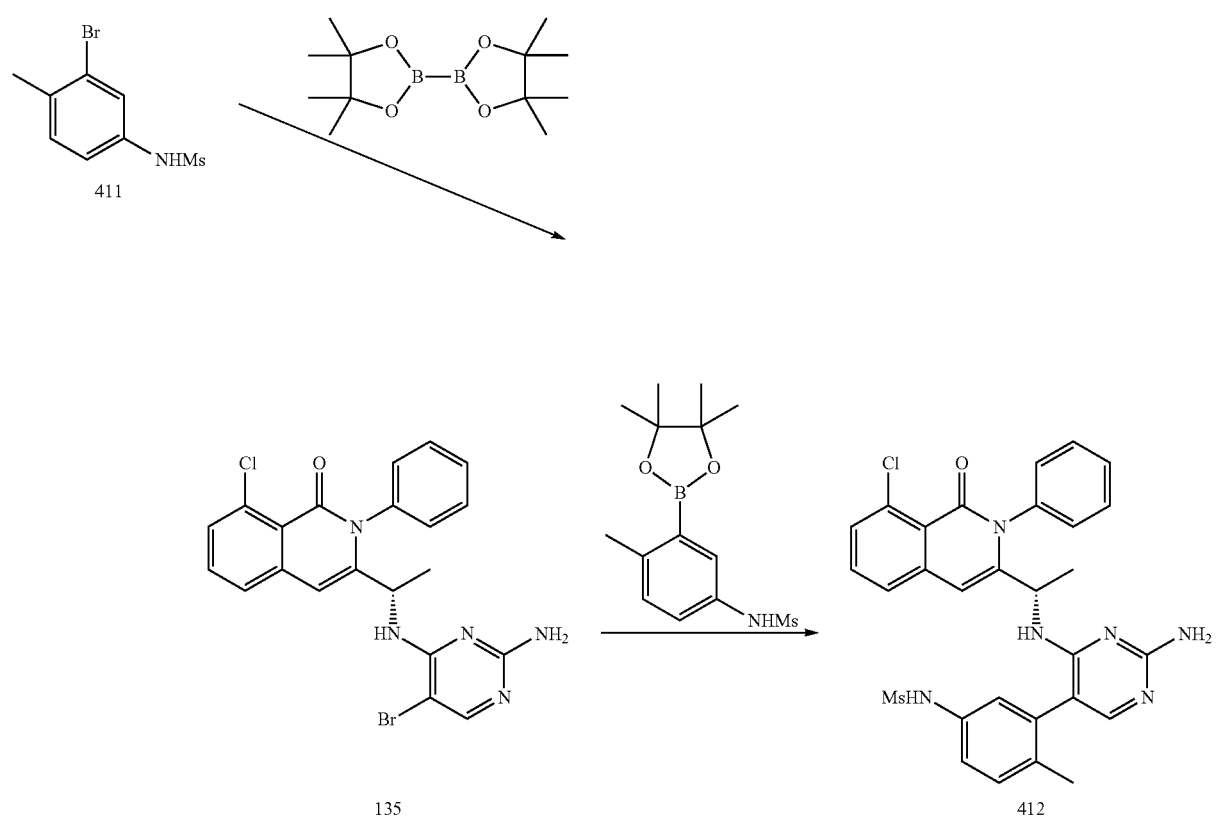

419

A mixture of bromide 411 (500 mg, 1.893 mmol), bis(pinacolato)diboron (577 mg, 2.272 mmol) and KOAc (557 mg, 5.68 mmol) in DMSO (6 mL) was bubbled with Ar for 10 min. The mixture was charged with Pd(dppf)$_2$Cl$_2$-DCM complex (155 mg, 0.189 mmol) and heated to 85° C. overnight. The reaction was cooled to room temperature and diluted with EtOAc. The organic layer was washed with water, dried over Na$_2$SO$_4$, filtered, and pre-adsorbed on SiO$_2$. The residue was purified on SiO$_2$ (20-40% EA/hex) to obtain the boronate ester. Compound 412 was prepared from the boronate ester and compound 135 according to Example 99. ESI-MS m/z: 575.2 [M+H]$^+$.

Example 233

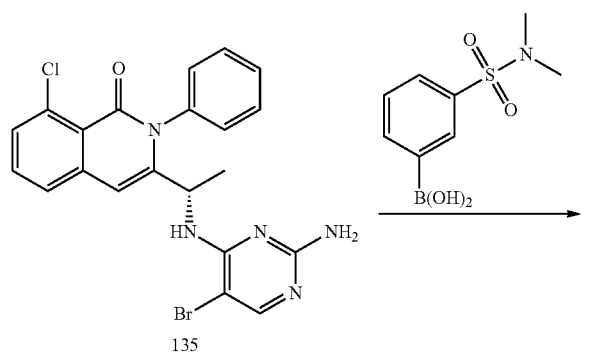

Compound 135 was prepared according to Example 87. Compound 413 was prepared according to Example 99 using 3-(N,N-dimethylsulfamoyl)phenylboronic acid. ESI-MS m/z: 575.2 [M+H]$^+$.

Example 234

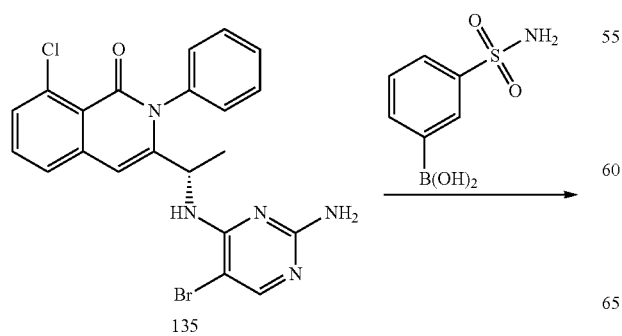

420

-continued

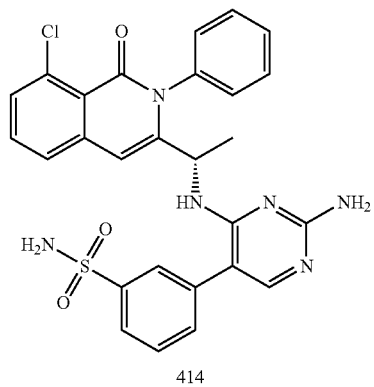

414

Compound 135 was prepared according to Example 87. Compound 414 was prepared according to Example 99 using 3-sulfamoylphenylboronic acid. ESI-MS m/z: 547.2 [M+H]$^+$.

Example 235

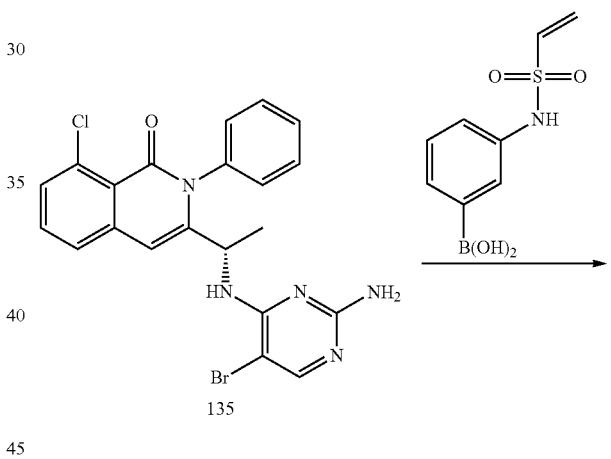

415

Compound 135 was prepared according to Example 87. Compound 415 was prepared according to Example 99 using N-(3-(4,4,5,5-tetramethyl-1,3,2-dioxaborolan-2-yl)phenyl) ethenesulfonamide instead of 3-(piperidin-1-ylsulfonyl)phenylboronic acid. ESI-MS m/z: 573.3 [M+H]$^+$.

Example 236

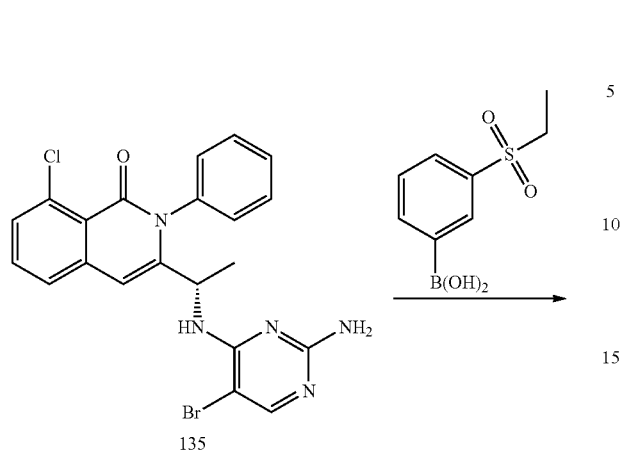

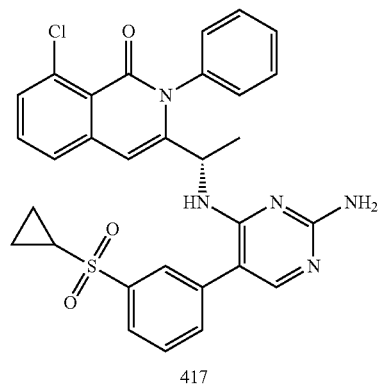

Compound 135 was prepared according to Example 87. Compound 416 was prepared according to Example 99 using 2-(3-(ethylsulfonyl)phenyl)-4,4,5,5-tetramethyl-1,3,2-dioxaborolane instead of 3-(piperidin-1-ylsulfonyl)phenylboronic acid. ESI-MS m/z: 560.2 [M+H]⁺.

Example 237

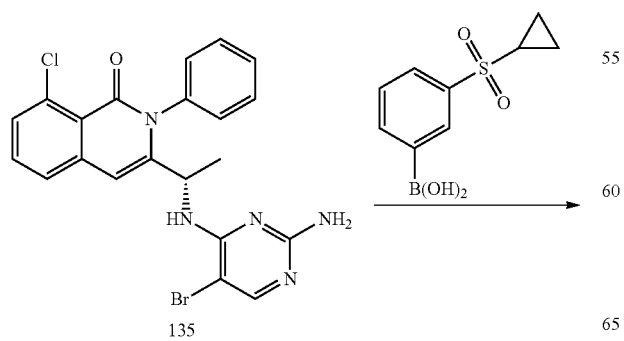

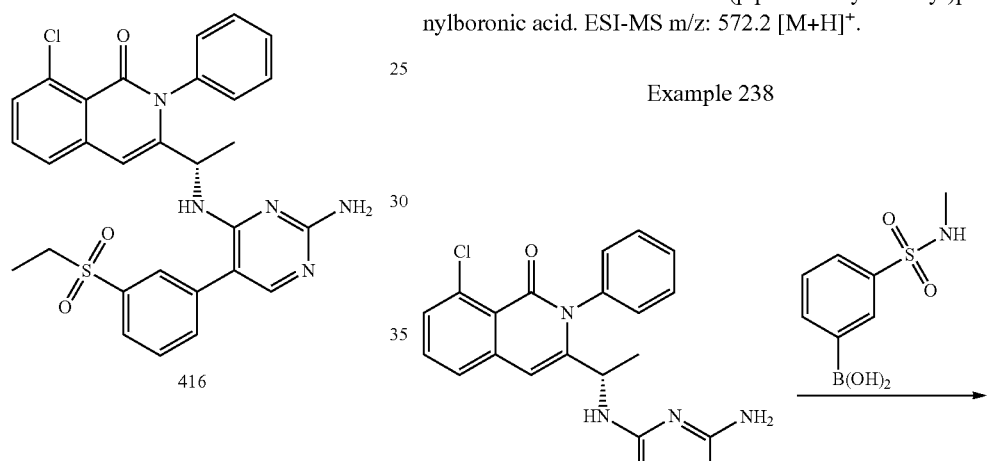

Compound 135 was prepared according to Example 87. Compound 417 was prepared according to Example 99 using 2-(3-(cyclopropylsulfonyl)phenyl)-4,4,5,5-tetramethyl-1,3,2-dioxaborolane instead of 3-(piperidin-1-ylsulfonyl)phenylboronic acid. ESI-MS m/z: 572.2 [M+H]⁺.

Example 238

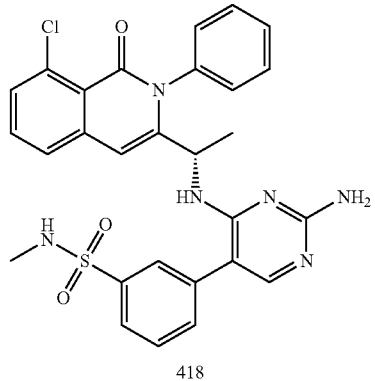

Compound 135 was prepared according to Example 87. Compound 418 was prepared according to Example 99 using 3-(N-methylsulfamoyl)phenylboronic acid. ESI-MS m/z: 561.2 [M+H]⁺.

Example 239

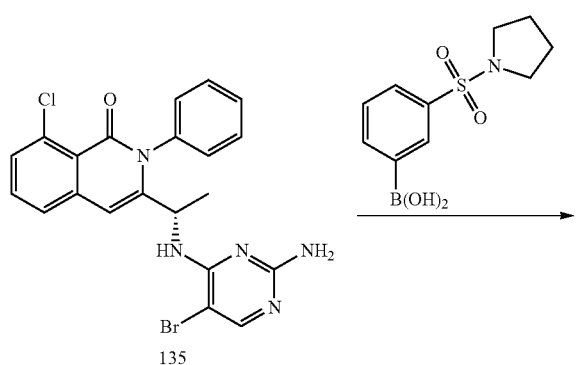

Compound 135 was prepared according to Example 87. Compound 419 was prepared according to Example 99 using 3-(pyrrolidin-1-ylsulfonyl)phenylboronic acid. ESI-MS m/z: 601.2 [M+H]+.

Example 240

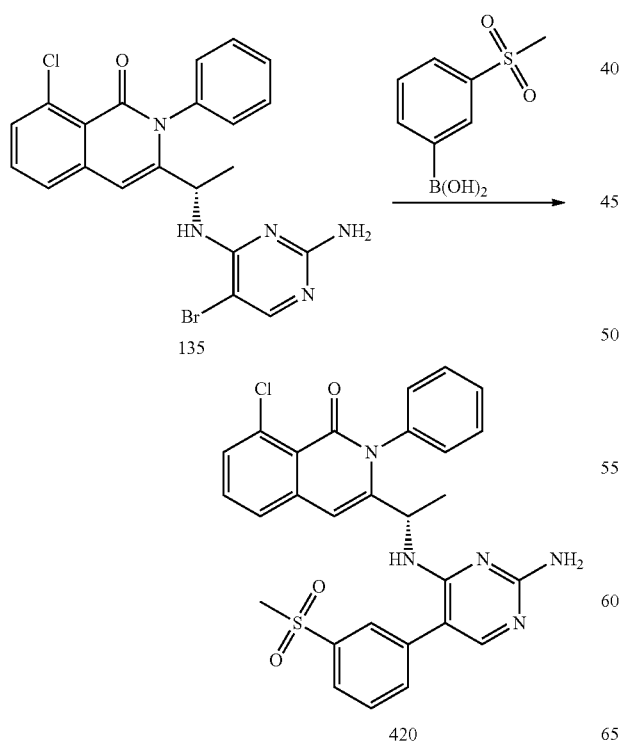

Compound 135 was prepared according to Example 87. Compound 420 was prepared according to Example 99 using 3-(methylsulfonyl)phenylboronic acid. ESI-MS m/z: 561.2 [M+H]+.

Example 241

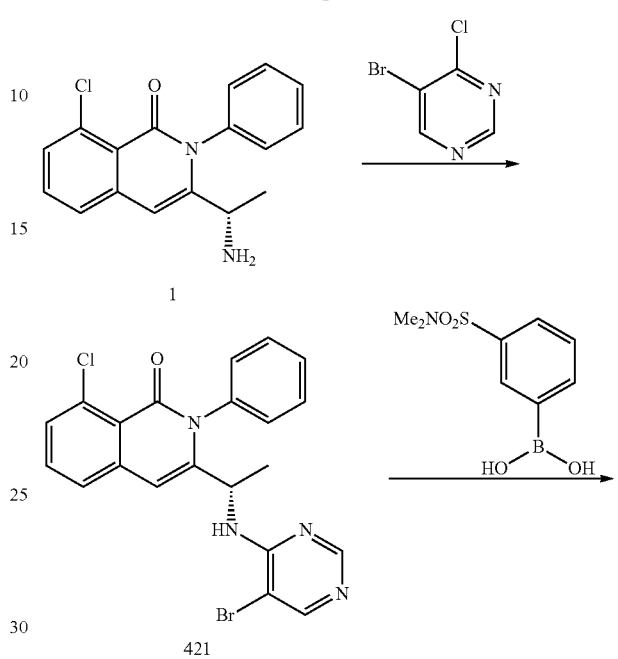

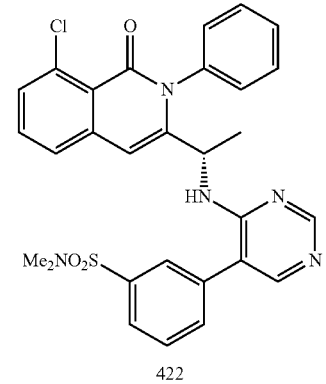

The amine 1 (4.00 g, 13.39 mmol) and 5-bromo-4-chloropyrimidine were suspended in 1-butanol (65 mL) and charged with Hunig's Base (2.338 ml, 13.39 mmol). The mixture was heated to reflux for 2 h. The reaction was cooled to room temperature, diluted with toluene (50 mL) and concentrated. The residue was suspended in toluene (50 mL) and heated to reflux until all solids dissolved to form a solution. The solution was then cooled to 0° C. The resulting solid was filtered and washed with cold toluene to give the bromide 421.

Bromide 421 (104 mg, 0.189 mmol) and boronic acid (65.1 mg, 0.284 mmol) were dissolved in dioxane (2 mL) and $Na_2CO_3$ aq. (253 μA, 0.379 mmol) The mixture was bubbled with Ar for 5 min then charged with $Pd(Ph_3P)_4$ (10.94 mg, 9.47 μmol). The mixture was heated to 90° C. for 3 h. The reaction was cooled to room temperature, and poured into saturated bicarbonate/EtOAc mixture. The phases were split and the organic layer was dried, filtered and pre-adsorbed on $SiO_2$ (1.5 g). The residue was purified on $SiO_2$ (12 g) (0-90 Acetone/DCM) to give the sulfonamide 422. ESI-MS m/z: 460.2 [M+H]+.

Example 242

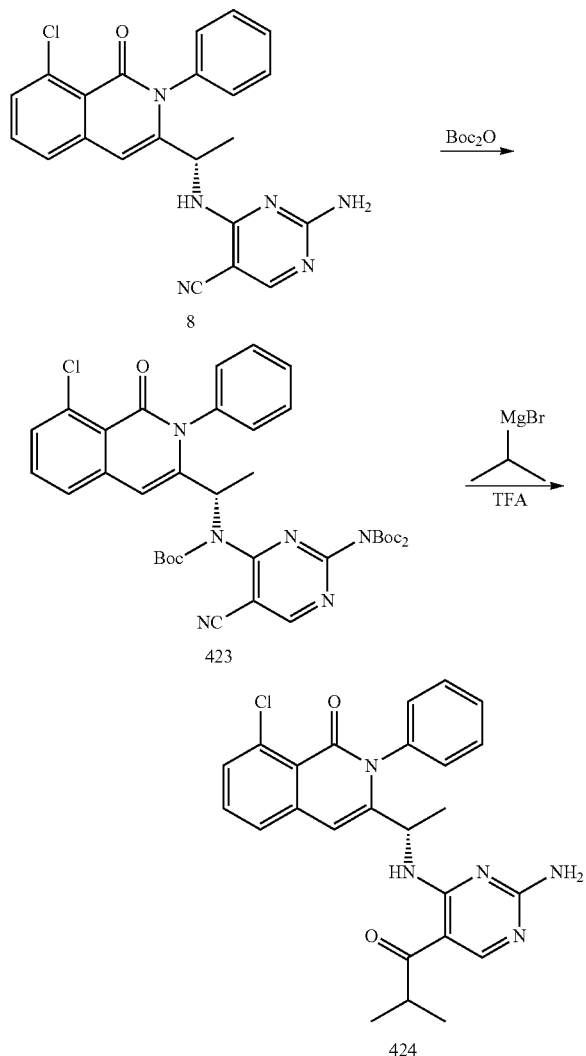

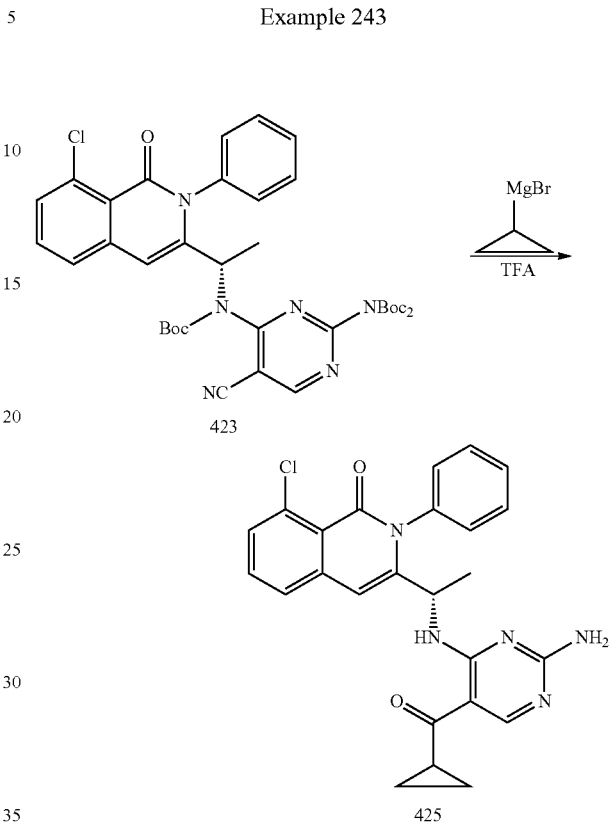

Compound 8 (284 mg, 0.681 mmol) was dissolved in THF (15 mL) and treated with DMAP (20.80 mg, 0.170 mmol) and Boc₂O (1189 mg, 5.45 mmol). The mixture was stirred for 2 h at reflux and further Boc₂O (4 eq) was added. The reaction was cooled and the product was extracted with EtOAc. The organic layer was washed with sodium bicarbonate and brine. The organic layers were dried on Na₂SO₄, filtered, then pre-absorbed on silica gel (2 g). The product was added to a silica gel (25 g) column and was eluted with EtOAc (5 to 50%)/Hexanes to give compound 423.

In a flame dry flask, compound 423 (120 mg, 0.167 mmol) was dissolved in cooled (0° C.) THF (5 mL). Isopropylmagnesium bromide in 2-MeTHF (0.115 ml, 0.335 mmol) was added dropwise, and the mixture was stirred to reflux overnight. The reaction was cooled down and treated with 2 M HCl (0.418 ml, 0.837 mmol) for 4 h. The product was extracted with DCM, which was washed with sodium bicarbonate. The organic layers were dried on Na₂SO₄, filtered and concentrated. The product was dissolved in DCM (5 mL) and treated with TFA (0.064 ml, 0.837 mmol) at room temperature overnight. The solvent was removed and the material was purified by HPLC to give the isopropyl ketone 424. ESI-MS m/z: 461.1 [M+H]⁺.

Example 243

Compound 423 was prepared according to Example 422. Compound 423 (125 mg, 0.174 mmol) was dissolved in cooled (0° C.) THF (5 mL). Cyclopropylmagnesium bromide (0.5 M; 0.115 ml, 0.335 mmol) was added dropwise and the mixture was stirred to reflux overnight. The reaction was cooled and treated with conc. HCl 0.418 ml, 0.837 mmol) for 4 h. The product was extracted with DCM, which was washed with sodium bicarbonate. The organic layers were dried on Na₂SO₄, filtered and concentrated. The product was dissolved in DCM (5 mL) and treated with TFA (3 mL) at room temperature overnight. The solvent was removed and the compound was purified by HPLC to give the cyclopropyl ketone 425. ESI-MS m/z: 459.1 [M+H]⁺.

Example 244

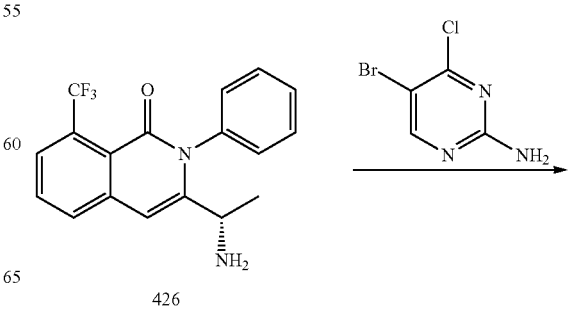

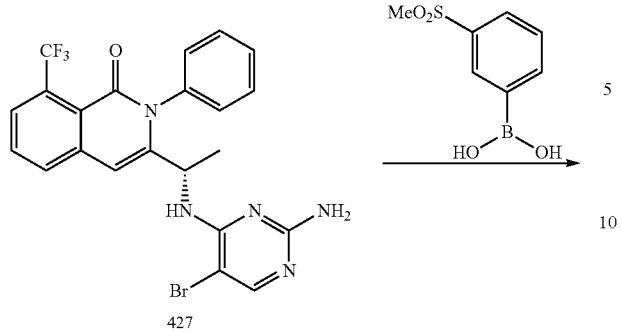

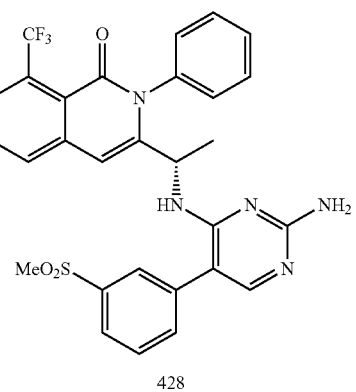

(S)-3-(1-aminoethyl)-1-8-(trifluoromethyl)isoquinolin-1(2H)-one 427, made according to Method C, was coupled to 5-bromo-4-chloropyrimidin-2-amine using Method G. Compound 428 was prepared from compound 427 according to Example 99 using (3-(methylsulfonyl)phenyl)boronic acid. ESI-MS m/z: 580.1 [M+H]⁺.

Example 245

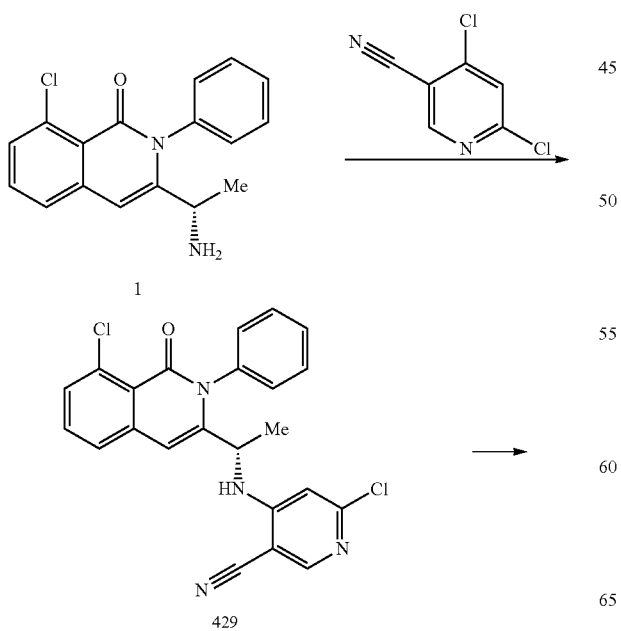

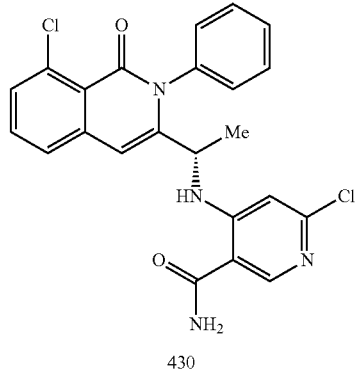

Compound 1 was prepared using 4,6-dichloronicotinonitrile according to Method G to provide compound 429. To a mixture of isoquinolinone 432 (0.23 mmol) and 1,4-dioxane (10 mL) was added ammonium hydroxide solution (10 mL) and the mixture was placed in a 110° C. bath overnight. The reaction mixture was cooled and diluted with 2 volumes of brine after which a solid is formed. Collection via vacuum filtration provided amide 430. ESI-MS m/z: 453.17 [M+H]⁺.

Example 246

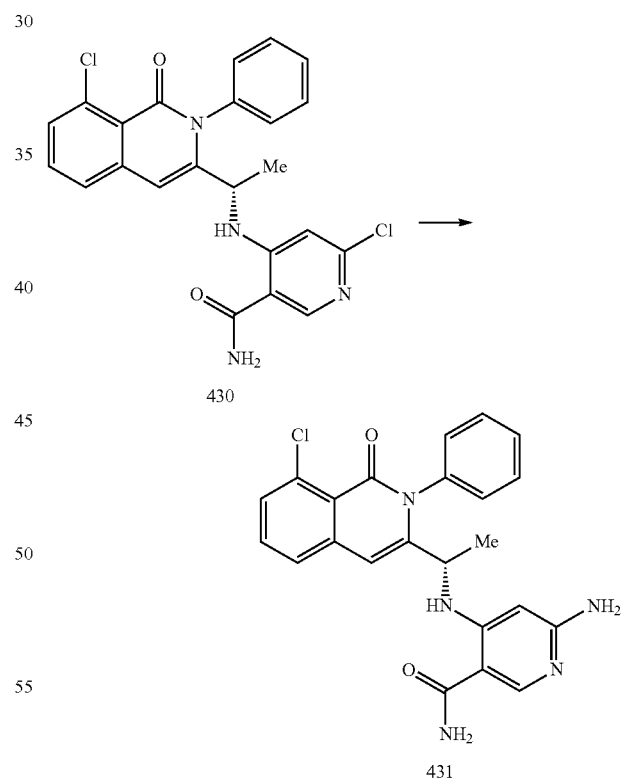

To a mixture of isoquinolinone 430 (0.14 mmol) and 1,4-dioxane (4 mL) was added ammonium hydroxide solution (30%, 5 mL). The mixture was placed in a 150° C. bath for 3 days. The mixture was then recharged with 5 mL of ammonium hydroxide (30%, 5 mL) and heated for an additional 24 h at 170° C. The reaction mixture was then added to excess methylene chloride and the layers were separated. The organic layer was washed with brine (1×) and water (1×), dried over Na₂SO₄ and concentrated to provide compound 431. ESI-MS m/z: 434.18 [M+H]⁺.

Example 247

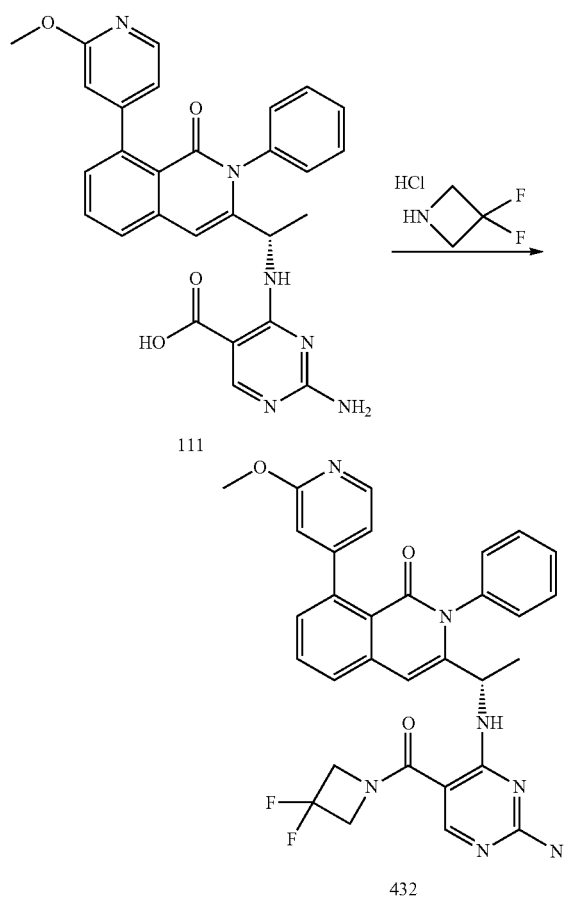

Compound 432 was prepared from compound III in analogous fashion to compound 112 in Example 73 except that difluoroazetidine hydrochloride was used in place of dimethylamine. ESI-MS m/z: 584.2 [M+H]+.

Example 248

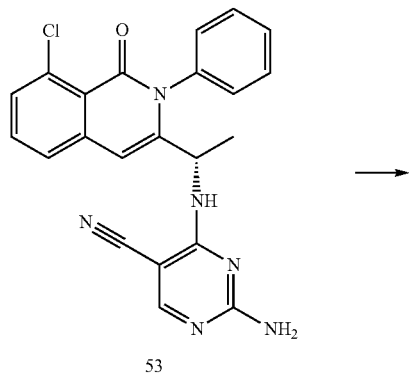

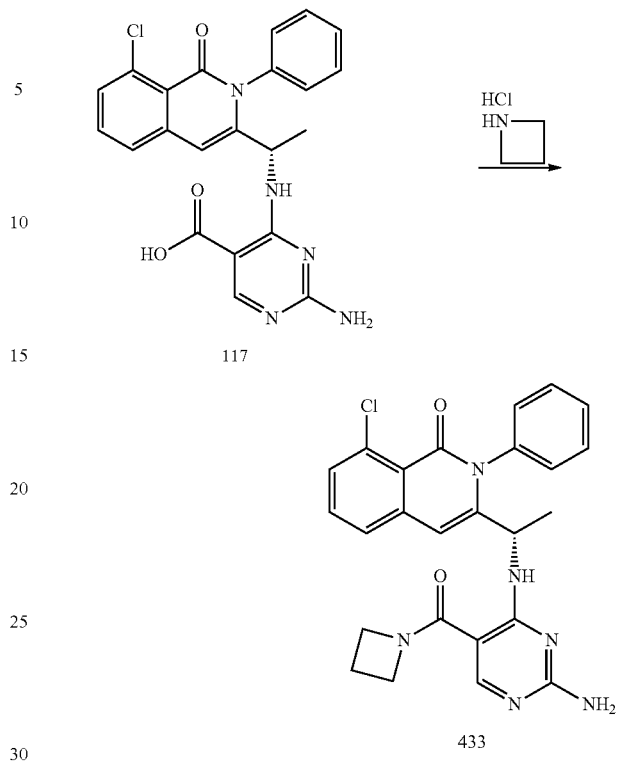

Compound 117 was prepared from compound 53 according to Example 78. Compound 433 was prepared from compound 117 according to Example 96. ESI-MS m/z: 475.0 [M+H]+.

Example 249

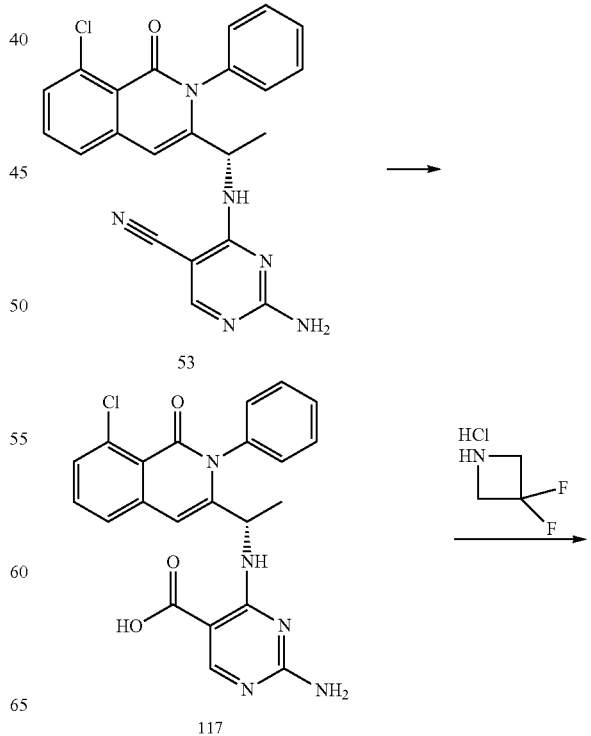

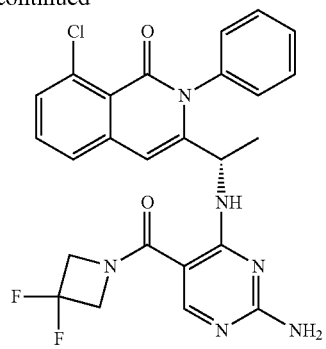

434

Compound 434 was prepared from compound 117 according to Example 249 using 2,2-difluoroazetidine hydrochloride. ESI-MS m/z: 511.1 [M+H]+.

Example 250

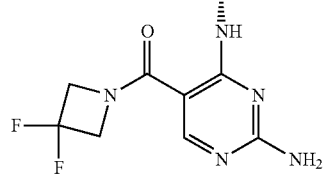

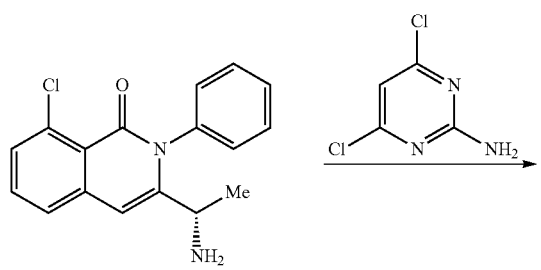

435

Compound 1 was coupled to 4,6-dichloropyrimidin-2-amine according to Method G to afford compound 435. ESI-MS m/z: 426.0 [M+H]+.

Example 251

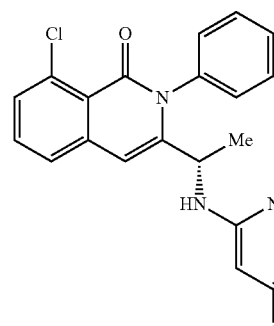

135

436

Compound 135 was prepared according to Example 87. Compound 436 was prepared according to Example 99 using 4-hydroxyphenylboronic acid instead of 3-(piperidin-1-yl-sulfonyl)phenylboronic acid. ESI-MS m/z: 484.2 [M+H]$^+$.

Example 252

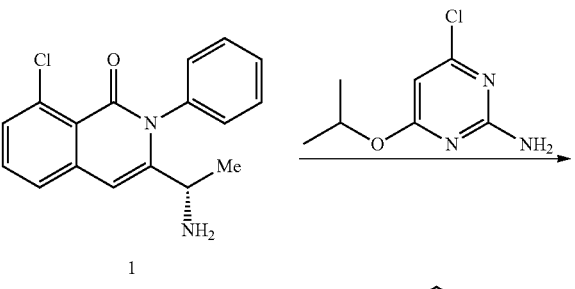

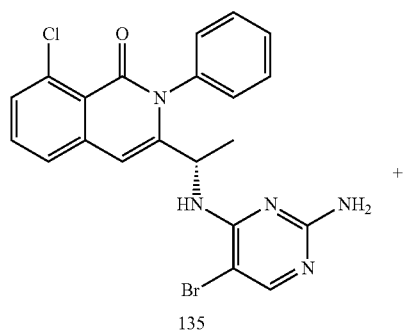

437

Compound 440 was prepared from compound 1 using 4-chloro-6-isopropoxypyrimidin-2-amine according to Method G. ESI-MS m/z: 450.1 [M+H]$^+$.

Example 253

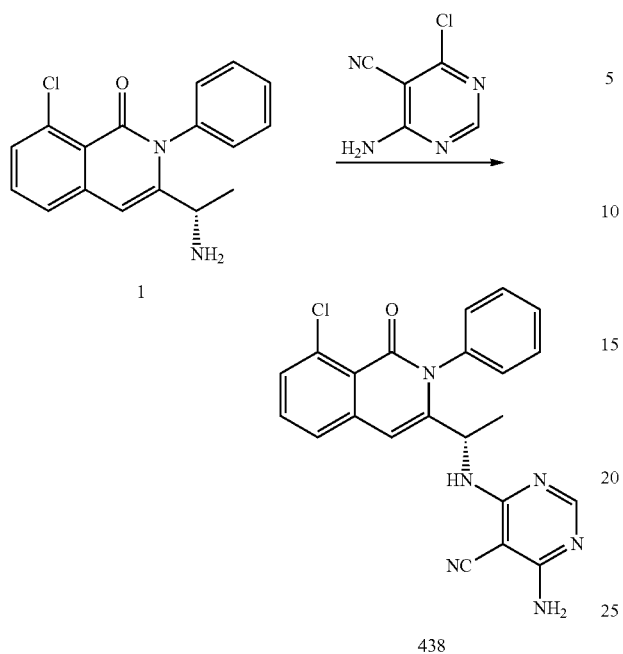

Compound 438 was prepared from compound 1 in analogous fashion to compound 325 in Example 176 using 4-amino-6-chloropyrimidine-5-carbonitrile. ESI-MS m/z: 450.1 [M+H]$^+$.

Example 254

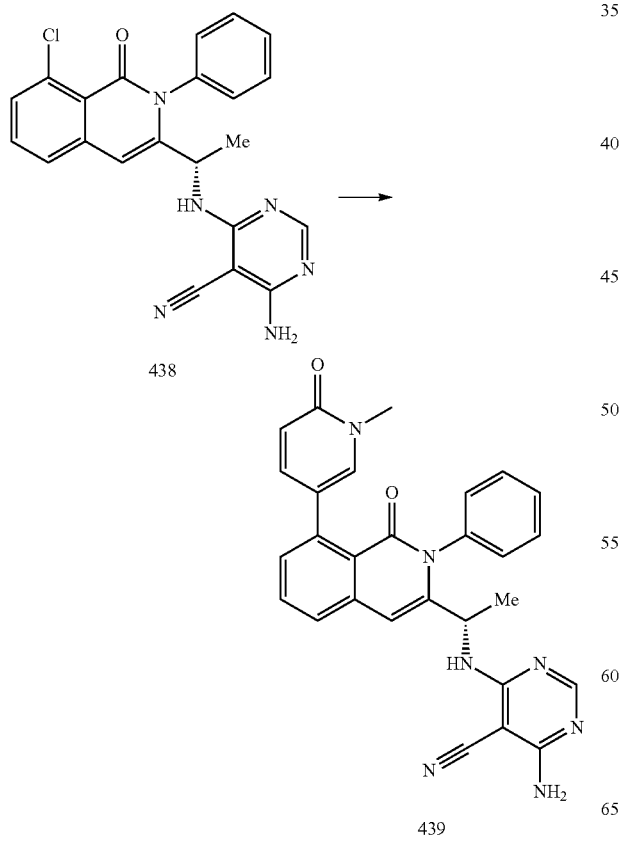

Compound 439 was prepared from compound 438 according to Example 176 using 2-methoxy-pyrimidin-5-ylboronic acid in the coupling according to Method J. ESI-MS m/z: 490.2 [M+H]$^+$.

Example 255

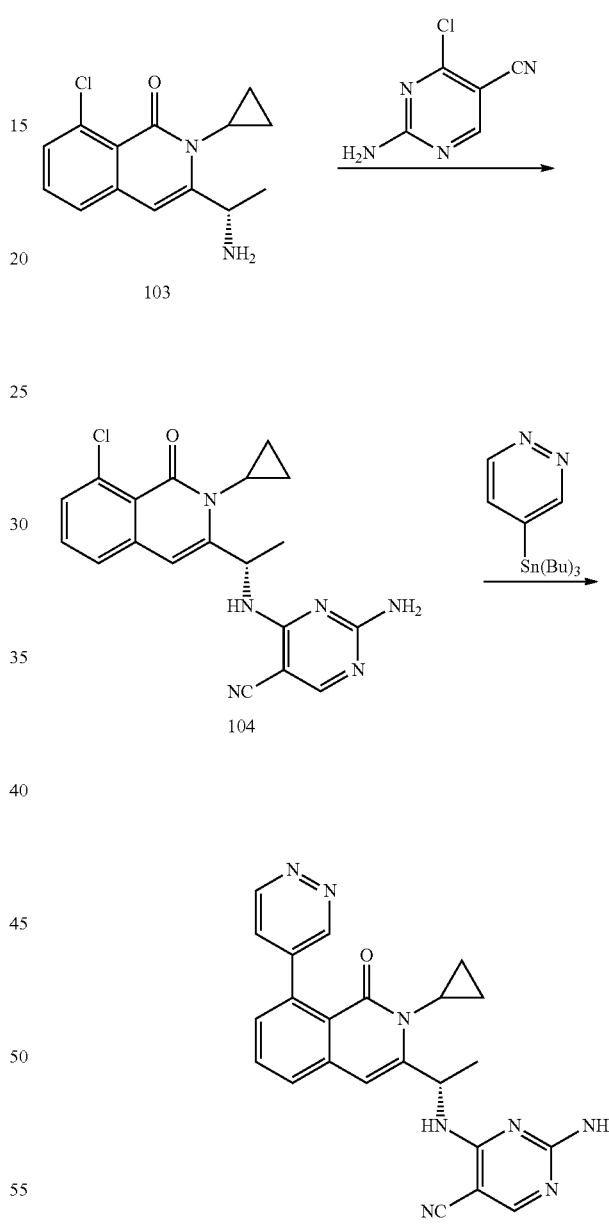

Following Example 59, amine 103 was prepared from commercially available 2-chloro-6-methylbenzoic acid according to Method A. Compound 103 was then coupled to 2-amino-4-chloropyrimidine-5-carbonitrile (E-2) according to Method G to afford compound 104. Compound 440 was prepared from compound 104 using 4-(tributylstannyl)pyridazine according to method I. ESI-MS m/z: 425.2 [M+H]$^+$.

Example 256

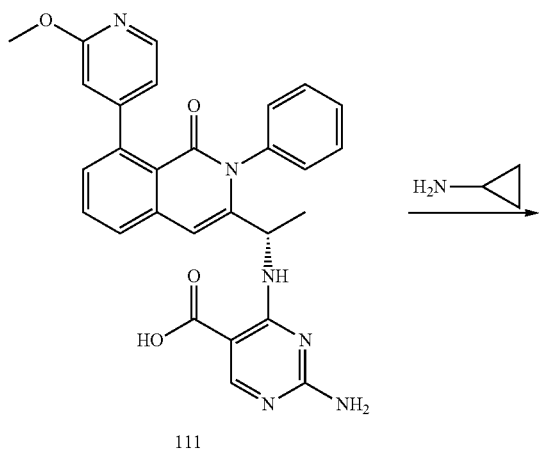

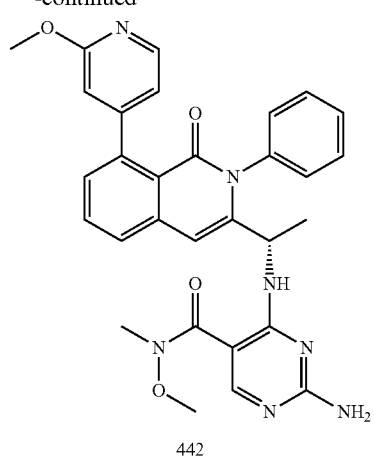

Compound 441 was prepared from compound III according to Example 73, where cyclopropylamine was used instead of dimethylamine. ESI-MS m/z: 545.8 [M+H]$^+$.

Example 257

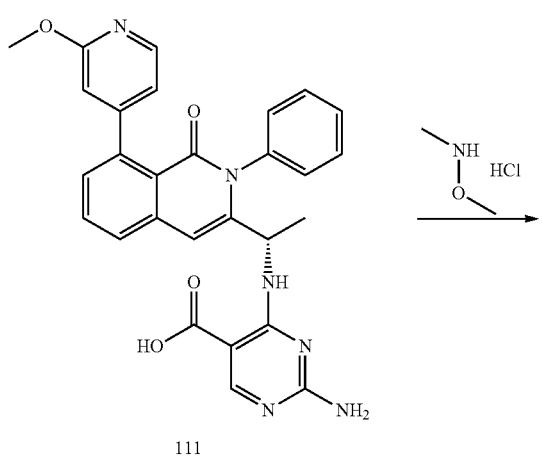

Compound 442 was prepared from compound III according to Example 73, where N,O-dimethylhydroxylamine was used instead of dimethylamine. ESI-MS m/z: 552.1 [M+H]$^+$.

Example 258

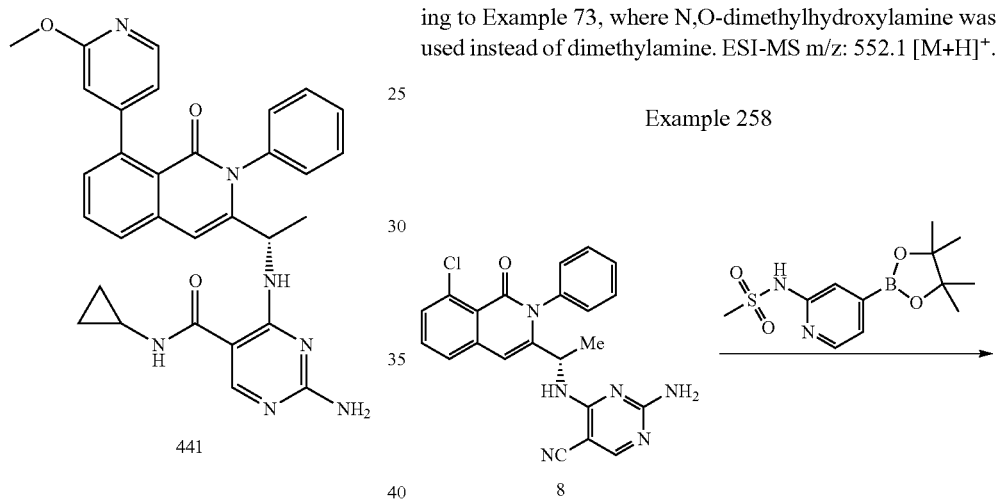

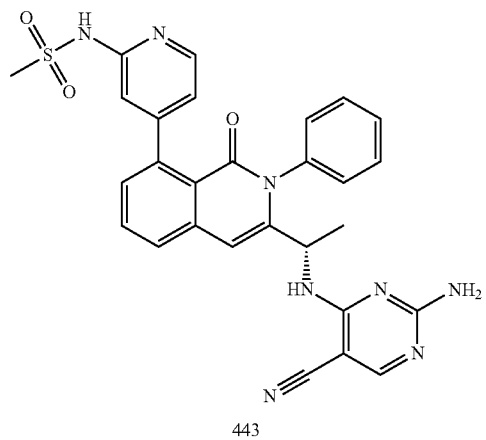

Compound 443 was prepared from compound 8 using N-(4-(4,4,5,5-tetramethyl-1,3,2-dioxaborolan-2-yl)pyridin-2-yl)methanesulfonamide according to Method J. ESI-MS m/z: 553.3 [M+H]$^+$.

TABLE 4

In Vitro IC$_{50}$ data for selected compounds.

| IC50 (nM) | Greater than 10 µM | Greater than 1 µM to 10 µM | 1 µM to 100 nM | Less than 100 nM |
|---|---|---|---|---|
| PI3K δ | 92, 111, 171, 173, 243 | 77, 82, 85, 104, 114, 119, 148, 154, 155, 175, 182, 191, 211, 220, 228, 270, 279, 291, 338, 354, 401, 402, 425, 429, 433, 434, 441 | 75, 78, 122, 128, 132, 133, 157, 168, 179, 204, 210, 214, 246, 258, 261, 273, 276, 288, 312, 316, 333, 335, 336, 337, 353, 366, 368, 375, 376, 378, 379, 383, 397, 408, 414, 416, 418, 422, 424, 428, 430, 432, 435, 436, 442 | 5, 8, 9, 10, 11, 12, 13, 15, 16, 18, 20, 22, 23, 24, 25, 26, 27, 28, 30, 31, 32, 33, 34, 35, 36, 37, 38, 39, 40, 41, 42, 43, 44, 45, 46, 47, 48, 49, 50, 51, 52, 53, 55, 57, 59, 60, 61, 62, 63, 65, 66, 68, 70, 72, 74, 76, 89, 91, 94, 96, 98, 100, 102, 105, 106, 107, 108, 112, 113, 115, 116, 124, 125, 126, 127, 129, 130, 136, 138, 140, 145, 151, 152, 153, 156, 159, 161, 163, 164, 165, 166, 167, 169, 177, 181, 183, 185, 187, 189, 192, 193, 196, 199, 203, 205, 206, 207, 217, 222, 223, 224, 226, 230, 231, 232, 233, 234, 235, 241, 242, 249, 252, 255, 264, 267, 282, 285, 297, 300, 303, 306, 309, 325, 326, 327, 328, 329, 332, 334, 356, 359, 360, 361, 364, 365, 367, 369, 370, 371, 372, 373, 374, 380, 382, 387, 389, 391, 393, 394, 396, 399, 403, 410, 412, 413, 415, 417, 419, 431, 440, 443 |
| PI3K γ | 92, 111, 128, 171, 243, 336, 354, 416, 429 | 75, 77, 78, 114, 119, 173, 175, 182, 211, 316, 328, 333, 334, 337, 353, 425, 434, 441 | 12, 30, 31, 57, 82, 85, 105, 122, 127, 133, 148, 155, 161, 205, 210, 220, 226, 228, 241, 242, 246, 276, 279, 285, 303, 312, 326, 327, 329, 335, 338, 356, 359, 366, 380, 396, 401, 402, 422, 424, 428, 430, 432, 435, 440 | 5, 8, 9, 10, 11, 13, 15, 16, 18, 20, 22, 23, 24, 25, 26, 27, 28, 32, 33, 34, 35, 36, 37, 38, 39, 40, 41, 42, 43, 44, 45, 46, 47, 48, 49, 50, 51, 52, 53, 55, 59, 60, 61, 62, 63, 65, 66, 68, 70, 72, 74, 76, 89, 91, 94, 96, 98, 100, 102, 104, 106, 107, 108, 112, 113, 115, 116, 124, 125, 126, 129, 130, 132, 136, 138, 140, 145, 151, 152, 153, 154, 156, 157, 159, 163, 164, 165, 166, 167, 168, 169, 177, 179, 181, 183, 185, 187, 189, 191, 192, 193, 196, 199, 203, 204, 206, 207, 214, 217, 222, 223, 224, 230, 231, 232, 233, 234, 235, 249, 252, 255, 258, 261, 264, 267, 270, 273, 282, 288, 291, 297, 300, 306, 309, 325, 332, 360, 361, 364, 365, 367, 368, 369, 370, 371, 372, 373, 374, 375, 376, 378, 379, |

TABLE 4-continued

In Vitro IC$_{50}$ data for selected compounds.

| IC50 (nM) | Greater than 10 μM | Greater than 1 μM to 10 μM | 1 μM to 100 nM | Less than 100 nM |
|---|---|---|---|---|
| | | | | 382, 383, 387, 389, 391, 393, 394, 397, 399, 403, 408, 410, 412, 413, 414, 415, 417, 418, 419, 431, 433, 436, 442, 443 |
| PI3K α | 11, 12, 16, 22, 30, 31, 60, 63, 75, 77, 78, 76, 82, 85, 92, 104, 111, 114, 119, 122, 124, 128, 130, 132, 145, 148, 151, 154, 155, 159, 161, 163, 166, 168, 171, 173, 175, 179, 182, 204, 205, 210, 211, 214, 220, 226, 228, 242, 243, 246, 252, 258, 261, 270, 273, 276, 279, 282, 288, 291, 297, 303, 306, 312, 328, 333, 334, 335, 336, 353, 354, 356, 366, 367, 368, 372, 373, 375, 376, 378, 379, 380, 382, 387, 391, 393, 402, 403, 410, 412, 419, 429, 430, 432, 433, 434, 435, 436, 440, 441, 442 | 5, 8, 13, 15, 18, 20, 24, 32, 33, 35, 38, 41, 42, 43, 44, 45, 51, 52, 55, 57, 59, 61, 62, 65, 66, 68, 70, 72, 74, 91, 94, 98, 102, 105, 108, 116, 125, 126, 127, 133, 136, 138, 152, 156, 164, 165, 167, 169, 177, 183, 185, 187, 189, 191, 196, 199, 203, 206, 207, 217, 222, 224, 230, 231, 232, 234, 241, 249, 255, 264, 267, 285, 300, 309, 316, 325, 326, 327, 329, 332, 337, 338, 359, 360, 361, 365, 369, 371, 383, 389, 396, 397, 399, 401, 408, 414, 416, 417, 418, 422, 424, 425, 428, 443 | 9, 10, 23, 25, 26, 27, 28, 34, 37, 39, 40, 46, 47, 48, 49, 65, 96, 100, 106, 107, 112, 113, 115, 129, 140, 153, 157, 181, 193, 223, 233, 235, 374, 394, 413, 415, 431 | 13, 36, 50, 53, 89, 192, 364, 370 |
| PI3K β | 5, 11, 12, 20, 22, 31, 41, 55, 57, 60, 63, 75, 77, 78, 82, 85, 92, 96, 111, 112, 114, 119, 122, 127, 128, 130, 132, 133, 148, 151, 152, 154, 155, 156, 159, 161, 163, 164, 165, 169, 171, 173, 175, 177, 179, 182, 185, 203, 204, 205, 206, 211, 226, 228, 231, 242, 243, 273, 312, 316, 327, 328, 333, 334, 335, 336, 337, 353, 354, 356, 378, 379, 380, 383, 387, 391, 393, 414, 422, 424, 425, 429, 430, 432, 433, 434, 435, 441, 442 | 10, 13, 16, 23, 24, 26, 27, 28, 30, 32, 34, 35, 36, 37, 38, 40, 42, 43, 44, 45, 46, 48, 49, 51, 52, 53, 61, 62, 66, 68, 70, 74, 94, 98, 100, 102, 104, 105, 115, 116, 124, 125, 126, 138, 140, 145, 153, 166, 167, 168, 181, 183, 187, 189, 191, 192, 196, 207, 210, 214, 220, 224, 230, 232, 233, 234, 235, 241, 246, 252, 258, 261, 270, 279, 282, 288, 291, 300, 303, 326, 329, 338, 359, 366, 367, 368, 373, 375, 376, 382, 389, 396, 397, 399, 401, 402, 403, 408, 412, 417, 428, 436, 443 | 9, 15, 18, 25, 33, 39, 47, 50, 59, 72, 76, 91, 99, 106, 108, 113, 136, 157, 193, 199, 217, 222, 255, 264, 267, 276, 285, 297, 306, 332, 360, 361, 364, 365, 371, 372, 374, 410, 413, 415, 416, 418, 419, 440 | 8, 89, 107, 129, 223, 249, 309, 325, 369, 370, 394, 431 |
| B cell proliferation EC50 (nM) | | 82, 204, 211, 441 | 92, 161, 163, 246, 252, 432 | 5, 8, 9, 10, 12, 13, 15, 16, 18, 20, 22, 23, 24, 25, 26, 27, 28, 30, 31, 41, 42, 43, 44, 45, 47, 48, 49, 50, 51, 52, 55, 57, 59, 60, 61, 62, 63, 66, 72, 74, 79, 89, 91, 94, 96, 98, 100, 102, 105, 106, 107, 108, 112, 115, 116, 124, 125, 126, 129, 130, 136, 140, 151, 152, 153, 156, 159, 164, 165, 166, 167, 169, 177, 181, 183, 185, 187, 189, 192, 193, 196, 199, 203, 206, 207, 217, 222, 223, 224, 230, |

TABLE 4-continued

In Vitro IC$_{50}$ data for selected compounds.

| IC50 (nM) | Greater than 10 μM | Greater than 1 μM to 10 μM | 1 μM to 100 nM | Less than 100 nM |
|---|---|---|---|---|
| | | | | 231, 232, 233, 234, 249, 297, 300, 306, 309, 325, 332, 360, 361, 365, 367, 369, 371, 372, 380, 431, 440, 443 |

TABLE 5

Structures of the Compounds for the IC$_{50}$ results described in Table 4 above and other exemplary compounds.

Structure

Compound 5

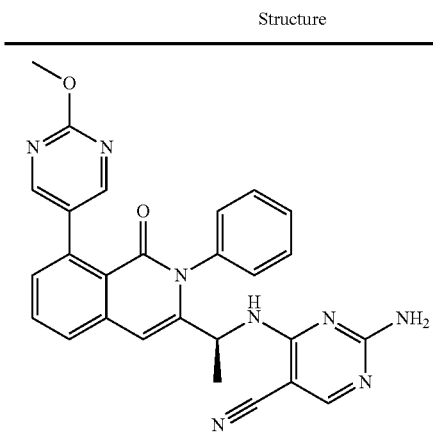

Compound 8

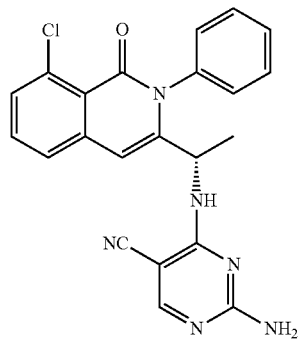 [SMILES: C[C@H](Nc1nc(N)ncc1C#N)c1cc2cccc(Cl)c2c(=O)n1-c1ccccc1]

Compound 9

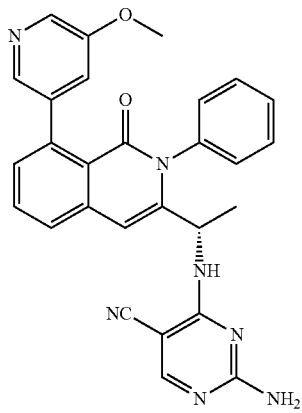 [SMILES: COc1cncc(-c2cccc3cc([C@H](C)Nc4nc(N)ncc4C#N)n(-c4ccccc4)c(=O)c23)c1]

TABLE 5-continued

Structures of the Compounds for the IC$_{50}$ results described in Table 4 above and other exemplary compounds.

Structure

Compound 10

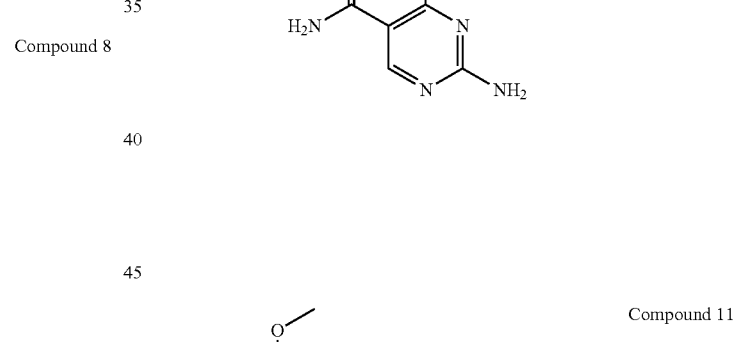

Compound 11

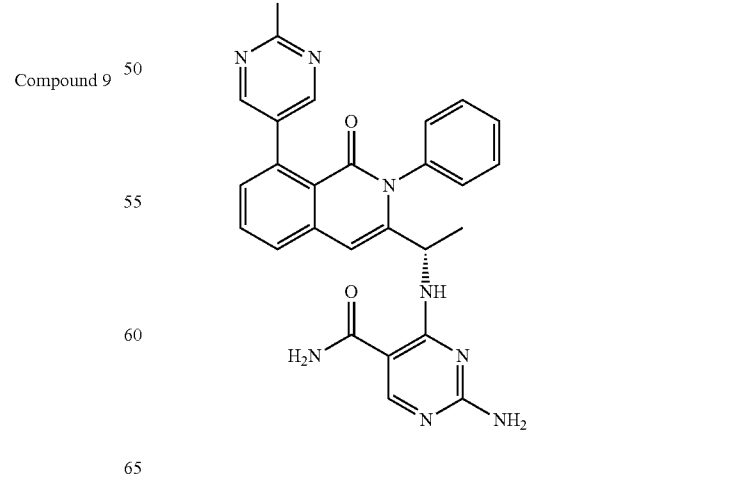

TABLE 5-continued

Structures of the Compounds for the IC$_{50}$ results described in Table 4 above and other exemplary compounds.

| Structure |
| --- |

Compound 12

Compound 13

Compound 15

Compound 16

TABLE 5-continued

Structures of the Compounds for the IC$_{50}$ results described in Table 4 above and other exemplary compounds.

| Structure |
| --- |

Compound 18

Compound 20

Compound 22

TABLE 5-continued
Structures of the Compounds for the IC$_{50}$ results described in Table 4 above and other exemplary compounds.
Structure
Compound 23
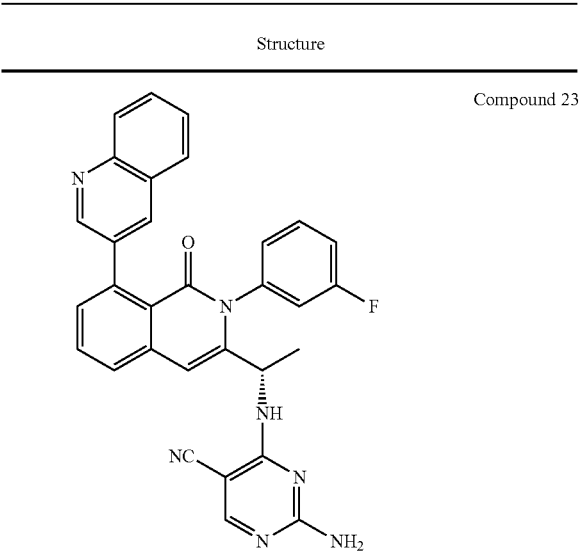
Compound 24
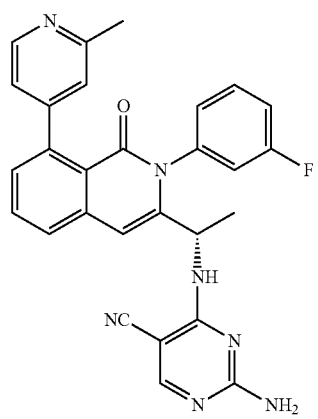 [SMILES: Cc1cc(-c2cccc3cc([C@H](C)Nc4nc(N)ncc4C#N)n(-c4cccc(F)c4)c(=O)c23)ccn1]
Compound 25
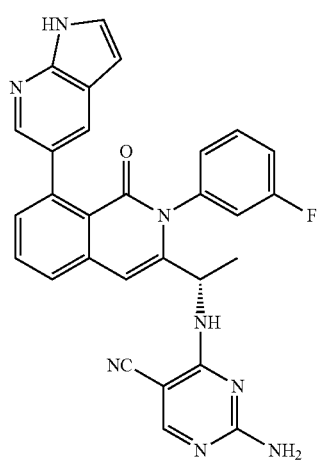 [SMILES: C[C@H](Nc1nc(N)ncc1C#N)c1cc2cccc(-c3cnc4[nH]ccc4c3)c2c(=O)n1-c1cccc(F)c1]
TABLE 5-continued
Structures of the Compounds for the IC$_{50}$ results described in Table 4 above and other exemplary compounds.
Structure
Compound 26
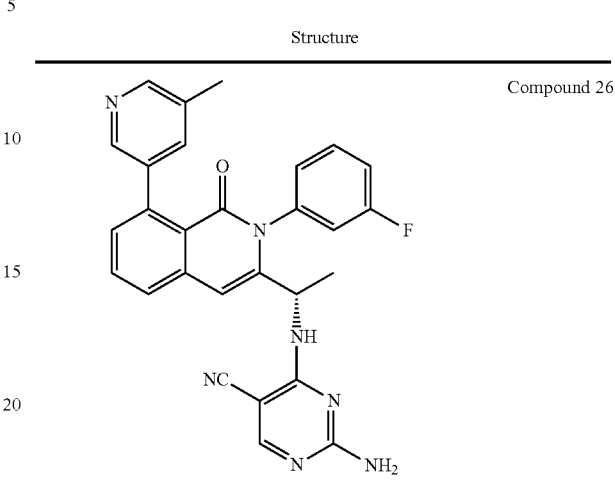
Compound 27
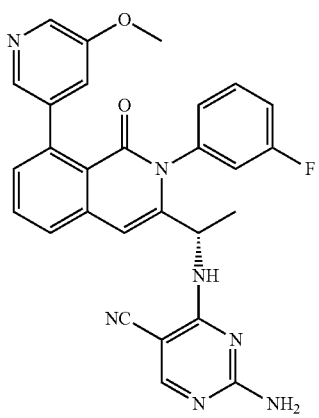 [SMILES: COc1cncc(-c2cccc3cc([C@H](C)Nc4nc(N)ncc4C#N)n(-c4cccc(F)c4)c(=O)c23)c1]
Compound 28
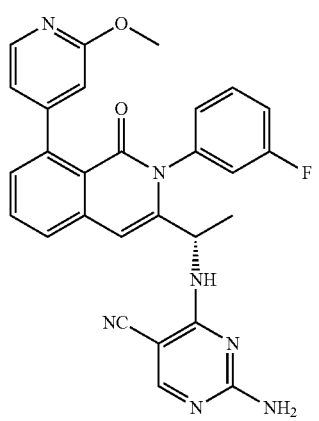 [SMILES: COc1cc(-c2cccc3cc([C@H](C)Nc4nc(N)ncc4C#N)n(-c4cccc(F)c4)c(=O)c23)ccn1]

TABLE 5-continued
Structures of the Compounds for the IC$_{50}$ results described in Table 4 above and other exemplary compounds.
Structure
Compound 30
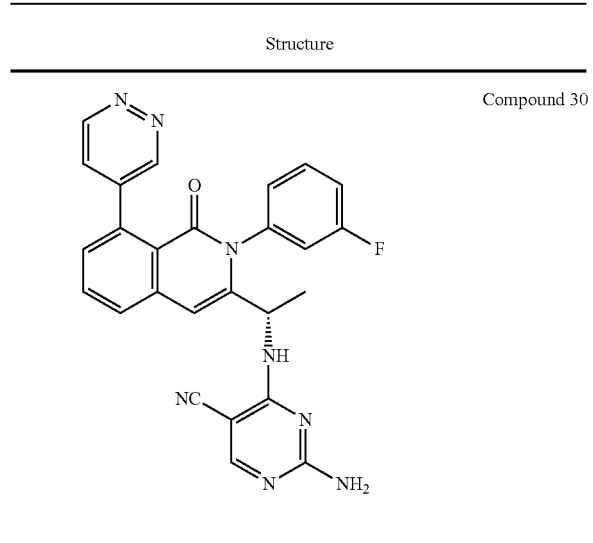
Compound 31
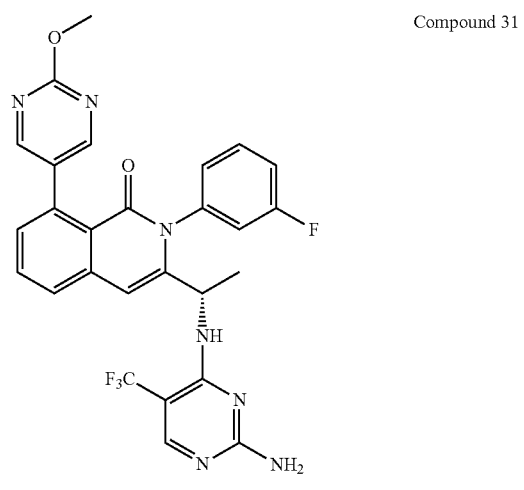
Compound 32
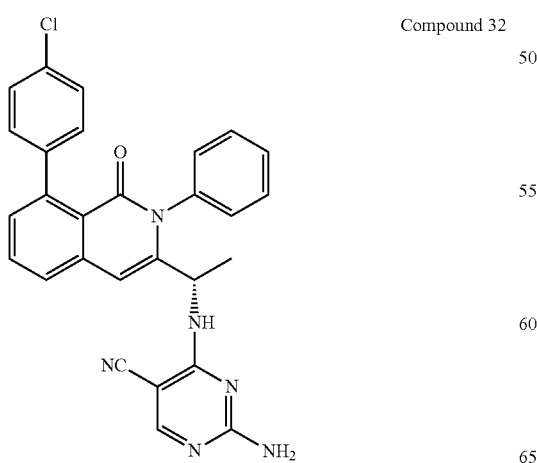
TABLE 5-continued
Structures of the Compounds for the IC$_{50}$ results described in Table 4 above and other exemplary compounds.
Structure
Compound 33
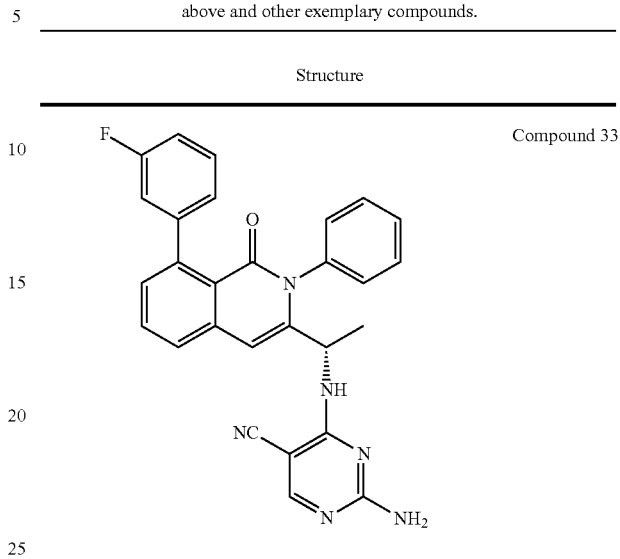
Compound 34
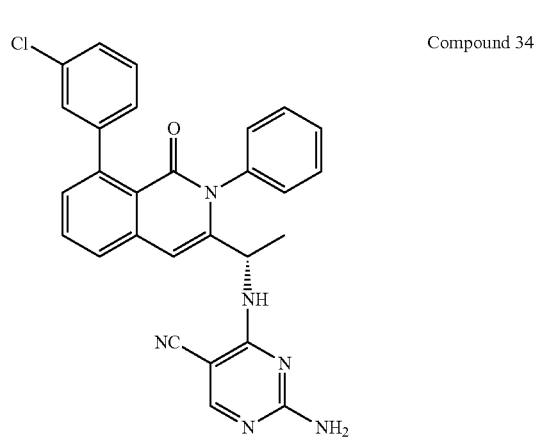
Compound 35
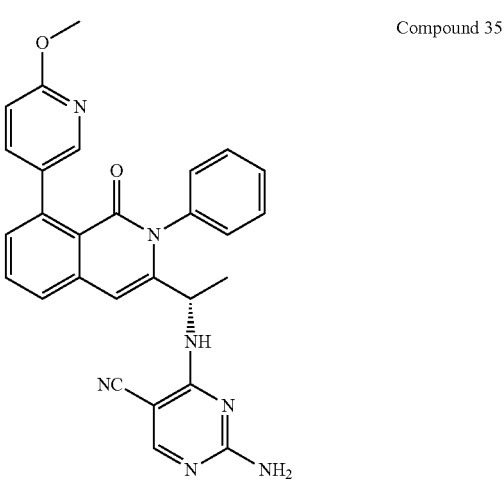

TABLE 5-continued
Structures of the Compounds for the $IC_{50}$ results described in Table 4 above and other exemplary compounds.
Structure
Compound 36
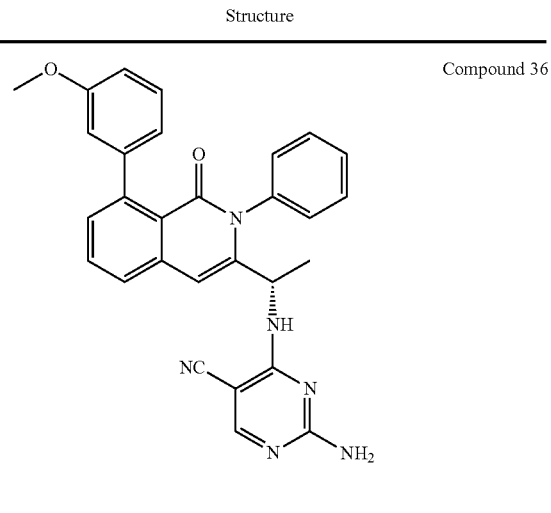
Compound 37
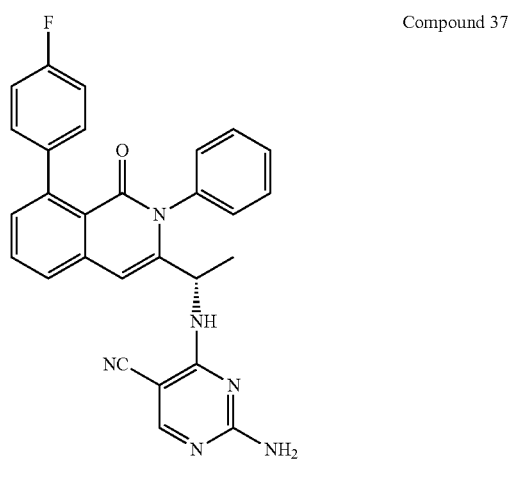
Compound 38
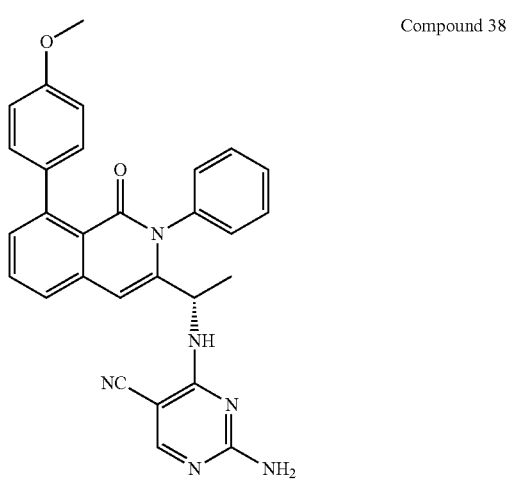
TABLE 5-continued
Structures of the Compounds for the $IC_{50}$ results described in Table 4 above and other exemplary compounds.
Structure
Compound 39
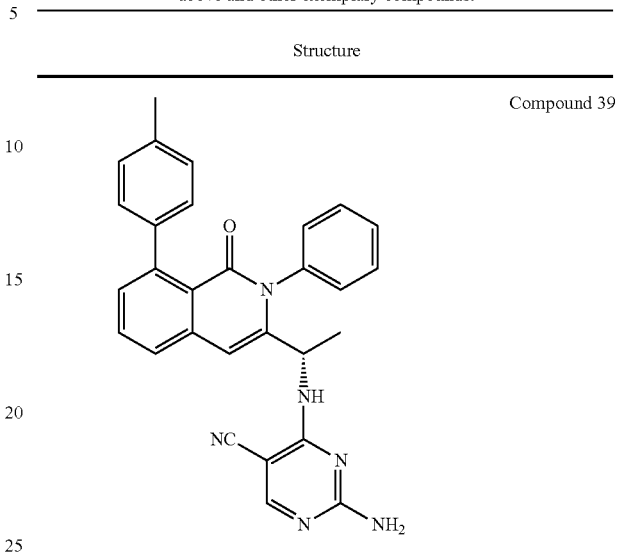
Compound 40
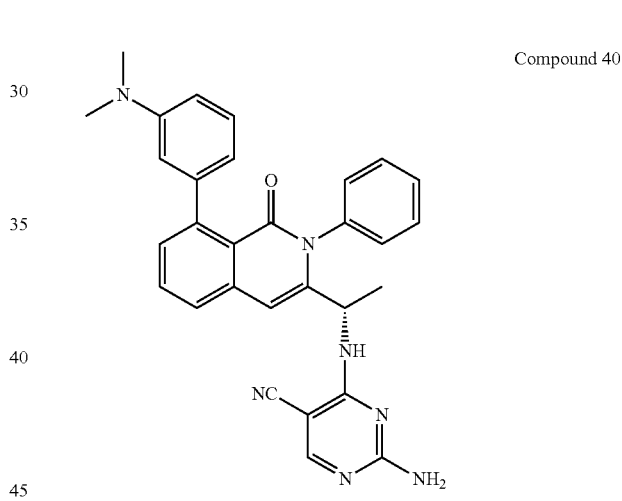
Compound 41
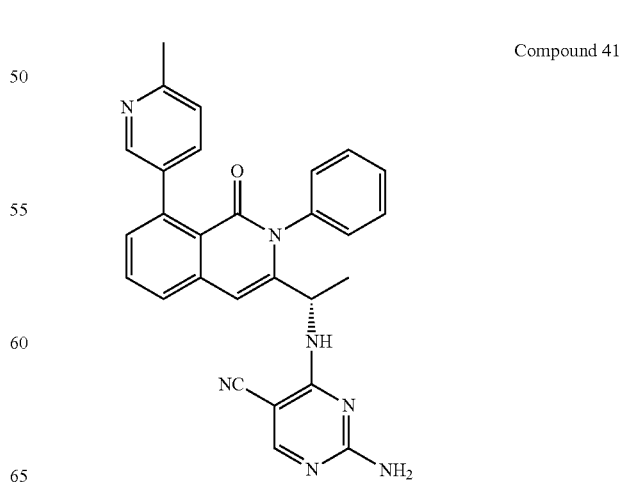

TABLE 5-continued
Structures of the Compounds for the IC$_{50}$ results described in Table 4 above and other exemplary compounds.
Structure
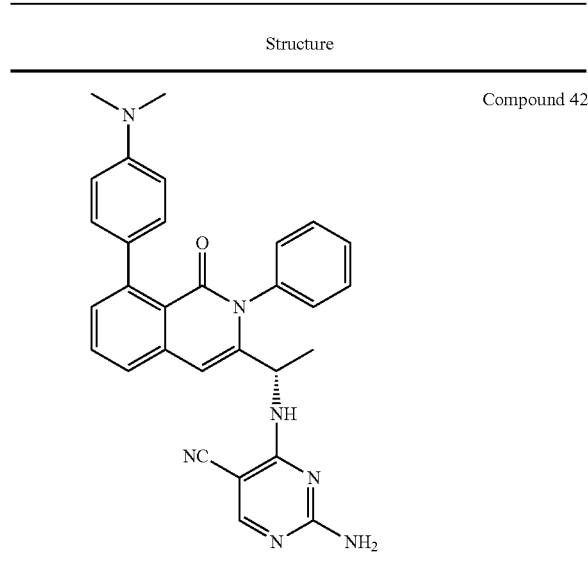
Compound 42
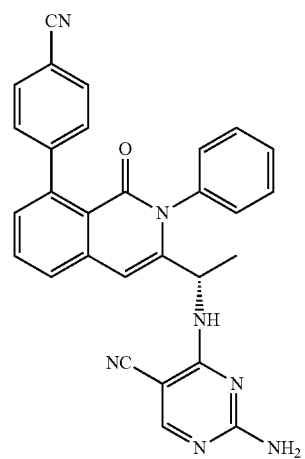 [SMILES: C[C@H](Nc1nc(N)ncc1C#N)c1cc2cccc(-c3ccc(Cl)cc3)c2c(=O)n1-c1ccccc1]
Compound 43
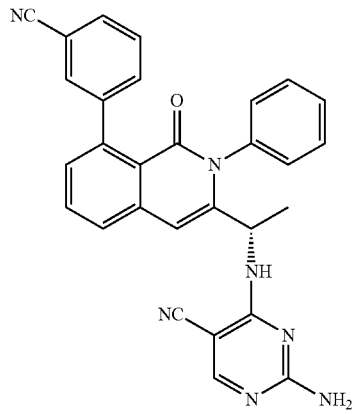 [SMILES: C[C@H](Nc1nc(N)ncc1C#N)c1cc2cccc(-c3cccc(C#N)c3)c2c(=O)n1-c1ccccc1]
Compound 44
TABLE 5-continued
Structures of the Compounds for the IC$_{50}$ results described in Table 4 above and other exemplary compounds.
Structure
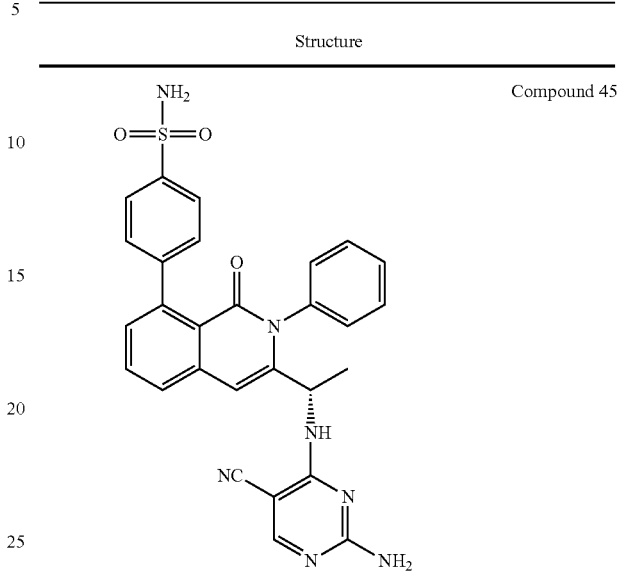
Compound 45
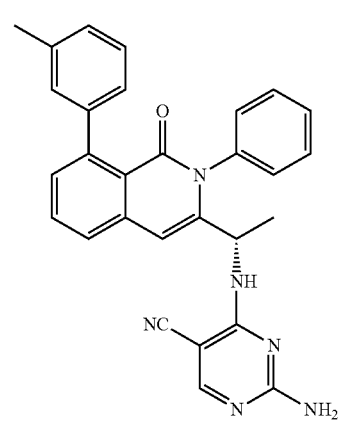 [SMILES: Cc1cccc(-c2cccc3cc([C@H](C)Nc4nc(N)ncc4C#N)n(-c4ccccc4)c(=O)c23)c1]
Compound 46
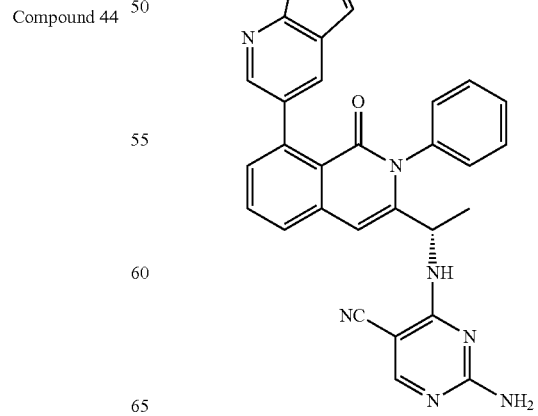
Compound 47

TABLE 5-continued
Structures of the Compounds for the IC$_{50}$ results described in Table 4 above and other exemplary compounds.
Structure
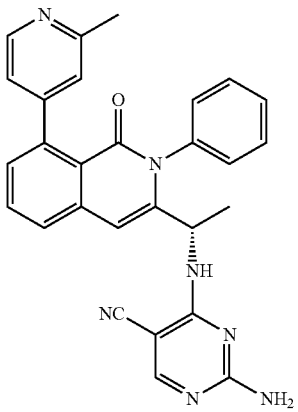 [SMILES: Cc1cc(-c2cccc3cc([C@H](C)Nc4nc(N)ncc4C#N)n(-c4ccccc4)c(=O)c23)ccn1]
Compound 48
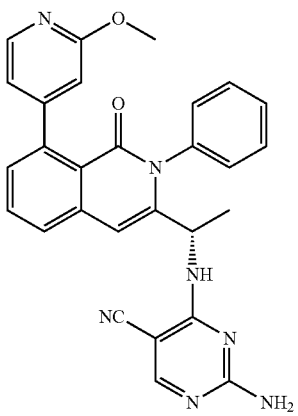 [SMILES: COc1cc(-c2cccc3cc([C@H](C)Nc4nc(N)ncc4C#N)n(-c4ccccc4)c(=O)c23)ccn1]
Compound 49
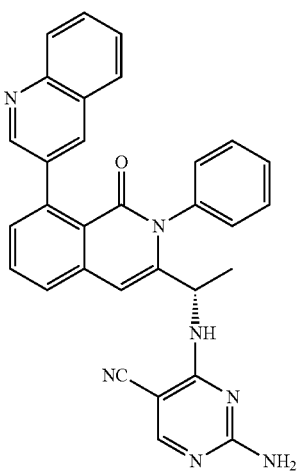 [SMILES: C[C@H](Nc1nc(N)ncc1C#N)c1cc2cccc(-c3cnc4ccccc4c3)c2c(=O)n1-c1ccccc1]
Compound 50
TABLE 5-continued
Structures of the Compounds for the IC$_{50}$ results described in Table 4 above and other exemplary compounds.
Structure
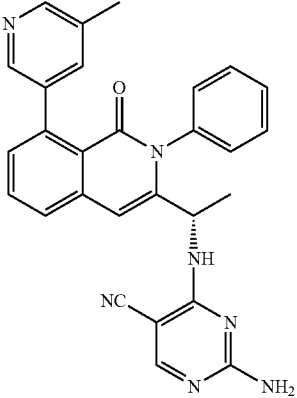 [SMILES: Cc1cncc(-c2cccc3cc([C@H](C)Nc4nc(N)ncc4C#N)n(-c4ccccc4)c(=O)c23)c1]
Compound 51
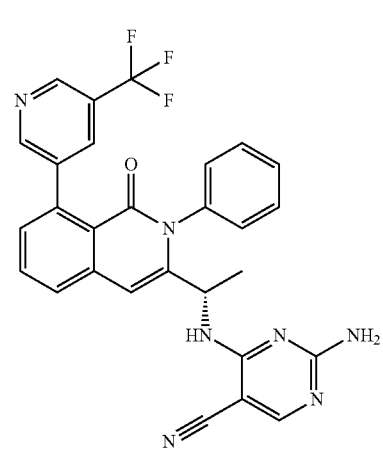 [SMILES: C[C@H](Nc1nc(N)ncc1C#N)c1cc2cccc(-c3cncc(C(F)(F)F)c3)c2c(=O)n1-c1ccccc1]
Compound 52
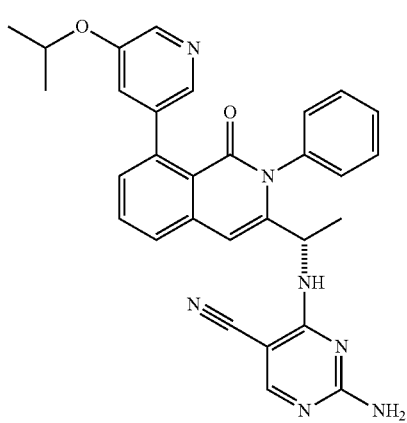 [SMILES: CC(C)Oc1cncc(-c2cccc3cc([C@H](C)Nc4nc(N)ncc4C#N)n(-c4ccccc4)c(=O)c23)c1]
Compound 53

TABLE 5-continued
Structures of the Compounds for the IC$_{50}$ results described in Table 4 above and other exemplary compounds.
Structure
Compound 55
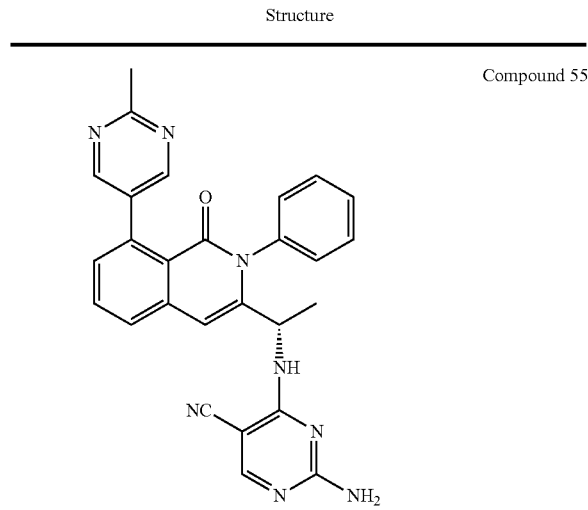
Compound 57
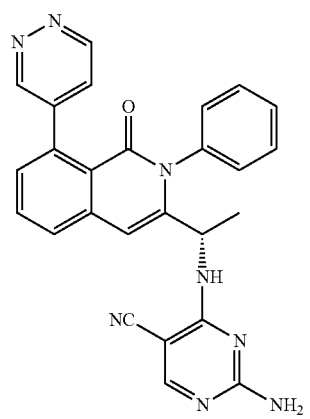 [SMILES: C[C@H](Nc1nc(N)ncc1C#N)c1cc2cccc(-c3ccnnc3)c2c(=O)n1-c1ccccc1]
Compound 59
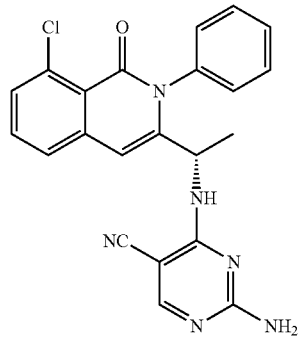 [SMILES: C[C@H](Nc1nc(N)ncc1C#N)c1cc2cccc(Cl)c2c(=O)n1-c1ccccc1]
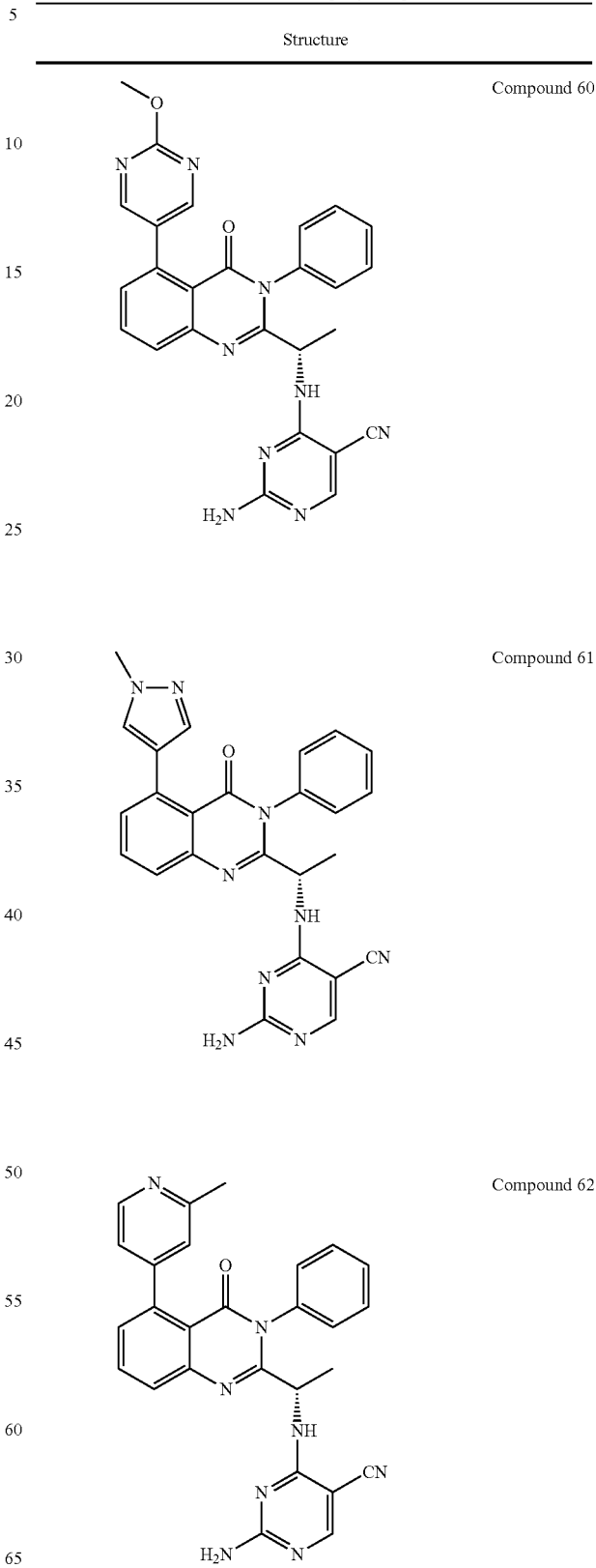

TABLE 5-continued
Structures of the Compounds for the IC$_{50}$ results described in Table 4 above and other exemplary compounds.
Structure
Compound 63
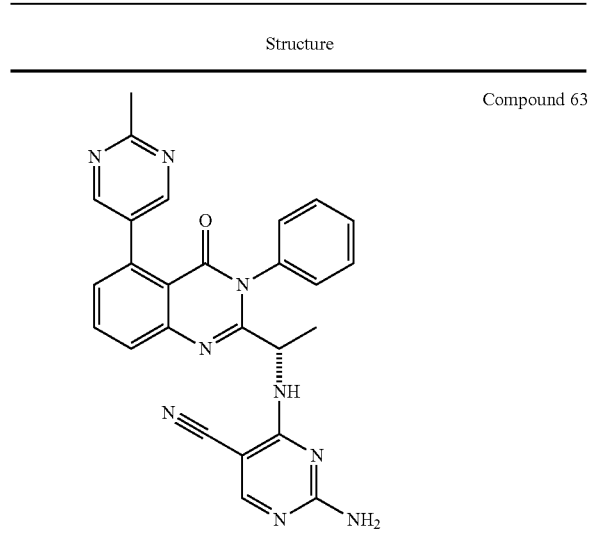
Compound 65
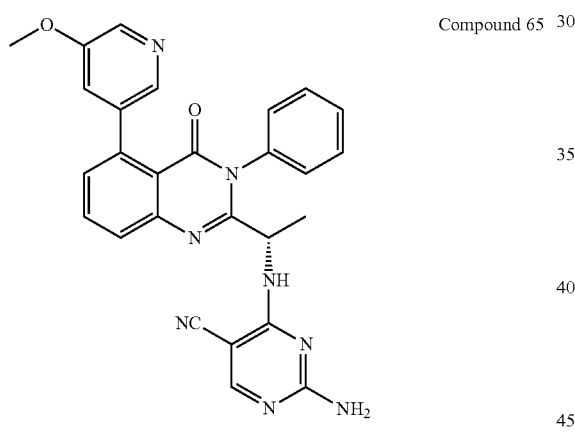
Compound 66
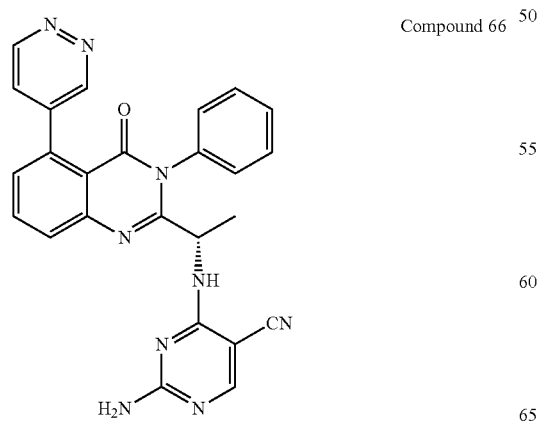
TABLE 5-continued
Structures of the Compounds for the IC$_{50}$ results described in Table 4 above and other exemplary compounds.
Structure
Compound 68
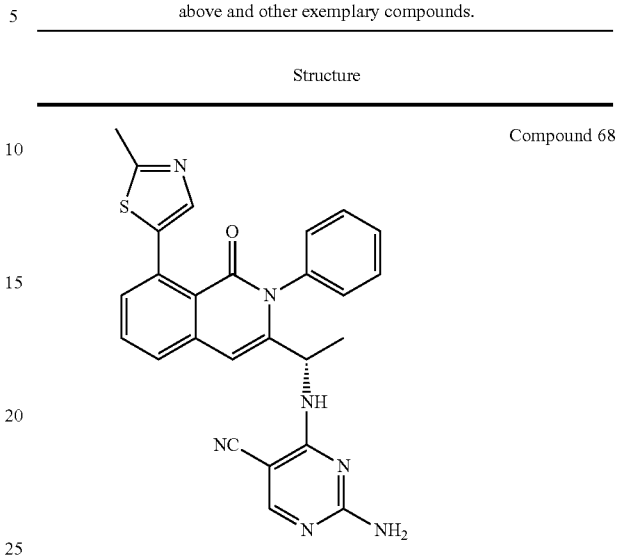
Compound 70
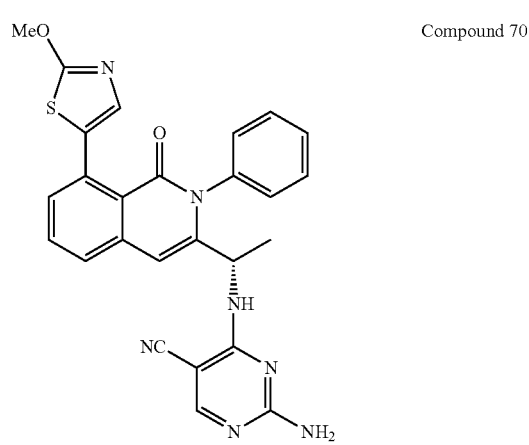
Compound 72
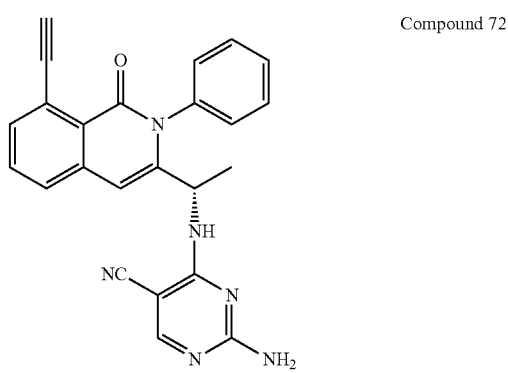

TABLE 5-continued
Structures of the Compounds for the IC$_{50}$ results described in Table 4 above and other exemplary compounds.
Structure
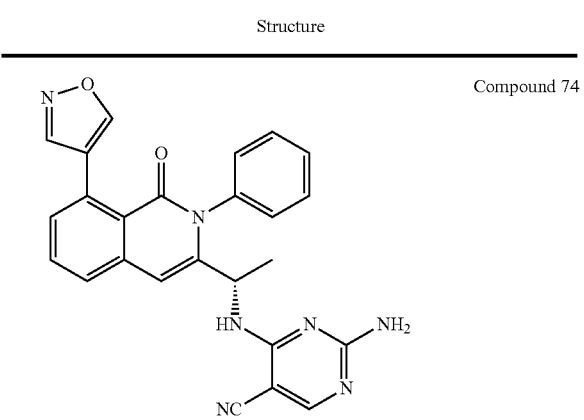
Compound 74
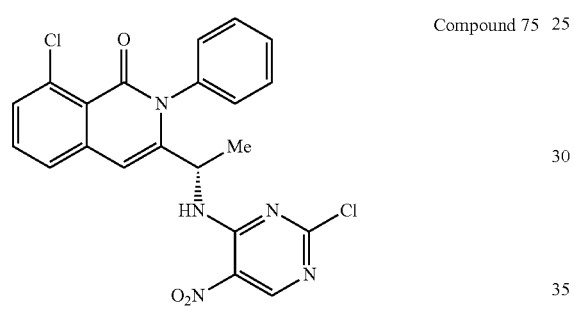
Compound 75
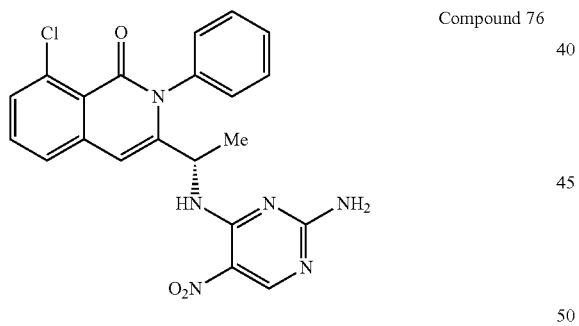
Compound 76
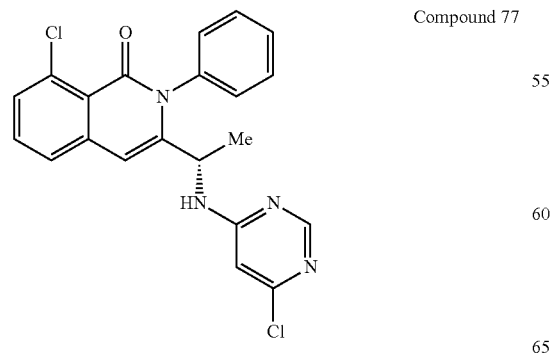
Compound 77
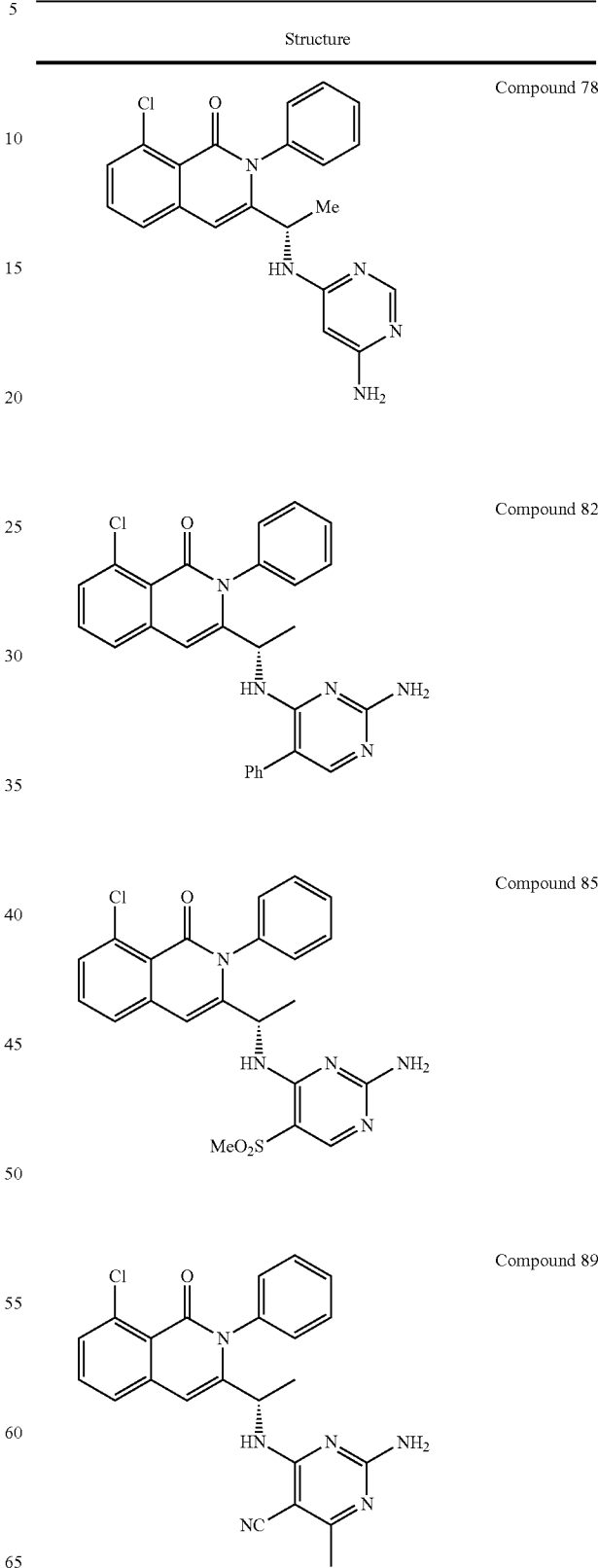
Compound 78
Compound 82
Compound 85
Compound 89

TABLE 5-continued
Structures of the Compounds for the IC$_{50}$ results described in Table 4 above and other exemplary compounds.
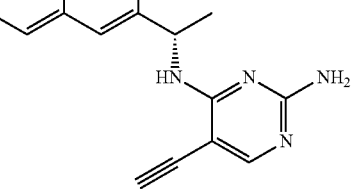
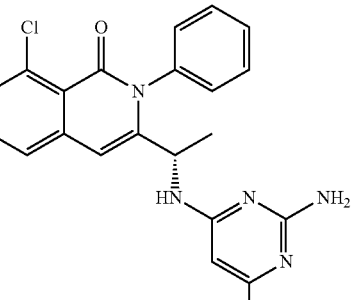
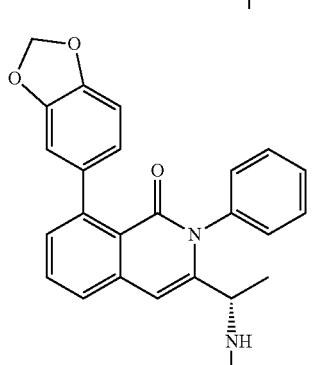
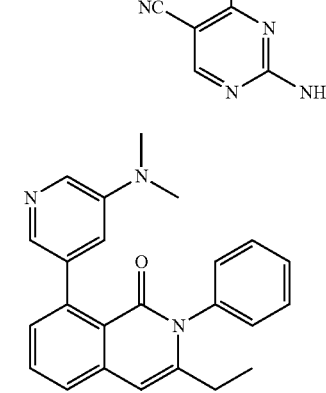

TABLE 5-continued
Structures of the Compounds for the $IC_{50}$ results described in Table 4 above and other exemplary compounds.
Structure
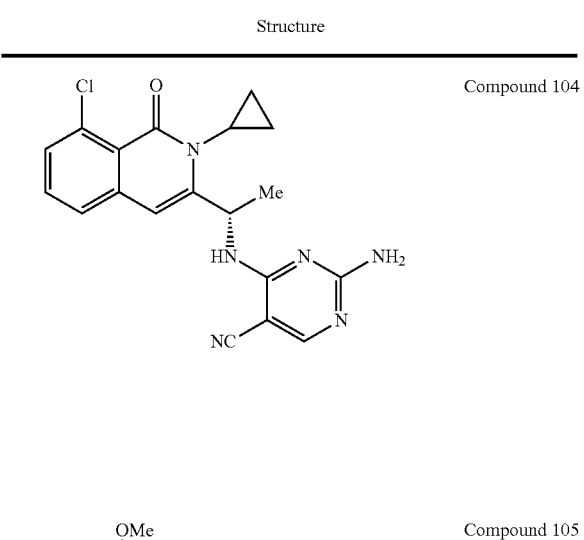
Compound 104
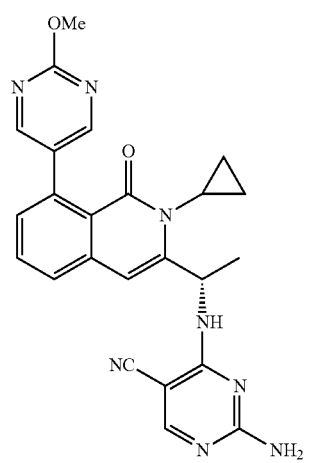 [SMILES: COc1ncc(-c2cccc3cc([C@H](C)Nc4nc(N)ncc4C#N)n(C4CC4)c(=O)c23)cn1]
Compound 105
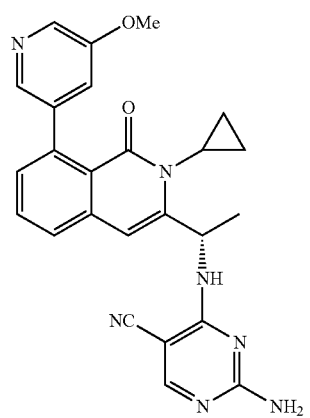 [SMILES: COc1cncc(-c2cccc3cc([C@H](C)Nc4nc(N)ncc4C#N)n(C4CC4)c(=O)c23)c1]
Compound 106
TABLE 5-continued
Structures of the Compounds for the $IC_{50}$ results described in Table 4 above and other exemplary compounds.
Structure
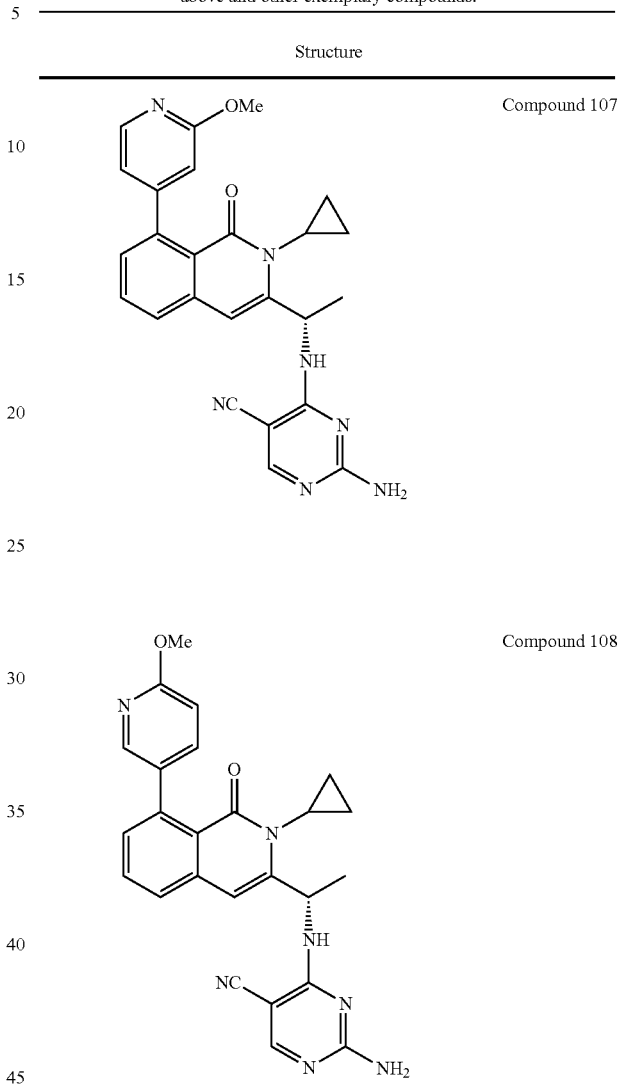
Compound 107
Compound 108
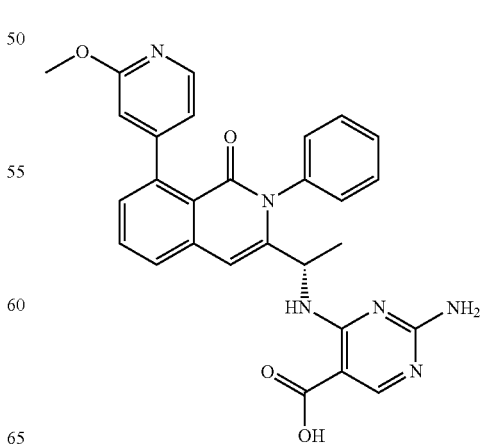
Compound 111

TABLE 5-continued
Structures of the Compounds for the IC$_{50}$ results described in Table 4 above and other exemplary compounds.
Structure
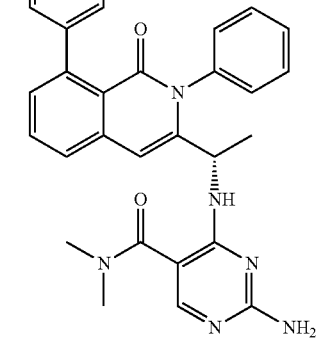
Compound 112
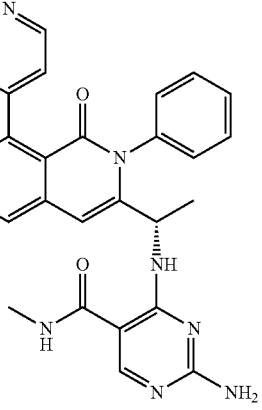
Compound 113
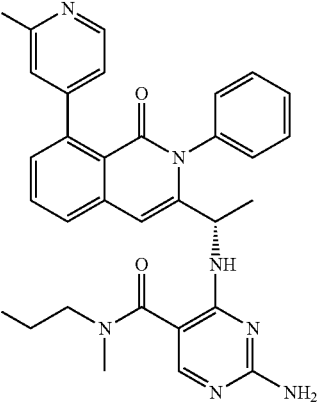
Compound 114
TABLE 5-continued
Structures of the Compounds for the IC$_{50}$ results described in Table 4 above and other exemplary compounds.
Structure
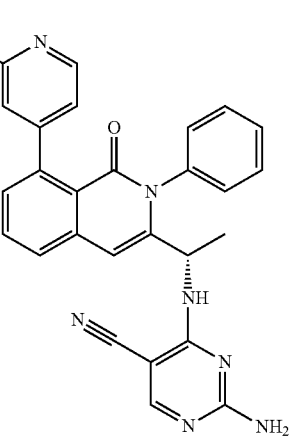
Compound 115
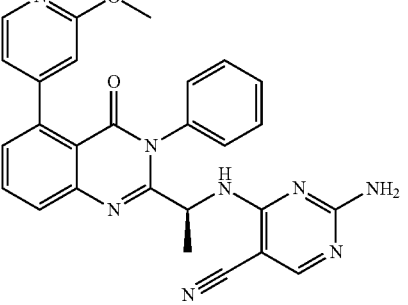
Compound 116
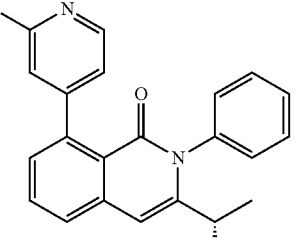
Compound 119
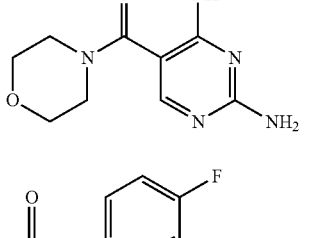
Compound 122

TABLE 5-continued
Structures of the Compounds for the $IC_{50}$ results described in Table 4 above and other exemplary compounds.
Structure
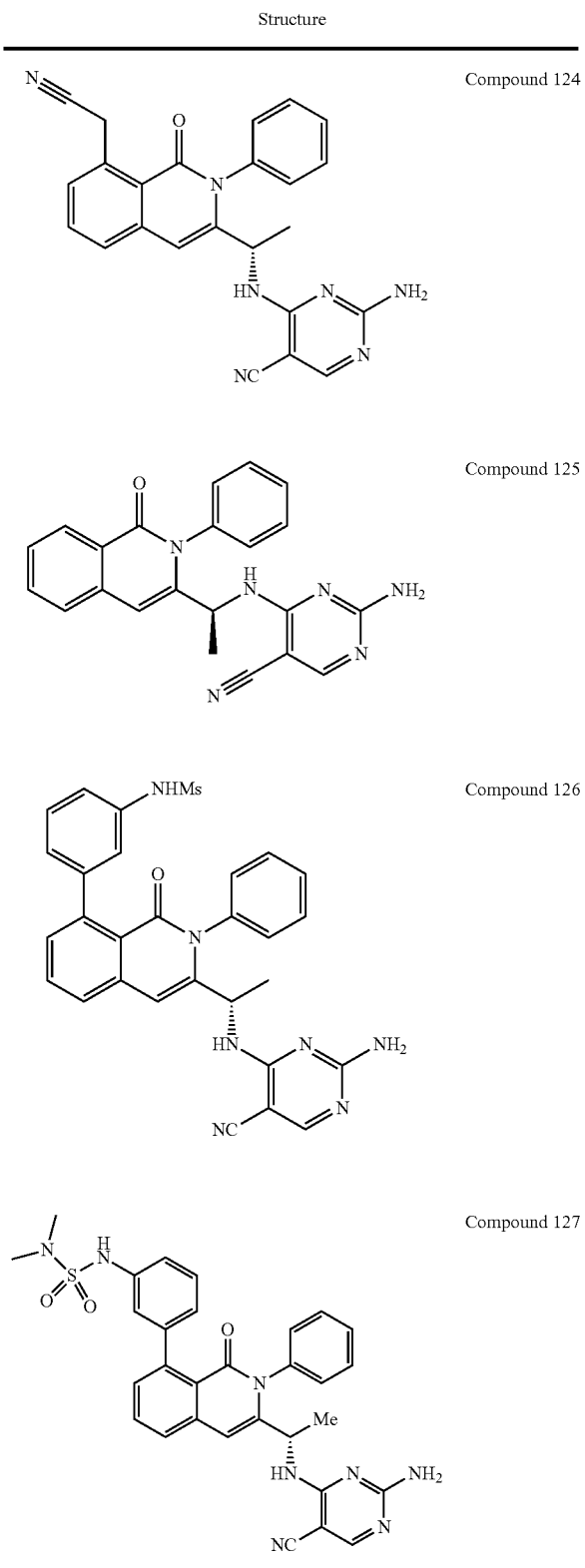
Compound 124
Compound 125
Compound 126
Compound 127
TABLE 5-continued
Structures of the Compounds for the $IC_{50}$ results described in Table 4 above and other exemplary compounds.
Structure
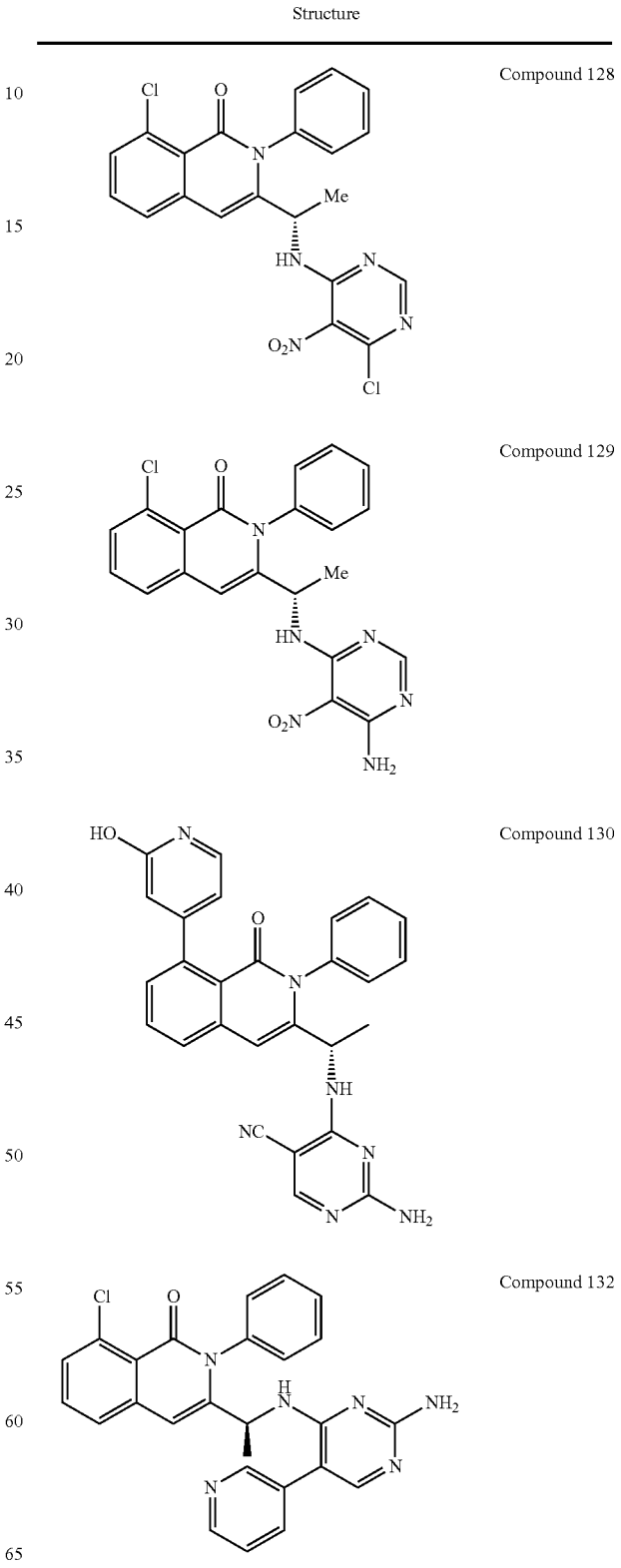
Compound 128
Compound 129
Compound 130
Compound 132

TABLE 5-continued

Structures of the Compounds for the IC$_{50}$ results described in Table 4 above and other exemplary compounds.

Structure

Compound 133

Compound 136

Compound 138

Compound 140

Compound 145

Compound 148

Compound 151

TABLE 5-continued
Structures of the Compounds for the IC$_{50}$ results described in Table 4 above and other exemplary compounds.
Structure
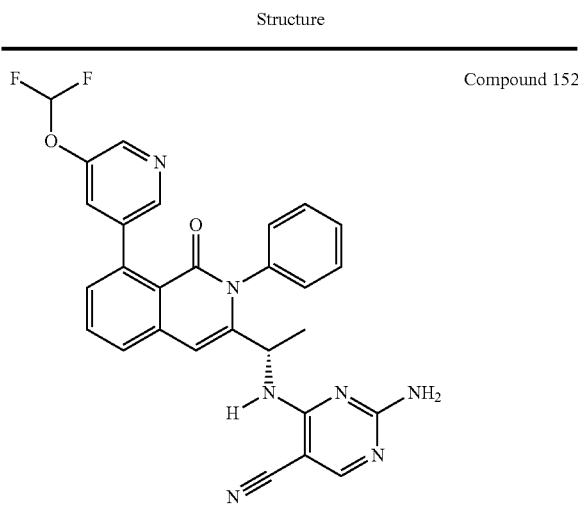
Compound 152
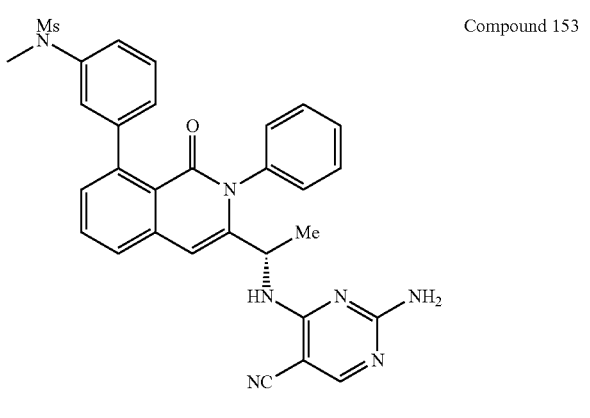
Compound 153
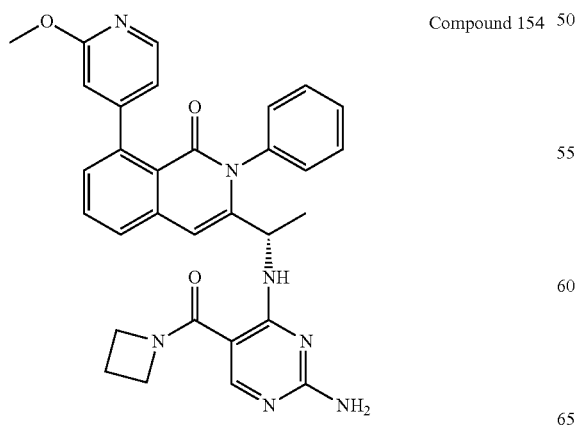
Compound 154
TABLE 5-continued
Structures of the Compounds for the IC$_{50}$ results described in Table 4 above and other exemplary compounds.
Structure
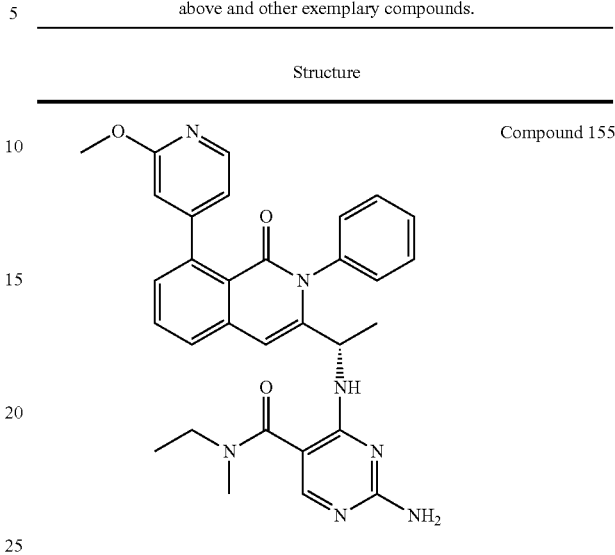
Compound 155
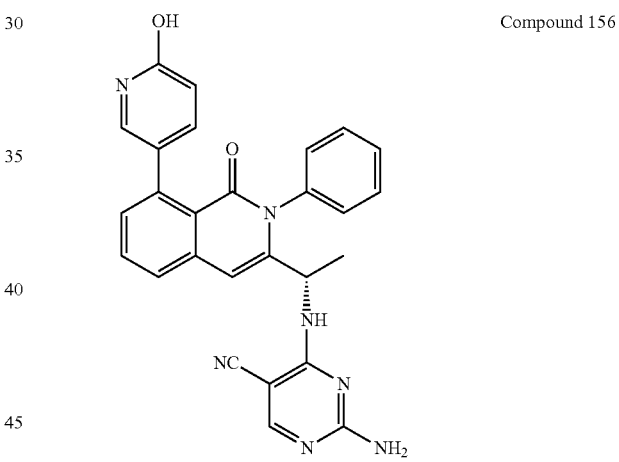
Compound 156
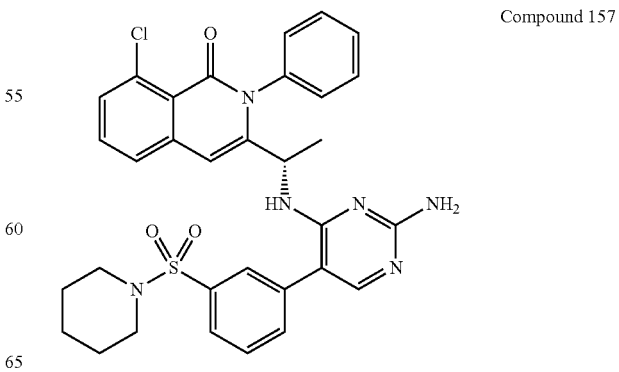
Compound 157

TABLE 5-continued
Structures of the Compounds for the IC$_{50}$ results described in Table 4 above and other exemplary compounds.
Structure
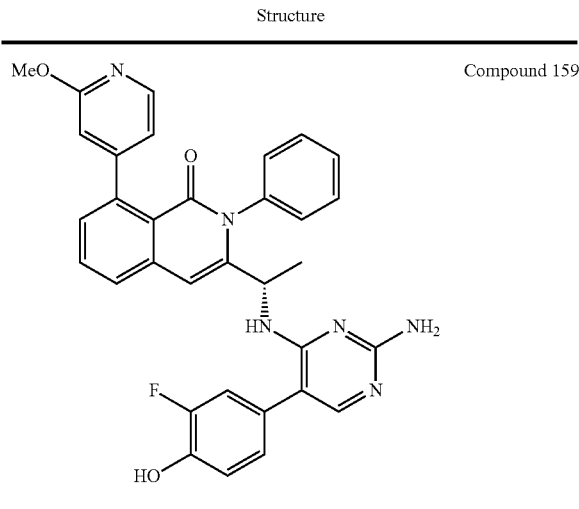
Compound 159
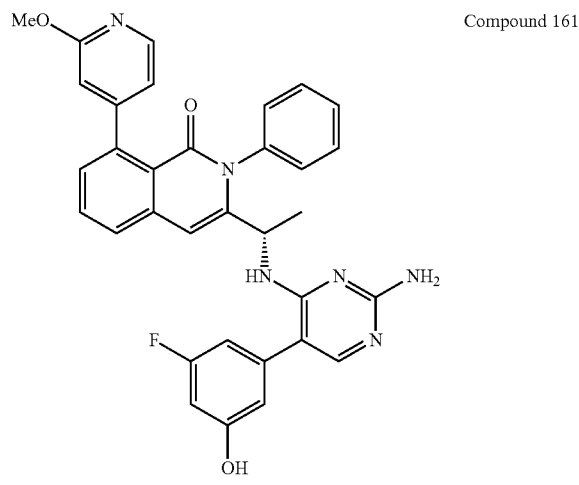
Compound 161
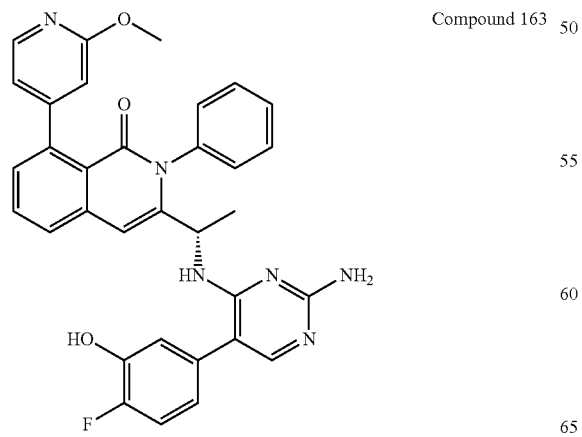
Compound 163
TABLE 5-continued
Structures of the Compounds for the IC$_{50}$ results described in Table 4 above and other exemplary compounds.
Structure
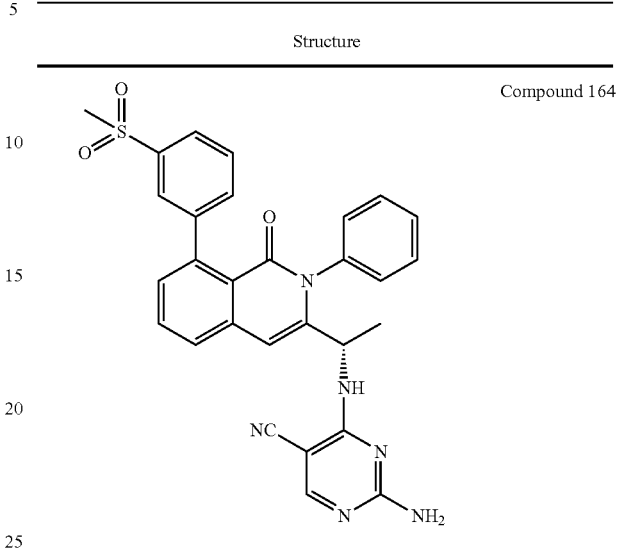
Compound 164
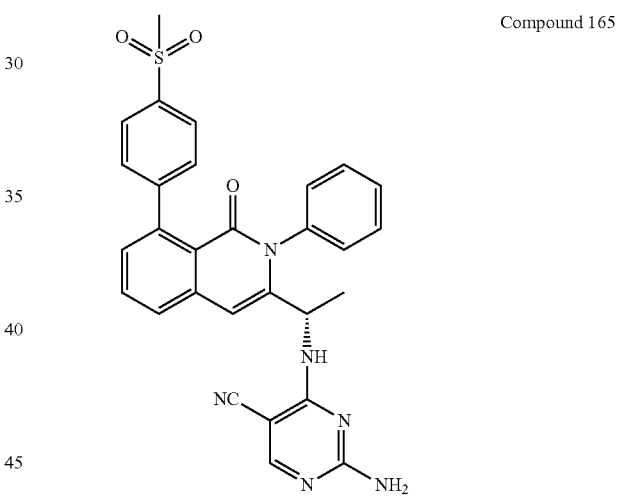
Compound 165
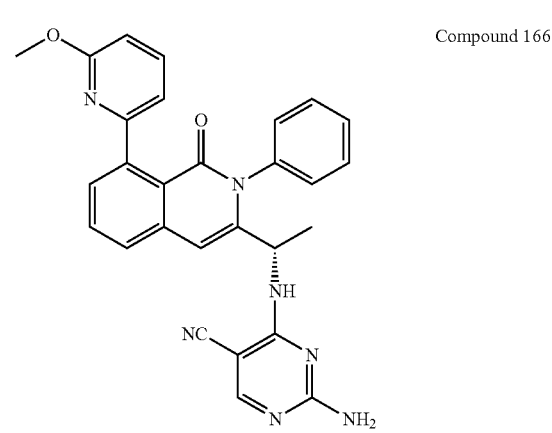
Compound 166

TABLE 5-continued
Structures of the Compounds for the $IC_{50}$ results described in Table 4 above and other exemplary compounds.
Structure
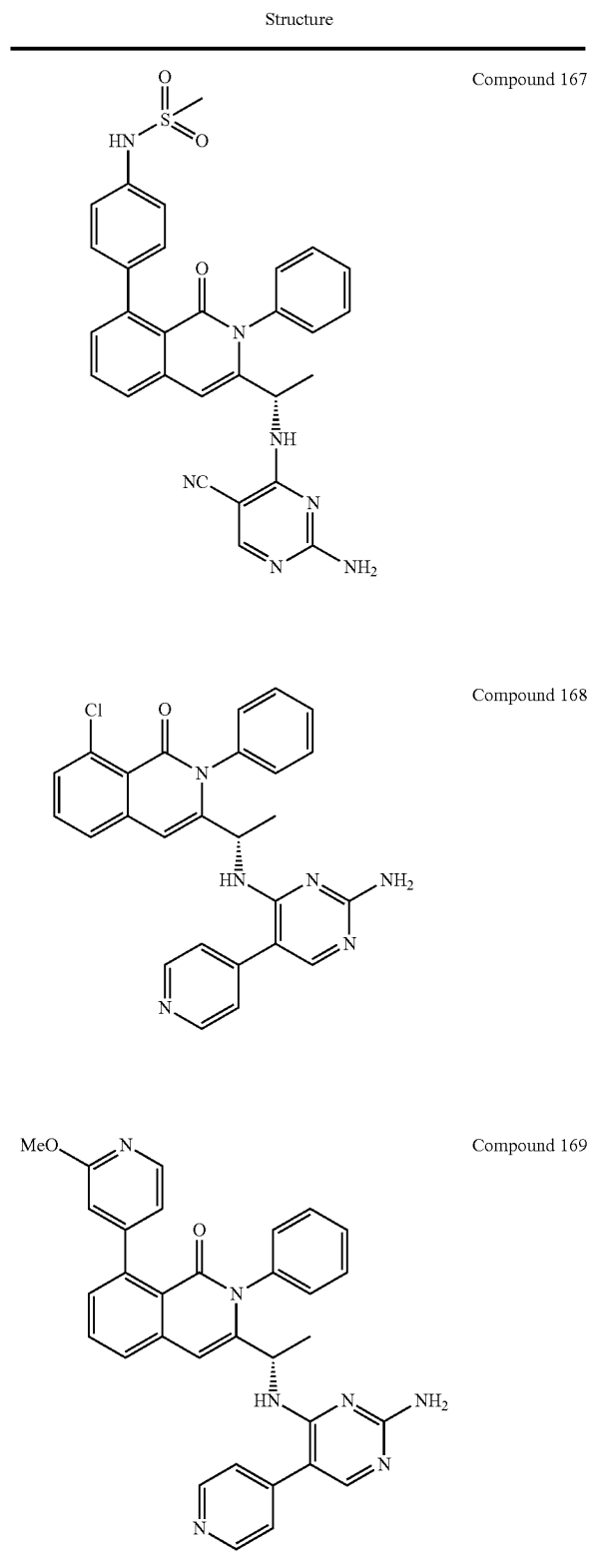
Compound 167
Compound 168
Compound 169
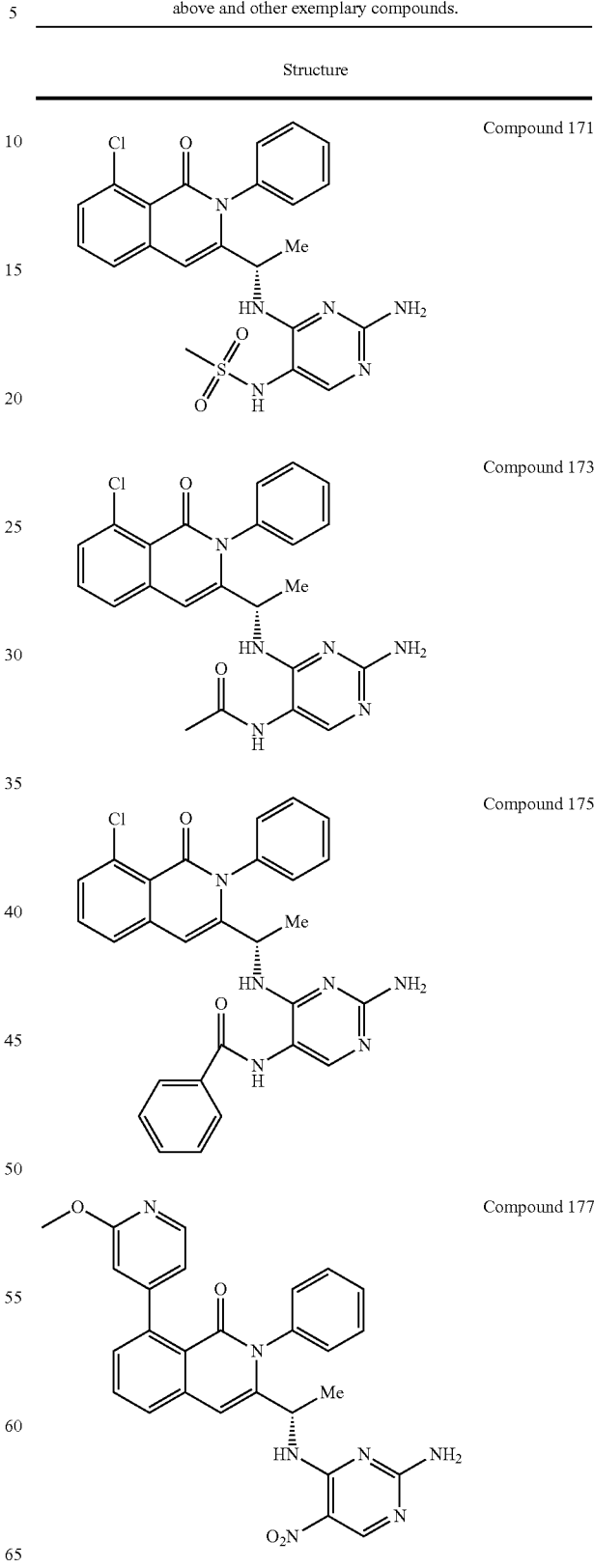
Compound 171
Compound 173
Compound 175
Compound 177

TABLE 5-continued
Structures of the Compounds for the IC$_{50}$ results described in Table 4 above and other exemplary compounds.
Structure
Compound 179
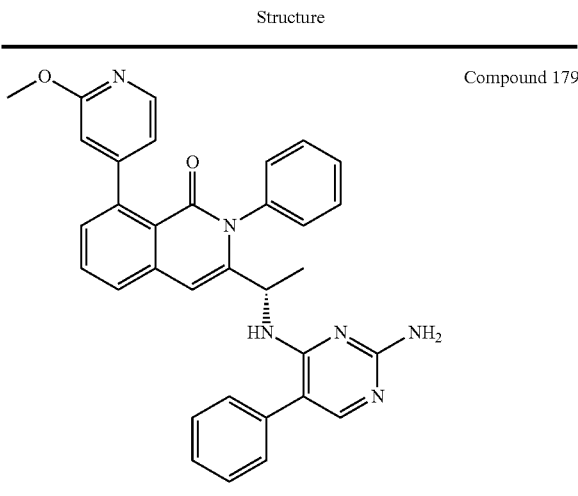
Compound 181
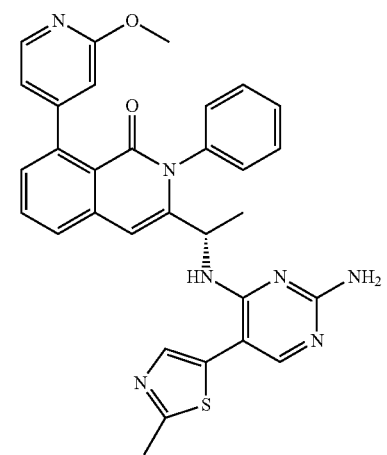 [SMILES: COc1cc(-c2cccc3cc([C@H](C)Nc4nc(N)ncc4-c4cnc(C)s4)n(-c4ccccc4)c(=O)c23)ccn1]
Compound 182
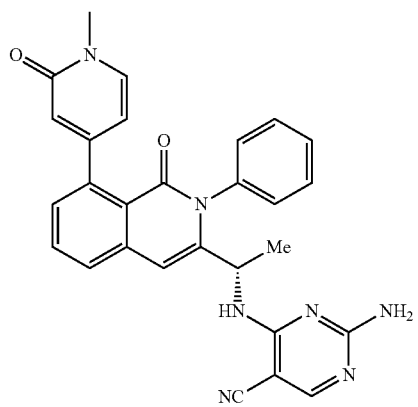 [SMILES: C[C@H](Nc1nc(N)ncc1C#N)c1cc2cccc(-c3ccn(C)c(=O)c3)c2c(=O)n1-c1ccccc1]
TABLE 5-continued
Structures of the Compounds for the IC$_{50}$ results described in Table 4 above and other exemplary compounds.
Structure
Compound 183
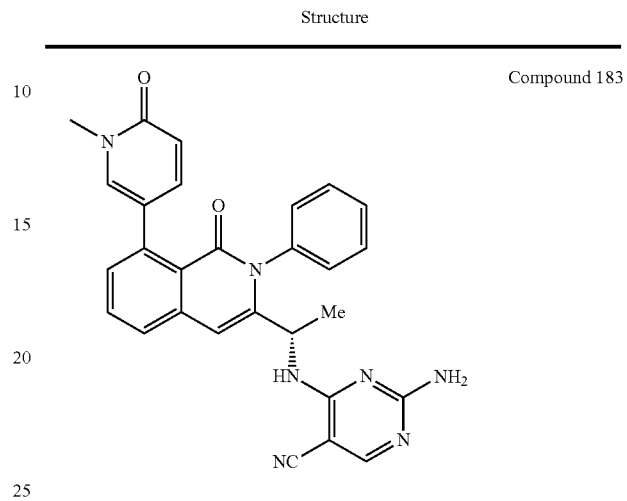
Compound 185
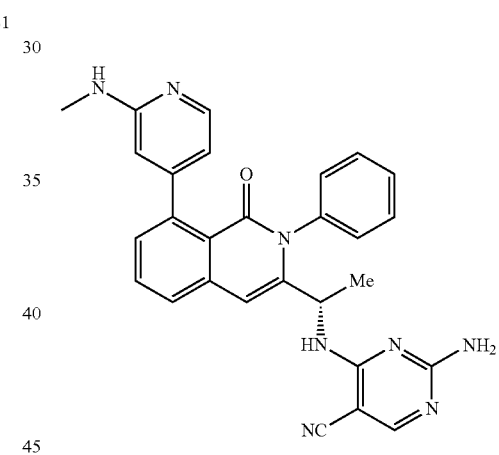
Compound 187
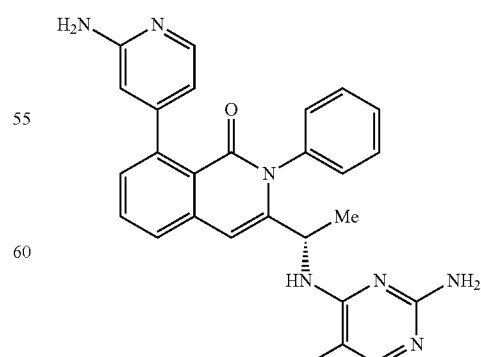

TABLE 5-continued
Structures of the Compounds for the IC$_{50}$ results described in Table 4 above and other exemplary compounds.
Structure
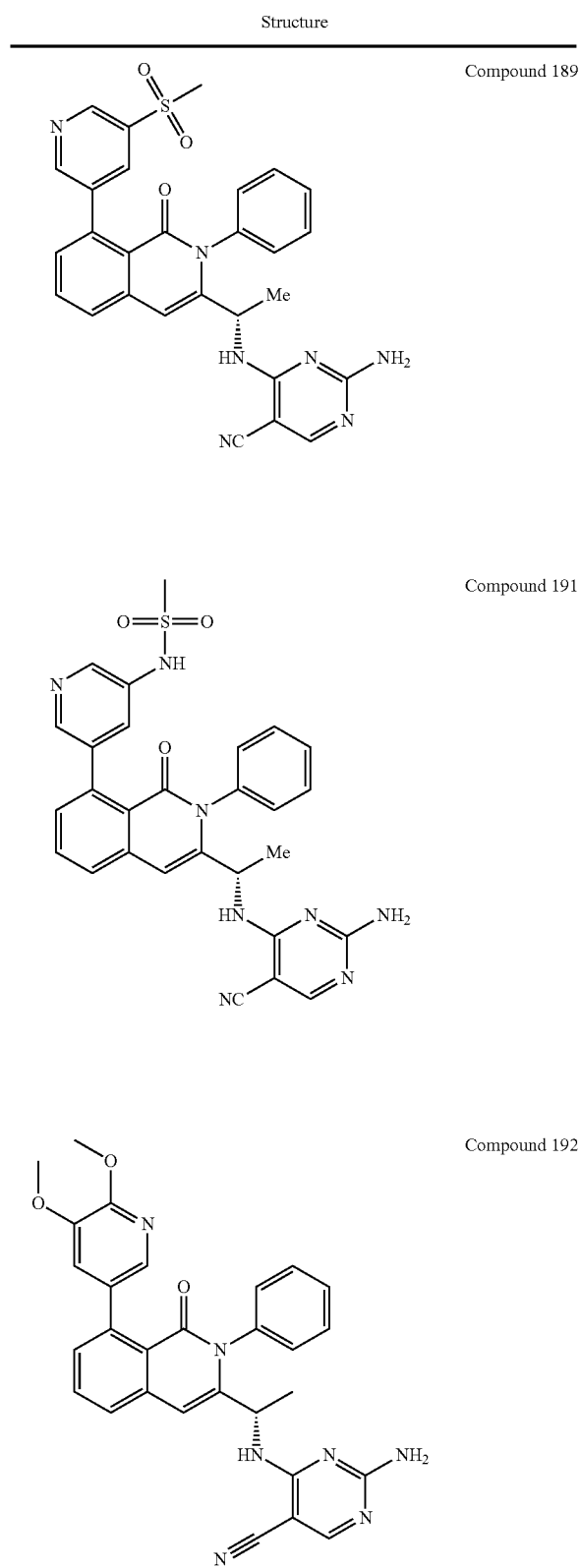
Compound 189
Compound 191
Compound 192
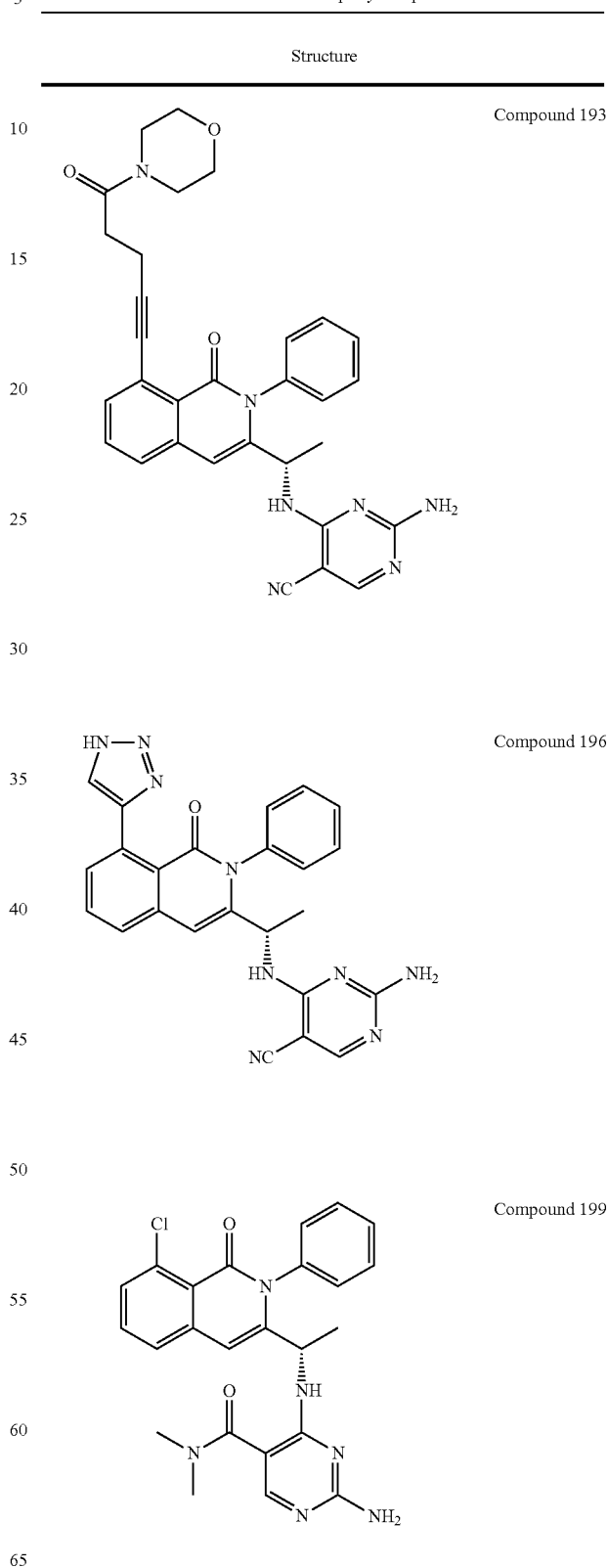
Compound 193
Compound 196
Compound 199

TABLE 5-continued

Structures of the Compounds for the IC$_{50}$ results described in Table 4 above and other exemplary compounds.

Structure

Compound 203

Compound 204

Compound 205

Compound 206

Compound 207

Compound 210

Compound 211

TABLE 5-continued

Structures of the Compounds for the IC$_{50}$ results described in Table 4 above and other exemplary compounds.

Structure

Compound 214

Compound 217

Compound 220

Compound 222

Compound 223

Compound 224

Compound 226

Compound 228

TABLE 5-continued
Structures of the Compounds for the IC$_{50}$ results described in Table 4 above and other exemplary compounds.
Structure
Compound 229
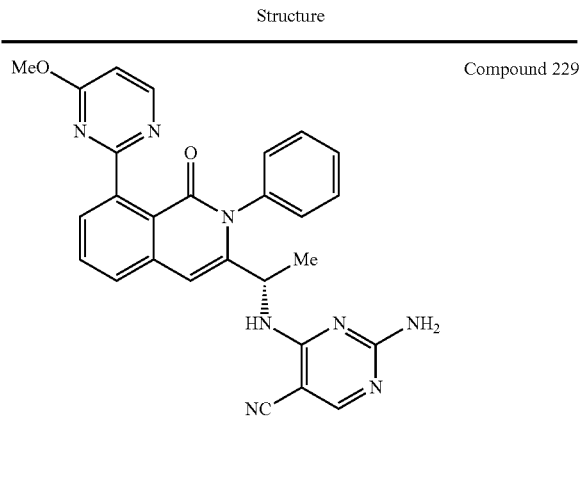
Compound 230
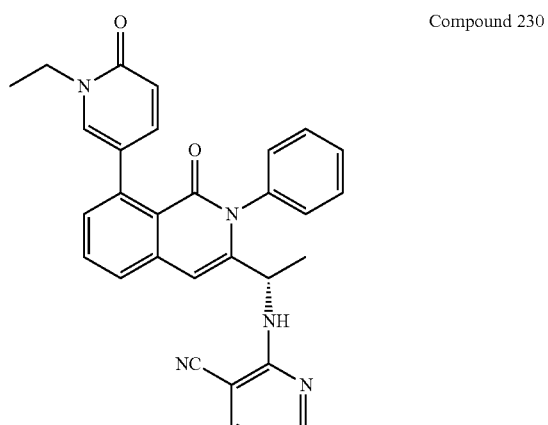
Compound 231
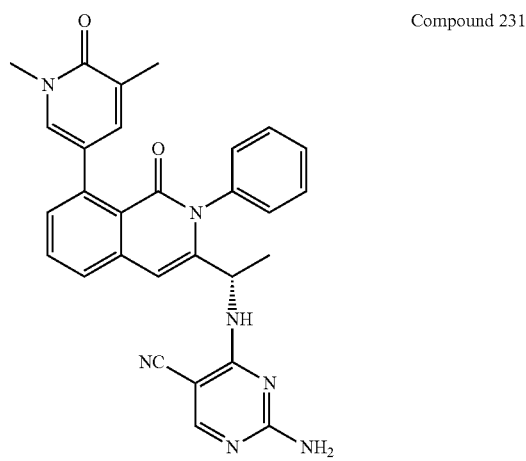
TABLE 5-continued
Structures of the Compounds for the IC$_{50}$ results described in Table 4 above and other exemplary compounds.
Structure
Compound 232
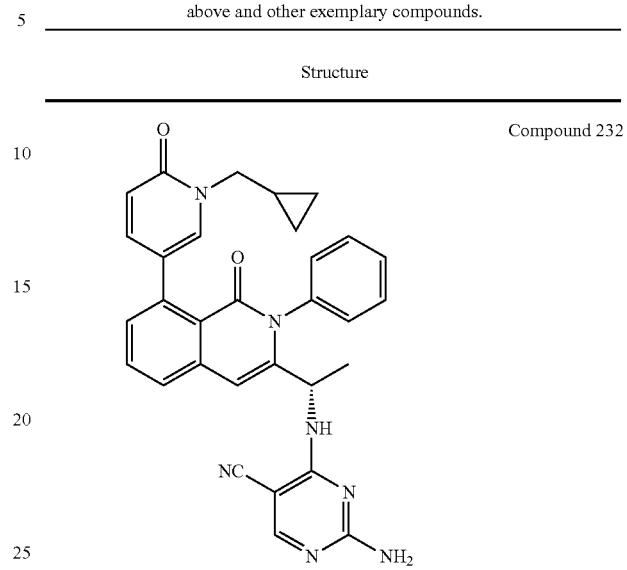
Compound 233
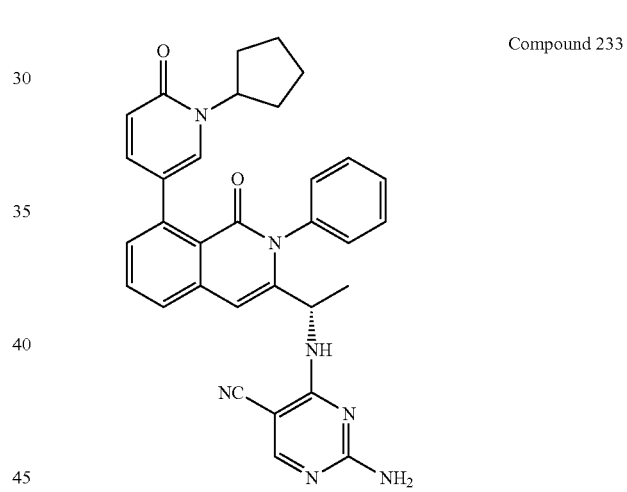
Compound 234
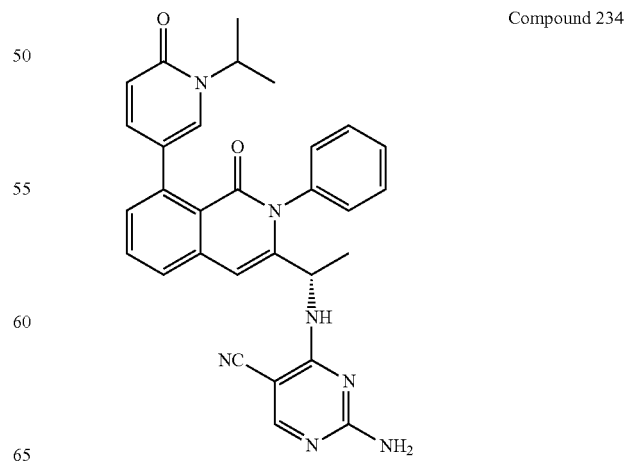

TABLE 5-continued

Structures of the Compounds for the IC$_{50}$ results described in Table 4 above and other exemplary compounds.

TABLE 5-continued
Structures of the Compounds for the IC$_{50}$ results described in Table 4 above and other exemplary compounds.
Structure
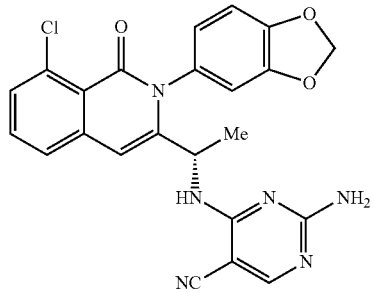 [SMILES: C[C@H](Nc1nc(N)ncc1C#N)c1cc2cccc(Cl)c2c(=O)n1-c1ccc2c(c1)OCO2]
Compound 261
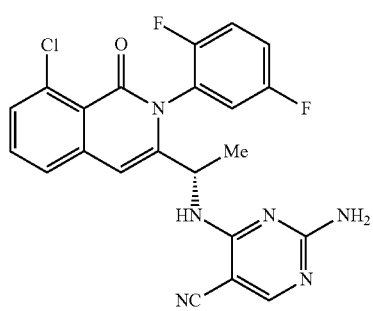 [SMILES: C[C@H](Nc1nc(N)ncc1C#N)c1cc2cccc(Cl)c2c(=O)n1-c1cc(F)ccc1F]
Compound 264
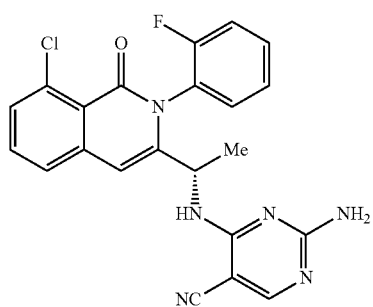 [SMILES: C[C@H](Nc1nc(N)ncc1C#N)c1cc2cccc(Cl)c2c(=O)n1-c1ccccc1F]
Compound 267
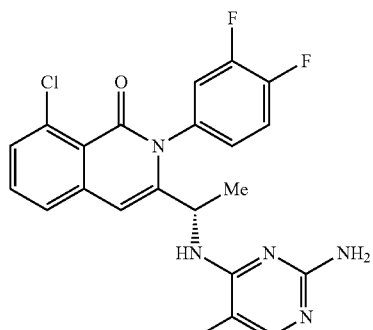
Compound 270
TABLE 5-continued
Structures of the Compounds for the IC$_{50}$ results described in Table 4 above and other exemplary compounds.
Structure
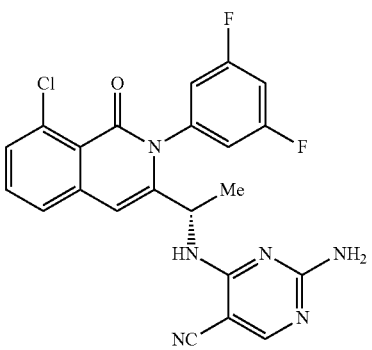 [SMILES: C[C@H](Nc1nc(N)ncc1C#N)c1cc2cccc(Cl)c2c(=O)n1-c1cc(F)cc(F)c1]
Compound 273
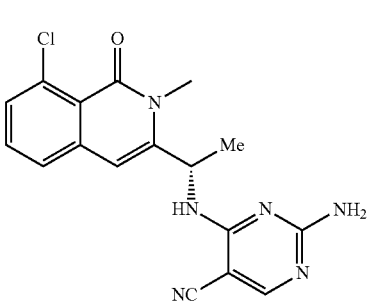 [SMILES: C[C@H](Nc1nc(N)ncc1C#N)c1cc2cccc(Cl)c2c(=O)n1C]
Compound 276
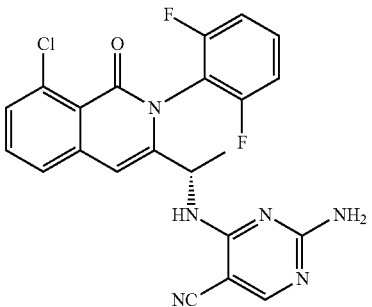 [SMILES: C[C@H](Nc1nc(N)ncc1C#N)c1cc2cccc(Cl)c2c(=O)n1-c1c(F)cccc1F]
Compound 279
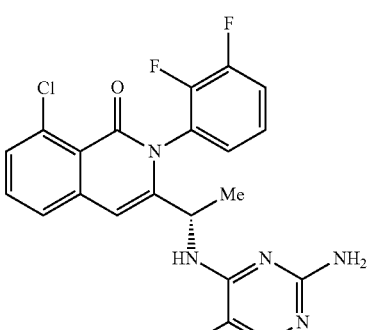
Compound 282

TABLE 5-continued
Structures of the Compounds for the IC$_{50}$ results described in Table 4 above and other exemplary compounds.
Structure
Compound 285
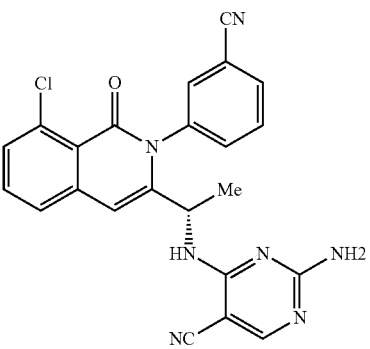 [SMILES: C[C@H](Nc1nc(N)ncc1C#N)c1cc2cccc(Cl)c2c(=O)n1-c1cccc(C#N)c1]
Compound 288
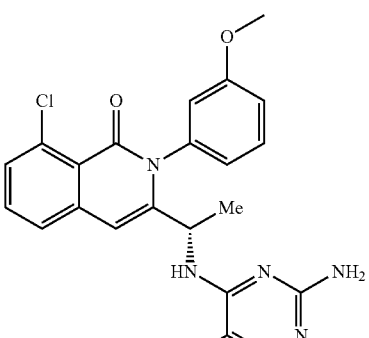
Compound 291
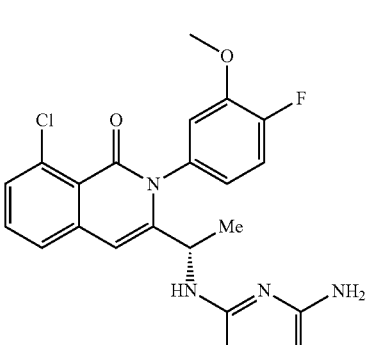
Compound 294
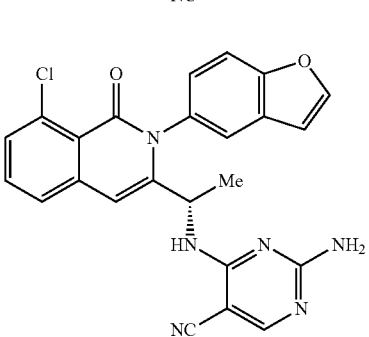
Compound 297
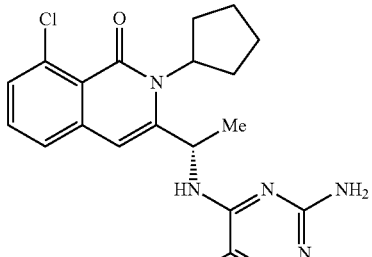
Compound 300
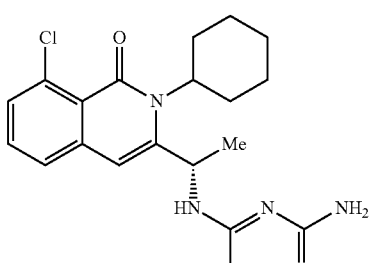
Compound 303
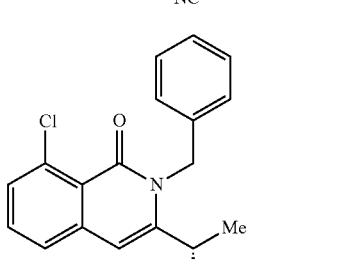
Compound 306
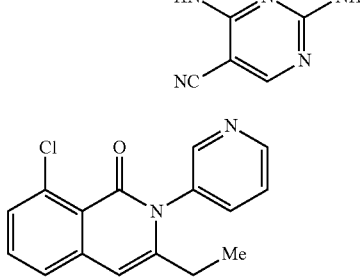
Compound 309
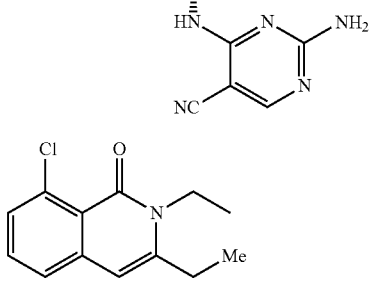

TABLE 5-continued

Structures of the Compounds for the IC$_{50}$ results described in Table 4 above and other exemplary compounds.

| Structure | |
|---|---|
| (structure) | Compound 312 |
| (structure) | Compound 313 |
| (structure) | Compound 316 |
| (structure) | Compound 319 |
| (structure) | Compound 322 |
| (structure) | Compound 325 |
| (structure) | Compound 326 |
| (structure) | Compound 327 |

TABLE 5-continued

Structures of the Compounds for the IC$_{50}$ results described in Table 4 above and other exemplary compounds.

Structure

Compound 328

Compound 329

Compound 332

Compound 333

Compound 334

Compound 335

Compound 336

TABLE 5-continued
Structures of the Compounds for the IC$_{50}$ results described in Table 4 above and other exemplary compounds.
Structure
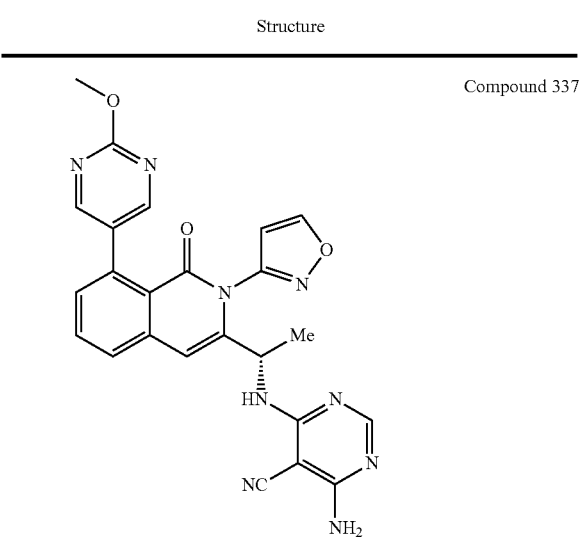
Compound 337
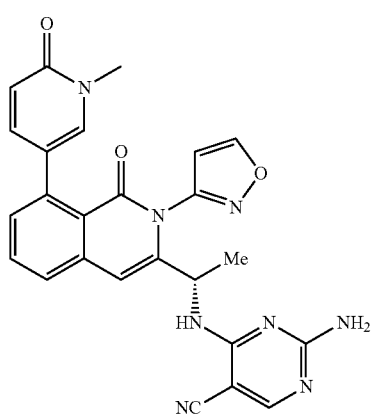 [SMILES: C[C@H](Nc1nc(N)ncc1C#N)c1cc2cccc(-c3ccc(=O)n(C)c3)c2c(=O)n1-c1ccon1]
Compound 338
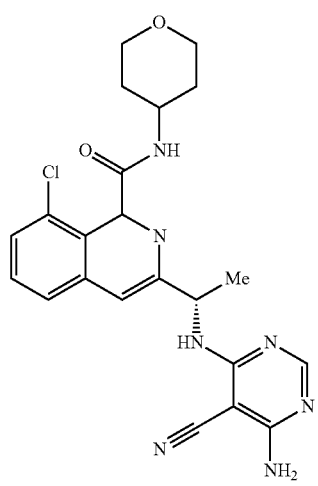 [SMILES: C[C@H](Nc1ncnc(N)c1C#N)C1=Cc2cccc(Cl)c2C(C(=O)NC2CCOCC2)N1]
Compound 353
TABLE 5-continued
Structures of the Compounds for the IC$_{50}$ results described in Table 4 above and other exemplary compounds.
Structure
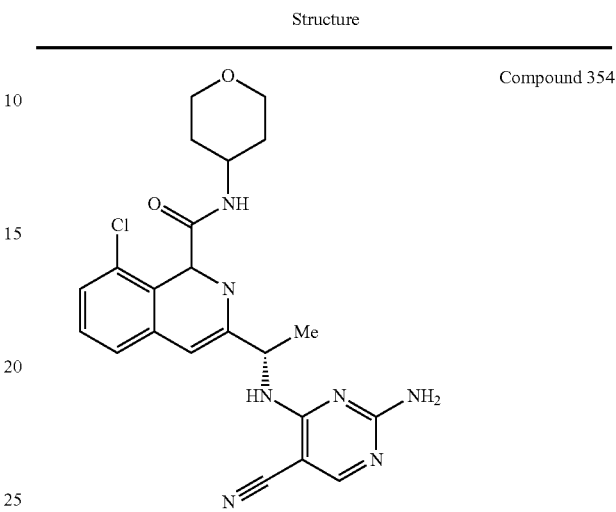
Compound 354
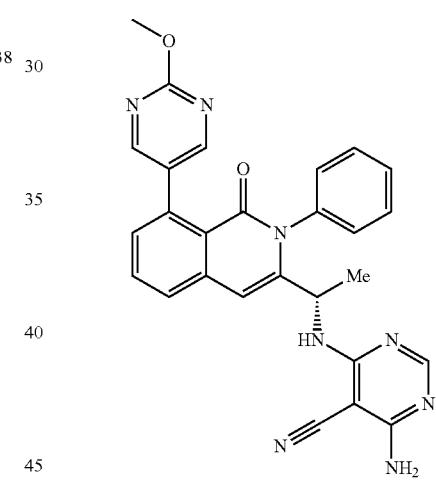
Compound 356
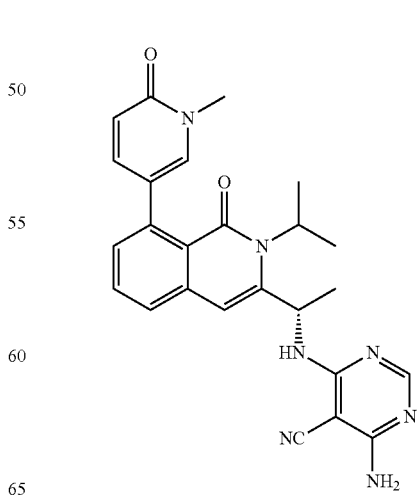
Compound 359

TABLE 5-continued

Structures of the Compounds for the IC$_{50}$ results described in Table 4 above and other exemplary compounds.

Structure

Compound 360

Compound 361

Compound 364

Compound 365

Compound 366

Compound 367

Compound 368

Compound 369

TABLE 5-continued
Structures of the Compounds for the IC$_{50}$ results described in Table 4 above and other exemplary compounds.
Structure
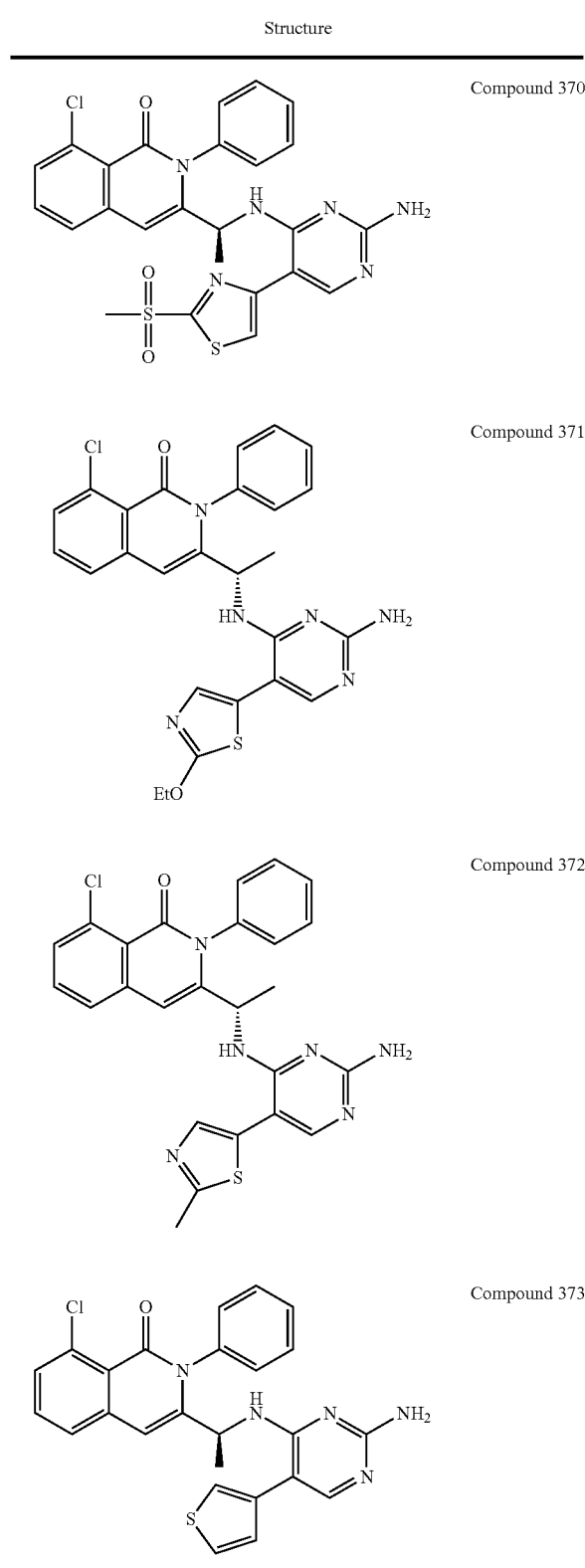
Compound 370
Compound 371
Compound 372
Compound 373
TABLE 5-continued
Structures of the Compounds for the IC$_{50}$ results described in Table 4 above and other exemplary compounds.
Structure
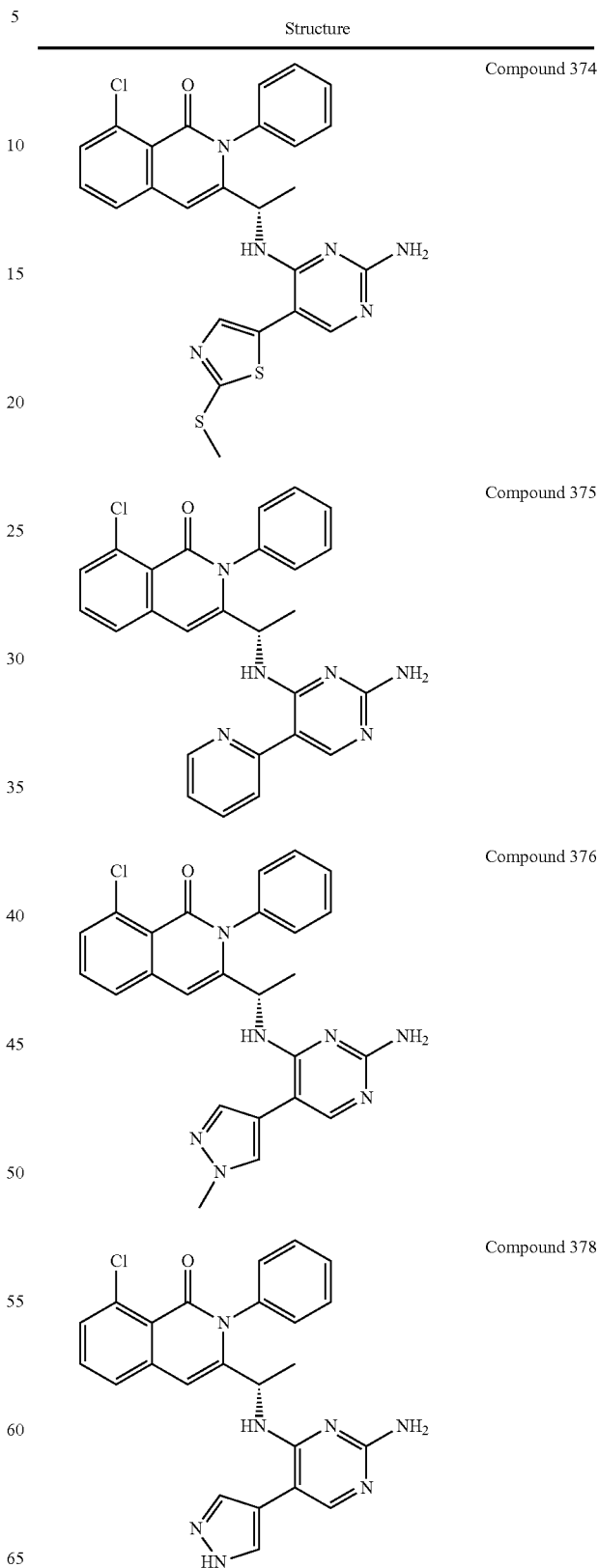
Compound 374
Compound 375
Compound 376
Compound 378

TABLE 5-continued

Structures of the Compounds for the IC$_{50}$ results described in Table 4 above and other exemplary compounds.

Structure

Compound 379

Compound 380

Compound 381

Compound 382

Compound 383

Compound 384

Compound 385

Compound 387

TABLE 5-continued

Structures of the Compounds for the IC$_{50}$ results described in Table 4 above and other exemplary compounds.

Structure

Compound 389

Compound 391

Compound 393

Compound 394

Compound 396

Compound 397

TABLE 5-continued

Structures of the Compounds for the IC$_{50}$ results described in Table 4 above and other exemplary compounds.

Structure

Compound 398

Compound 399

Compound 400

Compound 401

Compound 402

Compound 403

Compound 404

TABLE 5-continued
Structures of the Compounds for the IC$_{50}$ results described in Table 4 above and other exemplary compounds.
Structure
Compound 405
Compound 406
Compound 407
Compound 408
TABLE 5-continued
Structures of the Compounds for the IC$_{50}$ results described in Table 4 above and other exemplary compounds.
Structure
Compound 409
Compound 410
Compound 412
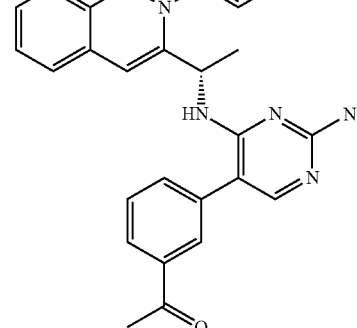

TABLE 5-continued
Structures of the Compounds for the $IC_{50}$ results described in Table 4 above and other exemplary compounds.
Structure
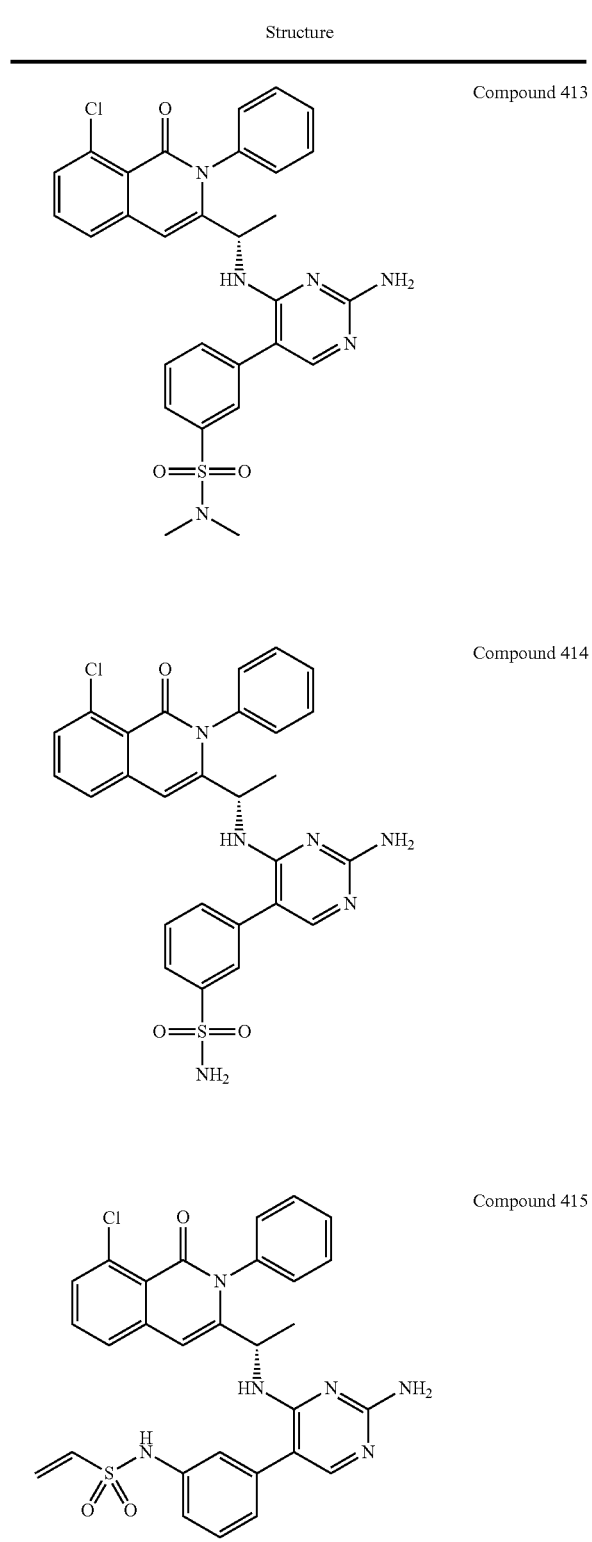
Compound 413
Compound 414
Compound 415
TABLE 5-continued
Structures of the Compounds for the $IC_{50}$ results described in Table 4 above and other exemplary compounds.
Structure
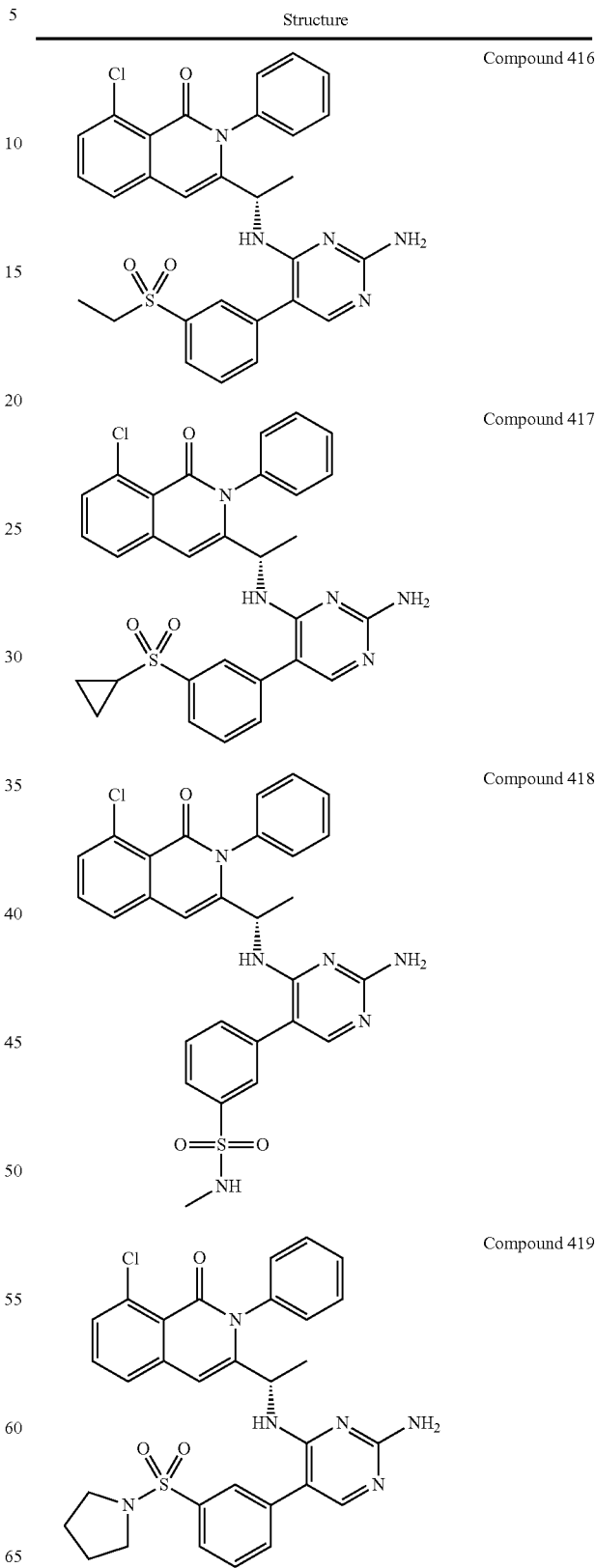
Compound 416
Compound 417
Compound 418
Compound 419

TABLE 5-continued

Structures of the Compounds for the IC$_{50}$ results described in Table 4 above and other exemplary compounds.

Structure

Compound 420, Compound 422, Compound 424, Compound 425, Compound 428, Compound 429, Compound 430, Compound 431

TABLE 5-continued
Structures of the Compounds for the $IC_{50}$ results described in Table 4 above and other exemplary compounds.
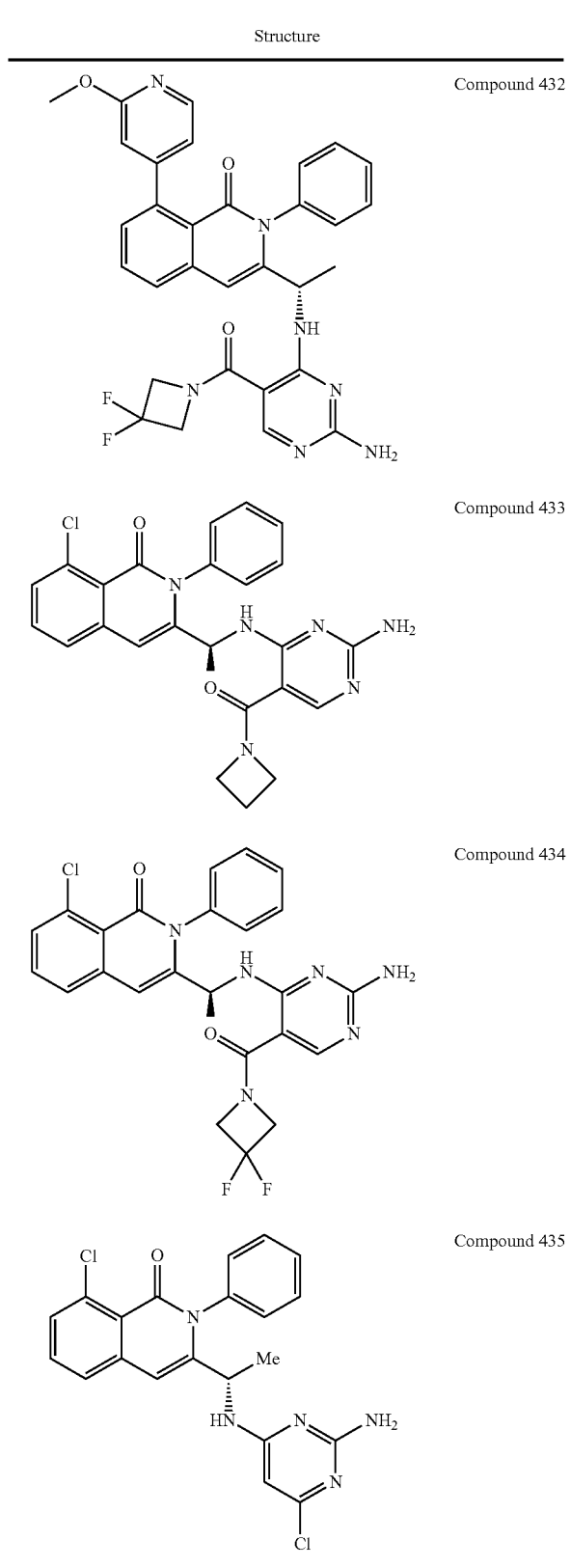
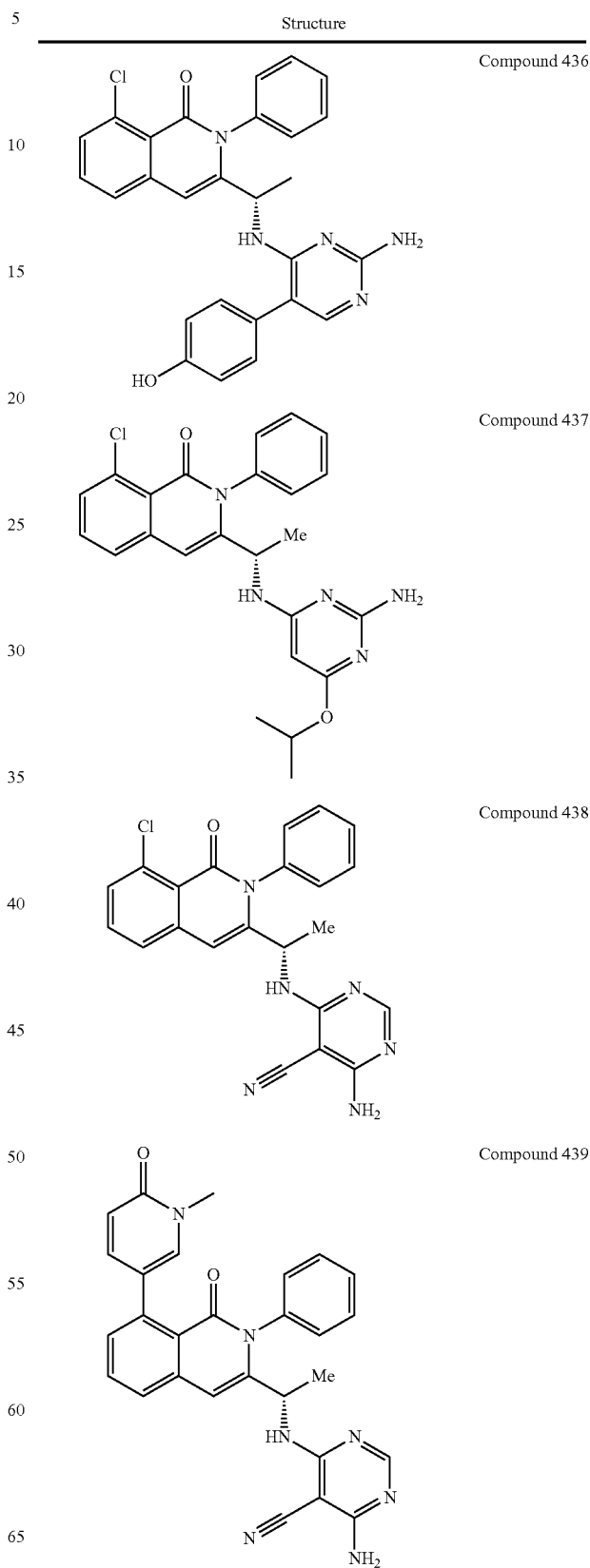

TABLE 5-continued
Structures of the Compounds for the IC$_{50}$ results described in Table 4 above and other exemplary compounds.
Structure
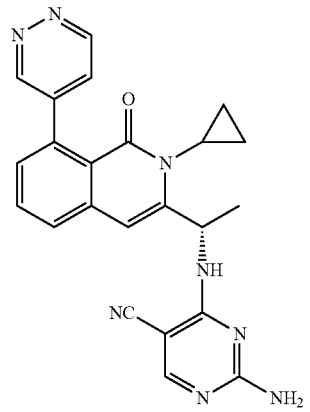 [SMILES: C[C@H](Nc1nc(N)ncc1C#N)c1cc2cccc(-c3ccnnc3)c2c(=O)n1C1CC1]
Compound 440
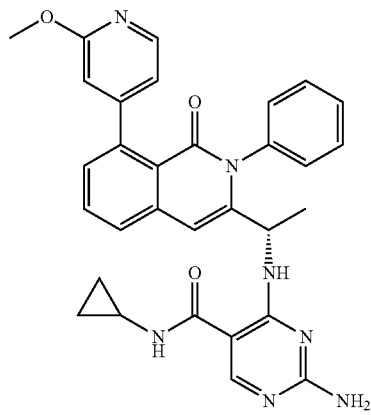 [SMILES: COc1cc(-c2cccc3cc([C@H](C)Nc4nc(N)ncc4C(=O)NC4CC4)n(-c4ccccc4)c(=O)c23)ccn1]
Compound 441
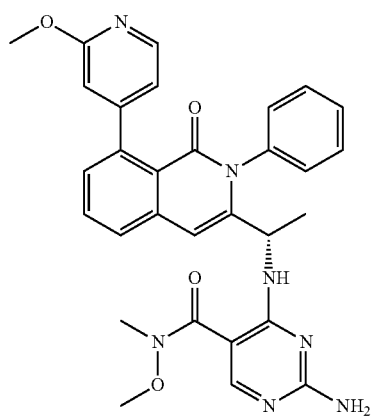 [SMILES: COc1cc(-c2cccc3cc([C@H](C)Nc4nc(N)ncc4C(=O)N(C)OC)n(-c4ccccc4)c(=O)c23)ccn1]
Compound 442
TABLE 5-continued
Structures of the Compounds for the IC$_{50}$ results described in Table 4 above and other exemplary compounds.
Structure
Compound 443
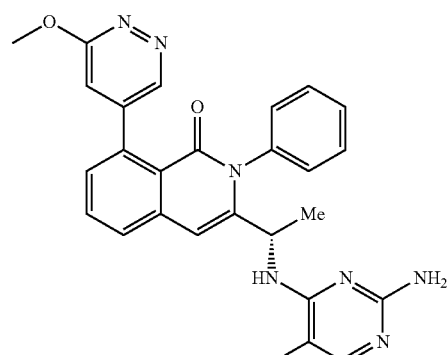
Compound 444
Compound 445
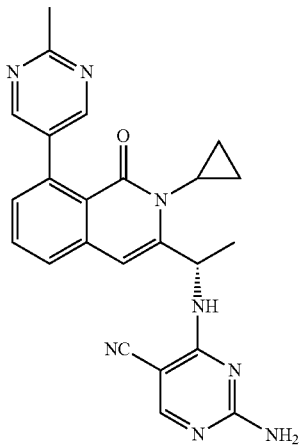 [SMILES: Cc1ncc(-c2cccc3cc([C@H](C)Nc4nc(N)ncc4C#N)n(C4CC4)c(=O)c23)cn1]

TABLE 5-continued

Structures of the Compounds for the IC$_{50}$ results described in Table 4 above and other exemplary compounds.

Structure

Compound 446

Compound 447

Compound 448

Compound 449

Compound 450

Compound 451

Compound 452

Compound 453

TABLE 5-continued
Structures of the Compounds for the IC$_{50}$ results described in Table 4 above and other exemplary compounds.
Structure
Compound 454
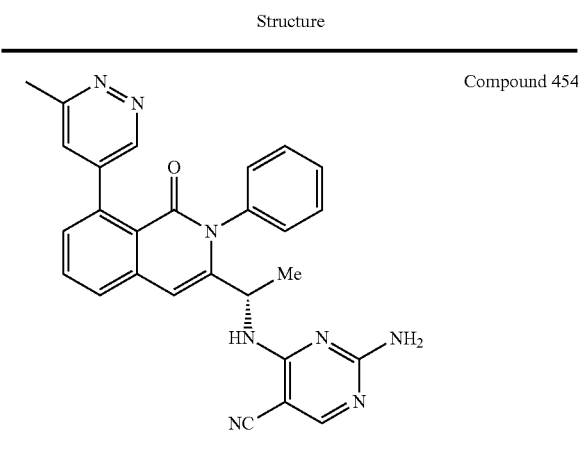
Compound 455
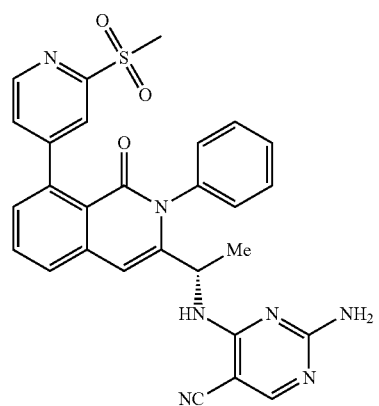 [SMILES: C[C@H](Nc1nc(N)ncc1C#N)c1cc2cccc(-c3ccnc(S(C)(=O)=O)c3)c2c(=O)n1-c1ccccc1]
Compound 456
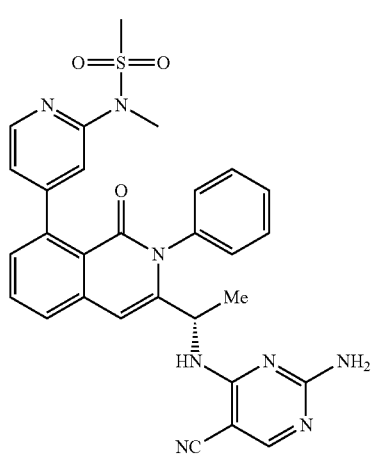 [SMILES: C[C@H](Nc1nc(N)ncc1C#N)c1cc2cccc(-c3ccnc(N(C)S(C)(=O)=O)c3)c2c(=O)n1-c1ccccc1]
TABLE 5-continued
Structures of the Compounds for the IC$_{50}$ results described in Table 4 above and other exemplary compounds.
Structure
Compound 457
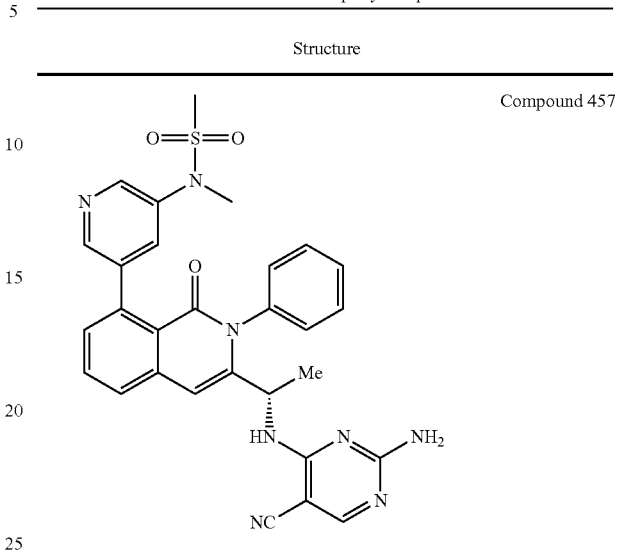
Compound 458
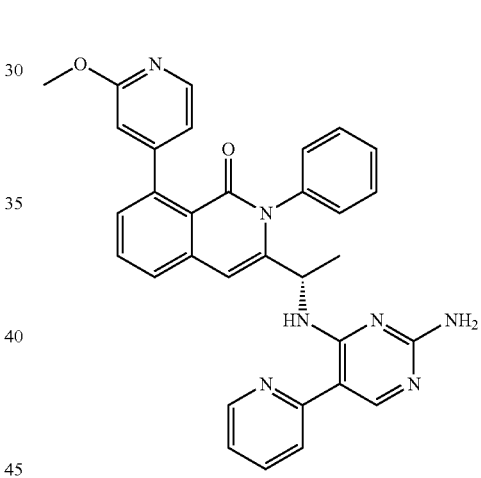
Compound 459
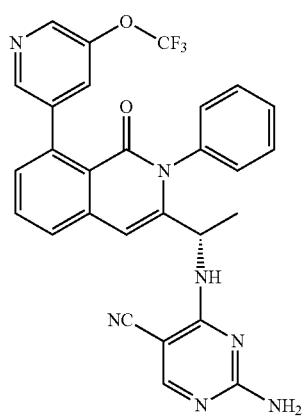 [SMILES: C[C@H](Nc1nc(N)ncc1C#N)c1cc2cccc(-c3cncc(OC(F)(F)F)c3)c2c(=O)n1-c1ccccc1]

TABLE 5-continued

Structures of the Compounds for the IC$_{50}$ results described in Table 4 above and other exemplary compounds.

| Structure | |
|---|---|
| 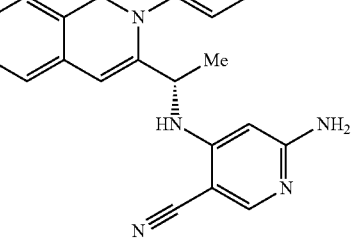 | Compound 460 |
| 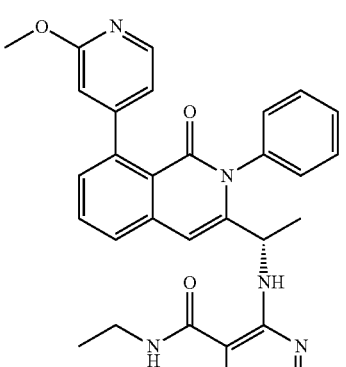 | Compound 461 |
| 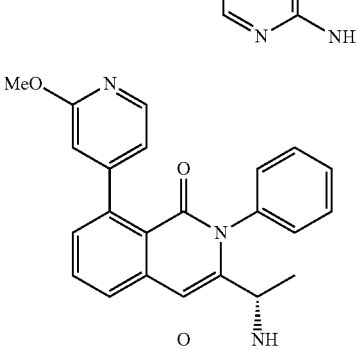 | Compound 462 |

BIOLOGICAL ACTIVITY ASSESSMENT

A PI3-Kinase HTRF® assay kit (cat No. 33-016) purchased from Millipore Corporation was used to screen compounds provided herein. This assay used specific, high affinity binding of the GRP1 pleckstrin homology (PH) domain to PIP3, the product of a Class 1A or 1B PI3 Kinase acting on its physiological substrate PIP2. During the detection phase of the assay, a complex was generated between the GST-tagged PH domain and biotinylated short chain PIP3. The biotinylated PIP3 and the GST-tagged PH domain recruited fluorophores (Streptavidin-Allophycocyanin and Europium-labeled anti-GST respectively) to form the fluorescence resonance energy transfer (FRET) architecture, generating a stable time-resolved FRET signal. The FRET complex was disrupted in a competitive manner by non-biotinylated PIP3, a product formed in the PI3 Kinase assay.

PI3 Kinase α, β, γ and δ activity was assayed using the PI3 Kinase HTRF® assay kit (catalogue No. 33-016) purchased from Millipore Corporation. Purified recombinant PI3Kα (catalogue No. 14-602-K), PI3Kβ (catalogue No. 14-603-K), PI3Kγ (catalogue No. 14-558-K) and PI3Kδ (catalogue No. 14-604-K) were obtained from Millipore Corporation. Purified recombinant PI3K enzyme was used to catalyze the phosphorylation of phosphatidylinositol 4,5-bisphosphate (PIP2 at 10 μM) to phosphatidylinositol 3,4,5-trisphosphate (PIP3) in the presence of 10 μM ATP. The assay was carried out in 384-well format and detected using a Perkin Elmer EnVision Xcite Multilabel Reader. Emission ratios were converted into percent inhibitions and imported into GraphPad Prism software. The concentration necessary to achieve inhibition of enzyme activity by 50% (IC$_{50}$) was calculated using concentrations ranging from 20 μM to 0.1 nM (12-point curve). IC$_{50}$ values were determined using a nonlinear regression model available in GraphPad Prism 5.

Example 259

Chemical Stability

The chemical stability of one or more subject compounds is determined according to standard procedures known in the art. The following details an exemplary procedure for ascertaining chemical stability of a subject compound. The default buffer used for the chemical stability assay is phosphate-buffered saline (PBS) at pH 7.4; other suitable buffers can be used. A subject compound is added from a 100 μM stock solution to an aliquot of PBS (in duplicate) to give a final assay volume of 400 μL, containing 5 μM test compound and 1% DMSO (for half-life determination a total sample volume of 700 μL is prepared). Reactions are incubated, with shaking, for 24 hours at 37° C.; for half-life determination samples are incubated for 0, 2, 4, 6, and 24 hours. Reactions are stopped by adding immediately 100 μL of the incubation mixture to 100 μL of acetonitrile and vortexing for 5 minutes. The samples are then stored at −20° C. until analysis by HPLC-MS/MS. Where desired, a control compound or a reference compound such as chlorambucil (5 μM) is tested simultaneously with a subject compound of interest, as this compound is largely hydrolyzed over the course of 24 hours. Samples are analyzed via (RP)HPLC-MS/MS using selected reaction monitoring (SRM). The HPLC conditions consist of a binary LC pump with autosampler, a mixed-mode, C12, 2×20 mm column, and a gradient program. Peak areas corresponding to the analytes are recorded by HPLC-MS/MS. The ratio of the parent compound remaining after 24 hours relative to the amount remaining at time zero, expressed as percent, is reported as chemical stability. In case of half-life determination, the half-life is estimated from the slope of the initial linear range of the logarithmic curve of compound remaining (%) vs. time, assuming first order kinetics.

Example 260

Expression and Inhibition Assays of p110α/p85γ, p110β/p85γ, p110δ/p85γ, and p110γ

Class I PI3-Ks can be either purchased (p110α/p85α, p110β/p85γ, p110δ/p85γ from Upstate, and p110γ from Sigma) or expressed as previously described (Knight et al., 2004). IC$_{50}$ values are measured using either a standard TLC assay for lipid kinase activity (described below) or a high-throughput membrane capture assay. Kinase reactions are performed by preparing a reaction mixture containing kinase, inhibitor (2% DMSO final concentration), buffer (25 mM HEPES, pH 7.4, 10 mM MgCl2), and freshly sonicated phosphatidylinositol (100 µg/ml). Reactions are initiated by the addition of ATP containing 10 µCi of γ-32P-ATP to a final concentration of 10 or 100 µM and allowed to proceed for 5 minutes at room temperature. For TLC analysis, reactions are then terminated by the addition of 105 µl 1N HCl followed by 160 µl CHCl$_3$:MeOH (1:1). The biphasic mixture is vortexed, briefly centrifuged, and the organic phase is transferred to a new tube using a gel loading pipette tip precoated with CHCl$_3$. This extract is spotted on TLC plates and developed for 3-4 hours in a 65:35 solution of n-propanol:1M acetic acid. The TLC plates are then dried, exposed to a phosphorimager screen (Storm, Amersham), and quantitated. For each compound, kinase activity is measured at 10-12 inhibitor concentrations representing two-fold dilutions from the highest concentration tested (typically, 200 µM). For compounds showing significant activity, IC$_{50}$ determinations are repeated two to four times, and the reported value is the average of these independent measurements.

Other commercial kits or systems for assaying PI3-K activities are available. The commercially available kits or systems can be used to screen for inhibitors and/or agonists of PI3-Ks including, but not limited to, PI 3-Kinase α, β, δ, and γ. An exemplary system is PI 3-Kinase (human) HTRF™ Assay from Upstate. The assay can be carried out according to the procedures suggested by the manufacturer. Briefly, the assay is a time resolved FRET assay that indirectly measures PIP3 product formed by the activity of a PI3-K. The kinase reaction is performed in a microtiter plate (e.g., a 384 well microtiter plate). The total reaction volume is approximately 20 µl per well. In the first step, each well receives 2 µl of test compound in 20% dimethylsulphoxide resulting in a 2% DMSO final concentration. Next, approximately 14.5 µl of a kinase/PIP2 mixture (diluted in 1× reaction buffer) is added per well for a final concentration of 0.25-0.3 µg/ml kinase and 10 µM PIP2. The plate is sealed and incubated for 15 minutes at room temperature. To start the reaction, 3.5 µl of ATP (diluted in 1× reaction buffer) is added per well for a final concentration of 10 µM ATP. The plate is sealed and incubated for 1 hour at room temperature. The reaction is stopped by adding 5 µl of Stop Solution per well and then 5 µl of Detection Mix is added per well. The plate is sealed, incubated for 1 hour at room temperature, and then read on an appropriate plate reader. Data is analyzed and IC$_{50}$s are generated using GraphPad Prism 5.

Example 261

B Cell Activation and Proliferation Assay

The ability of one or more subject compounds to inhibit B cell activation and proliferation is determined according to standard procedures known in the art. For example, an in vitro cellular proliferation assay is established that measures the metabolic activity of live cells. The assay is performed in a 96 well microtiter plate using Alamar Blue reduction. Balb/c splenic B cells are purified over a Ficoll-Paque™ PLUS gradient followed by magnetic cell separation using a MACS B cell Isolation Kit (Miletenyi). Cells are plated in 90 µl at 50,000 cells/well in B Cell Media (RPMI+10% FBS+Penn/Strep+50 µM bME+5 mM HEPES). A compound provided herein is diluted in B Cell Media and added in a 10 µl volume. Plates are incubated for 30 min at 37° C. and 5% CO$_2$ (0.2% DMSO final concentration). A 50 µl B cell stimulation cocktail is then added containing either 10 µg/ml LPS or 5 µg/ml F(ab')$_2$ Donkey anti-mouse IgM plus 2 ng/ml recombinant mouse IL4 in B Cell Media. Plates are incubated for 72 hours at 37° C. and 5% CO$_2$. A volume of 15 µL, of Alamar Blue reagent is added to each well and plates are incubated for 5 hours at 37° C. and 5% CO$_2$. Alamar Blue fluoresce is read at 560Ex/590Em, and IC$_{50}$ or EC$_{50}$ values are calculated using GraphPad Prism 5.

Example 262

Tumor Cell Line Proliferation Assay

The ability of one or more subject compounds to inhibit tumor cell line proliferation can be determined according to standard procedures known in the art. For instance, an in vitro cellular proliferation assay can be performed to measure the metabolic activity of live cells. The assay is performed in a 96 well microtiter plate using Alamar Blue reduction. Human tumor cell lines are obtained from ATCC (e.g., MCF7, U-87 MG, MDA-MB-468, PC-3), grown to confluency in T75 flasks, trypsinized with 0.25% trypsin, washed one time with Tumor Cell Media (DMEM+10% FBS), and plated in 90 µl at 5,000 cells/well in Tumor Cell Media. A compound provided herein is diluted in Tumor Cell Media and added in a 10 µl volume. Plates are incubated for 72 hours at 37° C. and 5% CO$_2$. A volume of 10 µL, of Alamar Blue reagent is added to each well and plates are incubated for 3 hours at 37° C. and 5% CO$_2$. Alamar Blue fluoresce is read at 560Ex/590Em, and IC$_{50}$ values are calculated using GraphPad Prism 5.

Example 263

Antitumor Activity In Vivo

The compounds described herein can be evaluated in a panel of human and murine tumor models.
Paclitaxel-Refractory Tumor Models
1. Clinically-Derived Ovarian Carcinoma Model.
This tumor model is established from a tumor biopsy of an ovarian cancer patient. Tumor biopsy is taken from the patient. The compounds described herein are administered to nude mice bearing staged tumors using an every 2 days×5 schedule.
2. A2780Tax Human Ovarian Carcinoma Xenograft (Mutated Tubulin).
A2780Tax is a paclitaxel-resistant human ovarian carcinoma model. It is derived from the sensitive parent A2780 line by co-incubation of cells with paclitaxel and verapamil, an MDR-reversal agent. Its resistance mechanism has been shown to be non-MDR related and is attributed to a mutation in the gene encoding the beta-tubulin protein. The compounds described herein can be administered to mice bearing staged tumors on an every 2 days×5 schedule.
3. HCT116/VM46 Human Colon Carcinoma Xenograft (Multi-Drug Resistant).
HCT116/VM46 is an MDR-resistant colon carcinoma developed from the sensitive HCT116 parent line. In vivo, grown in nude mice, HCT116/VM46 has consistently demonstrated high resistance to paclitaxel. The compounds described herein can be administered to mice bearing staged tumors on an every 2 days×5 schedule.
4. M5076 Murine Sarcoma Model
M5076 is a mouse fibrosarcoma that is inherently refractory to paclitaxel in vivo. The compounds described herein can be administered to mice bearing staged tumors on an every 2 days×5 schedule.

One or more compounds as provided herein can be used in combination other therapeutic agents in vivo in the multidrug resistant human colon carcinoma xenografts HCT/VM46 or any other model known in the art including those described herein.

Example 264

Microsome Stability Assay

The stability of one or more subject compounds is determined according to standard procedures known in the art. For example, stability of one or more subject compounds is established by an in vitro assay. For example, an in vitro microsome stability assay is established that measures stability of one or more subject compounds when reacting with mouse, rat or human microsomes from liver. The microsome reaction with compounds is performed in 1.5 mL Eppendorf tube. Each tube contains 0.1 µL, of 10.0 mg/ml NADPH; 75 mL of 20.0 mg/ml mouse, rat or human liver microsome; 0.4 µL, of 0.2 M phosphate buffer, and 425 mL of ddH$_2$O, Negative control (without NADPH) tube contains 75 µL, of 20.0 mg/ml mouse, rat or human liver microsome; 0.4 µL, of 0.2 M phosphate buffer, and 525 µL, of ddH$_2$O. The reaction is started by adding 1.0 µL, of 10.0 mM tested compound. The reaction tubes are incubated at 37° C. 100 µL, sample is collected into new Eppendorf tube containing 300 mL cold methanol at 0, 5, 10, 15, 30 and 60 minutes of reaction. Samples are centrifuged at 15,000 rpm to remove protein. Supernatant of centrifuged sample is transferred to new tube. Concentration of stable compound after reaction with microsome in the supernatant is measured by Liquid Chromatography/Mass Spectrometry (LC-MS).

Example 265

Plasma Stability Assay

The stability of one or more subject compounds in plasma is determined according to standard procedures known in the art. See, e.g., *Rapid Commun. Mass Spectrom.*, 10: 1019-1026. The following procedure is an HPLC-MS/MS assay using human plasma; other species including monkey, dog, rat, and mouse are also available. Frozen, heparinized human plasma is thawed in a cold water bath and spun for 10 minutes at 2000 rpm at 4° C. prior to use. A subject compound is added from a 400 µM stock solution to an aliquot of pre-warmed plasma to give a final assay volume of 400 mL (or 800 mL for half-life determination), containing 5 µM test compound and 0.5% DMSO. Reactions are incubated, with shaking, for 0 minutes and 60 minutes at 37° C., or for 0, 15, 30, 45 and 60 minutes at 37 C for half life determination. Reactions are stopped by transferring 50 mL of the incubation mixture to 200 mL of ice-cold acetonitrile and mixed by shaking for 5 minutes. The samples are centrifuged at 6000×g for 15 minutes at 4° C. and 120 µL of supernatant removed into clean tubes. The samples are then evaporated to dryness and submitted for analysis by HPLC-MS/MS.

In one embodiment, one or more control or reference compounds (5 µM) are tested simultaneously with the test compounds: one compound, propoxycaine, with low plasma stability and another compound, propantheline, with intermediate plasma stability.

Samples are reconstituted in acetonitrile/methanol/water (1/1/2, v/v/v) and analyzed via (RP)HPLC-MS/MS using selected reaction monitoring (SRM). The HPLC conditions consist of a binary LC pump with autosampler, a mixed-mode, C12, 2×20 mm column, and a gradient program. Peak areas corresponding to the analytes are recorded by HPLC-MS/MS. The ratio of the parent compound remaining after 60 minutes relative to the amount remaining at time zero, expressed as percent, is reported as plasma stability. In case of half-life determination, the half-life is estimated from the slope of the initial linear range of the logarithmic curve of compound remaining (%) vs. time, assuming first order kinetics.

Example 266

Kinase Signaling in Blood

PI3K/Akt/mTor signaling is measured in blood cells using the phosflow method (*Methods Enzymol.* (2007) 434:131-54). This method is by nature a single cell assay so that cellular heterogeneity can be detected rather than population averages. This allows concurrent distinction of signaling states in different populations defined by other markers. Phosflow is also highly quantitative. To test the effects of one or more compounds provided herein, unfractionated splenocytes, or peripheral blood mononuclear cells are stimulated with anti-CD3 to initiate T-cell receptor signaling. The cells are then fixed and stained for surface markers and intracellular phosphoproteins Inhibitors provided herein inhibit anti-CD3 mediated phosphorylation of Akt -S473 and S6, whereas rapamycin inhibits S6 phosphorylation and enhances Akt phosphorylation under the conditions tested.

Similarly, aliquots of whole blood are incubated for 15 minutes with vehicle (e.g., 0.1% DMSO) or kinase inhibitors at various concentrations, before addition of stimuli to crosslink the T cell receptor (TCR) (anti-CD3 with secondary antibody) or the B cell receptor (BCR) using anti-kappa light chain antibody (Fab'2 fragments). After approximately 5 and 15 minutes, samples are fixed (e.g., with cold 4% paraformaldehyde) and used for phosflow. Surface staining is used to distinguish T and B cells using antibodies directed to cell surface markers that are known to the art. The level of phosphorylation of kinase substrates such as Akt and S6 are then measured by incubating the fixed cells with labeled antibodies specific to the phosphorylated isoforms of these proteins. The population of cells are then analyzed by flow cytometry.

Example 267

Colony Formation Assay

Murine bone marrow cells freshly transformed with a p190 BCR-Abl retrovirus (herein referred to as p190 transduced cells) are plated in the presence of various drug combinations in M3630 methylcellulose media for about 7 days with recombinant human IL-7 in about 30% serum, and the number of colonies formed is counted by visual examination under a microscope.

Alternatively, human peripheral blood mononuclear cells are obtained from Philadelphia chromosome positive (Ph+) and negative (Ph−) patients upon initial diagnosis or relapse. Live cells are isolated and enriched for CD19+ CD34+ B cell progenitors. After overnight liquid culture, cells are plated in methocult GF+ H4435, Stem Cell Technologies) supplemented with cytokines (IL-3, IL-6, IL-7, G-CSF, GM-CSF, CF, Flt3 ligand, and erythropoietin) and various concentrations of known chemotherapeutic agents in combination with either compounds of the present disclosure. Colonies are counted by microscopy 12-14 days later. This method can be used to test for evidence of additive or synergistic activity.

Example 268

In Vivo Effect of Kinase Inhibitors on Leukemic Cells

Female recipient mice are lethally irradiated from a γ source in two doses about 4 hr apart, with approximately 5Gy each. About 1 hr after the second radiation dose, mice are injected i.v. with about $1\times10^6$ leukemic cells (e.g., Ph+ human or murine cells, or p190 transduced bone marrow cells). These cells are administered together with a radioprotective dose of about $5\times10^6$ normal bone marrow cells from 3-5 week old donor mice. Recipients are given antibiotics in the water and monitored daily. Mice who become sick after about 14 days are euthanized and lymphoid organs are harvested for analysis. Kinase inhibitor treatment begins about 10 days after leukemic cell injection and continues daily until the mice become sick or a maximum of approximately 35 days post-transplant. Inhibitors are given by oral lavage.

Peripheral blood cells are collected approximately on day 10 (pre-treatment) and upon euthanization (post treatment), contacted with labeled anti-hCD4 antibodies and counted by flow cytometry. This method can be used to demonstrate that the synergistic effect of one or more compounds provided herein in combination with known chemotherapeutic agents can reduce leukemic blood cell counts as compared to treatment with known chemotherapeutic agents (e.g., Gleevec) alone under the conditions tested.

Example 269

Treatment of Lupus Disease Model Mice

Mice lacking the inhibitory receptor FcγRIIb that opposes PI3K signaling in B cells develop lupus with high penetrance. FcγRIIb knockout mice (R2KO, Jackson Labs) are considered a valid model of the human disease as some lupus patients show decreased expression or function of FcγRIIb (S. Bolland and J. V. Ravtech 2000. *Immunity* 12:277-285).

The R2KO mice develop lupus-like disease with antinuclear antibodies, glomerulonephritis and proteinurea within about 4-6 months of age. For these experiments, the rapamycin analogue RAD001 (available from LC Laboratories) is used as a benchmark compound, and administered orally. This compound has been shown to ameliorate lupus symptoms in the B6.Sle1z.Sle3z model (T. Wu et al. *J. Clin Invest.* 117:2186-2196).

The NZB/W F1 mice spontaniously develop a systemic autoimmune disease with that is a model of lupus. The mice are treated starting at 20 weeks of age for a profilactic model and at 23 weeks of age for a therapeutic model. Blood and urine samples are obtained at approximately throughout the testing period, and tested for antinuclear antibodies (in dilutions of serum) or protein concentration (in urine). Serum is also tested for anti-ssDNA and anti-dsDNA antibodies by ELISA. Glomerulonephritis is assessed in kidney sections stained with H&E at the end of the study, or survival can be an endpoint. For example, the proteozome inhibitor Bortezimib is effective at blocking disease in the NZB/W model in both the profilactic and therapeuctic model with reductions in auto-antibody production, kidney damage, and improvements in survival (*Nature Medicine* 14, 748-755 (2008)).

Lupus disease model mice such as R2KO, BXSB or MLR/lpr are treated at about 2 months old, approximately for about two months. Mice are given doses of: vehicle, RAD001 at about 10 mg/kg, or compounds provided herein at approximately 1 mg/kg to about 500 mg/kg. Blood and urine samples are obtained at approximately throughout the testing period, and tested for antinuclear antibodies (in dilutions of serum) or protein concentration (in urine). Serum is also tested for anti-ssDNA and anti-dsDNA antibodies by ELISA Animals are euthanized at day 60 and tissues harvested for measuring spleen weight and kidney disease. Glomerulonephritis is assessed in kidney sections stained with H&E. Other animals are studied for about two months after cessation of treatment, using the same endpoints.

This established art model can be employed to demonstrate that the kinase inhibitors provided herein can suppress or delay the onset of lupus symptoms in lupus disease model mice.

Example 270

Murine Bone Marrow Transplant Assay

Female recipient mice are lethally irradiated from a γ ray source. About 1 hr after the radiation dose, mice are injected with about $1\times10^6$ leukemic cells from early passage p190 transduced cultures (e.g., as described in *Cancer Genet Cytogenet.* 2005 August; 161(1):51-6). These cells are administered together with a radioprotective dose of approximately $5\times10^6$ normal bone marrow cells from 3-5 wk old donor mice. Recipients are given antibiotics in the water and monitored daily. Mice who become sick after about 14 days are euthanized and lymphoid organs harvested for flow cytometry and/or magnetic enrichment. Treatment begins on approximately day 10 and continues daily until mice become sick, or after a maximum of about 35 days post-transplant. Drugs are given by oral gavage (p.o.). In a pilot experiment a dose of chemotherapeutic that is not curative but delays leukemia onset by about one week or less is identified; controls are vehicle-treated or treated with chemotherapeutic agent, previously shown to delay but not cure leukemogenesis in this model (e.g., imatinib at about 70 mg/kg twice daily). For the first phase p190 cells that express eGFP are used, and post-mortem analysis is limited to enumeration of the percentage of leukemic cells in bone marrow, spleen and lymph node (LN) by flow cytometry. In the second phase, p190 cells that express a tailless form of human CD4 are used and the post-mortem analysis includes magnetic sorting of hCD4+ cells from spleen followed by immunoblot analysis of key signaling endpoints: p Akt-T308 and S473; pS6 and p4EBP-1. As controls for immunoblot detection, sorted cells are incubated in the presence or absence of kinase inhibitors of the present disclosure inhibitors before lysis. Optionally, "phosflow" is used to detect p Akt —S473 and pS6-S235/236 in hCD4-gated cells without prior sorting. These signaling studies are particularly useful if, for example, drug-treated mice have not developed clinical leukemia at the 35 day time point. Kaplan-Meier plots of survival are generated and statistical analysis done according to methods known in the art. Results from p190 cells are analyzed separated as well as cumulatively.

Samples of peripheral blood (100-200 μl) are obtained weekly from all mice, starting on day 10 immediately prior to commencing treatment. Plasma is used for measuring drug concentrations, and cells are analyzed for leukemia markers (eGFP or hCD4) and signaling biomarkers as described herein.

This general assay known in the art can be used to demonstrate that effective therapeutic doses of the compounds provided herein can be used for inhibiting the proliferation of leukemic cells.

Example 271

Matrigel Plug Angiogenesis Assay

Matrigel containing test compounds are injected subcutaneously or intraocularly, where it solidifies to form a plug. The plug is recovered after 7-21 days in the animal and examined histologically to determine the extent to which blood vessels have entered it. Angiogenesis is measured by quantification of the vessels in histologic sections. Alternatively, fluorescence measurement of plasma volume is performed using fluorescein isothiocyanate (FITC)-labeled dextran 150. The results are expected to indicate one or more compounds provided herein that inhibit angiogenesis and are thus expected to be useful in treating ocular disorders related to aberrant angiogenesis and/or vascular permeability.

Example 272

Corneal Angiogenesis Assay

A pocket is made in the cornea, and a plug containing an angiogenesis inducing formulation (e.g., VEGF, FGF, or tumor cells), when introduced into this pocket, elicits the ingrowth of new vessels from the peripheral limbal vasculature. Slow-release materials such as ELVAX (ethylene vinyl copolymer) or Hydron are used to introduce angiogenesis inducing substances into the corneal pocket. Alternatively, a sponge material is used.

The effect of putative inhibitors on the locally induced (e.g., sponge implant) angiogenic reaction in the cornea (e.g., by FGF, VEGF, or tumor cells). The test compound is administered orally, systemically, or directly to the eye. Systemic administration is by bolus injection or, more effectively, by use of a sustained-release method such as implantation of osmotic pumps loaded with the test inhibitor. Administration to the eye is by any of the methods described herein including, but not limited to eye drops, topical administration of a cream, emulsion, or gel, intravitreal injection.

The vascular response is monitored by direct observation throughout the course of the experiment using a stereomicroscope in mice. Definitive visualization of the corneal vasculature is achieved by administration of fluorochrome-labeled high-molecular weight dextran. Quantification is performed by measuring the area of vessel penetration, the progress of vessels toward the angiogenic stimulus over time, or in the case of fluorescence, histogram analysis or pixel counts above a specific (background) threshold.

The results can indicate one or more compounds provided herein inhibit angiogenesis and thus can be useful in treating ocular disorders related to aberrant angiogenesis and/or vascular permeability.

Example 273

Microtiter-Plate Angiogenesis Assay

The assay plate is prepared by placing a collagen plug in the bottom of each well with 5-10 cell spheroids per collagen plug each spheroid containing 400-500 cells. Each collagen plug is covered with 1100 µl of storage medium per well and stored for future use (1-3 days at 37° C., 5% $CO_2$). The plate is sealed with sealing. Test compounds are dissolved in 200 µl assay medium with at least one well including a VEGF positive control and at least one well without VEGF or test compound as a negative control. The assay plate is removed from the incubator and storage medium is carefully pipeted away. Assay medium containing the test compounds are pipeted onto the collagen plug. The plug is placed in a humidified incubator for (37° C., 5% $CO_2$) 24-48 hours. Angiogenesis is quantified by counting the number of sprouts, measuring average sprout length, or determining cumulative sprout length. The assay can be preserved for later analysis by removing the assay medium, adding 1 ml of 10% paraformaldehyde in Hanks BSS per well, and storing at 4° C. The results are expected to identify compounds that inhibit angiogenesis in various cell types tested, including cells of ocular origin.

Example 274

Combination Use of PI3K-δ Inhibitors and Agents that Inhibit IgE Production or Activity The compounds as provided herein can present synergistic or additive efficacy when administered in combination with agents that inhibit IgE production or activity. Agents that inhibit IgE production include, for example, one or more of TEI-9874, 2-(4-(6-cyclohexyloxy-2-naphtyloxy)phenylacetamide)benzoic acid, rapamycin, rapamycin analogs (i.e., rapalogs), TORC1 inhibitors, TORC2 inhibitors, and any other compounds that inhibit mTORC1 and mTORC2. Agents that inhibit IgE activity include, for example, anti-IgE antibodies such as Omalizumab and TNX-901.

One or more of the subject compounds capable of inhibiting PI3K-δ can be efficacious in treatment of autoimmune and inflammatory disorders (AIID), for example, rheumatoid arthritis. If any of the compounds causes an undesired level of IgE production, one can choose to administer it in combination with an agent that inhibits IgE production or IgE activity. Additionally, the administration of PI3K-δ or PI3K-δ/γ inhibitors as provided herein in combination with inhibitors of mTOR can also exhibit synergy through enhanced inhibition of the PI3K pathway. Various in vivo and in vitro models can be used to establish the effect of such combination treatment on AIID including, but not limited to (a) in vitro B-cell antibody production assay, (b) in vivo TNP assay, and (c) rodent collagen induced arthritis model.

(a) B-Cell Assay

Mice are euthanized, and the spleens are removed and dispersed through a nylon mesh to generate a single-cell suspension. The splenocytes are washed (following removal of erythrocytes by osmotic shock) and incubated with anti-CD43 and anti-Mac-1 antibody-conjugated microbeads (Miltenyi Biotec). The bead-bound cells are separated from unbound cells using a magnetic cell sorter. The magnetized column retains the unwanted cells and the resting B cells are collected in the flow-through. Purified B-cells are stimulated with lipopolysaccharide or an anti-CD40 antibody and interleukin 4 Stimulated B-cells are treated with vehicle alone or with PI3K-δ inhibitors as provided herein with and without mTOR inhibitors such as rapamycin, rapalogs, or mTORC1/C2 inhibitors. The results are expected to show that in the presence of mTOR inhibitors (e.g., rapamycin) alone, there is little to no substantial effect on IgG and IgE response. However, in the presence of PI3K-δ and mTOR inhibitors, the B-cells are expected to exhibit a decreased IgG response as compared to the B-cells treated with vehicle alone, and the B-cells are expected to exhibit a decreased IgE response as compared to the response from B-cells treated with PI3K-δ inhibitors alone.

(b) TNP Assay

Mice are immunized with TNP-Ficoll or TNP-KHL and treated with: vehicle, a PI3K-δ inhibitor, an mTOR inhibitor, for example rapamycin, or a PI3K-δ inhibitor in combination with an mTOR inhibitor such as rapamycin. Antigen-specific serum IgE is measured by ELISA using TNP-BSA coated plates and isotype specific labeled antibodies. It is expected that mice treated with an mTOR inhibitor alone exhibit little or no substantial effect on antigen specific IgG3 response and no statistically significant elevation in IgE response as compared to the vehicle control. It is also expected that mice treated with both PI3K-δ inhibitor and mTOR inhibitor exhibit a reduction in antigen specific IgG3 response as compared to the mice treated with vehicle alone. Additionally, the mice treated with both PI3K-δ inhibitor and mTOR inhibitor exhibit a decrease in IgE response as compared to the mice treated with PI3K-δ inhibitor alone.

(c) Rat Collagen Induced Arthritis Model

Female Lewis rats are anesthetized and given collagen injections prepared and administered as described previously on day 0. On day 6, animals are anesthetized and given a second collagen injection. Caliper measurements of normal (pre-disease) right and left ankle joints are performed on day 9. On days 10-11, arthritis typically occurs and rats are randomized into treatment groups. Randomization is performed after ankle joint swelling is obviously established and there is good evidence of bilateral disease.

After an animal is selected for enrollment in the study, treatment is initiated. Animals are given vehicle, PI3K-δ inhibitor, or PI3K-δ inhibitor in combination with rapamycin. Dosing is administered on days 1-6. Rats are weighed on days 1-7 following establishment of arthritis and caliper measurements of ankles taken every day. Final body weights are taken on day 7 and animals are euthanized.

The combination treatment using a compound as provided herein and rapamycin can provide greater efficacy than treatment with PI3K-δ inhibitor alone.

Certain compounds provided herein (e.g., Compounds 5, 49, and 359) were tested in the rat Collagen Induced Arthritis Model using procedures substantially similar to those described above, and all of the tested compounds demonstrated $EC_{50}$ values of less than 50 mg/kg.

Example 275

Delayed Type Hypersensitivity Model

DTH was induced by sensitizing 60 BALB/c male mice on day 0 and day 1 with a solution of 0.05% 2,4 dinitrofluorobenzene (DNFB) in a 4:1 acetone/olive oil mixture. Mice were gently restrained while 20 μL of solution was applied to the hind foot pads of each mouse. The hind foot pads of the mice were used as they represent an anatomical site that can be easily isolated and immobilized without anesthesia. On day 5, mice were administered a single dose of vehicle, a compound provided herein at 10, 3, 1, or 0.3 mg/kg, or dexamethasone at a dose of 5 mg/kg by oral gavage. Thirty minutes later mice were anaesthetized, and a solution of 0.25% DNFB in a 4:1 acetone/olive oil solution was applied to the left inner and outer ear surface. This application resulted in the induction of swelling to the left ear and under these conditions, all animals responded to this treatment with ear swelling. A vehicle control solution of 4:1 acetone/olive oil was applied to the right inner and outer ear. Twenty four hours later, mice were anaesthetized, and measurements of the left and right ear were taken using a digital micrometer. The difference between the two ears was recorded as the amount of swelling induced by the challenge of DNFB. Drug treatment groups were compared to vehicle control to generate the percent reduction in ear swelling. Dexamethasone is routinely used as a positive control as it has broad anti-inflammatory activity.

Example 276

Peptidoglycan-Polysaccharide Rat Arthritic Model (a) Systemic Arthritis Model

All injections are performed under anesthesia. 60 female Lewis rats (150-170) are anesthetized by inhalation isoflurane using a small animal anesthesia machine. The animals are placed in the induction chamber until anesthetized by delivery of 4-5% isoflurane in $O_2$ and then held in that state using a nose cone on the procedure table. Maintenance level of isoflurane is at 1-2%. Animals are injected intraperitoneally (i.p.) with a single injection of purified PG-PS 10S Group A, D58 strain (concentration 25 μg/g of bodyweight) suspended in sterile 0.85% saline. Each animal receives a total volume of 500 microliters administered in the lower left quadrant of the abdomen using a 1 milliliter syringe with a 23 gauge needle. Placement of the needle is critical to avoid injecting the PG-PS 10S into either the stomach or caecum. Animals are under continuous observation until fully recovered from anesthesia and moving about the cage. An acute response of a sharp increase in ankle measurement, typically 20% above baseline measurement can peak in 3-5 days post injection. Treatment with test compounds can be PO, SC, IV or IP. Rats are dosed no more than two times in a 24 hour time span. Treatment can begin on day 0 or any day after that through day 30. The animals are weighed on days 0, 1, 2, 3, 4, 5, 6, 7 and beginning again on day 12-30 or until the study is terminated. Paw/ankle diameter is measured with a digital caliper on the left and right side on day 0 prior to injection and again on day 1, 2, 3, 4, 5, 6 and 7. On day 12, measurements begin again and continue on through day 30. At this time, animals can be anesthetized with isoflurane, as described above, and terminal blood samples can be obtained by tail vein draws for the evaluation of the compound blood levels, clinical chemistry or hematology parameters. Animals are them euthanized with carbon dioxide overdose. A thoracotomy can be conducted as a means of death verification.

(b) Monoarticular Arthritis Model

All injections are performed under anesthesia. 60 female Lewis rats (150-170) are anesthetized by inhalation isoflurane using a small animal anesthesia machine. The animals are placed in the induction chamber until anesthetized by delivery of 4-5% isoflurane in $O_2$ and then held in that state using a nose cone on the procedure table. Maintenance level of isoflurane is at 1-2%. Animals are injected intra-articular (i.a.) with a single injection of purified PG-PS 100P Group A, D58 strain (concentration 500 ug/mL) suspended in sterile 0.85% saline. Each rat receives a total volume of 10 microliters administered into the tibiotalar joint space using a 1 milliliter syringe with a 27 gauge needle. Animals are under continuous observation until fully recovered from anesthesia and moving about the cage. Animals that respond 2-3 days later with a sharp increase in ankle measurement, typically 20% above baseline measurement on the initial i.a. injection, are included in the study. On day 14, all responders are anesthetized again using the procedure previously described. Animals receive an intravenous (I.V.) injection of PG-PS (concentration 250 uL/mL). Each rat receives a total volume of 400 microliters administered slowly into the lateral tail vein using a 1 milliliter syringe with a 27 gauge needle. Baseline ankle measurements are measured prior to IV injection and continue through the course of inflammation or out to day 10. Treatment with test compounds will be PO, SC, IV or IP. Rats are dosed no more than two times in a 24 hour time span. Treatment can begin on day 0 or any day after that through day 24. The animals are weighed on days 0, 1, 2, 3, 4, 5, and beginning again on day 14-24 or until the study is terminated. Paw/ankle diameter is measured with a digital caliper on the left and right side on day 0 prior to injection and again on day 1, 2, 3, 4, 5, and beginning again on day 14-24 or until the study is terminated. At this time, animals can be anesthetized with isoflurane, as described above, and terminal blood samples can be obtained by tail vein draws for the evaluation of the compound blood levels, clinical chemistry or hematology parameters. Animals are them euthanized with carbon dioxide overdose. A thoracotomy can be conducted as a means of death verification.

Example 277

Mice Models for Asthma

Efficacy of a compound provided herein in treating, preventing and/or managing asthma can be assessed using an conventional animal models including various mice models described in, for example, Nials et al., *Dis Model Mech.* 1(4-5): 213-220 (2008).

(a) Acute Allergen Challenge Models

Several models are known in the art and any of such models can be used. Although various allergens can be used to induce asthma-like conditions, the principle is consistent throughout the methods. Briefly, asthma-like conditions are induced through multiple systemic administration of the allergen (e.g., ova, house dust mite extracts and cockroach extracts) in the presence of an adjuvant such as aluminum hydroxide. Alternatively, an adjuvant-free system can be used, but it usually requires a higher number of exposures to achieve suitable sensitization. Once induced, animals exhibit many key features of clinical asthma such as: elevated levels of IgE; airway inflammation; goblet cell hyperplasia; epithelial hypertrophy; AHR ro specific stimuli; and early and late phase bronchoconstriction. Potential efficacy of a compound thus can be assessed by determining whether one or more of these clinical features are reversed or mitigated.

(b) Chronic Allergen Challenge Models

Chronic allergen challenge models aim to reproduce more of the features of the clinical asthma, such as airway remodeling and persistent AHR, than acute challenge models. While allergens similar to those used in acute allergen challenge models can be used, in chronic allergen challenge models, animals are subjected to repeated exposure of the airways to low levels of allergen for a period of up to 12 weeks. Once induced, animals exhibit key features of human asthma such as: allergen-dependent sensitization; a Th2-dependent allergic inflammation characterized by eosinophillic influx into the airway mucosa; AHR; and airway remodeling as evidenced by goblet cell hyperplasia, epithelial hypertrophy, subepithelial or peribronchiolar fibrosis. Potential efficacy of a compound thus can be assessed by determining whether one or more of these clinical features are reversed or mitigated.

Example 278

Models for Psoriasis

Efficacy of a compound provided herein in treating, preventing and/or managing psoriasis can be assessed using an conventional animal models including various animal models described in, for example, Boehncke et al., *Clinics in Dermatology,* 25: 596-605 (2007).

As an example, the mouse model based on adoptive transfer of $CD4^+CD45RB^{hi}$ T cells described in Hong et al., *J. Immunol.,* 162: 7480-7491 (1999) can be made. Briefly, female BALB/cBY (donor) and C.B.-17/Prkdc scid/scid (recipient) mice are housed in a specific pathogen-free environment and are used between 6 and 8 weeks of age. CD4 T cells are enriched from BALB/cBy splenocytes using a mouse CD4 enrichment kit. The cells are then labeled with PE-conjugated anti-CD4, FITC-conjugated anti-CD45RB, and APC-conjugated anti-CD25 antibodies. Cells are sorted using a cell sorter. $CD4^+CD45RB^{hi}CD25$ cells are collected. Cells are resuspended in saline and $4 \times 10^8$ cells/mouse are injected i.p. into C.B.-17/Prkdc scid/scid mice. Mice may be dosed with LPS, cytokines, or antibodies as necessary. Mice are monitored for external signs of skin lesions twice each week. After the termination, ear, back skin, lymph nodes and spleen may be collected for further ex vivo studies.

Example 279

Models for Scleroderma

A compound's efficacy in treating scleroderma can be tested using animal models. An exemplary animal model is a mouse model for scleroderma induced by repeated local injections of bleomycin ("BLM") described, for example, in Yamamoto et al., *J Invest Dermatol* 112: 456-462 (1999), the entirety of which is incorporated herein by reference. This mouse model provides dermal sclerosis that closely resembles systemic sclerosis both histologically and biochemically. The sclerotic changes observed in the model include, but are not limited to: thickened and homogenous collagen bundles and cellular filtrates; gradual increase in number of mast cells; degranulation of mast cells; elevated histamine release; increase in hydroxyproline in skin; presence of anti-nuclear antibody in serum; and strong expression of transforming growth factor β-2 mRNA. Therefore, efficacy of a compound in treating scleroderma can be assessed by monitoring the lessening of one or more of these changes.

Briefly, the following exemplary procedures can be used to generate the mouse model for scleroderma: Specific pathogen-free, female BALB/C mice and C3H mice of 6 weeks old, weighing about 20 g, are purchased and maintained with food and water ad libitum. BLM is dissolved in PBS at differing concentrations and sterilized with filtration. Aliquots of each concentration of BLM or PBS are injected subcutaneously into the shaved back of the mice daily for 1-4 weeks with a needle. Alternatively, mice are injected every other day.

Histopathological and biochemical changes induced can be assessed using any methods commonly practiced in the field. For example, histopathological changes can be assessed using a standard avidine-biotin peroxidase technique with anti-L3T4 monoclonal antibody, anti-Lyt2 monoclonal antibody, anti-mouse pan-tissue-fixed macrophage antibody, anti-stem cell factor monoclonal antibody, anti-transforming growth factor-13 polyclonal antibody, and anti-decorin antibody. Cytokine expression of cellular infiltrates can be assessed by using several anti-cytokine antibodies. Hydroxyproline level can be assessed by hydrolyzing skin pieces with hydrochloric acid, neutralizing with sodium hydroxide, and colorimetrically assessing the hydrolates at 560 nm with p-dimethylaminobenzaldehyde. Pepsin-resistant collagen can be assessed by treating collagen sample extracted from biopsied tissues and analyzing by polyacrylamide stacking gel electrophoresis. Mast cells can be identified by toluidine blue, and cells containing matachromatic granules can be counted under high magnification of a light microscope. Serum levels of various cytokines can be assessed by enzyme-linked immunosorbent assay, and mRNA levels of the cytokines can be assessed by reverse-transcriptase polymerase chain reaction. Autoantibodies in serum can be detected using 3T3 fibroblasts as the substrate for the screening.

Example 280

Models for Myositis

A compound's efficacy in treating myositis (e.g., dermatomyositis) can be tested using animal models known in the art. One such example is the familial canine dermatomyositis model described in Hargis et al., *AJP* 120(2): 323-325 (1985). Another example is the rabbit myosin induced mouse model described in Phyanagi et al., *Arthritis & Rheumatism*, 60(10): 3118-3127 (2009).

Briefly, 5-week old male SJL/J mice are used. Purified myosin from rabbit skeletal muscle (6.6 mg/ml) is emulsified with an equal amount of Freund's complete adjuvant and 3.3 mg/ml *Mycobacterium butyricum*. The mice are immunized repeatedly with emulsified rabbit myosin. Once myositis is induced, inflammatory cell filtration and necrotic muscle fiber should be evident in the model. In the muscles of animals, $CD4^+$ T cells are mainly located in the perimysum and $CD8^+$ T cells are mainly located in the endomysium and surround non-necrotic muscle fibers. TNFα, IFNγ and perforin are up-regulated and intercellular adhesion molecule 1 is increased in the muscles.

To assess the efficacy of a compound, following administration of the compound through adequate route at specified dose, the mice are killed and muscle tissues are harvested. The muscle tissue is immediately frozen in chilled isopentane precooled in liquid nitrogen, and then cryostat sections are prepared. The sections are stained with hematoxylin and eosin for counting of number of infiltrated cells. Three sections from each mouse are prepared and photomicrographs are obtained. For immunohistochemical tests, cryostat sections of muscle are dried and fixed in cold acetone at $-20°$ C. The slides are rehydrated in PBS, and then endogenous peroxide activity is blocked by incubation in 1% hydrogen peroxide. The sections are incubated overnight with rat anti-mouse CD4 monoclonal antibody, rat anti-mouse CD8 monoclonal antibody, rat anti-mouse F4/80 monoclonal antibody or normal rat IgG in antibody diluent. The samples are washed with PBS and incubated with biotin-conjugated rabbit anti-rat IgG pretreated with 5% normal mouse serum. After washing with PBS, the samples are incubated with streptavidin-horseradish peroxidase. After washing PBS, diaminobenzidine is used for visualization.

Example 281

Models for Sjögren Syndrome

A compound's efficacy in treating Sjögren's syndrome can be tested using animal models known in the art, for example, those described in Chiorini et al., *Journal of Autoimmunity* 33: 190-196 (2009). Examples include: mouse model spontaneously developed in first filial generation of NZB mice crossed to NZW mice (see, e.g., Jonsson et al., *Clin Immunol Immunopathol* 42: 93-101 (1987); mouse model induced by i.p. injection of incomplete Freund's adjuvant (id.; Deshmukh et al., *J Oral Pathol Med* 38: 42-27 (2009)); NOD mouse models wherein Sjögren's phenotype is developed by specific genotypes (see, e.g., Cha et al., *Arthritis Rheum* 46: 1390-1398 (2002); Kong et al., *Clin Exp Rheumatol* 16: 675-681 (1998); Podolin et al., *J Exp Med* 178: 793-803 (1993); and Rasooly et al., *Clin Immunol Immunopathol* 81: 287-292 (1996)); mouse model developed in spontaneous lpr mutation; mouse model developed in Id3 knock-out mice (see, e.g., Li et al., *Immunity* 21: 551-560 (2004)); mouse model developed in PI3K knock-out mice (see, e.g., Oak et al., *Proc Natl Acad Sci USA* 103: 16882-16887 (2006)); mouse model developed in BAFF over-expressing transgenic mice (see, e.g., Groom et al., *J Clin Invest* 109: 59-68 (2002)); mouse model induced by injection of Ro antigen into BALB/c mice (see, e.g., Oh-Hora et al., *Nat. Immunol* 9: 432-443 (2008)); mouse model induced by injection of carbonic anhydrase II (see, e.g., Nishimori et al., *J Immunol* 154: 4865-4873 (1995); mouse model developed in IL-14 over-expressing transgenic mice (see, e.g., Shen et al., *J Immunol* 177: 5676-5686 (2006)); and mouse model developed in IL-12 expressing transgenic mice (see, e.g., McGrath-Morrow et al., *Am J Physiol Lung Cell Mol Physiol* 291: L837-846 (2006)).

Example 282

Models for Immune Complex Mediated Disease

The Arthus reaction is a type 3 immune response to immune complexes, and thus, can be a mechanistic model supporting therapeutic hypothesis for immune complex mediated diseases such as rheumatoid arthritis, lupus and other autoimmune diseases. For example, PI3Kγ and δ deficient mice can be used as experimental models of the Arthus reaction and provide assessment of therapeutic potential of a compound as to the treatment of immune complex mediated diseases. The Arthus reaction can be induced using the following exemplary procedures as described in Konrad et al., *Journal of Biological Chemistry* (2008 283(48): 33296-33303.

PI3Kγ- and PI3Kδ-deficient mice are maintained under dry barrier conditions. Mice are anesthetized with ketamine and xylazine, and the trachea is cannulated. Appropriate amount of protein G-purified anti-OVA IgG Ab is applied, and appropriate amount of OVA antigen is given intravenously. For PI3K blocking experiments, wortmanin is given intratracheally together with the application of anti-OVA IgG. Mice are killed at 2-4 hours after initiation of inflammation, and desired follow up assessments can be performed using methods known in the art.

Example 283

Isoform-Selective Cellular Assays (a) PI3Kδ Selective Assay

A compound's ability in selectively inhibiting PI3Kδ can be assessed using RAJI cells, i.e., B lymphocyte cells derived from lymphoma patients. Briefly, serum-starved RAJI cells are stimulated with anti-human IgM, thereby causing signaling through the B-cell receptors, as described in, for example, He et al., *Leukemia Research* (2009) 33: 798-802. B-cell receptor signaling is important for the activation, differentiation, and survival of B cells and certain B-cell derived cancers. Reduction of phospho-AKT is indicative of compounds that may inhibit B-cell proliferation and function in certain diseases. By monitoring the reduction of phospho-AKT in stimulated RAJI cells (using for example, phospho-AKT antibodies), a compound's potential efficacy in selectively inhibiting PI3Kδ can be assessed.

Certain compounds provided herein (e.g., Compounds 5, 49, 104, 138, 157, 191, 241, 242, 270, 273, 279, 285, 288, 291, 312, 316, 326, 327, 328, 329, 333, 334, 335, 336, 337, 338, 353, 354, 356, 359, 378, 379, 382, 383, 387, 389, 391, 393, 394, 396, 397, 399, 401, 402, 403, 408, 410, 412, 413, 414, 415, 416, 417, 418, 419, 422, 424, 425, and 428) were tested in RAJI cell model using procedures as described above. It was found that $IC_{50}$ values for phospho-AKT are as follows: Compounds 5, 49, 104, 138, 157, 191, 241, 242, 270, 273, 279, 285, 288, 291, 312, 316, 326, 327, 328, 329, 333, 334, 335, 336, 337, 338, 353, 354, 356, 359, 378, 379, 382, 383, 387, 389, 391, 393, 394, 396, 397, 399, 401, 402, 403, 408, 410, 412, 413, 414, 415, 416, 417, 418, 419, 422, 424, 425, and 428 in the range of less than 100 nM.

(b) PI3Kγ Selective Assay

A compound's ability in selectively inhibiting PI3Kγ can be assessed using RAW264.7 macrophages. Briefly, serum-starved PAW264.7 cells are stimulated with a known GPCR agonist C5a. (See, e.g., Camps et al., *Nature Medicine* (2005) 11(9): 936-943). Cells can be treated with test compounds prior to, simultaneously with, or subsequent to the stimulation by C5a. RAW 264.7 cells respond to the complement component fragment C5a through activation of the C5a receptor, and the C5a receptor activates macrophages and induces cell migration. Test compounds' ability to inhibit C5a-mediated AKT phosphorylation is indicative of selective inhibition of PI3Kγ. Thus, by monitoring the reduction of phospho-AKT in stimulated RAW 264.7 cells (using for example, phospho-AKT antibodies), a compound's potential efficacy in selectively inhibiting PI3Kγ can be assessed.

Certain compounds provided herein (e.g., Compounds 5, 49, 104, 127, 138, 157, 191, 241, 242, 270, 273, 276, 279, 285, 288, 291, 312, 316, 326, 327, 328, 329, 333, 334, 335, 336, 337, 338, 353, 354, 356, 359, 378, 379, 382, 383, 387, 389, 391, 393, 394, 396, 397, 399, 401, 402, 403, 408, 410, 412, 413, 414, 415, 416, 417, 418, 419, 422, 424, 425, and 428) were tested in RAW 264.7 cell model using procedures as described above. It was found that $IC_{50}$ values for phospho-AKT are as follows: Compounds 5, 49, 127, 138, 157, 241, 270, 276, 279, 285, 288, 291, 316, 379, 382, 383, 394, 397, 399, 403, 408, 410, 412, 413, 414, 415, 416, 417, 418, 419, 422, and 428 in the range of less than 100 nM; Compounds 104, 242, 273, 312, 326, 327, 328, 329, 335, 356, 378, 387, 389, 391, 393, 396, 401, 424, and 425 in the range of between 100 nM and 1 μM; Compounds 191, 333, 334, 336, 337, 338, 353, 354, 359, and 402 in the range of between 1 μM and 10 μM.

(c) PI3Kα Selective Assay

A compound's ability in selectively inhibiting PI3Kα can be assessed using SKOV-3 cells, i.e., human ovarian carcinoma cell line. Briefly, SKOV-3 cells, in which mutant PI3Kα is constitutively active, can be treated with test compounds. Test compounds' ability to inhibit AKT phosphorylation in SKOV-3 cells, therefore, is indicative of selective inhibition of PI3Kα. Thus, by monitoring the reduction of phospho-AKT in SKOV-3 cells (using for example, phospho-AKT antibodies), a compound's potential efficacy in selectively inhibiting PI3Kα can be assessed.

Certain compounds provided herein (e.g., Compounds 5, 49, 138, 326, 328, 354, 359, 389, and 391) were tested in SKOV-3 cell model using procedures as described above. It was found that $IC_{50}$ values for phospho-AKT are as follows: Compounds 138 and 328 in the range of between 100 nM and 1 μM; Compounds 5, 49, 326, 359, and 389 in the range of between 1 μM and 10 μM; and Compounds 354 and 391 in the range of greater than 10 μM.

(d) PI3K/β Selective Assay

A compound's ability in selectively inhibiting PI3Kβ can be assessed using 786-O cells, i.e., human kidney carcinoma cell line. Briefly, 786-O cells, in which PI3Kβ is constitutively active, can be treated with test compounds. Test compounds' ability to inhibit AKT phosphorylation in 786-O cells, therefore, is indicative of selective inhibition of PI3Kβ. Thus, by monitoring the reduction of phospho-AKT in 786-O cells (using for example, phospho-AKT antibodies), a compound's potential efficacy in selectively inhibiting PI3Kβ can be assessed.

Certain compounds provided herein (e.g., Compounds 5, 49, 138, 326, 328, 354, 359, 389, and 391) were tested in 786-O cell model using procedures as described above. It was found that $IC_{50}$ values for phospho-AKT are as follows: Compounds 326 and 359 in the range of between 100 nM and 1 μM; Compounds 49, 138, 328, 354, and 389 in the range of between 1 μM and 10 μM; and Compounds 5 and 391 in the range of greater than 10 μM.

What is claimed is:

1. A compound of Formula (IIb):

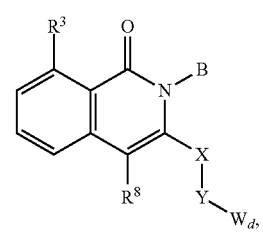

Formula (IIb)

or a pharmaceutically acceptable salt or stereoisomer thereof, wherein

B is alkyl;

X is —CH($R^9$)—;

Y is —O—, —S—, —S(=O)—, —S(=O)$_2$—, —N($R^9$)—, —(=O)—(CHR$^9$)$_z$—, —C(=O)—, —N($R^9$)—C(=O)NH—, or —N($R^9$)C($R^9$)$_2$—;

each z is independently 1, 2, 3 or 4;

$R^3$ is heterocyclyl, heteroaryl, $C_{2-6}$alkyl, fluoro, chloro, bromo, iodo, cycloalkyl, cycloalkylalkyl, aryl, aralkyl, heteroaralkyl, heterocyclylalkyl, alkenyl, or alkynyl, or $R^3$ is a heteroatom selected from N, S, and O, wherein the heteroatom has a covalent bond, either directly or through a $C_1$-$C_6$ alkyl group, to an aryl, heteroaryl or heterocyclyl; wherein each of the above substituents is optionally substituted with 1, 2, or 3 $R^{13}$;

$R^8$ is hydrogen, alkyl, alkenyl, alkynyl, cycloalkyl, heteroalkyl, alkoxy, amino, acyl, acyloxy, sulfonamido, halo, cyano, hydroxy, or nitro;

each $R^9$ is independently alkyl, hydrogen, cycloalkyl, heterocyclyl or heteroalkyl;

W_d is

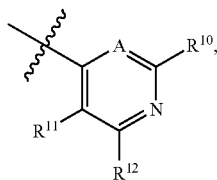

wherein A is N;

R[10], R[11], and R[12] are independently hydrogen, amino, cyano, alkyl, heteroalkyl, alkenyl, alkynyl, cycloalkyl, heterocyclyl, aryl, arylalkyl, heteroaryl, heteroarylalkyl, alkoxy, heterocyclyloxy, amido, acyl, acyloxy, sulfonamido, halo, hydroxy, nitro, phosphate, urea, carbonate, or NR'R" wherein R' and R" are taken together with nitrogen to form a cyclic moiety, and R[13] is independently hydrogen, amino, cyano, alkyl, heteroalkyl, alkenyl, alkynyl, cycloalkyl, heterocyclyl, aryl, arylalkyl, heteroaryl, heteroarylalkyl, alkoxy, heterocyclyloxy, amido, acyl, acyloxy, sulfonamido, halo, hydroxy, nitro, phosphate, urea, carbonate, oxo, or NR'R" wherein R' and R" are taken together with nitrogen to form a cyclic moiety.

2. The compound of claim 1, wherein

Y is —N(R[9])—;

R[3] is 6-membered heterocyclyl, 6-membered heteroaryl, or chloro;

R[8] is hydrogen;

each R[9] is independently alkyl or hydrogen;

R[10], R[11], and R[12] are independently hydrogen, amino, cyano, alkyl, or alkoxy; and R[13] is independently hydrogen, amino, cyano, alkyl, alkoxy, or oxo.

3. The compound of claim 1, wherein W_d is:

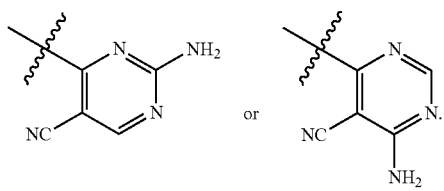 [SMILES: *c1nc(N)ncc1C#N ; *c1ncnc(N)c1C#N]

4. The compound of claim 1, or a pharmaceutically acceptable salt or stereoisomer thereof, wherein B is alkyl;

X is —CH(R[9])—;

Y is —NH—;

R[3] is chloro;

R[8] is hydrogen;

R[9] is alkyl;

W_d is

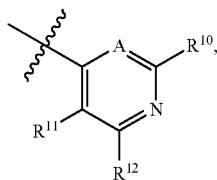

wherein A is N; and

R[10], R[11], and R[12] are independently hydrogen, amino, or cyano.

5. The compound of claim 4, having a structure of the Formula (IIIb-1):

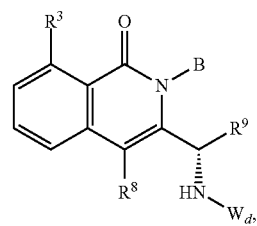

Formula (IIIb-1)

or a pharmaceutically acceptable salt or stereoisomer thereof.

6. The compound of claim 4, wherein the compound is:

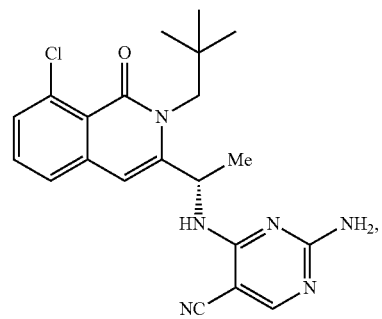

Compound 246

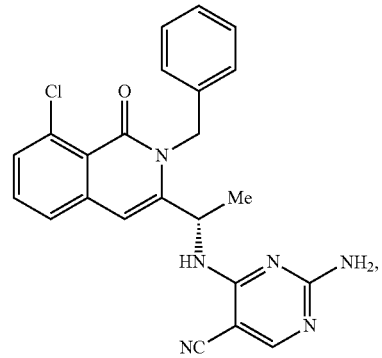

Compound 303

-continued

Compound 276
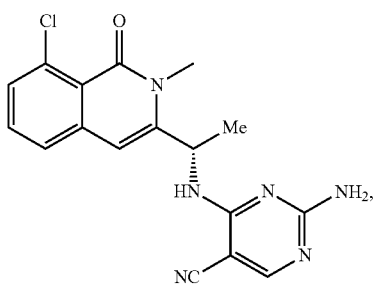

Compound 309
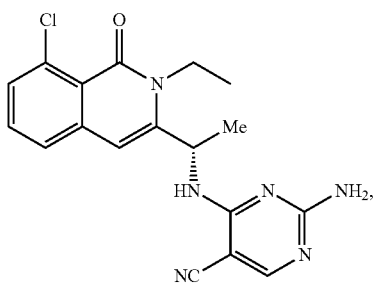

Compound 325
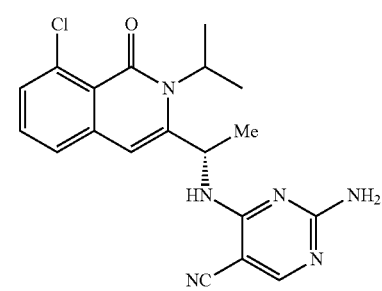

Compound 329
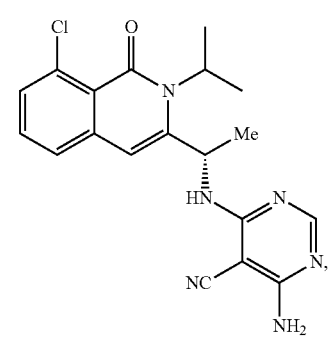

or a pharmaceutically acceptable salt or stereoisomer thereof.

7. A pharmaceutical composition comprising a compound according to claim 4 and one or more pharmaceutically acceptable excipients.

8. A pharmaceutical composition comprising a compound according to claim 1 and one or more pharmaceutically acceptable excipients.

9. A method of inhibiting phosphatidylinositol 3-kinase activity in a subject, the method comprising administering to said subject a therapeutically effective amount of a compound according to claim 4.

10. The method of claim 9, wherein the subject suffers from a disorder selected from cancer, an autoimmune disease, an inflammatory disease or a respiratory disease.

11. The method of claim 10, further comprising administering one or more therapeutic agents.

12. A method of inhibiting phosphatidylinositol 3-kinase activity in a subject, the method comprising administering to said subject a therapeutically effective amount of a compound according to claim 1.

13. A compound of Formula (IIb):

Formula (IIb)
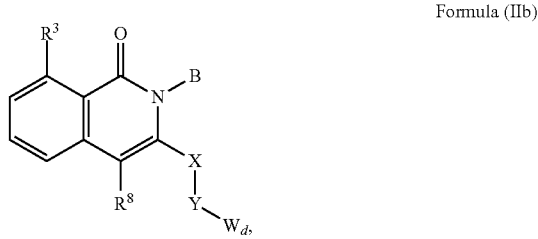

or a pharmaceutically acceptable salt or stereoisomer thereof, wherein
B is alkyl;
X is —CH($R^9$)—;
Y is —NH—;
$R^3$ is 6-membered heterocyclyl or 6-membered heteroaryl, wherein the heterocyclyl and heteroaryl are optionally substituted with 1, 2, or 3 $R^{13}$;
$R^8$ is hydrogen;
$R^9$ is alkyl;
$W_d$ is

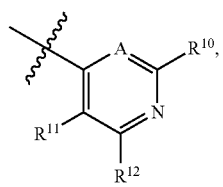

wherein A is N;
$R^{10}$, $R^{11}$, and $R^{12}$ are independently hydrogen, amino, or cyano; and
$R^{13}$ is independently alkyl, alkoxy, or oxo.

14. The compound of claim 13, wherein B is methyl, ethyl, or isopropyl.

15. The compound of claim 13, wherein B is isopropyl.

16. The compound of claim 13, wherein $W_d$ is:

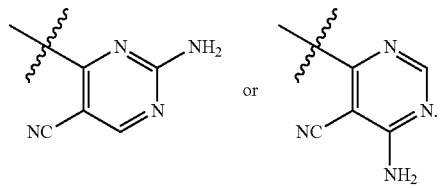 [SMILES: *c1nc(N)ncc1C#N ; *c1ncnc(N)c1C#N]

17. The compound of claim 13, wherein the compound has an (S)-enantiomeric excess of greater than 55%.

18. The compound of claim 13, wherein the compound has an (S)-enantiomeric excess of greater than 75%.

19. The compound of claim 13, wherein the compound has an (S)-enantiomeric excess of greater than 90%.

20. The compound of claim 13, wherein the compound has an (S)-enantiomeric excess of greater than 95%.

21. The compound of claim 13, wherein the compound has an (S)-enantiomeric excess of greater than 98%.

22. The compound of claim 13, having a structure of the Formula (IIIb-1):

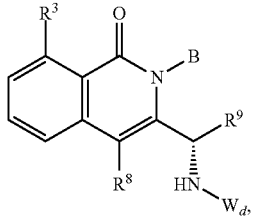

Formula (IIIb-1)

or a pharmaceutically acceptable salt or stereoisomer thereof.

23. The compound of claim 13, wherein the compound is:

Compound 326

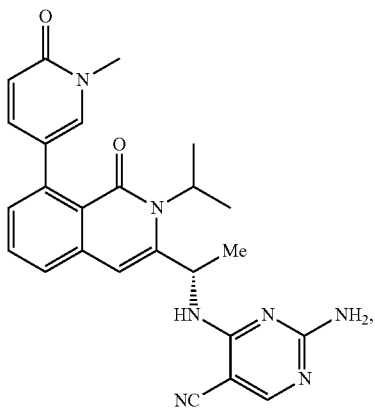

or a pharmaceutically acceptable salt or stereoisomer thereof.

24. The compound of claim 13, wherein the compound is:

Compound 327

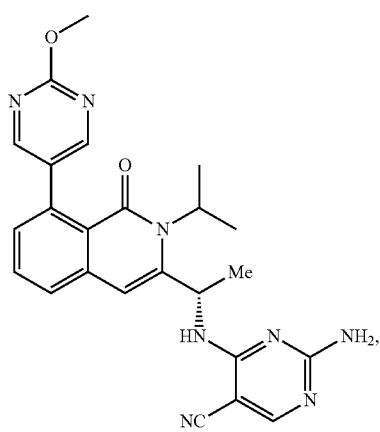

or a pharmaceutically acceptable salt or stereoisomer thereof.

25. The compound of claim 13, wherein the compound is:

Compound 328

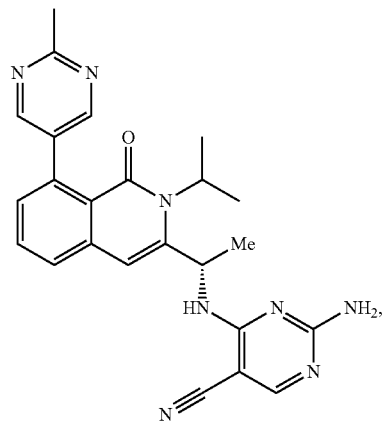

or a pharmaceutically acceptable salt or stereoisomer thereof.

26. The compound of claim 13, wherein the compound is:

Compound 359

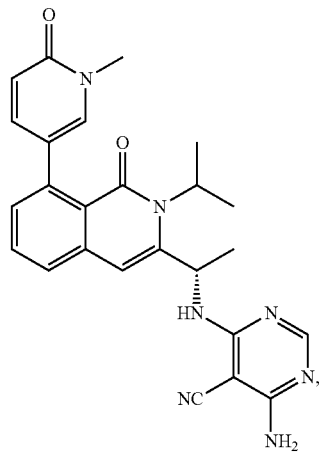

or a pharmaceutically acceptable salt or stereoisomer thereof.

27. The compound of claim 26, wherein the stereoisomer is an enantiomer.

28. The compound of claim 13, wherein the compound is:

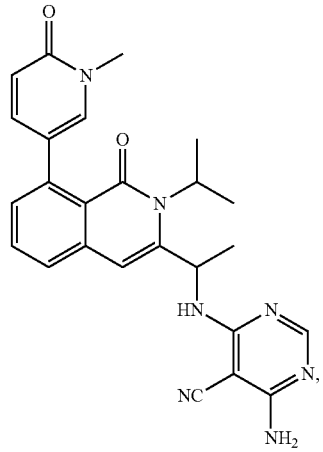

or a pharmaceutically acceptable salt or stereoisomer thereof.

29. The compound of claim 28, wherein the stereoisomer is an enantiomer.

30. The compound of claim 29, wherein the compound has an (S)-enantiomeric excess of greater than 55%.

31. The compound of claim 29, wherein the compound has an (S)-enantiomeric excess of greater than 75%.

32. The compound of claim 29, wherein the compound has an (S)-enantiomeric excess of greater than 90%.

33. The compound of claim 29, wherein the compound has an (S)-enantiomeric excess of greater than 95%.

34. The compound of claim 29, wherein the compound has an (S)-enantiomeric excess of greater than 98%.

35. A pharmaceutical composition comprising a compound according to claim 13 and one or more pharmaceutically acceptable excipients.

36. A method of inhibiting phosphatidylinositol 3-kinase activity in a subject, the method comprising administering to said subject a therapeutically effective amount of a compound according to claim 13.

37. The method of claim 36, wherein the subject suffers from a disorder selected from cancer, an autoimmune disease, an inflammatory disease or a respiratory disease.

38. The method of claim 37, wherein the disorder is cancer.

39. The method of claim 38, wherein the cancer is leukemia or lymphoma.

40. The method of claim 39, wherein the leukemia is acute lymphocytic leukemia, hairy cell leukemia, myelodysplasia, myeloproliferative disorders, natural killer cell leukemia, acute myelogenous leukemia, chronic myelogenous leukemia, mastocytosis, chronic lymphocytic leukemia, multiple myeloma or myelodysplastic syndrome.

41. The method of claim 39, wherein the lymphoma is diffuse large B-cell lymphoma, B-cell immunoblastic lymphoma, natural killer cell lymphoma, small non-cleaved cell lymphoma, Kaposi's sarcoma, viral-induced cancers, human lymphotropic virus-type 1 leukemia/lymphoma, adult T-cell leukemia/lymphoma, Hodgkin's disease, non-Hodgkin's lymphomas, mantle cell lymphoma or T-cell lymphoma.

42. The method of claim 38, wherein the cancer is acute lymphocytic leukemia, hairy cell leukemia, myelodysplasia, myeloproliferative disorders, natural killer cell leukemia, acute myelogenous leukemia, chronic myelogenous leukemia, mastocytosis, chronic lymphocytic leukemia, multiple myeloma, myelodysplastic syndrome, diffuse large B-cell lymphoma, B-cell immunoblastic lymphoma, natural killer cell lymphoma, small non-cleaved cell lymphoma, Kaposi's sarcoma, viral-induced cancers, human lymphotropic virus-type 1 leukemia/lymphoma, adult T-cell leukemia/lymphoma, Hodgkin's disease, non-Hodgkin's lymphomas, mantle cell lymphoma or T-cell lymphoma.

43. The method of claim 37, wherein the disorder is an inflammatory disease or an autoimmune disease.

44. The method of claim 43, wherein the inflammatory disease or autoimmune disease is asthma.

45. The method of claim 43, wherein the inflammatory disease or autoimmune disease is rheumatoid arthritis.

46. The method of claim 37, further comprising administering one or more therapeutic agents.

47. A compound of the formula:

Compound 359

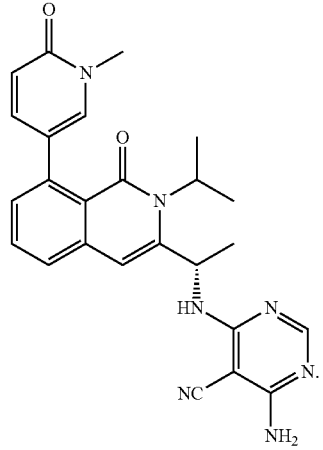 [SMILES: CC(Nc1ncnc(N)c1C#N)c1cc2cccc(-c3ccc(=O)n(C)c3)c2c(=O)n1C(C)C]

48. A pharmaceutical composition comprising a compound according to claim 47 and one or more pharmaceutically acceptable excipients.

49. A compound of the formula:

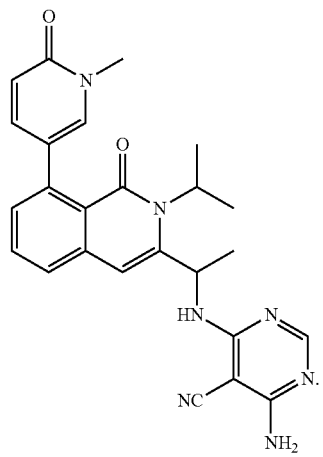 [SMILES: CC(Nc1ncnc(N)c1C#N)c1cc2cccc(-c3ccc(=O)n(C)c3)c2c(=O)n1C(C)C]

* * * * *

UNITED STATES PATENT AND TRADEMARK OFFICE
CERTIFICATE OF CORRECTION

PATENT NO. : 9,115,141 B2  
APPLICATION NO. : 14/099831  
DATED : August 25, 2015  
INVENTOR(S) : Castro et al.

It is certified that error appears in the above-identified patent and that said Letters Patent is hereby corrected as shown below:

In the claims

In column 540, line 50 (part of claim 1), replace the term "-(=O)-(CHR$^9$)$_z$-" with "-C(=O)-(CHR$^9$)$_z$-" to read:

-- -N(R$^9$)-, -C(=O)-(CHR$^9$)$_z$-, -C(=O)-, --.

Signed and Sealed this  
Ninth Day of August, 2016

Michelle K. Lee  
*Director of the United States Patent and Trademark Office*